(12) United States Patent
Barta et al.

(10) Patent No.: US 7,119,203 B2
(45) Date of Patent: Oct. 10, 2006

(54) PIPERIDINYL- AND PIPERAZINYL-SULFONYLMETHYL HYDROXAMIC ACIDS AND THEIR USE AS PROTEASE INHIBITORS

(75) Inventors: Thomas E. Barta, Evanston, IL (US);
Daniel P. Becker, Glenview, IL (US);
Louis J. Bedell, Mt. Prospect, IL (US);
Terri L. Boehm, Ballwin, MO (US);
David L. Brown, Chesterfield, MO (US); Jeffery N. Carroll, Columbia, IL (US); Yiyuan Chen, Skokie, IL (US);
Yvette M. Fobian, Wildwood, MO (US); John N. Freskos, Clayton, MO (US); Alan F. Gasiecki, Vernon Hills, IL (US); Margaret L. Grapperhaus, Troy, IL (US); Robert M. Heintz, Ballwin, MO (US); Susan L. Hockerman, Lincolnwood, IL (US);
Darren J. Kassab, O'Fallon, MO (US);
Ish K. Khanna, Libertyville, IL (US);
Stephen A. Kolodziej, Ballwin, MO (US); Mark A. Massa, Ballwin, MO (US); Joseph J. McDonald, Wildwood, MO (US); Brent V. Mischke, Defiance, MO (US); Deborah A. Mischke, Defiance, MO (US); Patrick B. Mullins, St. Louis, MO (US); Mark A. Nagy, Chesterfield, MO (US); Monica B. Norton, St. Louis, MO (US); Joseph G. Rico, Ballwin, MO (US); Michelle A. Schmidt, Belleville, IL (US);
Nathan W. Stehle, Grafton, WI (US);
John J. Talley, Cambridge, MA (US);
William F. Vernier, St. Louis, MO (US); Clara I. Villamil, Glenview, IL (US); Lijuan J. Wang, Wildwood, MO (US); Thomas A. Wynn, Chicago, IL (US)

(73) Assignee: Pharmacia Corporation, St. Louis, MO (US)

( * ) Notice: Subject to any disclaimer, the term of this patent is extended or adjusted under 35 U.S.C. 154(b) by 79 days.

(21) Appl. No.: 10/618,288

(22) Filed: Apr. 25, 2003

(65) Prior Publication Data
US 2005/0009838 A1 Jan. 13, 2005

Related U.S. Application Data

(60) Provisional application No. 60/375,598, filed on Apr. 25, 2002, provisional application No. 60/380,713, filed on May 15, 2002, provisional application No. 60/392,021, filed on Jun. 27, 2002.

(51) Int. Cl.
C07D 405/14 (2006.01)
C07D 405/12 (2006.01)
A61K 31/496 (2006.01)

(52) U.S. Cl. .................. 544/364; 544/130; 544/238; 544/295; 544/357; 544/360; 544/336; 544/366; 544/367; 544/369; 544/374; 544/383; 544/408; 546/187; 546/193; 546/194; 546/207; 546/210; 546/212; 546/214; 546/233; 514/235.5; 514/252.02; 514/252.03; 514/252.11; 514/252.18; 514/253.09; 514/253.12; 514/253.11; 514/254.1; 514/254.05; 514/255.02; 514/255.05; 514/254.03; 514/314; 514/316; 514/318; 514/323; 514/326; 514/327; 514/255.03

(58) Field of Classification Search ............... 544/295, 544/360, 364; 514/252.18, 253.11, 253.12
See application file for complete search history.

(56) References Cited

U.S. PATENT DOCUMENTS 4,595,700 A   6/1986  Donald et al. ............. 514/616

(Continued)

FOREIGN PATENT DOCUMENTS

EP          0 266 182       5/1988

(Continued)

OTHER PUBLICATIONS

Boehm et al. U.S. Appl. No. 10/877,450, filed Jul. 8, 2004.*

(Continued)

Primary Examiner—Emily Bernhardt
(74) Attorney, Agent, or Firm—Pharmacia Corporation

(57) ABSTRACT

This invention is directed generally to proteinase (also known as "protease") inhibitors, and, more particularly, to piperidinyl- and piperazinyl-sulfonylmethyl hydroxamic acids that, inter alia, inhibit matrix metalloproteinase (also known as "matrix metalloprotease" or "MMP") activity and/or aggrecanase activity. Such hydroxamic acids generally correspond in structure to the following formula:

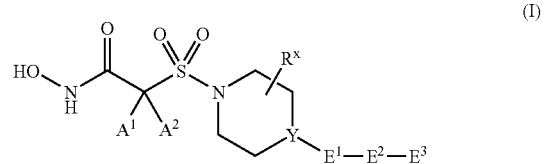

(I)

(wherein $A^1$, $A^2$, Y, $E^1$, $E^2$, $E^3$, and $R^x$ are as defined in this specification), and further include salts of such compounds. This invention also is directed to compositions of such hydroxamic acids, intermediates for the syntheses of such hydroxamic acids, methods for making such hydroxamic acids, and methods for treating conditions (particularly pathological conditions) associated with MMP activity and/or aggrecanase activity.

2 Claims, No Drawings

U.S. PATENT DOCUMENTS

| | | | |
|---|---|---|---|
| 5,451,676 A | 9/1995 | Whittaker et al. | 546/118 |
| 5,472,978 A | 12/1995 | Baker et al. | 514/443 |
| 5,475,138 A | 12/1995 | Pal et al. | 564/342 |
| 5,599,994 A | 2/1997 | Pal et al. | 564/355 |
| 5,932,595 A | 8/1999 | Bender et al. | 514/317 |
| 5,998,412 A | 12/1999 | Broka et al. | 514/250 |
| 6,013,649 A | 1/2000 | Freskos et al. | 514/237.8 |
| 6,300,514 B1 | 10/2001 | Takahashi et al. | 560/17 |
| 6,372,758 B1 | 4/2002 | DeCrescenzo et al. | 514/316 |
| 6,448,250 B1 | 9/2002 | DeCrescenzo et al. | 514/252 |
| 6,492,367 B1 | 12/2002 | DeCrescenzo et al. | 514/252 |
| 6,495,568 B1 | 12/2002 | Dack et al. | 514/318 |
| 6,683,078 B1 | 1/2004 | Barta et al. | 514/231.5 |
| 6,683,093 B1 | 1/2004 | Barta et al. | 514/316 |
| 6,689,794 B1 | 2/2004 | Freskos et al. | 514/318 |
| 6,800,646 B1 | 10/2004 | DeCrescenzo et al. | 514/316 |
| 2003/0073718 A1 | 4/2003 | Barta et al. | |
| 2003/0171404 A1 | 9/2003 | Barta et al. | |

FOREIGN PATENT DOCUMENTS

| | | |
|---|---|---|
| EP | 0 336 354 | 10/1989 |
| EP | 0 606 046 | 7/1994 |
| EP | 0 780 386 | 6/1997 |
| EP | 0 930 067 | 7/1999 |
| EP | 0 931 788 | 7/1999 |
| EP | 1081137 | 3/2001 |
| GB | 1067965 | 5/1967 |
| GB | 2263109 | 7/1993 |
| JP | 4-338331 | 11/1992 |
| WO | WO 90/05719 | 5/1990 |
| WO | WO 93/20047 | 10/1993 |
| WO | WO 94/02466 | 2/1994 |
| WO | WO 94/24140 | 10/1994 |
| WO | WO 95/04720 | 2/1995 |
| WO | WO 95/09841 | 4/1995 |
| WO | WO 95/13064 | 5/1995 |
| WO | WO 95/13289 | 5/1995 |
| WO | WO 95/29892 | 11/1995 |
| WO | WO 96/06074 | 2/1996 |
| WO | WO 96/11209 | 4/1996 |
| WO | WO 97/05865 | 2/1997 |
| WO | WO 97/20824 | 6/1997 |
| WO | WO 97/24117 | 7/1997 |
| WO | WO 97/48368 | 12/1997 |
| WO | WO 98/37877 | 9/1998 |
| WO | WO 98/38163 | 9/1998 |
| WO | WO 98/38859 | 9/1998 |
| WO | WO 98/39329 | 9/1998 |
| WO | WO 99/09000 | 2/1999 |
| WO | WO 99/24399 | 5/1999 |
| WO | WO 99/25687 | 5/1999 |
| WO | WO 99/29667 | 6/1999 |
| WO | WO 99/42436 | 8/1999 |
| WO | WO 00/38717 | 6/2000 |
| WO | WO 00/46221 | 8/2000 |
| WO | WO 00/50396 | 8/2000 |
| WO | WO 00/59874 | 10/2000 |
| WO | WO 00/69819 | 11/2000 |
| WO | WO 00/69821 | 11/2000 |
| WO | WO 00/74681 | 12/2000 |
| WO | WO 02/092588 | 11/2002 |
| WO | WO 03/007930 | 1/2003 |

OTHER PUBLICATIONS

McDonald et al. U.S. Appl. No. 10/700,202, filed Nov. 3, 2003.*
Barta et al. U.S. Appl. No. 09/311,837, filed May 14, 1999.*
Freskos et al. U.S. Appl. No. 10/142,737, filed May 10, 2002.*
Freskos et al. U.S. Appl. No. 10/291,983, filed Nov. 12, 2002.*
DeCrescenzo et al. U.S. Appl. No. 10/262,622, filed Sep. 30, 2002.*
Brown, "Synthetic Inhibitors of Matrix Metalloproteinases"; *Matrix Metalloproteinases*, pp. 243-261 (Academic Press, San Diego, CA, Eds. Park, W.C., & Mecham, R.P., 1998).
Dack, et al., "Preparation of N-hydroxytetrahydropyridylsulfonylacetamides and related compounds as matrix metalloprotease inhibitors," CA 131:44740 (1999) [CA Plus Accession No. 1999:388166].
Denis, et al., "Matrix metalloproteinase inhibitors: Present achievements and future prospects," *Invest New Drugs*, 15:175-185 (1997).
Freije, et al., "Molecular cloning and expression of collagenase-3, a novel human matrix metalloproteinase produced by breast carcinomas," *J. Biol. Chem.*, 269(24), pp. 16766-16773 (1994).
Gearing, et al., "Processing of tumour necrosis factor-α precursor by metalloproteinases," *Nature*, 370:555-557 (1994).
Gu, et al., "S-Nitrosylation of Matrix Metalloproteinases: Signaling Pathway to Neuronal Cell Death," *Science*, 297, 1186-1190 (2002).
Hughes, et al., "Monoclonal antibodies that specifically recognize neoepitope sequences generated by 'aggrecanase' and matrix metalloproteinase cleavage of aggrecan: application to catabolism *in situ* and *in vitro*," *Biochem. J.*, 305, 799-804 (1995).
Kenyon, et al., "A model of angiogenesis in the mouse cornea," *Invest Ophthalmol. Vis. Sci.*, 37(8):1625-1632 (1996).
Knight, et al., "A novel coumarin-labelled peptide for sensitive continuous assays of the matrix metalloproteinases," *FEBS Lett.*, 296(3):263-266 (1992).
Kuzmic, et al., "High-throughput screening of enzyme inhibitor: simultaneous determination of tright-binding inhibition constants and enzyme concentration," *Anal. Biochem.*, 286, 45-50 (2000).
Luckow, et al., "Insect Cell Expression Technology", *Protein Enginerring: Principles and Practice*, pp. 183-218 (John Wiley & Sons, Inc., New York, NY, Edited by J.L. Cleland et al., 1996).
Luckow, et al., "Efficient generation of infectious recombinant baculoviruses by site-specific transposon-mediated insertion of foreign genes into a baculovirus genome propagated in *Escherihia coli*," J. Virol., 67(8):4566-4579 (1993).
McClure, et al., "Matrix metalloprotease (MMP)-13 selective inhibitors for treatment of arthritis deformans and other MMP-related diseases," CA 131:125454 (1999) [CA Plus Accession No. 1999:468334].
McGeehan, et al., "Regulation of tumour necrosis factor-α processing by a metalloproteinase inhibitor," *Nature*, 370:558-561 (1994).
Mitchell, et al., "Cloning, expression, and type II collagenolytic activity of matrix metalloproteinase-13 from human osteoarthritic cartilage," *J. Clin. Invest.*, 97(3):761-768 (1996).
Rasmussen, et al., "Matrix metalloproteinase inhibition as a novel anticancer strategy: a review with special focus on batimastat and marimastat," *Pharmacol. Ther.*, 75(1):69-75 (1997).
Reboul, et al., "The new collagenase, collagnease-3, is expressed and synthesized by human chondrocytes but not by synoviocytes," *J. Clin. Invest.*, 97(9):2011-2019 (1996).
Schwartz, et al., "Synthetic inhibitors of bacterial and mammalian interstitial collagenases," *Prog. In Med. Chem.*, 29:271-334 (1992).
Tang, "ADAMTS: a novel family of extracellular matrix proteases," *Int'l J. Biochem. Cell Biol.*, 33, 33-44 (2001).
Woessner, "The Matrix Metalloproteinase Family," *Matrix Metalloproteinases*, pp. 1-14 (Academic Press, San Diego, CA, Eds. Parks, W.C. & Mecham, R.P., 1998).
A partial search report from PCT Appl. No. PCT/US03/13123.
Oct. 9, 2003 Search Report and Aug. 3, 2004 International Preliminary Examination Report from International Patent Application No. PCT/US03/13123.

* cited by examiner

US 7,119,203 B2

PIPERIDINYL- AND PIPERAZINYL-SULFONYLMETHYL HYDROXAMIC ACIDS AND THEIR USE AS PROTEASE INHIBITORS

PRIORITY CLAIM TO RELATED PATENT APPLICATIONS

This patent claims priority to U.S. Provisional Patent Application Ser. Nos. 60/375,598 (filed Apr. 25, 2002); 60/380,713 (filed May 15, 2002); and 60/392,021 (filed Jun. 27, 2002). The entire text of each of the above-referenced applications is incorporated by reference into this patent.

FIELD OF THE INVENTION

This invention is directed generally to proteinase (also known as "protease") inhibitors, and, more particularly, to piperidinyl- and piperazinyl-sulfonylmethyl hydroxamic acids and salts thereof that, inter alia, inhibit matrix metalloproteinase (also known as "matrix metalloprotease" or "MMP") activity and/or aggrecanase activity. This invention also is directed to compositions of such inhibitors, intermediates for the syntheses of such inhibitors, methods for making such inhibitors, and methods for treating conditions associated with proteinase activity (particularly pathological conditions associated with MMP activity and/or aggrecanase activity).

BACKGROUND OF THE INVENTION

Connective tissue is a required component of all mammals. It provides rigidity, differentiation, attachments, and, in some cases, elasticity. Connective tissue components include, for example, collagen, elastin, proteoglycans, fibronectin, and laminin. These biochemicals make up (or are components of) structures, such as skin, bone, teeth, tendon, cartilage, basement membrane, blood vessels, cornea, and vitreous humor.

Under normal conditions, connective tissue turnover and/or repair processes are in equilibrium with connective tissue production. Degradation of connective tissue is carried out by the action of proteinases released from resident tissue cells and/or invading inflammatory or tumor cells.

Matrix metalloproteinases, a family of zinc-dependent proteinases, make up a major class of enzymes involved in degrading connective tissue. Matrix metalloproteinases are divided into classes, with some members having several different names in common use. Examples are: MMP-1 (also known as collagenase 1, fibroblast collagenase, or EC 3.4.24.3); MMP-2 (also known as gelatinase A, 72 kDa gelatinase, basement membrane collagenase, or EC 3.4.24.24), MMP-3 (also known as stromelysin 1 or EC 3.4.24.17), proteoglycanase, MMP-7 (also known as matrilysin), MMP-8 (also known as collagenase II, neutrophil collagenase, or EC 3.4.24.34), MMP-9 (also known as gelatinase B, 92 kDa gelatinase, or EC 3.4.24.35), MMP-10 (also known as stromelysin 2 or EC 3.4.24.22), MMP-11 (also known as stromelysin 3), MMP-12 (also known as metalloelastase, human macrophage elastase or HME), MMP-13 (also known as collagenase 111), and MMP-14 (also known as MT1-MMP or membrane MMP). See, generally, Woessner, J. F., "The Matrix Metalloprotease Family" in *Matrix Metalloproteinases*, pp. 1–14 (Edited by Parks, W. C. & Mecham, R. P., Academic Press, San Diego, Calif. 1998).

Excessive breakdown of connective tissue by MMPs is a feature of many pathological conditions. Inhibition of MMPs therefore provides a control mechanism for tissue decomposition to treat these pathological conditions. Such pathological conditions generally include, for example, tissue destruction, fibrotic diseases, pathological matrix weakening, defective injury repair, cardiovascular diseases, pulmonary diseases, kidney diseases, liver diseases, and diseases of the central nervous system. Specific examples of such conditions include, for example, rheumatoid arthritis, osteoarthritis, septic arthritis, multiple sclerosis, a decubitis ulcer, corneal ulceration, epidermal ulceration, gastric ulceration, tumor metastasis, tumor invasion, tumor angiogenesis, periodontal disease, liver cirrhosis, fibrotic lung disease, emphysema, otosclerosis, atherosclerosis, proteinuria, coronary thrombosis, dilated cardiomyopathy, congestive heart failure, aortic aneurysm, epidermolysis bullosa, bone disease, Alzheimer's disease, defective injury repair (e.g., weak repairs, adhesions such as post-surgical adhesions, and scarring), chronic obstructive pulmonary disease, and post myocardial infarction. MMPs (particularly MMP-9) also have been reported to be associated with pathological conditions related to nitrosative and oxidative stress. See Gu, Zezong et al., "S-Nitrosylation of Matrix Metalloproteinases: Signaling Pathway to Neuronal Cell Death," *Science*, vol. 297, pp. 1186–90 (2002).

Matrix metalloproteinases also are involved in the biosynthesis of tumor necrosis factors (TNFs). Tumor necrosis factors are implicated in many pathological conditions. TNF-α, for example, is a cytokine that is presently thought to be produced initially as a 28 kD cell-associated molecule. It is released as an active, 17 kD form that can mediate a large number of deleterious effects in vitro and in vivo. TNF-α can cause and/or contribute to the effects of inflammation (e.g., rheumatoid arthritis), autoimmune disease, graft rejection, multiple sclerosis, fibrotic diseases, cancer, infectious diseases (e.g., malaria, mycobacterial infection, meningitis, etc.), fever, psoriasis, cardiovascular diseases (e.g., post-ischemic reperfusion injury and congestive heart failure), pulmonary diseases (e.g., hyperoxic alveolar injury), hemorrhage, coagulation, radiation damage, and acute phase responses like those seen with infections and sepsis and during shock (e.g., septic shock and hemodynamic shock). Chronic release of active TNF-α can cause cachexia and anorexia. TNF-α also can be lethal.

Inhibiting TNF (and related compounds) production and action is an important clinical disease treatment. Matrix metalloproteinase inhibition is one mechanism that can be used. MMP (e.g., collagenase, stromelysin, and gelatinase) inhibitors, for example, have been reported to inhibit TNF-α release. See, e.g., Gearing et al., *Nature*, 370, 555–557 (1994). See also, McGeehan et al., *Nature*, 370, 558–561 (1994). MMP inhibitors also have been reported to inhibit TNF-α convertase, a metalloproteinase involved in forming active TNF-α. See, e.g., WIPO Int'l Pub. No. WO 94/24140. See also, WIPO Int'l Pub. No. WO 94/02466. See also, WIPO Int'l Pub. No. WO 97/20824.

Matrix metalloproteinases also are involved in other biochemical processes in mammals. These include control of ovulation, post-partum uterine involution, possibly implantation, cleavage of APP (β-amyloid precursor protein) to the ainyloid plaque, and inactivation of ($α_1$-protease inhibitor ($α_1$-PI). Inhibiting MMPs therefore may be a mechanism that may be used to control of fertility. In addition, increasing and maintaining the levels of an endogenous or administered serine protease inhibitor (e.g., $α_1$-PI) supports the treatment of pathological conditions such as emphysema, pulmonary diseases, inflammatory diseases, and diseases of aging (e.g., loss of skin or organ stretch and resiliency).

Numerous metalloproteinase inhibitors are known. See, generally, Brown, P. D., "Synthetic Inhibitors of Matrix Metalloproteinases," in *Matrix Metalloproteinases*, pp. 243–61 (Edited by Parks, W. C. & Mecham, R. P., Academic Press, San Diego, Calif. 1998).

Metalloproteinase inhibitors include, for example, natural biochemicals, such as tissue inhibitor of metalloproteinase (TIMP), α2-macroglobulin, and their analogs and derivatives. These are high-molecular-weight protein molecules that form inactive complexes with metalloproteinases.

A number of smaller peptide-like compounds also have been reported to inhibit metalloproteinases. Mercaptoamide peptidyl derivatives, for example, have been reported to inhibit angiotensin converting enzyme (also known as ACE) in vitro and in vivo. ACE aids in the production of angiotensin II, a potent pressor substance in mammals. Inhibiting ACE leads to lowering of blood pressure.

A wide variety of thiol compounds have been reported to inhibit MMPs. See, e.g., WO95/13289. See also, WO96/11209. See also, U.S. Pat. No. 4,595,700. See also, U.S. Pat. No. 6,013,649.

A wide variety of hydroxamic acid compounds also have been reported to inhibit MMPs. Such compounds reportedly include hydroxamic acids having a carbon backbone. See, e.g., WIPO Int'l Pub. No. WO 95/29892. See also, WIPO Int'l Pub. No. WO 97/24117. See also, WIPO Int'l Pub. No. WO 97/49679. See also, European Patent No. EP 0 780 386. Such compounds also reportedly include hydroxamic acids having peptidyl backbones or peptidomimetic backbones. See, e.g., WIPO Int'l Pub. No. WO 90/05719. See also, WIPO Int'l Pub. No. WO 93/20047. See also, WIPO Int'l Pub. No. WO 95/09841. See also, WIPO Int'l Pub. No. WO 96/06074. See also, Schwartz et al., *Progr. Med. Chem.*, 29:271–334(1992). See also, Rasmussen et al., *Pharmacol. Ther.*, 75(1): 69–75 (1997). See also, Denis et al., *Invest New Drugs*, 15: 175–185 (1997). Various piperazinylsulfonylmethyl hydroxamic acids and piperidinylsulfonylmethyl hydroxamic acids have additionally been reported to inhibit MMPs. See, WIPO Int'l Pub. No. WO 00/46221. And various aromatic sulfone hydroxamic acids have been reported to inhibit MMPs. See, WIPO Int'l Pub. No. WO 99/25687. See also, WIPO Int'l Pub. No. WO 00/50396. See also, WIPO Int'l Pub. No. WO 00/69821.

It is often advantageous for an MMP inhibitor drug to target a certain MMP(s) over another MMP(s). For example, it is typically preferred to inhibit MMP-2, MMP-3, MMP-9, and/or MMP-13 (particularly MMP-13) when treating cancer, inhibiting of metastasis, and inhibiting angiogenesis. It also is typically preferred to inhibit MMP-13 when treating osteoarthritis. See, e.g., Mitchell et al., *J Clin. Invest.*, 97(3):761–768 (1996). See also, Reboul et al., *J Clin. Invest.*, 97(9):2011–2019 (1996). Normally, however, it is preferred to use a drug that has little or no inhibitory effect on MMP-1 and MMP-14. This preference stems from the fact that both MMP-1 and MMP-14 are involved in several homeostatic processes, and inhibition of MMP-1 and/or MMP-14 consequently tends to interfere with such processes.

Many known MMP inhibitors exhibit the same or similar inhibitory effects against each of the MMPs. For example, batimastat (a peptidomimetic hydroxamic acid) has been reported to exhibit $IC_{50}$ values of from about 1 to about 20 nM against each of MMP-1, MMP-2, MMP-3, MMP-7, and MMP-9. Marimastat (another peptidomimetic hydroxamic acid) has been reported to be another broad-spectrum MMP inhibitor with an enzyme inhibitory spectrum similar to batimastat, except that Marimastat reportedly exhibited an $IC_{50}$ value against MMP-3 of 230 nM. See Rasmussen et al., *Pharmacol. Ther.*, 75(1): 69–75 (1997).

Meta analysis of data from Phase I/II studies using Marimastat in patients with advanced, rapidly progressive, treatment-refractory solid tumor cancers (colorectal, pancreatic, ovarian, and prostate) indicated a dose-related reduction in the rise of cancer-specific antigens used as surrogate markers for biological activity. Although Marimastat exhibited some measure of efficacy via these markers, toxic side effects reportedly were observed. The most common drug-related toxicity of Marimastat in those clinical trials was musculoskeletal pain and stiffness, often commencing in the small joints in the hands, and then spreading to the arms and shoulder. A short dosing holiday of 1–3 weeks followed by dosage reduction reportedly permits treatment to continue. See Rasmussen et al., *Pharmacol. Ther.*, 75(1): 69–75 (1997). It is thought that the lack of specificity of inhibitory effect among the MMPs may be the cause of that effect.

Another enzyme implicated in pathological conditions associated with excessive degradation of connective tissue is aggrecanase, particularly aggrecanase-1 (also known as ADAMTS-4). Specifically, articular cartilage contains large amounts of the proteoglycan aggrecan. Proteoglycan aggrecan provides mechanical properties that help articular cartilage in withstanding compressive deformation during joint articulation. The loss of aggrecan fragments and their release into synovial fluid caused by proteolytic cleavages is a central pathophysiological event in osteoarthritis and rheumatoid arthritis. It has been reported that two major cleavage sites exist in the proteolytically sensitive interglobular domains at the N-terminal region of the aggrecan core protein. One of those sites has been reported to be cleaved by several matrix metalloproteases. The other site, however, has been reported to be cleaved by aggrecanase-1. Thus, inhibiting excessive aggrecanase activity provides an additional and/or alternative treatment method for inflammatory conditions. See generally, Tang, B. L., "ADAMTS: A Novel Family of Extracellular Matrix Proteases," *Int'l Journal of Biochemistry & Cell Biology*, 33, pp. 33–44 (2001). Such diseases reportedly include, for example, osteoarthritis, rheumatoid arthritis, joint injury, reactive arthritis, acute pyrophosphate arthritis, and psoriatic arthritis. See, e.g., European Patent Application Publ. No. EP 1 081 137 A1.

In addition to inflammatory conditions, there also is evidence that inhibiting aggrecanase may be used for treating cancer. For example, excessive levels of aggrecanase-1 reportedly have been observed with a ghoma cell line. It also has been postulated that the enzymatic nature of aggrecanase and its similarities with the MMPs would support tumor invasion, metastasis, and angiogenesis. See Tang, *Int'l Journal of Biochemistry & Cell Biology*, 33, pp. 33–44 (2001).

Various hydroxamic acid compounds have been reported to inhibit aggrecanase-1. Such compounds include, for example, those described in European Patent Application Publ. No. EP 1 081 137 A1. Such compounds also include, for example, those described in WIPO PCT Int'l Publ. No. WO 99/09000. Such compounds further include, for example, those described in WIPO PCT Int'l Publ. No. WO 00/59874.

In view of the importance of hydroxamic acid compounds in the treatment of several pathological conditions (particularly those associated with MMP and/or aggrecanase activity) and the lack of enzyme specificity exhibited by two of the more potent hydroxamic acid MMP-inhibitor drugs that have been in clinical trials, there continues to be a need for hydroxamic acids having greater enzyme specificity (particularly hydroxamic acids exhibiting little or no inhibitory activity toward MMP-1 and/or MMP-14). The following disclosure describes hydroxamic acid compounds that tend to exhibit such desirable activities.

SUMMARY OF THE INVENTION

This invention is directed to, for example, compounds and salts thereof that inhibit protease activity, particularly compounds that inhibit MMP-2, MMP-9, MIMP-13, and/or aggrecanase, while generally exhibiting relatively little or no inhibition against MMP-1 and MMP-14 activity. This invention also is directed to, for example, a method for inhibiting protease activity, particularly pathological MMP activity. Such a method is particularly suitable to be used with mammals, such as humans, other primates (e.g., monkeys, chimpanzees. etc.), companion animals (e.g., dogs, cats, horses, etc.), farm animals (e.g., goats, sheep, pigs, cattle, etc.), laboratory animals (e.g., mice, rats, etc.), and wild and zoo animals (e.g., wolves, bears, deer, etc.).

Briefly, therefore, this invention is directed, in part, to a compound that corresponds in structure to Formula I (or a salt thereof):

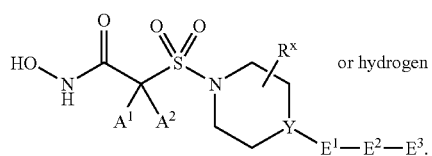

Generally, Y, $A^1$, $A^2$, $E^1$, $E^2$, and $E^3$ are defined as follows:

Y is nitrogen, carbon bonded to hydrogen, or carbon bonded to an $R^x$ substituent.

$A^1$ and $A^2$, together with the carbon to which they are bonded, form carbocyclyl or heterocyclyl. The carbocyclyl or heterocyclyl is optionally substituted with up to 3 independently selected $R^x$ substituents. Alternatively, $A^1$ and $A^2$ are independently selected from the group consisting of hydrogen, alkyl, alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, and heterocyclylalkylthioalkyl. Each such substituent (if substitutable) optionally is substituted with up to 3 independently selected $R^x$ substituents.

$E^1$ is carbocyclyl or heterocyclyl. The carbocyclyl or heterocyclyl (if substitutable at one or more positions other than the position occupied by -$E^2$-$E^3$) is optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

Alternatively, $E^1$ is alkyl optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional the alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

Alternatively, $E^1$ is -$E^{1A}$-$E^{1B}$. Here, $E^{1A}$ is —O—, —C(O)—, —C(O)—O—, —O—C(O)—, —N($R^a$)—, —C(O)—N($R^a$)—, —N($R^a$)—C(O)—, —C(O)—N($R^a$)—N($R^a$)—C(O)—, —S—, —S(O)—, —S(O)$_2$—, —N($R^a$)—S(O)$_2$—, —S(O)$_2$—N($R^a$)—, —O—S(O)$_2$—, —S(O)$_2$—O—, —C(NOH)—, or a bond. $E^{1B}$ is heterocylcylalkyl optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. Any member of such group optionally is substituted with one or more substituents independently selected from the group consisting of halogen, hydroxy, cyano, carboxy, thiol, sulfo, nitro, nitroso, oxo, thioxo, and imino.

$E^2$ is —O—, —C(O)—, —C(O)—O—, —O—C(O)—, —N($R^a$)—, —C(O)—N($R^a$)—, —N($R^a$)—C(O)—, —C(O)—N($R^a$)—N($R^a$)—C(O)—, —S—, —S(O)—, —S(O)$_2$—, —N($R^a$)—S(O)$_2$—, —S(O)$_2$—N($R^a$)—, —O—S(O)$_2$—, —S(O)$_2$—O—, —C(NH)—, —C(NOH)—, or a bond.

$E^3$ is hydrogen, halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Any such substituent (if substitutable) is optionally substituted with one or more substituents independently selected from the group consisting of halogen, hydroxy, cyano, carboxy, thiol, sulfo, nitro, nitroso, oxo, thioxo, imino, hydroxylimino, amino (optionally substituted with up to 2 substituents independently selected from the group consisting of alkyl and carbocyclylalkyl), alkyl, alkoxy, alkylthio, alkylsulfonyl, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

Each $R^x$ is independently selected from the group consisting of halogen, cyano, hydroxy, nitro, nitroso, oxo, alkyl, alkenyl, alkynyl, alkoxy, alkoxyalkyl, alkoxyalkoxy, $R^a$-oxyalkyl, alkenyloxy, alkynyloxy, alkylthio, alkylsulfonyl, $R^aR^a$-amino, $R^aR^a$-aminoalkyl, $R^aR^a$-aminoalkoxy, $R^aR^a$-aminoalkyl($R^a$)amino, $R^aR^a$-aminosulfonyl, carbocyclyl, carbocyclylalkyl, carbocyclyloxy, carbocyclyloxyalkoxy, carbocyclylthio, carbocyclylsulfonyl, heterocyclyl, heterocyclylalkyl, heterocyclyloxy, heterocyclyloxyalkoxy, heterocyclylthio, and heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy are optionally substituted with one or more substituents independently selected from the group consisting of halogen and hydroxy; and the amino is optionally substituted with up to 2 independently selected alkyl; and the imino is optionally substituted with hydroxy.

Each $R^a$ is independently selected from the group consisting of hydrogen, hydroxy, alkyl, alkenyl, alkynyl, alkoxy, alkoxyalkyl, bisalkoxyalkyl, alkylthioalkyl, alkylthioalkenyl, alkylsulfoxidoalkyl, alkylsulfonyl, alkylsulfonylalkyl, carbocyclyl, carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, carbocyclylsulfonylalkyl, heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonyl, heterocyclylsulfonylalkyl, aminoalkyl, aminosulfonyl, aminoalkylsulfonyl, and alkoxyalkylaminoalkyl. Each such substituent (if substitutable) is, in turn, optionally substituted:
  on any substitutable carbon with one or more substituents independently selected from the group consisting of halogen, hydroxy, cyano, carboxy, thiol, sulfo, nitro, nitroso, oxo, thioxo, and imino; and
  on any substitutable amino nitrogen with up to 2 substituents independently selected from the group consisting of alkyl, alkylcarbonyl, carbocyclyl, and carbocyclylalkyl;

This invention also is directed, in part, to a method for treating a condition associated with pathological matrix metalloprotease activity in a mammal having the condition or predisposed to having the condition. The method comprises administering an above-described compound or a pharmaceutically acceptable salt thereof to the mammal in an amount that is therapeutically-effective to treat the condition.

This invention also is directed, in part, to a method for treating a condition associated with pathological TNF-α convertase activity in a mammal having the condition or predisposed to having the condition. The method comprises administering an above-described compound or a pharmaceutically acceptable salt thereof to the mammal in an amount that is therapeutically-effective to treat the condition.

This invention also is directed, in part, to a method for treating a condition associated with pathological aggrecanase activity in a mammal having the condition or predisposed to having the condition. The method comprises administering an above-described compound or a pharmaceutically acceptable salt thereof to the mammal in an amount that is therapeutically-effective to treat the condition.

This invention also is directed, in part, to a method for treating a pathological condition in a mammal having the condition or predisposed to having the condition, wherein the pathological condition comprises tissue destruction, a fibrotic disease, pathological matrix weakening, defective injury repair, a cardiovascular disease, a pulmonary disease, a kidney disease, a liver disease, an ophthalmologic disease, and a central nervous system disease. The method comprises administering an above-described compound or a pharmaceutically acceptable salt thereof to the mammal in an amount that is therapeutically-effective to treat the condition.

This invention also is directed, in part, to a method for treating a pathological condition in a mammal having the condition or predisposed to having the condition, wherein the pathological condition comprises osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermal ulceration, epidermolysis bullosa, aortic aneurysm, defective injury repair, an adhesion, scarring, congestive heart failure, post myocardial infarction, coronary thrombosis, emphysema, proteinuria, Alzheimer's disease, bone disease, and chronic obstructive pulmonary disease. The method comprises administering an above-described compound or a pharmaceutically acceptable salt thereof to the mammal in an amount that is therapeutically-effective to treat the condition.

This invention also is directed, in part, to pharmaceutical compositions comprising a therapeutically-effective amount of an above-described compound or a pharmaceutically-acceptable salt thereof.

This invention also is directed, in part, to a use of an above-described compound or a pharmaceutically acceptable salt thereof to prepare a medicament for treating a condition associated with pathological matrix metalloprotease activity.

This invention also is directed, in part, to a use of an above-described compound or a pharmaceutically acceptable salt thereof to prepare a medicament for treating a condition associated with pathological TNF-α convertase activity.

This invention also is directed, in part, to a use of an above-described compound or a pharmaceutically acceptable salt thereof to prepare a medicament for treating a condition associated with pathological aggrecanase activity.

This invention also is directed, in part, to a use of an above-described compound or a pharmaceutically acceptable salt thereof to prepare a medicament for treating tissue destruction, a fibrotic disease, pathological matrix weakening, defective injury repair, a cardiovascular disease, a pulmonary disease, a kidney disease, a liver disease, an ophthalmologic disease, and a central nervous system disease. The method comprises administering an above-described compound or a pharmaceutically acceptable salt thereof to the mammal in an amount that is therapeutically-effective to treat the condition.

This invention also is directed, in part, to a use of an above-described compound or a pharmaceutically acceptable salt thereof to prepare a medicament for treating osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermal ulceration, epidermolysis bullosa, aortic aneurysm, defective injury repair, an adhesion, scarring, congestive heart failure, post myocardial infarction, coronary thrombosis, emphysema, proteinuria, Alzheimer's disease, bone disease, and chronic obstructive pulmonary disease. The method comprises administering an above-described compound or a pharmaceutically acceptable salt thereof to the mammal in an amount that is therapeutically-effective to treat the condition.

Further benefits of Applicants' invention will be apparent to one skilled in the art from reading this patent.

DETAILED DESCRIPTION OF THE PREFERRED EMBODIMENTS

This detailed description of preferred embodiments is intended only to acquaint others skilled in the art with Applicants' invention, its principles, and its practical application so that others skilled in the art may adapt and apply the invention in its numerous forms, as they may be best suited to the requirements of a particular use. This detailed description and its specific examples, while indicating preferred embodiments of this invention, are intended for purposes of illustration only. This invention, therefore, is not limited to the preferred embodiments described in this patent, and may be variously modified.

A. Compounds of this Invention

In accordance with this invention, it has been found that certain piperidinyl- and piperazinyl-sulfonylmethyl hydroxamic acid compounds and salts thereof tend to be effective for inhibiting proteases, particularly those associated with excessive (or otherwise pathological) breakdown of connective tissue. Specifically, Applicants have found that these compounds and salts tend to be effective for inhibiting proteases (particularly MMP-2, MMP-9, MMP-13, other MMP's associated with pathological conditions, and/or aggrecanase) that are often particularly destructive to tissue if present or generated in abnormally excessive quantities or concentrations. Moreover, Applicants have discovered that these compounds and salts tend to be selective toward inhibiting pathological protease activity, while avoiding excessive inhibition of other proteases (particularly MMP-1 and/or MMP-14) that are typically essential to normal bodily function (e.g., tissue turnover and repair).

A-1. Preferred Compound Structures

As noted above, the compounds of this invention generally have a structure corresponding to Formula I:

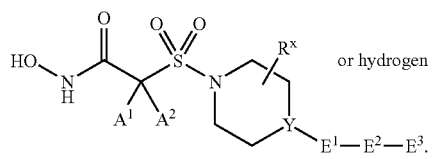
(I)

In many preferred embodiments, such compounds generally correspond in structure to the following formula (IA):

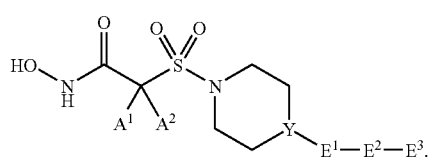
(IA)

In these formulas, Y, $A^1$, $A^2$, $E^1$, $E^2$, $E^3$, and $R^x$ are defined as follows:

General Description of Preferred Y Substituents

Y is generally (1) carbon bonded to hydrogen, (2) carbon bonded to an $R^x$ substituent, or (3) nitrogen.

If Y is carbon bonded to hydrogen, the compound corresponds in structure to Formula (IB-1):

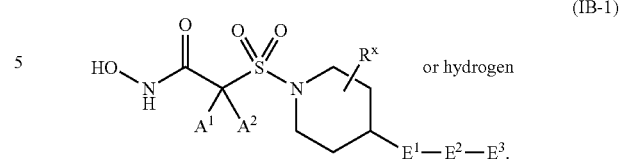
(IB-1)

If, on the other hand, Y is bonded to an $R^x$ substituent, the compound corresponds in structure to Formula (IB-2):

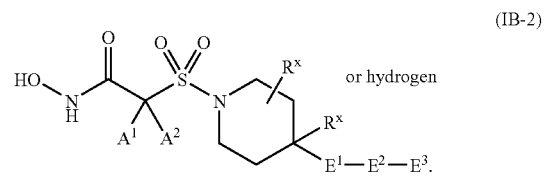
(IB-2)

In many such embodiments, the piperidine bridging the sulfonyl and $E^1$ is preferably not otherwise substituted with an $R^x$ substituent. In that instance, the compound corresponds in structure to Formula (IB-3):

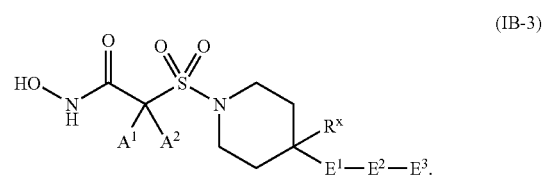
(IB-3)

In some such embodiments, Y is preferably carbon bonded to halogen. In other such embodiments, Y is preferably carbon bonded to hydroxy. In those embodiments, the compound corresponds in structure to Formula (IB-4)

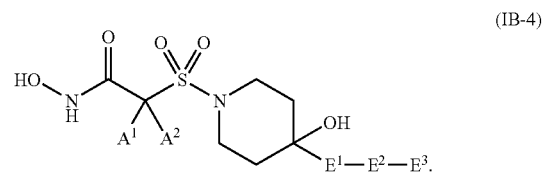
(IB-4)

If Y is nitrogen, the compound corresponds in structure to Formula (IB-5):

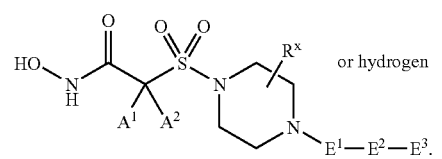
(IB-5)

General Description of Preferred $A^1$ and $A^2$ Substituents $A^1$ and $A^2$ (together with the carbon to which they are bonded) may form carbocyclyl or heterocyclyl. The carbocyclyl or heterocyclyl is, in turn, optionally substituted with up to 3 independently selected $R^x$ substituents. The phrase "optionally substituted with up to 3 independently selected $R^x$ substituents" means that the carbocyclyl or heterocyclyl may be either: (1) unsubstituted; or (2) substituted with 1, 2, or 3 $R^x$ substituents. Those $R^x$ substituents may be identical or different. The term "substituted" means that an $R^x$ substituent is in the place of a hydrogen on the carbocyclyl or heterocyclyl. If the ring structure has fewer than 3 substitutable positions (i.e., less than 3 hydrogens), then the number of optional $R^x$ substituents on the ring structure will be up to the number of substitutable positions on the ring structure. To illustrate, if $A^1$ and $A^2$ (together with the carbon to which they are bonded) form dioxazolyl:

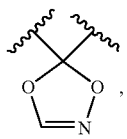

then the dioxazolyl is optionally substituted with up to one $R^x$ substituent. In other words, the compound will correspond in structure to one of the following:

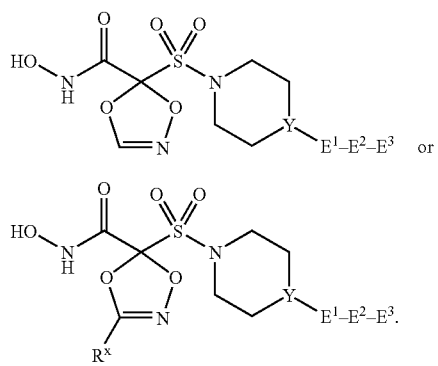

In some preferred embodiments, $A^1$ and $A^2$ (together with the carbon to which they are bonded) form carbocyclyl. The carbocyclyl is optionally substituted with up to 3 independently selected $R^x$ substituents.

In some preferred embodiments, $A^1$ and $A^2$ (together with the carbon to which they are bonded) form unsubstituted carbocyclyl.

In some preferred embodiments, $A^1$ and $A^2$ (together with the carbon to which they are bonded) form cycloalkenyl optionally substituted with up to 3 independently selected $R^x$ substituents.

In some preferred embodiments, $A^1$ and $A^2$ (together with the carbon to which they are bonded) form unsubstituted cycloalkenyl.

In some preferred embodiments, $A^1$ and $A^2$ (together with the carbon to which they are bonded) form cycloalkyl optionally substituted with up to 3 independently selected $R^x$ substituents.

In some preferred embodiments, $A^1$ and $A^2$ (together with the carbon to which they are bonded) form unsubstituted cycloalkyl.

In some preferred embodiments, $A^1$ and $A^2$ (together with the carbon to which they are bonded) form cyclopropyl optionally substituted with up to 3 independently selected $R^x$ substituents.

In some preferred embodiments, $A^1$ and $A^2$ (together with the carbon to which they are bonded) form unsubstituted cyclopropyl.

In some preferred embodiments, $A^1$ and $A^2$ (together with the carbon to which they are bonded) form cyclobutyl optionally substituted with up to 3 independently selected $R^x$ substituents.

In some preferred embodiments, $A^1$ and $A^2$ (together with the carbon to which they are bonded) form unsubstituted cyclobutyl.

In some preferred embodiments, $A^1$ and $A^2$ (together with the carbon to which they are bonded) form cyclopentyl optionally substituted with up to 3 independently selected $R^x$ substituents.

In some preferred embodiments, $A^1$ and $A^2$ (together with the carbon to which they are bonded) form unsubstituted cyclopentyl.

In some preferred embodiments, $A^1$ and $A^2$ (together with the carbon to which they are bonded) form cyclohexyl optionally substituted with up to 3 independently selected $R^x$ substituents.

In some preferred embodiments, $A^1$ and $A^2$ (together with the carbon to which they are bonded) form unsubstituted cyclohexyl.

In some preferred embodiments, $A^1$ and $A^2$ (together with the carbon to which they are bonded) form heterocyclyl. The heterocyclyl optionally is substituted with up to 3 independently selected $R^x$ substituents.

In some preferred embodiments, $A^1$ and $A^2$ (together with the carbon to which they are bonded) form unsubstituted heterocyclyl.

In some preferred embodiments, $A^1$ and $A^2$ (together with the carbon to which they are bonded) form heteroalkenyl. The heteroalkenyl optionally is substituted with up to 3 independently selected $R^x$ substituents.

In some preferred embodiments, $A^1$ and $A^2$ (together with the carbon to which they are bonded) form unsubstituted heteroalkenyl.

In some preferred embodiments, $A^1$ and $A^2$ (together with the carbon to which they are bonded) form heterocycloalkyl. The heteroalkenyl optionally is substituted with up to 3 independently selected $R^x$ substituents.

In some preferred embodiments, $A^1$ and $A^2$ (together with the carbon to which they are bonded) form unsubstituted heterocycloalkyl.

In some preferred embodiments, the

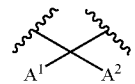

moiety corresponds in structure to one of the following:

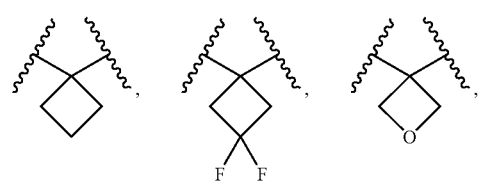

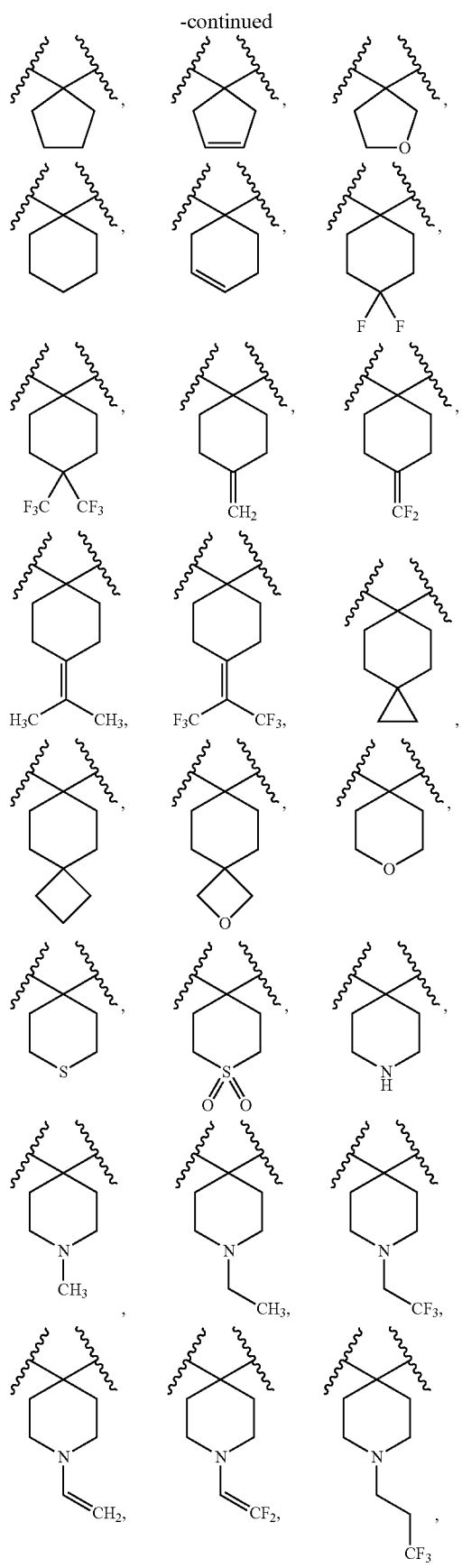
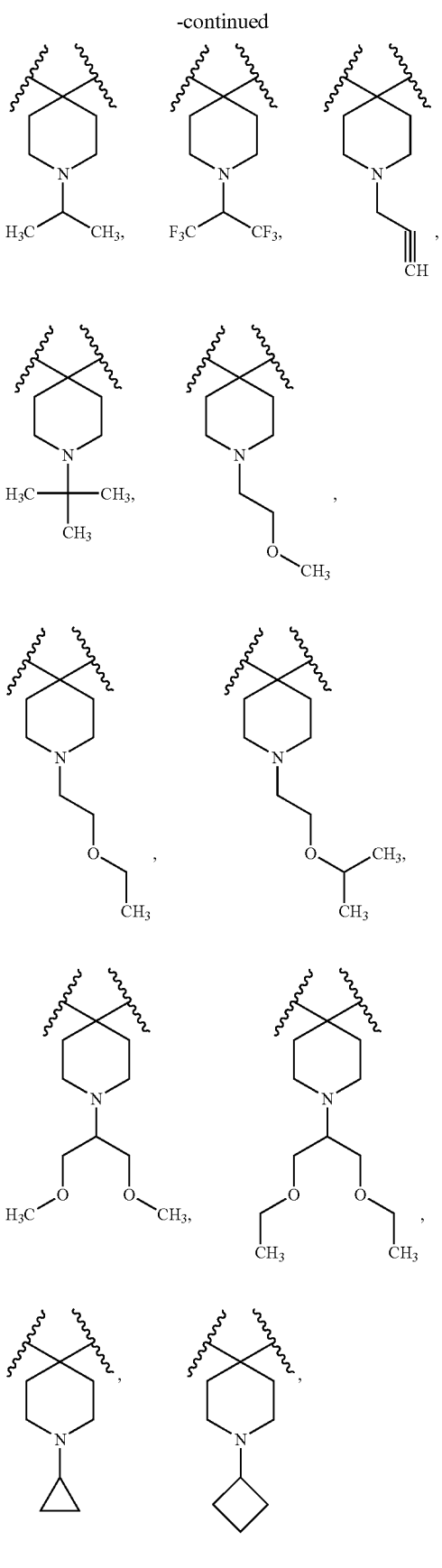

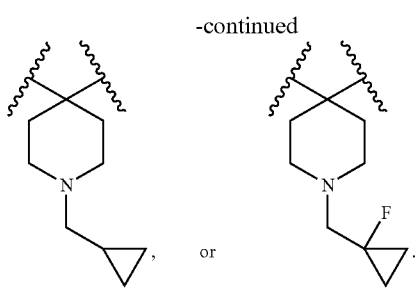

In some preferred embodiments, the

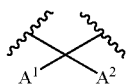

moiety corresponds in structure to the following formula:

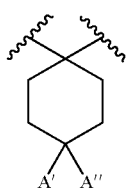

Here, A' and A" are independently selected from the group consisting of hydrogen and halogen (preferably fluoro).

In some preferred embodiments, the compound corresponds in structure to the following formula:

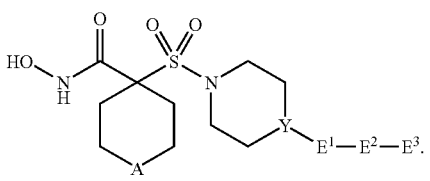
(ID)

Here, A is —O—, —N(H)—, —N($R^x$)—, —S—, —S(O)—, or —S(O)$_2$—.

In some preferred embodiments, A is —O—, i.e., the compound corresponds in structure to the following formula:

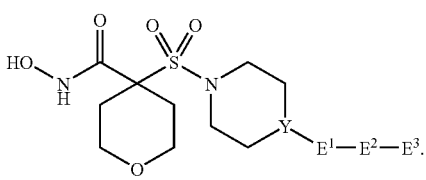
(ID-1)

In some preferred embodiments, A is —N(H)—, i.e., the compound corresponds in structure to the following formula:

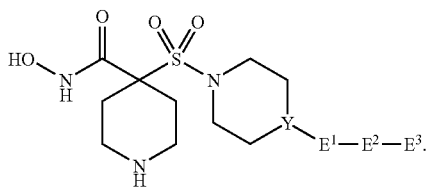
(ID-2)

In some preferred embodiments, A is —N($R^x$)—, i.e., the compound corresponds in structure to the following formula:

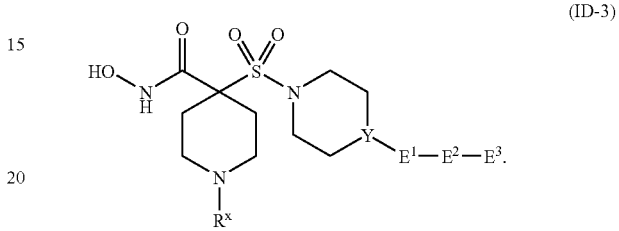
(ID-3)

In some preferred embodiments, A is —S—, i.e., the compound corresponds in structure to one of the following formula:

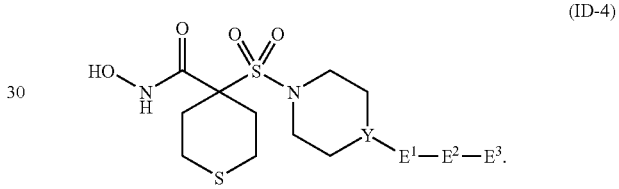
(ID-4)

In some preferred embodiments, A is —S(O)—, i.e., the compound corresponds in structure to one of the following formula:

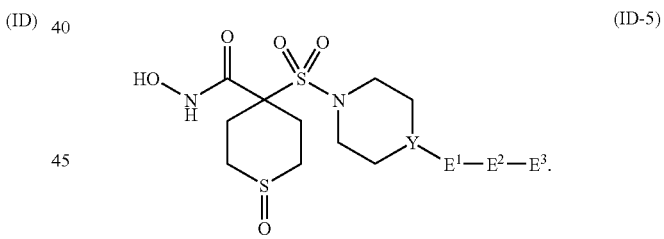
(ID-5)

In some preferred embodiments, A is —S(O)—, i.e., the compound corresponds in structure to one of the following formula:

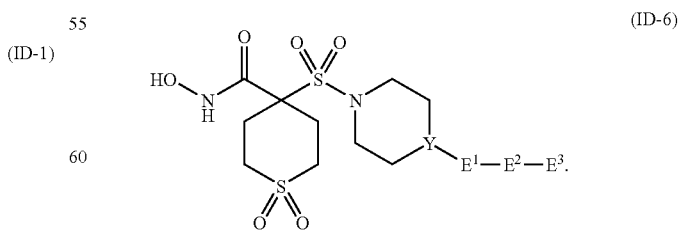
(ID-6)

$A^1$ and $A^2$ alternatively may be independently selected from the group consisting of hydrogen, alkyl, alkoxyalkyl, alkylthioalkyl, alkenyl, alkynyl, carbocyclyl, carbocyclylalkyl, carbocyclylalkenyl, carbocyclylalkynyl, carbocycly-loxyalkyl, carbocyclylalkoxyalkyl, carbocyclylalkylthio, carbocyclylthioalkyl, carbocyclylalkylthioalkyl, heterocy-clyl, heterocyclylalkyl, heterocyclylalkenyl, heterocycla-lkynyl, heterocycyloxyalkyl, heterocyclylalkoxyalkyl, het-erocyclylalkylthio, heterocyclylthioalkyl, and heterocyclylalkylthioalkyl. Each such substituent (if substi-tutable) optionally is substituted with up to 3 independently selected $R^x$ substituents.

In the above definition, where $A^1$ or $A^2$ can be hydrogen, the modifying phrase "if substitutable" excludes replacing that hydrogen with an $R^x$ substituent. Other contemplated $A^1$ or $A^2$ substituents that are not substitutable (i.e., have no hydrogens) include, for example, oxatriazolyl:

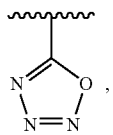

If the $A^1$ or $A^2$ substituent has less than 3 substitutable positions (i.e., less than 3 hydrogens), then the number of optional $R^x$ substituents will be up to the number of substi-tutable positions on the $A^1$ or $A^2$ substituent.

In some preferred embodiments, $A^1$ and $A^2$, together with the carbon to which they are bonded, form heterocyclyl or carbocyclyl. The heterocyclyl and carbocyclyl optionally are substituted with up to 3 independently selected $R^x$ substitu-ents. Alternatively, in such embodiments, $A^1$ and $A^2$ are independently selected as follows:

$A^1$ is hydrogen, alkyl, alkoxyalkyl, alkylthioalkyl, alk-enyl, alkynyl, carbocyclyl, carbocyclylalkyl, carbocy-clylalkenyl, carbocyclylalkynyl, carbocyclyloxyalkyl, carbocyclylalkoxyalkyl, carbocyclylalkylthio, carbocy-clylthioalkyl, carbocyclylalkylthioalkyl, heterocyclyl, heterocyclylalkyl, heterocyclylalkenyl, heterocyclyla-lkynyl, heterocyclyloxyalkyl, heterocyclylalkoxyalkyl, heterocyclylalkylthio, heterocyclylthioalkyl, or hetero-cyclylalkylthioalkyl. Any member of such group optionally is substituted with up to 3 independently selected $R^x$ substituents.

$A^2$ is alkyl, alkoxyalkyl, alkylthioalkyl, alkenyl, alkynyl, carbocyclyl, carbocyclylalkyl, carbocyclylalkenyl, car-bocyclylalkynyl, carbocyclyloxyalkyl, carbocyclyla-lkoxyalkyl, carbocyclylalkylthio, carbocyclylthioalkyl, carbocyclylalkylthioalkyl, heterocyclyl, heterocyclyla-lkyl, heterocyclylalkenyl, heterocyclylalkynyl, hetero-cyclyloxyalkyl, heterocyclylalkoxyalkyl, heterocycly-lalkylthio, heterocyclylthioalkyl, or heterocyclylalkylthioalkyl. Any member of such group optionally is substituted with up to 3 independently selected $R^x$ substituents.

In some preferred embodiments, $A^1$ and $A^2$ are indepen-dently selected from the group consisting of alkoxyalkyl, alkylthioalkyl, alkenyl, alkynyl, carbocyclyl, carbocyclyla-lkyl, carbocyclylalkenyl, carbocyclylalkynyl, carbocycly-loxyalkyl, carbocyclylalkoxyalkyl, carbocyclylalkylthio, carbocyclylthioalkyl, carbocyclylalkylthioalkyl, heterocy-clyl, heterocyclylalkyl, heterocyclylalkenyl, heterocyclyla-lkynyl, heterocyclyloxyalkyl, heterocyclylalkoxyalkyl, het-erocyclylalkylthio, heterocyclylthioalkyl, and heterocyclylalkylthioalkyl. Any member of such group optionally is substituted with up to 3 independently selected $R^x$ substituents.

In some preferred embodiments, one of $A^1$ and $A^2$ is hydrogen, e.g., the compound corresponds in structure to the following formula:

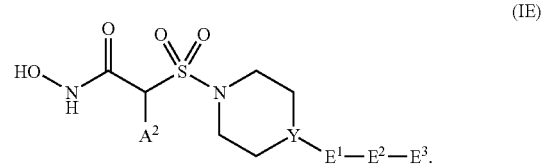

(IE)

In some preferred embodiments, $A^2$ is alkyl, and $A^1$ is hydrogen

General Description of Preferred $E^1$, $E^2$, and $E^3$ Substituents $E^1$ is generally carbocyclyl or heterocyclyl. The carbocy-clyl or heterocyclyl (if substitutable at one or more positions other than the position occupied by $-E^2-E^3$) is, in turn, optionally substituted with one or more substituents inde-pendently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alky-lamino, and di-alkylamino substituents are, in turn, option-ally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is heterocyclyl. The heterocyclyl is (if substitutable at one or more positions other than the position occupied by $-E^2-E^3$) optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is heterocyclyl. The heterocyclyl is (if substitutable at one or more positions other than the position occupied by $-E^2-E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is pyrazinyl, pyrim-idinyl, pyridazinyl, furanyl, tetrahydropyranyl, dihydrofura-nyl, tetrahydrofuranyl, thienyl, dihydrothienyl, tetrahy-drothienyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, oxazolidinyl, isoxazolidinyl, thiazolyl, isothiazolyl, thiazolinyl, isothiaz-olinyl, thiazolidinyl, isothiazolidinyl, thiodiazolyl, oxathia-zolyl, oxadiazolyl, oxatriazolyl, dioxazolyl, oxathiolyl, oxathiolanyl, pyranyl, dihydropyranyl, pyridinyl, piperidinyl, diazinyl, piperazinyl, triazinyl, oxazinyl, isoxazinyl, oxathiazinyl, oxadiazinyl, morpholinyl, azepinyl, oxepinyl, thiepinyl, diazepinyl, indolizinyl, pyrmndinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, or acridinyl. Each such substituent is (if substitutable at one or more positions other than the position occupied by -$E^2$-$E^3$) optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, thioxo, and imino.

In some preferred embodiments, $E^1$ is pyrazinyl, pyrimidinyl, pyridazinyl, furanyl, tetrahydropyranyl, dihydrofuranyl, tetrahydroftiranyl, thienyl, dihydrothienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, oxathiolyl, oxathiolanyl, pyranyl, dihydropyranyl, pyridinyl, piperidinyl, piperazinyl, triazinyl, oxazinyl, morpholinyl, azepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, or acridinyl. Each such substituent is (if substitutable at one or more positions other than the position occupied by -$E^2$-$E^3$) optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, thioxo, and imino.

In some preferred embodiments, $E^1$ is heterocycloalkyl. The heterocycloalkyl is optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is piperazinyl.

In some preferred embodiments, $E^1$ is heterocycloalkenyl. The heterocycloalkenyl is optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is heteroaryl. The heteroaryl (if substitutable at one or more positions other than the position occupied by -$E^2$-$E^3$) is optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is pyrazinyl, pyrimidinyl, pyridazinyl, furanyl, thienyl, pyrrolyl, isopyrrolyl, imidazolyl, isoimidazolyl, pyrazolyl, triazolyl, dithiolyl, oxathiolyl, oxazolyl, isoxazolyl, thiazolyl, isothiazolyl, thiodiazolyl, oxathiazolyl, oxadiazolyl, dioxazolyl, oxathiolyl, pyranyl, pyridinyl, diazinyl, triazinyl, tetrazolyl, oxazinyl, isoxazinyl, oxathiazinyl, oxadiazinyl, azepinyl, oxepinyl, thiepinyl, or diazepinyl. Each such substituent (if substitutable at one or more positions other than the position occupied by -$E^2$-$E^3$) is, in turn, optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, thioxo, and imino.

In some preferred embodiments, $E^1$ is pyrazinyl, pyrimidinyl, pyridazinyl, furanyl, thienyl, pyrrolyl, isopyrrolyl, imidazolyl, isoimidazolyl, pyrazolyl, triazolyl, dithiolyl, oxathiolyl, oxazolyl, isoxazolyl, thiazolyl, isothiazolyl, thiodiazolyl, oxathiazolyl, oxadiazolyl, dioxazolyl, oxathiolyl, pyranyl, pyridinyl, diazinyl, triazinyl, tetrazolyl, oxazinyl, isoxazinyl, oxathiazinyl, oxadiazinyl, azepinyl, oxepinyl, thiepinyl, or diazepinyl.

In some preferred embodiments, $E^1$ is pyrazinyl, pyrimidinyl, pyridazinyl, furanyl, thienyl, pyrrolyl, imidazolyl, pyrazolyl, triazolyl, oxazolyl, isoxazolyl, thiazolyl, isothiazolyl, thiodiazolyl, oxathiazolyl, oxadiazolyl, oxathiolyl, pyranyl, pyridinyl, triazinyl, tetrazolyl, oxazinyl, azepinyl, or diazepinyl. Each such substituent is optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. Such optional substituents, in turn, are optionally substituted with one or more substituents independently selected from the group consisting of halogen, hydroxy, cyano, carboxy, thiol, sulfo, nitro, nitroso, thioxo, and imino.

In some preferred embodiments, $E^1$ is pyrazinyl, pyrimidinyl, pyridazinyl, furanyl, thienyl, pyrrolyl, imidazolyl, pyrazolyl, triazolyl, oxazolyl, isoxazolyl, thiazolyl, isothiazolyl, thiodiazolyl, oxathiazolyl, oxadiazolyl, oxathiolyl, pyranyl, pyridinyl, triazinyl, tetrazolyl, oxazinyl, azepinyl, or diazepinyl.

In some preferred embodiments, $E^1$ is thienyl.

In some preferred embodiments, $E^1$ is thiazolyl.

In some preferred embodiments, $E^1$ is pyridinyl.

In some preferred embodiments, $E^1$ is 5-member heteroaryl. The heteroaryl is (if substitutable at one or more positions other than the position occupied by -$E^2$-$E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is thienyl, thiazolyl, isothiazolyl, oxadiazolyl, or thiodiazolyl.

In some preferred embodiments, $E^1$ is 6-member heteroaryl. The heteroaryl is (if substitutable at one or more positions other than the position occupied by -$E^2$-$E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is pyridinyl, pyrazinyl, pyrimidinyl, or pyridazinyl.

In some preferred embodiments, $E^1$ is multi-ring heteroaryl. The heteroaryl is (if substitutable at one or more positions other than the position occupied by -$E^2$-$E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional substituents are, in turn, optionally substituted with one or more substituents independently selected from the group consisting of halogen, hydroxy, cyano, carboxy, thiol, sulfo, nitro, nitroso, oxo, thioxo, and imino.

Examples of various contemplated compounds having a fused-ring heteroaryl at $E^1$ include, for example, those shown in Table 1A:

TABLE 1A

Examples of Various Suitable Compounds Wherein $E^1$ is Multi-Ring Heteroaryl

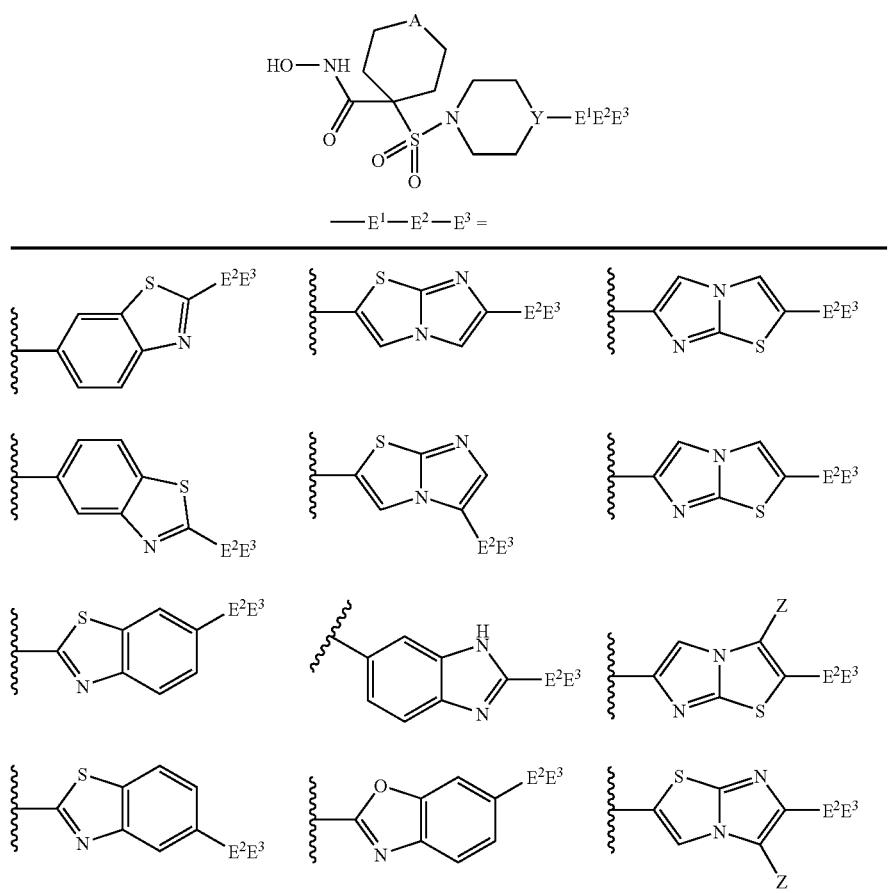

TABLE 1A-continued

Examples of Various Suitable Compounds Wherein $E^1$ is Multi-Ring Heteroaryl

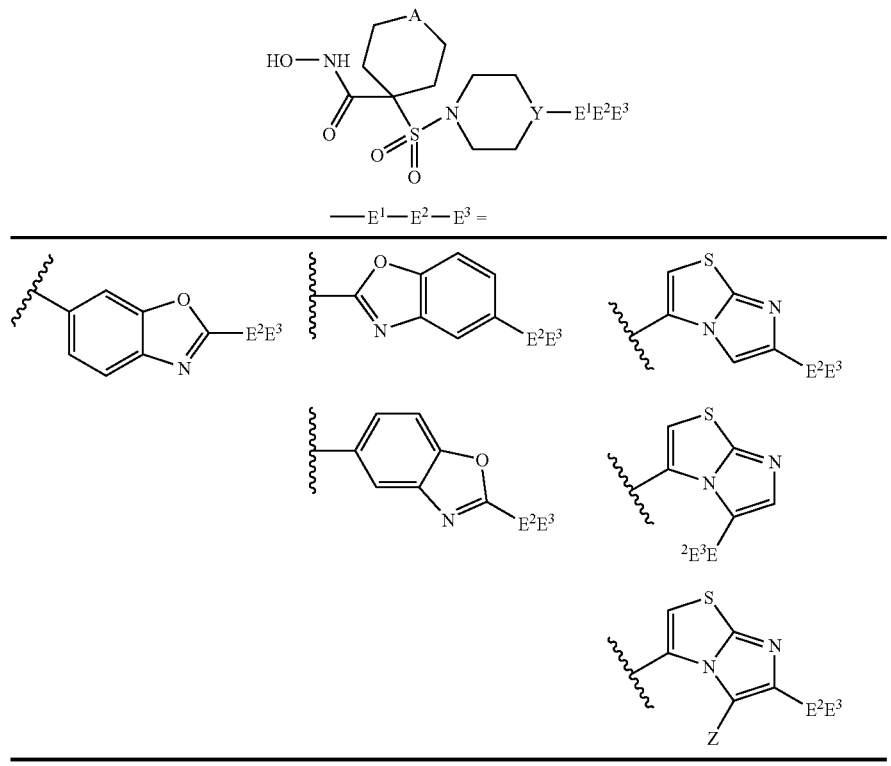

In Table 1, Z preferably is hydrogen, halogen, methyl, or (particularly trifluoromethyl).

Alternatively, $E^1$ may be alkyl optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional the alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, $E^1$ is alkyl.

In some preferred embodiments, $E^1$ is methyl.

$E^2$ is generally —O—, —C(O)—, —C(O)—O—, —O—C(O)—, —N($R^a$)—, —C(O)—N($R^a$)—, —N($R^a$)—C(O)—, —C(O)—N($R^a$)—N($R^a$)—C(O)—, —S—, —S(O)—, —S(O)$_2$—, —N($R^a$)—S(O)$_2$—, —S(O)$_2$—N($R^a$)—, —O—S(O)$_2$—, —S(O)$_2$—O—, —C(NH)—, —C(NOH)—, or a bond.

In some preferred embodiments, $E^2$ is —C(O)—, —C(O)—O—, —O—C(O)—, —N($R^a$)—, —C(O)—N($R^a$)—, —N($R^a$)—C(O)—, —C(O)—N($R^a$)—N($R^a$)—C(O)—, —S—, —S(O)—, —S(O)$_2$—, —N($R^a$)—S(O)$_2$—, —S(O)$_2$—N($R_a$)—, —O—S(O)$_2$—, —S(O)$_2$—O—, —C(NH)—, or —C(NOH)—.

In some preferred embodiments, $E^2$ is —O—, —C(O)—, —C(O)—O—, —O—C(O)—, —N($R^a$)—, —C(O)—N($R^a$)—, —N($R^a$)C(O)—, —C(O)—N($R^a$)—N($R^a$)—C(O)—, —S—, —S(O)—, —S(O)$_2$—, —N($R^a$)—S(O)$_2$—, —S(O)$_2$—N($R^a$)—, —O—S(O)$_2$—, —S(O)$_2$—O—, —C(NH)—, or —C(NOH)—.

In some preferred embodiments, $E^2$ is —C(O)—, —N(H)—, —S—, —S(O)$_2$—, —O—S(O)$_2$—, or —C(O)—N(H)—.

In some preferred embodiments, $E^2$ is —C(O)—, —C(O)—O—, —C(O)—N($R^a$)—, —S(O)$_2$—, —S(O)$_2$—N($R^a$)—, —C(NH)—, —C(NOH)—, or a bond.

In some preferred embodiments, $E^2$ is a bond.

In some preferred embodiments, $E^2$ is —O—.

In some preferred embodiments, $E^2$ is —N($R^a$)—.

In some preferred embodiments, $E^2$ is —N(H)—.

In some preferred embodiments, $E^2$ is —S—.

In some preferred embodiments, $E^2$ is —S(H)$_2$—.

In some preferred embodiments, $E^2$ is —C(O)—.

In some preferred embodiments, $E^2$ is —O—S(O)$_2$—.

In some preferred embodiments, $E^2$ is —C(O)—N(H)—.

In some preferred embodiments, -$E^1$-$E^2$ is —O—, —C(O)—, —C(O)—O—, —O—C(O)—, —N($R^a$)—, —C(O)—N($R^a$)—, —N($R^a$)—C(O)—, —C(O)—N($R^a$)—N($R^a$)—C(O)—, —S—, —S(O)—, —S(O)$_2$—, —N($R^a$)—S(O)$_2$—, —S(O)$_2$—N($R^a$)—, —O—S(O)$_2$—, —S(O)$_2$—O—, —C(NH)—, —C(NOH)—, or alkyl. The alkyl optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, -$E^1$-$E^2$ is alkyl.

In some preferred embodiments, -$E^1$-$E^2$ is methyl.

In some preferred embodiments, $E^1$-$E^2$ is —O—.

$E^3$ is generally hydrogen, halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is hydrogen, halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is hydrogen, halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, and amino.

In some preferred embodiments, $E^3$ is hydrogen, halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, and amino.

In some preferred embodiments, $E^3$ is halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is alkyl, alkenyl, alkynyl, alkoxyalkyl, alkoxyalkoxyalkyl, alkylthioalkyl, alkylthioalkylthioalkyl, alkylthioalkoxyalkyl, or alkoxyalkylthioalkyl; and more preferably alkyl, alkoxy, alkoxyalkyl, or alkoxyalkoxy. Each such substituent is, in turn, partially substituted with one or more independently selected halogen. The halogen are preferably selected from the group consisting of bromo, chloro, and fluoro; more preferably selected from the group consisting of chloro and fluoro; and even more preferably all fluoro.

In some preferred embodiments, $E^3$ is carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. As to such optional substituents:

the alkyl, alkoxy, alkylthio, carbocyclyl, and carbocyclylalkyl optionally are substituted with one or more substituents independently selected from the group consisting of halogen, hydroxy, cyano, carboxy, thiol, sulfo, nitro, nitroso, oxo, thioxo, imino, aminocarbonyl, and amino; and the amino nitrogen is substituted with up to 2 substituents independently selected from the group consisting of alkyl and carbocyclylalkyl.

In some preferred embodiments, $E^3$ is cyano, alkyl, alkenyl, alkynyl, alkoxyalkyl, alkoxyalkoxyalkyl, alkylthioalkyl, alkylthioalkylthioalkyl, alkylthioalkoxyalkyl, or alkoxyalkylthioalkyl. Each such substituent (if substitutable) is, in turn, substituted with one or more cyano.

In some preferred embodiments, $E^3$ is hydrogen, halogen, cyano, $C_1$–$C_9$-alkyl, $C_1$–$C_9$-alkoxy-$C_1$–$C_9$-alkyl, $C_3$–$C_6$-cycloalkyl, $C_3$–$C_6$-cycloalkyl-$C_1$–$C_6$-alkyl phenyl, $C_1$–$C_6$-alkylphenyl, $C_1$–$C_6$-alkoxyphenyl, phenyl-$C_1$–$C_6$-alkyl, heterocyclyl-$C_1$–$C_6$-alkyl, $C_1$–$C_6$-alkylheterocyclyl, or $C_1$–$C_6$-alkoxyheterocyclyl. Each such substituent (if substitutable) is, in turn, optionally substituted with one or more substituents independently selected from the group consisting of halogen and cyano. Any heterocyclyl of $E^3$ has 5 to 10 ring members, and, if divalently substitutable, is optionally substituted with up to 2 oxo.

In some preferred embodiments, $E^3$ is hydrogen, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. As to such optional substituents:

the alkyl, alkoxy, alkylthio, carbocyclyl, and carbocyclylalkyl optionally are substituted with one or more substituents independently selected from the group consisting of halogen, hydroxy, cyano, carboxy, thiol, sulfo, nitro, nitroso, oxo, thioxo, imino, aminocarbonyl, and amino; and the amino nitrogen is substituted with up to 2 substituents independently selected from the group consisting of alkyl and carbocyclylalkyl.

In some preferred embodiments, $E^3$ is hydrogen, $C_1$–$C_9$-alkyl, $C_1$–$C_9$-alkoxy-$C_1$–$C_9$-alkyl, $C_3$–$C_6$-cycloalkyl, $C_3$–$C_6$-cycloalkyl-$C_1$–$C_6$-alkyl, phenyl, $C_1$–$C_6$-alkylphenyl, $C_1$–$C_6$-alkoxyphenyl, phenyl-$C_1$–$C_6$-alkyl, heterocyclyl-$C_1$–$C_6$-alkyl, $C_1$–$C_6$-alkylheterocyclyl, and $C_1$–$C_6$-alkoxyheterocyclyl. Each such substituent (if substitutable) is, in turn, optionally substituted with one or more substituents independently selected from the group consisting of halogen and cyano. And any heterocyclyl of $E^3$ has 5 to 10 ring members, and, if divalently substitutable, is optionally substituted with up to 2 oxo.

In some preferred embodiments, $E^3$ is halogen, cyano, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. As to such optional substituents:

the alkyl, alkoxy, alkylthio, carbocyclyl, and carbocyclylalkyl optionally are substituted with one or more substituents independently selected from the group consisting of halogen, hydroxy, cyano, carboxy, thiol, sulfo, nitro, nitroso, oxo, thioxo, imino, aminocarbonyl, and amino; and the amino is substituted with up to 2 substituents independently selected from the group consisting of alkyl and carbocyclylalkyl.

In some preferred embodiments, $E^3$ is hydrogen, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) optionally is substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ comprises greater than 3 carbon atoms. In addition, $E^3$ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ comprises at least 2 carbon atoms. In addition, $E^3$ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is alkyl or alkoxyalkyl.

In some preferred embodiments, $E^3$ is alkoxyalkyl.

In some preferred embodiments, $E^3$ is haloalkyl.

In some preferred embodiments, $E^3$ is alkyl partially substituted with halogen.

In some preferred embodiments, $E^3$ is alkyl comprising a carbon atom bonded to at least one hydrogen atom and at least one halogen atom.

In some preferred embodiments, $E^3$ is alkyl.

In some preferred embodiments, $E^3$ is $C_6$–$C_{12}$-alkyl.

In some preferred embodiments, $E^3$ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Any substitutable member of such group optionally is substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is phenylalkyl optionally substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. The optional alkyl, alkoxy, alkylthio, carbocyclyl, and carbocyclylalkyl substituents are, in turn, optionally substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is alkenyl or alkynyl. The alkenyl and alkynyl optionally are substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is alkenyl.

In some preferred embodiments, $E^3$ comprises at least 5 carbon atoms and is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, or aminoalkyl. Any member of such group optionally is substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $-E^2-E^3$ comprises at least 2 carbon atoms. In addition, $-E^2-E^3$ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $-E^2-E^3$ is n-pentyl or n-butoxy. Here, the n-pentyl or n-butoxy, in turn, is optionally substituted with one or more independently selected halogen (preferably bromo, chloro, or fluoro; more preferably chloro or fluoro; and even more preferably fluoro).

In some preferred embodiments, $-E^2-E^3$ is butyl, pentyl, ethoxy, propoxy, methoxyethoxy, cyclobutyloxy, butoxy, trifluoromethylpropoxy, cyclopropylmethoxy, or phenyl.

In some preferred embodiments, $-E^2-E^3$ is alkoxyalkyl.

In some preferred embodiments, $-E^2-E^3$ is alkoxy.

In some preferred embodiments, $-E^2-E^3$ corresponds in structure to the following formula:

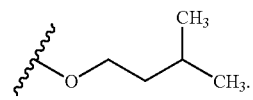

In some preferred embodiments, $-E^2-E^3$ corresponds in structure to the following formula:

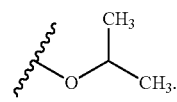

In some preferred embodiments, $-E^2-E^3$ is alkyl.

In some preferred embodiments, $-E^2-E^3$ corresponds in structure to the following formula:

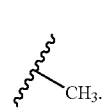

In some preferred embodiments, $-E^2-E^3$ corresponds in structure to the following formula:

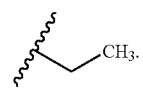

In some preferred embodiments, $-E^2-E^3$ corresponds in structure to the following formula:

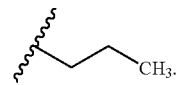

In some preferred embodiments, $-E^2-E^3$ corresponds in structure to the following formula:

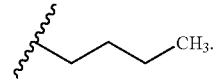

In some preferred embodiments, $-E^2-E^3$ corresponds in structure to the following formula:

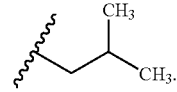

In some preferred embodiments, -E²-E³ corresponds in structure to the following formula:

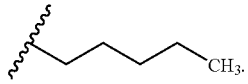

In some preferred embodiments, -E²-E³ corresponds in structure to the following formula:

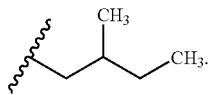

In some preferred embodiments, -E²-E³ corresponds in structure to the following formula:

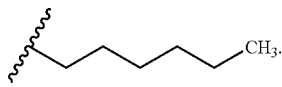

In some preferred embodiments, -E²-E³ corresponds in structure to the following formula:

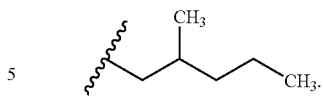

In some preferred embodiments, -E²-E³ corresponds in structure to the following formula:

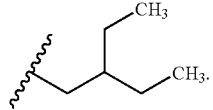

In some preferred embodiments, -E²-E³ corresponds in structure to the following formula:

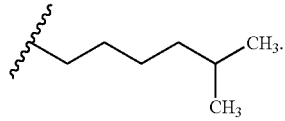

In some preferred embodiments, -E²-E³ is cyanoalkyl.
In some preferred embodiments, -E²-E³ is cyanoaryl.
In some preferred embodiments, -E²-E³ is cyano.
In some preferred embodiments, -E²-E³ is halogen.
In some preferred embodiments, -E²-E³ is hydrogen.
In some preferred embodiments, the -E²-E³ substituent is such that the compound corresponds in structure to a formula shown in Table Table 1B:

TABLE 1B

Examples of Compounds Having Various —E²—E³ Substituents

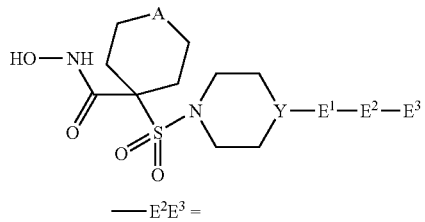

—E²E³ =

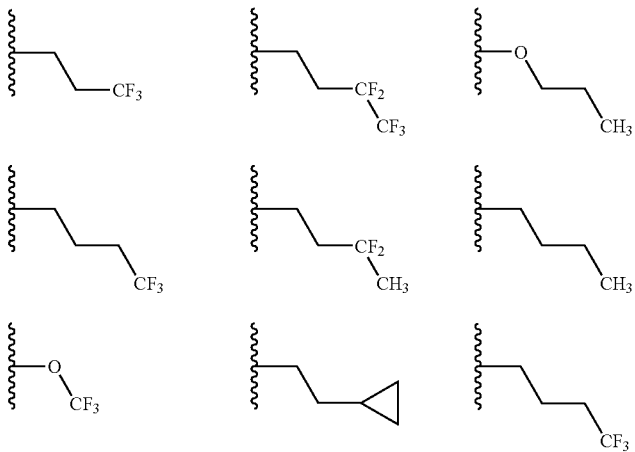

TABLE 1B-continued

Examples of Compounds Having Various —E²—E³ Substituents

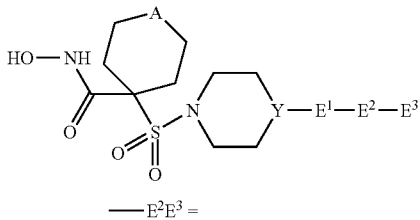

—E²E³ =

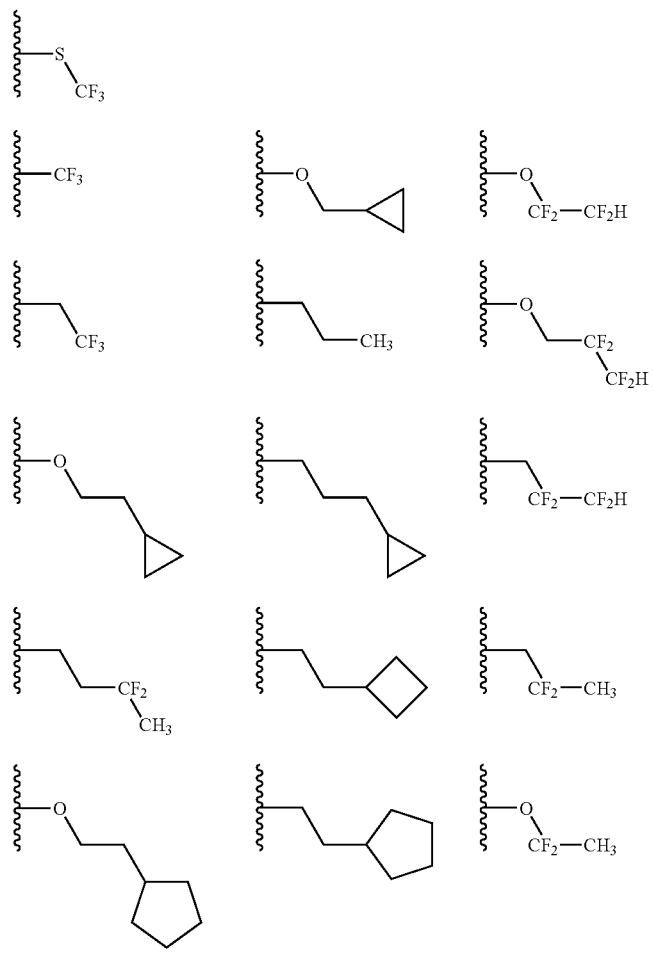

General Description of Preferred $R^x$ and $R^a$ Substituents

In general, each $R^x$ is independently selected from the group consisting of halogen, cyano, hydroxy, nitro, nitroso, oxo, alkyl, alkenyl, alkynyl, alkoxy, alkoxyalkyl, alkoxyalkoxy, $R^a$-oxyalkyl, alkenyloxy, alkynyloxy, alkylthio, alkylsulfonyl, $R^aR^a$-amino, $R^aR^a$-aminoalkyl, $R^aR^a$-aminoalkoxy, $R^aR^a$-aminoalkyl($R^a$)amino, $R^aR^a$-aminosulfonyl, carbocyclyl, carbocyclylalkyl, carbocyclyloxy, carbocyclyloxyalkoxy, carbocyclylthio, carbocyclylsulfonyl, heterocyclyl, heterocyclylalkyl, heterocyclyloxy, heterocyclyloxyalkoxy, heterocyclylthio, and heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

- the alkyl, alkoxy, alkoxyalkyl, and alkoxyalkoxy are optionally substituted with one or more substituents independently selected from the group consisting of halogen and hydroxy; and
- the amino is optionally substituted with up to 2 independently selected alkyl; and
- the imino is optionally substituted with hydroxy.

In some preferred embodiments, any heterocyclyl of $R^x$ is selected from the group consisting of pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, dioxazolyl, oxathiolyl, oxathiolanyl, pyranyl, dihydropyranyl, pyridinyl, piperidinyl, diazinyl, piperazinyl, triazinyl, oxazinyl, isoxazinyl, oxathiazinyl, oxadiazinyl, morpholinyl, azepinyl, oxepinyl, thiepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthrariilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl.

In some preferred embodiments, any heterocyclyl of $R^x$ is selected from the group consisting of pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, oxathiolyl, oxathiolanyl, pyranyl, dihydropyranyl, pyridinyl, piperidinyl, piperazinyl, triazinyl, oxazinyl, morpholinyl, azepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl.

In some preferred embodiments where $A^1$ and/or $A^2$ have one or more $R^x$ substituents, each such $R^x$ is independently selected from the group consisting of halogen, hydroxy, alkyl, alkoxy, alkoxyalkyl, cyno, acyl, carboxy, alkylsulfone, $R^aR^a$-amino, $R^aR^a$-aminoalkyl, $R^aR^a$-aminosulfonyl, carbocyclyl, carbocyclylalkyl, carbocyclyloxy, heterocyclyl, heterocyclylalkyl, heterocyclyloxy, and heterocyclylsulfonyl. Any substitutable member of such group optionally is substituted with one or more substituents independently selected from the group consisting of halogen, hydroxy, cyano, alkylamino, alkyl, alkoxy, and alkoxyalkyl. And any such optional substituent is, in turn, optionally substituted with one or more substituents independently selected from the group consisting of halogen, alkyl and hydroxy In some preferred embodiments where A is —N(R$_x$)—, $R^x$ is alkyl alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:
the alkyl, alkoxy, alkoxyalkyl, and alkoxyalkoxy are optionally substituted with one or more substituents independently selected from the group consisting of halogen and hydroxy; and
the amino is optionally substituted with up to 2 independently selected alkyl In some preferred embodiments where A is —N(R$^x$)—, $R^x$ is $R^c$-oxyalkyl, $R^cR^c$-aminoalkyl, carbocyclyl, carbocyclylalkyl, or carbocyclylsulfonyl. The carbocyclyl and the carbocyclyl of the carbocyclylalkyl, carbocyclyloxy, carbocyclyloxyalkoxy, carbocyclylthio, and carbocyclylsulfonyl are substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such substituents:
the alkyl, alkoxy, alkoxyalkyl, and alkoxyalkoxy optionally are substituted with one or more substituents independently selected from the group consisting of halogen and hydroxy; and
the amino is optionally substituted with up to 2 independently selected alkyl.

Here, each $R^c$ is independently selected from the group consisting of carbocyclyl, carbocyclylalkyl, carbocycyloxyalkyl, carbocyclylalkoxyalkyl, carbocyclylthioalkyl, carbocyclylthioalkenyl, carbocyclylsulfoxidoalkyl, carbocyclylsulfonyl, and carbocyclylsulfonylalkyl. The carbocyclyl and the carbocyclyl of the carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, and carbocyclylsulfonylalkyl are, in turn, substituted with one or more substituents independently selected from the group consisting of halogen, hydroxy, cyano, carboxy, thiol, sulfo, nitro, nitroso, oxo, thioxo, and imino.

In some preferred embodiments where A is —N(R$^x$)—, $R^x$ is $R^c$-oxyalkyl, $R^cR^c$-aminoalkyl, phenyl, phenylalkyl, or phenylsulfonyl. The phenyl and the phenyl of the phenylalkyl, phenyloxy, phenyloxyalkoxy, phenylthio, and phenylsulfonyl are, in turn, substituted with one or more substituents independently selected from the group consisting of halogen, hydroxy, cyano, amino, carboxy, thiol, sulfo, nitro, nitroso, alkyl, alkoxy, alkoxyalkyl, and alkoxyalkoxy. As to such substituents:
the alkyl, alkoxy, alkoxyalkyl, and alkoxyalkoxy optionally are substituted with one or more substituents independently selected from the group consisting of halogen and hydroxy; and
the amino optionally is substituted with up to 2 independently selected alkyl.

Here, each $R^c$ is independently selected from the group consisting of phenyl, phenylalkyl, phenyloxyalkyl, phenylalkoxyalkyl, phenylthioalkyl, phenylthioalkenyl, phenylsulfoxidoalkyl, phenylsulfonyl, and phenylsulfonylalkyl. The phenyl and the phenyl of the phenylalkyl, phenyloxyalkyl, phenylalkoxyalkyl, phenylthioalkyl, phenylthioalkenyl, phenylsulfoxidoalkyl, phenylsulfonyl, and phenylsulfonylalkyl are, in turn, substituted with one or more substituents independently selected from the group consisting of halogen, hydroxy, cyano, carboxy, thiol, sulfo, nitro, and nitroso.

In some preferred embodiments where A is —N(R$^x$)—, $R^x$ is phenyl substituted with one or more substituents independently selected from the group consisting of halogen, hydroxy, cyano, amino, carboxy, thiol, sulfo, $C_1$–$C_6$-alkyl (more preferably $C_1$–$C_2$-alkyl), $C_1$–$C_6$-alkoxy (more preferably $C_1$–$C_2$-alkoxy), $C_1$–$C_6$-alkoxy-$C_1$–$C_6$-alkyl (more preferably $C_1$–$C_2$-alkoxy-$C_1$–$C_2$-alkyl), and $C_1$–$C_6$-alkoxy-$C_1$–$C_6$-alkoxy (more preferably $C_1$–$C_2$-alkoxy-$C_1$–$C_2$-alkoxy). The alkyl, alkoxy, alkoxyalkyl, and alkoxyalkoxy optionally are substituted with one or more substituents independently selected from the group consisting of halogen and hydroxy. The amino, on the other hand, is optionally substituted with up to 2 independently selected $C_1$–$C_6$-alkyl (more preferably $C_1$–$C_2$-alkyl).

In some preferred embodiments where A is —N($R^x$)—, $R^x$ is aldehydo, $C_1$–$C_6$-alkyl, $C_3$–$C_6$-alkynyl, $C_1$–$C_6$-alkylcarbonyl, $C_1$–$C_6$-alkoxycarbonyl, $C_3$–$C_6$-alkenyloxycarbonyl, $C_3$–$C_6$-alkynyloxycarbonyl, amino, amino-$C_1$–$C_6$-alkyl, aminocarbonyl, amino-$C_1$–$C_6$-alkylcarbonyl, amino(thiocarbonyl), aminosulfonyl, $C_1$–$C_6$-alkylaminocarbonyl, $C_3$-cycloalkyl, $C_3$-cycloalkyl-$C_1$–$C_6$-alkyl, $C_3$-cycloalkylcarbonyl, phenyl, phenyl-$C_1$–$C_6$-alkyl, phenylcarbonyl, phenylsulfonyl, $C_1$–$C_6$-alkoxyphenyl, heterocyclyl, heterocyclyl-$C_1$–$C_6$-alkyl, heterocyclylcarbonyl, heterocyclylsulfonyl, or $C_1$–$C_6$-alkoxyheterocyclyl. Each such substituent (if substitutable) is, in turn, optionally substituted with one or more substituents independently selected from the group consisting of halogen, cyano, hydroxy, $C_1$–$C_6$-alkyl, and $C_1$–$C_6$-alkoxy. The optional alkyl and alkoxy substituents are, in turn, optionally substituted with one or more independently selected halogen. Any amino of $R^x$ optionally is substituted with up to 2 independently selected $C_1$–$C_6$-alkyl. And any heterocyclyl of $R^x$ has 5 to 10 ring members, and, if divalently substitutable, optionally is substituted with up to 2 oxo.

In some preferred embodiments where A is —N($R^x$)—, $R^x$ is butyl, methoxyethyl, cyclopropyl, methylphenyl, phenylmethyl, pyridinyl, pyrimidinyl, or pyridinylmethyl.

In some preferred embodiments where A is —N($R^x$)—, $R^x$ is $R^c$-oxyalkyl, $R^cR^c$-aminoalkyl, $R^cR^c$-aminosulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to these optional substituents:

the alkyl, alkoxy, alkoxyalkyl, and alkoxyalkoxy optionally are substituted with one or more substituents independently selected from the group consisting of halogen and hydroxy; and the amino optionally is substituted with up to two independently selected alkyl substituents.

Here, each $R^c$ is independently selected from the group consisting of heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonyl, and heterocyclylsulfonylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, and imino.

In some preferred embodiments where A is —N($R^x$)—, $R^x$ is heterocyclyl, heterocyclyl-$C_1$–$C_6$-alkyl, heterocyclylcarbonyl, heterocyclylsulfonyl, or $C_1$–$C_6$-alkoxyheterocyclyl. Each such substituent (if substitutable) optionally is substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, any heterocyclyl of $R^x$ has 5 to 10 ring members, and, if divalently substitutable, optionally is substituted with up to 2 oxo.

In some preferred embodiments where A is —N($R^x$)—, $R^x$ is heteroaryl optionally substituted with one or more substituents independently selected from the group consisting of halogen, cyano, hydroxy, $C_1$–$C_6$-alkyl, and $C_1$–$C_6$-alkoxy. Each optional alkyl or alkoxy is, in turn, optionally substituted with one or more independently selected halogen.

In some preferred embodiments where A is —N($R^x$)—, $R^x$ is 5-member heteroaryl optionally substituted with one or more substituents independently selected from the group consisting of halogen, cyano, hydroxy, $C_1$–$C_6$-alkyl, and $C_1$–$C_6$-alkoxy. Each optional alkyl or alkoxy is, in turn, optionally substituted with one or more independently selected halogen.

In some preferred embodiments where A is —N($R^x$)—, $R^x$ is 6-member heteroaryl optionally substituted with one or more substituents independently selected from the group consisting of halogen, cyano, hydroxy, $C_1$–$C_6$-alkyl, and $C_1$–$C_6$-alkoxy. Each optional alkyl or alkoxy is, in turn, optionally substituted with one or more independently selected halogen.

In some preferred embodiments where A is —N($R^x$)—, $R^x$ is 6-member heteroaryl optionally substituted with one or more substituents independently selected from the group consisting of halogen, cyano, hydroxy, $C_1$–$C_6$-alkyl, and $C_1$–$C_6$-alkoxy. Each optional alkyl or alkoxy is, in turn, optionally substituted with one or more independently selected halogen. In addition, the heteroaryl of $R^x$ has 1 or 2 nitrogen ring members, with the remaining ring members being carbon.

In some preferred embodiments where A is —N($R^x$)—, $R^x$ is 9- or 10-member heteroaryl optionally substituted with one or more substituents independently selected from the group consisting of halogen, cyano, hydroxy, $C_1$–$C_6$-alkyl, and $C_1$–$C_6$-alkoxy. Each optional alkyl or alkoxy is, in turn, optionally substituted with one or more independently selected halogen.

In some preferred embodiments where A is —N($R^x$)—, $R^x$ is heterocycloalkylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen.

In some preferred embodiments where A is —N($R^x$)—, $R^x$ is heterocycloalkylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heterocycloalkyl of the heterocycloalkylalkyl has 5 ring members.

In some preferred embodiments where A is —N($R^x$)—, $R^x$ is heterocycloalkylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heterocycloalkyl of the heterocycloalkylalkyl has 6 ring members.

In some preferred embodiments where A is —N($R^x$)—, $R^x$ is heteroarylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen.

In some preferred embodiments where A is —N($R^x$)—, $R^x$ is heteroarylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen.

In some preferred embodiments where A is —N($R^x$)—, $R^x$ is heteroarylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heteroaryl of the heteroarylalkyl has 6 ring members.

In some preferred embodiments where A is —N($R^x$)—, $R^x$ is heteroarylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heteroaryl of the heteroarylalkyl has 9 to 10 ring members.

In some preferred embodiments where A is —N($R^x$)—, $R^x$ is alkyl, alkenyl, alkynyl, $R^c$-oxyalkyl, alkylsulfonyl, $R^aR^a$-aminoalkyl, carbocyclyl, cycloalkylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino nitrogen is substituted by up to 2 independently selected alkyl. Here, $R^c$ is hydrogen, alkenyl, alkynyl, alkoxyalkyl, bisalkoxyalkyl, alkylthioalkyl, alkylthioalkenyl, alkylsulfoxidoalkyl, alkylsulfonylalkyl, carbocyclyl, carbocyclylalkyl, carbocycloxyalkyl, carbocyclylalkoxyalkyl, carbocyclylthioalkyl, carbocyclylthioalkenyl, carbocyclylsulfoxidoalkyl, carbocyclylsulfonylalkyl, heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonylalkyl, aminoalkyl, or alkoxyalkylaminoalkyl. Each such substituent (if substitutable) is, in turn, optionally substituted:

on any substitutable carbon with one or more substituents independently selected from the group consisting of halogen, hydroxy, cyano, carboxy, thiol, sulfo, nitro, nitroso, oxo, thioxo, and imino; and on any substitutable nitrogen with up to 2 substituents independently selected from the group consisting of alkyl, alkylcarbonyl, carbocyclyl, and carbocyclylalkyl.

In some preferred embodiments where A is —N($R^x$)—, $R^x$ is alkyl, alkynyl, aminoalkyl, cycloalkyl, aryl, or cycloalkylalkyl. Each such substituent optionally is substituted with one or more independently selected halogen. In addition, the nitrogen of the aminoalkyl optionally is substituted by up to 2 independently selected alkyl.

In some preferred embodiments where A is —N($R^x$)—, $R^x$ is aryl.

In some preferred embodiments where A is —N($R^x$)—, $R^x$ is haloalkyl, alkynyl, aminoalkyl, cycloalkyl, or cycloalkylalkyl. The nitrogen of the aminoalkyl optionally is substituted by 2 independently selected alkyl.

In some preferred embodiments where A is —N($R^x$)—, $R^x$ is alkyl, alkenyl, alkynyl, alkoxyalkyl, $R^a$-oxyalkyl, alkylsulfonyl, $R^aR^a$-aminoalkyl, carbocyclyl, cycloalkylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some preferred embodiments where A is —N($R^x$)—, $R^x$ is —$R^{x1}R^{c2}$.

$R^{x1}$ is —C(O)—, —C(S)—, —C(N$R^b$)—, or —S(O)$_2$—.

In some preferred embodiments, $R^{x1}$ is —S(O)$_2$—, i.e., the compound corresponds in structure to the following formula:

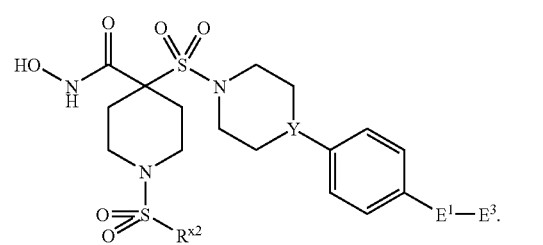

(IF-1)

In some preferred embodiments, $R^{x1}$ is —C(S)—, i.e., the compound corresponds in structure to the following formula:

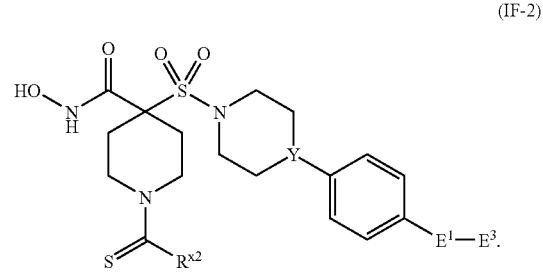

(IF-2)

In some preferred embodiments, $R^{x1}$ is —C(NR$^b$)—, i.e., the compound corresponds in structure to the following formula:

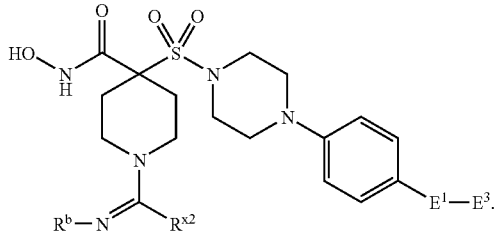

(IF-3)

In such embodiments, $R^b$ is hydrogen or hydroxy.

In some preferred embodiments, $R^{x1}$ is —C(O)—, i.e., the compound corresponds in structure to the following formula:

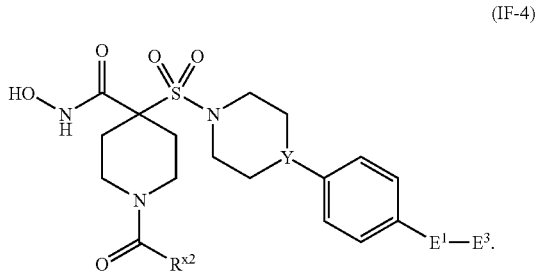

(IF-4)

$R^{x2}$ is hydrogen, hydroxy, alkyl, alkenyl, alkynyl, alkoxy, alkoxyalkyl, alkoxyalkoxy, $R^a$-oxyalkyl, alkenyloxy, alkynyloxy, $R^aR^a$-amino, $R^aR^a$-aminoalkyl, $R^aR^a$-aminoalkoxy, $R^aR^a$-aminoalkyl($R^a$)amino, carbocyclyl, carbocyclylalkyl, carbocyclyloxy, carbocyclyloxyalkoxy, heterocyclyl, heterocyclylalkyl, heterocyclyloxy, or heterocyclyloxyalkoxy. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to these optional substituents:
  the alkyl, alkoxy, alkoxyalkyl, and alkoxyalkoxy optionally are substituted with one or more substituents independently selected from the group consisting of halogen and hydroxy; and
  the amino optionally is substituted with up to two independently selected alkyl substituents.

In some preferred embodiments, $R^{x2}$ is hydrogen, amino, alkyl, alkoxy, alkoxyalkyl, alkoxyalkoxy, alkenyloxy, alkynyloxy, aminoalkyl, cycloalkyl, aryl, heterocycloalkyl, or heteroaryl. Here, the alkyl, alkoxy, alkoxyalkyl, alkoxyalkoxy, alkenyloxy, alkynyloxy, aminoalkyl, cycloalkyl, aryl, heterocycloalkyl, and heteroaryl (if substitutable) optionally are substituted with one or more substituents independently selected from the group consisting of halogen, oxo, hydroxy, and alkyl. The amino, on the other hand, is optionally substituted with up to two substituents independently selected from the group consisting of alkyl and alkoxyalkyl.

In some preferred embodiments, $R^{x2}$ is heterocycloalkyl or heteroaryl. The heterocycloalkyl and heteroaryl (if substitutable) optionally are substituted with one or more substituents independently selected from the group consisting of halogen, oxo, hydroxy, and alkyl.

In some preferred embodiments, $R^{x2}$ is more preferably optionally-substituted heterocycloalkyl.

In some preferred embodiments, $R^{x2}$ is more preferably optionally-substituted heteroaryl.

In some preferred embodiments, $R^{x2}$ is cycloalkyl or aryl. The cycloalkyl and aryl optionally are substituted with one or more substituents independently selected from the group consisting of halogen, oxo, hydroxy, and alkyl. In some such embodiments, $R_{x2}$ is more preferably optionally-substituted cycloalkyl. In other such embodiments, $R^{x2}$ is more preferably optionally-substituted aryl (preferably phenyl).

In some preferred embodiments where an $R^x$ substituent is a substituent of the piperazine or piperidine that is nitrogen linked to the sulfonyl, such $R^x$ is independently selected from the group consisting of hydrogen, alkyl, alkoxy, carbocyclyl, carbocyclylalkyl, carbocyclyloxy, heterocyclyl, and heterocyclylalkyl.

In some preferred embodiments where the carbon of Y has an $R^x$ substituent, such $R^x$ is independently selected from the group consisting of fluorine, hydroxy, alkyl, and alkoxy.

In general, each $R^a$ is independently selected from the group consisting of hydrogen, hydroxy, alkyl, alkenyl, alkynyl, alkoxy, alkoxyalkyl, bisalkoxyalkyl, alkylthioalkyl, alkylthioalkenyl, alkylsulfoxidoalkyl, alkylsulfonyl, alkylsulfonylalkyl, carbocyclyl, carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, carbocyclylsulfonylalkyl, heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonyl, heterocyclylsulfonylalkyl, aminoalkyl, aminosulfonyl, aminoalkylsulfonyl, and alkoxyalkylaminoalkyl. Such substituents are optionally substituted:
  on any substitutable carbon with one or more substituents independently selected from the group consisting of halogen, hydroxy, cyano, carboxy, thiol, sulfo, nitro, nitroso, oxo, thioxo, and imino; and
  on any substitutable nitrogen with up to 2 substituents independently selected from the group consisting of alkyl, alkylcarbonyl, carbocyclyl, and carbocyclylalkyl.

In some preferred embodiments, each $R^a$ is independently selected from the group consisting of hydrogen, alkyl, alkenyl, alkynyl, alkoxyalkyl, bisalkoxyalkyl, alkylthioalkyl, alkylthioalkenyl, alkylsulfoxidoalkyl, alkylsulfonyl, alkylsulfonylalkyl, carbocyclyl, carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, carbocyclylsulfonylalkyl, heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonyl, heterocyclylsulfonylalkyl, aminoalkyl, aminoalkylsulfonyl, and alkoxyalkylaminoalkyl. Each such substituent optionally is substituted:
  on any substitutable carbon with one or more substituents independently selected from the group consisting of halogen, hydroxy, cyano, carboxy, thiol, sulfo, nitro, nitroso, oxo, thioxo, and imino; and
  on any substitutable amino nitrogen with up to 2 substituents independently selected from the group consisting of alkyl, alkylcarbonyl, carbocyclyl, and carbocyclylalkyl.

In some preferred embodiments, each $R^a$ is independently selected from the group consisting of hydrogen, alkyl, alkoxyalkyl, bisalkoxyalkyl, alkylsulfonyl, alkylsulfonylalkyl, carbocyclyl, carbocyclylalkyl, carbocyclyloxyalkyl, carbocyclylalkoxyalkyl, carbocyclylsulfonyl, carbocyclylsulfonylalkyl, heterocyclyl, heterocyclylalkyl, heterocyclylalkoxyalkyl, heterocyclylsulfonyl, heterocyclylsulfonylalkyl. Each such substituent optionally is substituted on any substitutable carbon with one or more substituents independently selected from the group consisting of halogen, hydroxy, alkyl or alkoxy.

In some preferred embodiments, any heterocyclyl of any $R^a$ substituent is independently selected from the group consisting of pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, dioxazolyl, oxathiolyl, oxathiolanyl, pyranyl, dihydropyranyl, pyridinyl, piperidinyl, diazinyl, piperazinyl, triazinyl, oxazinyl, isoxazinyl, oxathiazinyl, oxadiazinyl, morpholinyl, azepinyl, oxepinyl, thiepinyl, diazepinyl, indolizinyl, pyrmndinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl.

In some preferred embodiments, any heterocyclyl of any $R^a$ substituent is independently selected from the group consisting of pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, oxathiolyl, oxathiolanyl, pyranyl, dihydropyranyl, pyridinyl, piperidinyl, piperazinyl, triazinyl, oxazinyl, morpholinyl, azepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl.

In some preferred embodiments, any heterocyclyl of $R^a$ and $R^x$ is independently selected from the group consisting of pyrazinyl, pyrimidinyl, pyridazinyl, furanyl, tetrahydropyranyl, dihydrofuranyl, tetrahydroftiranyl, thienyl, dihydrothienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, oxathiolyl, oxathiolanyl, pyranyl, dihydropyranyl, pyridinyl, piperidinyl, piperazinyl, triazinyl, oxazinyl, morpholinyl, azepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobeuzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl.

In some preferred embodiments, any heterocyclyl of $R^a$ and $R^x$ is independently selected from the group consisting of pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, dioxazolyl, oxathiolyl, oxathiolanyl, pyranyl, dihydropyranyl, pyridinyl, piperidinyl, diazinyl, piperazinyl, triazinyl, oxazinyl, isoxazinyl, oxathiazinyl, oxadiazinyl, morpholinyl, azepinyl, oxepinyl, thiepinyl, diazepinyl, indolizinyl, pyrmndinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl.

In some preferred embodiments, any heterocyclyl of $R^a$ and $R^x$ is independently selected from the group consisting of pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, oxathiolyl, oxathiolanyl, pyranyl, dihydropyranyl, pyridinyl, piperidinyl, piperazinyl, triazinyl, oxazinyl, morpholinyl, azepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobeuzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, and acridinyl.

DETAILED DESCRIPTION OF SEVERAL PREFERRED EMBODIMENTS

The above discussion describes the compounds and salts of this invention in general terms. The following discussion, in turn, describes in detail several preferred embodiments.

Preferred Embodiment No. 1

In some preferred embodiments, $E^1$ is heteroaryl. The -$E^2$-$E^3$ substituent is bonded to one position on the heteroaryl. The heteroaryl is (if substitutable at one or more positions other than the position occupied by -$E^2$-$E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

Particularly Preferred Embodiments of Embodiment No. 1

In some particularly preferred embodiments, the compound corresponds in structure to the following formula:

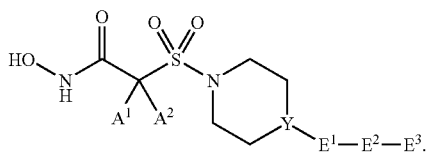

(2-1)

In some particularly preferred embodiments, Y is carbon bonded to an $R^x$ substituent. In some such embodiments, the compound preferably corresponds in structure to the following formula:

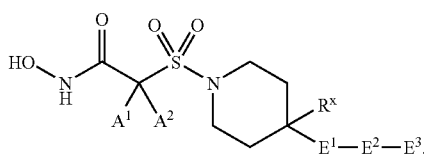

(3-1)

In some particularly preferred embodiments, Y is carbon bonded to halogen.

In some particularly preferred embodiments, Y is carbon bonded to hydroxy. In some such embodiments, the compound preferably corresponds in structure to the following formula:

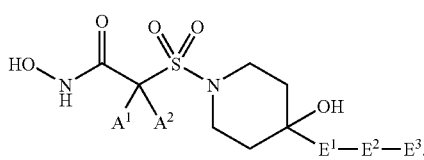

(4-1)

One such compound, for example, corresponds in structure to the following formula:

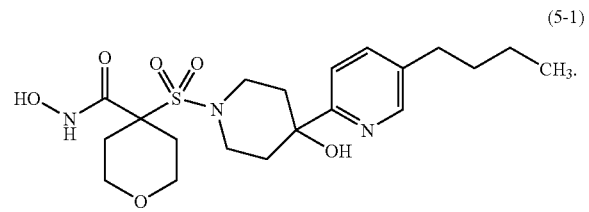

(5-1)

In some particularly preferred embodiments, Y is carbon bonded to hydrogen.

In some particularly preferred embodiments, Y is nitrogen.

In some particularly preferred embodiments, the compound corresponds in structure to the following formula:

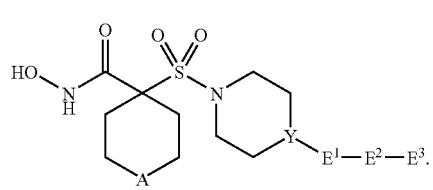

(19-1)

In some particularly preferred embodiments, A is —O—.

In some particularly preferred embodiments, A is —N(H)—.

In some particularly preferred embodiments, A is —N($R^x$)—. Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, the heteroaryl of $E^1$ is pyrazinyl, pyrimidinyl, pyridazinyl, furanyl, thienyl, pyrrolyl, imidazolyl, pyrazolyl, triazolyl, oxazolyl, isoxazolyl, thiazolyl, isothiazolyl, thiodiazolyl, oxathiazolyl, oxadiazolyl, oxathiolyl, pyranyl, pyridinyl, triazinyl, tetrazolyl, oxazinyl, azepinyl, or diazepinyl. Each such substituent (if substitutable at one or more positions other than the position occupied by -$E^2$-$E^3$) is, in turn, optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, thioxo, and imino.

In some particularly preferred embodiments, the heteroaryl of $E^1$ is not substituted, except to the extent it is substituted by an -$E^2$-$E^3$ substituent.

In some particularly preferred embodiments, $E^1$ is pyrazinyl, pyrimidinyl, pyridazinyl, furanyl, thienyl, pyrrolyl, isopyrrolyl, imidazolyl, isoimidazolyl, pyrazolyl, triazolyl, dithiolyl, oxathiolyl, oxazolyl, isoxazolyl, thiazolyl, isothiazolyl, thiodiazolyl, oxathiazolyl, oxadiazolyl, dioxazolyl, oxathiolyl, pyranyl, pyridinyl, diazinyl, triazinyl, tetrazolyl, oxazinyl, isoxazinyl, oxathiazinyl, oxadiazinyl, azepinyl, oxepinyl, thiepinyl, or diazepinyl.

In some particularly preferred embodiments, $E^1$ is pyrazinyl, pyrimidinyl, pyridazinyl, furanyl, thienyl, pyrrolyl, imidazolyl, pyrazolyl, triazolyl, oxazolyl, isoxazolyl, thiazolyl, isothiazolyl, thiodiazolyl, oxathiazolyl, oxadiazolyl, oxathiolyl, pyranyl, pyridinyl, triazinyl, tetrazolyl, oxazinyl, azepinyl, or diazepinyl.

In some particularly preferred embodiments, $E^2$ is a bond.

$E^3$ is halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, hydroxylimino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some preferred embodiments, $E^3$ is halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some particularly preferred embodiments, $E^1$ is thienyl. Examples of particularly preferred thienyl compounds include those corresponding in structure to the following formulas:

(23-1)

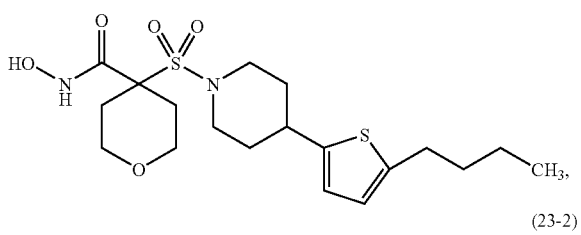

(23-2)

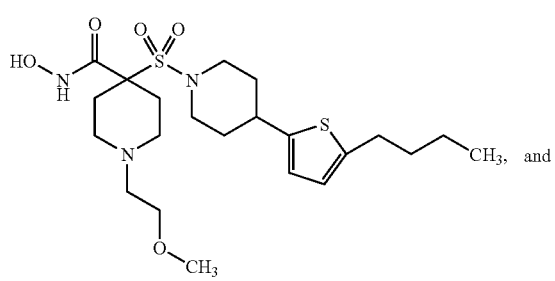

-continued (23-3)

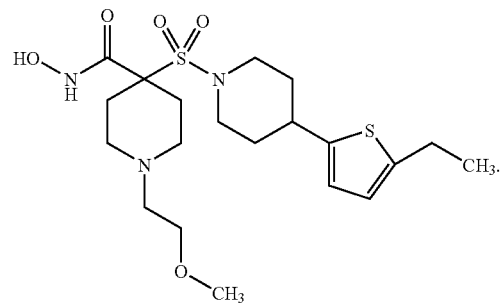

In some particularly preferred embodiments, $E^1$ is thiazolyl. Examples of particularly preferred thiazolyl compounds include those corresponding in structure to the following formulas:

(25-1)

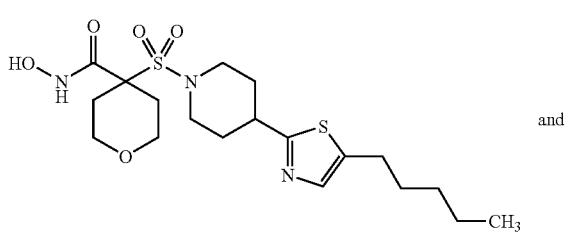

and (25-2)

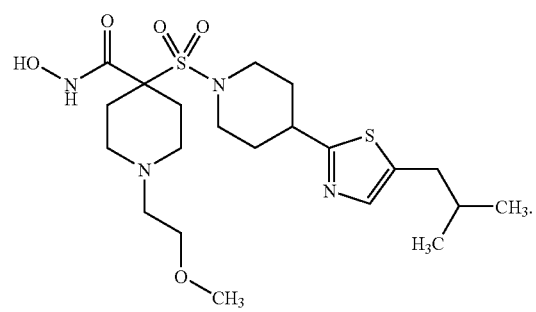

In some particularly preferred embodiments, $E^1$ is pyridinyl. Examples of particularly preferred pyridinyl compounds include those corresponding in structure to the following formulas:

(27-1)

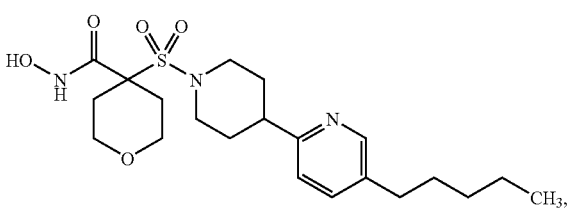

-continued
(27-2)
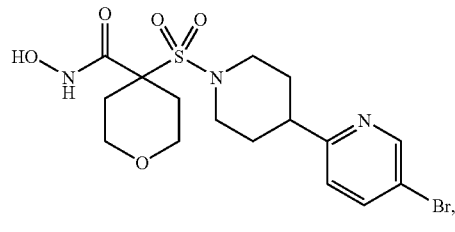
(27-8)
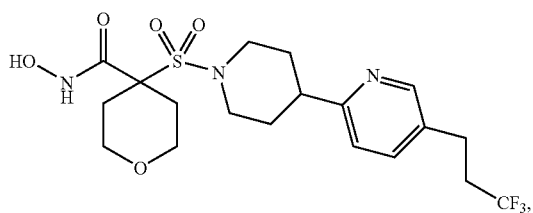
(27-3)
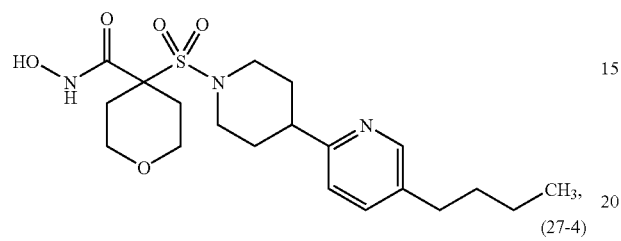
(27-9)
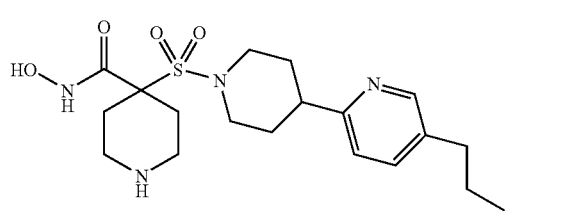
(27-4)
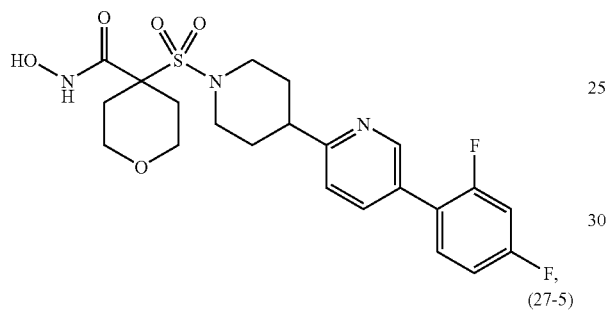
(27-10)
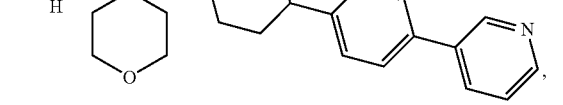
(27-5)
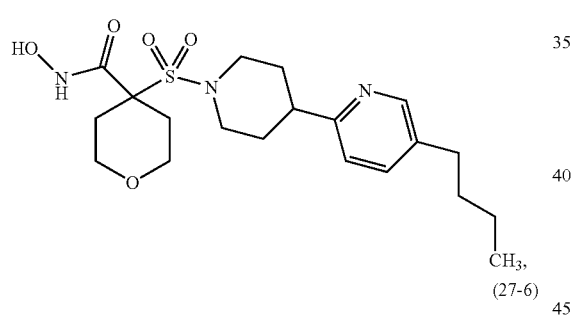
(27-11)
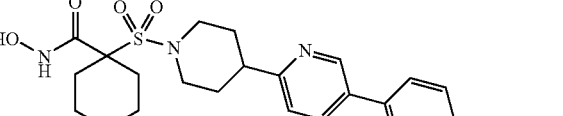
(27-6)
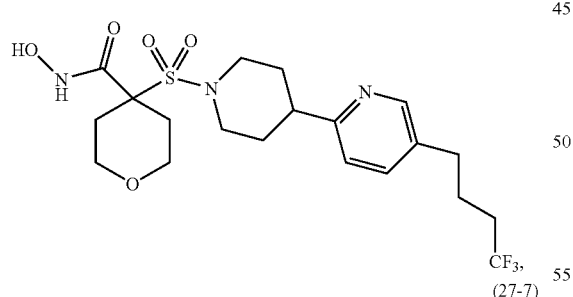
(27-12)
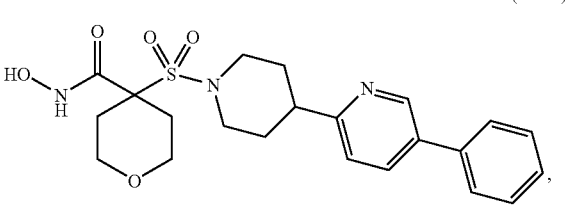
(27-7)
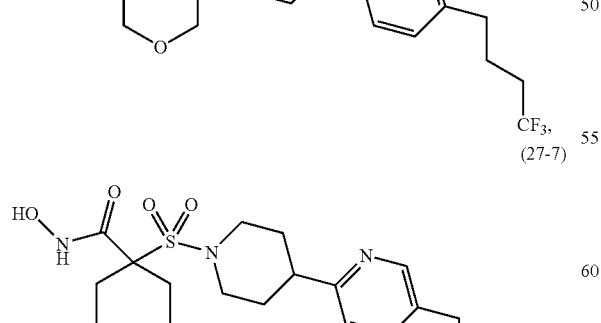
(27-13)
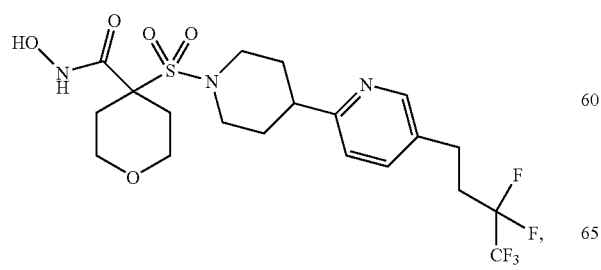

(27-14)
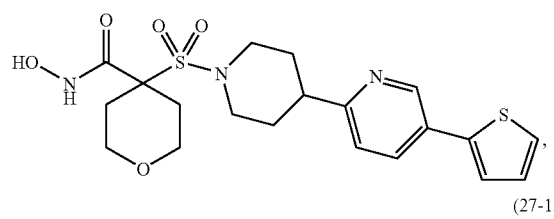
(27-15)
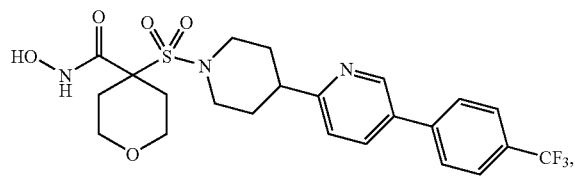
(27-16)
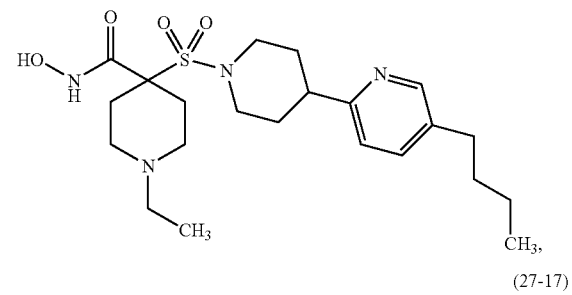
(27-17)
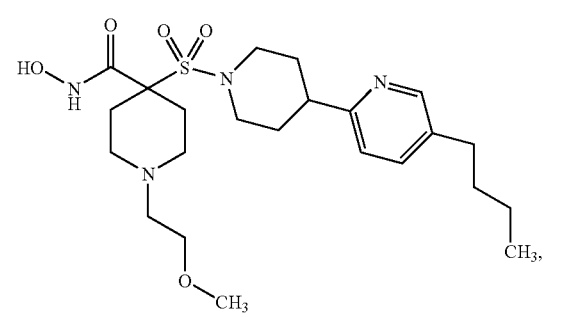
(27-18)
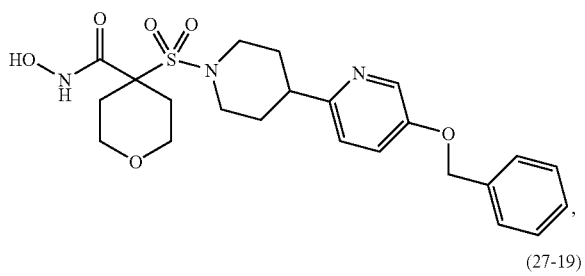
(27-19)
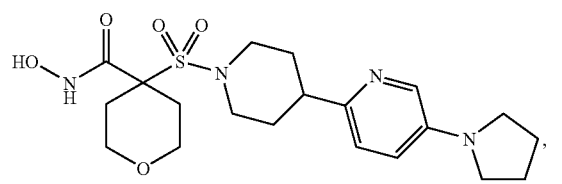
(27-20)
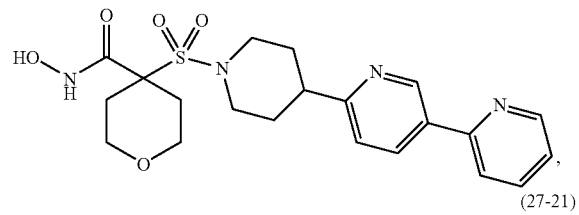
(27-21)
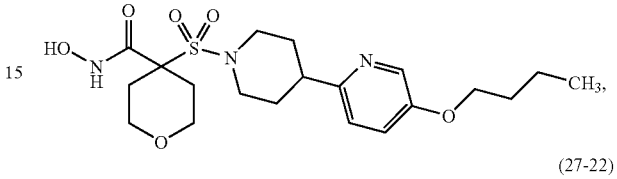
(27-22)
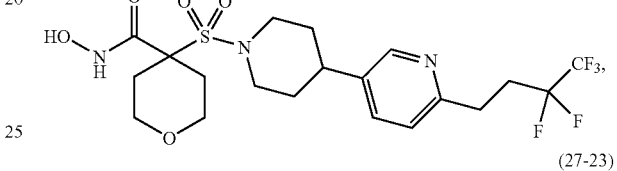
(27-23)
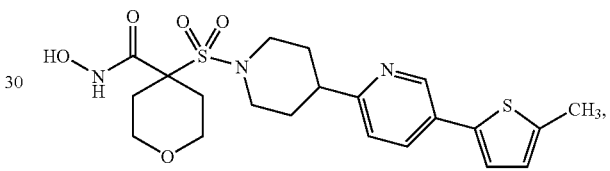
(27-24)
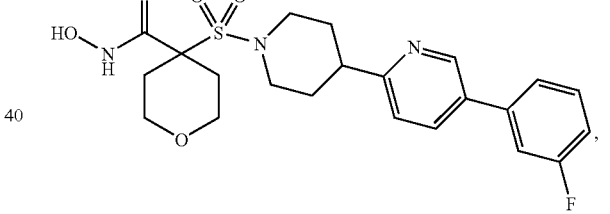
(34-1)
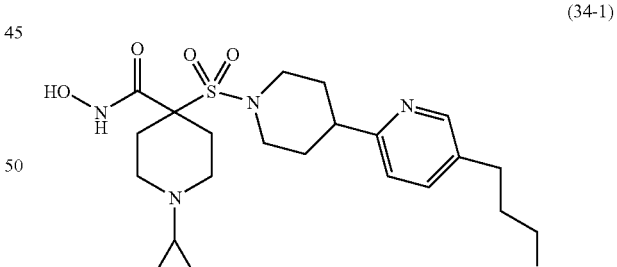
(35-1)
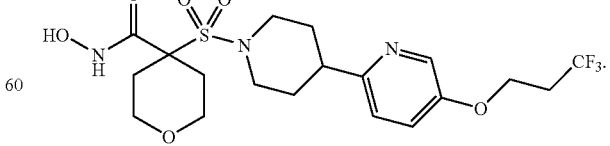

In some particularly preferred embodiments, $E^1$ is pyrazinyl. One example of a particularly preferred pyrazinyl compound corresponds in structure to the following formula:

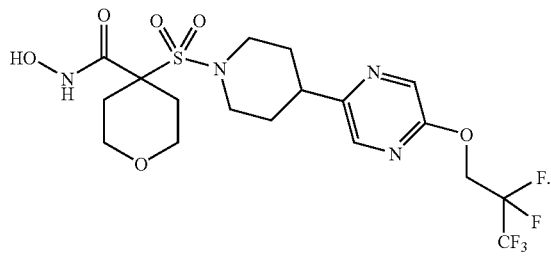

(37-1)

Preferred Embodiment No. 2

In some preferred embodiments, the compound corresponds in structure to the following formula:

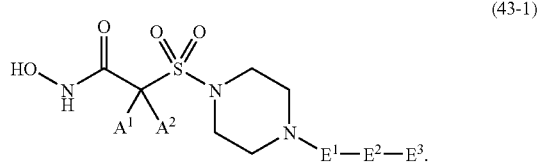

(43-1)

Here, $E^1$ is heterocyclyl. The heterocyclyl is (if substitutable at one or more positions other than the position occupied by $-E^2-E^3$) optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

Particularly Preferred Embodiments of Embodiment No. 2

In some particularly preferred embodiments, the compound corresponds in structure to the following formula:

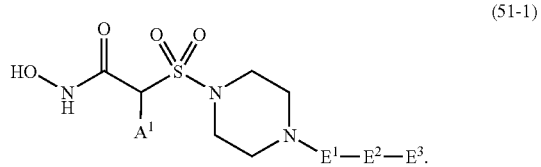

(51-1)

In some particularly preferred embodiments, $A^1$ is alkyl.

In some particularly preferred embodiments, the compound corresponds in structure to the following formula:

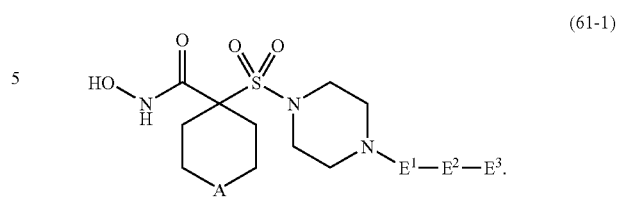

(61-1)

In some particularly preferred embodiments, A is —O—.
In some particularly preferred embodiments, A is —N(H)—.
In some particularly preferred embodiments, A is —N($R^x$)—. Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:
the alkyl, alkoxy, alkoxyalkyl, and alkoxyalkoxy optionally are substituted with one or more substituents independently selected from the group consisting of halogen and hydroxy; and
the amino optionally is substituted by up to 2 independently selected alkyl.

In some particularly preferred embodiments, A is —S—, —S(O)—, or —S(O)$_2$—.
In some particularly preferred embodiments, $E^2$ is a bond.
In some particularly preferred embodiments, $E^2$ is —O—.
In some particularly preferred embodiments, $E^2$ is —N($R^a$)—.
In some particularly preferred embodiments, $E^2$ is —N(H)—.

In some particularly preferred embodiments, $E^3$ is hydrogen, halogen, cyano, $C_1$–$C_9$-alkyl, $C_1$–$C_9$-alkoxy-$C_1$–$C_9$-alkyl, $C_3$–$C_6$-cycloalkyl, $C_3$–$C_6$-cycloalkyl-$C_1$–$C_6$-alkyl, phenyl, $C_1$–$C_6$-alkylphenyl, $C_1$–$C_6$-alkoxyphenyl, phenyl-$C_1$–$C_6$-alkyl, heterocyclyl-$C_1$–$C_6$-alkyl, $C_1$–$C_6$-alkylheterocyclyl, or $C_1$–$C_6$-alkoxyheterocyclyl. Each such substituent (if substitutable) optionally is substituted with one or more substituents independently selected from the group consisting of halogen and cyano. In addition, any heterocyclyl of $E^3$ has 5 to 10 ring members, and, if divalently substitutable, is optionally substituted with up to 2 oxo.

In some particularly preferred embodiments, $-E^2-E^3$ is selected from the group consisting of hydrogen, halogen, $C_1$–$C_9$-alkyl, $C_1$–$C_4$-alkoxy, methoxymethoxy, butoxy, butylamino, phenyl, methylphenyl, methoxyphenyl, phenylmethoxy, and phthalimidylbutyl. Each such substituent (if substitutable) optionally is substituted with one or more independently selected halogen (preferably bromo, chloro, or fluoro; more preferably chloro or fluoro; and even more preferably fluoro).

In some particularly preferred embodiments, $R^x$ is aldehydo, $C_1$–$C_6$-alkyl, $C_3$–$C_6$-alkynyl, $C_1$–$C_6$-alkylcarbonyl, $C_1$–$C_6$-alkoxycarbonyl, $C_3$–$C_6$-alkenyloxycarbonyl, $C_3$–$C_6$-alkynyloxycarbonyl, amino, amino-$C_1$–$C_6$-alkyl, aminocarbonyl, amino-$C_1$–$C_6$-alkylcarbonyl, amino(thiocarbonyl), aminosulfonyl, $C_1$–$C_6$-alkylaminocarbonyl, $C_3$-cycloalkyl, $C_3$-cycloalkyl-$C_1$–$C_6$-alkyl, $C_3$-cycloalkylcarbonyl, phenyl, phenyl-$C_1$–$C_6$-alkyl, phenylcarbonyl, phenylsulfonyl, $C_1$–$C_6$-alkoxyphenyl, heterocyclyl, heterocyclyl-$C_1$–$C_6$- alkyl, heterocyclylcarbonyl, heterocyclylsulfonyl, or $C_1$–$C_6$-alkoxyheterocyclyl. Each such substituent (if substitutable) optionally is substituted with one or more substituents independently selected from the group consisting of halogen, cyano, hydroxy, $C_1$–$C_6$-alkyl, and $C_1$–$C_6$-alkoxy. The optional alkyl are alkoxy are, in turn, optionally substituted with one or more independently selected halogen. Any amino of $R^x$ optionally is substituted with up to 2 independently selected $C_1$–$C_6$-alkyl. Any heterocyclyl of $R^x$ has 5 to 10 ring members, and, if divalently substitutable, optionally is substituted with up to 2 oxo.

In some particularly preferred embodiments, $R^x$ is butyl, methoxyethyl, cyclopropyl, methylphenyl, phenylmethyl, pyridinyl, pyrimidinyl, or pyridinylmethyl.

In some particularly preferred embodiments, $R^x$ is 2-methoxyethyl, pyridinyl, or pyrimidinyl.

In some particularly preferred embodiments, $E^1$ is heterocyclyl that is (if substitutable at one or more positions other than the position occupied by -$E^2$-$E^3$) optionally substituted with one or more substituents independently selected from the group consisting of halogen, hydroxy, amino, mono-alkylamino, di-alkylaamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some particularly preferred embodiments, $E^1$ is pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, dioxazolyl, oxathiolyl, oxathiolanyl, pyranyl, dihydropyranyl, pyridinyl, piperidinyl, diazinyl, piperazinyl, triazinyl, oxazinyl, isoxazinyl, oxathiazinyl, oxadiazinyl, morpholinyl, azepinyl, oxepinyl, thiepinyl, diazepinyl, indolizinyl, pyrmndinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, or acridinyl. Each such substituent is (if substitutable at one or more positions other than the position occupied by -$E^2$-$E^3$) optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, thioxo, and imino.

In some particularly preferred embodiments, $E^1$ is pyrazinyl, pyrimidinyl, pyridazinyl, furanyl, tetrahydropyranyl, dihydrofuranyl, tetrahydrofuranyl, thienyl, dihydrothienyl, tetrahydrothienyl, pyrrolyl, pyrrolinyl, pyrrolidinyl, imidazolyl, imidazolinyl, imidazolidinyl, pyrazolyl, pyrazolinyl, pyrazolidinyl, triazolyl, tetrazolyl, oxazolyl, isoxazolyl, oxazolidinyl, isoxazolidinyl, thiazolyl, isothiazolyl, thiazolinyl, isothiazolinyl, thiazolidinyl, isothiazolidinyl, thiodiazolyl, oxathiazolyl, oxadiazolyl, oxatriazolyl, oxathiolyl, oxathiolanyl, pyranyl, dihydropyranyl, pyridinyl, piperidinyl, piperazinyl, triazinyl, oxazinyl, morpholinyl, azepinyl, diazepinyl, indolizinyl, pyrindinyl, pyranopyrrolyl, 4H-quinolizinyl, purinyl, naphthyridinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofiiranyl, benzothienyl, isobenzothienyl, benzothiazolyl, benzothiadiazolyl, benzimidazolyl, benzotriazolyl, benzoxazinyl, benzisoxazinyl, tetrahydroisoquinolinyl, carbazolyl, xanthenyl, or acridinyl. Each such substituent is (if substitutable at one or more positions other than the position occupied by -$E^2$-$E^3$) optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, thioxo, and imino.

In some particularly preferred embodiments, $E^1$ is heterocycloalkyl. The heterocycloalkyl is optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some particularly preferred embodiments, $E^1$ is heterocycloalkenyl. The heterocycloalkenyl is optionally substituted with one or more substituents independently selected from the group consisting of halogen, hydroxy, oxo, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

One particularly preferred example of a heterocyclylpiperazinyl-sulfonylmethyl hydroxamic acid compound wherein $E^1$ is substituted heterocycloalkenyl is:

(65-1)

Examples of heterocyclylpiperazinyl-sulfonylmethyl hydroxamic acid compounds wherein $E^1$ is substituted heterocycloalkenyl include:

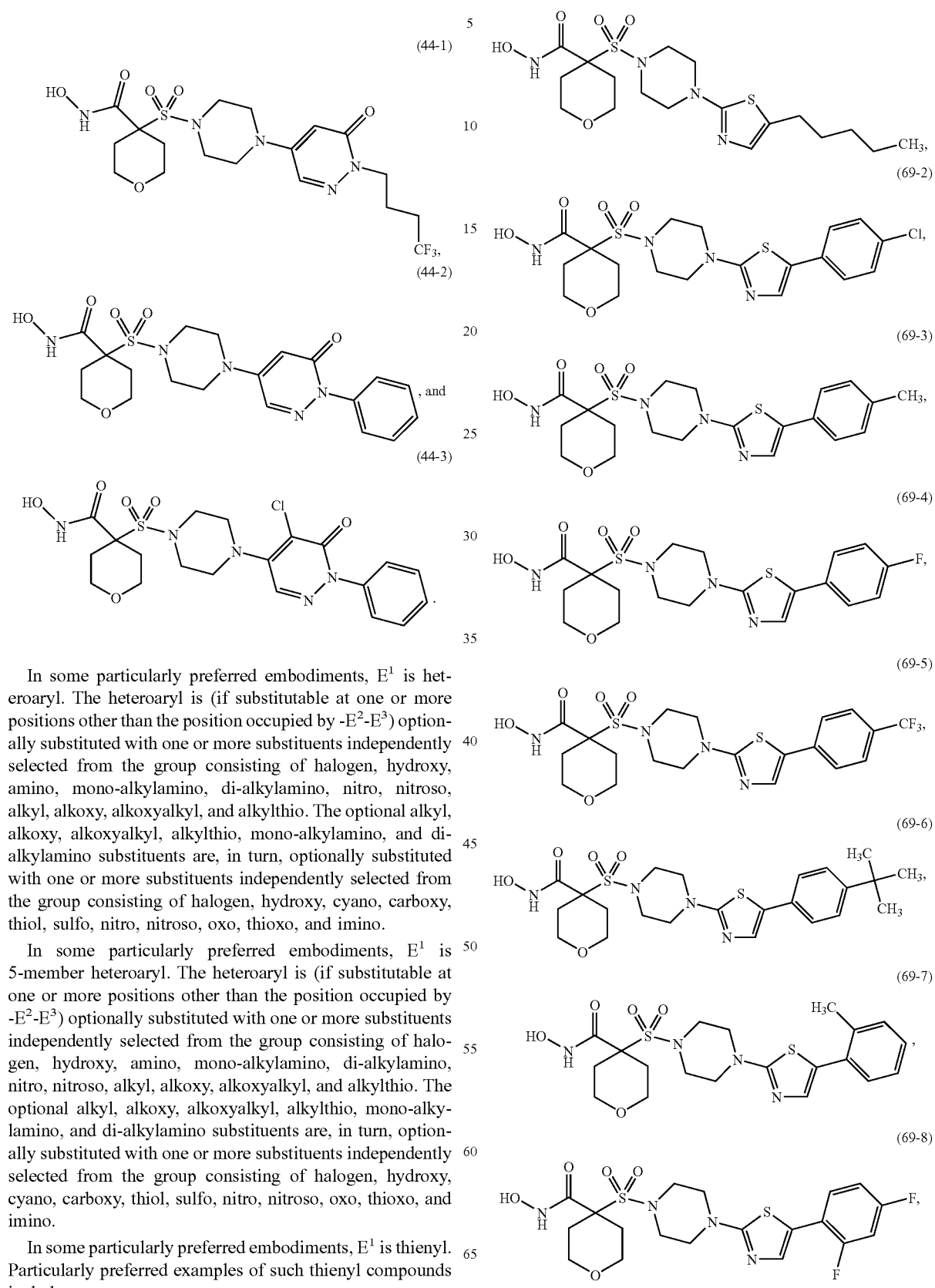

In some particularly preferred embodiments, $E^1$ is heteroaryl. The heteroaryl is (if substitutable at one or more positions other than the position occupied by -$E^2$-$E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some particularly preferred embodiments, $E^1$ is 5-member heteroaryl. The heteroaryl is (if substitutable at one or more positions other than the position occupied by -$E^2$-$E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some particularly preferred embodiments, $E^1$ is thienyl. Particularly preferred examples of such thienyl compounds include:

-continued
(69-9)
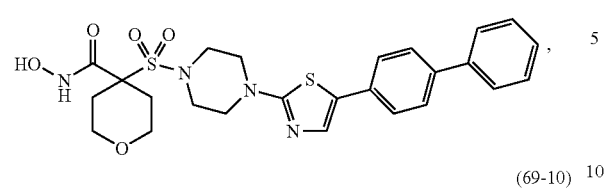
(69-10)
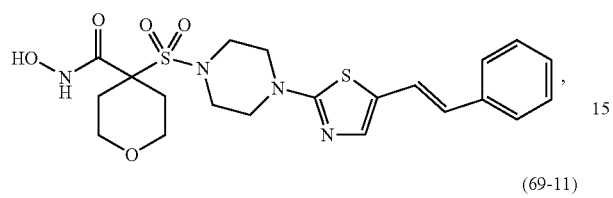
(69-11)
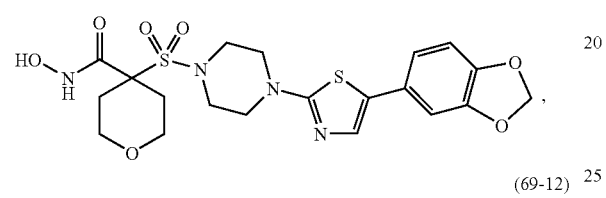
(69-12)
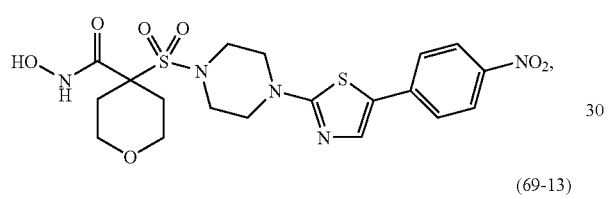
(69-13)
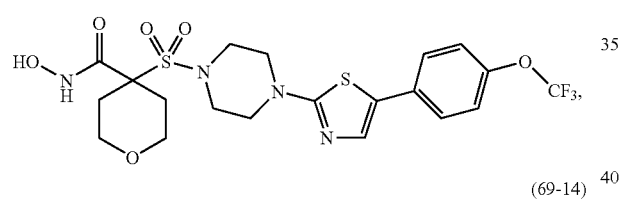
(69-14)
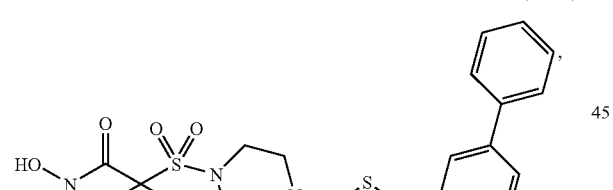
(69-15)
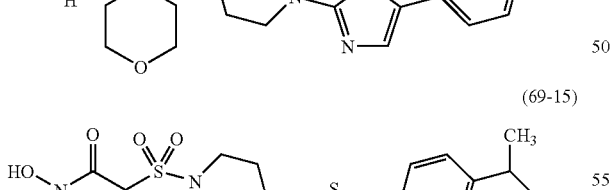
(69-16)

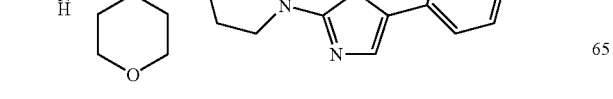
(69-17)
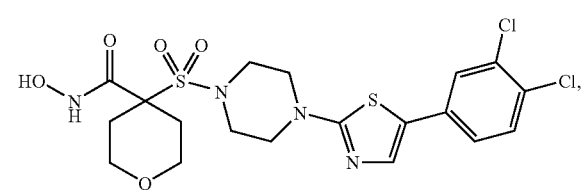
(69-18)
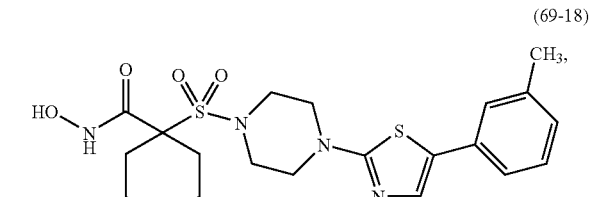
(69-19)

(69-20)
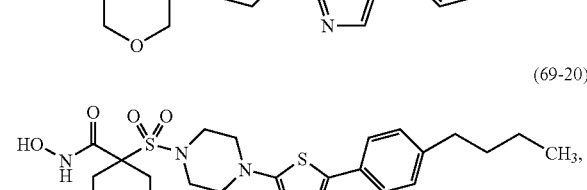
(69-21)
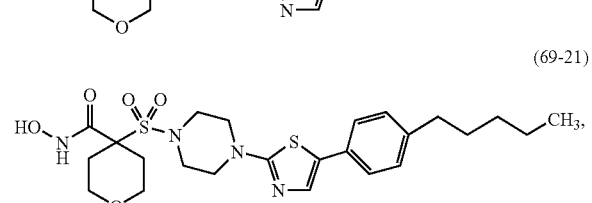
(69-22)
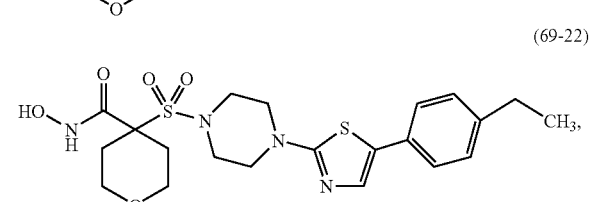
(69-23)
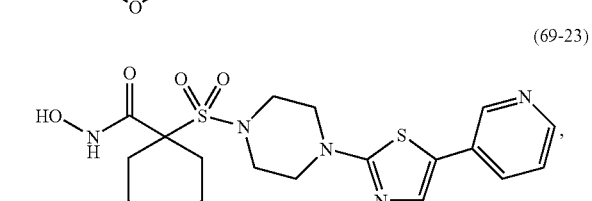
(69-24)
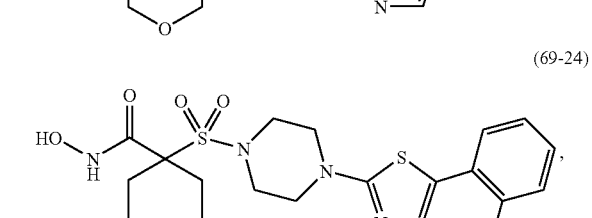

-continued (69-25)
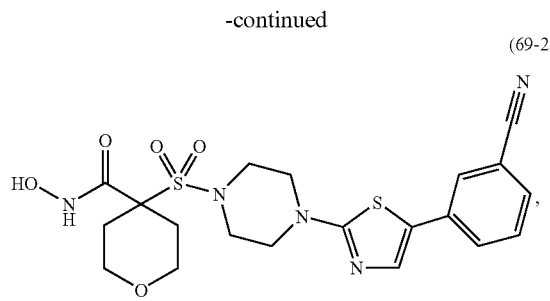

(69-26)
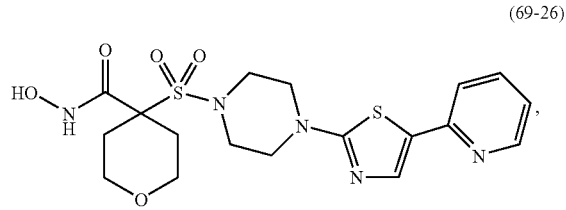

(69-27)
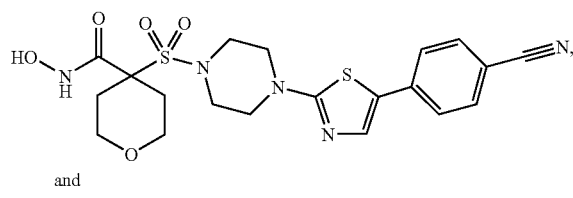

and (69-28)
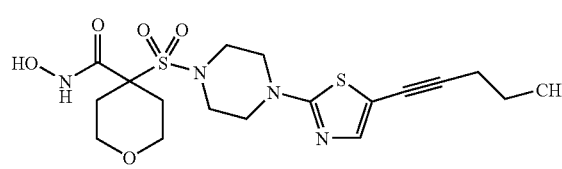

Particularly preferred thienyl compounds also include, for example, the following compounds:

(70-1)
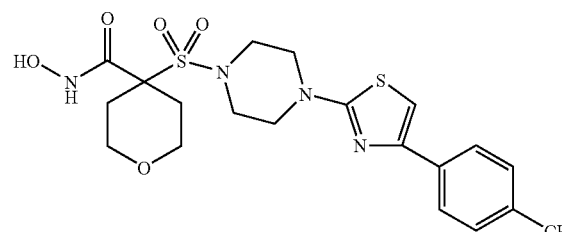

(70-2)
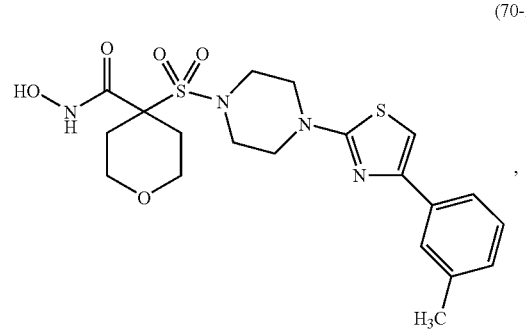

-continued (70-3)
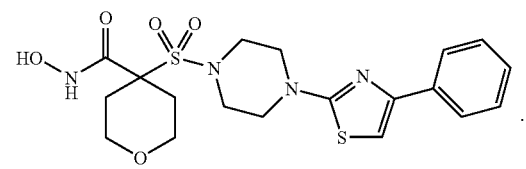

(70-4)
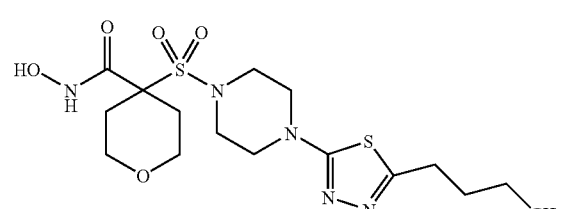

In some particularly preferred embodiments, $E^1$ is thiazolyl, isothiazolyl, oxadiazolyl, or thiodiazolyl. Particularly preferred examples of such compounds include:

(73-1)
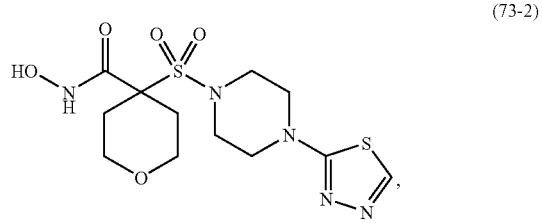

(73-2)

(73-3)
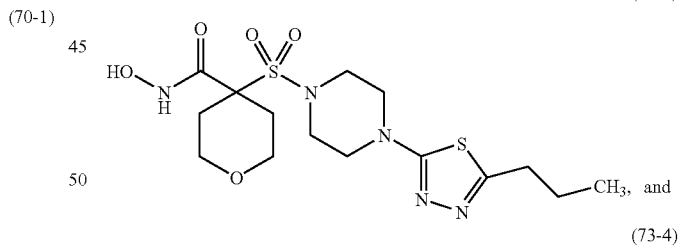

and (73-4)
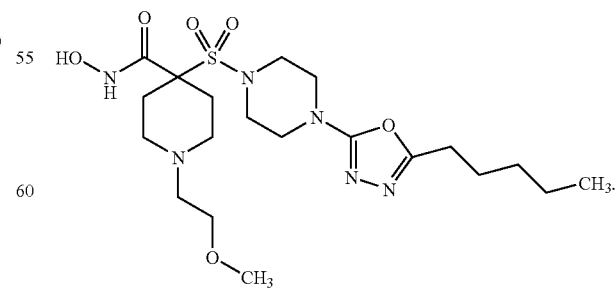

In some particularly preferred embodiments, $E^1$ is 6-member heteroaryl. The heteroaryl is (if substitutable at one or more positions other than the position occupied by -E²-E³) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some particularly preferred embodiments, $E^1$ is pyridinyl. Particularly preferred examples of compounds wherein $E^1$ is pyridinyl include:

(76-1)

(76-2)

(76-3)

(76-4)

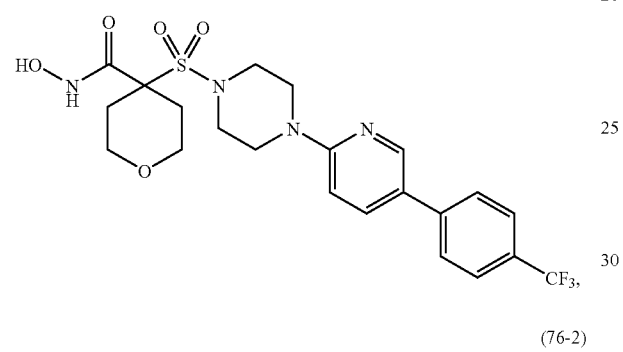

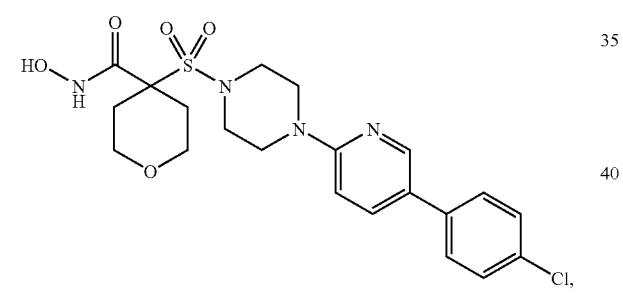

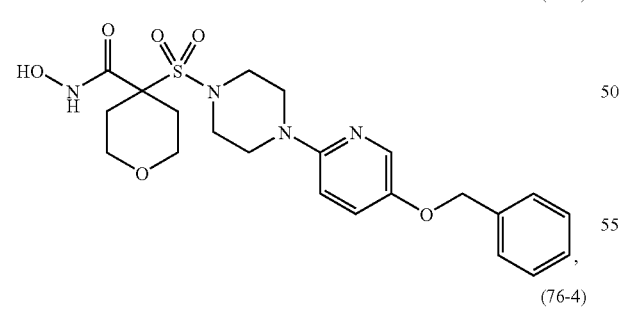

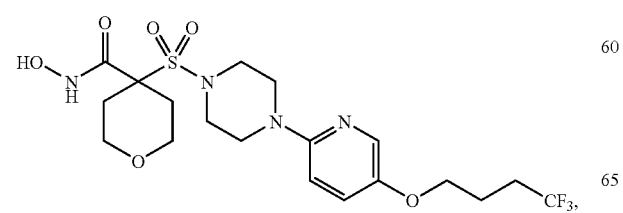

-continued (76-9)

(76-10)

(76-11)

(76-12)

(76-17)

(76-18)

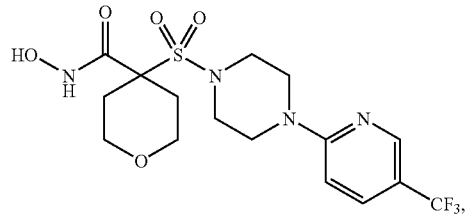

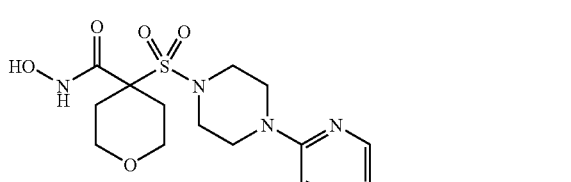

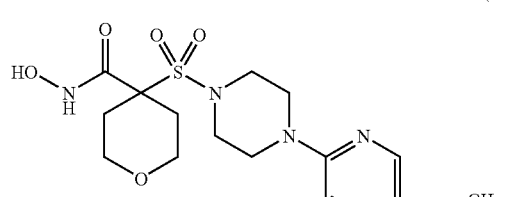

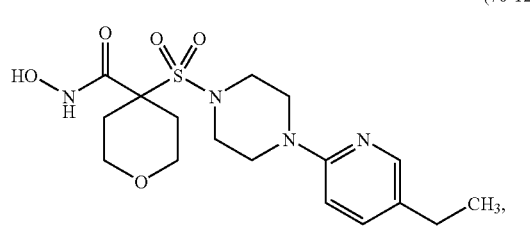

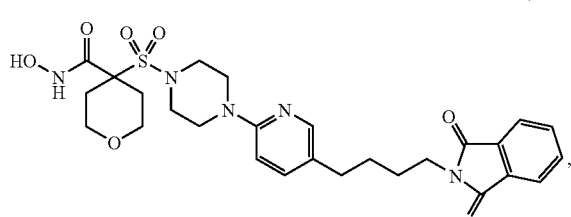

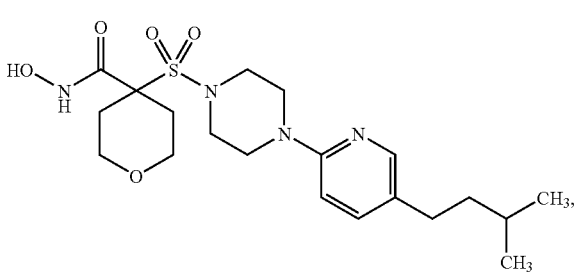

(76-19)
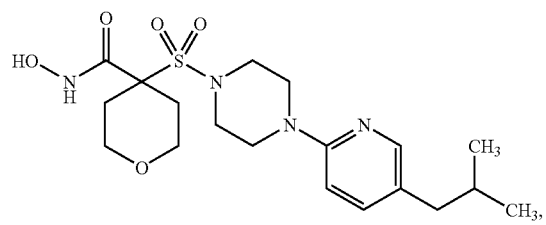
(76-20)
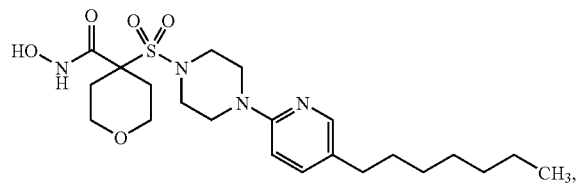
(76-21)
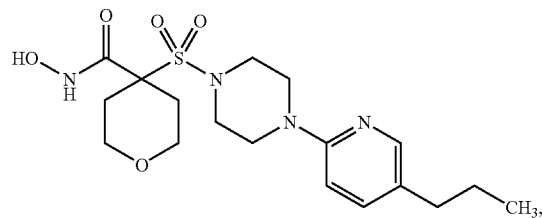
(76-22)
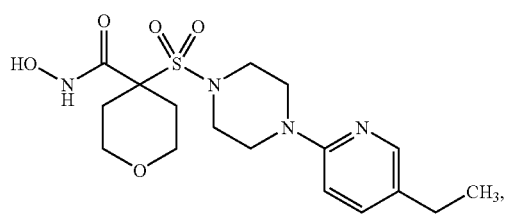
(76-23)
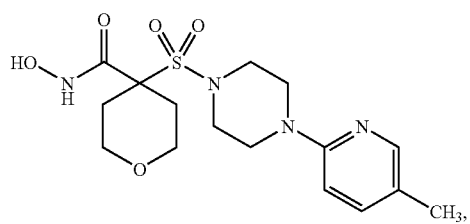
(76-24)
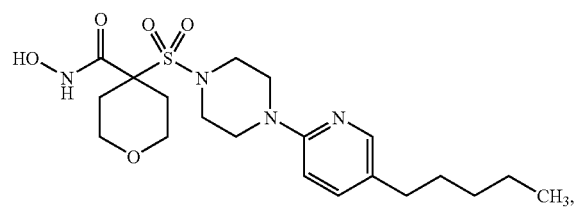
(76-25)
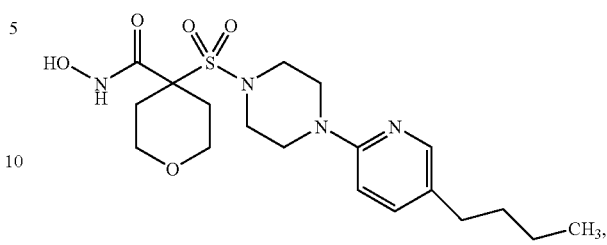
(76-26)
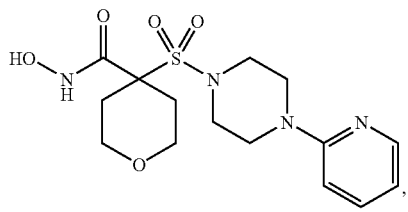
(76-27)
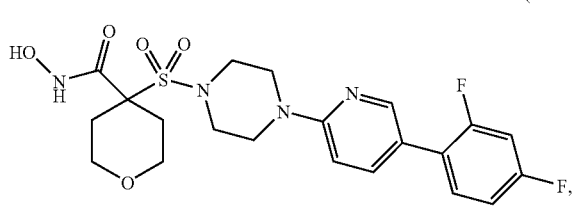
(76-28)
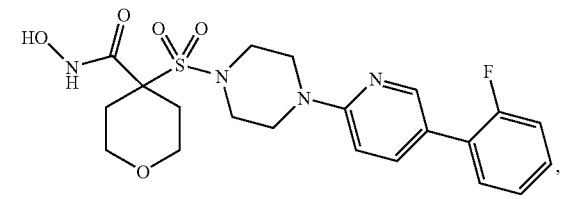
(76-29)
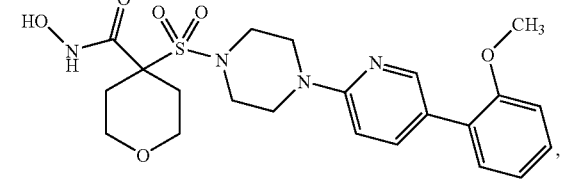
(76-30)
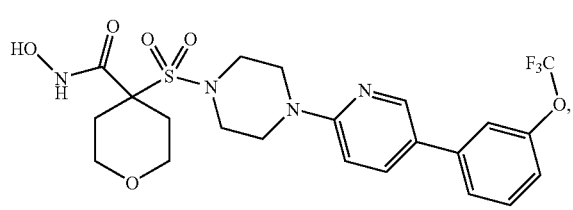

(76-31)
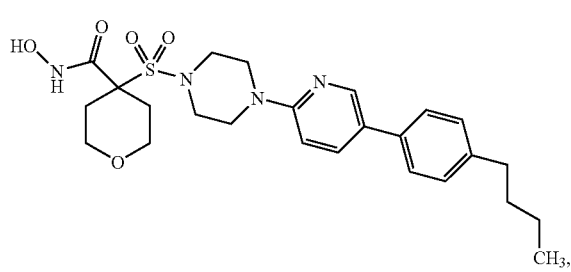
(76-32)
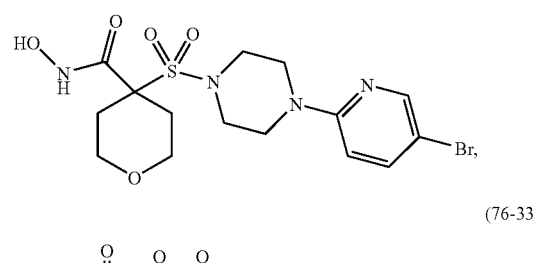
(76-33)
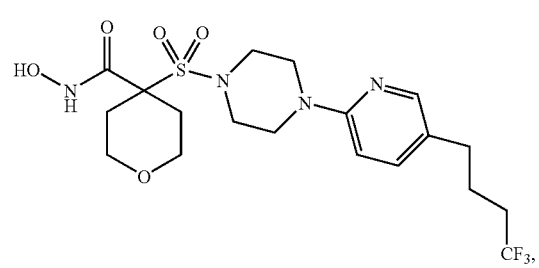
(76-34)
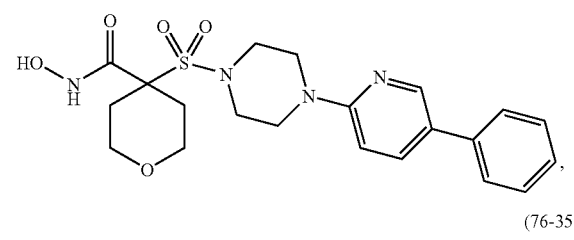
(76-35)
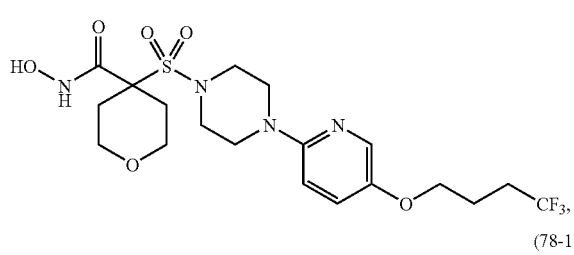
(78-1)
(79-1)
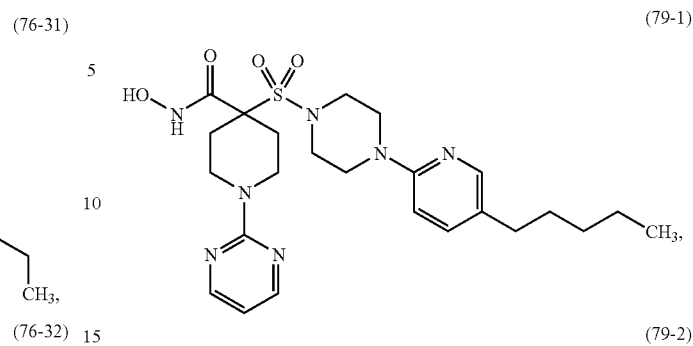
(79-2)
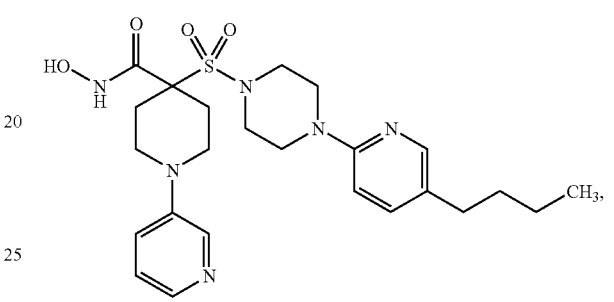
(79-3)
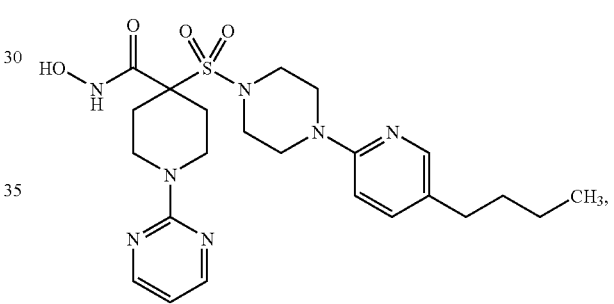
(79-4)
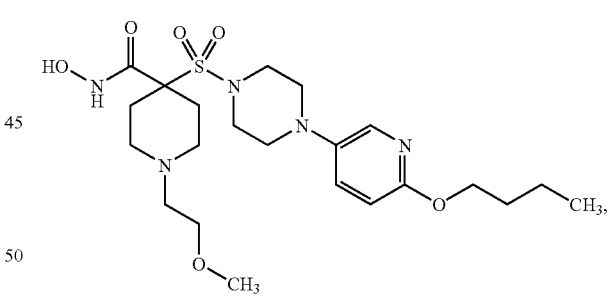
(79-5)
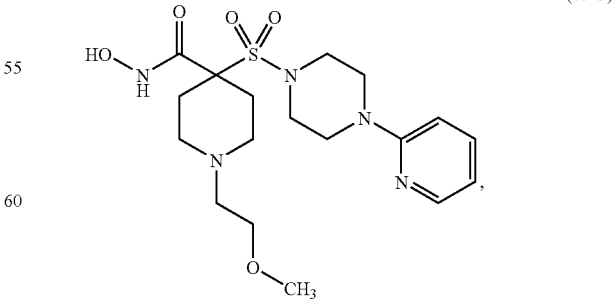

-continued
(79-6)
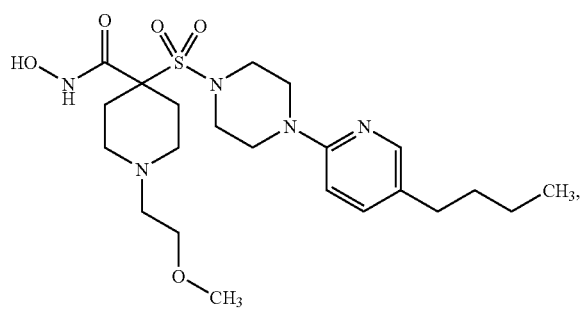
(79-7)
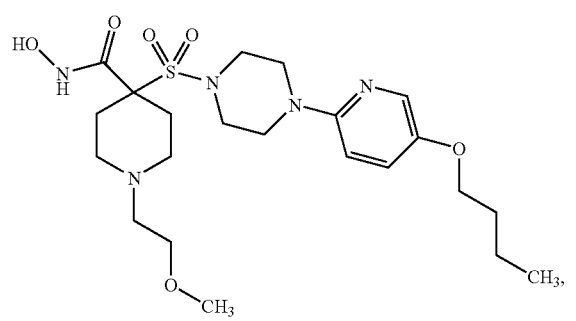
(53-1)
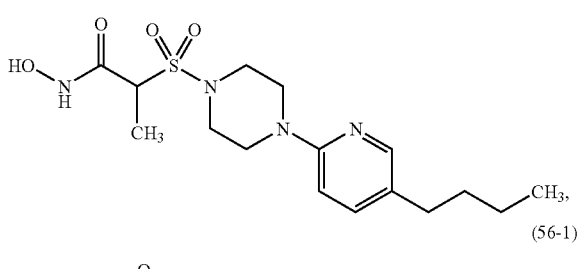
(56-1)
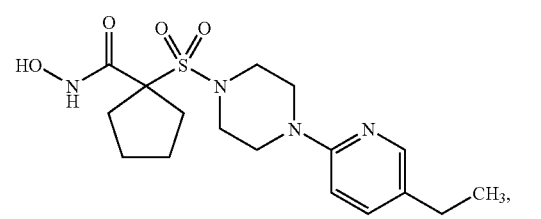
(58-1)
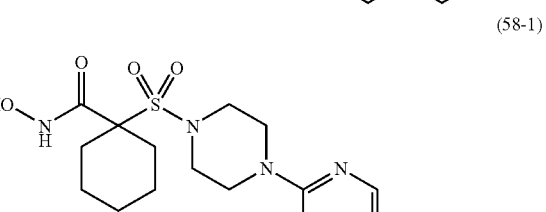
(58-2)
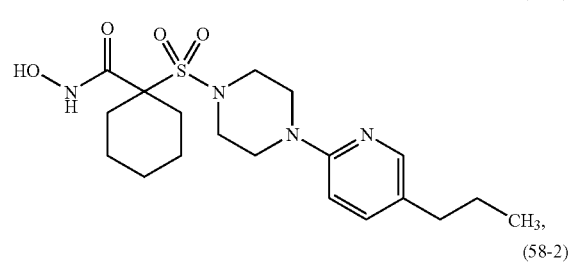
and
-continued
(60-1)
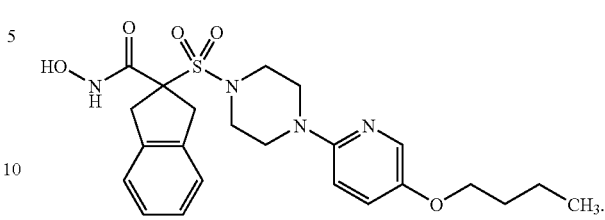
In some particularly preferred embodiments, $E^1$ is pyrazinyl. Particularly preferred examples of compounds wherein $E^1$ is pyrazinyl include:
(81-1)
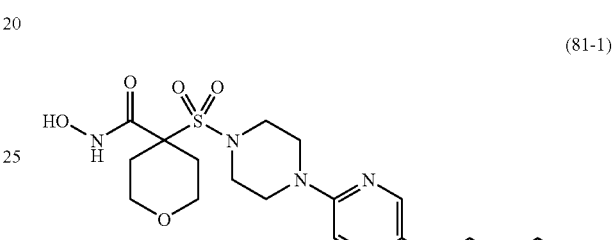
(81-2)
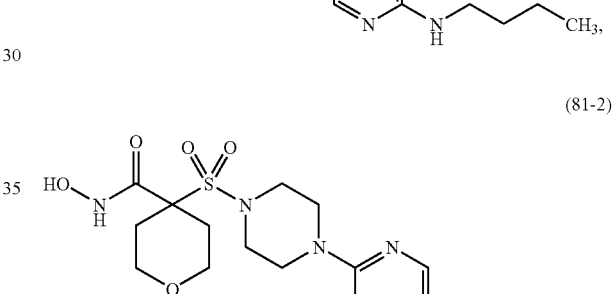
(81-3)
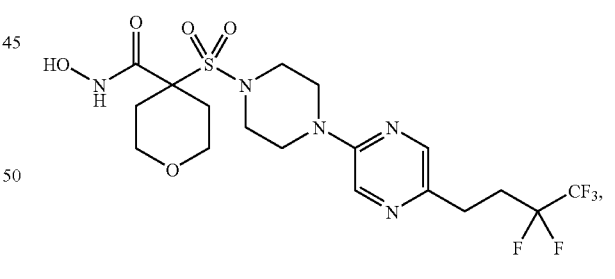
(81-4)
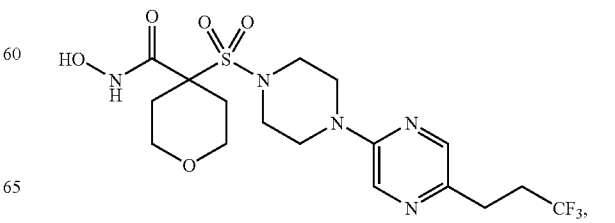

(82-1)
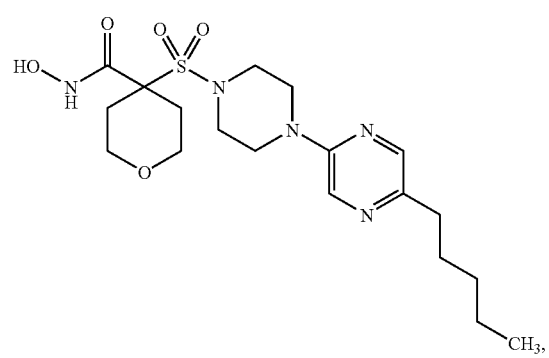
(83-1)
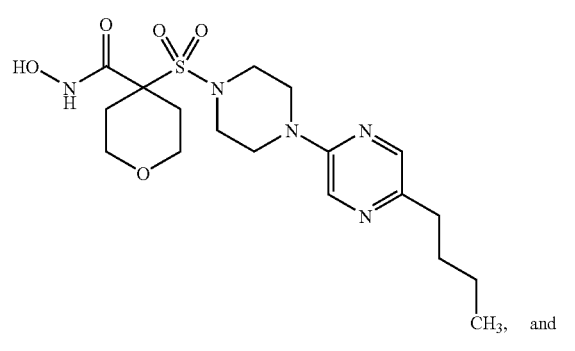
and
(84-1)
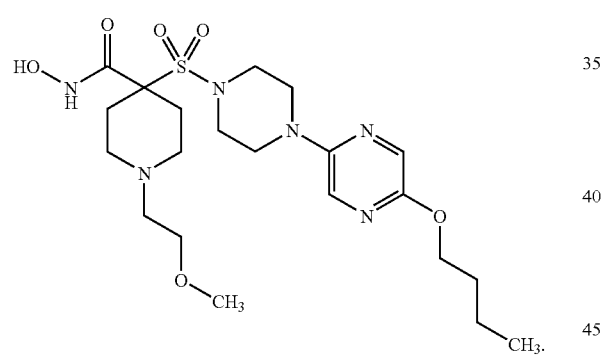
In some particularly preferred embodiments, $E^1$ is pyrimidinyl. Particularly preferred examples of compounds wherein $E^1$ is pyrimidinyl include:
(86-1)
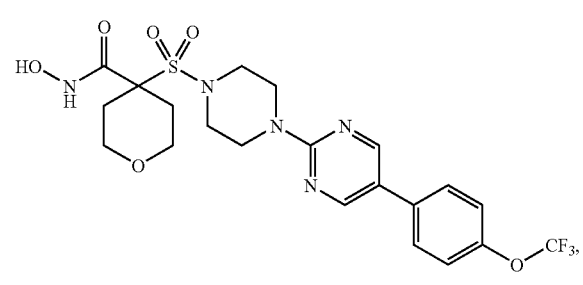
(86-2)
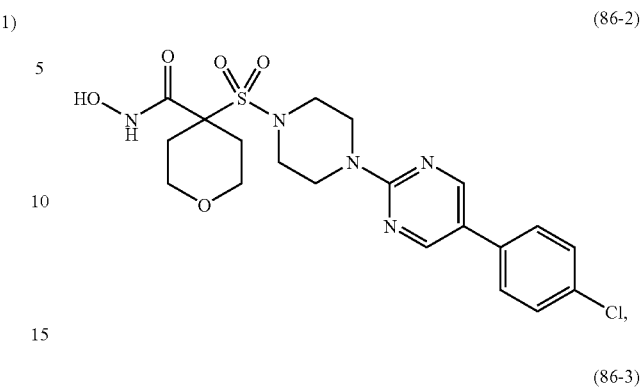
(86-3)
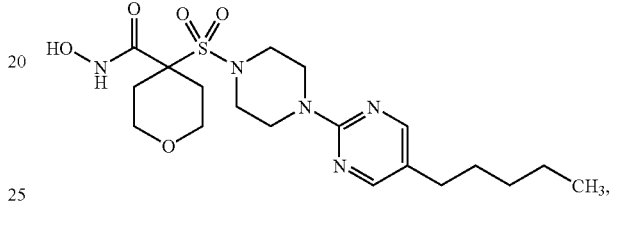
(86-4)
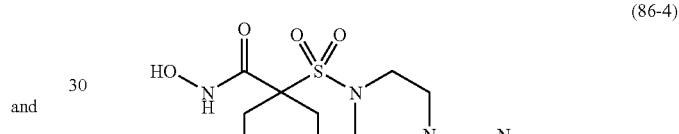
(86-5)
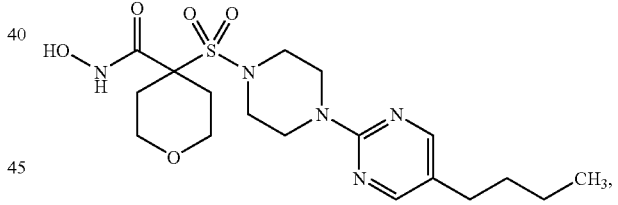
(86-6)
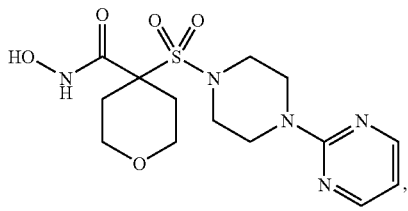
(86-7)
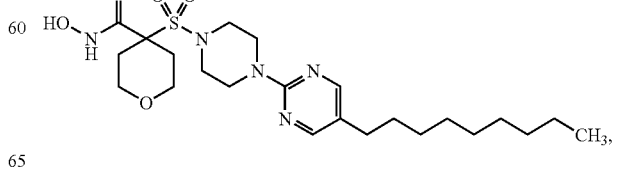

-continued (87-1)
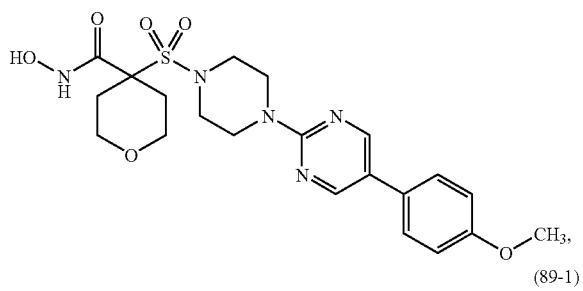

(89-1)
(89-2)
(89-3)
(89-4)
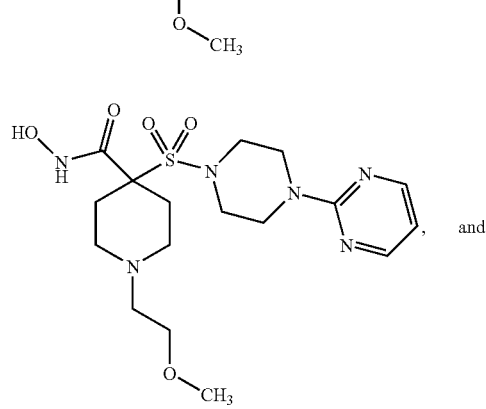
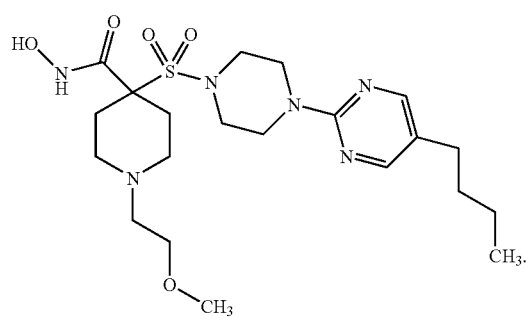

In some particularly preferred embodiments, $E^1$ is pyridazinyl. Particularly preferred examples of compounds wherein $E^1$ is pyridazinyl include:

(91-1)
(91-2)
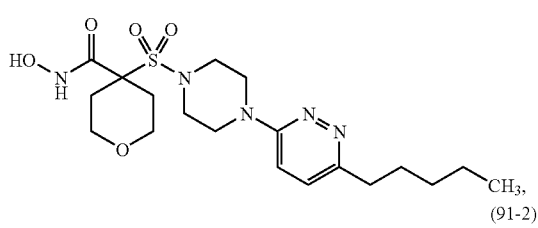
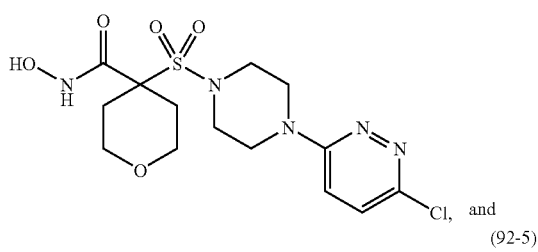

(92-5)
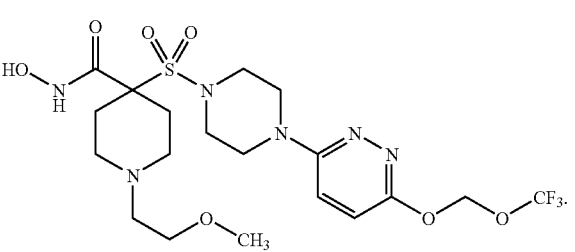

In some particularly preferred embodiments, $E^1$ is multi-ring heteroaryl. The heteroaryl is (if substitutable at one or more positions other than the position occupied by -$E^2$-$E^3$) optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino. Particularly preferred compounds wherein $E^1$ is optionally-substituted, multi-ring heteroaryl include, for example:

(94-1)
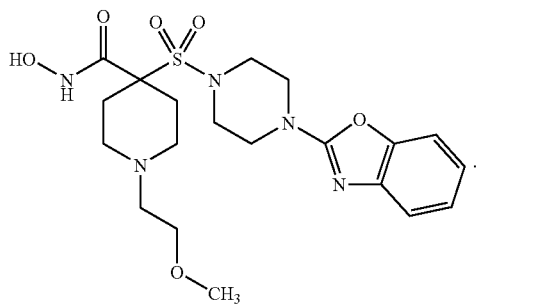

Preferred Embodiment No. 3

In some preferred embodiments, the compound corresponds in structure to the following formula:

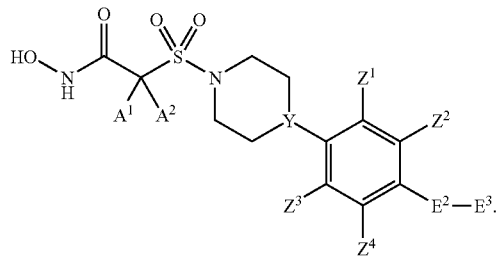
(PE-3)

Here, $Z^1$, $Z^2$, $Z^3$, and $Z^4$ are independently selected from the group consisting of hydrogen, halogen, hydroxy, amino, mono-alkylamino, di-alkylamino, nitro, nitroso, alkyl, alkoxy, alkoxyalkyl, and alkylthio. The alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, at least one of $Z^1$, $Z^2$, $Z^3$, and $Z^4$ is halogen, hydroxy, amino, mono-alkylamino, di-alkylamino, nitro, nitroso, alkyl, alkoxy, alkoxyalkyl, and alkylthio. The alkyl, alkoxy, alkoxyalkyl, alkylthio, mono-alkylamino, and di-alkylamino substituents is, in turn, optionally substituted with one or more substituents independently selected from the group consisting of halogen, hydroxy, cyano, carboxy, thiol, sulfo, nitro, nitroso, oxo, thioxo, and imino.

In some preferred embodiments, at least one of $Z^1$, $Z^2$, $Z^3$, $Z^4$, and -$E^2$-$E^3$ is halogen (preferably bromo, chloro or fluoro, more preferably chloro or fluoro, and often even more preferably fluoro).

In some preferred embodiments, at least one of $Z^1$, $Z^2$, $Z^3$, and $Z^4$ is halogen (preferably bromo, chloro or fluoro, more preferably chloro or fluoro, and often even more preferably fluoro).

In some preferred embodiments, $Z^1$, $Z^2$, $Z^3$, and $Z^4$ are independently selected from the group consisting of hydrogen and halogen (preferably bromo, chloro or fluoro, more preferably chloro or fluoro, and often even more preferably fluoro).

In some preferred embodiments, at least 2 of $Z^1$, $Z^2$, $Z^3$, and $Z^4$ are hydrogen.

In some preferred embodiments, three of $Z^1$, $Z^2$, $Z^3$, and $Z^4$ are hydrogen; and one of $Z^1$, $Z^2$, $Z^3$, and $Z^4$ is not hydrogen. In that instance, the compound corresponds in structure to one of the following formulas:

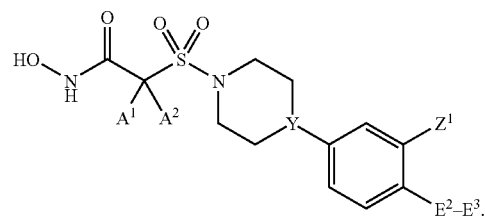
(PE-3A)

or

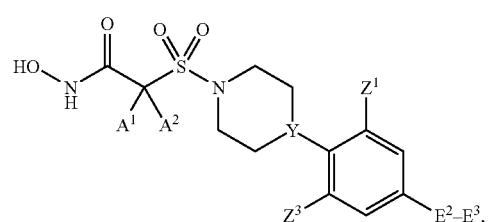
(PE-3B)

In some such embodiments, the $Z^1$ or $Z^2$ that is not hydrogen preferably is bromo, chloro, or fluoro; more preferably chloro or fluoro; and even more preferably fluoro.

In some preferred embodiments, two of $Z^1$, $Z^2$, $Z^3$, and $Z^4$ are hydrogen; and one of $Z^1$, $Z^2$, $Z^3$, and $Z^4$ is not hydrogen. In that instance, the compound corresponds in structure to one of the following formulas:

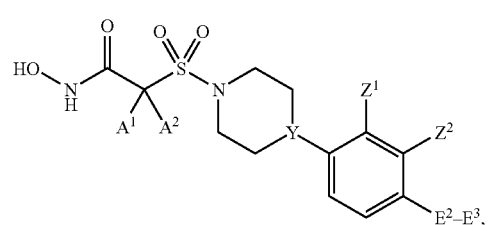
(PE-3C)

(PE-3D)

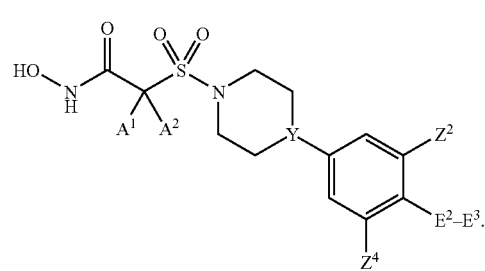

or (PE-3E)

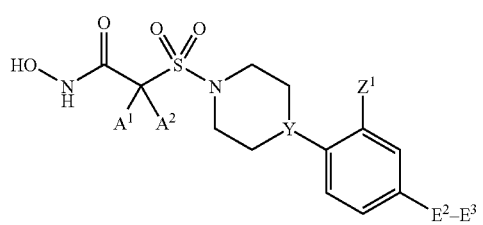

In some such embodiments, the two of $Z^1$, $Z^2$, $Z^3$, and $Z^4$ that are not hydrogen preferably are independently selected from the group consisting of bromo, chloro, and fluoro; more preferably independently selected from the group consisting of chloro and fluoro; and even more preferably both fluoro.

In some preferred embodiments, $Z^1$, $Z^2$, $Z^3$, and $Z^4$ are hydrogen. In that instance, the compound corresponds in structure to the following formula:

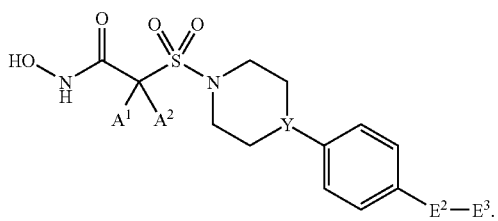

(PE-3F)

In some preferred embodiments:

Z¹ and Z³ are independently selected from the group consisting of hydrogen, halogen, hydroxy, amino, mono-alkylamino, di-alkylamino, nitro, nitroso, alkyl, alkoxy, alkoxyalkyl, and alkylthio. Any such substituent optionally is substituted with one or more substituents independently selected from the group consisting of halogen, hydroxy, cyano, carboxy, thiol, sulfo, nitro, nitroso, oxo, thioxo, and imino; and Z² and Z⁴ are independently selected from the group consisting of hydrogen, halogen, hydroxy, amino, mono-alkylamino, di-alkylamino, nitro, nitroso, alkyl, alkoxy, alkoxyalkyl, and alkylthio. Here:

the alkoxyalkyl, alkylthio, mono-alkylamino, and di-alkylamino optionally are substituted with one or more substituents independently selected from the group consisting of halogen, hydroxy, cyano, carboxy, thiol, sulfo, nitro, nitroso, oxo, thioxo, and imino; and the alkyl and alkoxy comprise at least two carbons and/or are substituted with one or more substituents independently selected from the group consisting of halogen, hydroxy, cyano, carboxy, thiol, sulfo, nitro, nitroso, oxo, thioxo, and imino.

Preferred Embodiment No. 3-A

In some preferred embodiments, E³ is alkyl, alkenyl, alkynyl, alkoxyalkyl, alkoxyalkoxyalkyl, alkylthioalkyl, alkylthioalkylthioalkyl, alkylthioalkoxyalkyl, or alkoxyalkylthioalkyl. Each such substituent is, in turn, partially substituted with one or more independently selected halogen (preferably bromo, chloro, or fluoro; more preferably chloro or fluoro; and even more preferably fluoro).

Particularly Preferred Embodiments of Embodiment No. 3-A

In some particularly preferred embodiments, Y is carbon bonded to hydrogen.

In some particularly preferred embodiments, Y is nitrogen.

In some particularly preferred embodiments, the compound corresponds in structure to the following formula:

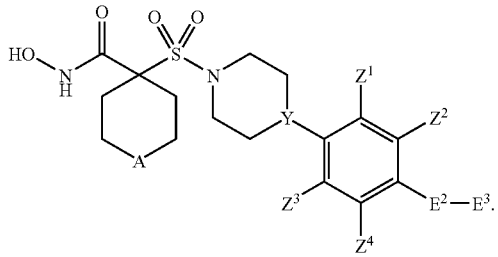

(104-1)

In some particularly preferred embodiments, A is —O—.

In some particularly preferred embodiments, A is —N(H)—.

In some particularly preferred embodiments, A is —N(R$^x$)—. Here, R$^x$ is alkyl, alkenyl, alkynyl, alkoxyalkyl, R$^a$-oxyalkyl, alkylsulfonyl, R$^a$R$^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, E² is a bond.

In some particularly preferred embodiments, E² is —O—.

In some particularly preferred embodiments, -E²-E³ is alkyl, alkoxy, alkoxyalkyl, or alkoxyalkoxy. Each such substituent is, in turn, partially substituted with one or more independently selected halogen (preferably selected from bromo, chloro, and fluoro; more preferably selected from bromo and chloro; and even more preferably all fluoro).

In some particularly preferred embodiments, -E²-E³ is alkyl, alkoxy, alkoxyalkyl, or alkoxyalkoxy. Each such substituent is, in turn, partially substituted with trihalomethyl, preferably trichloromethyl or trifluoromethyl, and more preferably trifluoromethyl. Particularly preferred examples of such compounds include:

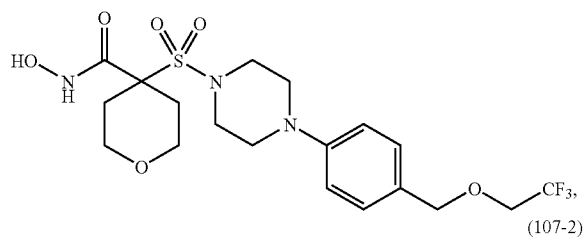

(107-1)

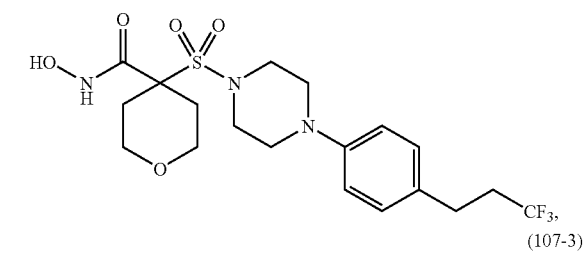

(107-2)

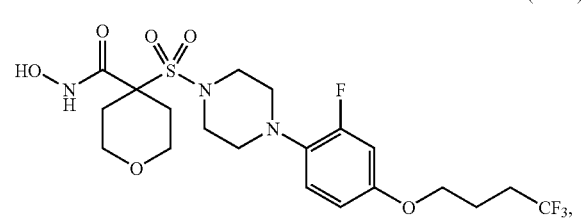

(107-3)

-continued
(107-4)
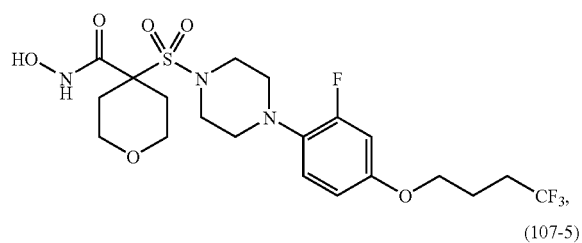
(107-5)
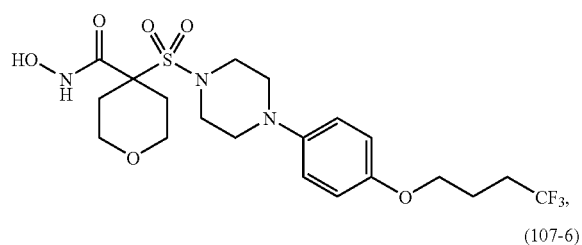
(107-6)
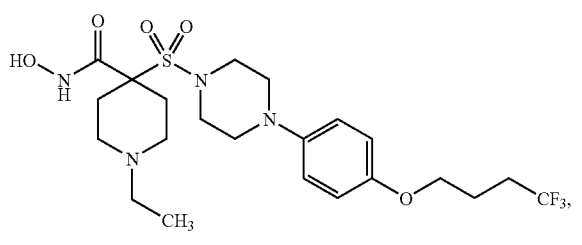
(111-1)
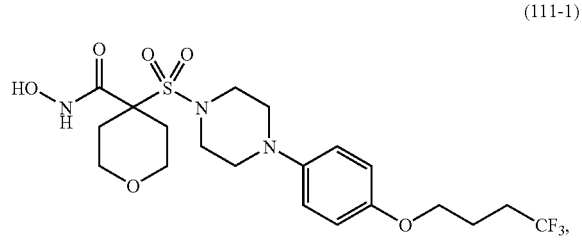
(112-1)
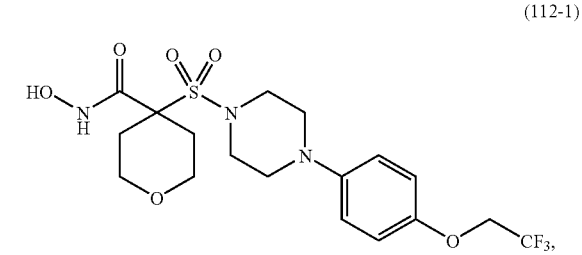
(109-1)
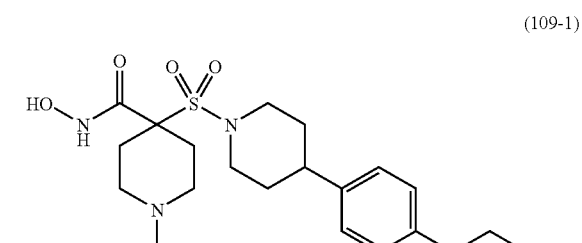
-continued
(110-1)
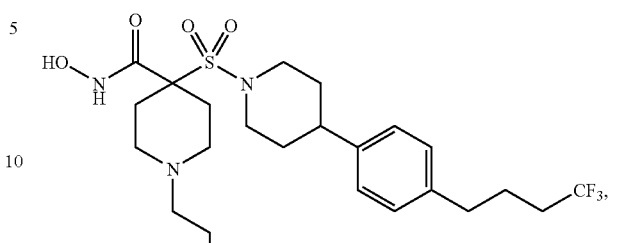
(107-7)
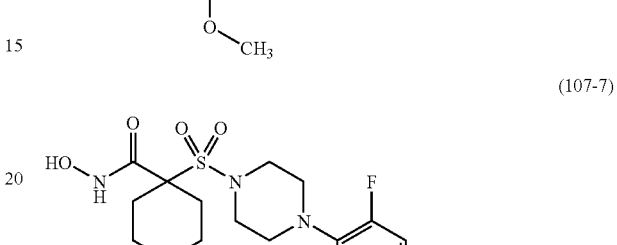
(107-8)
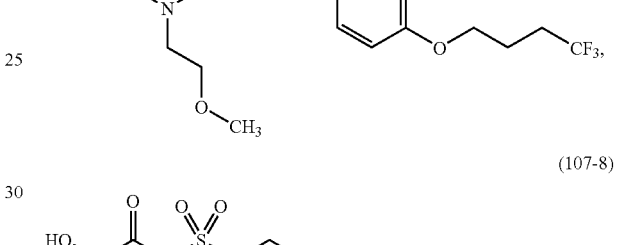
(107-9)
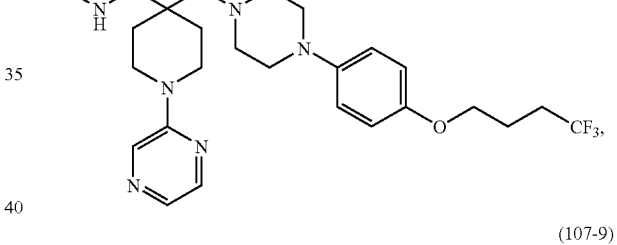
(107-10)
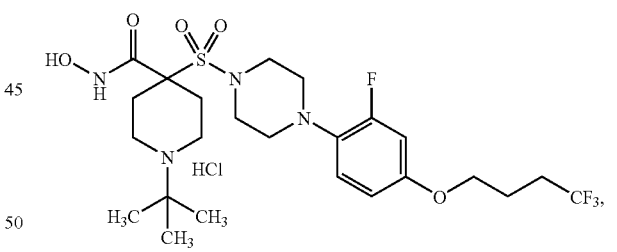
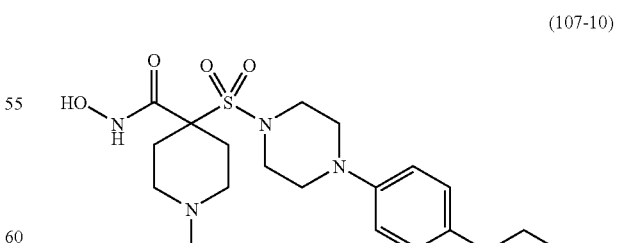
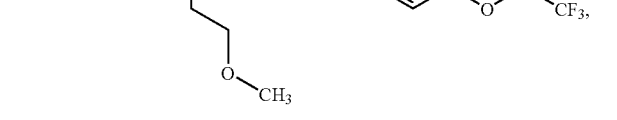

(107-11)
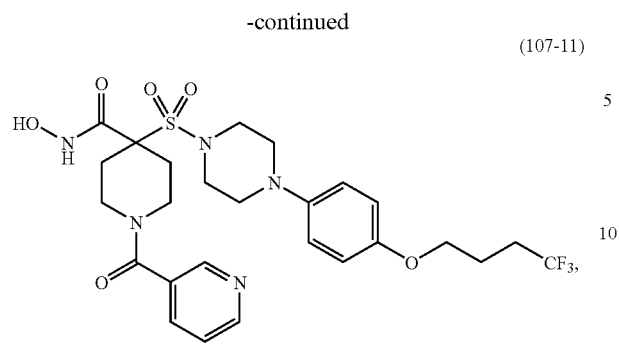
(107-12)
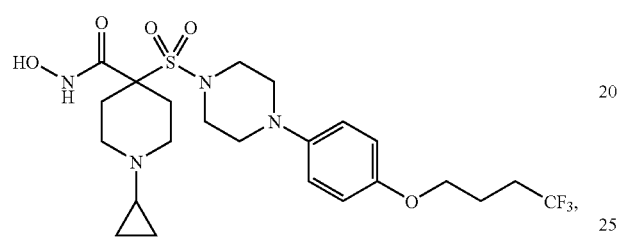
(107-13)
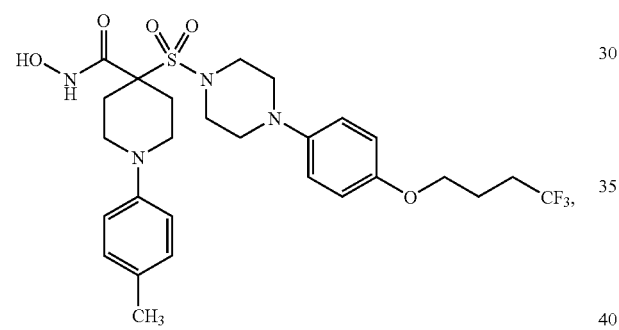
(107-14)
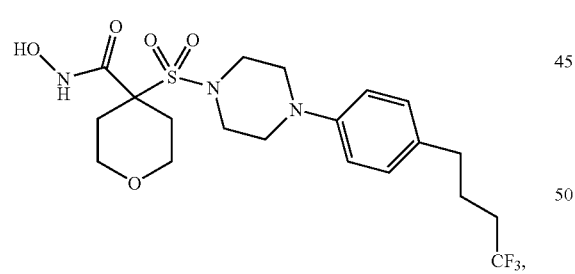
(107-15)
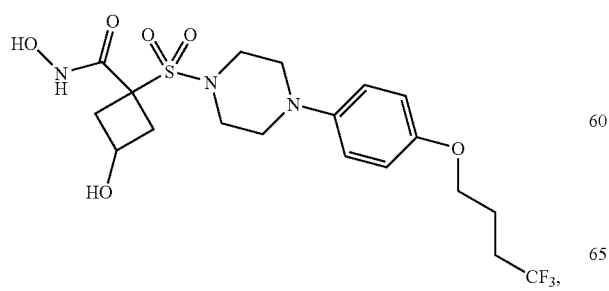
(107-16)
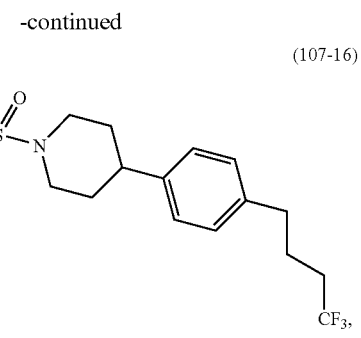
(107-17)
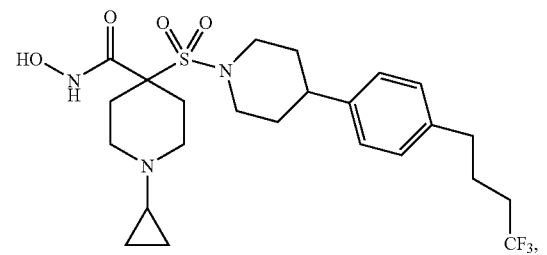
(107-18)
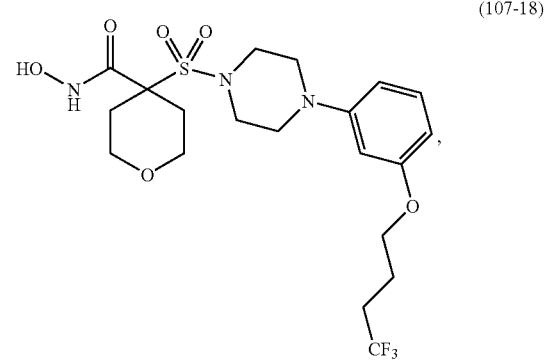
(107-19)
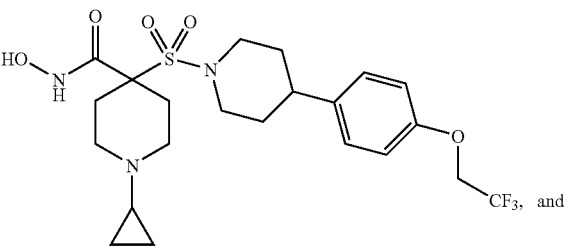
(113-1)

(114-1)
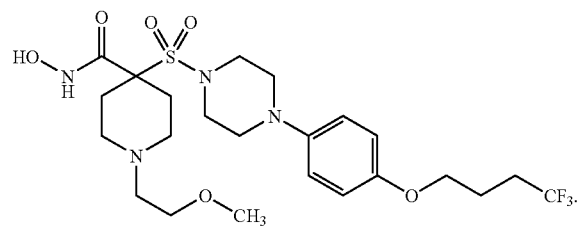

In some particularly preferred embodiments, -E²-E³ is haloalkyl, haloalkoxy, halo-substituted alkoxyalkyl, or halo-substituted alkoxyalkoxy (preferably fluoroalkyl, fluoroalkoxy, fluoro-substituted alkoxyalkyl, fluoro-substituted alkoxyalkoxy, chloroalkyl, chloroalkoxy, chloro-substituted alkoxyalkyl, or chloro-substituted alkoxyalkoxy; and more preferably fluoroalkyl, fluoroalkoxy, fluoro-substituted alkoxyalkyl, or fluoro-substituted alkoxyalkoxy). Each such substituent is, in turn, partially substituted with trihalomethyl, preferably trichloromethyl or trifluoromethyl, and more preferably trifluoromethyl. Particularly preferred examples of such compounds include:

(116-1)
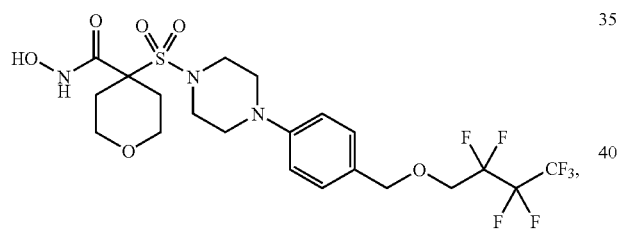

(116-2)
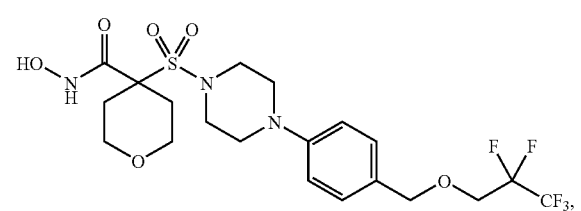

(116-3)
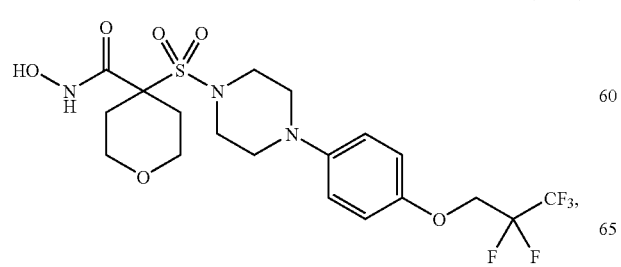

(116-4)
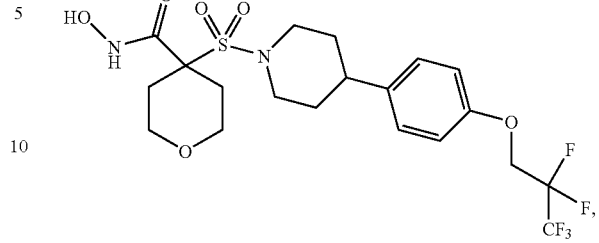

(116-5)
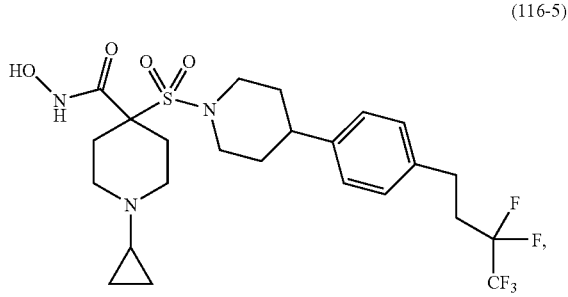

(117-1)
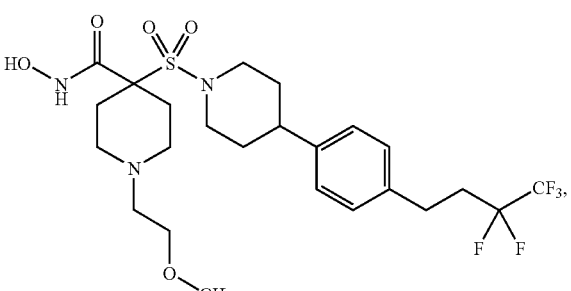

(118-1)
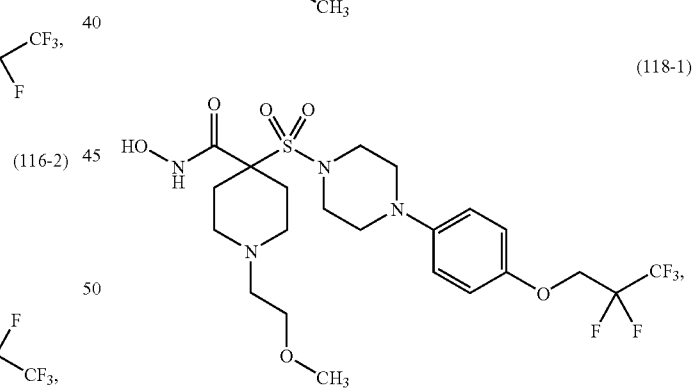

(119-1)
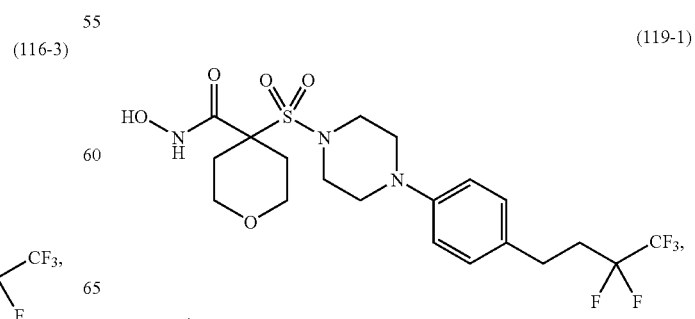

and (120-1)

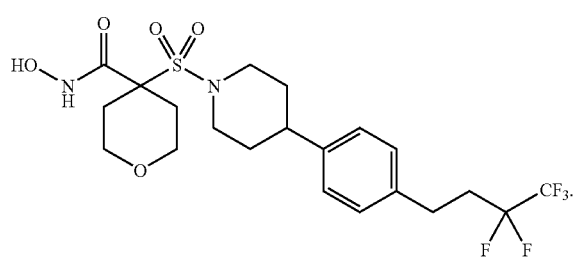

In some particularly preferred embodiments, E³ comprises a carbon atom bonded to at least one hydrogen and at least one halogen (preferably bromo, chloro, or fluoro; more preferably chloro or fluoro; and even more preferably fluoro). Particularly preferred examples of such compounds include:

(122-1)

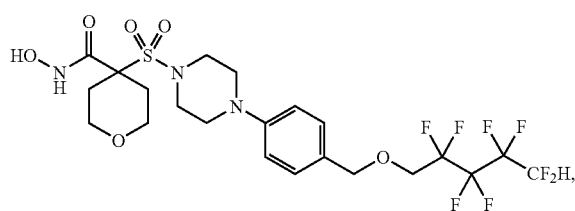

(122-2)

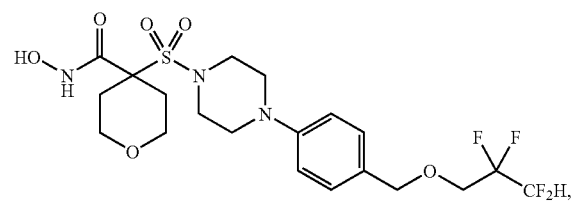

(122-3)

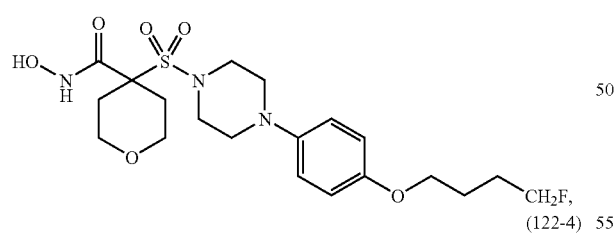

(122-4)

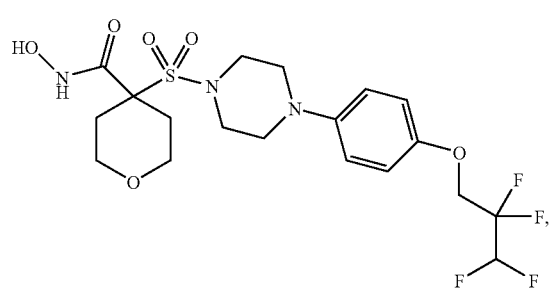

(122-5)

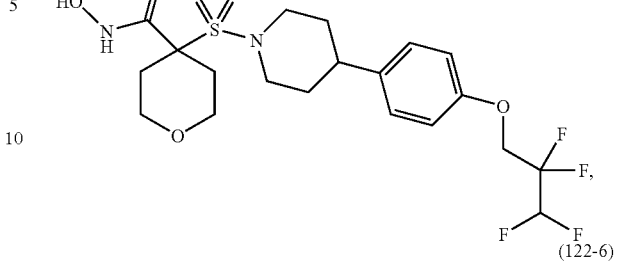

(122-6)

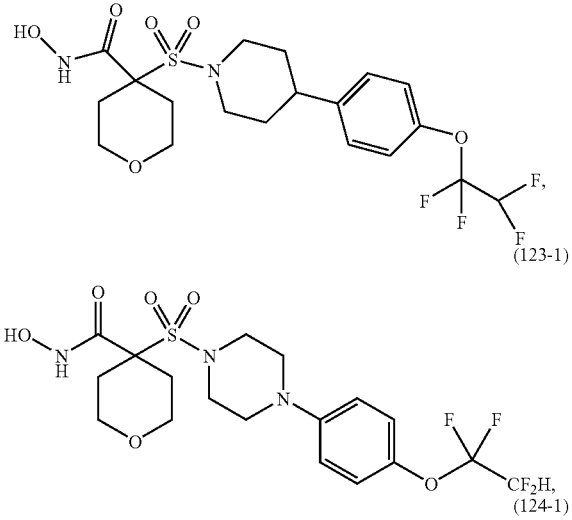

(123-1)

(124-1)

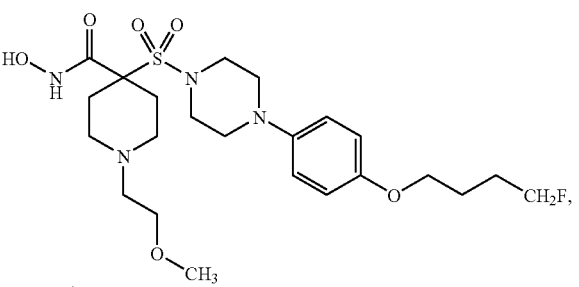

and (125-1)

Preferred Embodiment No. 3-B

In some preferred embodiments:

E³ is carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. As to such optional substituents:
- the alkyl, alkoxy, alkylthio, carbocyclyl, and carbocyclylalkyl optionally are substituted with one or more substituents independently selected from the group consisting of halogen, hydroxy, cyano, carboxy, thiol, sulfo, nitro, nitroso, oxo, thioxo, imino, aminocarbonyl, and amino; and
- the amino nitrogen is substituted with up to 2 substituents independently selected from the group consisting of alkyl and carbocyclylalkyl.

$A^1$ and $A^2$, together with the carbon to which they are bonded, form heterocyclyl or carbocyclyl. The heterocyclyl and carbocyclyl optionally are substituted with up to 3 independently selected $R^x$ substituents. Alternatively, $A^1$ and $A^2$ are independently selected as follows:
- $A^1$ is hydrogen, alkyl, alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, or heterocyclylalkylthioalkyl. Any member of such group optionally is substituted with up to 3 independently selected $R^x$ substituents; and
- $A^2$ is alkyl, alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, or heterocyclylalkylthioalkyl. Any member of such group optionally is substituted with up to 3 independently selected $R^x$ substituents.

As to $Z^1$, $Z^2$, $Z^3$, and $Z^4$:
- $Z^1$ and $Z^3$ are independently selected from the group consisting of hydrogen, halogen, hydroxy, amino, mono-alkylamino, di-alkylamino, nitro, nitroso, alkyl, alkoxy, alkoxyalkyl, and alkylthio. Any such substituent optionally is substituted with one or more substituents independently selected from the group consisting of halogen, hydroxy, cyano, carboxy, thiol, sulfo, nitro, nitroso, oxo, thioxo, and imino; and
- $Z^2$ and $Z^4$ are independently selected from the group consisting of hydrogen, halogen, hydroxy, amino, mono-alkylamino, di-alkylamino, nitro, nitroso, alkyl, alkoxy, alkoxyalkyl, and alkylthio. Here:
  - the alkoxyalkyl, alkylthio, mono-alkylamino, and di-alkylamino optionally are substituted with one or more substituents independently selected from the group consisting of halogen, hydroxy, cyano, carboxy, thiol, sulfo, nitro, nitroso, oxo, thioxo, and imino; and
  - the alkyl and alkoxy comprise at least two carbons and/or are substituted with one or more substituents independently selected from the group consisting of halogen, hydroxy, cyano, carboxy, thiol, sulfo, nitro, nitroso, oxo, thioxo, and imino.

Particularly Preferred Embodiments of Embodiment No. 3-B

In some particularly preferred embodiments, Y is carbon bonded to hydrogen.

In some particularly preferred embodiments, Y is nitrogen.

In some particularly preferred embodiments, $A^1$ and $A^2$ are independently selected from the group consisting of alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, and heterocyclylalkylthioalkyl. Any member of such group optionally is substituted with up to 3 independently selected $R^x$ substituents.

In some particularly preferred embodiments, the compound corresponds in structure to the following formula:

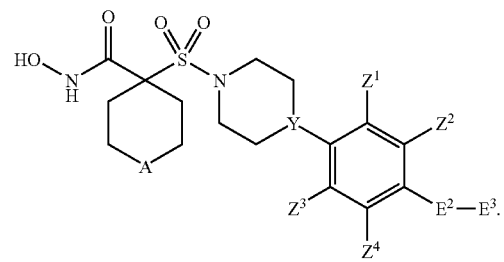

(128-1)

In some particularly preferred embodiments, A is —O—.

In some particularly preferred embodiments, A is —N(H)—.

In some particularly preferred embodiments, A is —N($R^x$)—. Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:
- the alkyl, alkoxy, alkoxyalkyl, and alkoxyalkoxy optionally are substituted with one or more substituents independently selected from the group consisting of halogen and hydroxy; and
- the amino optionally is substituted by up to 2 independently selected alkyl.

In some particularly preferred embodiments, A is —S—, —S(O)—, or —S(O)$_2$—.

In some particularly preferred embodiments, $Z^1$, $Z^2$, $Z^3$, and $Z^4$ are hydrogen.

In some particularly preferred embodiments, $E^2$ is a bond.

In some particularly preferred embodiments, E2 is —O—.

In some particularly preferred embodiments, $E^3$ is optionally-substituted carbocyclyl or optionally-substituted carbocyclylalkyl.

In some particularly preferred embodiments where $E^3$ is optionally-substituted carbocyclyl or optionally-substituted carbocyclylalkyl, the carbocyclyl portion of E³ is cycloalkyl. Particularly preferred examples of such compounds include:

(131-1)
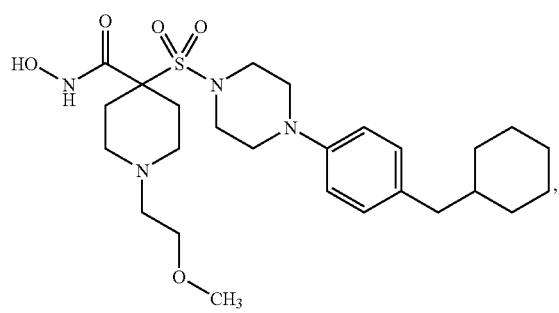

(131-2)
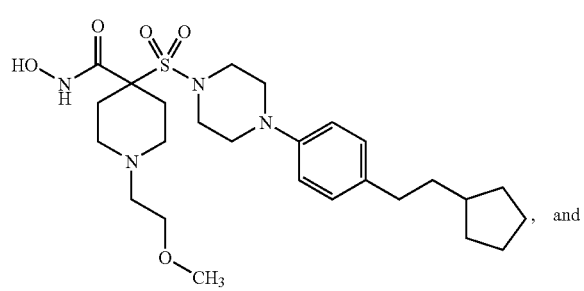
, and (131-3)
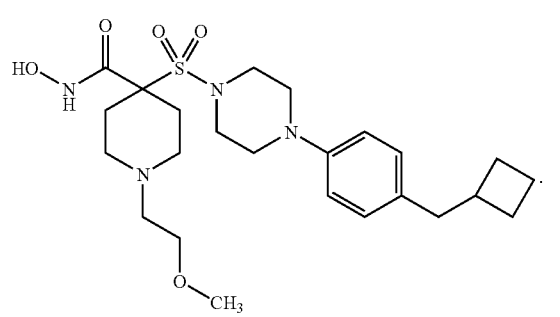

In some particularly preferred embodiments where E³ is optionally-substituted carbocyclyl or optionally-substituted carbocyclylalkyl, the carbocyclyl portion of E³ is aryl, and preferably phenyl. Particularly preferred examples of such compounds include:

(133-1)
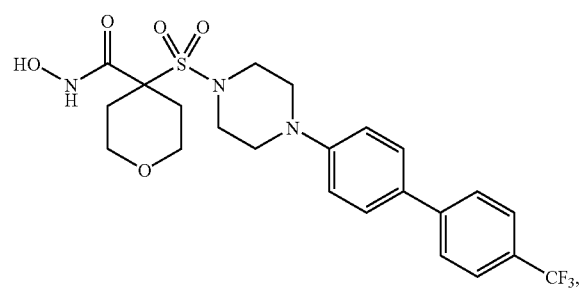

(133-2)
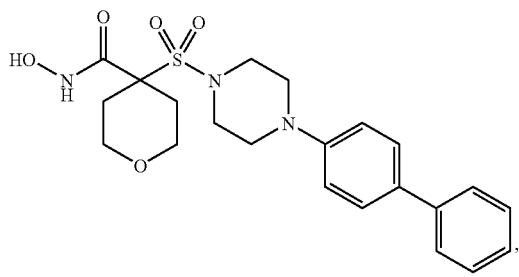
, (133-3)
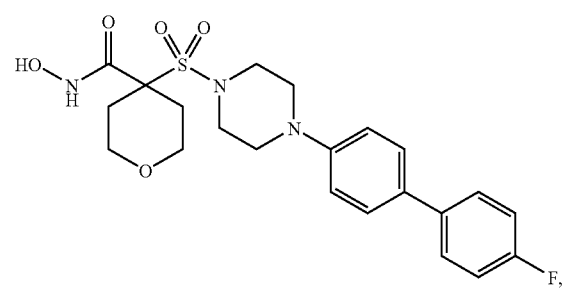
, (133-4)
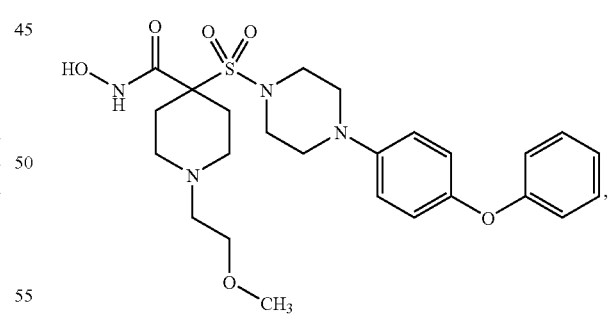
, (133-5)
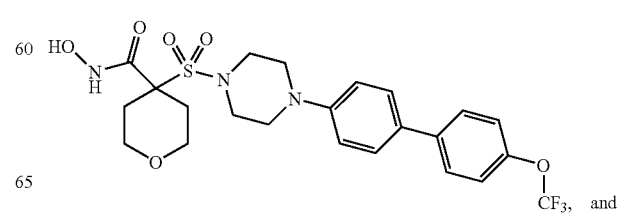
, (133-6)

-continued (133-7)

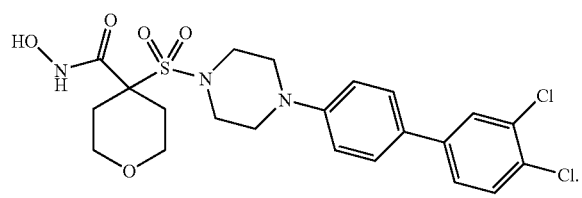

In some particularly preferred embodiments, E³ is more preferably optionally-substituted heterocyclyl or optionally-substituted heterocyclylalkyl.

In some particularly preferred embodiments where E³ is optionally-substituted heterocyclylalkyl or optionally-substituted heterocyclylalkyl, the heterocyclyl portion of E³ is heteroaryl.

In some particularly preferred embodiments where E³ is optionally-substituted heterocyclylalkyl or optionally-substituted heterocyclylalkyl, the heterocyclyl portion of E³ is heteroaryl. An example of one such particularly preferred compound corresponds in structure to the following formula:

(135-1)

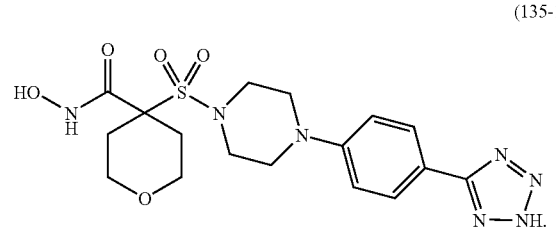

In some particularly preferred embodiments where E³ is optionally-substituted heterocyclylalkyl or optionally-substituted heterocyclylalkyl, the heterocyclyl portion of E³ is heterocycloalkyl. Particularly preferred examples of such compounds include:

(138-1)

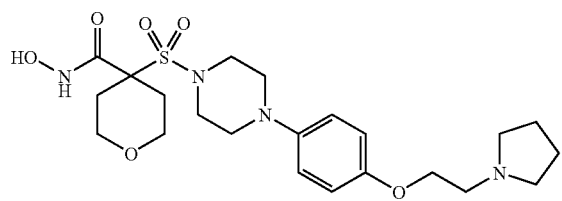

Preferred Embodiment No. 3-C

In some preferred embodiments, E³ is cyano, alkyl, alkenyl, alkynyl, alkoxyalkyl, alkoxyalkoxyalkyl, alkylthioalkyl, alkylthioalkylthioalkyl, alkylthioalkoxyalkyl, or alkoxyalkylthioalkyl. Each such substituent (except cyano) is, in turn, substituted with one or more cyano.

Particularly Preferred Embodiments of Embodiment No. 3-C

In some particularly preferred embodiments, Y is carbon bonded to hydrogen.

In some particularly preferred embodiments, Y is nitrogen.

In some particularly preferred embodiments, the compound corresponds in structure to the following formula:

(141-1)

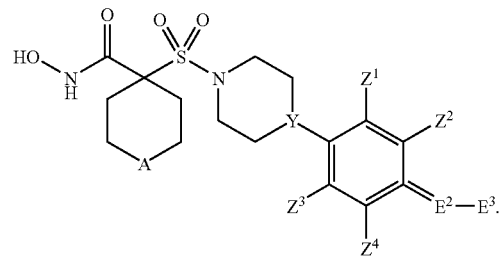

In some particularly preferred embodiments, A is —O—.

In some particularly preferred embodiments, A is —N(H)—.

In some particularly preferred embodiments, A is —N(R$^x$)—. Here, R$^x$ is alkyl, alkenyl, alkynyl, alkoxyalkyl, R$^a$-oxyalkyl, alkylsulfonyl, R$^a$R$^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, Z¹, Z², Z³, and Z⁴ are hydrogen.

In some particularly preferred embodiments, E² is a bond.

In some particularly preferred embodiments, -E²E³ is cyano. One particularly preferred example of such a compound is:

(145-1)

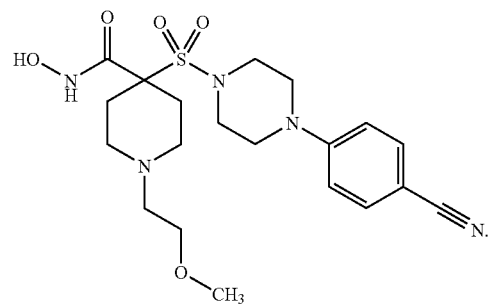

In some particularly preferred embodiments, -E²-E³ is cyanoalkyl. Particularly preferred examples of such compounds include:

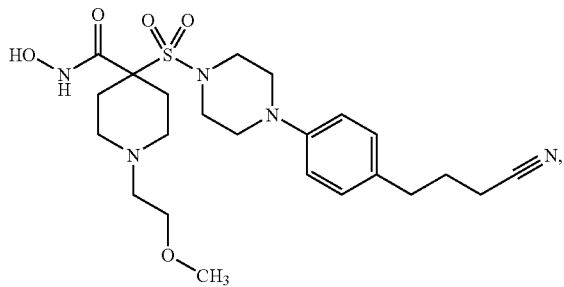

(148-1)

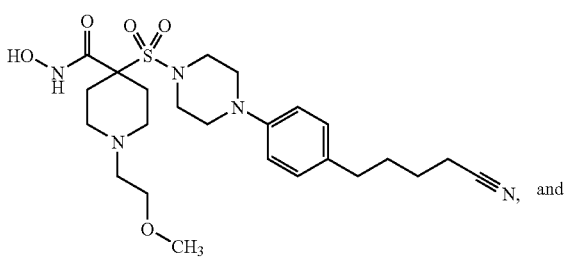

(148-2)

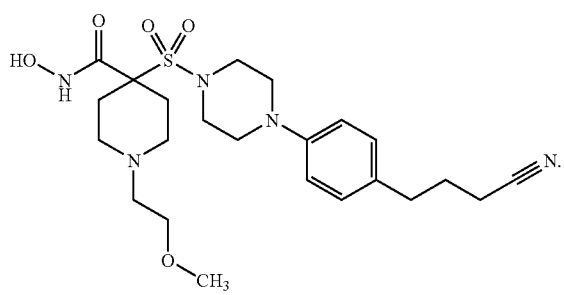

(148-3)

In some particularly preferred embodiments, -E²-E³ is cyanoaryl. One particularly preferred example of such a compound is:

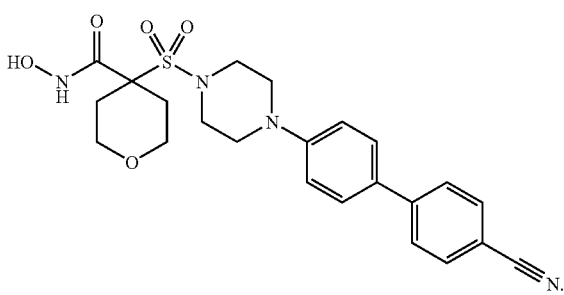

(143-1)

Preferred Embodiment No. 3-D

In some preferred embodiments, the compounds correspond in structure to Formula (149-1):

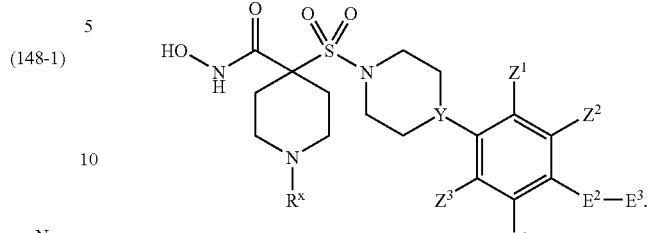

(149-1)

In these embodiments:

R$^x$ is R$^c$-oxyalkyl, R$^c$R$^c$-aminoalkyl, carbocyclyl, carbocyclylalkyl, or carbocyclylsulfonyl. The carbocyclyl and the carbocyclyl of the carbocyclylalkyl, carbocyclyloxy, carbocyclyloxyalkoxy, carbocyclylthio, and carbocyclylsulfonyl are substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such substituents:

the alkyl, alkoxy, alkoxyalkyl, and alkoxyalkoxy optionally are substituted with one or more substituents independently selected from the group consisting of halogen and hydroxy; and the amino nitrogen optionally is substituted with up to 2 independently selected alkyl.

Each R$^c$ is independently selected from the group consisting of carbocyclyl, carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, and carbocyclylsulfonylalkyl. The carbocyclyl and the carbocyclyl of the carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, and carbocyclylsulfonylalkyl are, in turn, substituted with one or more substituents independently selected from the group consisting of halogen, hydroxy, cyano, carboxy, thiol, sulfo, nitro, nitroso, oxo, thioxo, and imino.

Particularly Preferred Embodiments of Embodiment No. 3-D

In some particularly preferred embodiments, Y is carbon bonded to hydrogen.

In some particularly preferred embodiments, Y is nitrogen.

In some particularly preferred embodiments, Z$^1$, Z$^2$, Z$^3$, and Z$^4$ are hydrogen.

In some particularly preferred embodiments, E² is a bond.

In some particularly preferred embodiments, E2 is —O—.

In some particularly preferred embodiments, R$^x$ is R$^c$-oxyalkyl, R$^c$R$^c$-aminoalkyl, phenyl, phenylalkyl, or phenylsulfonyl. The phenyl and the phenyl of the phenylalkyl, phenyloxy, phenyloxyalkoxy, phenylthio, and phenylsulfonyl are, in turn, substituted with one or more substituents independently selected from the group consisting of halogen, hydroxy, cyano, amino, carboxy, thiol, sulfo, nitro, nitroso, alkyl, alkoxy, alkoxyalkyl, and alkoxyalkoxy. As to such substituents:

the alkyl, alkoxy, alkoxyalkyl, and alkoxyalkoxy optionally are substituted with one or more substituents independently selected from the group consisting of halogen and hydroxy; and the amino optionally is substituted with up to 2 independently selected alkyl.

Here, each $R^c$ is independently selected from the group consisting of phenyl, phenylalkyl, phenyloxyalkyl, phenylalkoxyalkyl, phenylthioalkyl, phenylthioalkenyl, phenylsulfoxidoalkyl, phenylsulfonyl, and phenylsulfonylalkyl. The phenyl and the phenyl of the phenylalkyl, phenyloxyalkyl, phenylalkoxyalkyl, phenylthioalkyl, phenylthioalkenyl, phenylsulfoxidoalkyl, phenylsulfonyl, and phenylsulfonylalkyl are, in turn, substituted with one or more substituents independently selected from the group consisting of halogen, hydroxy, cyano, carboxy, thiol, sulfo, nitro, and nitroso.

In some particularly preferred embodiments, $R^x$ is phenyl substituted with one or more substituents independently selected from the group consisting of halogen, hydroxy, cyano, amino, carboxy, thiol, sulfo, $C_1$–$C_6$-alkyl (more preferably $C_1$–$C_2$-alkyl), $C_1$–$C_6$-alkoxy (more preferably $C_1$–$C_2$-alkoxy), $C_1$–$C_6$-alkoxy-$C_1$–$C_6$-alkyl (more preferably $C_1$–$C_2$-alkoxy-$_1C$ -$C_2$-alkyl), and $C_1$–$C_6$-alkoxy-$C_1$–$C_6$-alkoxy (more preferably $C_1$–$C_2$-alkoxy-$C_1$–$C_2$-alkoxy). The alkyl, alkoxy, alkoxyalkyl, and alkoxyalkoxy optionally 10 are substituted with one or more substituents independently selected from the group consisting of halogen and hydroxy. The amino, on the other hand, is optionally substituted with up to 2 independently selected $C_1$–$C_6$-alkyl (more preferably $C_1$–$C_2$-alkyl). Particularly preferred examples of such compounds include:

(153-1)

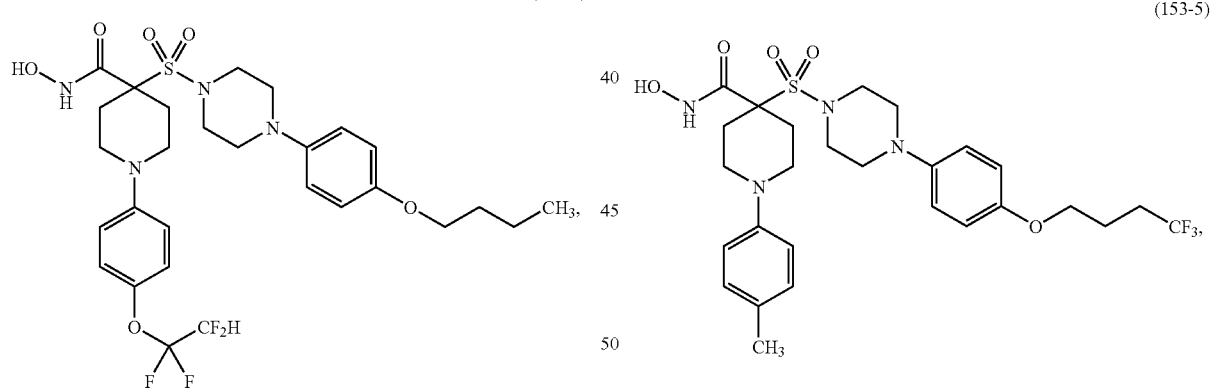

(153-2)

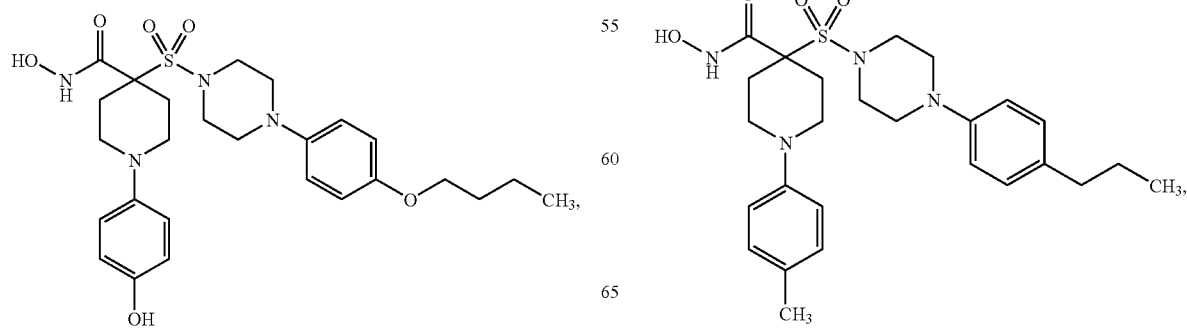

(153-3)

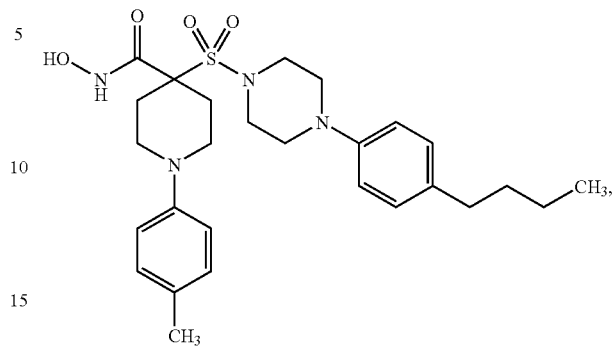

(153-4)

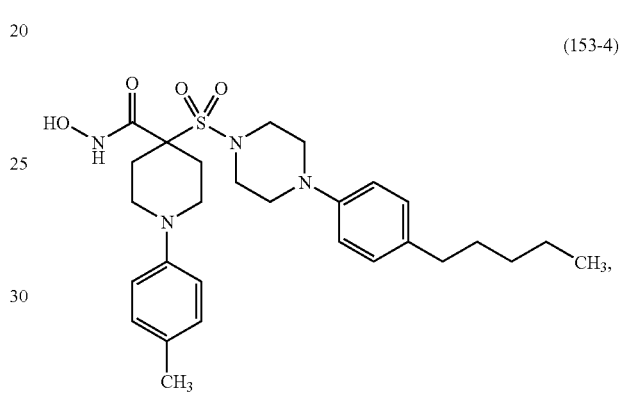

(153-5)

(153-6)

(153-7)
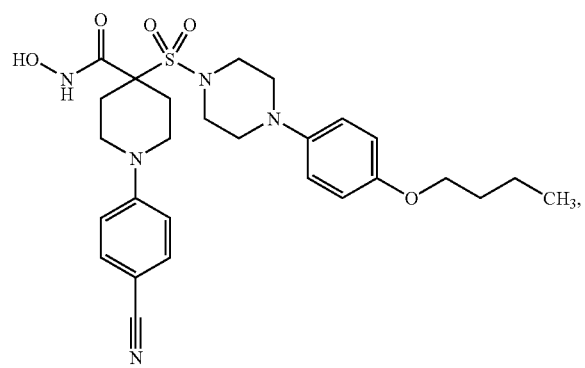
(153-8)
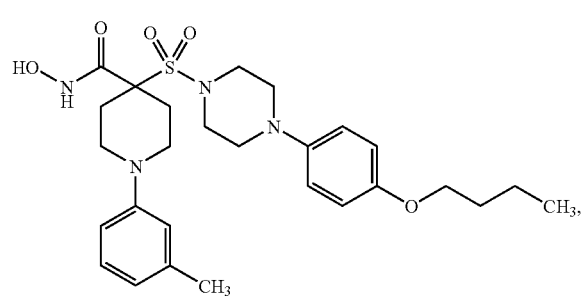
(153-9)
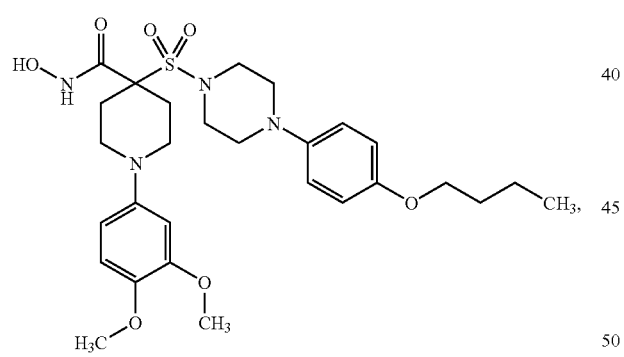
(153-10)
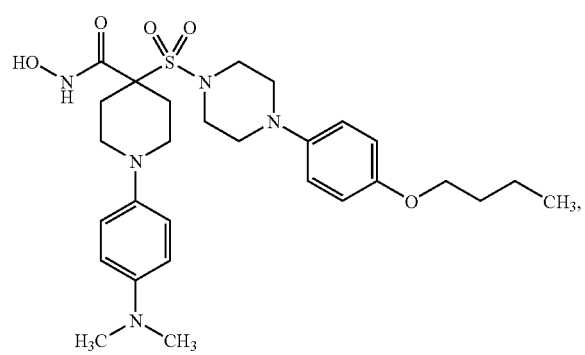
(153-11)
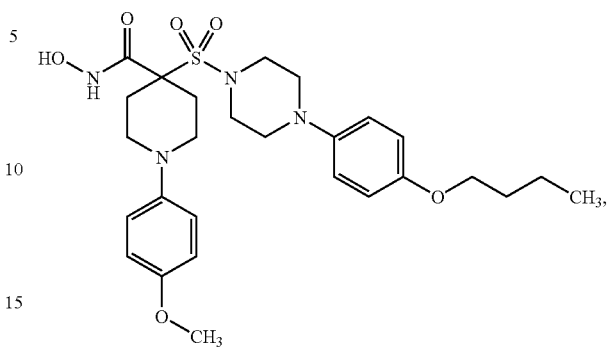
(153-12)
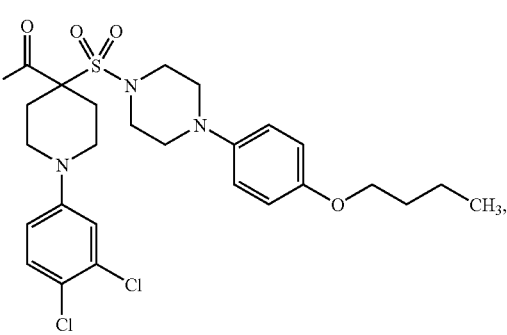
(153-13)
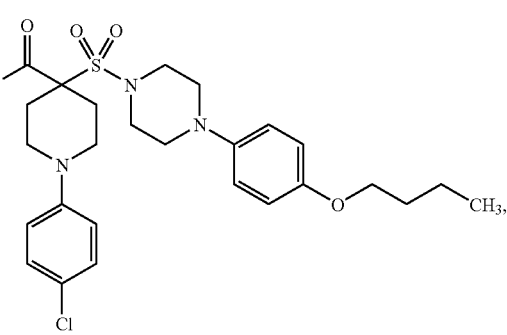
(153-14)
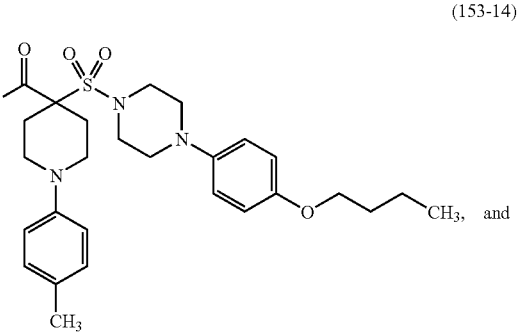 and -continued (153-15)

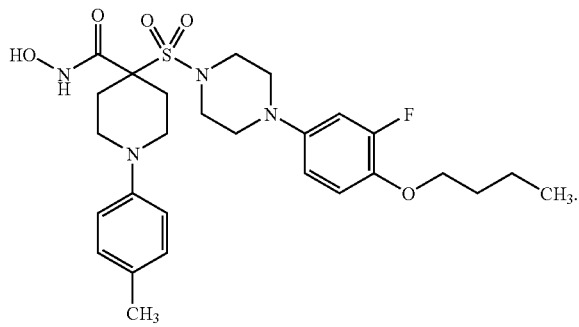

Preferred Embodiment No. 3-E

In some preferred embodiments, the compounds correspond in structure to Formula (154-1), (154-1)

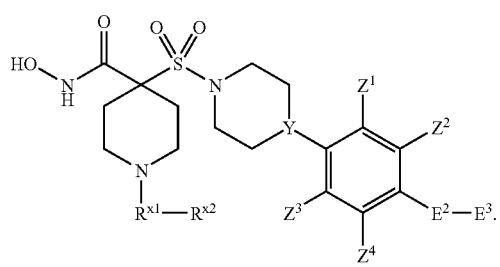

In these embodiments:

$R^{x1}$ is —C(O)—, —C(S)—, —C(NR$^b$)—, or —S(O)$_2$—.

$R^b$ is hydrogen or hydroxy.

$R^{x2}$ is hydrogen, hydroxy, alkyl, alkenyl, alkynyl, alkoxy, alkoxyalkyl, alkoxyalkoxy, $R^a$-oxyalkyl, alkenyloxy, alkynyloxy, $R^aR^a$-amino, $R^aR^a$-aminoalkyl, $R^aR^a$-aminoalkoxy, $R^aR^a$-aminoalkyl($R^a$)amino, carbocyclyl, carbocyclylalkyl, carbocyclyloxy, carbocyclyloxyalkoxy, heterocyclyl, heterocyclylalkyl, heterocyclyloxy, or heterocyclyloxyalkoxy. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to these optional substituents:

the alkyl, alkoxy, alkoxyalkyl, and alkoxyalkoxy optionally are substituted with one or more substituents independently selected from the group consisting of halogen and hydroxy; and the amino optionally is substituted with up to two independently selected alkyl substituents.

Particularly Preferred Embodiments of Embodiment No. 3-E

In some particularly preferred embodiments, Y is carbon bonded to hydrogen.

In some particularly preferred embodiments, Y is nitrogen.

In some particularly preferred embodiments, $Z^1$, $Z^2$, $Z^3$, and $Z^4$ are hydrogen.

In some particularly preferred embodiments, $E^2$ is a bond.

In some particularly preferred embodiments, $E^2$ is —O—.

In some particularly preferred embodiments, $R^{x2}$ is hydrogen, amino, alkyl, alkoxy, alkoxyalkyl, alkoxyalkoxy, alkenyloxy, alkynyloxy, aminoalkyl, cycloalkyl, aryl, heterocycloalkyl, or heteroaryl. Here, the alkyl, alkoxy, alkoxyalkyl, alkoxyalkoxy, alkenyloxy, alkynyloxy, aminoalkyl, cycloalkyl, aryl, heterocycloalkyl, and heteroaryl (if substitutable) optionally are substituted with one or more substituents independently selected from the group consisting of halogen, oxo, hydroxy, and alkyl. The amino, on the other hand, is optionally substituted with up to two substituents independently selected from the group consisting of alkyl and alkoxyalkyl.

In some particularly preferred embodiments, $R^{x2}$ is heterocycloalkyl or heteroaryl. The heterocycloalkyl and heteroaryl (if substitutable) optionally are substituted with one or more substituents independently selected from the group consisting of halogen, oxo, hydroxy, and alkyl. In some such embodiments, $R^{x2}$ is more preferably optionally-substituted heterocycloalkyl. In other such embodiments, $R^{x2}$ is more preferably optionally-substituted heteroaryl.

In some particularly preferred embodiments, $R^{x2}$ is cycloalkyl or aryl. The cycloalkyl and aryl optionally are substituted with one or more substituents independently selected from the group consisting of halogen, oxo, hydroxy, and alkyl. In some such embodiments, $R^{x2}$ is more preferably optionally-substituted cycloalkyl. In other such embodiments, $R^{x2}$ is more preferably optionally-substituted aryl (preferably phenyl).

In some particularly preferred embodiments, $R^{x1}$ is —S(O)$_2$—, i.e., the compound corresponds in structure to the following formula:

(157-1)

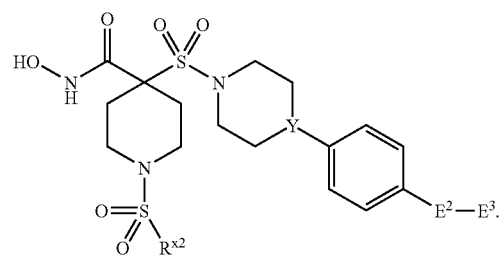

Particularly preferred examples of such compounds include:

(158-1)

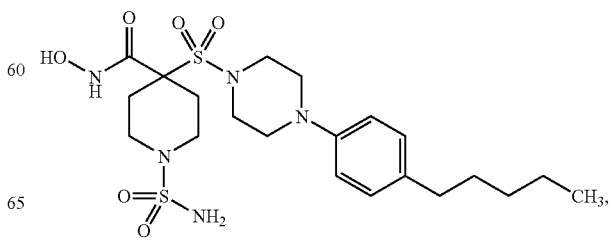

-continued (158-2)
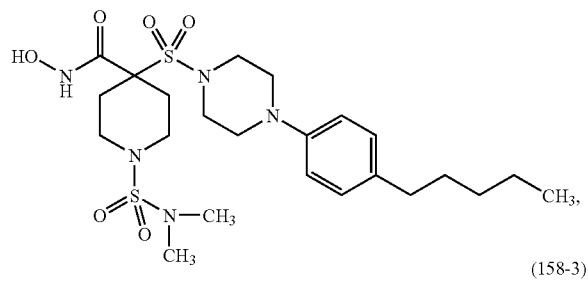

(158-3)
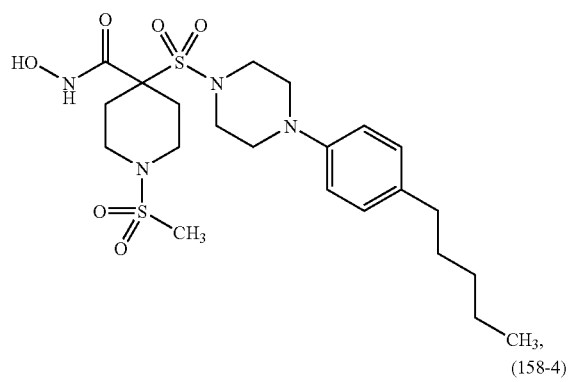

(158-4)
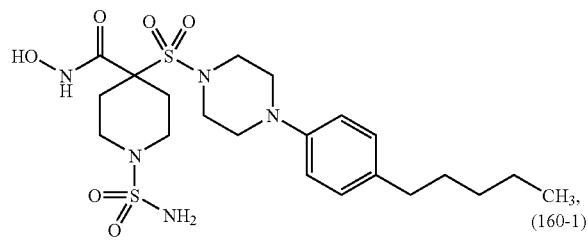

(160-1)
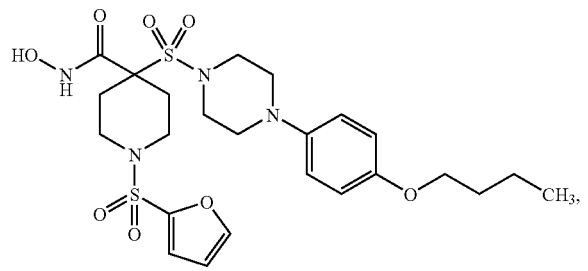

In some particularly preferred embodiments, $R^{x1}$ is —C(S)—, i.e., the compound corresponds in structure to the following formula:

(161-1)
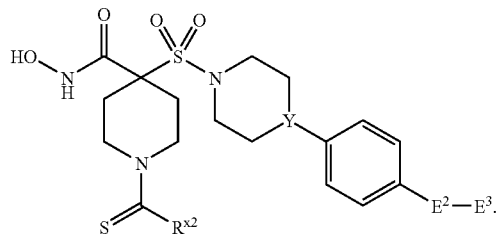

One particularly preferred example of such a compound is:

(162-1)
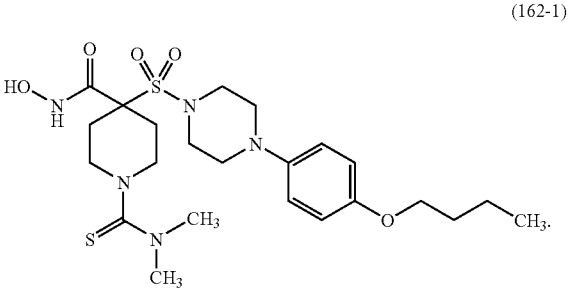

In some particularly preferred embodiments, $R^{x1}$ is —C($NR^b$)—, i.e., the compound corresponds in structure to the following formula:

(163-1)
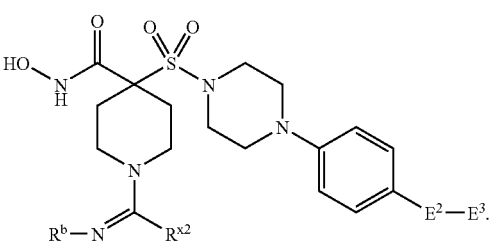

One particularly preferred example of such a compound is:

(164-1)
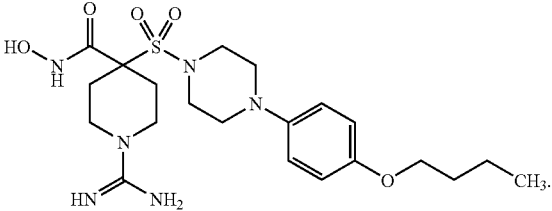

In some particularly preferred embodiments, $R^{x1}$ is —C(O)—, i.e., the compound corresponds in structure to the following formula:

(165-1)
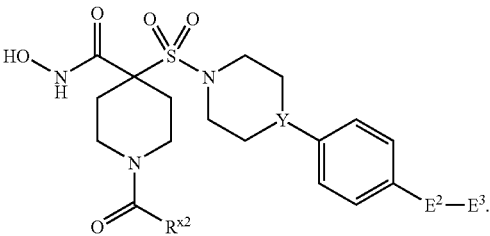

Particularly preferred examples of such compounds include:
(166-1)
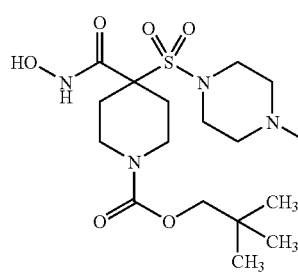
(166-2)
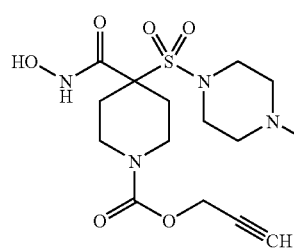
(166-3)
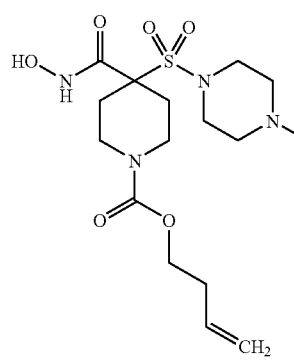
(166-4)
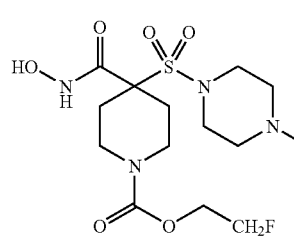
(166-5)
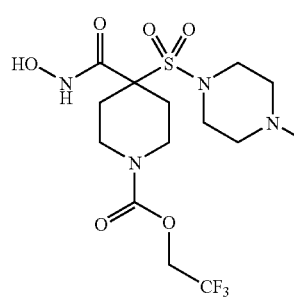
-continued
(166-6)
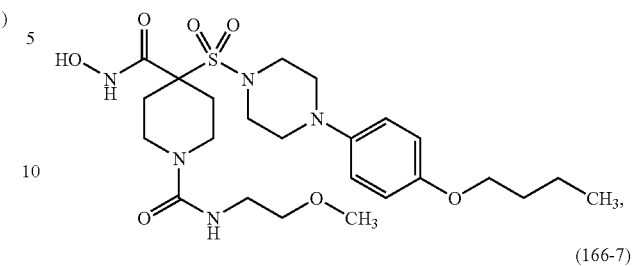
(166-7)
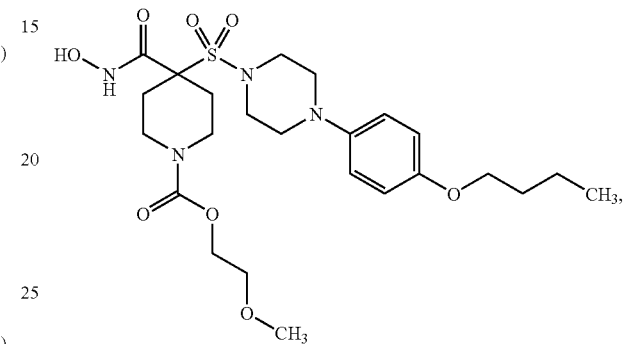
(166-8)
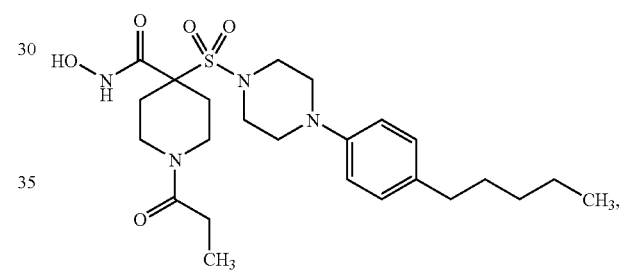
(166-9)
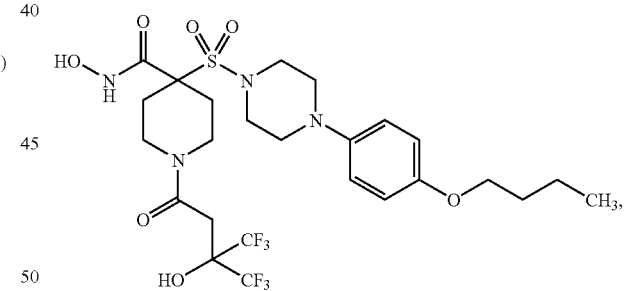
(166-10)
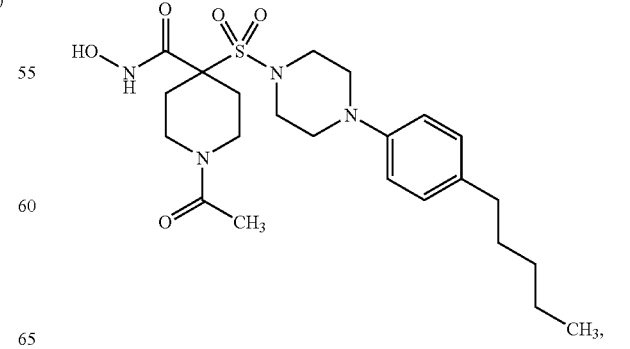

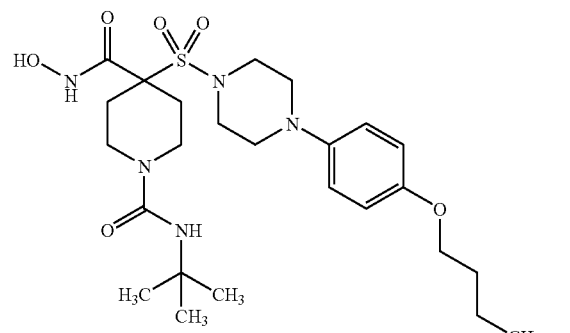
(166-11)
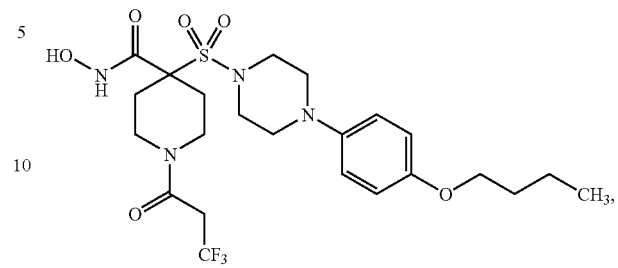
(166-16)
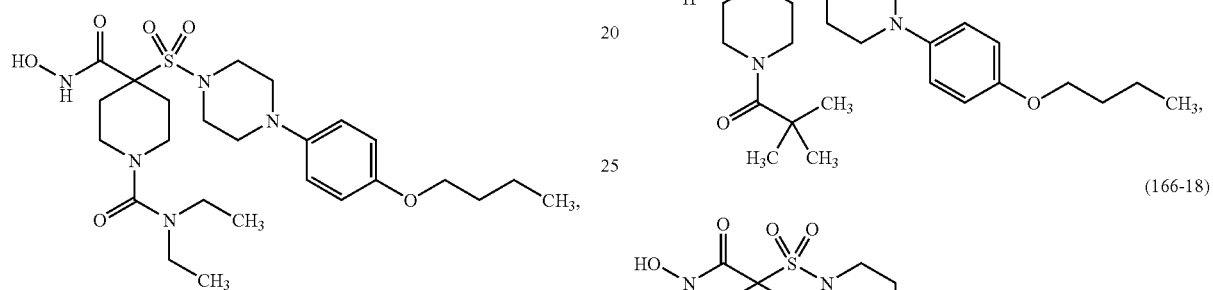
(166-12), (166-17)
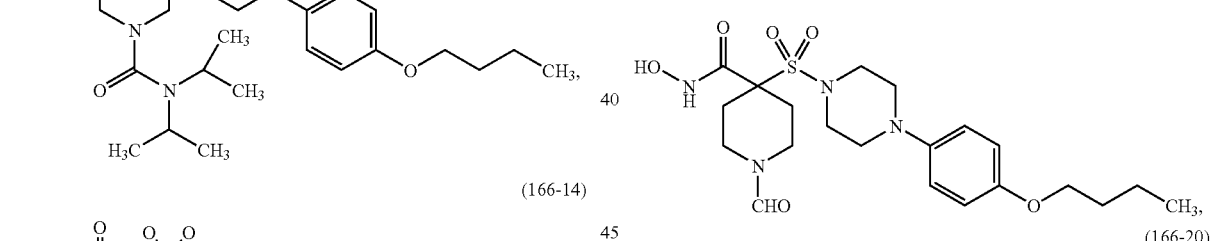
(166-13), (166-18)
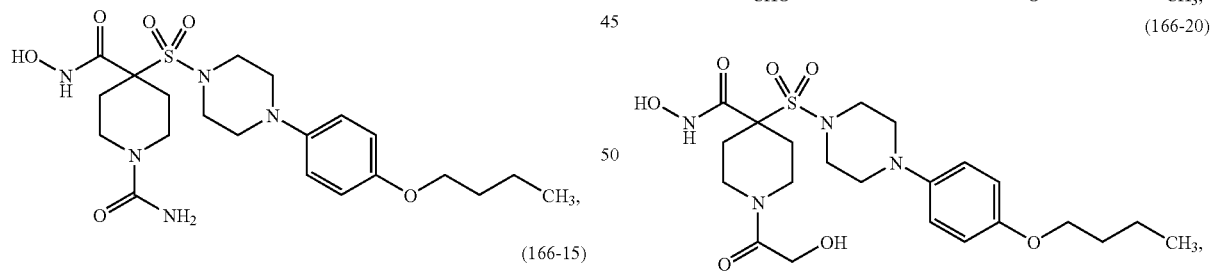
(166-14), (166-19)
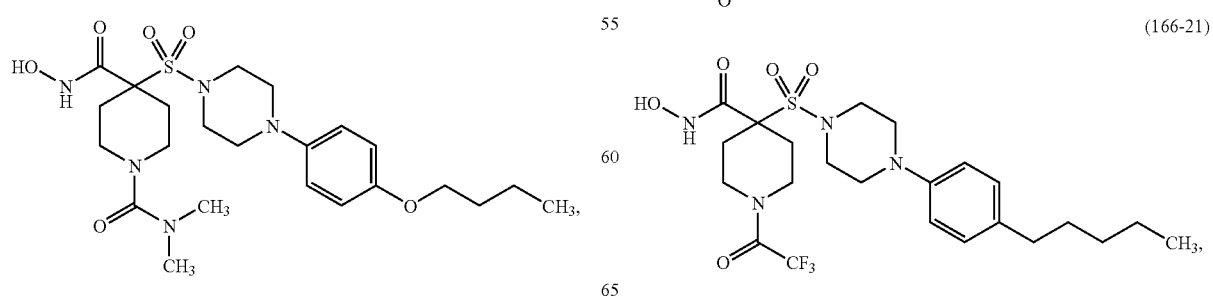
(166-15), (166-20), (166-21)

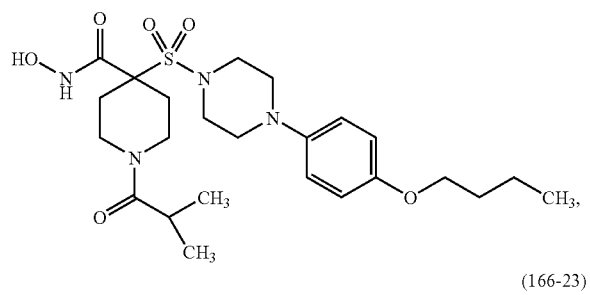
(166-22)
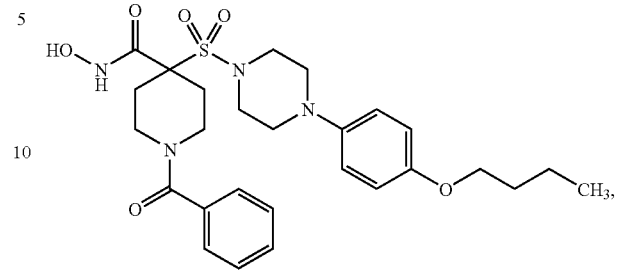
(168-1)
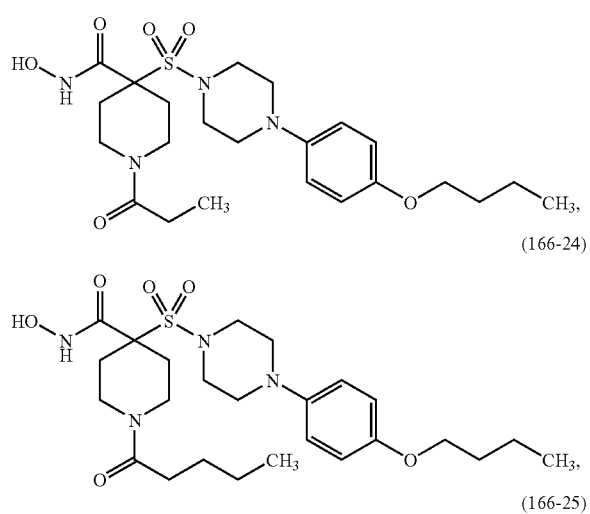
(166-23)
(166-24)
(166-25)
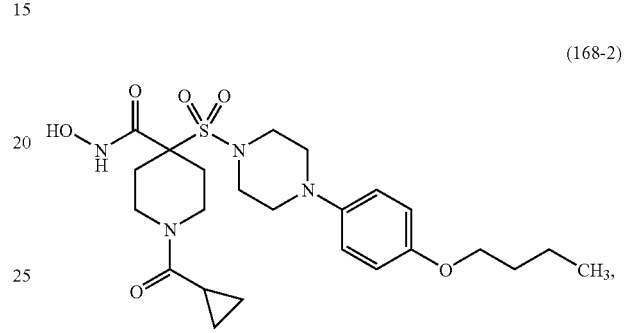
(168-2)
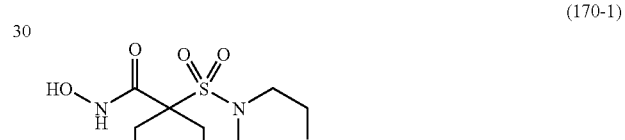
(170-1)
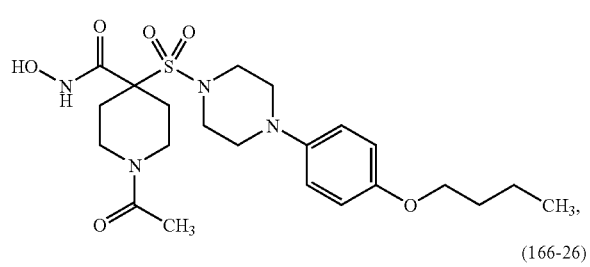
(166-26)
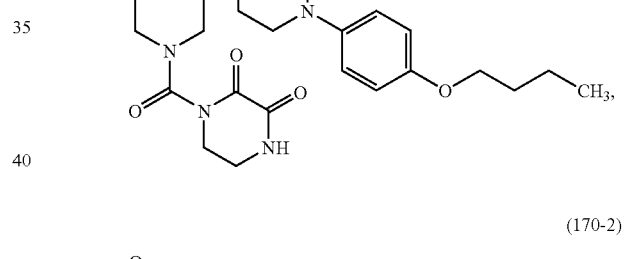
(170-1)
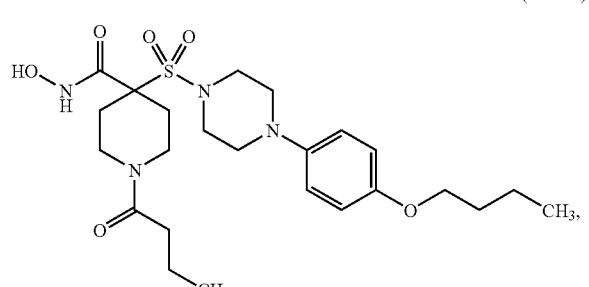
(166-27)
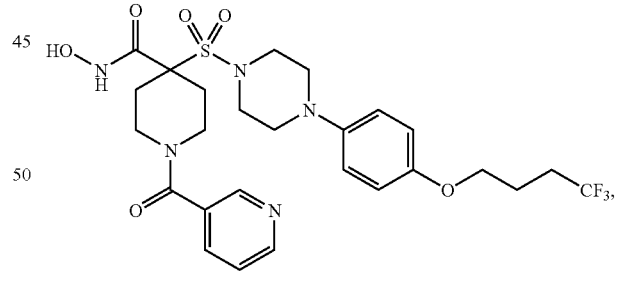
(170-2)
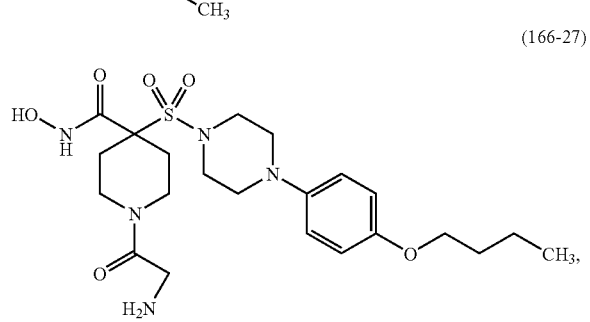
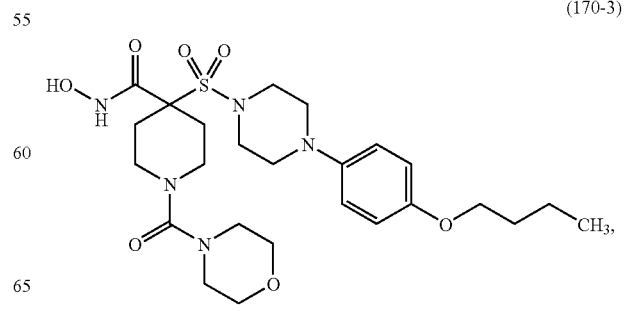
(170-3)

(170-4)
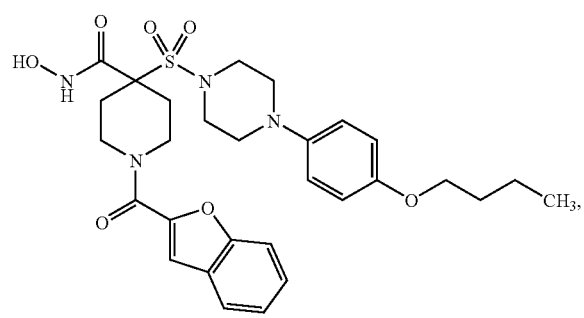
(170-5)
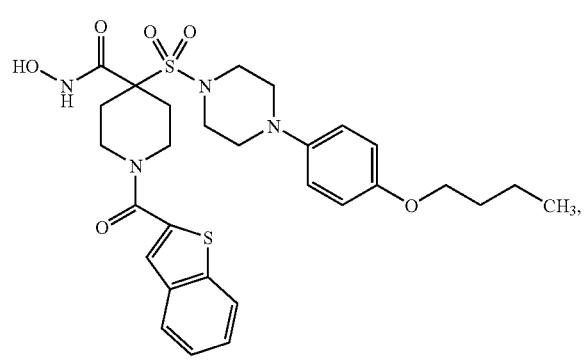
(170-6)
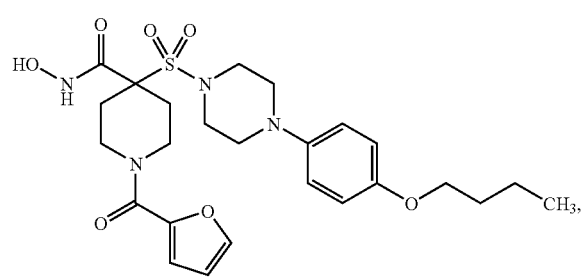
(170-7)
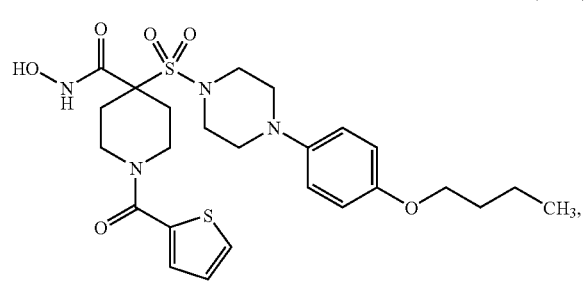
(170-8)
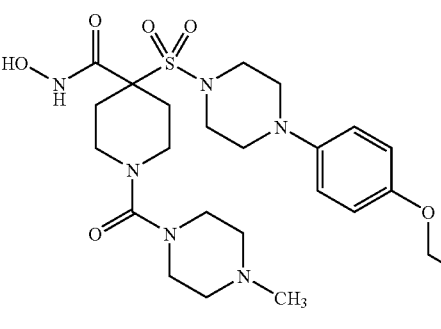
(170-9)
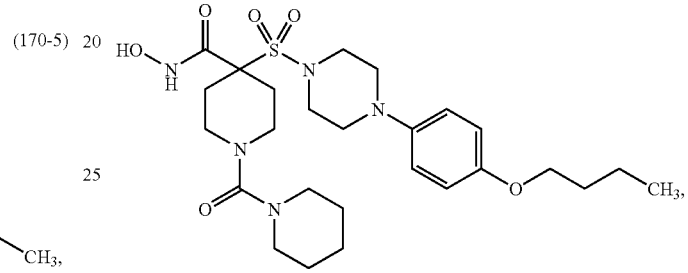
(170-10)
(170-11)
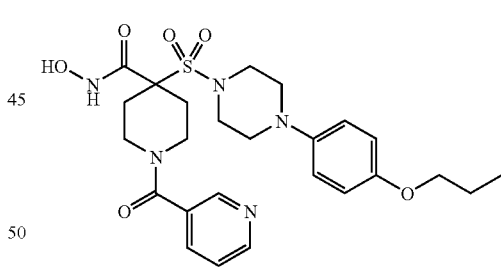
and
(170-12)
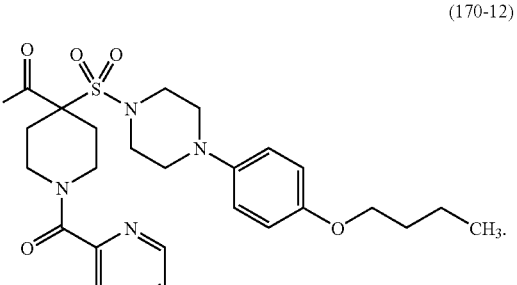

Preferred Embodiment No. 3-F

In some preferred embodiments, the compounds correspond in structure to Formula (171-1):

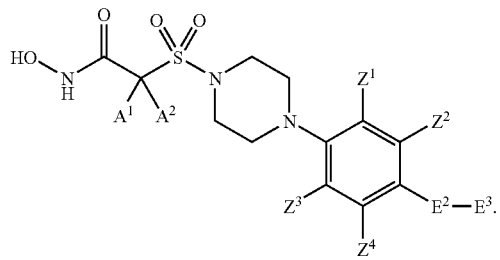

(171-1)

Here, at least one of $Z^1$, $Z^2$, $Z^3$, $Z^4$, and -$E^2$-$E^3$ is halogen.

Particularly Preferred Embodiments of Embodiment No. 3-F

In some particularly preferred embodiments, the compound corresponds in structure to the following formula:

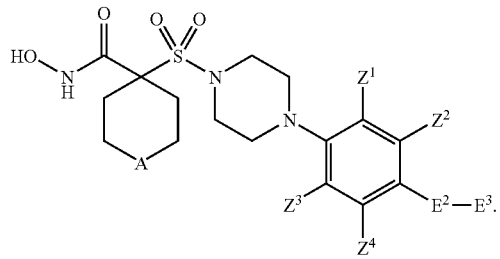

(184-1)

In some particularly preferred embodiments, A is —O—.

In some particularly preferred embodiments, A is —N(H)—.

In some particularly preferred embodiments, A is —N($R^x$)—. Here, $R^x$ is alkyl, alkenyl, alkynyl, alkoxyalkyl, $R^a$-oxyalkyl, alkylsulfonyl, $R^a R^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:
  the alkyl, alkoxy, alkoxyalkyl, and alkoxyalkoxy optionally are substituted with one or more substituents independently selected from the group consisting of halogen and hydroxy; and
  the amino optionally is substituted by up to 2 independently selected alkyl.

In some particularly preferred embodiments, A is —S—, —S(O)—, or —S(O)$_2$—.

In some particularly preferred embodiments, $E^2$ is a bond.

In some particularly preferred embodiments, $E^2$ is —O—.

In some particularly preferred embodiments, $R^x$ is aldehydo, $C_1$–$C_6$-alkyl, $C_3$–$C_6$-alkynyl, $C_1$–$C_6$-alkylcarbonyl, $C_1$–$C_6$-alkoxycarbonyl, $C_3$–$C_6$-alkenyloxycarbonyl, $C_3$–$C_6$-alkynyloxycarbonyl, amino, amino-$C_1$–$C_6$-alkyl, aminocarbonyl, amino-$C_1$–$C_6$-alkylcarbonyl, amino(thiocarbonyl), aminosulfonyl, $C_1$–$C_6$-alkylaminocarbonyl, $C_3$-cycloalkyl, $C_3$-cycloalkyl-$C_1$–$C_6$-alkyl, $C_3$-cycloalkylcarbonyl, phenyl, phenyl-$C_1$–$C_6$-alkyl, phenylcarbonyl, phenylsulfonyl, $C_1$–$C_6$-alkoxyphenyl, heterocyclyl, heterocyclyl-$C_1$–$C_6$-alkyl, heterocyclylcarbonyl, heterocyclylsulfonyl, or $C_1$–$C_6$-alkoxyheterocyclyl. Each such substituent (if substitutable) is, in turn, optionally substituted with one or more substituents independently selected from the group consisting of halogen, cyano, hydroxy, $C_1$–$C_6$-alkyl, and $C_1$–$C_6$-alkoxy. The optional alkyl and alkoxy substituents are, in turn, optionally substituted with one or more independently selected halogen. Any amino of $R^x$ optionally is substituted with up to 2 independently selected $C_1$–$C_6$-alkyl. And any heterocyclyl of $R^x$ has 5 to 10 ring members, and, if divalently substitutable, optionally is substituted with up to 2 oxo.

In some particularly preferred embodiments, $R^x$ is butyl, methoxyethyl, cyclopropyl, methylphenyl, phenylmethyl, pyridinyl, pyrimidinyl, or pyridinylmethyl.

In some particularly preferred embodiments, $E^3$ is selected from the group consisting of hydrogen, halogen, cyano, $C_1$–$C_9$-alkyl, $C_1$–$C_9$-alkoxy-$C_1$–$C_9$-alkyl, $C_3$–$C_6$-cycloalkyl, $C_3$–$C_6$-cycloalkyl-$C_1$–$C_6$-alkyl, phenyl, $C_1$–$C_6$-alkylphenyl, $C_1$–$C_6$-alkoxyphenyl, phenyl-$C_1$–$C_6$-alkyl, heterocyclyl-$C_1$–$C_6$-alkyl, $C_1$–$C_6$-alkylheterocyclyl, and $C_1$–$C_6$-alkoxyheterocyclyl. Each such substituent (if substitutable) is, in turn, optionally substituted with one or more substituents independently selected from the group consisting of halogen and cyano. Any heterocyclyl of $E^3$ has 5 to 10 ring members, and, if divalently substitutable, is optionally substituted with up to 2 oxo.

In some particularly preferred embodiments, -$E^2$-$E^3$ is selected from the group consisting of butyl, pentyl, ethoxy, propoxy, methoxyethoxy, cyclobutyloxy, butoxy, trifluoromethylpropoxy, cyclopropylmethoxy, and phenyl.

In some particularly preferred embodiments, -$E^2$-$E^3$ is halogen. One particularly preferred example of such a compound is:

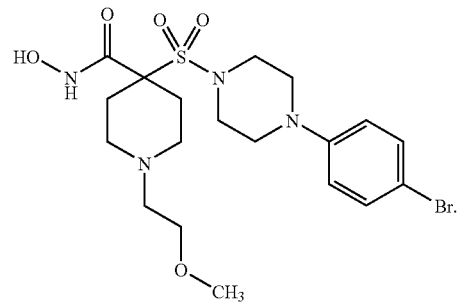

(177-1)

In some particularly preferred embodiments, at least one of $Z^1$, $Z^2$, $Z^3$, and $Z^4$ is halogen. In some such embodiments, $Z^1$, $Z^2$, $Z^3$, and $Z^4$ are independently selected from the group consisting of hydrogen and halogen (preferably bromo, chloro, or fluoro; more preferably chloro or fluoro; and most preferably fluoro).

In some particularly preferred embodiments, three of $Z^1$, $Z^2$, $Z^3$, and $Z^4$ are hydrogen; and one of $Z^1$, $Z^2$, $Z^3$, and $Z^4$ is halogen (preferably bromo, chloro, or fluoro; more preferably chloro or fluoro; and most preferably fluoro).

In some particularly preferred embodiments, the compound corresponds in structure to the following formula:

(PE-3-FA)

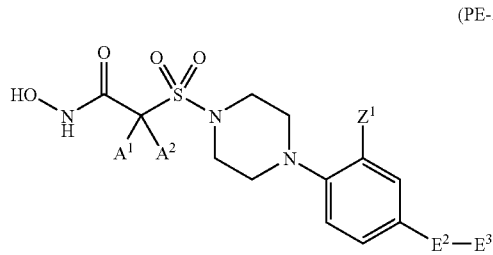

wherein $Z^1$ is halogen. Examples of particularly preferred compounds include tetrahydropyranyl compounds, such as those corresponding in structure to the following formulas:

(188-1)

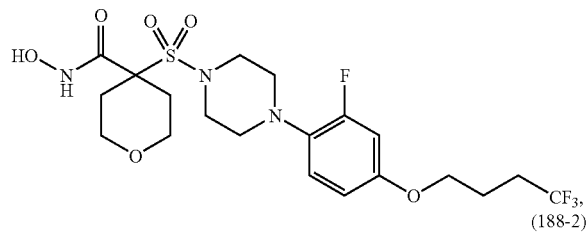

(188-2)

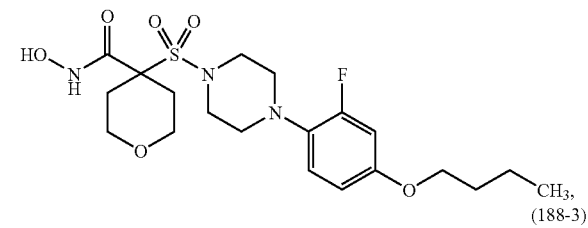

(188-3)

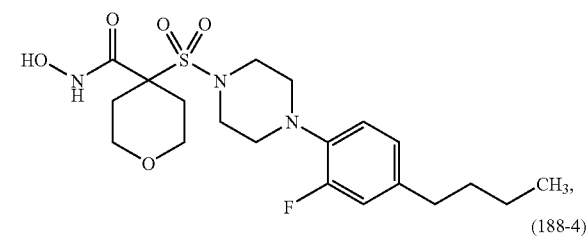

(188-4)

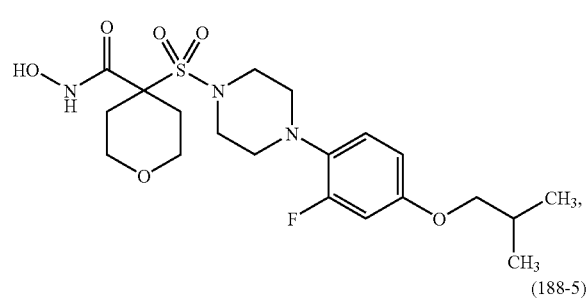

(188-5)

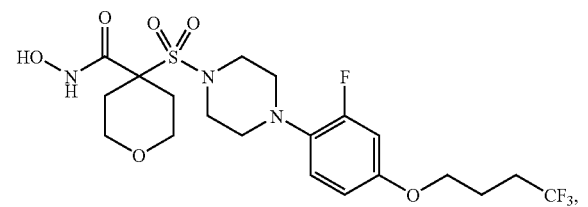

(189-1)

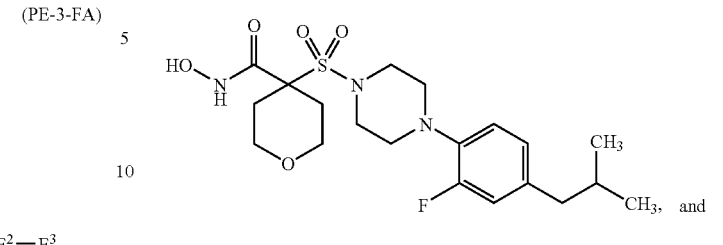

and (190-1)

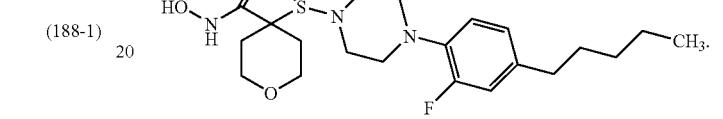

Examples of particularly preferred compounds also include piperidine compounds, such as those corresponding in structure to the following formulas:

(188-6)

(188-7)

(188-8)

, and (188-9)

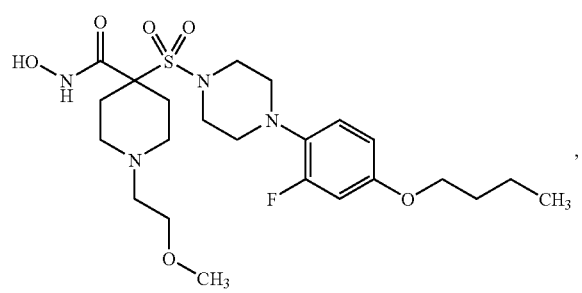

(194-1)

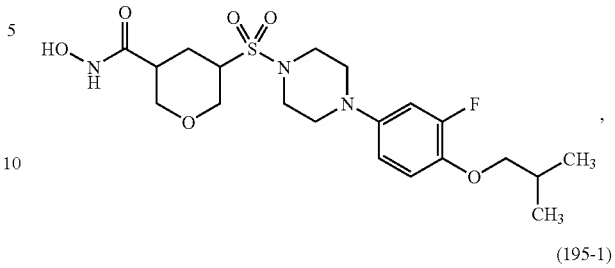

(195-1)

In some particularly preferred embodiments, the compound corresponds in structure to the following formula:

(PE-3-FB)

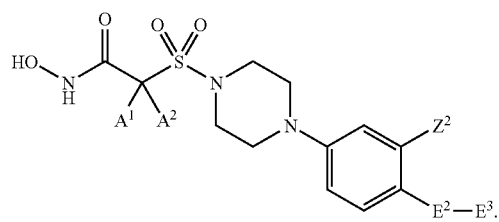

(192-9)

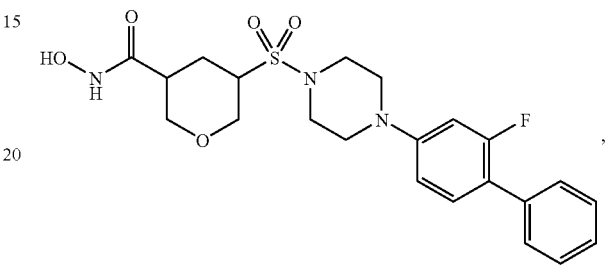

wherein $Z^2$ is halogen. Examples of particularly preferred compounds include heterocycloalkyl compounds, such as the compound corresponding in structure to the following formula:

(192-11)

(183-1)

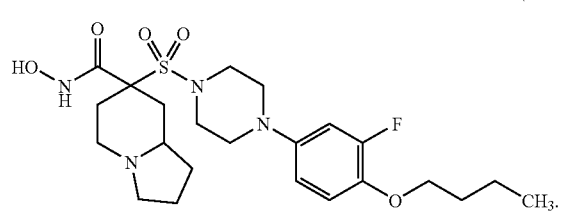

(192-12)

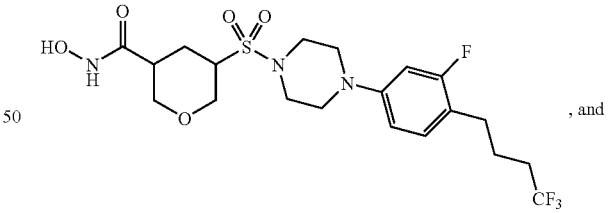

Examples of particularly preferred compounds also include tetrahydropyranyl compounds, such as those corresponding in structure to the following formulas:

, and (192-13)

(193-1)

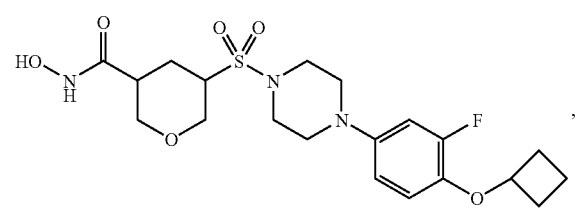

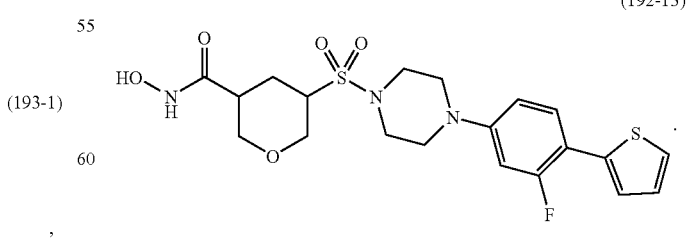

Examples of particularly preferred compounds also include piperidinyl compounds, such as those corresponding in structure to the following formulas:

-continued
(192-1)
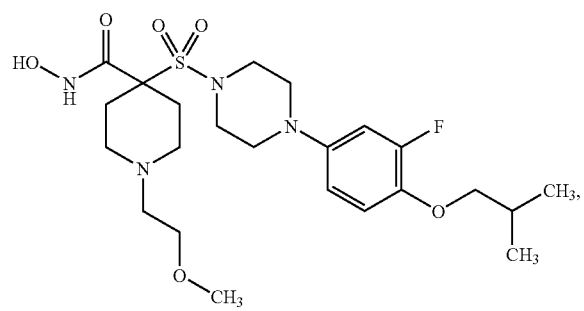
(192-6)
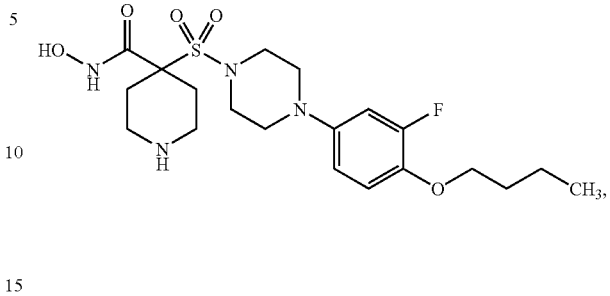
(192-2)
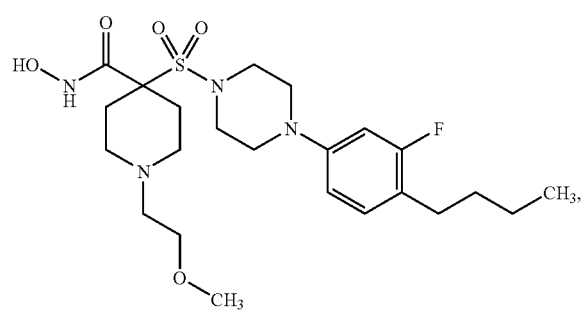
(192-7)
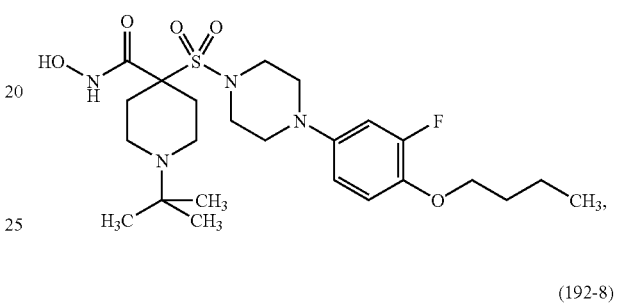
(192-3)
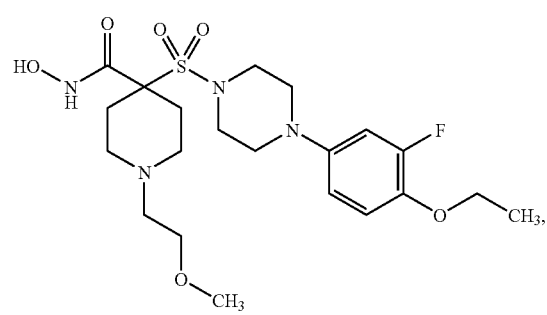
(192-8)
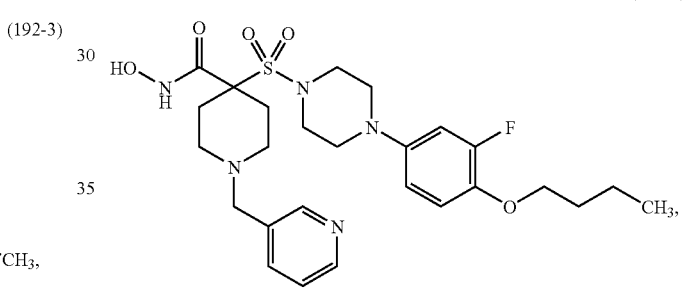
(192-4)
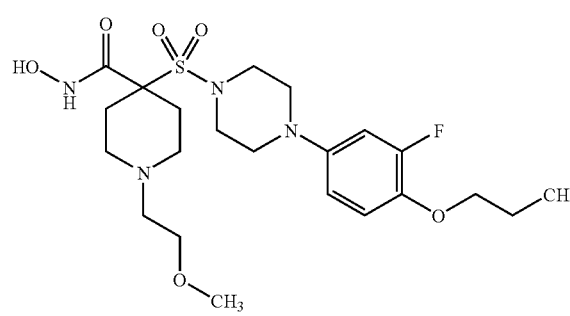
(196-1)
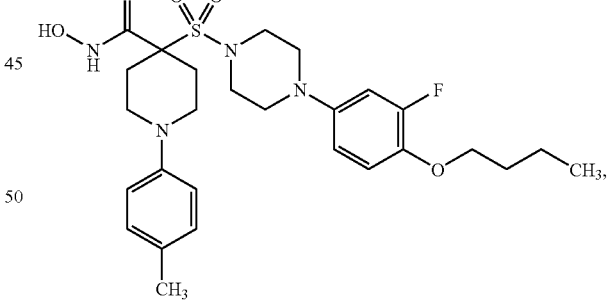
(192-5)
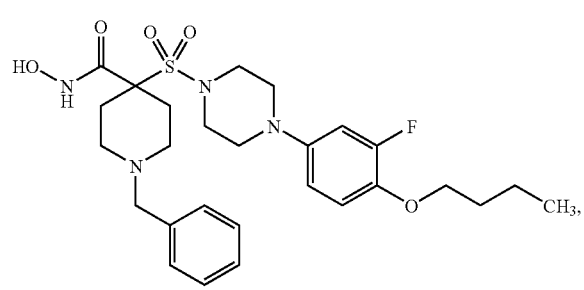
(197-1)
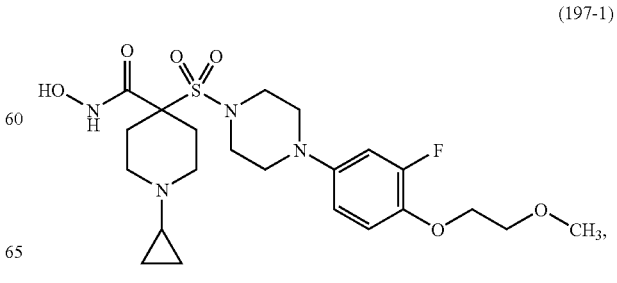

-continued

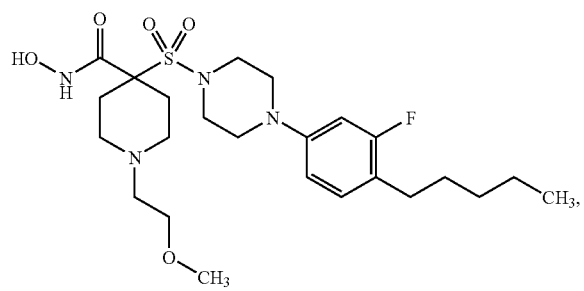
(198-1)

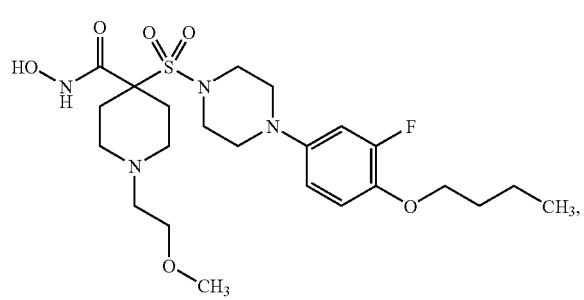
(199-1)

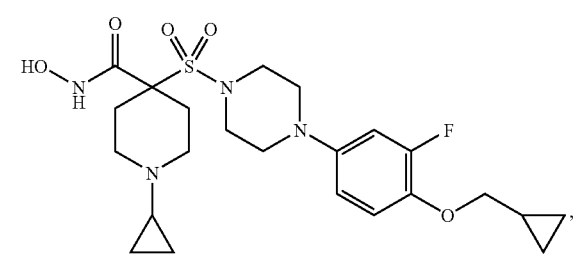
(200-1)

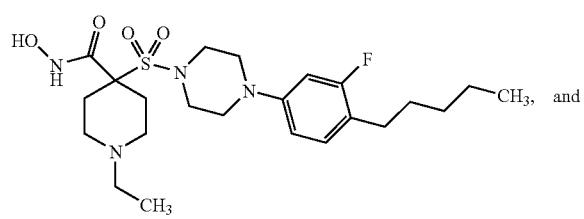
(201-1)

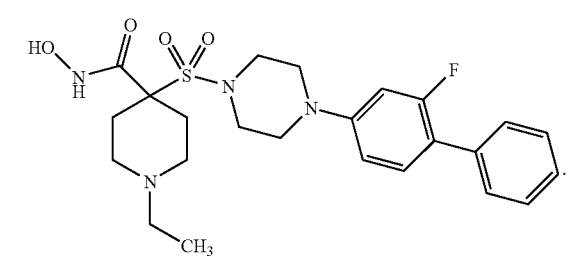
(192-10)

In some particularly preferred embodiments, two of $Z^1$, $Z^2$, $Z^3$, and $Z^4$ are hydrogen; and two of $Z^1$, $Z^2$, $Z^3$, and $Z^4$ is halogen (preferably bromo, chloro, or fluoro; more preferably chloro or fluoro; and most preferably fluoro).

In some particularly preferred embodiments, the compound corresponds in structure to the following formula:

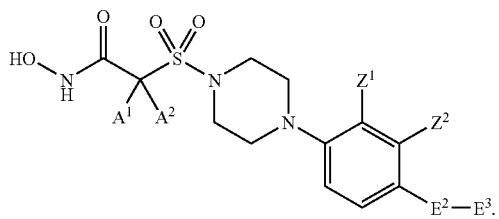
(PE-3-FC)

wherein $Z^1$ and $Z^2$ are independently selected halogen.

In some particularly preferred embodiments, the compound corresponds in structure to the following formula:

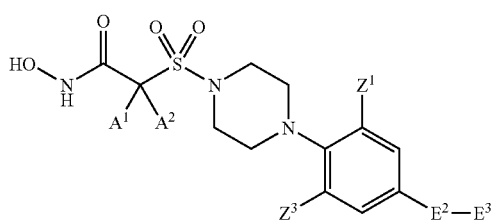
(PE-3-FD).

wherein $Z^1$ and $Z^3$ are independently selected halogen.

In some particularly preferred embodiments, the compound corresponds in structure to the following formula:

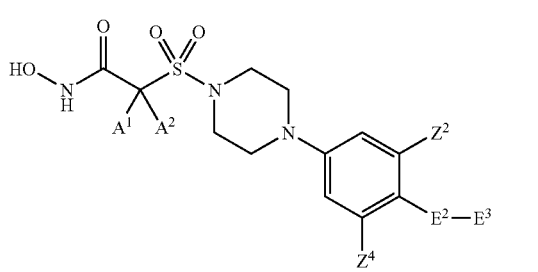
(PE-3-FE)

wherein $Z^2$ and $Z^4$ are independently selected halogen. One particularly preferred example of such a compound is:

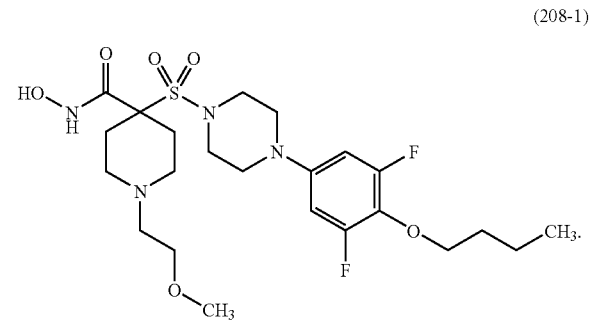
(208-1)

Preferred Embodiment No. 3-G

In some preferred embodiments, the compounds correspond in structure to Formula (209-1):

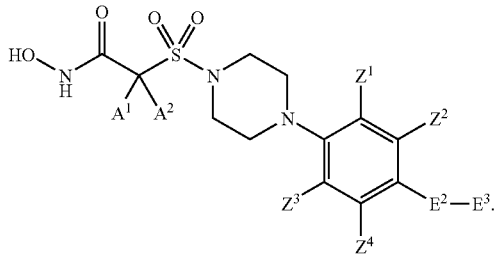

(209-1)

In these embodiments:

$E^2$ is —C(O)—, —C(O)—O—, —O—C(O)—, —N(R$^a$)—, —C(O)—N(R$^a$)—, —N(R$^a$)—C(O)—, —C(O)—N(R$^a$)—N(R$^a$)—C(O)—, —S—, —S(O)—, —S(O)$_2$—, —N(R$^a$)—S(O)$_2$—, —S(O)$_2$—N(R$^a$)—, —O—S(O)$_2$—, —S(O)$_2$—O—, —C(NH)—, or —C(NOH)—.

$E^3$ is hydrogen, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. As to such optional substituents:

the alkyl, alkoxy, alkylthio, carbocyclyl, and carbocyclylalkyl optionally are substituted with one or more substituents independently selected from the group consisting of halogen, hydroxy, cyano, carboxy, thiol, sulfo, nitro, nitroso, oxo, thioxo, imino, aminocarbonyl, and amino; and the amino nitrogen is substituted with up to 2 substituents independently selected from the group consisting of alkyl and carbocyclylalkyl.

Particularly Preferred Embodiments of Embodiment No. 3-G

In some particularly preferred embodiments, the compound corresponds in structure to the following formula:

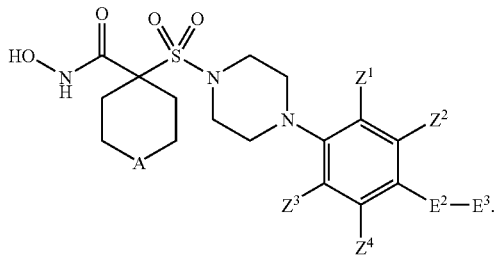

(210-1)

In some particularly preferred embodiments, A is —O—.

In some particularly preferred embodiments, A is —N(H)—.

In some particularly preferred embodiments, A is —N(R$^x$)—. Here, R$^x$ is alkyl, alkenyl, alkynyl, alkoxyalkyl, R$^a$-oxyalkyl, alkylsulfonyl, R$^a$R$^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, $Z^1$, $Z^2$, $Z^3$, and $Z^4$ are hydrogen.

In some particularly preferred embodiments, $E^3$ is hydrogen, $C_1$–$C_9$-alkyl, $C_1$–$C_9$-alkoxy-$C_1$–$C_9$-alkyl, $C_3$–$C_6$-cycloalkyl, $C_3$–$C_6$-cycloalkyl-$C_1$–$C_6$-alkyl, phenyl, $C_1$–$C_6$-alkylphenyl, $C_1$–$C_6$-alkoxyphenyl, phenyl-$C_1$–$C_6$-alkyl, heterocyclyl-$C_1$–$C_6$-alkyl, $C_1$–$C_6$-alkylheterocyclyl, and $C_1$–$C_6$-alkoxyheterocyclyl. Each such substituent (if substitutable) is, in turn, optionally substituted with one or more substituents independently selected from the group consisting of halogen and cyano. And any heterocyclyl of $E^3$ has 5 to 10 ring members, and, if divalently substitutable, is optionally substituted with up to 2 oxo.

In some particularly preferred embodiments, $E^2$ is —C(O)—, —N(H)—, —S—, —S(O)$_2$—, —O—S(O)$_2$—, or —C(O)—N(H)—.

In some particularly preferred embodiments, $E^2$ preferably is —S—. Examples of particularly preferred compounds include the compounds corresponding in structure to the following formulas:

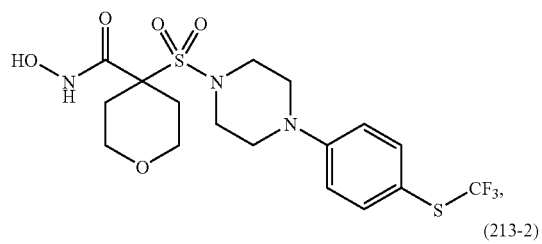

(213-1)

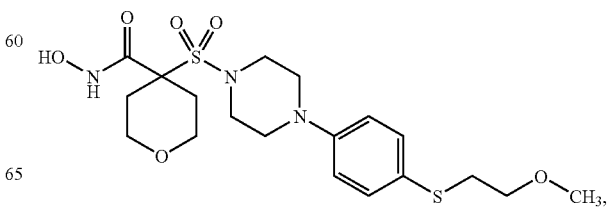

(213-2)

-continued (213-3)
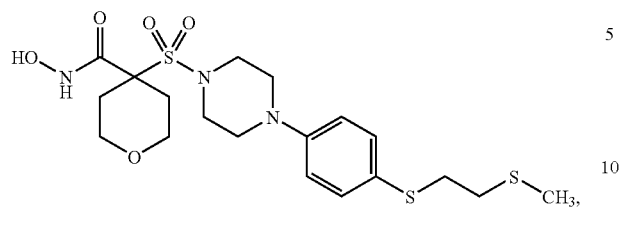

(213-4)
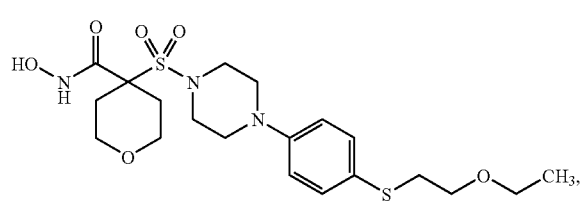

(213-5)
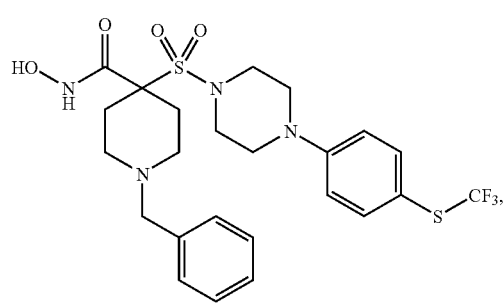

(213-6)
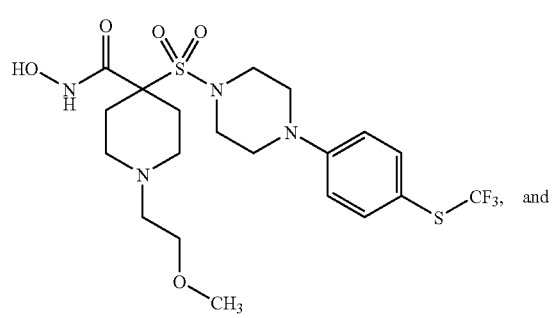

(213-7)
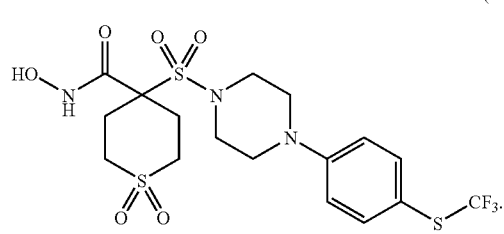

In some particularly preferred embodiments, $E^2$ preferably is —S(O)$_2$—. One particularly preferred example of such a compound is:

(215-1)
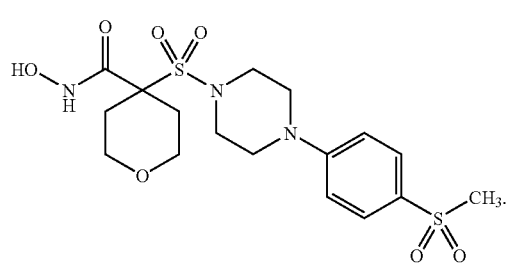

In some particularly preferred embodiments, $E^2$ preferably is —C(O)—. Examples of particularly preferred compounds include the compounds corresponding in structure to the following formulas:

(218-1)
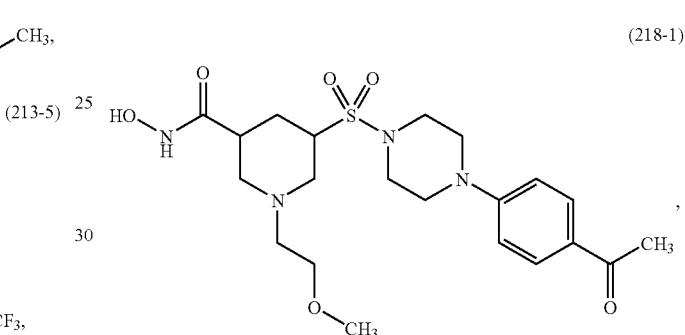

(218-2)
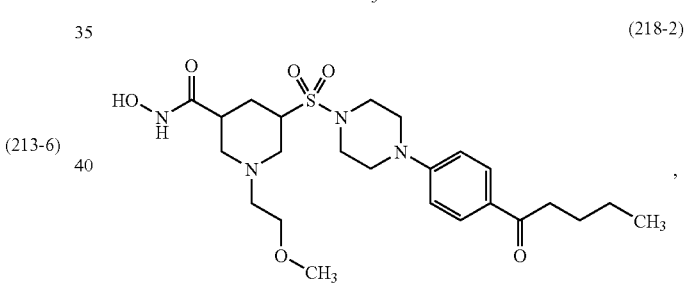

(218-3)
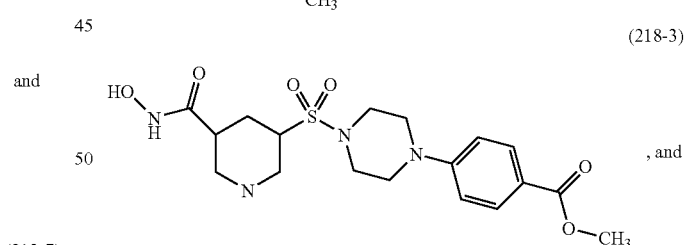

, and (218-4)
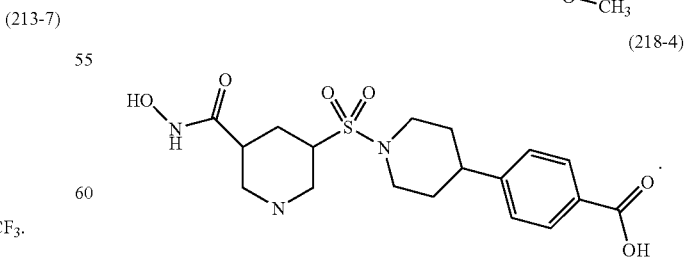

In some particularly preferred embodiments, $E^2$ preferably is —O—S(O)$_2$—. One particularly preferred example of such a compound is:

(220-1)

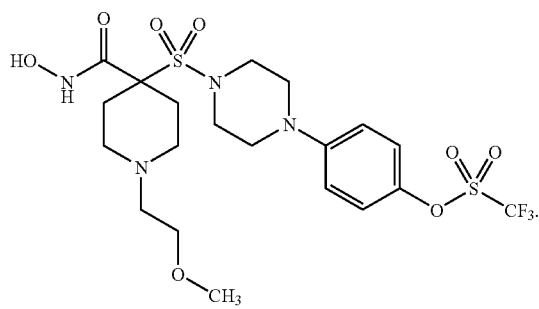

In some particularly preferred embodiments, $E^2$ preferably is —C(O)—N(H)—. One particularly preferred example of such a compound is:

(222-1)

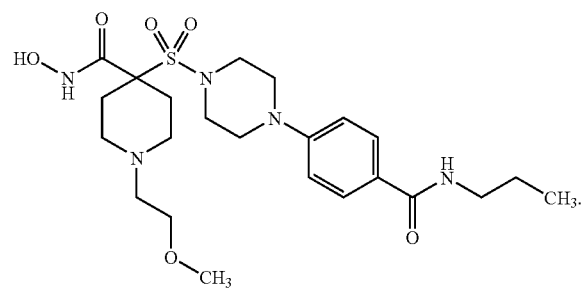

Preferred Embodiment No. 3-H

In some preferred embodiments, the compounds correspond in structure to Formula (223-1):

(223-1)

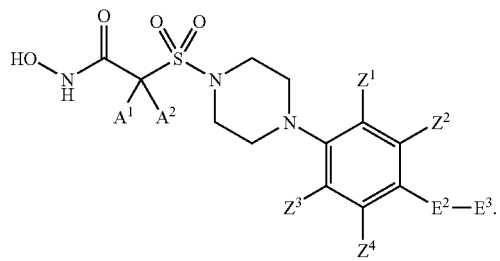

In this embodiment, $E^3$ is halogen, cyano, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. As to such optional substituents:

the alkyl, alkoxy, alkylthio, carbocyclyl, and carbocyclylalkyl optionally are substituted with one or more substituents independently selected from the group consisting of halogen, hydroxy, cyano, carboxy, thiol, sulfo, nitro, nitroso, oxo, thioxo, imino, aminocarbonyl, and amino; and the amino is substituted with up to 2 substituents independently selected from the group consisting of alkyl and carbocyclylalkyl.

Particularly Preferred Embodiments of Embodiment No. 3-H

In some particularly preferred embodiments, the compound corresponds in structure to the following formula:

(PE-3-HA)

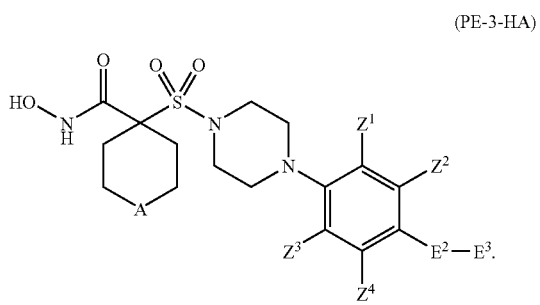

In some particularly preferred embodiments, A is —O—.

In some particularly preferred embodiments, A is —N(H)—.

In some particularly preferred embodiments, A is —N($R^x$)—. Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, $Z^1$, $Z^2$, $Z^3$, and $Z^4$ are hydrogen.

In some particularly preferred embodiments, $E^2$ is a bond.

In some particularly preferred embodiments, $E^3$ is alkoxyalkyl. In some such embodiments, -$E^2$-$E^3$ is alkoxyalkyl. Examples of particularly preferred compounds include the compounds corresponding in structure to the following formulas:

(226-1)

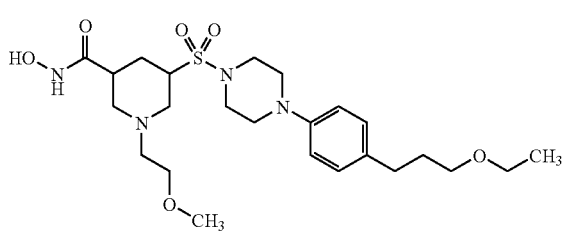

and

-continued

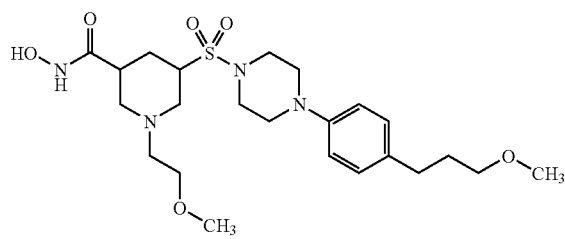

(226-2)

Preferred Embodiment No. 3-I

In some preferred embodiments, the compounds correspond in structure to Formula (227-1):

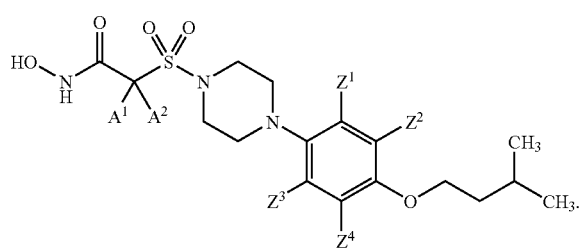

(227-1)

Particularly Preferred Embodiments of Embodiment No. 3-I

In some particularly preferred embodiments, the compound corresponds in structure to the following formula:

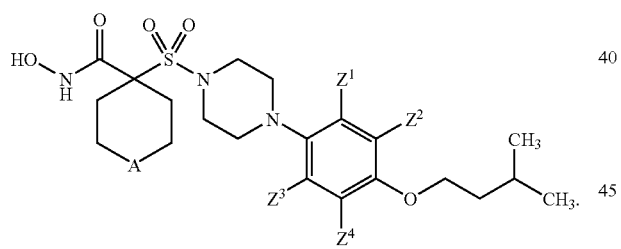

(228-1)

In some particularly preferred embodiments, A is —O—.

In some particularly preferred embodiments, A is —N(H)—.

In some particularly preferred embodiments, A is —N($R^x$)—. Here, $R^x$ is alkyl, alkenyl, alkynyl, alkoxyalkyl, $R^a$-oxyalkyl, alkylsulfonyl, $R^a R^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, $Z^1$, $Z^2$, $Z^3$, and $Z^4$ are hydrogen.

An example of a particularly preferred compound is the compound corresponding in struture to the following formula:

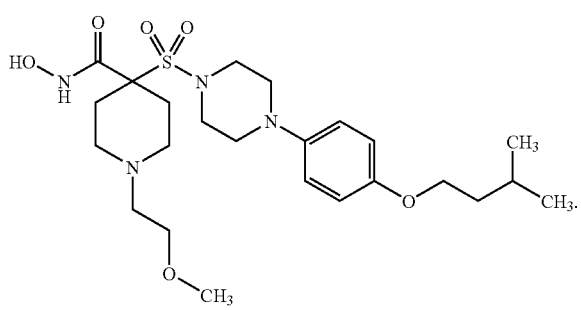

(229-1)

Preferred Embodiment No. 3-J

In some preferred embodiments, the compounds correspond in structure to Formula (227-2):

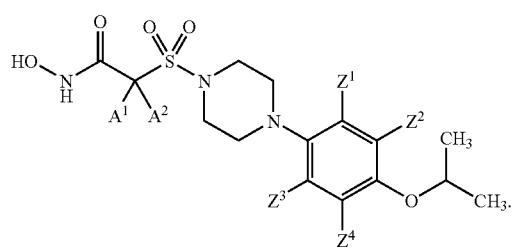

(227-2)

Particularly Preferred Embodiments of Embodiment No. 3-J

In some particularly preferred embodiments, the compound corresponds in structure to the following formula:

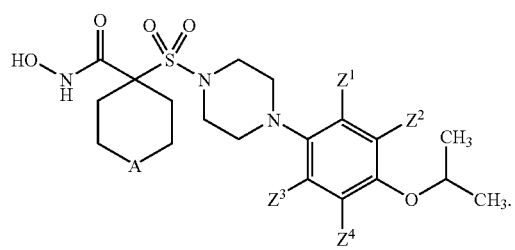

(230-1)

In some particularly preferred embodiments, A is —O—.

In some particularly preferred embodiments, A is —N(H)—.

In some particularly preferred embodiments, A is —N($R^x$)—. Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, $Z^1$, $Z^2$, $Z^3$, and $Z^4$ are hydrogen.

An example of a particularly preferred compounds is the compound corresponding in structure to the following formula:

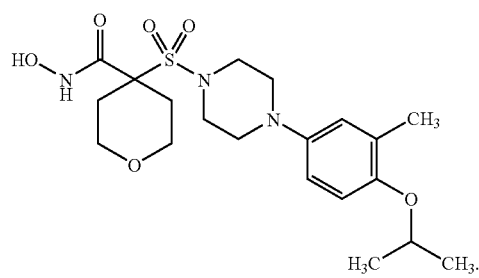

(231-1)

Preferred Embodiment No. 3-K

In some preferred embodiments, the compounds correspond in structure to Formula (232-1):

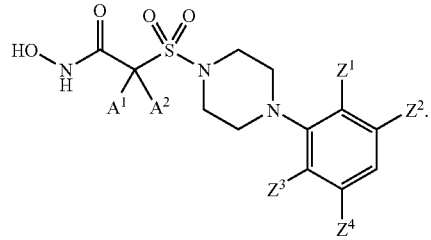

(232-1)

Here, at least one of $Z^1$, $Z^2$, $Z^3$, and $Z^4$ is not hydrogen.

Particularly Preferred Embodiments of Embodiment No. 3-K

In some particularly preferred embodiments, the compound corresponds in structure to the following formula:

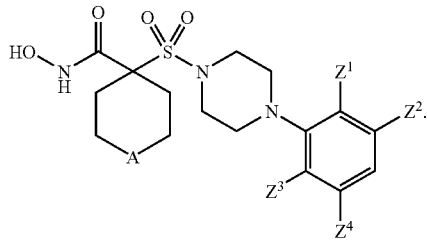

(233-1)

In some particularly preferred embodiments, A is —O—.

In some particularly preferred embodiments, A is —N(H)—.

In some particularly preferred embodiments, A is —N($R^x$)—. Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

Examples of particularly preferred compounds include the compound corresponding in structure to a formula selected from the group consisting of:

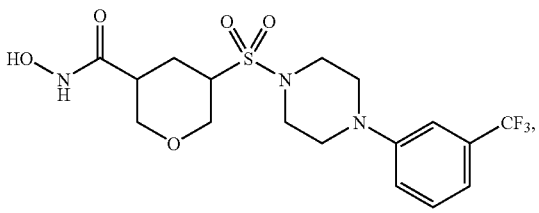

(234-1)

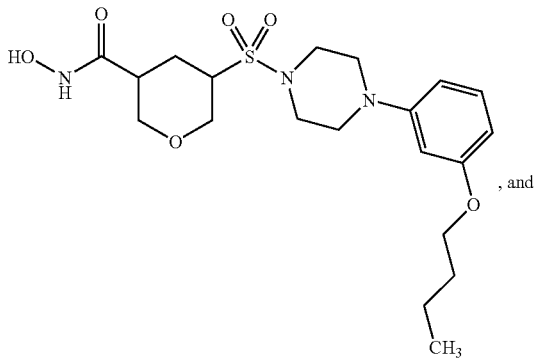

(234-2)

, and

-continued

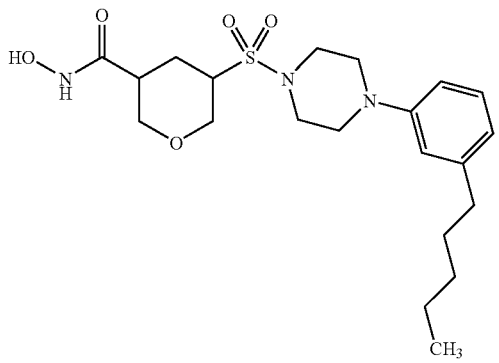

(234-3)

Preferred Embodiment No. 3-L

In some preferred embodiments, the compounds correspond in structure to Formula (235-1):

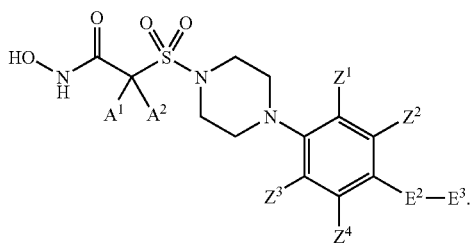

(235-1)

In this embodiment, $A^1$ and $A^2$ (together with the carbon to which they are bonded) form carbocyclyl that is optionally substituted with up to 3 independently selected $R^x$ substituents.

Particularly Preferred Embodiments of Embodiment No. 3-L

In some particularly preferred embodiments, $Z^1$, $Z^2$, $Z^3$, and $Z^4$ are hydrogen.

In some particularly preferred embodiments, $E^2$ is a bond.

In some particularly preferred embodiments, $E^2$ is —O—.

In some particularly preferred embodiments, $A^1$ and $A^2$ (together with the carbon to which they are bonded) form unsubstituted carbocyclyl.

In some particularly preferred embodiments, $A^1$ and $A^2$ (together with the carbon to which they are bonded) form cycloalkenyl optionally substituted with up to 3 independently selected $R^x$ substituents.

In some particularly preferred embodiments, $A^1$ and $A^2$ (together with the carbon to which they are bonded) form unsubstituted cycloalkenyl.

In some particularly preferred embodiments, $A^1$ and $A^2$ (together with the carbon to which they are bonded) form cycloalkyl optionally substituted with up to 3 independently selected $R^x$ substituents.

In some particularly preferred embodiments, $A^1$ and $A^2$ (together with the carbon to which they are bonded) form unsubstituted cycloalkyl.

In some particularly preferred embodiments, $A^1$ and $A^2$ (together with the carbon to which they are bonded) form cyclopropyl optionally substituted with up to 3 independently selected $R^x$ substituents.

In some particularly preferred embodiments, $A^1$ and $A^2$ (together with the carbon to which they are bonded) form unsubstituted cyclopropyl. One example of a particularly preferred compound is:

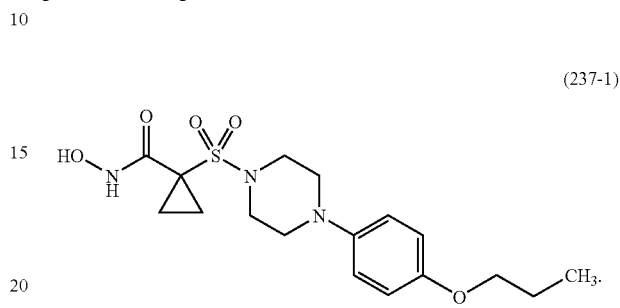

(237-1)

In some particularly preferred embodiments, $A^1$ and $A^2$ (together with the carbon to which they are bonded) form cyclobutyl optionally substituted with up to 3 independently selected $R^x$ substituents.

In some particularly preferred embodiments, $A^1$ and $A^2$ (together with the carbon to which they are bonded) form unsubstituted cyclobutyl.

In some particularly preferred embodiments, $A^1$ and $A^2$ (together with the carbon to which they are bonded) form cyclopentyl optionally substituted with up to 3 independently selected $R^x$ substituents.

In some particularly preferred embodiments, $A^1$ and $A^2$ (together with the carbon to which they are bonded) form unsubstituted cyclopentyl. One example of a particularly preferred compound is:

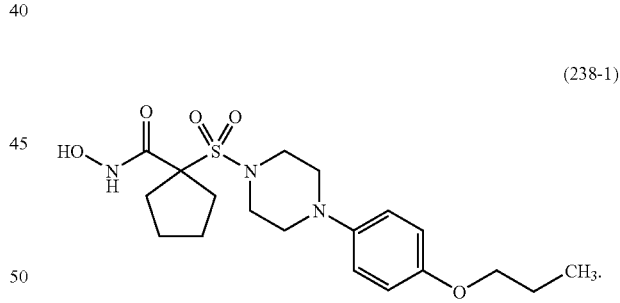

(238-1)

In some particularly preferred embodiments, $A^1$ and $A^2$ (together with the carbon to which they are bonded) form cyclohexyl optionally substituted with up to 3 independently selected $R^x$ substituents.

In some particularly preferred embodiments, $A^1$ and $A^2$ (together with the carbon to which they are bonded) form unsubstituted cyclohexyl.

Preferred Embodiment No. 3-M

In some preferred embodiments, the compounds correspond in structure to Formula (239-1):

(239-1)

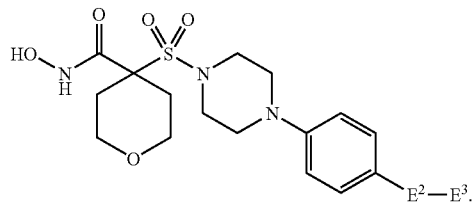

In this embodiment, $E^3$ is alkyl or alkoxyalkyl.

Particularly Preferred Embodiments of Embodiment No. 3-M

In some particularly preferred embodiments, $E^2$ is a bond.
In some particularly preferred embodiments, $E^2$ is —O—.

Examples of particularly preferred compounds include the compounds corresponding in structure to the following formulas:

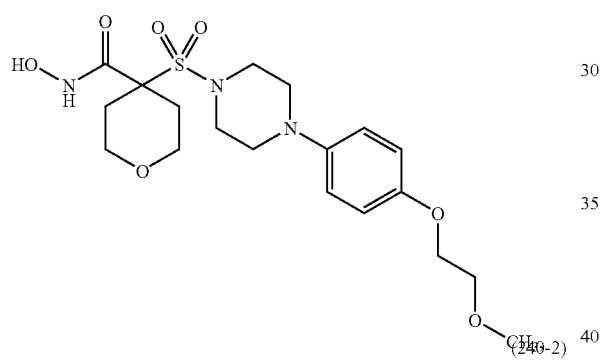

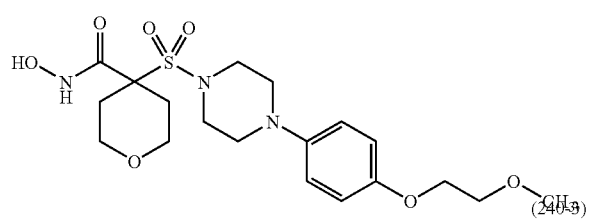

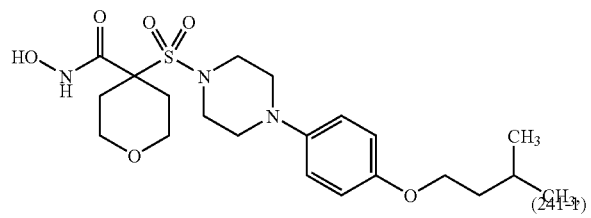

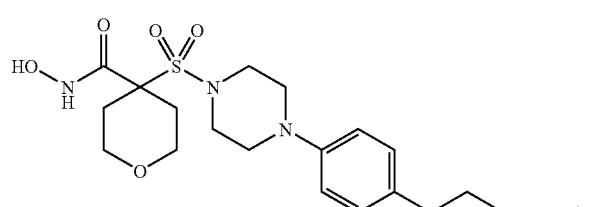

-continued (242-1)

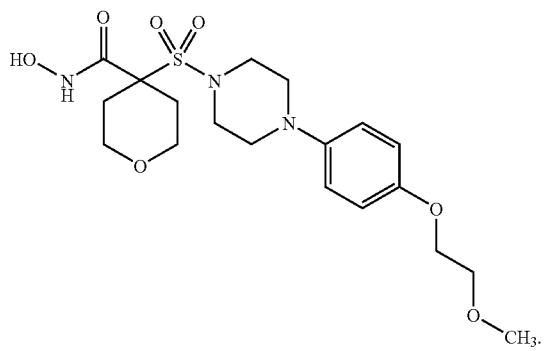

Preferred Embodiment No. 3-N

In some preferred embodiments, the compounds correspond in structure to Formula (243-1):

(243-1)

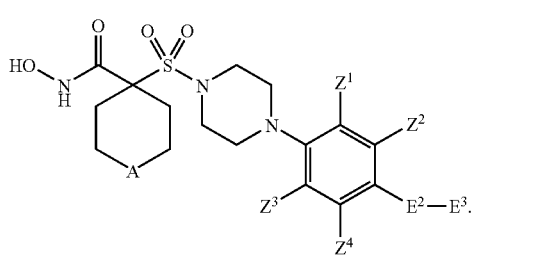

In this embodiment, A is —S—, —S(O)—, or —S(O)$_2$—.

Particularly Preferred Embodiments of Embodiment No. 3-N

In some particularly preferred embodiments, $Z^1$, $Z^2$, $Z^3$, and $Z^4$ are hydrogen.
In some particularly preferred embodiments, $E^2$ is a bond.
In some particularly preferred embodiments, $E^2$ is —O—.
In some particularly preferred embodiments, A is —S—.
One example of a particularly preferred compound is:

(245-1)

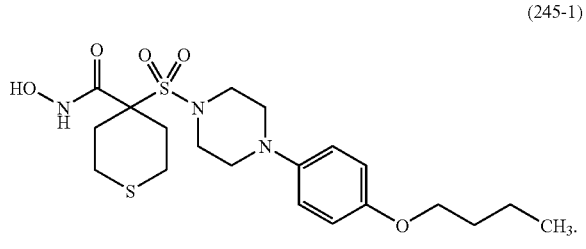

In some particularly preferred embodiments, A is —S(O)—.

In some particularly preferred embodiments, A is —S(O)$_2$—. One example of a particularly preferred compound is:

(247-1)

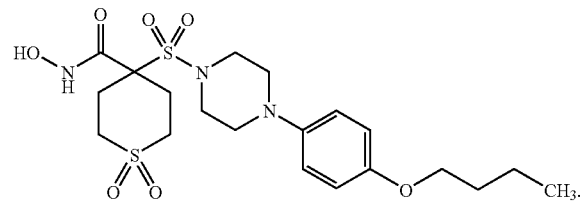

Preferred Embodiment No. 3-O

In some preferred embodiments, the compounds correspond in structure to Formula (248-1):

(248-1)

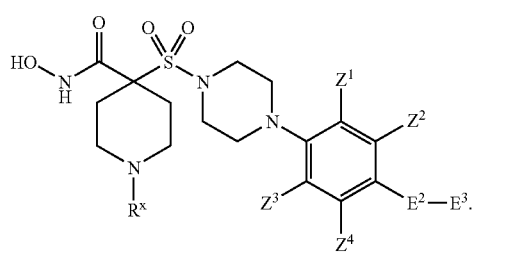

In these embodiments:

R$^x$ is R$^c$-oxyalkyl, R$^c$R$^c$-aminoalkyl, R$^c$R$^c$-aminosulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to these optional substituents:
- the alkyl, alkoxy, alkoxyalkyl, and alkoxyalkoxy optionally are substituted with one or more substituents independently selected from the group consisting of halogen and hydroxy; and
- the amino optionally is substituted with up to two independently selected alkyl substituents.

Each R$^c$ is independently selected from the group consisting of heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonyl, and heterocyclylsulfonylalkyl. Each such substituent (if substitutable) is, in turn, optionally substituted with one or more substituents independently selected from the group consisting of halogen, hydroxy, cyano, carboxy, thiol, sulfo, nitro, nitroso, oxo, thioxo, and imino.

Particularly Preferred Embodiments of Embodiment No. 3-O

In some particularly preferred embodiments, Z$^1$, Z$^2$, Z$^3$, and Z$^4$ are hydrogen.

In some particularly preferred embodiments, E$^2$ is a bond.

In some particularly preferred embodiments, E$^2$ is —O—.

In some particularly preferred embodiments, R$^x$ is heterocyclyl, heterocyclyl-C$_1$–C$_6$-alkyl, heterocyclylcarbonyl, heterocyclylsulfonyl, or C$_1$–C$_6$-alkoxyheterocyclyl. Each such substituent (if substitutable) optionally is substituted with one or more substituents independently selected from the group consisting of halogen, cyano, hydroxy, oxo, C$_1$–C$_6$-alkyl, and C$_1$–C$_6$-alkoxy. Each optional alkyl or alkoxy is, in turn, optionally substituted with one or more independently selected halogen. In addition, any heterocyclyl of R$^x$ has 5 to 10 ring members, and, if divalently substitutable, optionally is substituted with up to 2 oxo.

In some particularly preferred embodiments, R$^x$ is heteroaryl optionally substituted with one or more substituents independently selected from the group consisting of halogen, cyano, hydroxy, C$_1$–C$_6$-alkyl, and C$_1$–C$_6$-alkoxy. Each optional alkyl or alkoxy is, in turn, optionally substituted with one or more independently selected halogen.

In some particularly preferred embodiments, R$^x$ is 5-member heteroaryl optionally substituted with one or more substituents independently selected from the group consisting of halogen, cyano, hydroxy, C$_1$–C$_6$-alkyl, and C$_1$–C$_6$-alkoxy. Each optional alkyl or alkoxy is, in turn, optionally substituted with one or more independently selected halogen. Examples of particularly preferred compounds include the compounds corresponding in structure to the following formulas:

(252-1)

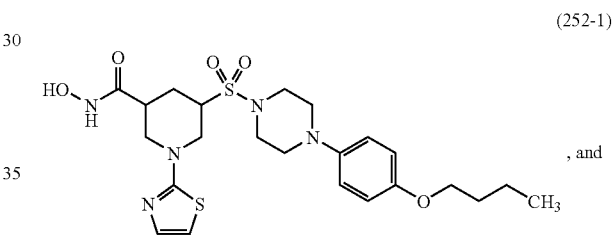

, and (252-2)

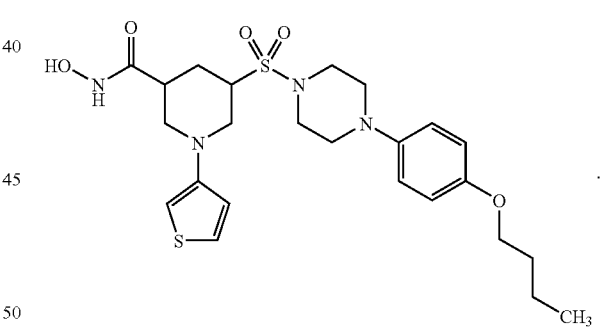

In some particularly preferred embodiments, R$^x$ is 6-member heteroaryl optionally substituted with one or more substituents independently selected from the group consisting of halogen, cyano, hydroxy, C$_1$–C$_6$-alkyl, and C$_1$–C$_6$-alkoxy. Each optional alkyl or alkoxy is, in turn, optionally substituted with one or more independently selected halogen.

In some particularly preferred embodiments, R$^x$ is 6-member heteroaryl optionally substituted with one or more substituents independently selected from the group consisting of halogen, cyano, hydroxy, C$_1$–C$_6$-alkyl, and C$_1$–C$_6$-alkoxy. Each optional alkyl or alkoxy is, in turn, optionally substituted with one or more independently selected halogen. In addition, the heteroaryl of R$^x$ has 1 or 2 nitrogen ring members, with the remaining ring members being carbon. Examples of particularly preferred compounds include the compounds corresponding in structure to the following formulas:
(255-1)
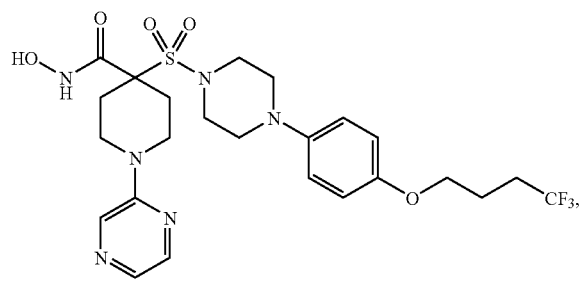
(255-2)
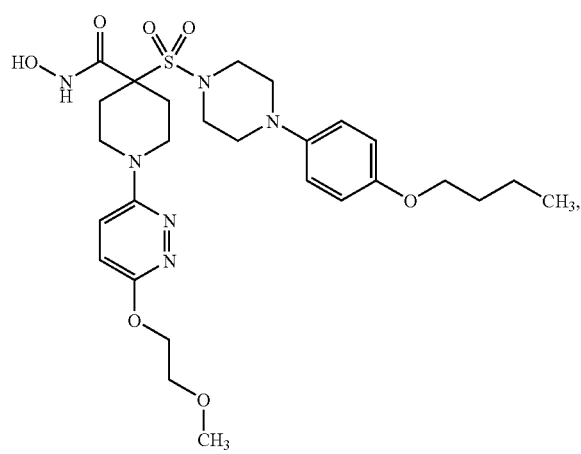
(255-3)
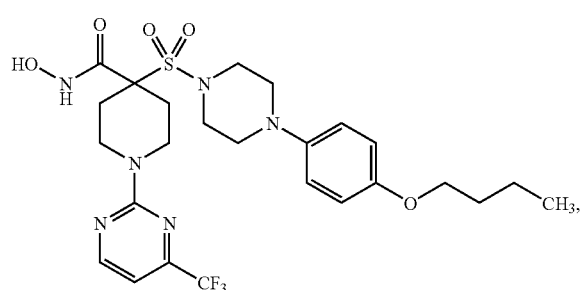
(255-4)
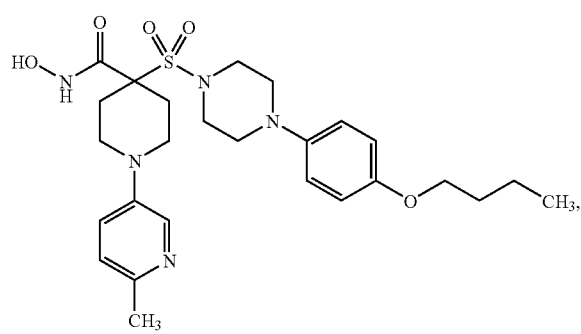
-continued
(255-5)
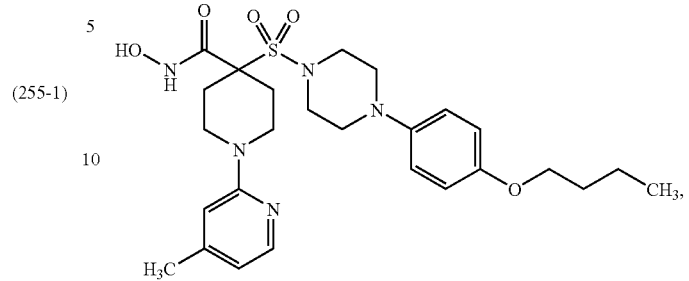
(255-6)
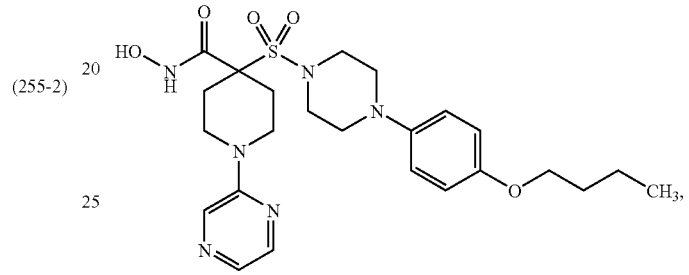
(255-7)
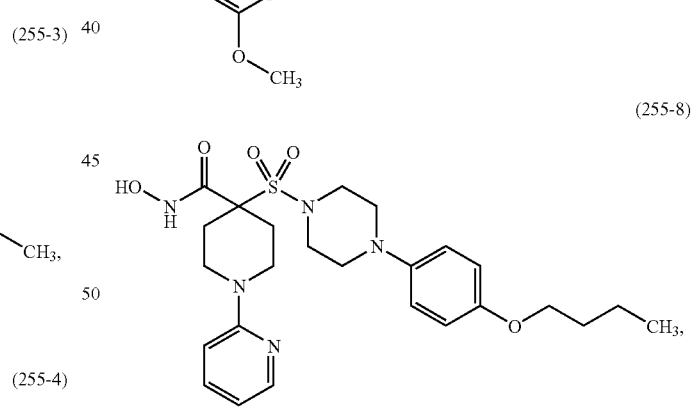
(255-8)
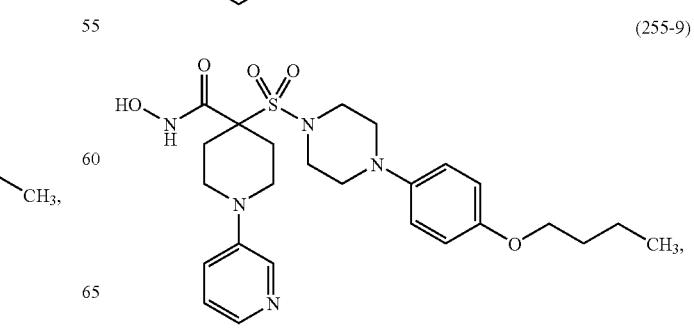
(255-9)

-continued (255-10)
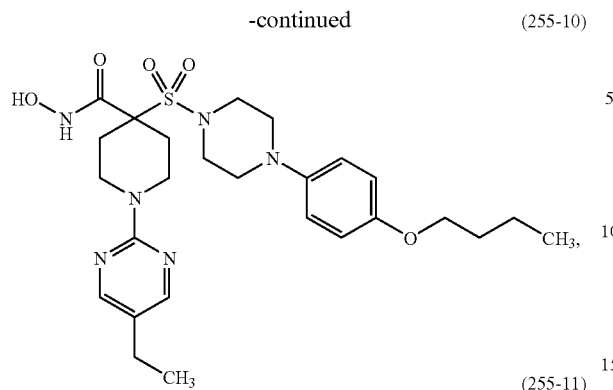

(255-11)
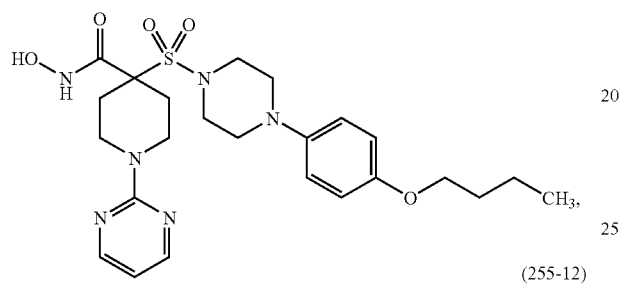

(255-12)
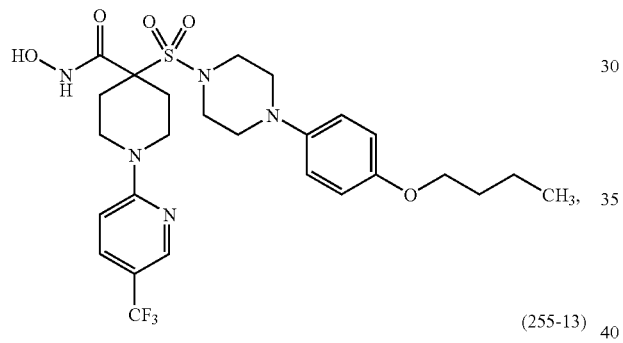

(255-13)

(255-14)
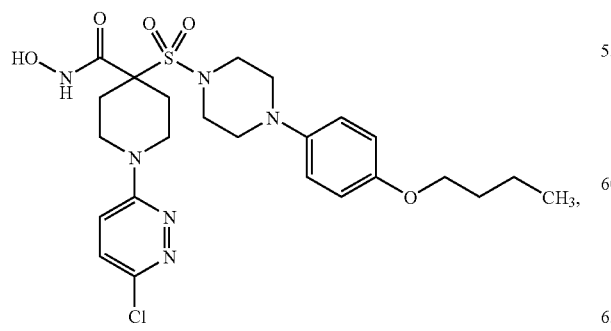

-continued (255-15)
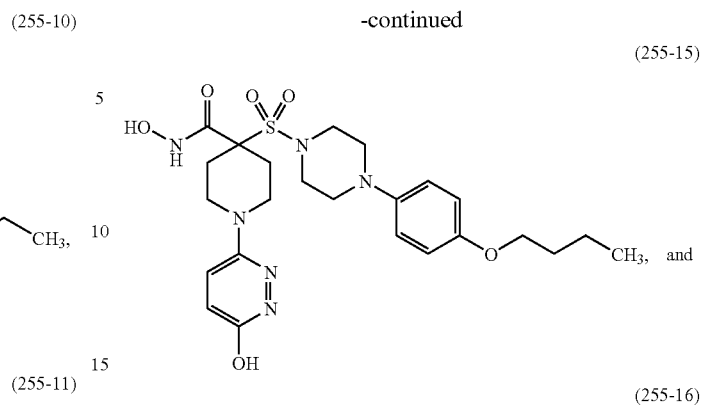

(255-16)
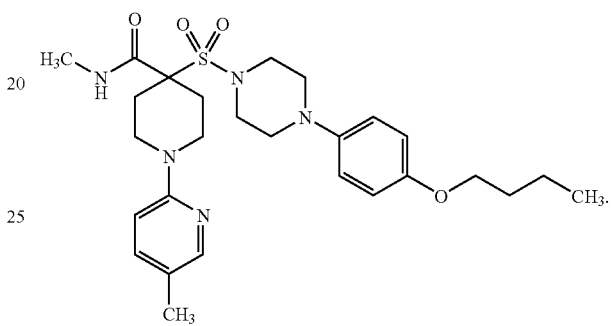

In some particularly preferred embodiments, $R^x$ is 9- or 10-member heteroaryl optionally substituted with one or more substituents independently selected from the group consisting of halogen, cyano, hydroxy, $C_1$–$C_6$-alkyl, and $C_1$–$C_6$-alkoxy. Each optional alkyl or alkoxy is, in turn, optionally substituted with one or more independently selected halogen. Examples of particularly preferred compounds include the compounds corresponding in structure to the following formulas:

(257-1)
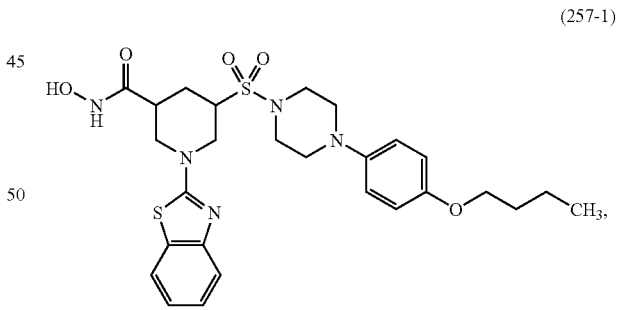

(257-2)
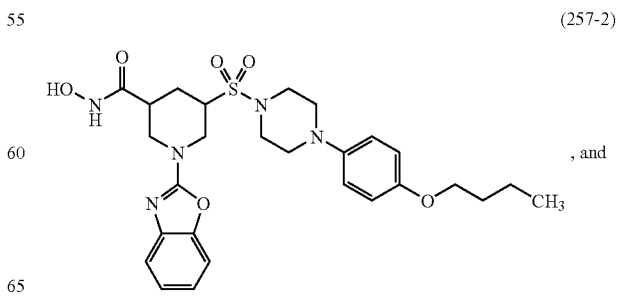

-continued

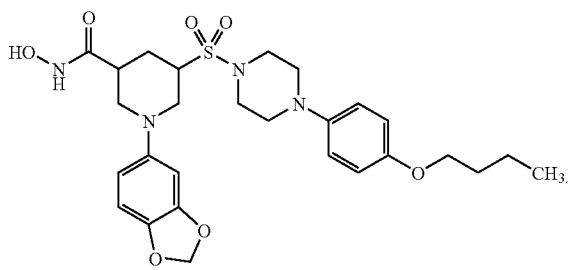
(257-3)

In some particularly preferred embodiments, $R^x$ is heterocycloalkylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen.

In some particularly preferred embodiments, $R^x$ is heterocycloalkylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heterocycloalkyl of the heterocycloalkylalkyl has 5 ring members. One example of a particularly preferred compound is:

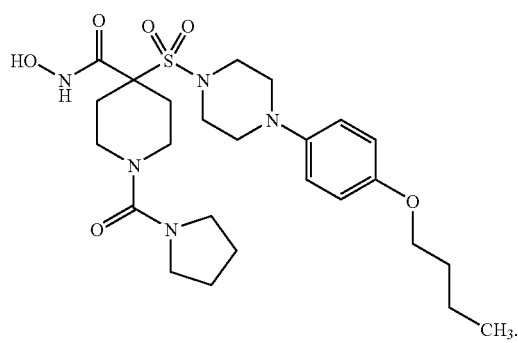
(260-1)

In some particularly preferred embodiments, $R^x$ is heterocycloalkylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heterocycloalkyl of the heterocycloalkylalkyl has 6 ring members. Examples of particularly preferred compounds include the compounds corresponding in structure to the following formulas:

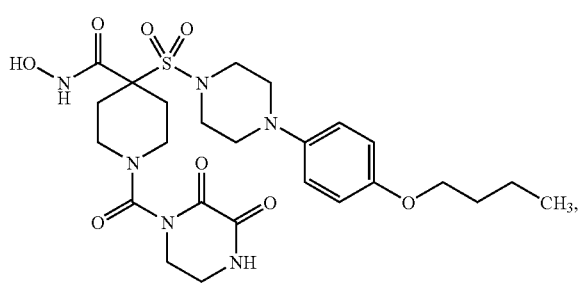
(262-1)

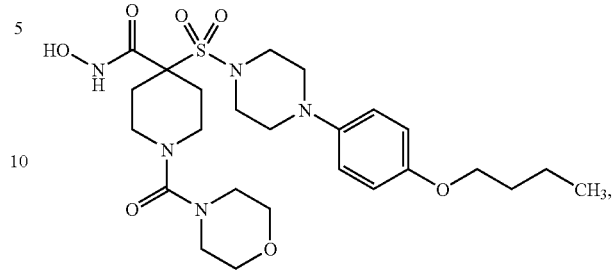
(262-2)

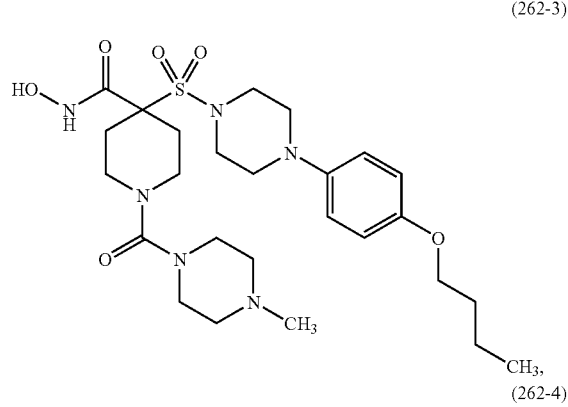
(262-3)

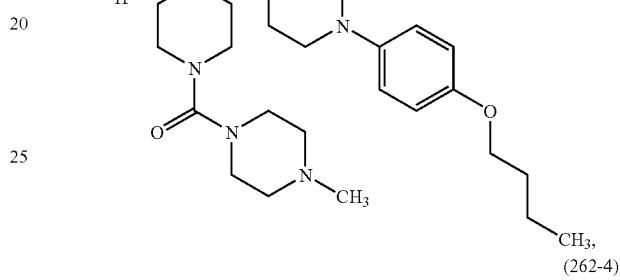
(262-4)

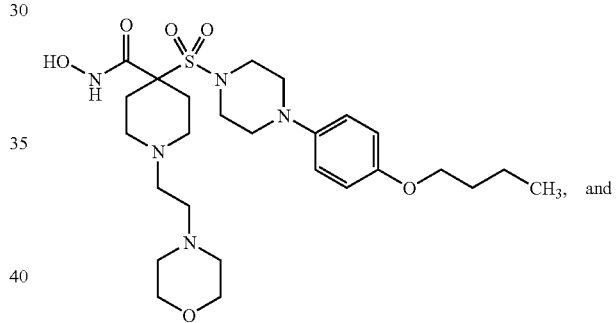

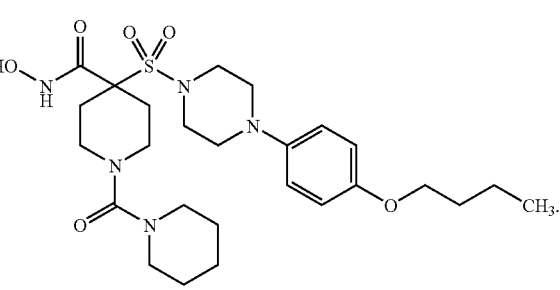
(262-5)

In some particularly preferred embodiments, $R^x$ is heteroarylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen.

In some particularly preferred embodiments, $R^x$ is heteroarylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heteroaryl of the heteroarylalkyl has 5 ring members. Examples of particularly preferred compounds include the compounds corresponding in structure to the following formulas:

(264-1)
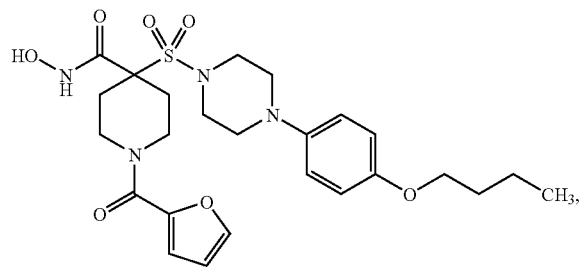

(264-2)
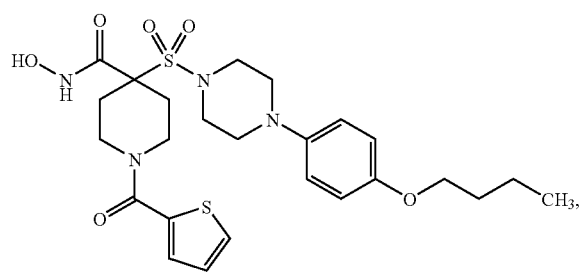

(264-3)
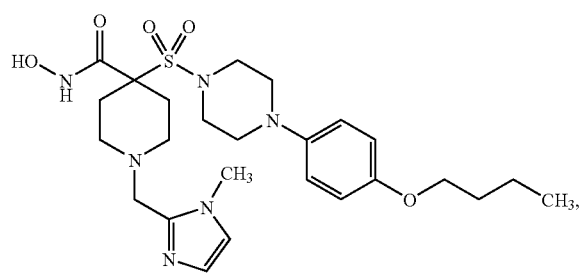

(264-4)
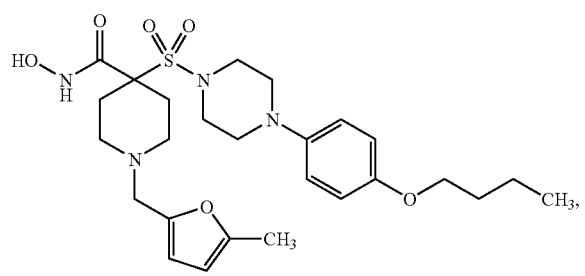

(264-5)
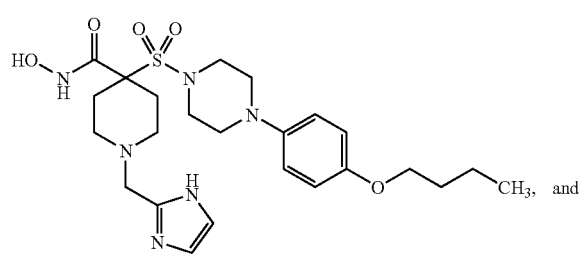, and (264-6)
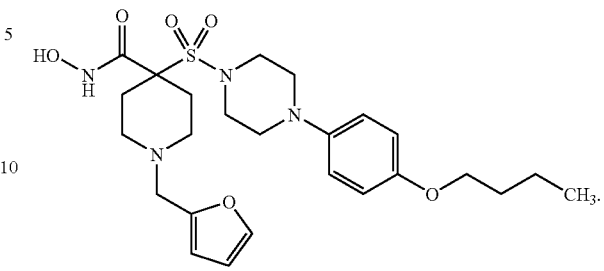

In some particularly preferred embodiments, $R^x$ is heteroarylalkyl optionally substituted with one or more substituents independently selected from the group consisting of halogen, cyano, hydroxy, oxo, $C_1$–$C_6$-alkyl, and $C_1$–$C_6$-alkoxy. Each optional alkyl or alkoxy is, in turn, optionally substituted with one or more independently selected halogen. In addition, the heteroaryl of the heteroarylalkyl has 6 ring members. Examples of particularly preferred compounds include the compounds corresponding in structure to the following formulas:

(266-1)
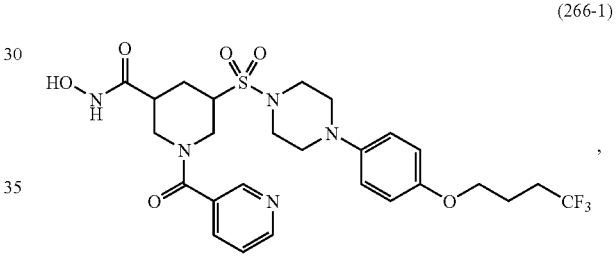, (266-2)
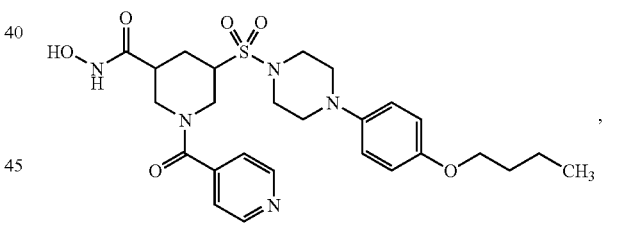, (266-3)
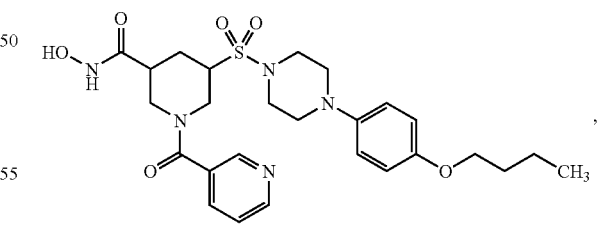, (266-4)
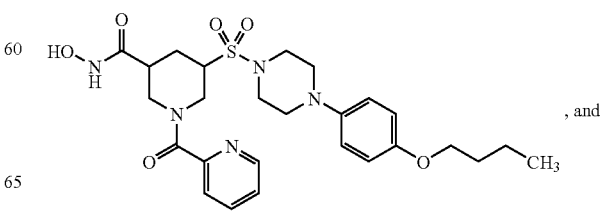, and -continued (266-5)

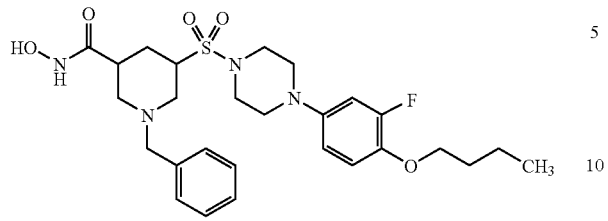

In some particularly preferred embodiments, R$^x$ is heteroarylalkyl optionally substituted with one or more substituents independently selected from the group consisting of halogen, cyano, hydroxy, oxo, C$_1$–C$_6$-alkyl, and C$_1$–C$_6$-alkoxy. Each optional alkyl or alkoxy is, in turn, optionally substituted with one or more independently selected halogen. In addition, the heteroaryl of the heteroarylalkyl has 9 to 10 ring members. Examples of particularly preferred compounds include the compounds corresponding in structure to the following formulas:

(268-1)

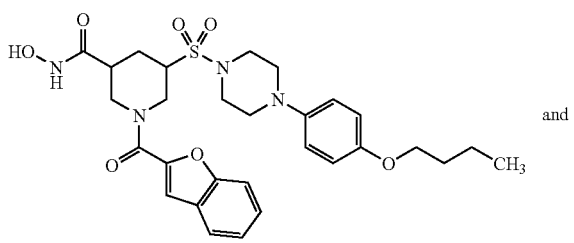

and (268-2)

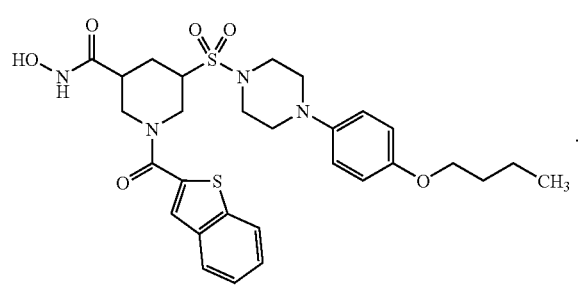

Preferred Embodiment No. 3-P

In some preferred embodiments, the compound corresponds in structure to one of the following formulas:

(269-1)

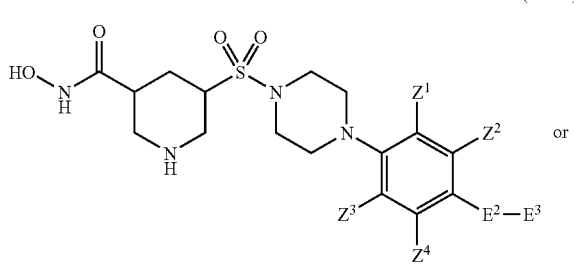

or

-continued (269-2)

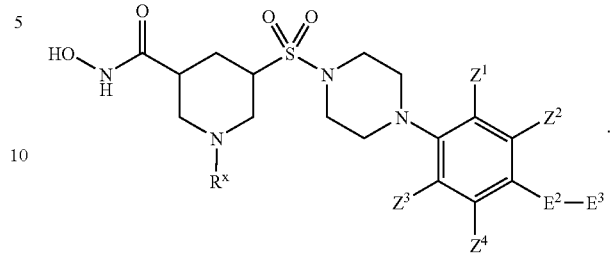

In these embodiments:

R$^x$ is alkyl, alkenyl, alkynyl, R$^c$-oxyalkyl, alkylsulfonyl, R$^a$R$^a$-aminoalkyl, carbocyclyl, cycloalkylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino nitrogen is substituted by up to 2 independently selected alkyl.

R$^c$ is hydrogen, alkenyl, alkynyl, alkoxyalkyl, bisalkoxyalkyl, alkylthioalkyl, alkylthioalkenyl, alkylsulfoxidoalkyl, alkylsulfonylalkyl, carbocyclyl, carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonylalkyl, heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonylalkyl, aminoalkyl, or alkoxyalkylaminoalkyl. Each such substituent (if substitutable) is, in turn, optionally substituted:

on any substitutable carbon with one or more substituents independently selected from the group consisting of halogen, hydroxy, cyano, carboxy, thiol, sulfo, nitro, nitroso, oxo, thioxo, and imino; and on any substitutable nitrogen with up to 2 substituents independently selected from the group consisting of alkyl, alkylcarbonyl, carbocyclyl, and carbocyclylalkyl.

Particularly Preferred Embodiments of Embodiment No. 3-P

In some particularly preferred embodiments, Z$^1$, Z$^2$, Z$^3$, and Z$^4$ are hydrogen.

In some particularly preferred embodiments, E$^2$ is a bond.

In some particularly preferred embodiments, E$^2$ is —O—.

In some particularly preferred embodiments, the compound corresponds in structure to the following formula:

(270-1)

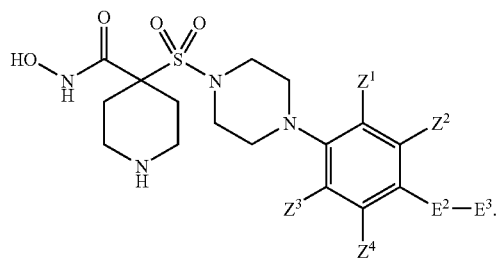

(277-1)

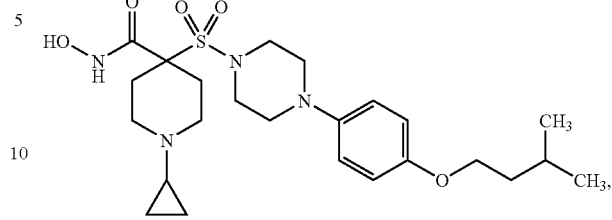

One example of a particularly preferred compound is:

(271-1)

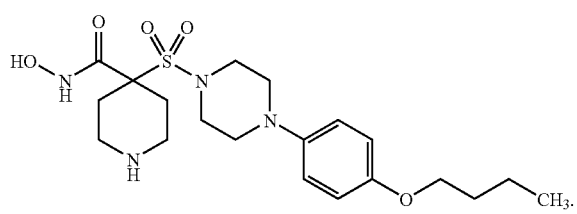

(277-2)

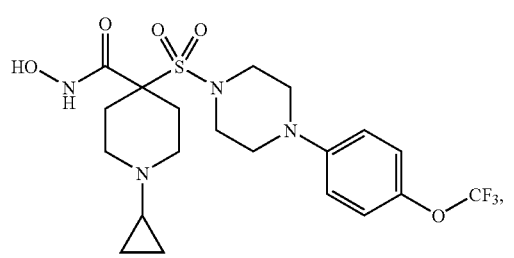

In some particularly preferred embodiments, the compound corresponds in structure to the following formula:

(272-1)

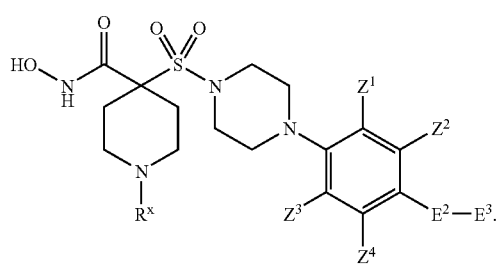

(277-3)

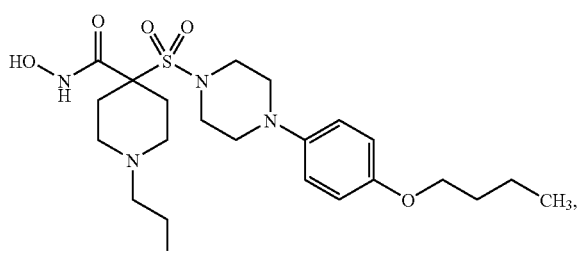

In some particularly preferred embodiments, $R^x$ is alkyl, alkynyl, aminoalkyl, cycloalkyl, aryl, or cycloalkylalkyl. Each such substituent optionally is substituted with one or more independently selected halogen. In addition, the nitrogen of the aminoalkyl optionally is substituted by up to 2 independently selected alkyl.

In some particularly preferred embodiments, $R^x$ is aryl. One example of a particularly preferred compound is:

(275-1)

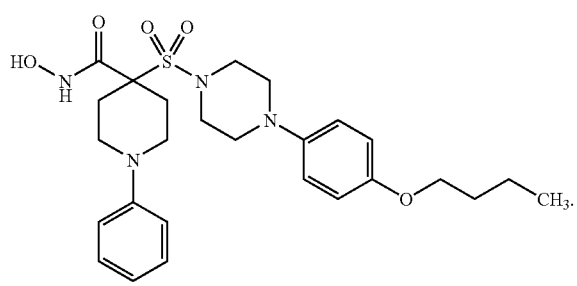

(277-4)

(277-5)

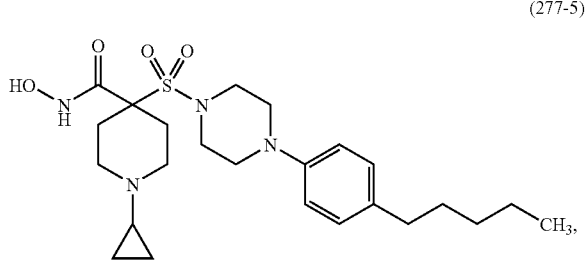

In some particularly preferred embodiments, $R^x$ is haloalkyl, alkynyl, aminoalkyl, cycloalkyl, or cycloalkylalkyl. The nitrogen of the aminoalkyl optionally is substituted by 2 independently selected alkyl. Examples of particularly preferred compounds include the compounds corresponding in structure to one of the following formulas:

(277-6)

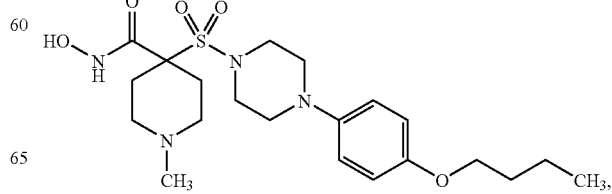

-continued (277-7)
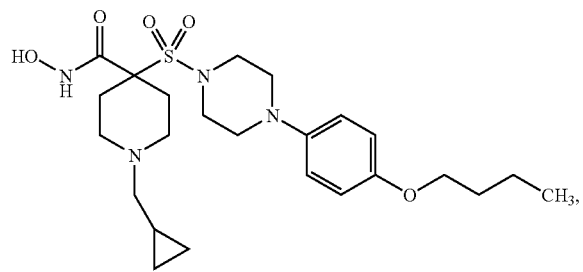

(277-8)
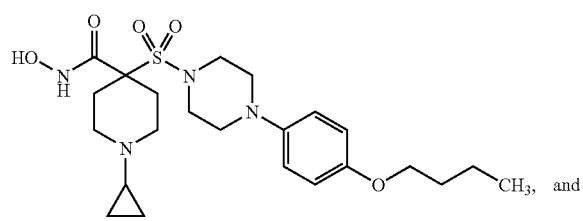
and (277-9)
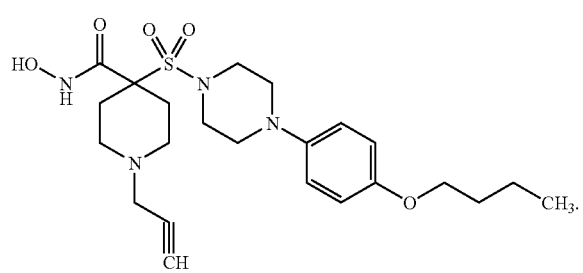

Preferred Embodiment No. 3-Q

In some preferred embodiments, the compound corresponds in structure to one of the following formulas:

(278-1)
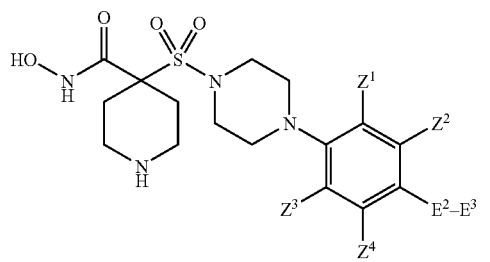
or (278-2)
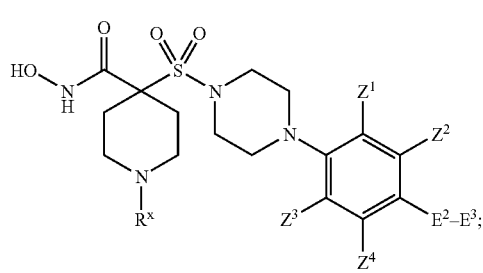

In these embodiments:

$E^3$ is haloalkyl.

$R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy, and the amino nitrogen is substituted by up to 2 independently selected alkyl.

Particularly Preferred Embodiments of Embodiment No. 3-Q

In some particularly preferred embodiments, $Z^1$, $Z^2$, $Z^3$, and $Z^4$ are hydrogen.

In some particularly preferred embodiments, $E^2$ is a bond.

In some particularly preferred embodiments, $E^2$ is —O—.

In some particularly preferred embodiments, the compound corresponds in structure to the following formula:

(278-1)
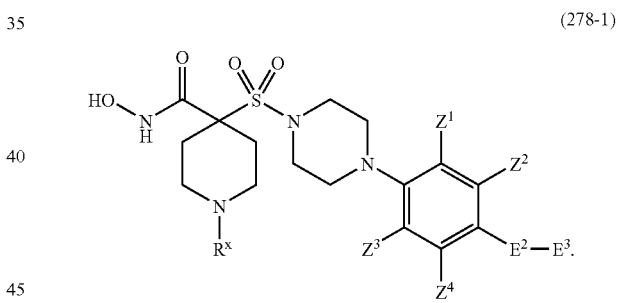

Examples of particularly preferred compounds include the compounds corresponding in structure to one of the following formulas:

(279-1)
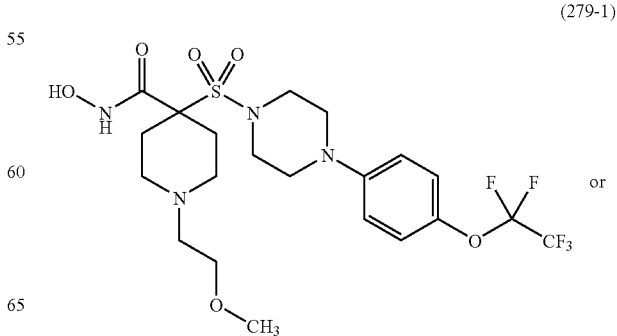
or (279-2)

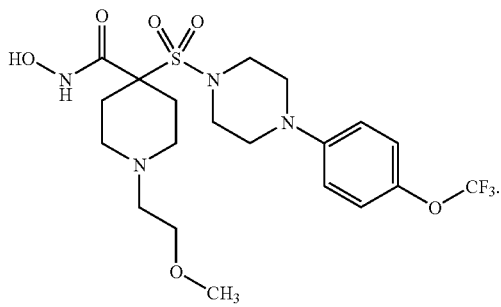

Preferred Embodiment No. 3-R

In some preferred embodiments, the compound corresponds in structure to one of the following formulas:

(280-1)

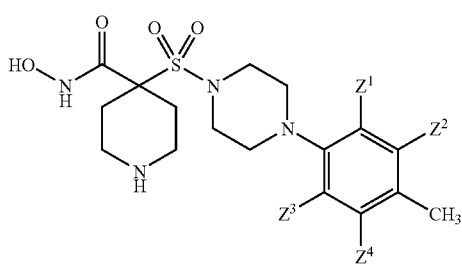

or (280-2)

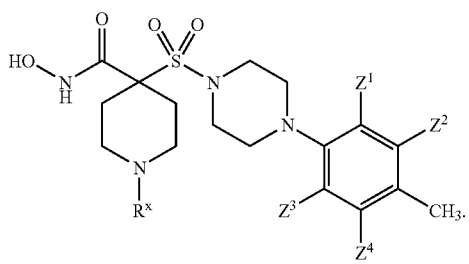

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:
 the alkyl, alkoxy, alkoxyalkyl, and alkoxyalkoxy optionally are substituted with one or more substituents independently selected from the group consisting of halogen and hydroxy; and
 the amino optionally is substituted by up to 2 independently selected alkyl.

Particularly Preferred Embodiments of Embodiment No. 3-R

In some particularly preferred embodiments, the compound corresponds in structure to the following formula:

(281-1)

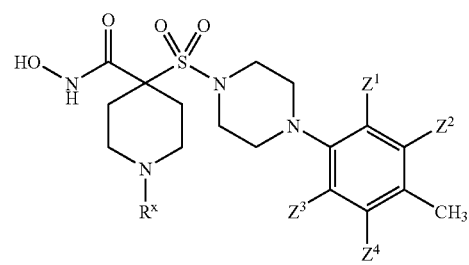

In some particularly preferred embodiments, $Z^1$, $Z^2$, $Z^3$, and $Z^4$ are hydrogen.

An example of a particularly preferred compound is:

(282-1)

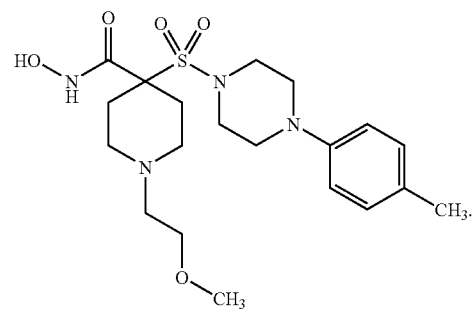

Preferred Embodiment No. 3-S

In some preferred embodiments, the compound corresponds in structure to one of the following formulas:

(280-3)

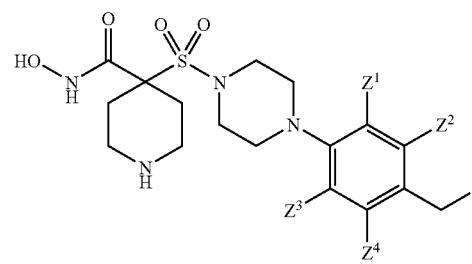

or (280-4)

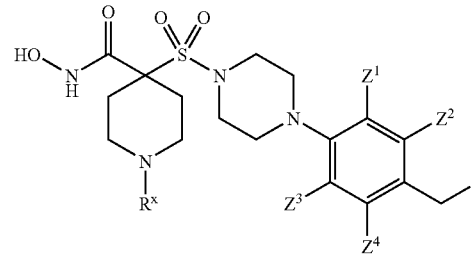

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-S

In some particularly preferred embodiments, the compound corresponds in structure to the following formula:

(281-2)

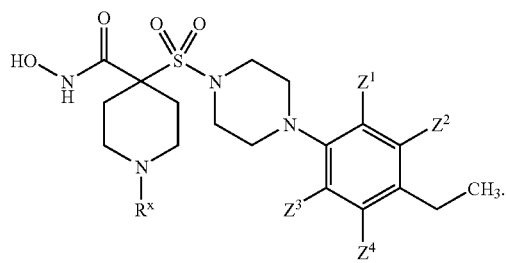

In some particularly preferred embodiments, $Z^1$, $Z^2$, $Z^3$, and $Z^4$ are hydrogen.

One example of a particularly preferred compound is:

(282-2)

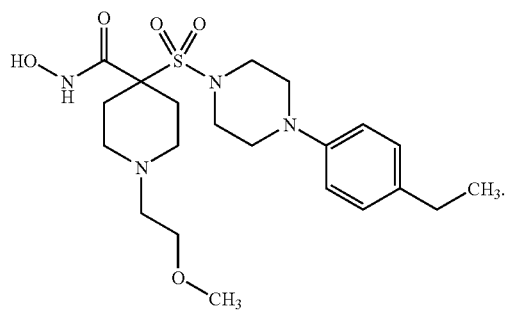

Preferred Embodiment No. 3-T

In some preferred embodiments, the compound corresponds in structure to one of the following formulas:

(280-5)

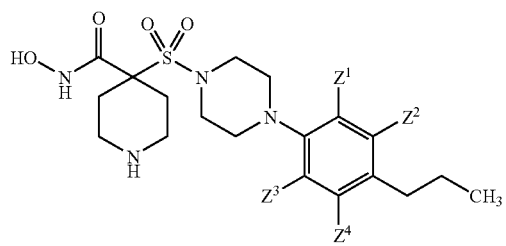

or (280-6)

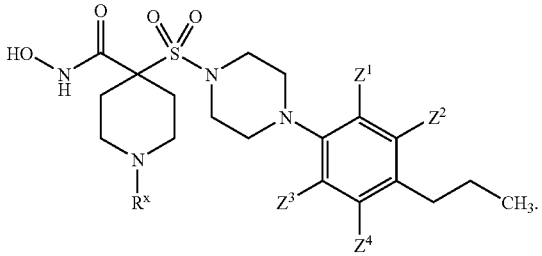

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-T

In some particularly preferred embodiments, the compound corresponds in structure to the following formula:

(281-3)

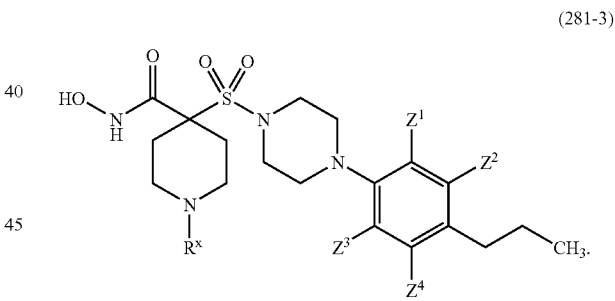

In some particularly preferred embodiments, $Z^1$, $Z^2$, $Z^3$, and $Z^4$ are hydrogen.

One example of a particularly preferred compound is:

(282-3)

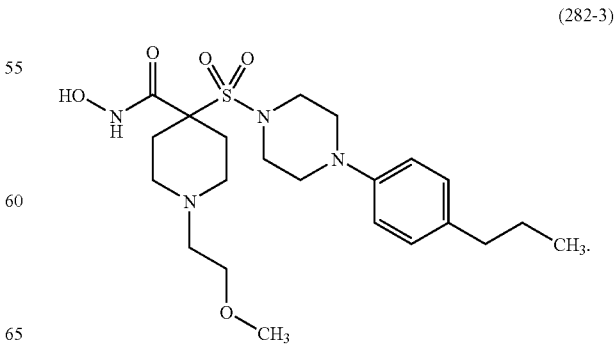

Preferred Embodiment No. 3-U

In some preferred embodiments, the compound corresponds in structure to one of the following formulas:

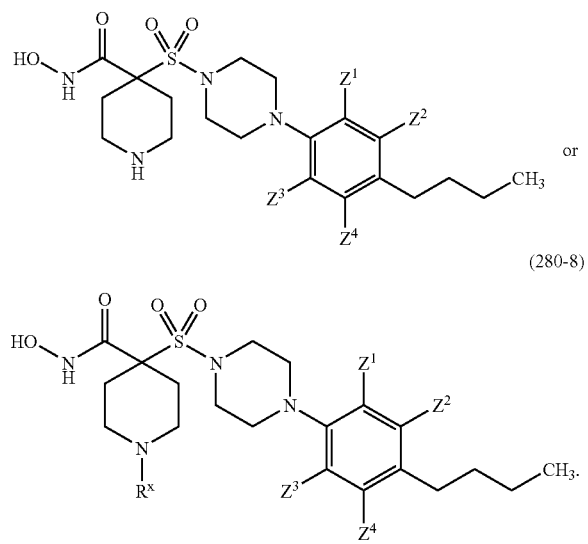

(280-7)

or (280-8)

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-U

In some particularly preferred embodiments, the compound corresponds in structure to the following formula:

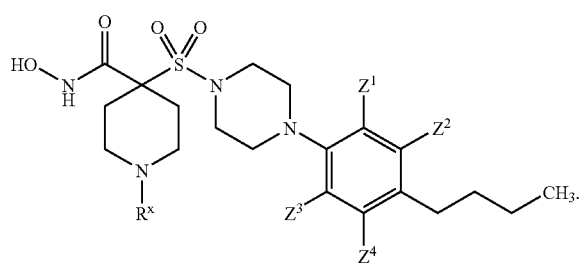

(281-4)

In some particularly preferred embodiments, $Z^1$, $Z^2$, $Z^3$, and $Z^4$ are hydrogen.

One example of a particularly preferred compound is:

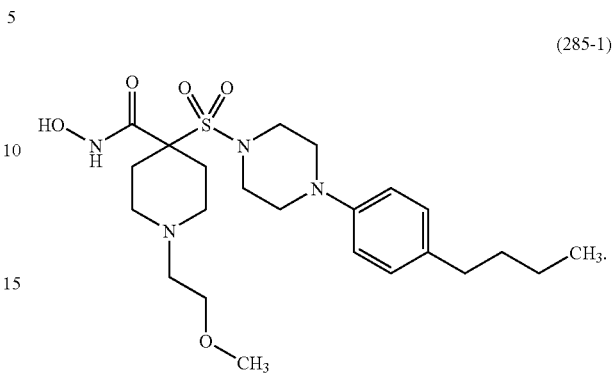

(285-1)

Preferred Embodiment No. 3-V

In some preferred embodiments, the compound corresponds in structure to one of the following formulas:

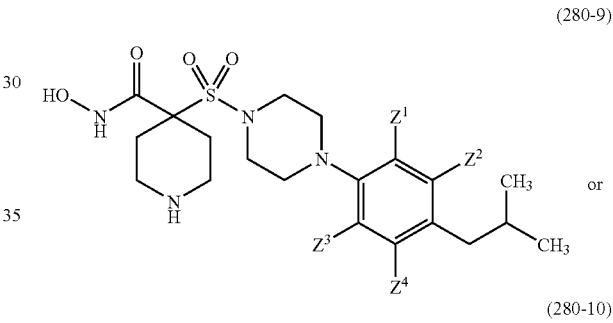

(280-9)

or (280-10)

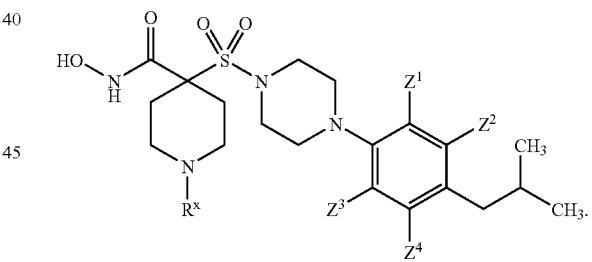

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-V

In some particularly preferred embodiments, the compound corresponds in structure to the following formula:

(281-5)

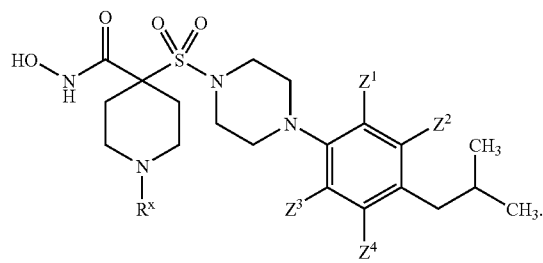

In some particularly preferred embodiments, $Z^1$, $Z^2$, $Z^3$, and $Z^4$ are hydrogen.

One example of a particularly preferred compound is:

(282-4)

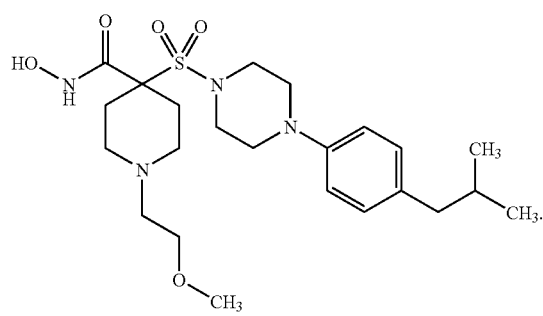

Preferred Embodiment No. 3-W

In some preferred embodiments, the compound corresponds in structure to one of the following formulas:

(280-11)

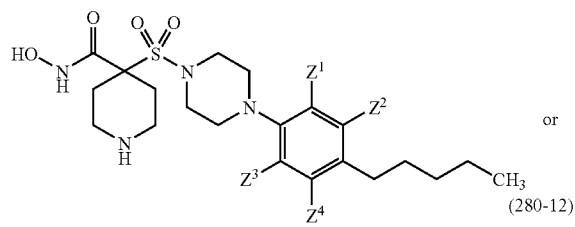

or (280-12)

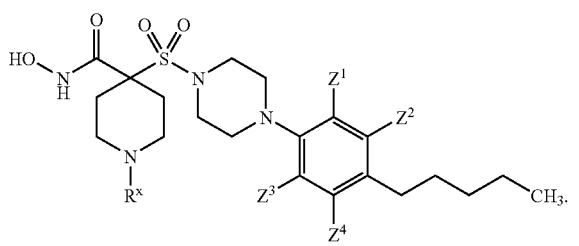

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-W

In some particularly preferred embodiments, the compound corresponds in structure to the following formula:

(281-6)

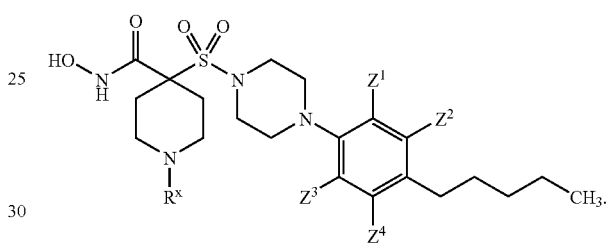

In some particularly preferred embodiments, $Z^1$, $Z^2$, $Z^3$, and $Z^4$ are hydrogen.

One example of a particularly preferred compound is:

(286-1)

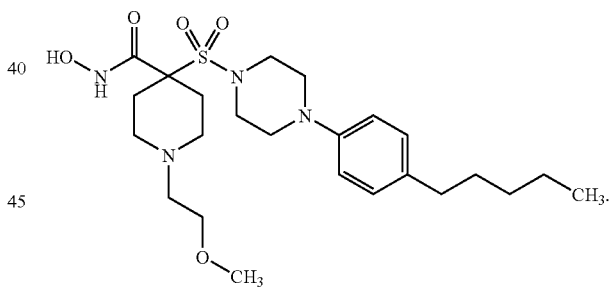

Preferred Embodiment No. 3-X

In some preferred embodiments, the compound corresponds in structure to one of the following formulas:

(280-13)

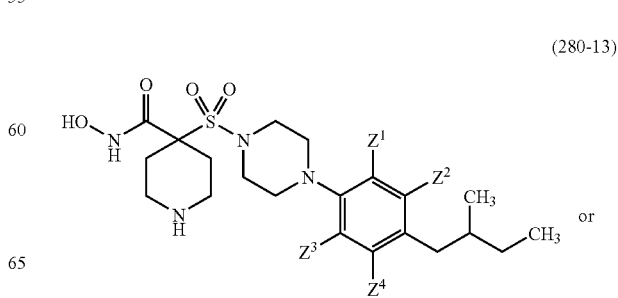

or

-continued (280-14)

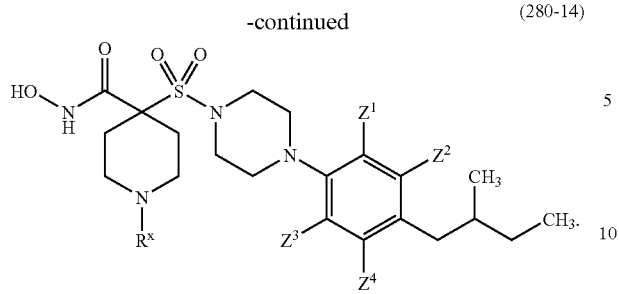

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-X

In some particularly preferred embodiments, the compound corresponds in structure to the following formula:

(281-7)

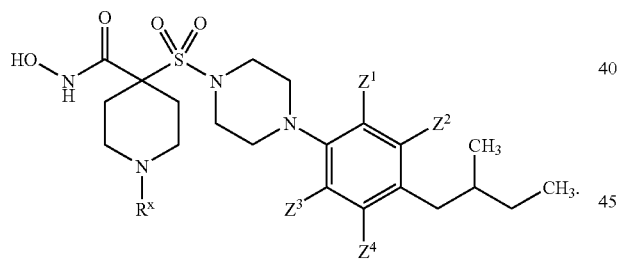

In some particularly preferred embodiments, $Z^1$, $Z^2$, $Z^3$, and $Z^4$ are hydrogen.

One example of a particularly preferred compound is:

(282-5)

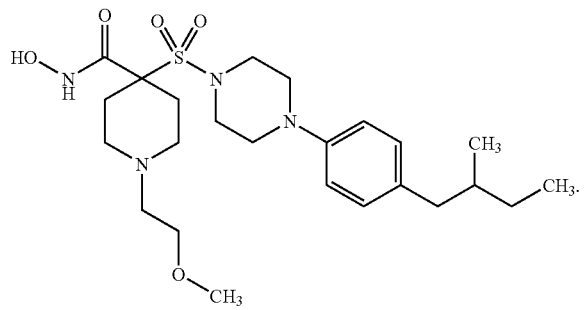

Preferred Embodiment No. 3-Y

In some preferred embodiments, the compound corresponds in structure to one of the following formulas:

(280-15)

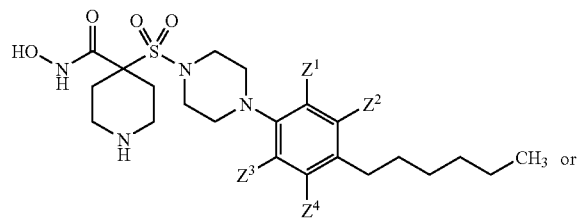

or (280-16)

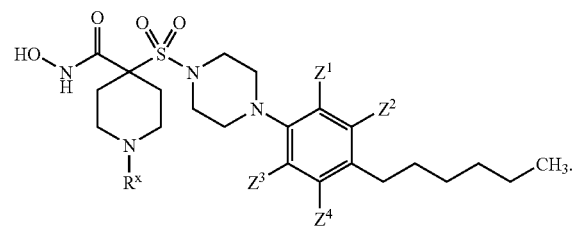

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-Y

In some particularly preferred embodiments, the compound corresponds in structure to the following formula:

(281-8)

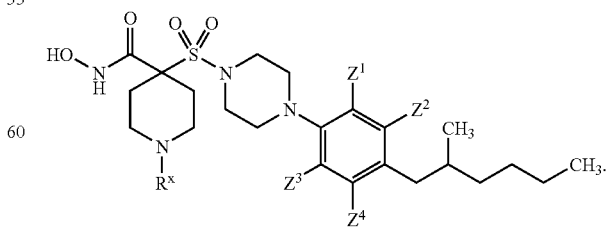

In some particularly preferred embodiments, $Z^1$, $Z^2$, $Z^3$, and $Z^4$ are hydrogen.

One example of a particularly preferred compound is:

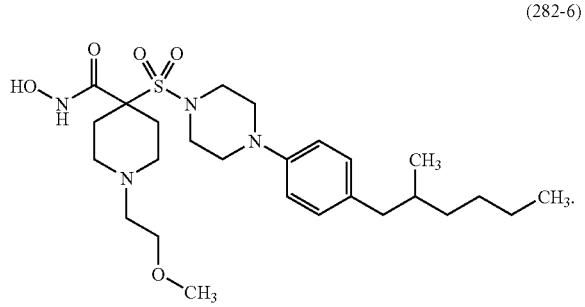

(282-6)

Preferred Embodiment No. 3-Z

In some preferred embodiments, the compound corresponds in structure to one of the following formulas:

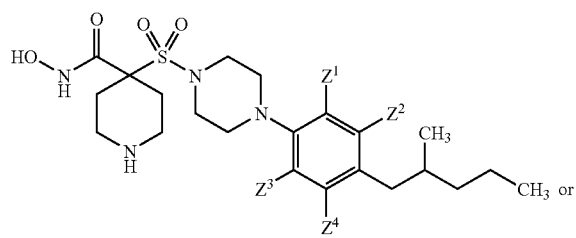

(280-17)

or (280-18)

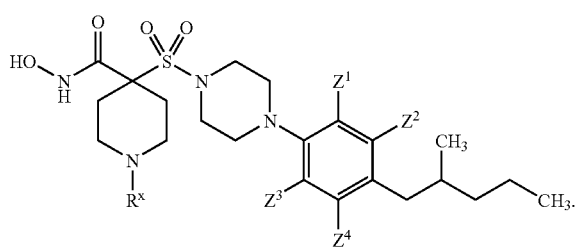

Here, $R^x$ is alkyl, alkenyl, alkynyl, alkoxyalkyl, $R^a$-oxyalkyl, alkylsulfonyl, $R^a R^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

Particularly Preferred Embodiments of Embodiment No. 3-Z

In some particularly preferred embodiments, the compound corresponds in structure to the following formula:

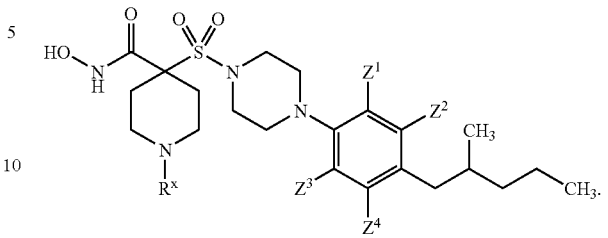

(281-9)

In some particularly preferred embodiments, $Z^1$, $Z^2$, $Z^3$, and $Z^4$ are hydrogen.

One example of a particularly preferred compound is:

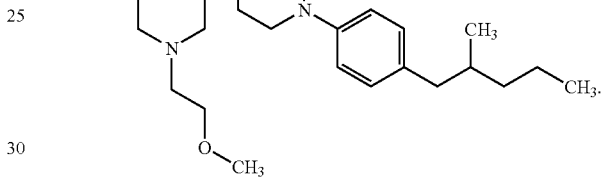

(282-7)

Preferred Embodiment No. 3-AA

In some preferred embodiments, the compound corresponds in structure to one of the following formulas:

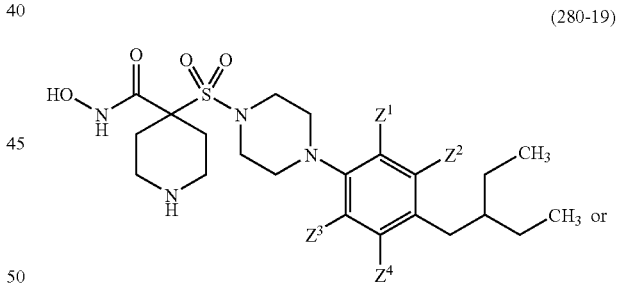

(280-19)

or (280-20)

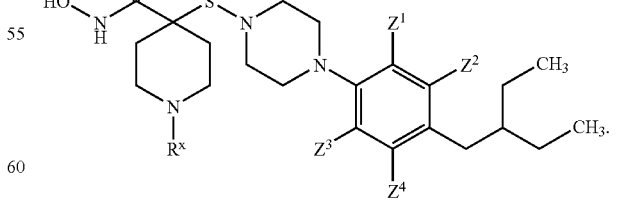

Here, $R^x$ is alkyl, alkenyl, alkynyl, alkoxyalkyl, $R^a$-oxyalkyl, alkylsulfonyl, $R^a R^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

- the alkyl, alkoxy, alkoxyalkyl, and alkoxyalkoxy optionally are substituted with one or more substituents independently selected from the group consisting of halogen and hydroxy; and
- the amino optionally is substituted by up to 2 independently selected alkyl.

Particularly Preferred Embodiments of Embodiment No. 3-AA

In some particularly preferred embodiments, the compound corresponds in structure to the following formula:

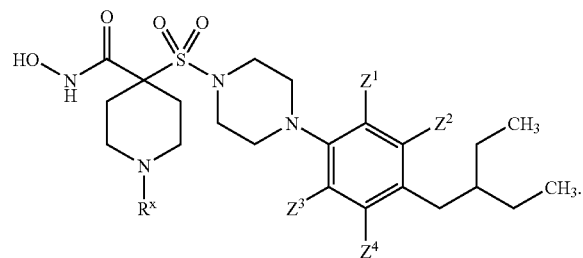

(281-10)

In some particularly preferred embodiments, $Z^1$, $Z^2$, $Z^3$, and $Z^4$ are hydrogen.

One example of a particularly preferred compound is:

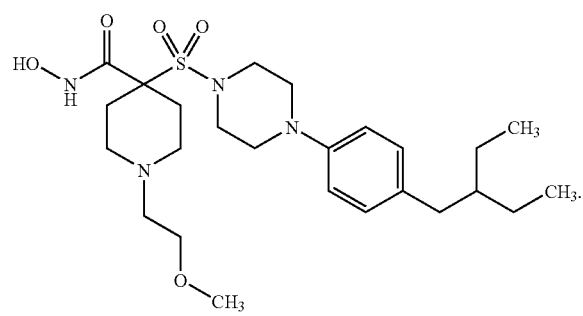

(284-1)

Preferred Embodiment No. 3-BB

In some preferred embodiments, the compound corresponds in structure to one of the following formulas:

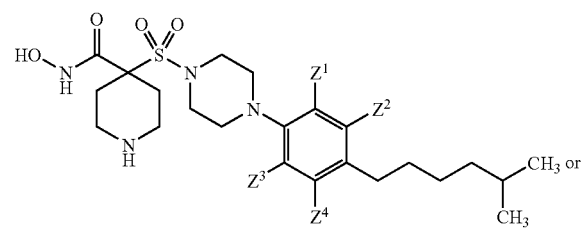

(280-21)

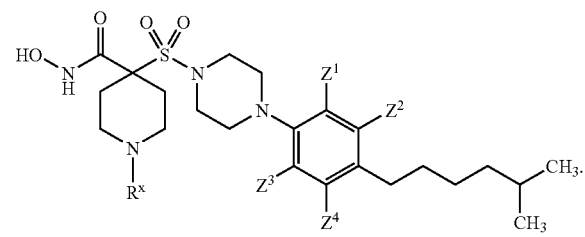

(280-22)

Here, $R^x$ is alkyl, alkenyl, alkynyl, alkoxyalkyl, $R^a$-oxyalkyl, alkylsulfonyl, $R^aR^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

- the alkyl, alkoxy, alkoxyalkyl, and alkoxyalkoxy optionally are substituted with one or more substituents independently selected from the group consisting of halogen and hydroxy; and
- the amino optionally is substituted by up to 2 independently selected alkyl.

Particularly Preferred Embodiments of Embodiment No. 3-BB

In some particularly preferred embodiments, the compound corresponds in structure to the following formula:

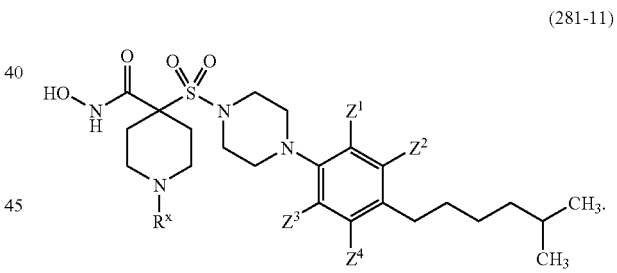

(281-11)

In some particularly preferred embodiments, $Z^1$, $Z^2$, $Z^3$, and $Z^4$ are hydrogen.

One example of a particularly preferred compound is:

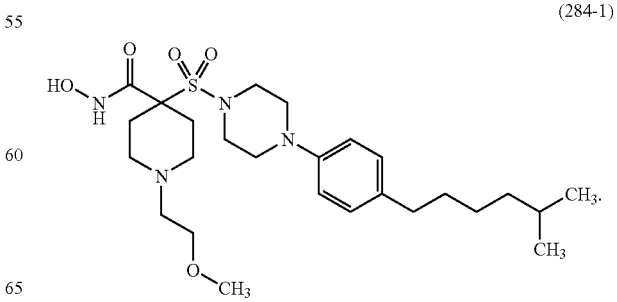

(284-1)

Preferred Embodiment No. 3-CC

In some preferred embodiments, the compound corresponds in structure to one of the following formulas:

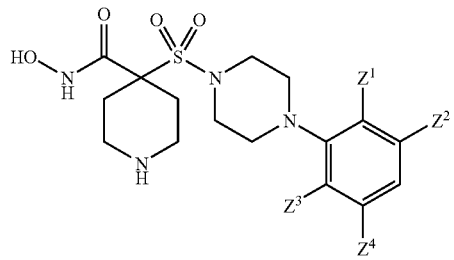

(287-1)

or

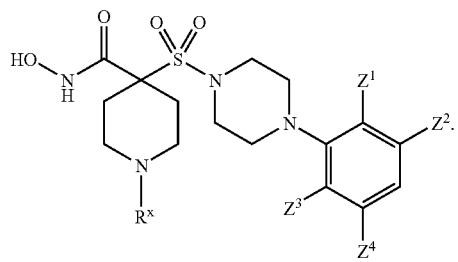

(287-2)

In these embodiments:

$R^x$ is alkyl, alkenyl, alkynyl, alkoxyalkyl, $R^a$-oxyalkyl, alkylsulfonyl, $R^aR^a$-aminoalkyl, carbocyclyl, cycloalkylalkyl, carbocyclylsulfonyl, heterocyclyl, heterocyclylalkyl, or heterocyclylsulfonyl. Each such substituent (if substitutable) is, in turn, optionally substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:
- the alkyl, alkoxy, alkoxyalkyl, and alkoxyalkoxy optionally are substituted with one or more substituents independently selected from the group consisting of halogen and hydroxy; and
- the amino optionally is substituted by up to 2 independently selected alkyl.

Each $R^a$ is independently selected from the group consisting of hydrogen, alkyl, alkenyl, alkynyl, alkoxyalkyl, bisalkoxyalkyl, alkylthioalkyl, alkylthioalkenyl, alkylsulfoxidoalkyl, alkylsulfonyl, alkylsulfonylalkyl, carbocyclyl, carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, carbocyclylsulfonylalkyl, heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonyl, heterocyclylsulfonylalkyl, aminoalkyl, aminoalkylsulfonyl, and alkoxyalkylaminoalkyl. Each such substituent optionally is substituted:
- on any substitutable carbon with one or more substituents independently selected from the group consisting of halogen, hydroxy, cyano, carboxy, thiol, sulfo, nitro, nitroso, oxo, thioxo, and imino; and
- on any substitutable amino nitrogen with up to 2 substituents independently selected from the group consisting of alkyl, alkylcarbonyl, carbocyclyl, and carbocyclylalkyl.

Particularly Preferred Embodiments of Embodiment No. 3-CC

In some particularly preferred embodiments, $Z^1$, $Z^2$, $Z^3$, and $Z^4$ are hydrogen.

One example of a particularly preferred compound is:

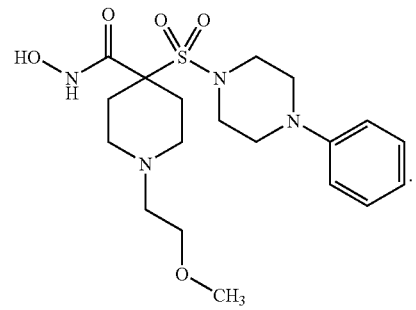

(288-1)

Preferred Embodiment No. 3-DD

In some preferred embodiments, the compounds correspond in structure to Formula (289-1):

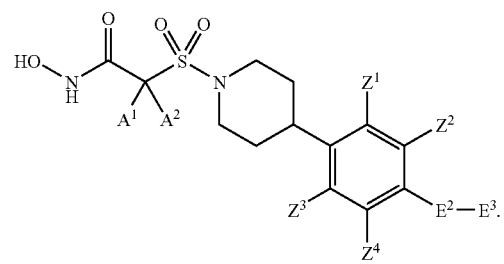

(289-1)

In these embodiments:

$A^1$ and $A^2$, together with the carbon to which they are bonded, form heterocyclyl or carbocyclyl. The heterocyclyl and carbocyclyl optionally are substituted with up to 3 independently selected $R^x$ substituents. Alternatively, $A^1$ and $A^2$ are independently selected as follows:

$A^1$ is hydrogen, alkyl, alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, or heterocyclylalkylthioalkyl. Any member of such group optionally is substituted with up to 3 independently selected $R^x$ substituents.

$A^2$ is alkyl, alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, or heterocyclylalkylthioalkyl. Any member of such group optionally is substituted with up to 3 independently selected R$^x$ substituents.

E$^2$ is selected from the group consisting of: —O—, —C(O)—, —C(O)—O—, —O—C(O)—, —N(R$^a$)—, —C(O)—N(R$^a$)—, —N(R$^a$)—C(O)—, —C(O)—N(R$^a$)—N(R$^a$)—C(O)—, —S—, —S(O)—, —S(O)$_2$—, —N(R$^a$)—S(O)$_2$—, —S(O)$_2$—N(R$^a$)—, —O—S(O)$_2$—, —S(O)$_2$—O—, —C(NH)—, and —C(NOH)—.

E$^3$ comprises greater than 3 carbon atoms. In addition, E$^3$ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

Particularly Preferred Embodiments of Embodiment No. 3-DD

In some particularly preferred embodiments, A$^1$ and A$^2$ are independently selected from the group consisting of alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, and heterocyclylalkylthioalkyl. Any member of such group optionally is substituted with up to 3 independently selected R$^x$ substituents.

In some particularly preferred embodiments, the compound corresponds in structure to the following formula:

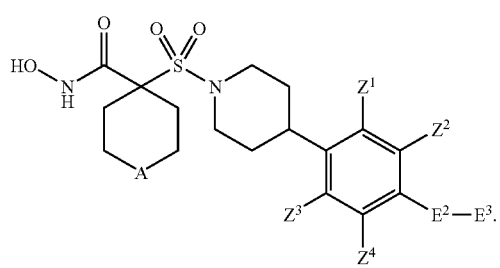

(290-1)

In some particularly preferred embodiments, A is —O—.
In some particularly preferred embodiments, A is —N(H)—.
In some particularly preferred embodiments, A is —N(R$^x$)—. Here, R$^x$ is alkyl, alkenyl, alkynyl, alkoxyalkyl, R$^a$-oxyalkyl, alkylsulfonyl, R$^a$R$^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, Z$^1$, Z$^2$, Z$^3$, and Z$^4$ are hydrogen.

In some particularly preferred embodiments, E$^2$ is —O—.

In some particularly preferred embodiments, -E$^2$-E$^3$ is alkoxy.

Examples of particularly preferred compounds include the compounds corresponding in structure to one of the following formulas:

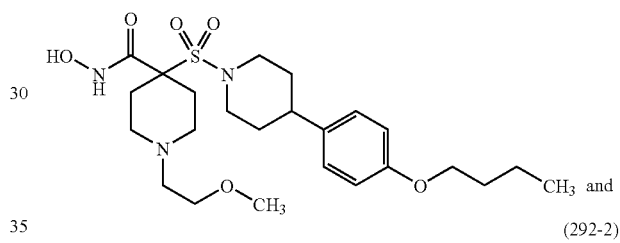

(292-1)

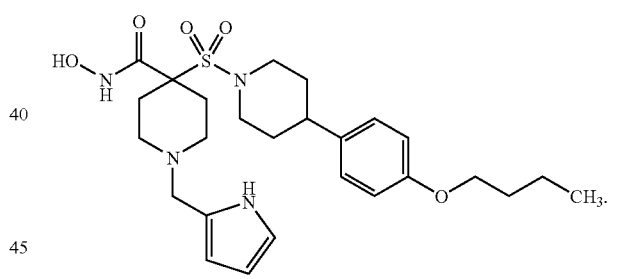

(292-2)

Preferred Embodiment No. 3-EE

In some preferred embodiments, the compounds correspond in structure to Formula (293-1):

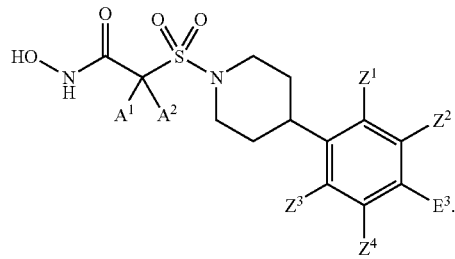

(293-1)

In these embodiments:

A¹ and A², together with the carbon to which they are bonded, form heterocyclyl or carbocyclyl. The heterocyclyl and carbocyclyl optionally are substituted with up to 3 independently selected R$^x$ substituents. Alternatively, A¹ and A² are independently selected as follows:

A¹ is hydrogen, alkyl, alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, or heterocyclylalkylthioalkyl. Any member of such group optionally is substituted with up to 3 independently selected R$^x$ substituents.

A² is selected from the group consisting of alkyl, alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, and heterocyclylalkylthioalkyl. Any member of such group optionally is substituted with up to 3 independently selected R$^x$ substituents.

E³ comprises at least 2 carbon atoms. In addition, E³ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, alkylsulfonyl, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

Each R$^a$ is independently selected from the group consisting of hydrogen, alkyl, alkenyl, alkynyl, alkoxyalkyl, bisalkoxyalkyl, alkylthioalkyl, alkylthioalkenyl, alkylsulfoxidoalkyl, alkylsulfonyl, alkylsulfonylalkyl, carbocyclyl, carbocyclylalkyl, carbocyclyloxyalkyl, carbocyclylalkoxyalkyl, carbocyclylthioalkyl, carbocyclylthioalkenyl, carbocyclylsulfoxidoalkyl, carbocyclylsulfonyl, carbocyclylsulfonylalkyl, heterocyclyl, heterocyclylalkyl, heterocyclyloxyalkyl, heterocyclylalkoxyalkyl, heterocyclylthioalkyl, heterocyclylsulfoxidoalkyl, heterocyclylsulfonyl, heterocyclylsulfonylalkyl, aminoalkyl, aminoalkylsulfonyl, and alkoxyalkylaminoalkyl. Each such substituent is, in turn, optionally substituted:

on any substitutable carbon with one or more substituents independently selected from the group consisting of halogen, hydroxy, cyano, carboxy, thiol, sulfo, nitro, nitroso, oxo, thioxo, and imino; and on any substitutable amino nitrogen with up to 2 substituents independently selected from the group consisting of alkyl, alkylcarbonyl, carbocyclyl, and carbocyclylalkyl.

As to Z¹, Z², Z³, and Z⁴:

Z¹ and Z³ are independently selected from the group consisting of hydrogen, halogen, hydroxy, amino, mono-alkylamino, di-alkylamino, nitro, nitroso, alkyl, alkoxy, alkoxyalkyl, and alkylthio. Any such substituent optionally is substituted with one or more substituents independently selected from the group consisting of halogen, hydroxy, cyano, carboxy, thiol, sulfo, nitro, nitroso, oxo, thioxo, and imino; and Z² and Z⁴ are independently selected from the group consisting of hydrogen, halogen, hydroxy, amino, mono-alkylamino, di-alkylamino, nitro, nitroso, alkyl, alkoxy, alkoxyalkyl, and alkylthio. Here:

the alkoxyalkyl, alkylthio, mono-alkylamino, and di-alkylamino optionally are substituted with one or more substituents independently selected from the group consisting of halogen, hydroxy, cyano, carboxy, thiol, sulfo, nitro, nitroso, oxo, thioxo, and imino; and the alkyl and alkoxy comprise at least two carbons and/or are substituted with one or more substituents independently selected from the group consisting of halogen, hydroxy, cyano, carboxy, thiol, sulfo, nitro, nitroso, oxo, thioxo, and imino.

Particularly Preferred Embodiments of Embodiment No. 3-EE

In some particularly preferred embodiments, A¹ and A² are independently selected from the group consisting of alkoxyalkyl, alkylthioalkyl, alkenyl, alkynyl, carbocyclyl, carbocyclylalkyl, carbocyclylalkenyl, carbocyclylalkynyl, carbocyclyloxyalkyl, carbocyclylalkoxyalkyl, carbocyclylalkylthio, carbocyclylthioalkyl, carbocyclylalkylthioalkyl, heterocyclyl, heterocyclylalkyl, heterocyclylalkenyl, heterocyclylalkynyl, heterocyclyloxyalkyl, heterocyclylalkoxyalkyl, heterocyclylalkylthio, heterocyclylthioalkyl, and heterocyclylalkylthioalkyl. Any member of such group optionally is substituted with up to 3 independently selected R$^x$ substituents.

In some particularly preferred embodiments, the compound corresponds in structure to the following formula:

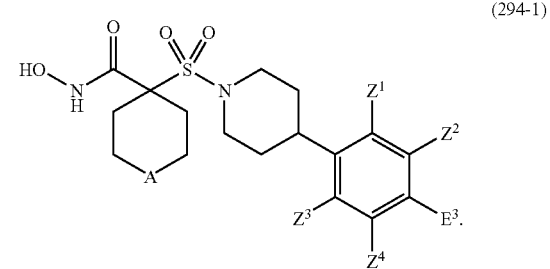

(294-1)

In some particularly preferred embodiments, A is —O—.

In some particularly preferred embodiments, A is —N(H)—.

In some particularly preferred embodiments, A is —N(R$^x$)—. Here, R$^x$ is alkyl, alkenyl, alkynyl, alkoxyalkyl, R$^a$-oxyalkyl, alkylsulfonyl, R$^a$R$^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, $E^3$ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent is, in turn, optionally substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

In some particularly preferred embodiments, $Z^1$, $Z^2$, $Z^3$, and $Z^4$ are hydrogen.

In some particularly preferred embodiments, -$E^3$ is alkyl.

One example of a particularly preferred compound is:

(296-1)

Preferred Embodiment No. 3-FF

In some preferred embodiments, $E^3$ is perhaloalkyl and comprises at least two carbon atoms.

Particularly Preferred Embodiments of Embodiment No. 3-FF

In some particularly preferred embodiments,

In some particularly preferred embodiments, $Z^1$, $Z^2$, $Z^3$, and $Z^4$ are hydrogen.

In some particularly preferred embodiments, Y is nitrogen.

In some particularly preferred embodiments, Y is carbon bonded to hydrogen.

In some particularly preferred embodiments, $E^2$ is —O—.

In some particularly preferred embodiments, $E^3$ is perfluroalkyl.

One example of a particularly preferred compound is:

(301-1)

Preferred Embodiment No. 4

In some preferred embodiments, the compounds correspond in structure to Formula (302-1):

(302-1)

In these embodiments:

$E^2$ is —C(O)—, —C(O)—O—, —C(O)—N($R^a$)—, —S(O)$_2$—, —S(O)$_2$—N($R^a$)—, —C(NH)—, —C(NOH)—, or a bond.

$E^3$ is hydrogen, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Each such substituent (if substitutable) optionally is substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

Particularly Preferred Embodiments of Embodiment No. 4

In some particularly preferred embodiments, the compound corresponds in structure to the following formula:

(303-1)

In some particularly preferred embodiments, A is —O—.

In some particularly preferred embodiments, A is —N(H)—.

In some particularly preferred embodiments, A is —N(R$^x$)—. Here, R$^x$ is alkyl, alkenyl, alkynyl, alkoxyalkyl, R$^a$-oxyalkyl, alkylsulfonyl, R$^a$R$^a$-aminoalkyl, carbocyclyl, carbocyclylalkyl, carbocyclylsulfonyl, heterocyclyl, heterocyclylalkyl, or heterocyclylsulfonyl. Each such substituent (if substitutable) optionally is substituted with one or more substituents independently selected from the group consisting of halogen, hydroxy, cyano, amino, carboxy, thiol, sulfo, nitro, nitroso, oxo, thioxo, imino, alkyl, alkoxy, alkoxyalkyl, and alkoxyalkoxy. As to such optional substituents:

the alkyl, alkoxy, alkoxyalkyl, and alkoxyalkoxy optionally are substituted with one or more substituents independently selected from the group consisting of halogen and hydroxy; and the amino optionally is substituted by up to 2 independently selected alkyl.

In some particularly preferred embodiments, A is —S—, —S(O)—, or —S(O)$_2$—.

In some particularly preferred embodiments, E$^2$ is a bond. One example of a particularly preferred compound is:

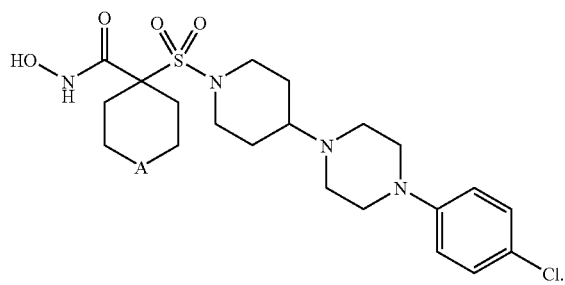

(305-1)

Preferred Embodiment No. 5

In some preferred embodiments, the compounds correspond in structure to Formula (307-1):

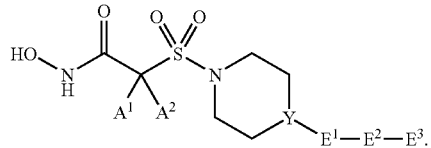

(307-1)

In these embodiments:

E$^1$ is alkyl optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional the alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

E$^2$ is —O—, —C(O)—, —C(O)—O—, —O—C(O)—, —N(R$^a$)—, —C(O)—N(R$^a$)—, —N(R$^a$)—C(O)—, —C(O)—N(R$^a$)—N(R$^a$)—C(O)—, —S—, —S(O)—, —S(O)$_2$—, —N(R$^a$)—S(O)$_2$—, —S(O)$_2$—N(R$^a$)—, —O—S(O)$_2$—, —S(O)$_2$—O—, —C(NH)—, or —C(NOH)—.

E$^3$ is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Any substitutable member of such group optionally is substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

Particularly Preferred Embodiments of Embodiment No. 5

In some particularly preferred embodiments, Y is nitrogen.

In some particularly preferred embodiments, Y is carbon bonded to hydrogen.

In some particularly preferred embodiments, E$^1$ is alkyl.

In some particularly preferred embodiments, E$^1$ is methyl.

In some particularly preferred embodiments, E$^2$ is —O—.

In some particularly preferred embodiments, E$^3$ is alkyl or carbocyclylalkyl. The alkyl and carbocyclylalkyl optionally are substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. The optional alkyl, alkoxy, alkylthio, carbocyclyl, and carbocyclylalkyl substituents are, in turn, optionally substituted with one or more substituents independently selected from the group consisting of halogen, hydroxy, cyano, carboxy, thiol, sulfo, nitro, nitroso, oxo, thioxo, imino, aminocarbonyl, and amino.

In some particularly preferred embodiments, E$^3$ is alkyl partially substituted with halogen. Examples of such compounds include those corresponding in structure to one of the following formulas:

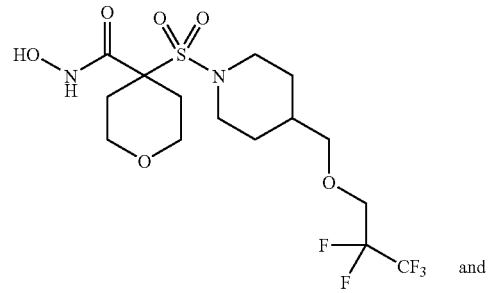

(319-1)

and

-continued (319-2)
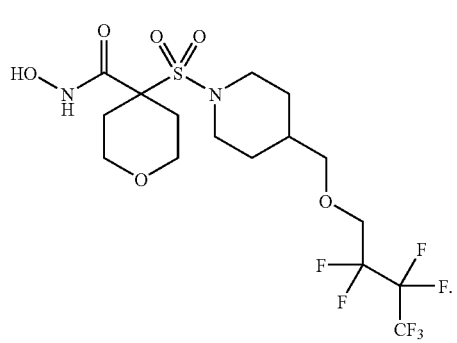

(325-1)
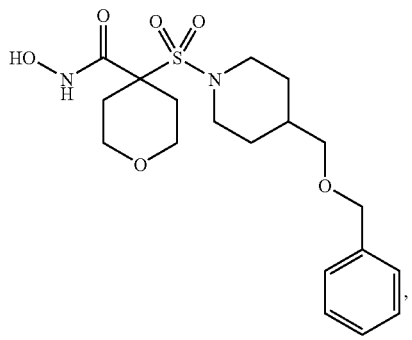

In some particularly preferred embodiments, E³ is alkyl comprising a carbon bonded to at least one hydrogen and at least one halogen. Examples of such compounds include those corresponding in structure to one of the following formulas:

(325-2)
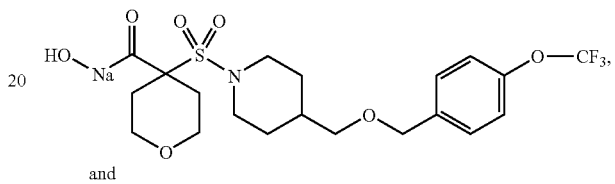

and (323-1)
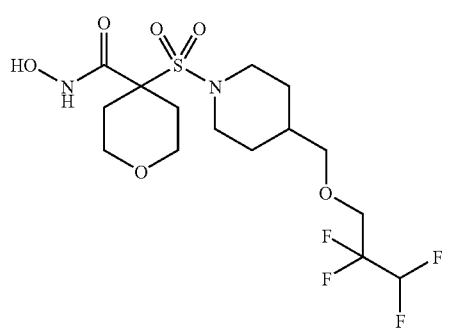

and (325-3)
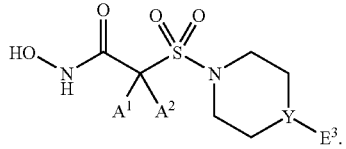

Preferred Embodiment No. 6

In some preferred embodiments, the compounds correspond in structure to Formula (339-1):

(339-1)

(323-2)
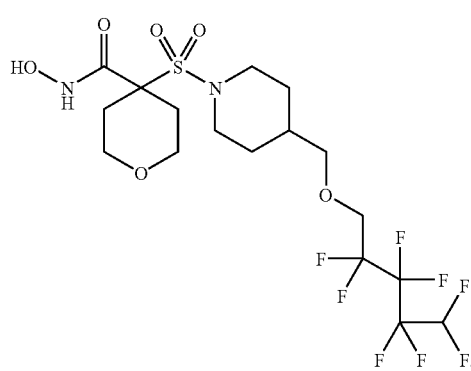

In some particularly preferred embodiments, E³ is phenylalkyl. Here, the phenylalkyl optionally is substituted with one or more substituents independently selected from the group consisting of halogen, hydroxy, cyano, carboxy, thiol, sulfo, nitro, nitroso, oxo, thioxo, imino, amino, alkyl, alkoxy, alkylthio, carbocyclyl, and carbocyclylalkyl. The optional the alkyl, alkoxy, alkylthio, carbocyclyl, and carbocyclylalkyl substituents are, in turn, optionally substituted with one or more substituents independently selected from the group consisting of halogen, hydroxy, cyano, carboxy, thiol, sulfo, nitro, nitroso, oxo, thioxo, imino, aminocarbonyl, and amino. Examples of such compounds include those corresponding in structure to one of the following formulas:

In these embodiments, E³ is alkenyl or alkynyl. The alkenyl and alkynyl optionally are substituted with one or more substituents independently selected from the group consisting of halogen, hydroxy, cyano, carboxy, thiol, sulfo, nitro, nitroso, oxo, thioxo, imino, amino (optionally substituted with up to 2 substituents independently selected from the group consisting of alkyl and carbocyclylalkyl), alkyl, alkoxy, alkylthio, carbocyclyl, and carbocyclylalkyl. Such optional substituents, in turn, optionally are substituted with one or more substituents independently selected from the group consisting of halogen, hydroxy, cyano, carboxy, thiol, sulfo, nitro, nitroso, oxo, thioxo, imino, aminocarbonyl, and amino.

Particularly Preferred Embodiments of Embodiment No. 6

In some particularly preferred embodiments, Y is nitrogen.

In some particularly preferred embodiments, Y is carbon bonded to hydrogen.

In some particularly preferred embodiments, $E^3$ is alkenyl. Examples of such compounds include those corresponding in structure to one of the following formulas:

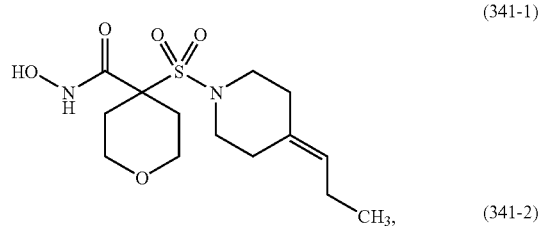
(341-1)

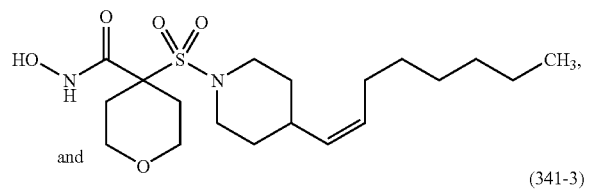
(341-2)

and

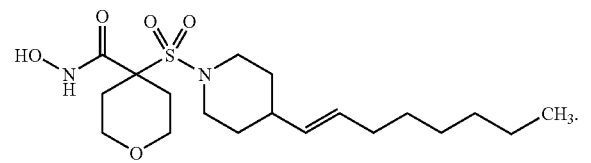
(341-3)

Preferred Embodiment No. 7

In some preferred embodiments, the compounds correspond in structure to Formula (342-1):

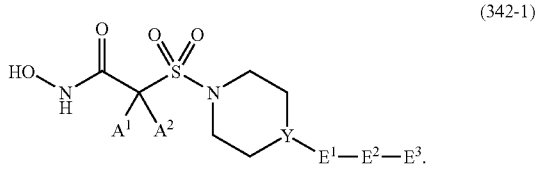
(342-1)

In these embodiments:

$-E^1-E^2$ is —O—, —C(O)—, —C(O)—O—, —O—C(O)—, —N(R$^a$)—, —C(O)—N(R$^a$)—, —N(R$^a$)—C(O)—, —C(O)—N(R$^a$)—N(R$^a$)—C(O)—, —S—, —S(O)—, —S(O)$_2$—, —N(R$^a$)—S(O)$_2$—, —S(O)$_2$—N(R$^a$)—, —O—S(O)$_2$—, —S(O)$_2$—O—, —C(NH)—, —C(NOH)—, or alkyl. The alkyl optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. The optional alkyl, alkoxy, alkoxyalkyl, alkylthio, mono-alkylamino, and di-alkylamino substituents are, in turn, optionally substituted with one or more substituents independently selected from the group consisting of halogen, hydroxy, cyano, carboxy, thiol, sulfo, nitro, nitroso, oxo, thioxo, and imino.

$E^3$ comprises at least 5 carbon atoms and is alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, or aminoalkyl. Any member of such group optionally is substituted with one or more substituents independently selected from the group consisting of halogen, hydroxy, cyano, carboxy, thiol, sulfo, nitro, nitroso, oxo, thioxo, imino, amino (which is optionally substituted with up to 2 substituents independently selected from the group consisting of alkyl and carbocyclylalkyl), alkyl, alkoxy, alkylthio, carbocyclyl, and carbocyclylalkyl. Such optional substituents are, in turn, optionally substituted with one or more substituents independently selected from the group consisting of halogen, hydroxy, cyano, carboxy, thiol, sulfo, nitro, nitroso, oxo, thioxo, imino, aminocarbonyl, and amino Particularly Preferred Embodiments of Embodiment No. 7

In some particularly preferred embodiments, Y is nitrogen.

In some particularly preferred embodiments, Y is carbon bonded to hydrogen.

In some particularly preferred embodiments, $E^3$ is $C_6$–$C_{12}$-alkyl.

In some particularly preferred embodiments, $-E^1-E^2$ is alkyl.

In some particularly preferred embodiments, $-E^1-E^2$ is methyl. One example of a particularly preferred compound is:

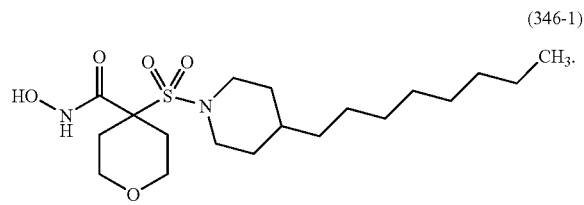
(346-1)

In some particularly preferred embodiments, $E^1-E^2$ is —O—. One example of a particularly preferred compound is:

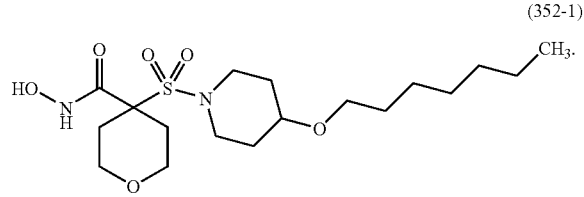
(352-1)

Preferred Embodiment No. 8

In some preferred embodiments, the compounds correspond in structure to Formula (360-1):

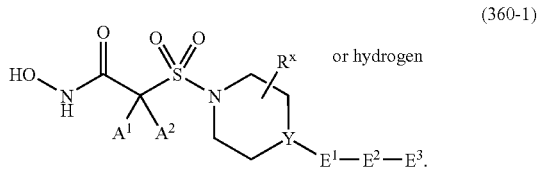
(360-1)

In these embodiments:

$E^1$ is $-E^{1A}-E^{1B}$.

$E^{1A}$ is —O—, —C(O)—, —C(O)—O—, —O—C(O)—, —N(R$^a$)—, —C(O)—N(R$^a$)—, —N(R$^a$)—C(O)—, —C(O)—N(R$^a$)—N(R$^a$)—C(O)—, —S—, —S(O)—, —S(O)$_2$—, —N(R$^a$)—S(O)$_2$—, —S(O)$_2$—N(R$^a$)—, —O—S(O)$_2$—, —S(O)$_2$—O—, —C(NH)—, —C(NOH)—, or a bond.

$E^{1B}$ is heterocylcylalkyl optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. Any member of such group optionally is substituted with one or more substituents independently selected from the group consisting of halogen, hydroxy, cyano, carboxy, thiol, sulfo, nitro, nitroso, oxo, thioxo, and imino.

$E^2$ is —O—, —C(O)—, —C(O)—O—, —O—C(O)—, —N($R^a$)—, —C(O)—N($R^a$)—, —N($R^a$)—C(O)—, —C(O)—N($R^a$)—N($R^a$)—C(O)—, —S—, —S(O)—, —S(O)$_2$—, —N($R^a$)—S(O)$_2$—, —S(O)$_2$—N($R^a$)—, —O—S(O)$_2$—, —S(O)$_2$—O—, —C(NH)—, —C(NOH)—, or a bond.

$E^3$ is halogen, cyano, alkyl, alkenyl, alkynyl, alkoxyalkyl, alkoxyalkoxyalkyl, alkylthioalkyl, alkylthioalkylthioalkyl, alkylthioalkoxyalkyl, alkoxyalkylthioalkyl, aminoalkyl, carbocyclyl, carbocyclylalkyl, heterocyclyl, or heterocyclylalkyl. Any member of such group optionally is substituted with one or more substituents independently selected from the group consisting of halogen, hydroxy, cyano, carboxy, thiol, sulfo, nitro, nitroso, oxo, thioxo, imino, hydroxyimino, amino (optionally substituted with up to two substituents independently selected from alkyl and carbocyclylalkyl), alkyl, alkoxy, alkylthio, carbocyclyl, and carbocyclylalkyl. And any such optional substituent is, in turn, optionally substituted with one or more substituents independently selected from the group consisting of halogen, hydroxy, cyano, carboxy, thiol, sulfo, nitro, nitroso, oxo, thioxo, imino, aminocarbonyl, and amino.

Particularly Preferred Embodiments of Embodiment No. 8

In some particularly preferred embodiments, Y is nitrogen.

In some particularly preferred embodiments, Y is carbon bonded to hydrogen.

In some particularly preferred embodiments, the compound corresponds in structure to Formula (361-1):

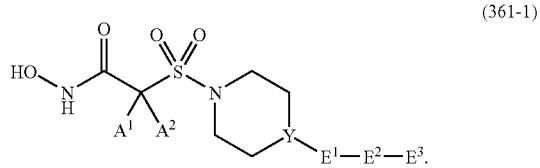

(361-1)

In some particularly preferred embodiments, $E^1$ is pyrazinyl-$C_2$–$C_6$-alkyl, pyrimidyl-$C_2$–$C_6$-alkyl, pyridazinyl-$C_2$–$C_6$-alkyl, furanyl-$C_2$–$C_6$-alkyl, thienyl-$C_2$–$C_6$-alkyl, pyrrolyl-$C_2$–$C_6$-alkyl, imidazolyl-$C_2$–$C_6$-alkyl, pyrazolyl-$C_2$–$C_6$-alkyl, triazolyl-$C_2$–$C_6$-alkyl, oxazolyl-$C_2$–$C_6$-alkyl, isoxazolyl-$C_2$–$C_6$-alkyl, thiazolyl-$C_2$–$C_6$-alkyl, isothiazolyl-$C_2$–$C_6$-alkyl, thiodiazolyl-$C_2$–$C_6$-alkyl, oxathiazolyl-$C_2$–$C_6$-alkyl, oxadiazolyl-$C_2$–$C_6$-alkyl, oxathiolyl-$C_2$–$C_6$-alkyl, pyranyl-$C_2$–$C_6$-alkyl, pyridinyl-$C_2$–$C_6$-alkyl, triazinyl-$C_2$–$C_6$-alkyl, tetrazolyl-$C_2$–$C_6$-alkyl, oxazinyl-$C_2$–$C_6$-alkyl, azepinyl-$C_2$–$C_6$-alkyl, diazepinyl-$C_2$–$C_6$-alkyl, pyrazinyl-$C_1$–$C_5$-alkoxy, pyrimidyl-$C_1$–$C_5$-alkoxy, pyridazinyl-$C_1$–$C_5$-alkoxy, furanyl-$C_1$–$C_5$-alkoxy, thienyl-$C_1$–$C_5$-alkoxy, pyrrolyl-$C_1$–$C_5$-alkoxy, imidazolyl-$C_1$–$C_5$-alkoxy, pyrazolyl-$C_1$–$C_5$-alkoxy, triazolyl-$C_1$–$C_5$-alkoxy, oxazolyl-$C_1$–$C_5$-alkoxy, isoxazolyl-$C_1$–$C_5$-alkoxy, thiazolyl-$C_1$–$C_5$-alkoxy, isothiazolyl-$C_1$–$C_5$-alkoxy, thiodiazolyl-$C_1$–$C_5$-alkoxy, oxathiazolyl-$C_1$–$C_5$-alkoxy, oxadiazolyl-$C_1$–$C_5$-alkoxy, oxathiolyl-$C_1$–$C_5$-alkoxy, pyranyl-$C_1$–$C_5$-alkoxy, pyridinyl-$C_1$–$C_5$-alkoxy triazinyl-$C_1$–$C_5$-alkoxy, tetrazolyl-$C_1$–$C_5$-alkoxy, oxazinyl-$C_1$–$C_5$-alkoxy, azepinyl-$C_1$–$C_5$-alkoxy, or diazepinyl-$C_1$–$C_5$-alkoxy. Each such substituent is optionally substituted with one or more substituents independently selected from the group consisting of halogen, hydroxy, amino, mono-alkylamino, di-alkylamino, nitro, nitroso, alkyl, alkoxy, alkoxyalkyl, and alkylthio. Each such optional substuituent, in turn, is optionally substituted with one or more substituents independently selected from the group consisting of halogen, hydroxy, cyano, carboxy, thiol, sulfo, nitro, nitroso, thioxo, and imino.

In some particularly preferred embodiments, $E^1$ is pyrazinyl-$C_3$–$C_4$-alkyl, pyrimidinyl-$C_3$–$C_4$-alkyl, pyridazinyl-$C_3$–$C_4$-alkyl, furanyl-$C_3$–$C_4$-alkyl, thienyl-$C_3$–$C_4$-alkyl, pyrrolyl-$C_3$–$C_4$-alkyl, imidazolyl-$C_3$–$C_4$-alkyl, pyrazolyl-$C_3$–$C_4$-alkyl, triazolyl-$C_3$–$C_4$-alkyl, oxazolyl-$C_3$–$C_4$-alkyl, isoxazolyl-$C_3$–$C_4$-alkyl, thiazolyl-$C_3$–$C_4$-alkyl, isothiazolyl-$C_3$–$C_4$-alkyl, thiodiazolyl-$C_3$–$C_4$-alkyl, oxathiazolyl-$C_3$–$C_4$-alkyl, oxadiazolyl-$C_3$–$C_4$-alkyl, oxathiolyl-$C_3$–$C_4$-alkyl, pyranyl-$C_3$–$C_4$-alkyl, pyridinyl-$C_3$–$C_4$-alkyl, triazinyl-$C_3$–$C_4$-alkyl, tetrazolyl-$C_3$–$C_4$-alkyl, oxazinyl-$C_3$–$C_4$-alkyl, azepinyl-$C_3$–$C_4$-alkyl, diazepinyl-$C_3$–$C_4$-alkyl, pyrazinyl-$C_2$–$C_3$-alkoxy, pyrimidinyl-$C_2$–$C_3$-alkoxy, pyridazinyl-$C_2$–$C_3$-alkoxy, furanyl-$C_2$–$C_3$-alkoxy, thienyl-$C_2$–$C_3$-alkoxy pyrrolyl-$C_2$–$C_3$-alkoxy, imidazolyl-$C_2$–$C_3$-alkoxy, pyrazolyl-$C_2$–$C_3$-alkoxy, triazolyl-$C_2$–$C_3$-alkoxy, oxazolyl-$C_2$–$C_3$-alkoxy, isoxazolyl-$C_2$–$C_3$-alkoxy, thiazolyl-$C_2$–$C_3$-alkoxy, isothiazolyl-$C_2$–$C_3$-alkoxy, thiodiazolyl-$C_2$–$C_3$-alkoxy, oxathiazolyl-$C_2$–$C_3$-alkoxy, oxadiazolyl-$C_2$–$C_3$-alkoxy, oxathiolyl-$C_2$–$C_3$-alkoxy, pyranyl-$C_2$–$C_3$-alkoxy, pyridinyl-$C_2$–$C_3$-alkoxy, triazinyl-$C_2$–$C_3$-alkoxy, tetrazolyl-$C_2$–$C_3$-alkoxy, oxazinyl-$C_2$–$C_3$-alkoxy, azepinyl-$C_2$–$C_3$-alkoxy, or diazepinyl-$C_2$–$C_3$-alkoxy.

In some particularly preferred embodiments, $E^1$ is oxadiazolyl-$C_3$–$C_4$-alkyl, tetrazolyl-$C_3$–$C_4$-alkyl, oxadiazolyl-$C_2$–$C_3$-alkoxy, or tetrazolyl-$C_2$–$C_3$-alkoxy.

In some particularly preferred embodiments, $E^2$ is a bond.

Examples of particularly preferred compounds include the following:

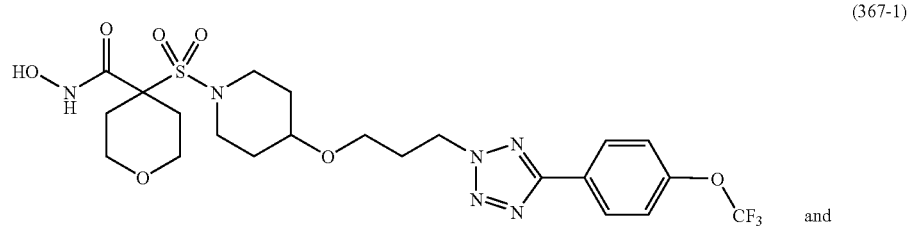

(367-1)

and

-continued

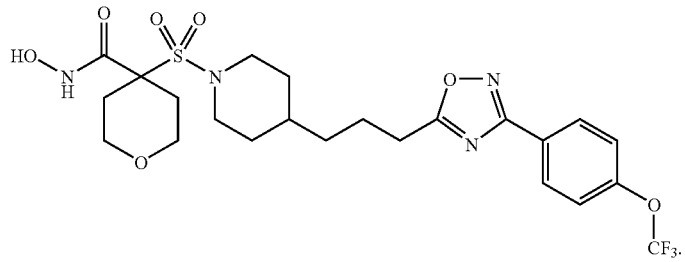

(367-2)

Other particularly preferred compounds include the following:

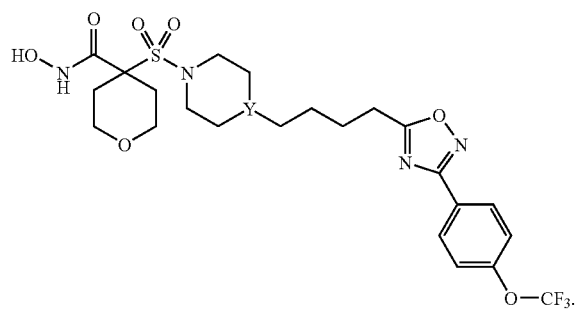

(368-1)

A-2. Preferred MMP Selectivities

The hydroxamic acid compound or salt preferably has an inhibitory activity against MMP-1 or MMP-14 that is substantially less than its inhibitory activity against MMP-2, MMP-9, or MMP-13. In other words, the hydroxamic acid compound or salt preferably has an in inhibition constant ($K_i$) against at least one of MMP-2, MMP-9, and MMP-13 that is no greater than about 0.1 times its inhibition constant(s) against at least one of MMP-1 and MMP-14. The inhibition constant of a compound or salt thereof may be determined using an in vitro inhibition assay, such as the $K_i$ assay described below in Examples 28–54.

In some particularly preferred embodiments, the hydroxamic acid compound or salt preferably has a $K_i$ against MMP-2 that is no greater than about 0.1 (more preferably no greater than about 0.01, even more preferably no greater than about 0.001, still more preferably no greater than about 0.0001, and still even more preferably no greater than about 0.00001) times its $K_i(s)$ against one or both of MMP-1 and MMP-14.

In some particularly preferred embodiments, the hydroxamic acid compound or salt preferably has a $K_i$ against MMP-9 that is no greater than about 0.1 (more preferably no greater than about 0.01, even more preferably no greater than about 0.001, still more preferably no greater than about 0.0001, and still even more preferably no greater than about 0.00001) times its $K_i(s)$ against one or both of MMP-1 and MMP-14. It is believed that such a selectivity profile is often particularly preferred when treating, for example, a pathological condition of the central nervous system associated with nitrosative or oxidative stress. Such a pathological condition may be, for example, cerebral ischemia, stroke, or other neurodegenerative disease.

In some particularly preferred embodiments, the hydroxamic acid compound or salt preferably has a $K_i$ against MMP-13 that is no greater than about 0.1 (more preferably no greater than about 0.01, even more preferably no greater than about 0.001, still more preferably no greater than about 0.0001, and still even more preferably no greater than about 0.00001) times its $K_i(s)$ against one or both of MMP-1 and MMP-14. It is believed that such a selectivity profile is often particularly preferred when treating, for example, a cardiovascular condition or arthritis.

In some particularly preferred embodiments, the hydroxamic acid compound or salt preferably has $K_i$'s against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $K_i(s)$ against one or both of MMP-1 and MMP-14. It is believed that such a selectivity profile is often particularly preferred when treating, for example, cancer, a cardiovascular condition, or an ophthalmologic condition.

In some particularly preferred embodiments, the hydroxamic acid compound or salt preferably has $K_i$'s against all of MMP-2, MMP-9, and MMP-13 that are no greater than about 0.1 (more preferably no greater than about 0.01, even more preferably no greater than about 0.001, still more preferably no greater than about 0.0001, and still even more preferably no greater than about 0.00001) times its $K_i(s)$ against one or both of MMP-1 and MMP-14. It is believed that such a selectivity profile is often particularly preferred when treating, for example, cancer, a cardiovascular condition, arthritis, or an ophthalmologic condition.

In some particularly preferred embodiments, the hydroxamic acid compound or salt preferably has a $K_i$ against MMP-2 that is no greater than about 0.1 (more preferably no greater than about 0.01, even more preferably no greater than about 0.001, still more preferably no greater than about 0.0001, and still even more preferably no greater than about 0.00001) times its $K_i$'s against both MMP-1 and MMP-14.

In some particularly preferred embodiments, the hydroxamic acid compound or salt preferably has a $K_i$ against MMP-9 that is no greater than about 0.1 (more preferably no greater than about 0.01, even more preferably no greater than about 0.001, still more preferably no greater than about 0.0001, and still even more preferably no greater than about 0.00001) times its $K_i$'s against both MMP-1 and MMP-14. It is believed that such a selectivity profile is often particularly preferred when treating, for example, a pathological condition of the central nervous system associated with nitrosative or oxidative stress. Such a pathological condition may be, for example, cerebral ischemia, stroke, or other neurodegenerative disease.

In some particularly preferred embodiments, the hydroxamic acid compound or salt preferably has a $K_i$ against MMP-13 that is no greater than about 0.1 (more preferably no greater than about 0.01, even more preferably no greater than about 0.001, still more preferably no greater than about 0.0001, and still even more preferably no greater than about 0.00001) times its $K_i$'s against both MMP-1 and MMP-14. It is believed that such a selectivity profile is often particularly preferred when treating, for example, a cardiovascular condition or arthritis.

In some particularly preferred embodiments, the hydroxamic acid compound or salt preferably has $K_i$'s against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $K_i$'s against both of MMP-1 and MMP-14. It is believed that such a selectivity profile is often particularly preferred when treating, for example, cancer, a cardiovascular condition, or an ophthalmologic condition.

In some particularly preferred embodiments, the hydroxamic acid compound or salt preferably has $K_i$'s against all of MMP-2, MMP-9, and MMP-13 that are no greater than about 0.1 (more preferably no greater than about 0.01, even more preferably no greater than about 0.001, still more preferably no greater than about 0.0001, and still even more preferably no greater than about 0.00001) times its $K_i$'s against both of MMP-1 and MMP-14. It is believed that such a selectivity profile is often particularly preferred when treating, for example, cancer, a cardiovascular condition, arthritis, or an ophthalmologic condition.

The activity and selectivity of a hydroxamic acid compound or salt may alternatively be determined using an in vitro $IC_{50}$ assay, such as the $IC_{50}$ assay described below in Examples 28–54. In that instance, the hydroxamic acid compound or salt preferably has an $IC_{50}$ value against at least one of MMP-2, MMP-9, and MMP-13 that is no greater than about 0.1 times its $IC_{50}$ value(s) against at least one of MMP-1 and MMP-14.

In some particularly preferred embodiments, the hydroxamic acid compound or salt preferably has an $IC_{50}$ value against MMP-2 that is no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14.

In some particularly preferred embodiments, the hydroxamic acid compound or salt preferably has an $IC_{50}$ value against MMP-9 that is no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14. It is believed that such a selectivity profile is often particularly preferred when treating, for example, a pathological condition of the central nervous system associated with nitrosative or oxidative stress. Such a pathological condition may be, for example, cerebral ischemia, stroke, or other neurodegenerative disease.

In some particularly preferred embodiments, the hydroxamic acid compound or salt preferably has an $IC_{50}$ value against MMP-13 that is no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14. It is believed that such a selectivity profile is often particularly preferred when treating, for example, a cardiovascular condition or arthritis.

In some particularly preferred embodiments, the hydroxamic acid compound or salt preferably has $IC_{50}$ values against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14. It is believed that such a selectivity profile is often particularly preferred when treating, for example, cancer, a cardiovascular condition, or an ophthalmologic condition.

In some particularly preferred embodiments, the hydroxamic acid compound or salt preferably has $IC_{50}$ values against all of MMP-2, MMP-9, and MMP-13 that are no greater than about 0.1 (more preferably no greater than about 0.01, even more preferably no greater than about 0.001, still more preferably no greater than about 0.0001, and still even more preferably no greater than about 0.00001) times its $IC_{50}$ value(s) against one or both of MMP-1 and MMP-14. It is believed that such a selectivity profile is often particularly preferred when treating, for example, cancer, a cardiovascular condition, arthritis, or an ophthalmologic condition.

In some particularly preferred embodiments, the hydroxamic acid compound or salt preferably has an $IC_{50}$ value against MMP-2 that is no greater than about 0.1 (more preferably no greater than about 0.01, even more preferably no greater than about 0.001, still more preferably no greater than about 0.0001, and still even more preferably no greater than about 0.00001) times its $IC_{50}$ values against both MMP-1 and MMP-14.

In some particularly preferred embodiments, the hydroxamic acid compound or salt preferably has an $IC_{50}$ value against MMP-9 that is no greater than about 0.1 (more preferably no greater than about 0.01, even more preferably no greater than about 0.001, still more preferably no greater than about 0.0001, and still even more preferably no greater than about 0.00001) times its $IC_{50}$ values against both MMP-1 and MMP-14. It is believed that such a selectivity profile is often particularly preferred when treating, for example, a pathological condition of the central nervous system associated with nitrosative or oxidative stress. Such a pathological condition may be, for example, cerebral ischemia, stroke, or other neurodegenerative disease.

In some particularly preferred embodiments, the hydroxamic acid compound or salt preferably has an $IC_{50}$ value against MMP-13 that is no greater than about 0.1 (more preferably no greater than about 0.01, even more preferably no greater than about 0.001, still more preferably no greater than about 0.0001, and still even more preferably no greater than about 0.00001) times its $IC_{50}$ values against both MMP-1 and MMP-14. It is believed that such a selectivity profile is often particularly preferred when treating, for example, a cardiovascular condition or arthritis.

In some particularly preferred embodiments, the hydroxamic acid compound or salt preferably has $IC_{50}$ values against both MMP-2 and MMP-9 that are no greater than about 0.1 (more preferably no greater than about 0.01, even more preferably no greater than about 0.001, still more preferably no greater than about 0.0001, and still even more preferably no greater than about 0.00001) times its $IC_{50}$ values against both of MMP-1 and MMP-14. It is believed that such a selectivity profile is often particularly preferred when treating, for example, cancer, a cardiovascular condition, or an ophthalmologic condition.

In some particularly preferred embodiments, the hydroxamic acid compound or salt preferably has $IC_{50}$ values against all of MMP-2, MMP-9, and MMP-13 that are no greater than about 0.1 (more preferably no greater than about 0.01, even more preferably no greater than about 0.001, still more preferably no greater than about 0.0001, and still even more preferably no greater than about 0.00001) times its $IC_{50}$ values against both of MMP-1 and MMP-14. It is believed that such a selectivity profile is often particularly preferred when treating, for example, cancer, a cardiovascular condition, arthritis, or an ophthalmologic condition.

B. Salts of the Compounds of this Invention

The compounds of this invention can be used in the form of salts derived from inorganic or organic acids. Depending on the particular compound, a salt of the compound may be advantageous due to one or more of the salt's physical properties, such as enhanced pharmaceutical stability in differing temperatures and humidities, or a desirable solubility in water or oil. In some instances, a salt of a compound also may be used as an aid in the isolation, purification, and/or resolution of the compound.

Where a salt is intended to be administered to a patient (as opposed to, for example, being used in an in vitro context), the salt preferably is pharmaceutically acceptable. Pharmaceutically acceptable salts include salts commonly used to form alkali metal salts and to form addition salts of free acids or free bases. In general, these salts typically may be prepared by conventional means with a compound of this invention by reacting, for example, the appropriate acid or base with the compound.

Pharmaceutically-acceptable acid addition salts of the compounds of this invention may be prepared from an inorganic or organic acid. Examples of suitable inorganic acids include hydrochloric, hydrobromic acid, hydroiodic, nitric, carbonic, sulfuric, and phosphoric acid. Suitable organic acids generally include, for example, aliphatic, cycloaliphatic, aromatic, araliphatic, heterocyclic, carboxylic, and sulfonic classes of organic acids. Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), ethanesulfonate, benzenesulfonate, pantothenate, 2-hydroxyethanesulfonate, sulfanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Pharmaceutically-acceptable base addition salts of the compounds of this invention include, for example, metallic salts and organic salts. Preferred metallic salts include alkali metal (group Ia) salts, alkaline earth metal (group IIa) salts, and other physiologically acceptable metal salts. Such salts may be made from aluminum, calcium, lithium, magnesium, potassium, sodium, and zinc. Preferred organic salts can be made from amines, such as tromethamine, diethylamine, N,N'-dibenzylethylenediamine, chloroprocaine, diethanolamine, ethylenediamine, meglumine (N-methylglucamine), and procaine. Basic nitrogen-containing groups can be quaternized with agents such as lower alkyl ($C_1$–$C_6$)halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), aralkyl halides (e.g., benzyl and phenethyl bromides), and others.

Particularly preferred salts of the compounds of this invention include hydrochloric acid (HCl) salts and trifluoroacetate ($CF_3COOH$ or "TFA") salts.

C. Treating Conditions Using the Compounds and Salts of this Invention

One embodiment of this invention is directed to a process for treating a pathological condition associated with MMP activity in a mammal (e.g., a human, companion animal, farm animal, laboratory animal, zoo animal, or wild animal) having or disposed to having such a condition. Such a condition may be, for example, tissue destruction, a fibrotic disease, pathological matrix weakening, defective injury repair, a cardiovascular disease, a pulmonary disease, a kidney disease, a liver disease, an ophthalmologic disease, or a central nervous system disease. Specific examples of such conditions include osteoarthritis, rheumatoid arthritis, septic arthritis, tumor invasion, tumor metastasis, tumor angiogenesis, a decubitis ulcer, a gastric ulcer, a corneal ulcer, periodontal disease, liver cirrhosis, fibrotic lung disease, otosclerosis, atherosclerosis, multiple sclerosis, dilated cardiomyopathy, epidermal ulceration, epidermolysis bullosa, aortic aneurysm, weak injury repair, an adhesion, scarring, congestive heart failure, post myocardial infarction, coronary thrombosis, emphysema, proteinuria, bone disease, chronic obstructive pulmonary diseases, Alzheimer's disease, and diseases of the central nervous system associated with nitrosative or oxidative stress (e.g., stroke, cerebral ischemia, and other neurodegenerative diseases).

In some particularly preferred embodiments, the condition comprises arthritis.

In some particularly preferred embodiments, the condition comprises tumor invasion, tumor metastasis, or tumor angiogenesis.

In some particularly preferred embodiments, the condition comprises periodontal disease.

In some particularly preferred embodiments, the condition comprises atherosclerosis.

In some particularly preferred embodiments, the condition comprises multiple sclerosis.

In some particularly preferred embodiments, the condition comprises dilated cardiomyopathy.

In some particularly preferred embodiments, the condition comprises post myocardial infarction.

In some particularly preferred embodiments, the condition comprises congestive heart failure.

In some particularly preferred embodiments, the condition comprises chronic obstructive pulmonary disease.

In some particularly preferred embodiments, the condition comprises a disease of the central nervous system associated with nitrosative or oxidative stress. Such a disease may be, for example, stroke, cerebral ischemia, and other neurodegenerative diseases.

The condition may alternatively (or additionally) be associated with TNF-α convertase activity. Examples of such a condition include inflammation (e.g., rheumatoid arthritis), autoimmune disease, graft rejection, multiple sclerosis, a fibrotic disease, cancer, an infectious disease (e.g., malaria, mycobacterial infection, meningitis, etc.), fever, psoriasis, a cardiovascular disease (e.g., post-ischemic reperfusion injury and congestive heart failure), a pulmonary disease, hemorrhage, coagulation, hyperoxic alveolar injury, radiation damage, acute phase responses like those seen with infections and sepsis and during shock (e.g., septic shock, hemodynamic shock, etc.), cachexia, and anorexia.

The condition may alternatively (or additionally) be associated with aggrecanase activity. Examples of such a condition include inflammation diseases (e.g., osteoarthritis, rheumatoid arthritis, joint injury, reactive arthritis, acute pyrophosphate arthritis, and psoriatic arthritis) and cancer.

In this specification, the phrase "treating a condition" means ameliorating, suppressing, eradicating, preventing, reducing the risk of, or delaying the onset of the condition. The pathological condition may be (a) the result of pathological aggrecanase and/or MMP activity itself, and/or (b) affected by aggrecanase and/or MMP activity (e.g., diseases associated with TNF-α).

A wide variety of methods may be used alone or in combination to administer the hydroxamic acids and salt thereof described above. For example, the hydroxamic acids or salts thereof may be administered orally, parenterally, by inhalation spray, rectally, or topically.

Typically, a compound (or pharmaceutically acceptable salt thereof) described in this patent is administered in an amount effective to inhibit a target MMP(s) or aggrecanase. The target MMP is/are typically MMP-2, MMP-9, and/or MMP-13, with MMP-13 often being a particularly preferred target. The preferred total daily dose of the hydroxamic acid or salt thereof (administered in single or divided doses) is typically from about 0.001 to about 100 mg/kg, more preferably from about 0.001 to about 30 mg/kg, and even more preferably from about 0.01 to about 10 mg/kg (i.e., mg hydroxamic acid or salt thereof per kg body weight). Dosage unit compositions can contain such amounts or submultiples thereof to make up the daily dose. In many instances, the administration of the compound or salt will be repeated a plurality of times. Multiple doses per day typically may be used to increase the total daily dose, if desired.

Factors affecting the preferred dosage regimen include the type, age, weight, sex, diet, and condition of the patient; the severity of the pathological condition; the route of administration; pharmacological considerations, such as the activity, efficacy, pharmacokinetic, and toxicology profiles of the particular hydroxamic acid or salt thereof employed; whether a drug delivery system is utilized; and whether the hydroxamic acid or salt thereof is administered as part of a drug combination. Thus, the dosage regimen actually employed can vary widely, and, therefore, can deviate from the preferred dosage regimen set forth above.

D. Pharmaceutical Compositions Containing the Compounds and Salts of this Invention This invention also is directed to pharmaceutical compositions comprising a hydroxamic acid or salt thereof described above, and to methods for making pharmaceutical compositions (or medicaments) comprising a hydroxamic acid or salt thereof described above.

The preferred composition depends on the method of administration, and typically comprises one or more conventional pharmaceutically acceptable carriers, adjuvants, and/or vehicles. Formulation of drugs is generally discussed in, for example, Hoover, John E., *Remington's Pharmaceutical Sciences* (Mack Publishing Co., Easton, Pa.: 1975). See also, Liberman, H. A. See also, Lachman, L., eds., *Pharmaceutical Dosage Forms* (Marcel Decker, New York, N.Y., 1980).

Solid dosage forms for oral administration include, for example, capsules, tablets, pills, powders, and granules. In such solid dosage forms, the hydroxamic acids or salts thereof are ordinarily combined with one or more adjuvants. If administered per os, the hydroxamic acids or salts thereof can be mixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation, as can be provided in a dispersion of the hydroxamic acid or salt thereof in hydroxypropylmethyl cellulose. In the case of capsules, tablets, and pills, the dosage forms also can comprise buffering agents, such as sodium citrate, or magnesium or calcium carbonate or bicarbonate. Tablets and pills additionally can be prepared with enteric coatings.

Liquid dosage forms for oral administration include, for example, pharmaceutically acceptable emulsions, solutions, suspensions, syrups, and elixirs containing inert diluents commonly used in the art (e.g., water). Such compositions also can comprise adjuvants, such as wetting, emulsifying, suspending, flavoring (e.g., sweetening), and/or perfuming agents.

"Parenteral administration" includes subcutaneous injections, intravenous injections, intramuscular injections, intrasternal injections, and infusion. Injectable preparations (e.g., sterile injectable aqueous or oleaginous suspensions) can be formulated according to the known art using suitable dispersing, wetting agents, and/or suspending agents. Acceptable vehicles and solvents include, for example, water, 1,3-butanediol, Ringer's solution, isotonic sodium chloride solution, bland fixed oils (e.g., synthetic mono- or diglycerides), fatty acids (e.g., oleic acid), dimethyl acetamide, surfactants (e.g., ionic and non-ionic detergents), and/or polyethylene glycols.

Formulations for parenteral administration may, for example, be prepared from sterile powders or granules having one or more of the carriers or diluents mentioned for use in the formulations for oral administration. The hydroxamic acids or salts thereof can be dissolved in water, polyethylene glycol, propylene glycol, ethanol, corn oil, cottonseed oil, peanut oil, sesame oil, benzyl alcohol, sodium chloride, and/or various buffers.

Suppositories for rectal administration can be prepared by, for example, mixing the drug with a suitable nonirritating excipient that is solid at ordinary temperatures, but liquid at the rectal temperature and will therefore melt in the rectum to release the drug. Suitable excipients include, for example, such as cocoa butter; synthetic mono-, di-, or triglycerides; fatty acids; and/or polyethylene glycols "Topical administration" includes the use of transdermal administration, such as transdermal patches or iontophoresis devices.

Other adjuvants and modes of administration well-known in the pharmaceutical art may also be used.

E. Definitions

The term "alkyl" (alone or in combination with another term(s)) means a straight-or branched-chain saturated hydrocarbyl substituent typically containing from 1 to about 20 carbon atoms, more typically from 1 to about 8 carbon atoms, and even more typically from 1 to about 6 carbon atoms. Examples of such substituents include methyl, ethyl, n-propyl, isopropyl, n-butyl, isobutyl, sec-butyl, tert-butyl, pentyl, iso-amyl, hexyl, octyl, and the like.

The term "alkenyl" (alone or in combination with another term(s)) means a straight- or branched-chain hydrocarbyl substituent containing one or more double bonds and typically from 2 to about 20 carbon atoms, more typically from about 2 to about 8 carbon atoms, and even more typically from about 2 to about 6 carbon atoms. Examples of such substituents include ethenyl (vinyl); 2-propenyl; 3-propenyl; 1,4-pentadienyl; 1,4-butadienyl; 1-butenyl; 2-butenyl; 3-butenyl; decenyl; and the like.

The term "alkynyl" (alone or in combination with another term(s)) means a straight- or branched-chain hydrocarbyl substituent containing one or more triple bonds and typically from 2 to about 20 carbon atoms, more typically from about 2 to about 8 carbon atoms, and even more typically from about 2 to about 6 carbon atoms. Examples of such substituents include ethynyl, 2-propynyl, 3-propynyl, decynyl, 1-butynyl, 2-butynyl, 3-butynyl, and the like.

The term "carbocyclyl" (alone or in combination with another term(s)) means a saturated cyclic (i.e., "cycloalkyl"), partially saturated cyclic (i.e., "cycloalkenyl"), or completely unsaturated (i.e., "aryl") hydrocarbyl substituent containing from 3 to 14 carbon ring atoms ("ring atoms" are the atoms bound together to form the ring or rings of a cyclic substituent). A carbocyclyl may be a single ring, which typically contains from 3 to 6 ring atoms. Examples of such single-ring carbocyclyls include cyclopropanyl, cyclobutanyl, cyclopentyl, cyclopentenyl, cyclopentadienyl, cyclohexyl, cyclohexenyl, cyclohexadienyl, and phenyl. A carbocyclyl alternatively may be 2 or 3 rings fused together, such as naphthalenyl, tetrahydronaphthalenyl (also known as "tetralinyl"), indenyl, isoindenyl, indanyl, bicyclodecanyl, anthracenyl, phenanthrene, benzonaphthenyl (also known as "phenalenyl"), fluoreneyl, decalinyl, and norpinanyl.

The term "cycloalkyl" (alone or in combination with another term(s)) means a saturated cyclic hydrocarbyl substituent containing from 3 to 14 carbon ring atoms. A cycloalkyl may be a single carbon ring, which typically contains from 3 to 6 carbon ring atoms. Examples of single-ring cycloalkyls include cyclopropyl (or "cyclopropanyl"), cyclobutyl (or "cyclobutanyl"), cyclopentyl (or "cyclopentanyl"), and cyclohexyl (or "cyclohexanyl"). A cycloalkyl alternatively may be 2 or 3 carbon rings fused together, such as, decalinyl or norpinanyl.

The term "aryl" (alone or in combination with another term(s)) means an aromatic carbocyclyl containing from 6 to 14 carbon ring atoms. Examples of aryls include phenyl, naphthalenyl, and indenyl.

In some instances, the number of carbon atoms in a hydrocarbyl substituent (e.g., alkyl, alkenyl, alkynyl, or cycloalkyl) is indicated by the prefix "$C_x$–$C_y$—", wherein x is the minimum and y is the maximum number of carbon atoms in the substituent. Thus, for example, "$C_1$–$C_6$-alkyl" refers to an alkyl substituent containing from 1 to 6 carbon atoms. Illustrating further, $C_3$–$C_6$-cycloalkyl means a saturated hydrocarbyl ring containing from 3 to 6 carbon ring atoms.

The term "hydrogen" (alone or in combination with another term(s)) means a hydrogen radical, and may be depicted as —H.

The term "hydroxy" (alone or in combination with another term(s)) means —OH.

The term "nitro" (alone or in combination with another term(s)) means —$NO_2$.

The term "cyano" (alone or in combination with another term(s)) means —CN, which also may be depicted:

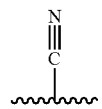

The term "keto" (alone or in combination with another term(s)) means an oxo radical, and may be depicted as =O.

The term "carboxy" (alone or in combination with another term(s)) means —C(O)—OH, which also may be depicted as:

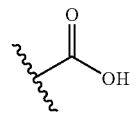

The term "amino" (alone or in combination with another term(s)) means —$NH_2$. The term "monosubstituted amino" (alone or in combination with another term(s)) means an amino substituent wherein one of the hydrogen radicals is replaced by a non-hydrogen substituent. The term "disubstituted amino" (alone or in combination with another term(s)) means an amino substituent wherein both of the hydrogen atoms are replaced by non-hydrogen substituents, which may be identical or different.

The term "halogen" (alone or in combination with another term(s)) means a fluorine radical (which may be depicted as —F), chlorine radical (which may be depicted as —Cl), bromine radical (which may be depicted as —Br), or iodine radical (which may be depicted as —I). Typically, a fluorine radical or chlorine radical is preferred, with a fluorine radical often being particularly preferred.

A substituent is "substitutable" if it comprises at least one carbon or nitrogen atom that is bonded to one or more hydrogen atoms. Thus, for example, hydrogen, halogen, and cyano do not fall within this definition.

If a substituent is described as being "substituted", a non-hydrogen radical is in the place of a hydrogen radical on a carbon or nitrogen of the substituent. Thus, for example, a substituted alkyl substituent is an alkyl substituent wherein at least one non-hydrogen radical is in the place of a hydrogen radical on the alkyl substituent. To illustrate, monofluoroalkyl is alkyl substituted with a fluoro radical, and difluoroalkyl is alkyl substituted with two fluoro radicals. It should be recognized that if there are more than one substitutions on a substituent, each non-hydrogen radical may be identical or different (unless otherwise stated).

If a substituent is described as being "optionally substituted", the substituent may be either (1) not substituted or (2) substituted. If a substituent is described as being optionally substituted with up to a particular number of non-hydrogen radicals, that substituent may be either (1) not substituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical. Further illustrations of this definition may be found above at, for example, the sub-section entitled "General Description of Preferred $A^1$ and $A^2$ Substituents."

This specification uses the terms "substituent" and "radical" interchangeably.

The prefix "halo" indicates that the substituent to which the prefix is attached is substituted with one or more independently selected halogen radicals. For example, haloalkyl means an alkyl substituent wherein at least one hydrogen radical is replaced with a halogen radical. Examples of haloalkyls include chloromethyl, 1-bromoethyl, fluoromethyl, difluoromethyl, trifluoromethyl, 1,1,1-trifluoroethyl, and the like. Illustrating further, "haloalkoxy" means an alkoxy substituent wherein at least one hydrogen radical is replaced by a halogen radical. Examples of haloalkoxy substituents include chloromethoxy, 1-bromoethoxy, fluoromethoxy, difluoromethoxy, trifluoromethoxy (also known as "perfluoromethyloxy"), 1,1,1,-trifluoroethoxy, and the like. It should be recognized that if a substituent is substituted by more than one halogen radical, those halogen radicals may be identical or different (unless otherwise stated).

The prefix "perhalo" indicates that every hydrogen radical on the substituent to which the prefix is attached is replaced with independently selected halogen radicals, i.e., each hydrogen radical on the substituent is replaced with a halogen radical. If all the halogen radicals are identical, the prefix typically will identify the halogen radical. Thus, for example, the term "perfluoro" means that every hydrogen radical on the substituent to which the prefix is attached is substituted with a fluorine radical. To illustrate, the term "perfluoroalkyl" means an alkyl substituent wherein a fluorine radical is in the place of each hydrogen radical. Examples of perfluoroalkyl substituents include trifluoromethyl (—$CF_3$), perfluorobutyl, perfluoroisopropyl, perfluorododecyl, perfluorodecyl, and the like. To illustrate further, the term "perfluoroalkoxy" means an alkoxy substituent wherein each hydrogen radical is replaced with a fluorine radical. Examples of perfluoroalkoxy substituents include trifluoromethoxy (—O—$CF_3$), perfluorobutoxy, perfluoroisopropoxy, perfluorododecoxy, perfluorodecoxy, and the like.

The term "carbonyl" (alone or in combination with another term(s)) means —C(O)—, which also may be depicted as:

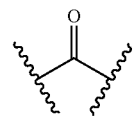

This term also is intended to encompass a hydrated carbonyl substituent, i.e., —$C(OH)_2$—.

The term "aminocarbonyl" (alone or in combination with another term(s)) means —C(O)—$NH_2$, which also may be depicted as:

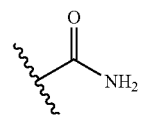

The term "oxy" (alone or in combination with another term(s)) means an ether substituent, and may be depicted as —O—.

The term "alkoxy" (alone or in combination with another term(s)) means an alkylether substituent, i.e., —O-alkyl. Examples of such a substituent include methoxy (—O—$CH_3$), ethoxy, n-propoxy, isopropoxy, n-butoxy, iso-butoxy, sec-butoxy, tert-butoxy, and the like.

The term "alkylcarbonyl" (alone or in combination with another term(s)) means —C(O)-alkyl. For example, "ethylcarbonyl" may be depicted as:

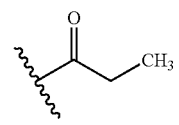

The term "aminoalkylcarbonyl" (alone or in combination with another term(s)) means —C(O)-alkyl—$NH_2$. For example, "aminomethylcarbonyl" may be depicted as:

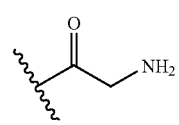

The term "alkoxycarbonyl" (alone or in combination with another term(s)) means —C(O)—O-alkyl. For example, "ethoxycarbonyl" may be depicted as:

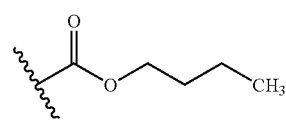

The term "carbocyclylcarbonyl" (alone or in combination with another term(s)) means —C(O)-carbocyclyl. For example, "phenylcarbonyl" may be depicted as:

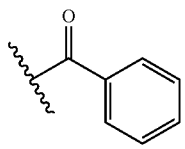

Similarly, the term "heterocyclylcarbonyl" (alone or in combination with another term(s)) means —C(O)-heterocyclyl.

The term "carbocyclylalkylcarbonyl" (alone or in combination with another term(s)) means —C(O)-alkyl-carbocyclyl. For example, "phenylethylcarbonyl" may be depicted as:

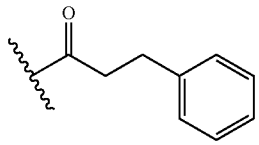

Similarly, the term "heterocyclylalkylcarbonyl" (alone or in combination with another term(s)) means —C(O)-alkyl-heterocyclyl.

The term "carbocyclyloxycarbonyl" (alone or in combination with another term(s)) means —C(O)—O-carbocyclyl. For example, "phenyloxycarbonyl" may be depicted as:

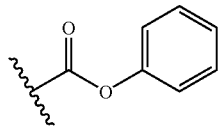

The term "carbocyclylalkoxycarbonyl" (alone or in combination with another term(s)) means —C(O)—O-alkyl-carbocyclyl. For example, "phenylethoxycarbonyl" may be depicted as:

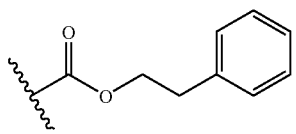

The term "thio" or "thia" (alone or in combination with another term(s)) means a thiaether substituent, i.e., an ether substituent wherein a divalent sulfur atom is in the place of the ether oxygen atom. Such a substituent may be depicted as —S—. This, for example, "alkyl-thio-alkyl" means alkyl—S-alkyl.

The term "thiol" or "sulfhydryl" (alone or in combination with another term(s)) means a sulfhydryl substituent, and may be depicted as —SH.

The term "(thiocarbonyl)" (alone or in combination with another term(s)) means a carbonyl wherein the oxygen atom has been replaced with a sulfur. Such a substituent may be depicted as —C(S)—, and also may be depicted as:

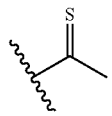

The term "sulfonyl" (alone or in combination with another term(s)) means —S(O)$_2$—, which also may be depicted as:

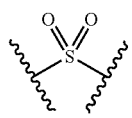

Thus, for example, "alkyl-sulfonyl-alkyl" means alkyl-S(O)$_2$-alkyl.

The term "aminosulfonyl" (alone or in combination with another term(s)) means —S(O)$_2$—NH$_2$, which also may be depicted as:

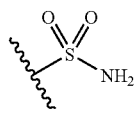

The term "sulfoxido" (alone or in combination with another term(s)) means —S(O)—, which also may be depicted as:

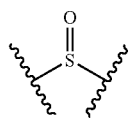

Thus, for example, "alkyl-sulfoxido-alkyl" means alkyl-S(O)-alkyl.

The term "heterocyclyl" (alone or in combination with another term(s)) means a saturated (i.e., "heterocycloalkyl"), partially saturated (i.e., "heterocycloalkenyl"), or heteroaryl ring structure containing a total of 3 to 14 ring atoms. At least one of the ring atoms is a heteroatom (i.e., oxygen, nitrogen, or sulfur), with the remaining ring atoms being independently selected from the group consisting of carbon, oxygen, nitrogen, and sulfur.

A heterocyclyl may be a single ring, which typically contains from 3 to 7 ring atoms, more typically from 3 to 6 ring atoms, and even more typically 5 to 6 ring atoms. Examples of single-ring heterocyclyls include furanyl, dihydrofumayl, tetradydrofumayl, thiophenyl (also known as "thiofuranyl"), dihydrothiophenyl, tetrahydrothiophenyl, pyrrolyl, isopyrrolyl, pyrrolinyl, pyrrolidinyl, imidazolyl, isoimidazolyl, imidazolinyl, imidazolidinyl, pyrazolyl, pyrazolinyl, pyrazolidinyl, triazolyl, tetrazolyl, dithiolyl, oxathiolyl, oxazolyl, isoxazolyl, thiazolyl, isothiazolyl, thiazolinyl, isothiazolinyl, thiazolidinyl, isothiazolidinyl, thiodiazolyl, oxathiazolyl, oxadiazolyl (including 1,2,3-oxadiazolyl, 1,2,4-oxadiazolyl (also known as "azoximyl"), 1,2,5-oxadiazolyl (also known as "furazanyl"), and 1,3,4-oxadiazolyl), oxatriazolyl (including 1,2,3,4-oxatriazolyl and 1,2,3,5-oxatriazolyl), dioxazolyl (including 1,2,3-dioxazolyl, 1,2,4-dioxazolyl, 1,3,2-dioxazolyl, and 1,3,4-dioxazolyl), oxathiolanyl, pyranyl (including 1,2-pyranyl and 1,4-pyranyl), dihydropyranyl, pyridinyl, piperidinyl, diazinyl (including pyridazinyl (also known as "1,2-diazinyl"), pyrimidinyl (also known as "1,3-diazinyl"), and pyrazinyl (also known as "1,4-diazinyl")), piperazinyl, triazinyl (including s-triazinyl (also known as "1,3,5-triazinyl"), as-triazinyl (also known 1,2,4-triazinyl), and v-triazinyl (also known as "1,2,3-triazinyl")), oxazinyl (including 1,2,3-oxazinyl, 1,3,2-oxazinyl, 1,3,6-oxazinyl (also known as "pentoxazolyl"), 1,2,6-oxazinyl, and 1,4-oxazinyl), isoxazinyl (including o-isoxazinyl and p-isoxazinyl), oxazolidinyl, isoxazolidinyl, oxathiazinyl (including 1,2,5-oxathiazinyl and 1,2,6-oxathiazinyl), oxadiazinyl (including 1,4,2-oxadiazinyl and 1,3,5,2-oxadiazinyl), morpholinyl, azepinyl, oxepinyl, thiepinyl, and diazepinyl.

A heterocyclyl alternatively may be 2 or 3 rings fused together, such as, for example, indolizinyl, pyrindinyl, pyranopyrrolyl, 4H-quinolizinyl, purinyl, pyridopyridinyl (including pyrido[3,4-b]-pyridinyl, pyrido[3,2-b]-pyridinyl, pyrido[4,3-b]-pyridinyl, and naphthyridinyl), and pteridinyl. Other examples of fused-ring heterocyclyls include benzo-fused heterocyclyls, such as indolyl, isoindolyl, indoleninyl (also known as "pseudoindolyl"), isoindazolyl (also known as "benzpyrazolyl"), benzazinyl (including quinolinyl (also known as "1-benzazinyl") and isoquinolinyl (also known as "2-benzazinyl")), phthalazinyl, quinoxalinyl, benzodiazinyl (including cinnolinyl (also known as "1,2-benzodiazinyl") and quinazolinyl (also known as "1,3-benzodiazinyl")), benzopyranyl (including chromenyl and isochromenyl), benzothiopyranyl (also known as thiochromenyl), benzoxazolyl, indoxazinyl (also known as "benzisoxazolyl"), anthranilyl, benzodioxolyl, benzodioxanyl, benzoxadiazolyl, benzofuranyl (also known as "coumaronyl"), isobenzofuranyl, benzothienyl (also known as "benzothiophenyl", "thionaphthenyl", or "benzothiofuranyl"), isobenzothienyl (also known as "isobenzothiophenyl", "isothionaphthenyl", or "isobenzothiofuranyl"), benzothiazolyl, benzothiadiazolyl, benzimidazolyl, benzotriazolyl, benzoxazinyl (including 1,3,2-benzoxazinyl, 1,4,2-benzoxazinyl, 2,3,1-benzoxazinyl, and 3,1,4-benzoxazinyl), benzisoxazinyl (including 1,2-benzisoxazinyl and 1,4-benzisoxazinyl), tetrahydroisoquinolinyl, carbazolyl, xanthenyl, and acridinyl.

The term 2-fused-ring heterocyclyl (alone or in combination with another term(s)) means a saturated, partially saturated, or aryl heterocyclyl containing 2 fused rings. Examples of 2-fused-ring heterocyclyls include indolizinyl, pyrindinyl, pyranopyrrolyl, 4H-quinolizinyl, purinyl, pyridopyridinyl, pteridinyl, indolyl, isoindolyl, indoleninyl, isoindazolyl, benzazinyl, phthalazinyl, quinoxalinyl, quinazolinyl, benzodiazinyl, benzopyranyl, benzothiopyranyl, benzoxazolyl, indoxazinyl, anthranilyl, benzodioxolyl, benzodioxanyl, benzoxadiazolyl, benzofuranyl, isobenzofuranyl, benzothienyl, isobenzothienyl, benzothiazolyl, benzothiadiazolyl, benzimidazolyl, benzotriazolyl, benzoxazinyl, benzisoxazinyl, and tetrahydroisoquinolinyl.

The term "heteroaryl" (alone or in combination with another term(s)) means an aromatic heterocyclyl containing from 5 to 14 ring atoms. A heteroaryl may be a single ring or 2 or 3 fused rings. Examples of heteroaryl substituents include 6-membered ring substituents such as pyridinyl, pyrazinyl, pyrimidinyl, pyridazinyl, and 1,3,5-, 1,2,4-, and 1,2,3-triazinyl; 5-membered ring substituents such as imidazolyl, furanyl, thiophenyl, pyrazolyl, oxazolyl, isoxazolyl, thiazolyl, 1,2,3-, 1,2,4-, 1,2,5-, and 1,3,4-oxadiazolyl, and isothiazolyl; 6/5-membered fused ring substituents such as benzothiofuranyl, isobenzothiofuranyl, benzisoxazolyl, benzoxazolyl, purinyl, and anthranilyl; and 6/6-membered fused rings such as quinolinyl, isoquinolinyl, cinnolinyl, and quinazolinyl.

A carbocyclyl or heterocyclyl can optionally be substituted with, for example, one or more substituents independently selected from the group consisting of halogen, hydroxy, carboxy, keto, alkyl, alkoxy, alkoxyalkyl, alkylcarbonyl (also known as "alkanoyl"), aryl, arylalkyl, arylalkoxy, arylalkoxyalkyl, arylalkoxycarbonyl, cycloalkyl, cycloalkylalkyl, cycloalkylalkoxy, cycloalkylalkoxyalkyl, and cycloalkylalkoxycarbonyl. More typically, a carbocyclyl or heterocyclyl may optionally be substituted with, for example, one or more substituents independently selected from the group consisting of halogen, —OH, —C(O)—OH, keto, $C_1$–$C_6$-alkyl, $C_1$–$C_6$-alkoxy, $C_1$–$C_6$-alkoxy-$C_1$–$C_6$-alkyl, $C_1$–$C_6$-alkylcarbonyl, aryl, aryl-$C_1$–$C_6$-alkyl, aryl-$C_1$–$C_6$-alkoxy, aryl-$C_1$–$C_6$-alkoxy-$C_1$–$C_6$-alkyl, aryl-$C_1$–$C_6$-alkoxycarbonyl, cycloalkyl, cycloalkyl-$C_1$–$C_6$-alkyl, cycloalkyl-$C_1$–$C_6$-alkoxy, cycloalkyl-$C_1$–$C_6$-alkoxy-$C_1$–$C_6$-alkyl, and cycloalkyl-$C_1$–$C_6$-alkoxycarbonyl. The alkyl, alkoxy, alkoxyalkyl, alkylcarbonyl, aryl, arylalkyl, arylalkoxy, arylalkoxyalkyl, or arylalkoxycarbonyl substituent(s) may further be substituted with, for example, one or more halogen. The aryls or cycloalkyls are typically single-ring substituents containing from 3 to 6 ring atoms, and more typically from 5 to 6 ring atoms.

An aryl or heteroaryl can optionally be substituted with, for example, one or more substituents independently selected from the group consisting of halogen, —OH, —CN, —NO$_2$, —SH, —C(O)—OH, amino, aminocarbonyl, aminoalkyl, alkyl, alkylthio, carboxyalkylthio, alkylcarbonyl, alkylcarbonyloxy, alkoxy, alkoxyalkyl, alkoxycarbonyl, alkoxycarbonylalkoxy, alkoxyalkylthio, alkoxycarbonylalkylthio, carboxyalkoxy, alkoxycarbonylalkoxy, carbocyclyl, carbocyclylalkyl, carbocyclyloxy, carbocyclylthio, carbocyclylalkylthio, carbocyclylamino, carbocyclylalkylamino, carbocyclylcarbonylamino, carbocyclylcarbonyl, carbocyclylalkyl, carbocyclylcarbonyloxy, carbocyclyloxycarbonyl, carbocyclylalkoxycarbonyl, carbocyclyloxyalkoxycarbonyl, carbocyclylthioalkylthiocarbocyclyl, carbocyclylthioalkoxycarbocyclyl, carbocyclyloxyalkylthiocarbocyclyl, heterocyclyl, heterocyclylalkyl, heterocyclyloxy, heterocyclylthio, heterocyclylalkylthio, heterocyclylamino, heterocyclylalkylamino, heterocyclylcarbonylamino, heterocyclylcarbonyl, heterocyclylalkylcarbonyl, heterocyclyloxycarbonyl, heterocyclylcarbonyloxy, heterocyclylalkoxycarbonyl, heterocyclyloxyalkoxyheterocyclyl, heterocyclylthioalkylthioheterocyclyl, heterocyclylthioalkoxyheterocyclyl, and heterocyclyloxyalkylthioheterocyclyl. More typically, an aryl or heteroaryl may, for example, optionally be substituted with one or more substituents independently selected from the group consisting of halogen, —OH, —CN, —NO$_2$, —SH, —C(O)—OH, amino, aminocarbonyl, amino-$C_1$–$C_6$-alkyl, $C_1$–$C_6$-alkyl, $C_1$–$C_6$-alkylthio, carboxy-$C_1$–$C_6$-alkylthio, $C_1$–$C_6$-alkylcarbonyl, $C_1$–$C_6$-alkylcarbonyloxy, $C_1$–$C_6$-alkoxy, $C_1$–$C_6$-alkoxy-$C_1$–$C_6$-alkyl, $C_1$–$C_6$-alkylcarbonyl, $C_1$–$C_6$-alkoxycarbonyl-$C_1$–$C_6$-alkoxy, $C_1$–$C_6$-alkoxy-$C_1$–$C_6$-alkylthio, $C_1$–$C_6$-alkoxycarbonyl-$C_1$–$C_6$-alkylthio, carboxy-$C_1$–$C_6$-alkoxy, $C_1$–$C_6$-alkoxycarbonyl-$C_1$–$C_6$-alkoxy, aryl, aryl-$C_1$–$C_6$-alkyl, aryloxy, arylthio, aryl-$C_1$–$C_6$-alkylthio, arylamino, aryl-$C_1$–$C_6$-alkylamino, arylcarbonylamino, arylcarbonyl, aryl-$C_1$–$C_6$-alkylcarbonyl, arylcarbonyloxy, aryloxycarbonyl, aryl-$C_1$–$C_6$-alkoxycarbonyl, aryloxy-$C_1$–$C_6$-alkoxyaryl, arylthio-$C_1$–$C_6$-alkylthioaryl, arylthio-$C_1$–$C_6$-alkoxyaryl, aryloxy-$C_1$–$C_6$-alkylthioaryl, cycloalkyl, cycloalkyl-$C_1$–$C_6$-alkyl, cycloalkyloxy, cycloalkylthio, cycloalkyl-$C_1$–$C_6$-alkylthio, cycloalkylamino, cycloalkyl-$C_1$–$C_6$-alkylamino, cycloalkylcarbonylamino, cycloalkylcarbonyl, cycloalkyl-$C_1$–$C_6$-alkylcarbonyl, cycloalkylcarbonyloxy, cycloalkyloxycarbonyl, cycloalkyl-$C_1$–$C_6$-alkoxycarbonyl, heteroaryl, heteroaryl-$C_1$–$C_6$-alkyl, heteroaryloxy, heteroarylthio, heteroaryl-$C_1$–$C_6$-alkylthio, heteroarylamino, heteroaryl-$C_1$–$C_6$-alkylamino, heteroarylcarbonylamino, heteroarylcarbonyl, heteroaryl-$C_1$–$C_6$-alkylcarbonyl, heteroaryloxycarbonyl, heteroarylcarbonyloxy, and heteroaryl-$C_1$–$C_6$-alkoxycarbonyl. Here, one or more hydrogen bound to a carbon in any such substituent may, for example, optionally be replaced with halogen. In addition, the cycloalkyl, aryl, and heteroaryl are typically single-ring substituents containing 3 to 6 ring atoms, and more typically 5 or 6 ring atoms.

A prefix attached to a multi-component substituent only applies to the first component. To illustrate, the term "alkylcycloalkyl" contains two components: alkyl and cycloalkyl. Thus, the $C_1$–$C_6$-prefix on $C_1$–$C_6$-alkylcycloalkyl means that the alkyl component of the alkylcycloalkyl contains from 1 to 6 carbon atoms; the $C_1$–$C_6$-prefix does not describe the cycloalkyl component. To illustrate fuirther, the prefix "halo" on haloalkoxyalkyl indicates that only the alkoxy component of the alkoxyalkyl substituent is substituted with one or more halogen radicals. If halogen substitution may alternatively or additionally occur on the alkyl component, the substituent would instead be described as "halogen-substituted alkoxyalkyl" rather than "haloalkoxyalkyl." And finally, if the halogen substitution may only occur on the alkyl component, the substituent would instead be described as "alkoxyhaloalkyl."

If substituents are described as being "independently selected" from a group, each substituent is selected independent of the other. Each substituent therefore may be identical to or different from the other substituent(s).

When words are used to describe a substituent, the rightmost-described component of the substituent is the component that has the free valence. To illustrate, benzene substituted with methoxyethyl has the following structure:

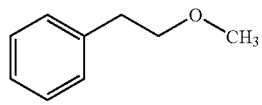

As can be seen, the ethyl is bound to the benzene, and the methoxy is the component of the substituent that is the component furthest from the benzene. As further illustration, benzene substituted with cyclohexanylthiobutoxy has the following structure:

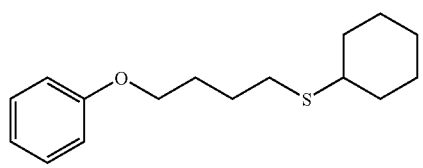

When words are used to describe a linking element between two other elements of a depicted chemical structure, the rightmost-described component of the substituent is the component that is bound to the left element in the depicted structure. To illustrate, if the chemical structure is X-L-Y and L is described as methylcyclohexanylethyl, then the chemical would be X-ethyl-cyclohexanyl-methyl-Y.

When a chemical formula is used to describe a substituent, the dash on the left side of the formula indicates the portion of the substituent that has the free valence. To illustrate, benzene substituted with —C(O)—OH has the following structure:

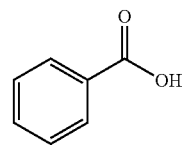

When a chemical formula is used to describe a linking element between two other elements of a depicted chemical structure, the leftmost dash of the substituent indicates the portion of the substituent that is bound to the left element in the depicted structure. The rightmost dash, on the other hand, indicates the portion of the substituent that is bound to the right element in the depicted structure. To illustrate, if the depicted chemical structure is X-L-Y and L is described as —C(O)—N(H)—, then the chemical would be:

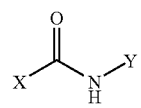

The term "pharmaceutically acceptable" is used adjectivally in this patent to mean that the modified noun is appropriate for use as a pharmaceutical product or as a part of a pharmaceutical product.

With reference to the use of the words "comprise" or "comprises" or "comprising" in this patent (including the claims), Applicants note that unless the context requires otherwise, those words are used on the basis and clear understanding that they are to be interpreted inclusively, rather than exclusively, and that Applicants intend each of those words to be so interpreted in construing this patent, including the claims below.

F. Compound Preparation

The detailed examples below illustrate preparation of compounds and salts of this invention. Other compounds and salts of this invention may be prepared using the methods illustrated in these examples, either alone or in combination with techniques generally known in the art. Such known techniques include, for example, those disclosed in WIPO Int'l Publ. No. WO 00/46221 (PCT Patent Application No. PCT/US00/03061 published on Aug. 10, 2000) (incorporated herein by reference).

EXAMPLES

The following examples are merely illustrative, and not limiting to the remainder of this disclosure in any way.

Example 1

Preparation of 4-{[4-(5-butylpyrazin-2-yl)piperazin-1-yl]sulfonyl}-N-hydroxytetrahydro-2H-pyran-4-carboxamide dihydrochloride

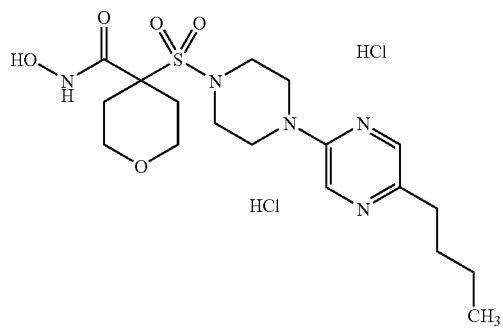

Part A. Preparation of

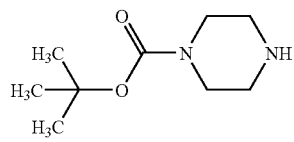

To a DMSO solution (350 mL) of chloropyrazine (21.3 g, 187 mmol) and 1-Boc-piperazine (31.6 g, 170 mmol) was added $Cs_2CO_3$ (77 g, 237 mmol). The slurry was stirred at 60° C. for 24 hr, and at 100° C. for an additional 24 hr. The cooled mixture was diluted with water (800 mL), and extracted with diethyl ether (3×500 mL). The combined organic extracts were washed with brine, dried over $MgSO_4$, and evaporated to a brown oil. The crude material was purified on a plug (200 g) of silica gel eluting with 10–40% ethyl acetate in hexane to produce 31.7 g (71%) of the desired compound in the form of a pale yellow solid. MS: m/z=265.1 (M+H).

Part B:

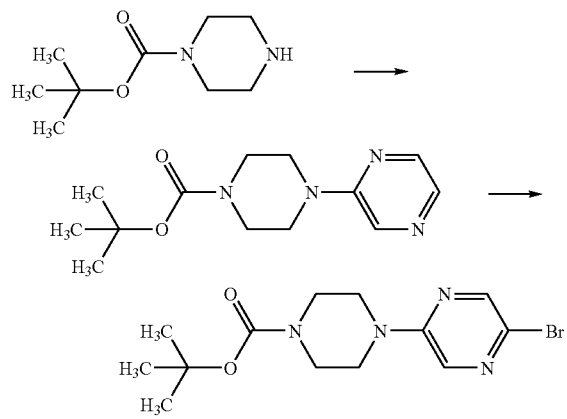

To a $CH_2Cl_2$ (350 mL) solution of Part A (30.5 g, 115 mmol) in an ice bath was added solid N-bromosuccinimide (23.7 g, 133 mmol). The slurry was stirred for 3 hr at room temperature. An additional portion of N-bromosuccinimide (4.09 g, 23 mmol) was added, and the reaction mixture was stirred for 1 hr. The solution was poured onto a pad of silica gel and eluted with 30% ethyl acetate in hexane to produce a yellow solid. Recrystallization from diethyl ether/hexane produced 17.4 g (44%) of the desired compound in the form of an off-white solid. MS: m/z=343.0, 345.0 (M+H).

Part C:

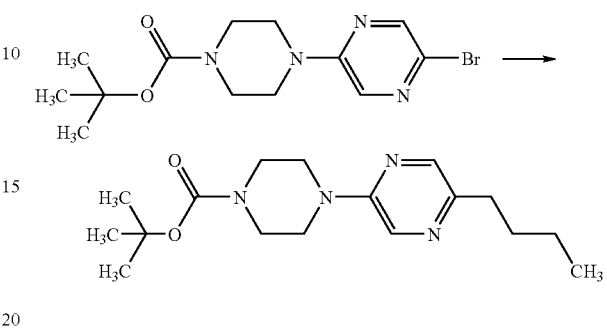

To a THF solution of $ZnCl_2$ (70 mL, 0.5 M, 35 mmol) in an ice bath was added a diethyl ether solution of butylmagnesium chloride (17.5 mL, 2.0M, 35 mmol). The ice bath was removed, and the solution was stirred for 15 min to produce a white precipitate. To this slurry was added a THF (10 mL) solution of the product of Part B (6.2 g, 18.0 mmol) and $Pd(PPh_3)_4$ (2.0 g, 1.7 mmol). The reaction mixture was refluxed for 2 hr. Additional butylmagnesium chloride (4.0 mL, 2.0M, 8.0 mmol) was added, and the slurry was refluxed for 30 min. The cooled reaction mixture was poured into saturated $NH_4Cl$ (150 mL) and extracted with ethyl acetate (2×100 mL). The combined organic extracts were washed with brine, dried over $MgSO_4$, and evaporated to produce a yellow solid. The crude material was purified on silica gel eluting with 5–40% ethyl acetate in hexane to produce 4.0 g (69%) of the desired iodide product in the form of a yellow oil which solidified upon standing. MS: m/z=321.2 (M+H).

Part D:

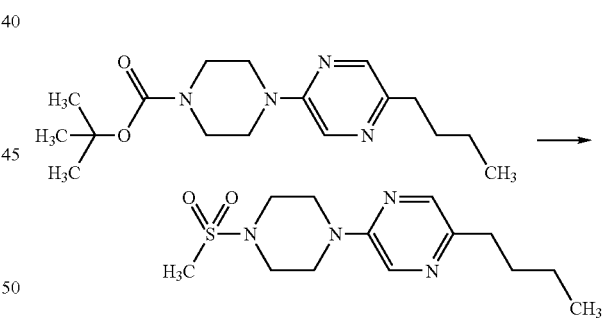

To a solution of Part C (3.96 g, 12.4 mmol) in $CH_2Cl_2$ (10 mL) was added trifluoroacetic acid (5 mL). The resulting mixture was stirred for 3 hr at room temperature. The solution was stripped in vacuo, and the remaining oil was partitioned between ethyl acetate (100 mL) and saturated $NaHCO_3$ (25 mL). The pH was adjusted to 10 using solid $K_2CO_3$. The organic layer was separated, and the aqueous layer was extracted with additional ethyl acetate (100 mL) and $CH_2Cl_2$ (2×50 mL). The combined organic extracts were washed with brine, dried over $MgSO_4$, and evaporated to produce a crude piperazine produce in the form of an orange solid (MS: m/z=221.1 (M+H)). The resulting crude product was dissolved in $CH_2Cl_2$ (50 mL), and cooled in an ice bath. To the solution was added $Et_3N$ (2.2 mL, 16 mmol) and methanesulfonyl chloride (1.05 mL, 13.6 mmol). The solution was stirred for 16 hr at room temperature. The reaction mixture was washed with water and brine, dried over MgSO₄, and evaporated to produce 2.55 g (69%) of the desired sulfonamide in the form of a pale yellow solid. MS: m/z=299.1 (M+H).

Part E:

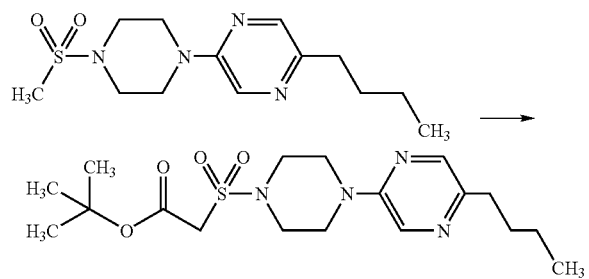

To a slurry of Part D (2.50 g, 8.38 mmol) in THF (40 mL) at −78° C. was added a THF solution of lithium bis(trimethylsilyl)amide (25 mL, 1 M, 25 mmol) dropwise (internal temperature <−65° C.). After stirring for 45 min, a THF (5 mL) solution of di-tert-butyl dicarbonate (2.38 g, 10.9 mmol) was added. Stirring was continued for 15 min at −78° C. The orange slurry was warmed to 0° C., stirred for 10 min, and quenched with saturated NH₄Cl (50 mL). The THF was removed by rotary evaporation, and the aqueous was extracted with ethyl acetate (100 mL). The organic layer was washed with brine, dried over MgSO₄, and evaporated to an oil. The crude material was purified by flash column chromatography on silica gel, eluting with 15% ethyl acetate in hexane to produce 2.00 g (60%) of the desired compound in the form of a white solid. LCMS: m/z=399.1 (M+H).

Part F:

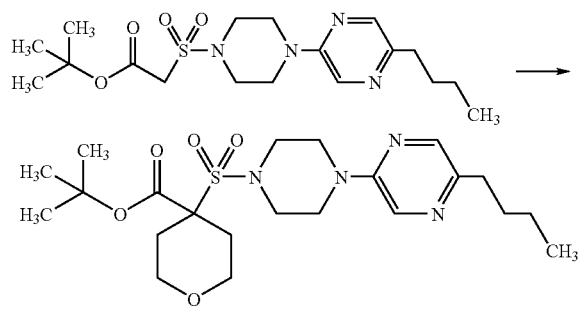

To a DMF (9 mL) solution of Part E (1.08 g, 2.71 mmol) was added K₂CO₃ (1.12 g, 8.16 mmol), 18-crown-6 (0.21 g, 0.80 mmol), and bis(2-bromoethyl)ether (0.37 mL, 2.9 mmol). The slurry was stirred at 60° C. for 72 hr. Additional bis(2-bromoethyl)ether was added at 24 hr (0.4 mmol) and 48 hr (1.2 mmol). The solvent was stripped in vacuo, and the residue was partitioned between ethyl acetate (50 mL) and water (30 mL). The organic layer was separated, dried over MgSO₄, and evaporated to an oil. Recrystallization from diethyl ether produced 0.88 g (69%) of the desired compound in the form of a white solid. LCMS: m/z=469.2 (M+H).

Part G:

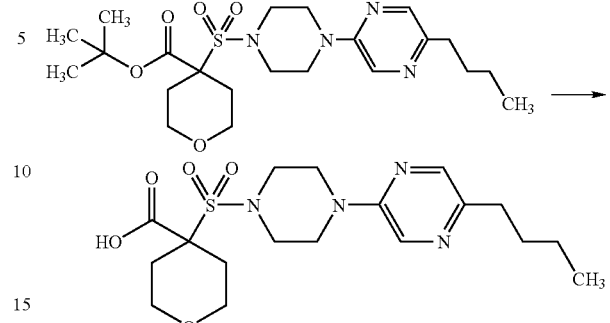

To a CH₂Cl₂ (2 mL) solution of Part F (0.75 g, 1.6 mmol) was added was added trifluoroacetic acid (3 mL). The solution was stirred 3 hr, and stripped in vacuo. The resulting oil was triturated with diethyl ether, and the precipitate was isolated by filtration to produce 0.62 g (94%) of the desired acid in the form of an off-white solid. LCMS: m/z=413.1 (M+H).

Part H:

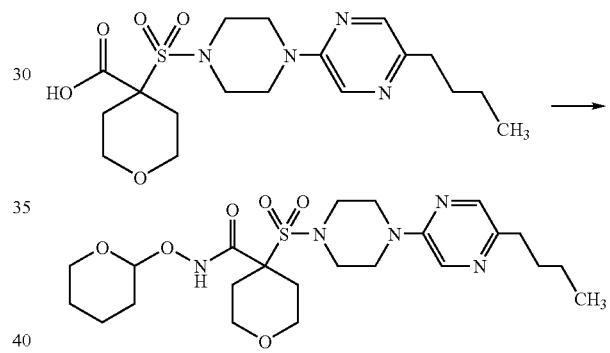

To a slurry of Part G (0.60 g, 1.46 mmol) in DMF (10 mL) was added triethylamine (0.80 mL, 5.8 mmol), O-(tetrahydro-2H-pyran-2-yl)hydroxyamine (0.51 g, 4.4 mmol), 1-(3-dimethylaminopropyl)-3-ethylcarbodiimide hydrochloride (0.83 mmol, 4.4 mmol), and 1-hydroxybenzotriazole (0.59 g, 4.4 mmol). The reaction mixture was stirred 16 hr at room temperature. The solvent was stripped in vacuo, and the residue partitioned between ethyl acetate and water. The organic layer was separated, washed with saturated NaHCO₃, brine, dried over MgSO₄, and evaporated to an oil. The crude material was purified by flash column chromatography on silica gel eluting with 30% ethyl acetate (containing 10% MeOH) in hexane to produce 0.67 g (89%) of the desired THP protected hydroxamic acid in the form of a white solid. LCMS: m/z=512.3 (M+H).

Part I:

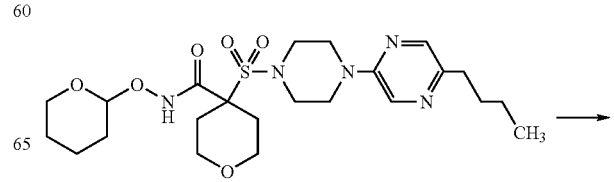

-continued

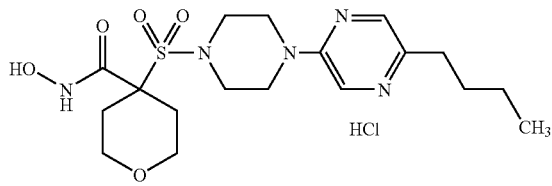

To the solid of Part H (0.45 g, 0.88 mmol) was added MeOH (0.4 mL) and 4 N HCl in dioxane (4.0 mL). The resulting yellow solution was stirred for 1.5 hr and added dropwise to rapidly stirring diethyl ether (50 mL). The slurry was stirred 3 hr and filtered. The resulting solid was washed with diethyl ether (2×20 mL). The precipitate was dried in vacuo for 16 hr to produce 0.34 g (77%) of the desired compound as a dihydrochloride salt. LCMS: m/z=428.1 (M+H). HRMS calcd. for $C_{18}H_{30}N_5O_5S$: m/z=428.1962 [M+H]$^+$; found: 428.1972.

Example 2

Preparation of N-hydroxy-4-({4-[4-(2,2,2-trifluoroethoxy)phenyl]piperazin-1-yl}sulfonyl)tetrahydro-2H-pyran-4-carboxamide hydrochloride

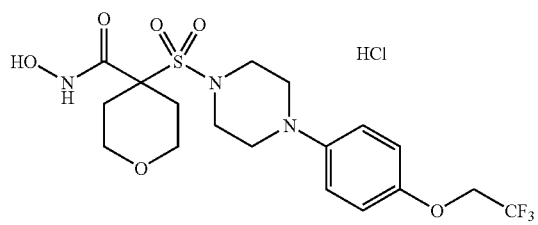

Part A:

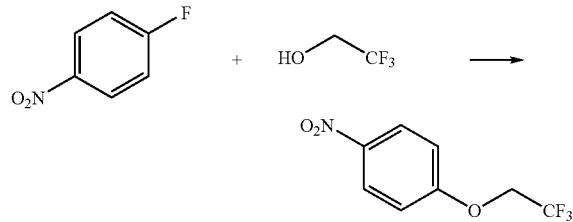

To a solution of 4-fluoro-nitrosobenzene (Aldrich, 20.0 g, 141 mmol) in N,N-dimethylformamide (100 ml) was added potassium carbonate (Aldrich, 45 g, 283 mmol) followed by 3,3,3-trifluoroethanol (25 g, 250 mmol). The reaction stirred at 80° C. for 18 hr. After cooling to room temperature, the mixture was diluted with water and the resulting solid filtered. The filter cake was washed with water and dried in vacuo to produce the desired compound in the form of a yellow solid (29 g, 94% yield). $^1$H NMR was consistent with the desired structure.

Part B:

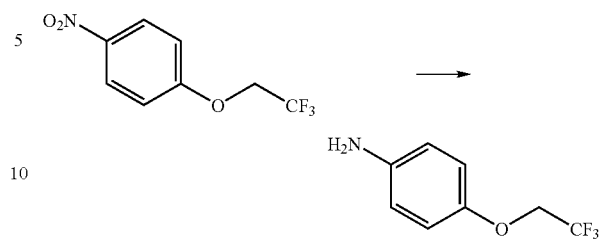

To a solution of the nitrosobenzyl ether from Part A (20.0 g, 90.4 mmol) in methanol (140 ml) was added 10% Pd/C Degussa catalyst (Aldrich, 4.0 g, 10% load). The reaction vessel was purged with $N_2$ followed by $H_2$ via a Parr Shaker apparatus. The reaction was ran at 50 psi of $N_2$, maintaining a temperature under 50° C. Once $H_2$ uptake ceased, the reaction mixture was left at 50 psi and shook for 1 hr to ensure completion. Work up consisted of filtering the mixture through a Celite pad, and concentrating the filtrate to produce the desired compound in the form of a greenish-gray solid product (17.3 g, 100% yield). $^1$H NMR was consistent with the desired structure.

Part C:

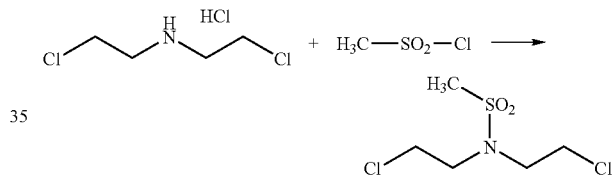

The bis(chloroethyl)amine hydrochloride (Aldrich, 100.0 g, 560 mmol) was suspended in methylene chloride (920 ml) and cooled to 0° C. Triethylamine (Aldrich, 156 ml, 1.12 mol) was added followed by the dropwise addition of a mesylchloride (Aldrich, 45.5 ml, 588 mmol) solution in methylene chloride (200 ml). The ice bath was removed and the reaction stirred at room temperature 15 hr. The reaction mixture was diluted with 10% HCl$_{aq}$ (1 L). The organic layer was separated and washed with 10% HCl$_{aq}$ (2×500 ml), water (3×500 ml) then dried of sodium sulfate, filtered, and concentrated to produce the desired compound in the form of a tan oil that crystallized to a hard solid (123 g, 100% yield). $^1$H NMR was consistent with the desired structure.

Part D:

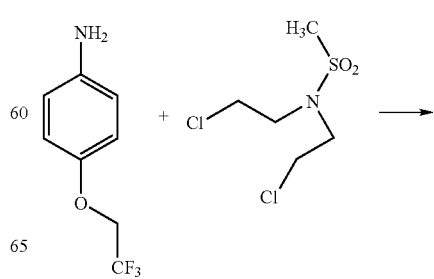

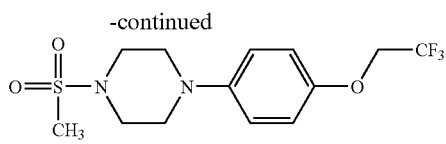

The product from Part B (13.2 g, 62.8 mmol) and the product from Part C (10.0 g, 52.3 mmol) were dissolved in 1-butanol (200 ml) then treated with di-isopropylethyinamine (Aldrich, 10.0 ml, 57.5 ml). The mixture stirred for 18 hr at 110° C. for completion. Workup consisted of cooling to room temperature and pouring into water (1 L). Resulting solid was filtered, washed with hexanes, and dried to produce the desired compound in the form of a gray solid (11.5 g, 64% yield). $^1$H NMR was consistent with the desired structure.

Part E:

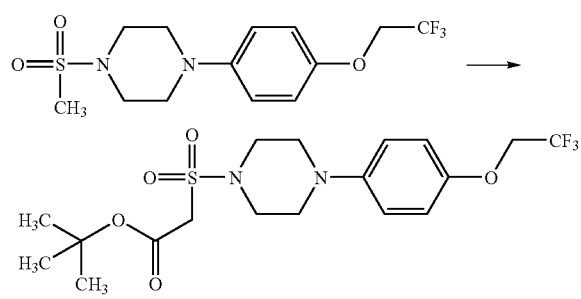

Oven-dried glassware was charged with the piperazine mesylate product of Part D (7.7 g, 21.9 mmol) and t-butyl-carboxlyate anhydride (Aldrich, 5.2 g, 24.1 mmol) in tetrahydrofuran (40 ml), and then cooled to −75° C. Lithium bis(trimethylsilyl)amide (Aldrich, 1.0 M in tetrahydrofuran, 65.6 ml, 65.6 mmol) was slowly added, keeping the temperature at less than −60° C. After addition, the reaction mixture was warmed to 0° C. and stirred for 1 hr. The reaction mixture was then cooled back to −75° C., and slowly quenched with saturated NH$_4$Cl$_{aq}$ (100 ml), keeping the temperature at less than −20° C. The aqueous layer froze into a solid chunks of ice. After warming to 5° C., the mixture was separated, and the aqueous layer was extracted with ethylacetate (3×-120 ml). The organics were washed with saturated NH$_4$Cl (2×-100 ml), water (1×-200 ml), and brine (1×-200 ml); dried over Na$_2$SO$_4$; and concentrated to produce a white solid. The solid was recrystallized from methanol to produce the desired compound (7.2 g, 75% yield). $^1$H NMR was consistent with the desired structure.

Part F:

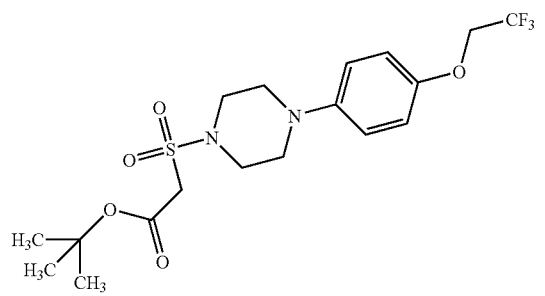

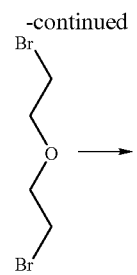

To a solution of the product of Part E (6.8 g, 15.5 mmol), potassium carbonate (Aldrich, 7.5 g, 54.3 mmol), and 18-crown-6 (Aldrich, 0.5 g, cat. amt) in N,N-dimethylformamide (30 ml) was added dibromo-diethylether (Aldrich, 2.9 ml, 23.2 mmol). The mixture was heated at 60° C. for 18 hr, and then worked up by cooling and pouring into water (50 ml). The mixture was extracted via ethylacetate (2×-150 ml). The organics were combined and washed with 5% HCl$_{aq}$ (1×-50 ml), water (1×-100 ml), and brine (2×-100 ml); dried over Na$_2$SO$_4$; and concentrated to afford a yellow oil that solidified. The solid was recrystallized from methanol to produce the desired compound in the form of a white solid (4.8 g, 76% yield). $^1$H NMR was consistent with the desired structure.

Part G:

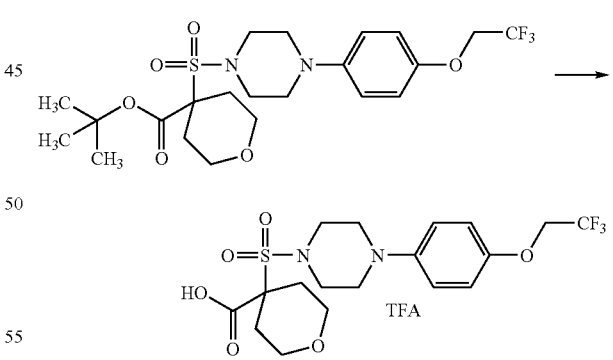

To a solution of the product of Part F (3.5 g, 6.9 mmol) in methylene chloride (10 ml) was added trifluoroacetic acid (Aldrich, 10 ml, 130 mmol). The reaction mixture was stirred overnight at room temperature. The mixture was concentrated to one-third volume. The resulting residue was dripped into stirring diethylether (500 ml). The resulting solid was collected, washed with diethylether, and dried to product the desired TFA salt (3.5 g, 90% yield). $^1$H NMR was consistent with the desired structure.

Part H:

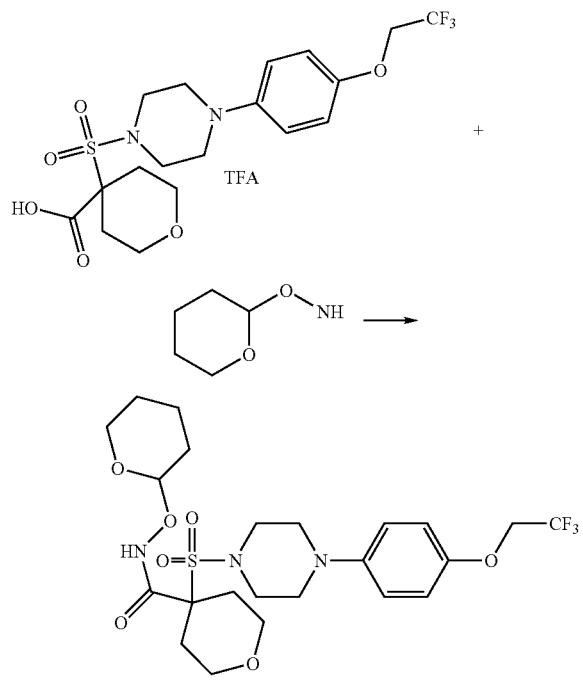

To a solution of the product of Part G (3.5 g, 6.2 mmol) in N,N-dimethylformamide (12 ml) was added triethylamine (Aldrich, 2.2 ml, 15.4 mmol), followed by N-hydroxybenzotriazole hydrate (Aldrich, 1.8 g, 13.6 mmol), O-(tetrahydro-2H-pyran-2-yl)hydroxyamine (1.4 g, 12.4 mmol), and, lastly, 1-(3-dimethylaminopropyl)-3-ethylcarbodiimide hydrochloride (Sigma, 3.0 g, 15.4 mmol). The mixture was stirred at room temperature for 15 hr, and then diluted with water (15 ml) and ethylacetate (100 ml). The organics were separated, and the aqueous layer was further extracted with ethylacetate (2×-75 ml). The organics were combined and washed with saturated NaHCO$_3$ $_{aq}$ (2×-150 ml), water (2×-100 ml), and brine (1×-200 ml). After drying over sodium sulfate, the organics were concentrated to produce a foamy solid that was recrystallized from methanol to produce the desired compound in the form of a white solid (3.1 g, 91% yield). $^1$H NMR was consistent with the desired structure.

Part I:

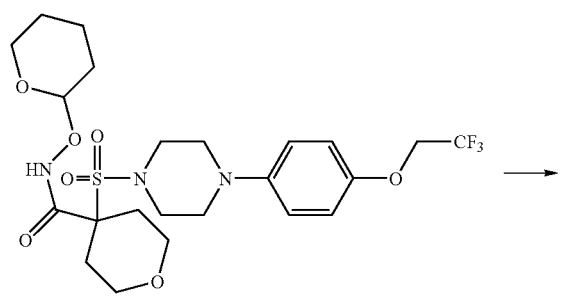

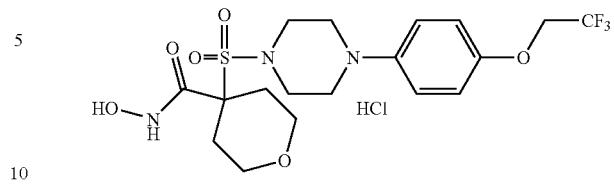

To the product of Part H (3.1 g, 5.6 mmol) was added methanol (2 ml) and 4 N HCl in dioxane (20 ml) for one hr. The solvent was concentrated to one-third volume and then diethylether was added. The resulting solid was filtered, washed with diethylether, and dried to produce the desired compound as white solid (2.6 g, 84% yield). $^1$H NMR was consistent with the desired structure. HRMS for $C_{18}H_{24}F_3N_3O_6S$ showed $M^{+H}_{found}$=468.1421 ($M^{+H}_{calc}$=468.1411).

Example 3

Preparation of 4-{[4-(4-ethoxyphenyl)piperazinyl]sulfonyl}perhydro-2H-pyran-4-carbohydroxamic acid

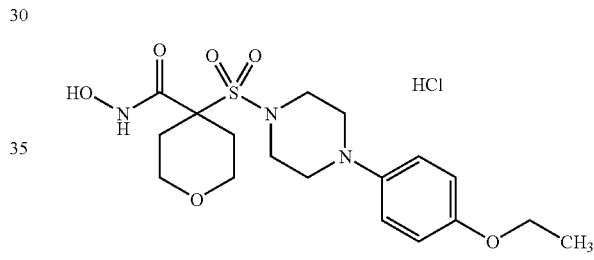

Part A: Preparation of tert-butyl 4-{[4-(4-ethoxyphenyl)piperazinyl]sulfonyl}perhydro-2H-pyran-4-carboxyate

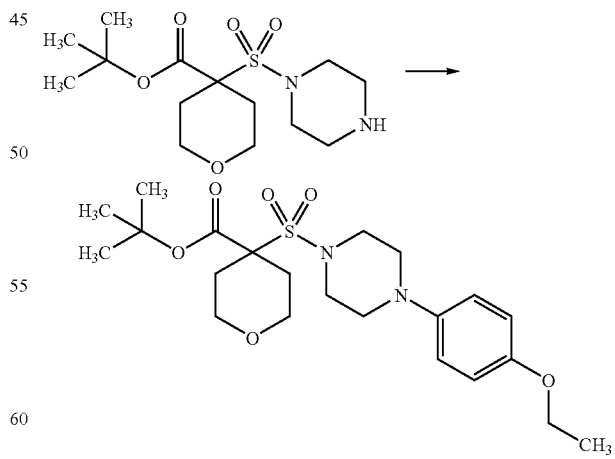

To a solution of tert-butyl 4-(piperazinyisulfonyl)perhydro-2H-pyran-4-carboxyate (715 mg, 2.14 mmol, supplied by CarboGen) in toluene (15 mL) under N$_2$ were added 1-bromo-4-ethoxybenzene (473 mg, 2.35 mmol), sodium tert-butoxide (514 mg, 5.35 mmol), palladium(II) acetate (5.0 mg, 0.021 mmol), and tri-tert-butylphosphine (3.5 mg, 0.17 mmol). The reaction was continued overnight at 60° C. under N₂. No starting material remained at this time, so the reaction mixture was diluted with methanol and concentrated under reduced pressure. The residue was partially dissolved in dichloromethane and filtered. The filtrate was concentrated under reduced pressure, and the resulting dark material was triturated with diethyl ether to produce a white solid, which was collected by suction filtration to produce 640 mg of clean product (66%). ¹H NMR and mass spectrometry (MH⁺=455) were consistent with the desired structure.

Part B. Preparation of 4-{[4-(4-ethoxyphenyl)piperazinyl]sulfonyl}perhydro-2H-pyran-4-carboxyic acid

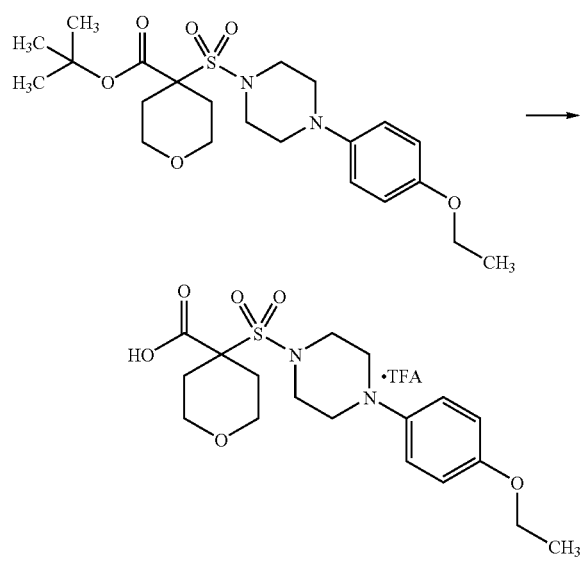

The product from Part A (620 mg, 1.37 mmol) was dissolved in 1:1 trifluoroacetic acid/dichloromethane (10 mL). The reaction was continued overnight at room temperature. Subsequently, no starting material detectable by HPLC. The mixture was concentrated under reduced pressure. Additional dichloromethane was added, and the solvent was once again removed under reduced pressure to produce the desired compound in the form of a tan solid (700 mg, quantitative yield). ¹H NMR and mass spectrometry (MH⁺=399) were consistent with the desired structure.

Part C. Preparation of (4-{[4-(4-ethoxyphenyl)piperazinyl]sulfonyl}perhydro-2H-pyran-4-yl)-N-perhydro-2H-pyran-2-yloxycarboxamide:

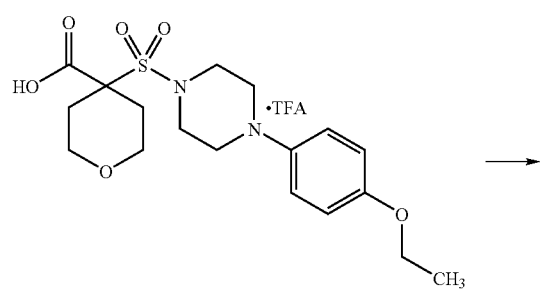

-continued

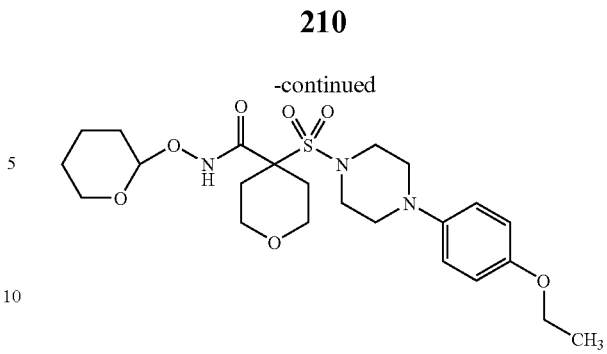

To a solution of the product from Part B (680 mg, 1.33 mmol) in N,N-dimethylformamide (10 mL) were added N-hydroxybenzotriazole (251 mg, 1.86 mmol), 4-methylmorpholine (537 mg, 0.584 mL, 5.31 mmol), 1-(3-dimethylaminopropyl)-3-ethylcarbodiimide hydrochloride (637 mg, 3.32 mmol), and O-(tetrahydro-2H-pyran-2-yl)hydroxyamine (390 mg, 3.32 mmol). The reaction was continued overnight at 45° C. under N₂. Subsequently, no starting material was detectable by HPLC. After cooling to room temperature, the reaction mixture was diluted with ethyl acetate. The combined organic layer was extracted with water (3 times) and saturated sodium bicarbonate (3 times); washed with saturated sodium chloride; and dried over anhydrous sodium sulfate. Filtration and evaporation of the solvent under reduced pressure produced a yellow oil (590 mg). The crude material was purified by flash chromatography using dichloromethane with a methanol gradient (0–1%) to produce the desired compound in the form of a white foam (480 mg, 73% yield). ¹H NMR and mass spectrometry (MH⁺=498) were consistent with the desired structure.

Part D. Preparation of 4-{[4-(4-ethoxyphenyl)piperazinyl]sulfonyl}perhydro-2H-pyran-4-carbohydroxamic acid

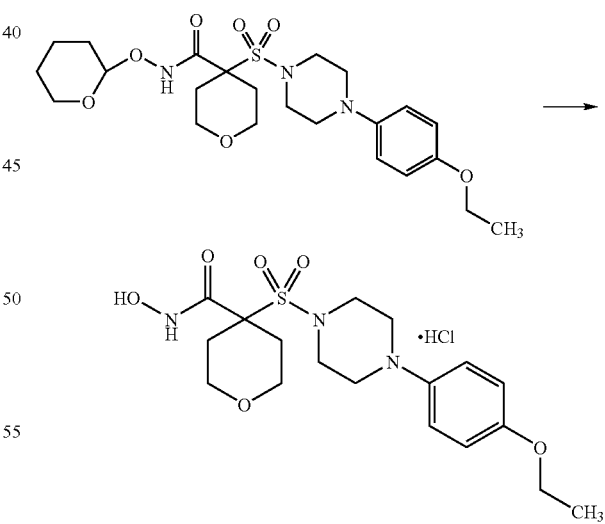

The product from Part C (440 mg, 0.89 mmol) was dissolved in dioxane (4 mL), 4N HCl in dioxane (5 mL), and methanol (0.5 mL). The reaction was continued at ambient temperature for 1 hr. HPLC indicated that the reaction was complete. The mixture was concentrated under reduced pressure. The residue was triturated with diethyl ether, and the resulting tan solid was collected by suction filtration (469 mg, quantitative yield). ¹H NMR and mass spectrometry (MH⁺=414) were consistent with the desired structure.

Example 4

Preparation of 4-({4-[4-(1,1,2,2-tetrafluoroethoxy) phenyl]piperazinyl}sulfonyl)perhydro-2H-pyran-4-carbohydroxamic acid

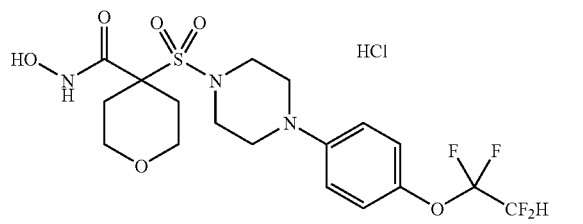

Part A. Preparation of tert-butyl 4-({4-[4-(1,1,2,2-tetrafluoroethoxy)phenyl]piperazinyl}sulfonyl)perhydro-2H-pyran-4-carboxyate

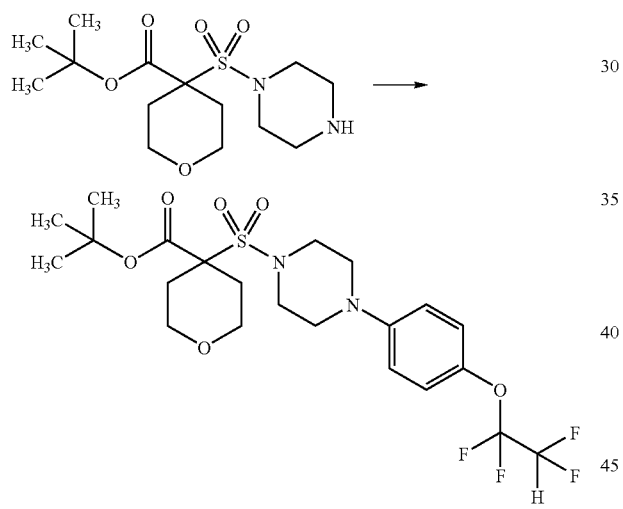

To a solution of tert-butyl 4-(piperazinylsulfonyl)perhydro-2H-pyran-4-carboxyate 1 (7.80 g, 23.3 mmol, supplied by CarboGen) in toluene (150 mL) under N₂ were added 1-bromo-4-tetrafluoroethoxybenzene (6.90 g, 25.6 mmol), sodium tert-butoxide (5.60 g, 5.83 mmol), palladium(II) acetate (0.52 g, 2.33 mmol), and tri-tert-butylphosphine (0.38 g, 1.86 mmol). The reaction mixture was heated at 80° C. under N₂ for 4 hr. Afterward, no starting material was detected. The mixture was diluted with methanol and concentrated under reduced pressure. The resulting residue was partially dissolved in dichloromethane and filtered. The filtrate was concentrated under reduced pressure, and the resulting dark material was triturated with diethyl ether to produce a tan solid, which was collected by suction filtration to produce 10.6 g of clean product (86%). ¹H NMR and mass spectrometry (MH⁺=527) were consistent with the desired structure.

Part B. Preparation of 4-({4-[4-(1,1,2,2-tetrafluoroethoxy)phenyl]piperazinyl}sulfonyl)perhydro-2H-pyran-4-carboxyic acid

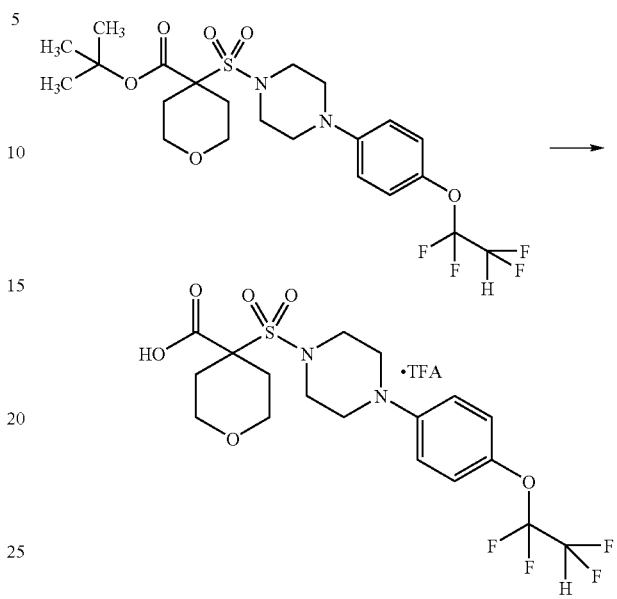

The product from Part A (10.5 g, 20.0 mmol) was dissolved in 1:1 trifluoroacetic acid/dichloromethane (100 mL). The reaction was continued overnight at room temperature. Subsequently, no starting material was detectable by HPLC. The reaction mixture was concentrated under reduced pressure. Additional dichloromethane was added, and the solvent was once again removed under reduced pressure to produce the desired compound in the form of a tan solid (14.0 g, quantitative yield for the "di-TFA" salt). Mass spectrometry (MH⁺=471) was consistent with the desired structure.

Part C. Preparation of N-perhydro-2H-pyran-2-yloxy[4-({4-[4-(1,1,2,2-tetrafluoroethoxy)phenyl] piperazinyl}sulfonyl)perhydro-2H-pyran-4-yl]carboxamide

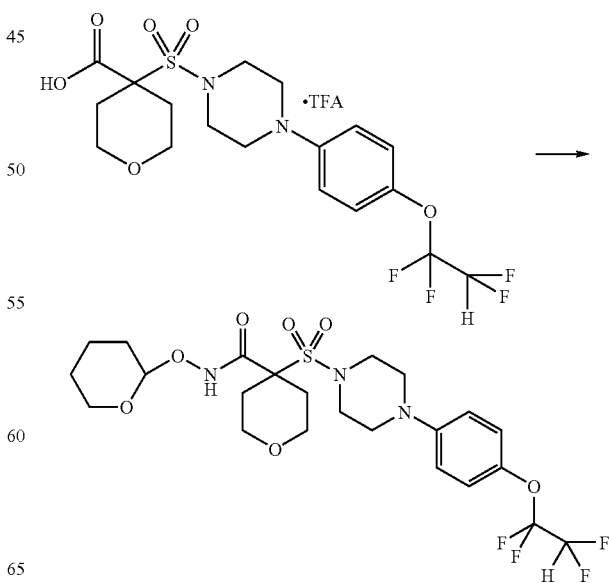

To a solution of the product from Part B (14.0 g, 20.1 mmol for "di-TFA") in N,N-dimethylformamide (200 mL) were added N-hydroxybenzotriazole (3.80 g, 28.1 mmol), 4-methylmorpholine (10.2 g, 11 mL, 100.5 mmol), 1-(3-dimethylaminopropyl)-3-ethylcarbodiimide hydrochloride (13.5 g, 70.4 mmol), and O-(tetrahydro-2H-pyran-2-yl)hydroxyamine (8.3 g, 70.4 mmol). The reaction was continued overnight at 45° C. under $N_2$. Subsequently, no starting material was detectable by HPLC. After cooling to room temperature, the reaction mixture was diluted with ethyl acetate. The combined organic layer was extracted with water (3 times), saturated sodium bicarbonate (3 times), and washed with saturated sodium chloride before drying over anhydrous sodium sulfate. Filtration and evaporation of the solvent under reduced pressure produced a yellow solid (11.4 g). The crude material was purified by flash chromatography using dichloromethane with a methanol gradient (0–2%) to produce the desired compound in the form of a white foam (10.4 g, 91% yield). $^1$H NMR and mass spectrometry ($MH^+$=570) were consistent with the desired structure.

Part D. Preparation of 4-({4-[4-(1,1,2,2-tetrafluoroethoxy)phenyl]piperazinyl}sulfonyl)perhydro-2H-pyran-4-carbohydroxamic acid

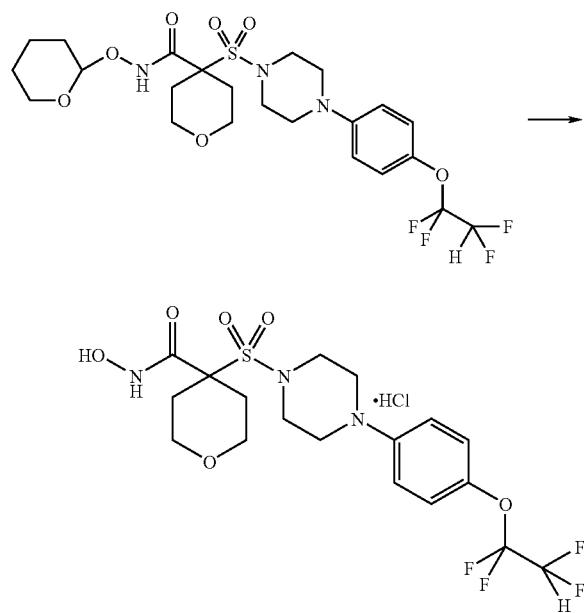

The product from Part C (10.4 g, 18.3 mmol) was dissolved in dioxane (70 mL), 4N HCl in dioxane (90 mL), and methanol (9 mL). The reaction was continued at ambient temperature for 2 hr. HPLC indicated that the reaction was complete, so it was concentrated under reduced pressure. The residue was triturated with diethyl ether, and the resulting white solid was collected by suction filtration (9 g, quantitative yield). $^1$H NMR and mass spectrometry ($MH^+$=485) were consistent with the desired structure.

Example 5

4-{[4-(4-butylphenyl)piperazin-1-yl]sulfonyl}-N-hydroxy-1-(2-methoxyethyl)piperidine-4-carboxamide dihydrochloride

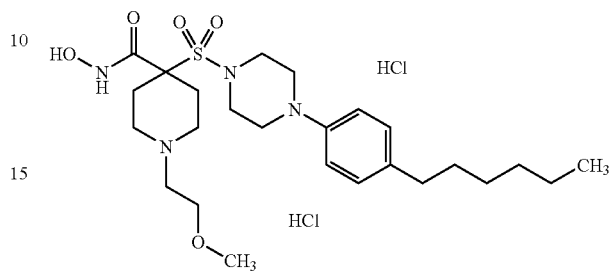

Part A. Preparation of 1-(4-Bromophenyl)-4-(methylsulfonyl)piperazine. A slurry of 1-(4-bromophenyl)piperazine (30.04 g, 0.108 mole) in dichloromethane (300 mL) was stirred at room temperature in a 3-necked, 1.0 liter round-bottomed flask under $N_2$. Methane sulfonyl chloride (10.9 mL, 0.141 mole) was added dropwise, followed by slow addition of triethylamine (37.6 mL, 0.27 mole). The temperature of the reaction mixture increased to 33° C. with the addition. The resultant mixture was stirred overnight at room temperature. The reaction mixture was then transferred to a 1.0 liter separatory funnel, and extracted twice with water (300 mL). The organic layer was dried over magnesium sulfate, and concentrated in vacuo to approximately one-forth of the original volume. Hexane was then added to precipitate a solid product. The solid was collected by vacuum filtration and further dried in vacuo to yield 27.2 g of the desired compound in the form of a pale yellow solid (79%). $^1$H NMR ($CDCl_3$) δ 2.81 (s, 3H), 3.24 (m, 4H), 3.35 (m, 4H), 6.79 (d, J=9 Hz, 2H), 7.36 (d, J=9 Hz, 2H). Electrospray mass spectroscopy showed m/z 319 (M+H).

Part B. Preparation of methyl {[4-(4-bromophenyl)piperazin-1-yl]sulfonyl}acetate. The 1-(4-Bromophenyl)-4-(methylsulfonyl)piperazine product from Part A (16.5 g, 51.7 mmol) was dissolved in dry tetrahydrofuran (350 mL) in an oven-dried 1.0 L, 3-necked round-bottomed flask under $N_2$. The flask was immersed in a dry ice/acetone bath. A 1.0 M solution of lithium hexamethyldisilazide in tetrahydrofuiran (155 mL, 155 mmol) was then added slowly, maintaining a temperature below −70° C. After complete addition, the mixture was stirred with cooling for 1 hr. A solution of methyl chloroformate (4.8 mL, 62 mmol) in tetrahydrofuran (10 mL) was then added dropwise while maintaining temperature at less than −70° C. After complete addition, the flask was stirred with cooling for 20 min. Afterward, the flask was immersed in an ice water bath and stirred for 30 min. The reaction mixture was quenched by slow addition of saturated aqueous ammonium chloride (100 mL). The mixture was warmed to room temperature, and the volatiles were removed in vacuo. The residue was partitioned between ethyl acetate (500 mL) and water (300 mL). The organic layer was washed with 5% HCl, water, and brine (300 mL each). After drying over magnesium sulfate, the solvent was removed in vacuo, leaving 17.46 g of the desired compound in the form of a tan solid (93%). $^1$H NMR ($CDCl_3$) δ 3.23 (m, 4H), 3.53 (m, 4H), 3.81 (s, 3H), 3.98 (s, 2H), 6.79 (d, J=9.3 Hz, 2H), 7.36 (d, J=9.3 Hz, 2H).

Part C. Preparation of Methyl 4-{[4-(4-bromophenyl)piperazin-1-yl]sulfonyl}-1-(2-methoxyethyl)piperidine-4-carboxyate. A solution of the methyl {[4-(4-bromophenyl)piperazin-1-yl]sulfonyl}acetate product from Part B (17 g, 45.1 mmol) in dimethylformamide (65 mL) was added to a rapidly stirred mixture of N,N-bis(2-chloroethyl)-N-(2-methoxyethyl)amine hydrochloride (12.8 g, 54 mmol), powdered potassium carbonate (37.3 g, 0.27 mol), 18-crown-6 (3.57 g, 13.5 mmol), and dimethylformamide (50 mL) at 60° C. in a 500 mL round-bottomed flask. After complete addition, the mixture was stirred at 60° C. for 24 hr. The reaction mixture was cooled to room temperature. The solvent was then removed in vacuo. The residue was partitioned between ethyl acetate (300 mL) and water (500 mL), and the organic layer was further washed with water (3×300 mL) and brine (200 mL). The organic layer was then dried over magnesium sulfate and concentrated in vacuo to yield 21.5 g of a dark yellow semi-solid. Purification by recrystallization from a mixture of ethyl acetate and hexane yielded 8.35 g of the desired compound in the form of a pale yellow solid (37%). $^1$H NMR (CDCl$_3$) δ 2.0 (m, 2H), 2.3 (m, 2H), 2.45–2.7 (m, 4H), 3.15 (m, 4H), 3.33 (s, 3H), 3.52 (m, 4H), 3.84 (s, 3H), 6.76 (d, J=9 Hz, 2H), 7.45 (d, J=9 Hz, 2H); ES/MS showed m/z=526 (M+NH4).

Part D. Methyl 4-{[4-(4-butylphenyl)piperazin-1-yl]sulfonyl}-1-(2-methoxyethyl)piperidine-4-carboxyate. To a solution of the methyl 4-{[4-(4-bromophenyl)piperazin-1-yl]sulfonyl}-1-(2-methoxyethyl)piperidine-4-carboxyate product from Part C (1.90 g, 3.77 mmol) in dry tetrahydrofuran (8 mL) in a 50 mL round-bottomed flask was added a 1 M solution of tri-n-butylborane in tetrahydrofuran (4.14 mL, 4.14 mmol), followed by 2 M aqueous potassium phosphate (5.6 mL, 11.3 mmol) and [1,1'-bis(diphenylphosphino)ferrocene] dichloropalladium (II), complex with dichloromethane (1:1) (154 mg, 0.19 mmol). The reaction mixture was heated to reflux for 2 hr, and then cooled to room temperature. The mixture was partitioned between ethyl acetate (100 mL) and water (100 mL). The organic layer was washed with water (50 mL) and brine (50 mL), dried over magnesium sulfate, and concentrated in vacuo to produce 1.90 g of a black semi-solid. Purification by filtration through a 1.5×2 inch pad of silica gel, followed by recrystallization from ethyl acetate and hexane, produced 0.997 g of pure 4-butylphenyl piperazine intermediate in the form of a tan solid. ES/MS showed m/z=482 (M+H).

Part E. Preparation of 4-{[4-(4-Butylphenyl)piperazin-1-yl]sulfonyl}-1-(2-methoxyethyl)piperidine-4-carboxyic acid. A solution of the product from Part D above (0.995 mg, 2.07 mmol) in tetrahydrofuran (4 mL) and ethyl alcohol (4 mL) was treated with 50% sodium hydroxide (1 mL, 12.5 mmol), and heated to 50° C. for 1 hr. After cooling to room temperature, the reaction mixture was diluted with water (20 mL). 5% HCl (aqueous) was then added until the pH of the solution was approximately 7. A white precipitate formed with the addition of the HCl solution, and this was collected by vacuum filtration. The solid was washed with water and hexane and then dried in vacuo for 24 hr to produce 0.923 g (95%) of a carboxyic acid in the form of a tan solid. ES/MS showed m/z=468 (M+H).

Part F. Preparation of 4-{[4-(4-Butylphenyl)piperazin-1-yl]sulfonyl}-1-(2-methoxyethyl)-N-(tetrahydro-2H-pyran-2-yloxy)piperidine-4-carboxamide. To a solution of the carboxyic acid product from Part E (0.912 g, 1.95 mmol) in dimethylformamide (5 mL) was added sequentially: 1-(3-dimethylaminopropyl)-3-ethylcarbodiimide hydrochloride (0.559 g, 2.93 mmol), 1-hydroxybenzotriazole hydrate (0.448 g, 2.93 mmol), 1-methylmorpholine (0.64 mL, 5.85 mmol), and O-(tetrahydro-2H-pyran-2-yl)hydroxyamine (0.457 g, 3.90 mmol). The reaction mixture was heated to 60° C. for 48 hr. Additional 1-(3-dimethylaminopropyl)-3-ethylcarbodiimide hydrochloride (0.559 g, 2.93 mmol), 1-methylmorpholine (0.64 mL, 5.85 mmol), and O-(tetrahydro-2H-pyran-2-yl)hydroxyamine (0.457 g, 3.90 mmol) were then added, and the mixture was stirred for an additional 24 hr. After 24 hr of heating, the reaction mixture was cooled to room temperature. The mixture was partitioned between ethyl acetate (100 mL) and water (100 mL), and the organic layer was washed with water (100 mL) and brine (100 mL). After drying over magnesium sulfate, the organic layer was concentrated in vacuo to produce 0.68 g tan solid. Purification by reverse-phase high pressure liquid chromatography produced a tetrahydropyranyl hydroxamic acid.

Part G. Preparation of 4-{[4-(4-butylphenyl)piperazin-1-yl]sulfonyl}-N-hydroxy-1-(2-methoxyethyl)piperidine-4-carboxamide dihydrochloride. The product from Part F was dissolved in methyl alcohol (2 mL) and dioxane (2 mL), and a 4 N HCl solution in dioxane (2 mL) was added dropwise. The solution was stirred for 15 min at room temperature. The volatiles were then removed in vacuo. Addition of 4 N HCl in dioxane was repeated for an additional 15 min, followed by removal of solvent in vacuo. This produced 0.468 g of the desired compound in the form of a white solid (42% over two steps). ES/MS showed m/z=483 (M+H).

Example 6

Preparation of N-Hydroxy-1-(2-methoxyethyl)-4-{[4-(4-pentylphenyl)piperazin-1-yl]sulfonyl}piperidine-4-carboxamide dihydrochloride

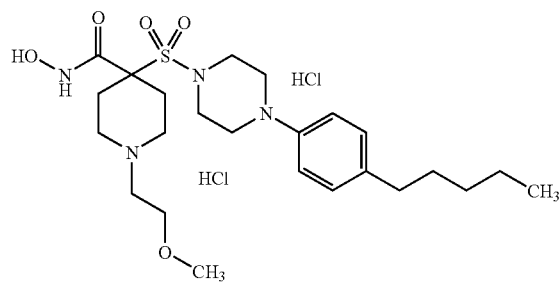

Part A. Preparation of 9-pentyl-9-borobicyclononane in tetrahydrofuran. A solution of 1-pentene (1.1 g, 15.7 mmol) in dry tetrahydrofuran (20 mL) in a 100 mL round-bottomed flask was immersed into an ice bath. A 0.5 M solution of 9-borobicyclononane in tetrahydroftiran (28 mL, 14 mmol) was added dropwise, maintaining a temperature of less than 5° C. After complete addition, the flask was removed from the ice bath and slowly warmed to room temperature. The mixture was stirred for 24 hr, producing a 0.29 M solution of 9-pentyl-9-borobicyclononane in tetrahydrofuran.

Part B. Preparation of 4-pentylphenyl piperazine. To a solution of methyl 4-{[4-(4-bromophenyl)piperazin-1-yl]sulfonyl}-1-(2-methoxyethyl)piperidine-4-carboxyate (0.402 g, 0.80 mmol, prepared as described in Part C of Example 5) in the 0.29 M solution of 9-pentyl-9-borobicyclononane in tetrahydrofuran from Part A (4.1 mL, 1.2 mmol) was added 2 M potassium phosphate (1.2 mL, 2.4 mmol) and [1,1'-bis(diphenylphosphino)ferrocene] dichloropalladium (II), complex with dichloromethane (1:1) (33 mg, 0.04 mmol). The reaction mixture turned dark brown with the addition of the palladium species. The mixture was heated to reflux for 1 hr, and then cooled to room temperature. The volatiles were removed in vacuo, and the resulting residue was partitioned between ethyl acetate (50 mL) and water (50 mL). The organic layer was dried over magnesium sulfate, and concentrated in vacuo to produce 0.5 g of a brown solid. Purification by flash column chromatography on silica gel produced 0.257 g of the pure 4-pentylphenyl piperazine in the form of white crystals (65%). ES/MS showed m/z=496.71 (M+H).

Part C. Preparation of 1-(2-Methoxyethyl)-4-{[4-(4-pentylphenyl)piperazin-1-yl]sulfonyl}piperidine-4-carboxyic acid. A solution of the intermediate from Part B (0.257 g, 0.52 mmol) in dry tetrahydrofuran (3 mL) was treated with 90% potassium trimethylsilanolate (0.22 g, 1.56 mmol) at room temperature for 6 hr. The volatiles were removed in vacuo. The residue was then dissolved in water (25 mL). A 5% solution of HCl in water was added to the reaction solution until the pH was approximately 3. A white precipitate formed, which was collected by vacuum filtration. The solid was washed with water and hexane, and then dried in vacuo to produce 0.21 g of a carboxyic acid product in the form of a white solid (84%). ES/MS showed m/z=496.71 (M+H).

Part D. Preparation of 1-(2-Methoxyethyl)-4-{[4-(4-pentylphenyl)piperazin-1-yl]sulfonyl}-N-(tetrahydro-2H-pyran-2-yloxy)piperidine-4-carboxamide. To a solution of the carboxyic acid from Part C (0.181 g, 0.376 mmol) in 1-methylpyrrolidinone (2 mL) was added sequentially 1-(3-dimethylaminopropyl)-3-ethylcarbodiimide hydrochloride (0.101 g, 0.526 mmol), 1-hydroxybenzotriazole hydrate (0.086 g, 0.564 mmol), 1-methylmorpholine (0.124 mL, 1.13 mmol), and O-(tetrahydro-2H-pyran-2-yl)hydroxyamine (0.066 g, 0.564 mmol). The reaction mixture was heated to 60° C. for 24 hr, and then additional 1-(3-dimethylaminopropyl)-3-ethylcarbodiimide hydrochloride (0.101 g, 0.526 mmol), 1-methylmorpholine (0.124 mL, 1.13 mmol), and O-(tetrahydro-2H-pyran-2-yl)hydroxyamine (0.066 g, 0.564 mmol) were added. The mixture was then stirred for an additional 24 hr. After 24 hr of heating, the reaction mixture was cooled to room temperature. The mixture was partitioned between ethyl acetate (50 mL) and water (50 mL), and the organic layer was washed with water (50 mL) and brine (50 mL). After drying over magnesium sulfate, the organic layer was concentrated in vacuo to produce 0.18 g of a tan solid. Purification by reverse-phase HPLC produced 80.5 mg of a tetrahydropyranyl hydroxamic acid.

Part E. Preparation of N-Hydroxy-1-(2-methoxyethyl)-4-{[4-(4-pentylphenyl)piperazin-1-yl]sulfonyl}piperidine-4-carboxamide dihydrochloride. The product from Part D was dissolved in methyl alcohol (1 mL) and dioxane (1 mL), and a 4 N solution of HCl in dioxane (1 mL) was added dropwise. The solution was stirred for 15 min at room temperature. The reaction solution was then poured into rapidly stirred diethyl ether (50 mL). A white precipitate formed, which was collected by vacuum filtration, washed with diethyl ether, and dried in vacuo. This yielded 57 mg of the desired compound in the form of a white solid (73%). HRMS: calculated for $C_{24}H_{41}N_4O_5S_1$: 497.2792; found: 497.2794.

Example 7

Preparation of N-hydroxy-4-({4-[4-(4,4,4-trifluorobutoxy)phenyl]piperazin-1-yl}sulfonyl)tetrahydro-2H-pyran-4-carboxamide hydrochloride

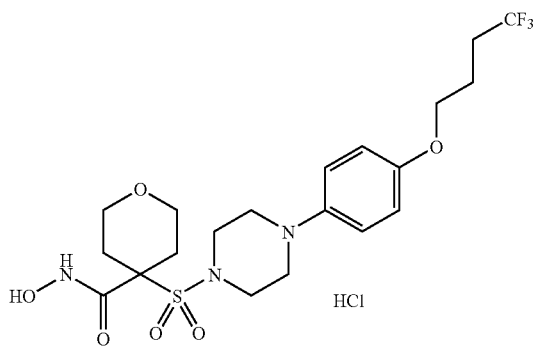

Part A. Preparation of 1-acetyl-4-[4-(4,4,4-trifluorobutoxy)phenyl]piperazine

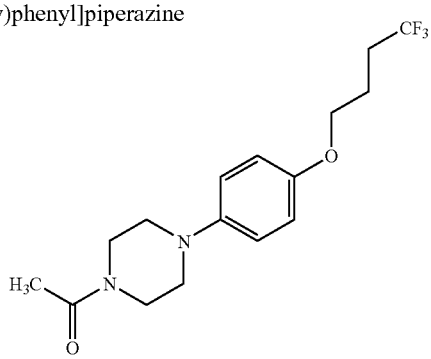

To a solution of 1-acetyl-4-(4-hydroxyphenyl)-piperizine (Aldrich, 20 g, 90 mmol) in dimethylformamide (100 mL) was added potassium carbonate (19 g, 136 mmol), followed by bromo-trifluromethylbutane (25 g, 130 mmol). The reaction mixture was stirred vigorously for 16 hr at 60° C. Afterward, water was added to the mixture at 25° C. The resulting precipitate was filtered and dried under vacuum to produce 30 grams (100% yield) of the desired compound in the form of a tan solid. Proton NMR and MS were consistent with the desired structure.

Part B. Preparation of 1-[4-(4,4,4-trifluorobutoxy)phenyl]piperazine

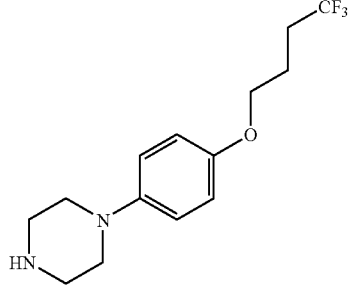

To 30 g of the 1-acetyl-4-[4-(4,4,4-trifluorobutoxy)phenyl]piperazine product from Part A was added aqueous 6 N HCl (100 mL). The resulting solution was heated to 60° C. for 16 hr. Afterward, the solution was cooled to ambient temperature, and aqueous NaOH (100 mL, 2.5N) was added. The milky mixture was placed into a refrigerator to cool for 2 hr. A solid (20 g, 77% yield) separated from the reaction mixture, and was subsequently filtered and dried under vacuum. Proton NMR and MS were consistent with the structure.

Part. C. Preparation of 1-(methylsulfonyl)-4-[4-(4,4,4-trifluorobutoxy)phenyl]piperazine

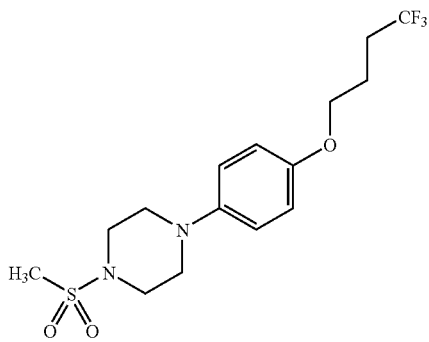

To a solution of the 1-[4-(4,4,4-trifluorobutoxy)phenyl]piperazine product from Part B (5 g, 17 mmol) in methylene chloride (50 mL) was added triethyl amine (4 mL). The mixture was cooled to 0° C. Methane sulfonyl chloride (2.4 g, 21 mmol) in a solution of methylene chloride (10 mL) was then added dropwise. After 2 hr, the reaction was complete. The solvent was removed under reduced pressure to produce a solid residue. To this solid was added water (100 mL). The resulting mixture was filtered and washed with water, and then dried under high vacuum to produce 6 g (95% yield) of the desired compound in the form of a tan solid. Proton NMR and MS were consistent with the desired structure.

Part D. Preparation of tert-butyl ({4-[4-(4,4,4-trifluorobutoxy)phenyl]piperazin-1-yl}sulfonyl)acetate

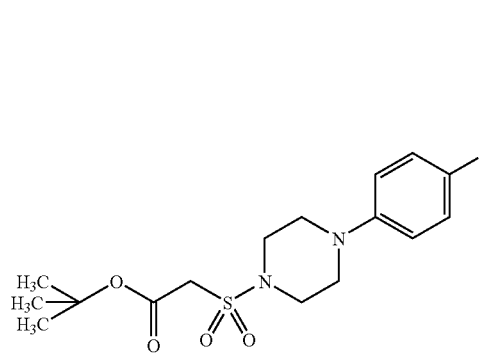

A solution of the 1-(methylsulfonyl)-4-[4-(4,4,4-trifluorobutoxy)phenyl]piperazine product from Part C (10 g, 27 mmol) and di-tert-butyl dicarbonate(6.2 g, 28 mmol) in tetrahydrofuran (50 mL) was cooled to −78° C. Lithium hexamethyldisilazane (80 mL, mmol) was added dropwise. The reaction mixture was stirred as the temperature slowly rose to 0° C. After the reaction completed, aqueous ammonium chloride was added, and the mixture was extracted with ethylacetate and dried over sodium sulfate. The solvent was removed under reduced pressure to produce 7 g (92% yield) of the desired product in the form of a white solid (after washing with methanol). Proton NMR and MS were consistent with the desired structure.

Part E. Preparation of tert-butyl 4-({4-[4-(4,4,4-trifluorobutoxy)phenyl]piperazin-1-yl}sulfonyl)tetrahydro-2H-pyran-4-carboxyate

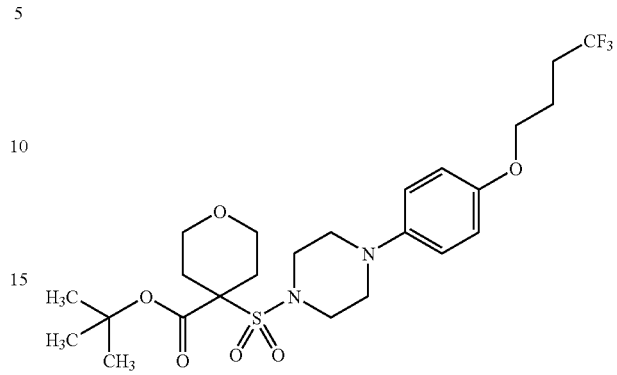

To a solution of the methylene sulfonamide product from Part D (4.66 g, 6.4 mmol) in dimethylacetamide (25 mL) was added potassium carbonate (3 g, 21 mmol), bis-bromoethyl ether (1.5 g, 6.4 mmol), and 18-Crown-6 (500 mg). The slurry was stirred at 60° C. for 24 hr. Afterward, potassium carbonate (1 g, 7 mmol) and bis-bromoethyl ether (0.5 g, 2 mmol) were added, and the mixture was stirred at 60° C. After a total of 48 hr, the reaction mixture was concentrated in vacuo. The residue was taken up in ethyl acetate, washed with water 3 times, washed with saturated NaCl solution, dried over $Na_2SO_4$, filtered, and concentrated in vacuo. Methanol (2 mL/g) was then added to the resulting the oil. The resulting solid (2.5 g, 71% yield) was collected and allowed to air dry. Proton NMR and MS were consistent with the desired structure.

Part F. Preparation of 4-({4-[4-(4,4,4-trifluorobutoxy)phenyl]piperazin-1-yl}sulfonyl)tetrahydro-2H-pyran-4-carboxyic acid

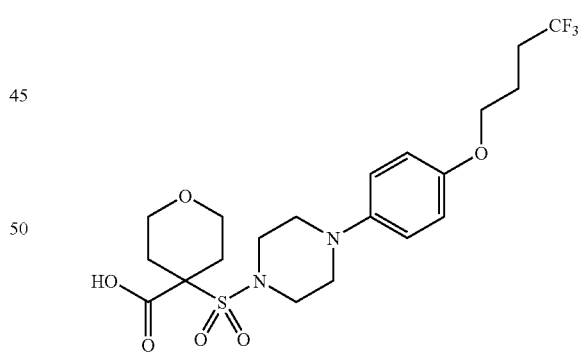

The alpha-tetrahydropyran sulfonamide product from Part E (2.5.0 g, 4.6 mmol) was dissolved in methylene chloride (10 mL) and trifluoracetic acid (10 mL). The resulting mixture was stirred at ambient temperature for 5 hr. Afterward, the solution was concentrated in vacuo. The resulting residue was taken up in diethyl ether (50 mL) and stirred vigorously. This produced a solid, which was collected by filtration and dried to produce the carboxyic acid product in the form of a white solid (2.1 g, 95%). Proton NMR and MS were consistent with the structure.

221

Part G: Preparation of N-(tetrahydro-2H-pyran-2-yloxy)-4-({4-[4-(4,4,4-trifluorobutoxy)phenyl]piperazin-1-yl}sulfonyl)tetrahydro-2H-pyran-4-carboxamide

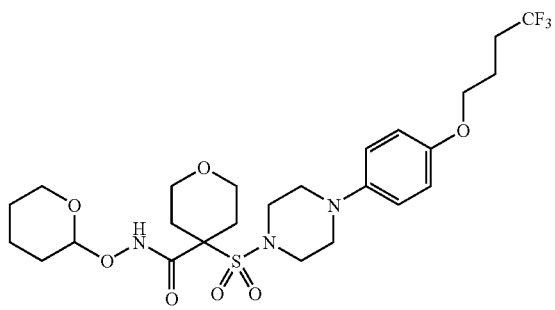

In dry equipment under N₂, the carboxyic acid product from Part F (2 g, 4.2 mmol) was dissolved in dry dimethylacetamide (25 mL). The following reagents were then added to the solution in the following order: N-hydroxybenzotriazole hydrate (0.85 g, 6.28 mmol), triethylamine (1.75 mL, 12.56 mmol), O-(tetrahydro-2H-pyran-2-yl)hydroxyamine (0.74 g, 6.28 mmol), and 1-(3-dimethylaminopropyl)-3-ethylcarbodiimide hydrochloride (1.6 g, 8.37 mmol). The reaction mixture was stirred at 40° C. for 24 hr. Afterward, the reaction mixture was concentrated in vacuo. The residue was taken up in ethyl acetate, washed with water, washed with saturated NaHCO₃, washed with saturated sodium chloride solution, dried over Na₂SO₄, filtered, and concentrated in vacuo to produce the desired THP hydroxamic acid compound in the form of a clear oil. Proton NMR and MS were consistent with the desired structure.

Part H: Preparation of N-hydroxy-4-({4-[4-(4,4,4-trifluorobutoxy)phenyl]piperazin-1-yl}sulfonyl)tetrahydro-2H-pyran-4-carboxamide hydrochloride

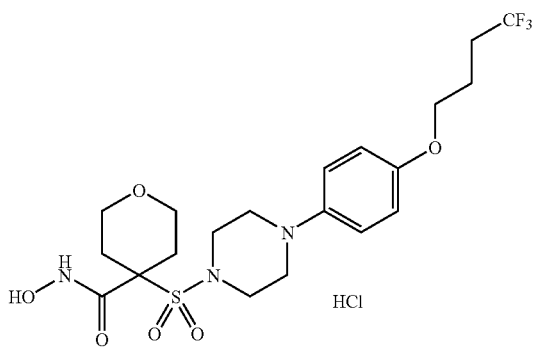

To a solution of the THP hydroxamic acid product from Part G in diethyl ether (3 mL) was added 4N HCl dioxane solution (6.2 mL) and methanol (0.6 mL). After 1 hr at ambient temperature, the reaction mixture was diluted with diethyl ether (30 mL), stirred for 30 min, and filtered under N₂. The resulting solid was washed with diethyl ether (10 mL), and dried in vacuo to produce the desired compound in the form of a white solid (800 mg). HRMS (ES+) M+hr⁺ calculated for C₂₀H₂₈F₃N₃O₆S. ClH=532.98; found=532.30. Proton NMR and MS were consistent with the desired structure.

222

Example 8

Preparation of N-hydroxy-4-({4-[5-(4-methoxyphenyl)pyrimidin-2-yl]piperazin-1-yl}sulfonyl)tetrahydro-2H-pyran-4-carboxamide hydrochloride

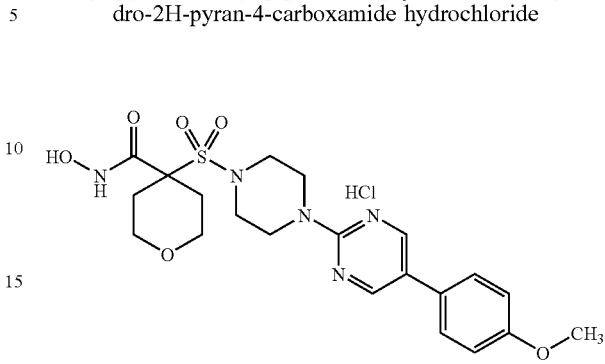

Part A: Preparation of tert-butyl 4-{[4-(5-bromopyrimidin-2-yl)piperazin-1-yl]sulfonyl}tetrahydro-2H-pyran-4-carboxyate

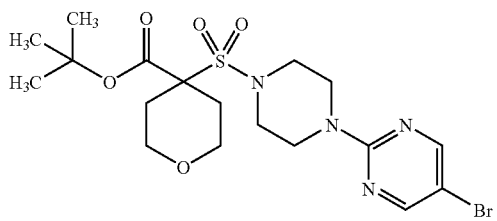

To a solution of tert-butyl 4-(piperazin-1-ylsulfonyl)tetrahydro-2H-pyran-4-carboxyate (3.31 gm, 9.9 mmol, supplied by CarboGen)) in toluene (50 mL) was added 2-chloro-5-bromopyrimidine (2.0 g, 10 mmol) and triethyl amine (5.5 mL, 39.6 mmol). The resulting solution was refluxed for 18 hr, diluted with water (25 mL), and extracted with ethyl acetate. The organic layer was washed with water, washed with saturated NaCl, dried over MgSO₄, filtered, and concentrated in vacuo to produce a solid. The solid was triturated with diethyl ether, and filtered to produce the desired compound in the form of a white solid. (4.7 gm, 99%). MS MH+ calculated for C₁₈H₂₈N₄O₅SBr: 492; found: 492.00.

Part B. Preparation of tert-butyl 4-({4-[5-(4-methoxyphenyl)pyrimidin-2-yl]piperazin-1-yl}sulfonyl)tetrahydro-2H-pyran-4-carboxyate

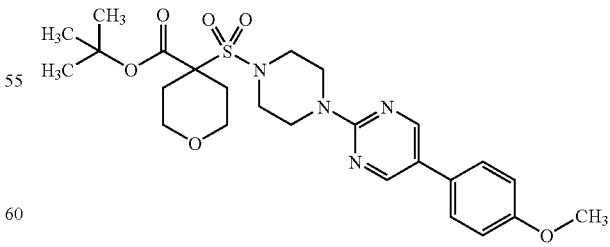

To the tert-butyl 4-{[4-(5-bromopyrimidin-2-yl)piperazin-1-yl]sulfonyl}tetrahydro-2H-pyran-4-carboxyate product from Part A (500 mg, 1.02 mmol) in ethylene glycol dimethyl ether (DME, 7 mL) was added 4-methoxybenzene boronic acid (170 mg, 1.11 mmol), cesium carbonate (665 mg, 2.04 mmol) in water (4 mL), and tetrakis(triphenylphosphine)palladium (0) (85 mg, 0.74 mmol). The resulting mixture was stirred at 80° C. for 18 hr, diluted with water (15 mL), and extracted with ethyl acetate. The organic layer was washed with water, washed with saturated NaCl, dried over MgSO$_4$, filtered, and concentrated in vacuo to produce an oil. Chromatography (on silica, 10% ethyl acetate/hexane) produced the desired compound in the form of a solid (313 mg, 59%). HRMS MH+ calculated for $C_{25}H_{34}N_4SO_6$: 519.2277; found: 519.2327.

Part C. Preparation of 4-({4-[5-(4-methoxyphenyl)pyrimidin-2-yl]piperazin-1-yl}sulfonyl)tetrahydro-2H-pyran-4-carboxyic acid trifluoroacetate

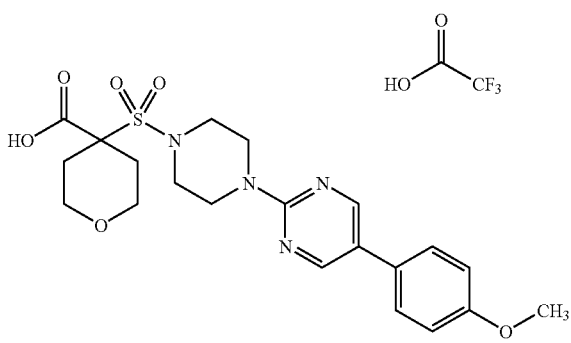

To
the tert-butyl 4-({4-[5-(4-methoxyphenyl)pyrimidin-2-yl]piperazin-1-yl}sulfonyl)tetrahydro-2H-pyran-4-carboxyate product of Part B (300 mg, 0.57 mmol) was added triflouroacetic acid (3 mL, 39.6 mmol). The resulting solution was stirred at ambient temperature for 2 hr. The solution was then concentrated in vacuo to produce the desired acid in the form of a solid (100%). HRMS MH+ calculated for $C_{21}H_{26}N_4SO_6$=463.1651; found=463.1628.

Part D. Preparation of 4-({4-[5-(4-methoxyphenyl)pyrimidin-2-yl]piperazin-1-yl}sulfonyl)-N-(tetrahydro-2H-pyran-2-yloxy)tetrahydro-2H-pyran-4-carboxamide

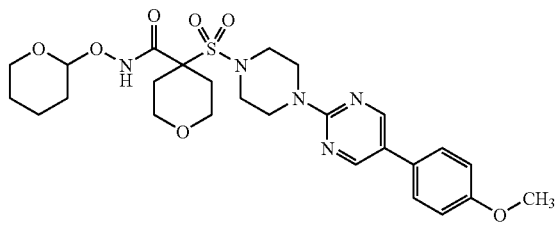

A
solution of the tert-butyl 4-({4-[5-(4-methoxyphenyl)pyrimidin-2-yl]piperazin-1-yl}sulfonyl)tetrahydro-2H-pyran-4-carboxyate acid trifluoroacetate product from Part C (266 mg, 0.57 mmol), N-hydroxybenzotriazole (97.2 mg, 0.72 mmol), 4-methylmorpholine (0.20 mL, 1.8 mmol), O-tetrahydro-2H-pyran-2-yl-hydroxyamine (105 mg, 0.9 mmol), and 1-(3-dimethylaminopropyl)-3-ethylcarbodiimide hydrochloride (161 mg, 0.84 mmol) in DMF (11 mL) was stirred at ambient temperature under an argon atmosphere for 18 hr. Afterward, the solution was concentrated in vacuo, diluted with water (20 mL), and extracted with ethyl acetate. The organic layer was washed with water, washed with saturated NaCl, dried over MgSO$_4$, and concentrated in vacuo to produce a solid. Chromatography (on silica, 5% methanol/acetate) produced the desired compound in the form of a solid (128 mg, 39%). MS H+ calculated for $C_{26}H_{35}N_5SO_7$: 562; found: 562.20

Part E. N-hydroxy-4-({4-[5-(4-methoxyphenyl)pyrimidin-2-yl]piperazin-1-yl}sulfonyl)tetrahydro-2H-pyran-4-carboxamide hydrochloride

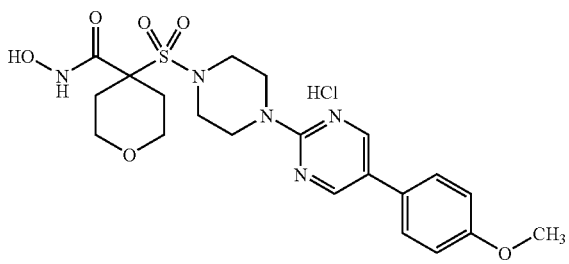

To
a suspension of the protected hydroxamic acid from Part D (128 mg, 0.228 mmol) in methanol (1 mL) was added 4N HCl (1 mL). The resulting mixture was stirred at ambient temperature under an argon atmosphere for 2 hr. The mixture was then concentrated in vacuo to produce a solid. The solid was triturated with diethyl ether and then filtered to produce the desired hydroxamic acid as white solid (95 mg, 81%). HRMS MH+ calculated for $C_{21}H_{27}N_5SO_6$: 478.1760; found 478.1786.

Example 9

Preparation of N-hydroxy-1-(2-methoxyethyl)-4-({4-[4-(4,4,4-trifluorobutoxy)phenyl]piperazin-1-yl}sulfonyl)piperidine-4-carboxamide dihydrochloride

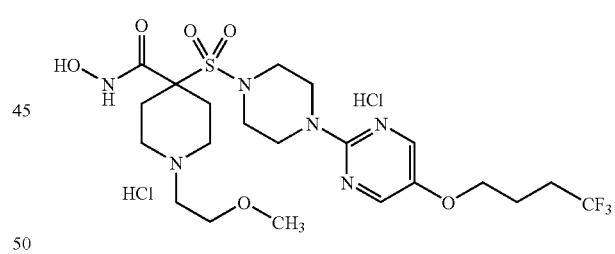

Part A. Preparation of tert-butyl 1-(2-methoxyethyl)-4-({4-[4-(4,4,4-trifluorobutoxy)phenyl]piperazin-1-yl}sulfonyl)piperidine-4-carboxyate. To a solution of the methylene sulfonamide (4.66 g, 10 mmol, prepared according to Part D of Example 7) in dimethylacetamide (25 mL) was added potassium carbonate (4.83 g, 35 mmol), bis-[N-(2-chloroethyl)]-N-(2-methoxyethyl)amine hydrochloride (2.6 g, 11 mmol), and 18-Crown-6 (500 mg). The resulting slurry was stirred at 60° C. for 24 hr. Afterward, potassium carbonate (0.48 g, 3.5 mmol) and bis-N-(2-chloroethyl)-N-(2-methoxyethyl)amine hydrochloride (0.26 g, 1.1 mmol) were added, and the resulting mixture was stirred at 60° C. for 48 hr. Afterward, the mixture was concentrated in vacuo. The resulting residue was taken up in ethyl acetate, washed with water 3 times, washed with saturated NaCl solution, dried over Na$_2$SO$_4$, filtered, and concentrated in vacuo. Chromatography (on silica, ethyl acetate with 10% methanolihexanes) produced the desired alpha-piperidine substituted sulfonamide in the form of a light yellow foam (3.15 g, 53%).

Part B: Preparation of 1-(2-methoxyethyl)-4-({4-[4-(4,4,4-trifluorobutoxy)phenyl]piperazin-1-yl}sulfonyl)piperidine-4-carboxyic acid. The alpha-piperidine substituted sulfonamide product from Part A (3.0 g, 5.06 mmol) was dissolved in methylene chloride (5.0 mL) and trifluoracetic acid (10 mL). The resulting mixture was stirred at ambient temperature for 5 hr. Afterward, the solution was concentrated in vacuo. The resulting residue was taken up in methylene chloride (25 mL), and then concentrated in vacuo. The resulting residue was dissolved in 2.5 N NaOH (30 mL), extracted with ethyl acetate (25 mL), and cooled to 5° C. The aqueous solution was treated with 6N HCl until the pH was 7. The solid was collected by filtration, and dried to produce the desired carboxyic acid product in the form of a white solid (2.35 g, 86%).

Part C. Preparation of 1-(2-methoxyethyl)-N-(tetrahydro-2H-pyran-2-yloxy)-4-({4-[4-(4,4,4-trifluorobutoxy)phenyl]piperazin-1-yl}sulfonyl)piperidine-4-carboxamide. In dry equipment under $N_2$, the carboxyic acid from Part B (2.25 g, 4.18 mmol) was dissolved in dry dimethylacetamide (25 mL). Afterward, additional reagents were added in the following order: N-hydroxybenzotriazole hydrate (0.85 g, 6.28 mmol), triethylamine (1.75 mL, 12.56 mmol), O-(tetrahydro-2H-pyran-2-yl)hydroxyamine (0.74 g, 6.28 mmol), and 1-(3-dimethylaminopropyl)-3-ethylcarbodiimide hydrochloride (1.6 g, 8.37 mmol). The reaction mixture was stirred at 40° C. for 24 hr. Afterward, the reaction mixture was concentrated in vacuo. The residue was taken up in ethyl acetate, washed with water, washed with 5% $KHSO_4$, washed with saturated $NaHCO_3$, washed with saturated sodium chloride solution, dried over $Na_2SO_4$, filtered, and concentrated in vacuo. Chromatography (on silica, ethyl acetate with 10% methanol/hexanes) produced the desired THP hydroxamic acid in the form of a light yellow foam (1.73 g, 65%).

Part D. Preparation of N-hydroxy-1-(2-methoxyethyl)-4-({4-[4-(4,4,4-trifluorobutoxy)phenyl]piperazin-1-yl}sulfonyl)piperidine-4-carboxamide dihydrochloride. To a solution of the THP hydroxamic acid product from Part C (1.57 g, 2.43 mmol) in 1,4-dioxane (3 mL) was added 4N HCl dioxane solution (6.2 mL) and methanol (0.6 mL). After 1 hr at ambient temperature, the mixture was diluted with diethyl ether (30 mL), stirred for 30 min, and filtered under $N_2$. The resulting solid was washed with acetonitrile (10 mL), and dried over phosphorus pentoxide in vacuo to produce the desired compound in the form of a white solid (1.47 g, 95%). HRMS (ES+) M+hr$^+$ calculated for $C_{23}H_{35}N_4O_6S_1F_3$: 553.2302; found 553.2315.

Example 10

Preparation of 1-cyclopropyl-4-[[4-[4-(cyclopropylmethoxy)-3-fluorophenyl]-1-piperazinyl]sulfonyl]-N-hydroxy-4-piperidinecarboxamide, dihydrochloride

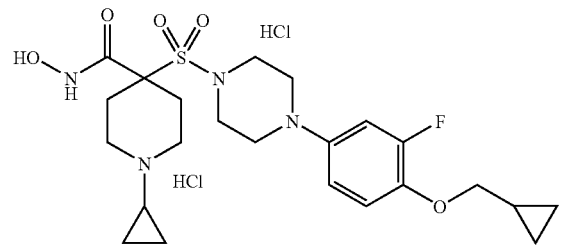

Part A. Preparation of aryl bromide intermediate. 4-Bromo-2-fluorophenol (5.21 g; 27.2 mmol), cesium carbonate (8.866 g; 27.2 mmol), tetrabutylammonium iodide (0.250 g, 0.7 mmol), and bromomethylcyclopropane (4.334 g; 32.1 mmol) were suspended in N-methylpyrrolidinone (15 mL). The resulting mixture was warmed to 80° C. for 10 min. The temperature was then lowered to 50° C. After 2 hr, the mixture was allowed to cool, diluted with water (200 mL), and extracted with ethyl ether (200 mL; then 2×100 mL). The combined organic phases were dried over magnesium sulfate, filtered through a silica plug, and concentrated to produce an aryl bromide product (6.58 g; 99%). The product was characterized by nuclear magnetic resonance and liquid chromatography mass spectroscopy.

Part B. Preparation of aryl piperazine intermediate. The aryl bromide from Part A (6.58 g; 26.9 mmol) was combined with t-butylpiperazine carboxyate (5.98 g; 32 mmol), rac-2,2'-bis(diphenylphosphino)-1,1'-binaphthyl (0.665 g; 1.06 mmol), sodium t-butoxide (3.6 g; 37.4 mmol), 1,4-dioxane (25 mL), and, lastly, tris(dibenzylideneacetone)dipalladium (0) (0.507 g; 0.55 mmol). The mixture was stirred while lowering the temperature in an oil bath set to 50° C. The temperature of the bath was then raised to 100° C. over 30 min. After 1.5 hr, thin layer chromatography of the mixture indicated that the reaction was complete. The mixture was allowed to cool, diluted with water (300 mL), and extracted with dichloromethane (2×150 mL). The combined organic layers were dried using magnesium sulfate. Filtration through a silica plug followed by concentration produced an aryl BOC piperazine product in the form of a dark oil (12.28 g, quantitative), which was characterized by nuclear magnetic resonance and liquid chromatography mass spectroscopy. The crude aryl BOC piperazine product was diluted with methanol (200 mL). Acetyl chloride (12.5 mL, 175 mmol) was then added over 5 min, and the resulting solution was warmed to reflux. After 1 hr, the reaction was finished. The mixture was allowed to cool to ambient temperature, causing a preciptate to begin forming. The solution was decanted into dry ether (500 mL), causing more precipitate to form. The precipitate was collected and dried under vacuum, producing 8.65 g of an aryl piperazine product in the form of a white crystalline product (~quantitative).

Part C. Preparation of aryl sulfonamide intermediate. The aryl piperazine from Part B (8.65 g, 30 mmol) was diluted with triethylamine (11 mL, 79 mmol), N,N-dimethylformamide (7 mL), and dichloromethane (150 mL). The mixture was stirred while being cooled to 0° C. Methanesulfonylchloride (2.9 mL; 37.5 mmol) was then added over 5 min. Afterward, the mixture was warmed to room temperature and stirred continuously for 2 hr. The resulting residue was diluted with water (500 mL), and extracted with dichloromethane (2×100 mL). The combined organic layers were filtered through silica. Removal of the organic solvent produced an aryl sulfonamide in the form of a white solid (8.6 g, 87%).

Part D. Preparation of carboxyic acid intermediate. The aryl sulfonamide (4.8 g; 14.6 mmol) from Part C was dissolved in dry tetrahydrofuran (50 mL) and cooled to −78° C. Lithium bis(trimethylsilyl)amide (1 M in THF, 43 mL) was added dropwise. The reaction then warmed to ambient temperature, and changed from a suspension mixture into a homogenous orange solution. The mixture was re-cooled to −78° C., and dimethyl carbonate (1.42 mL, 15.8 mmol) was added all at once. The reaction mixture was warmed to 0° C., and poured into a saturated solution of ammonium chloride. The solution was extracted with ethyl acetate (3×100 mL). The combined organic layer was dried over magnesium sulfate. Filtration through a silica plug, followed by removing the solvent, produced (4.15 g, 73%) of a carboxyic acid in the form of a crude product.

Part E. Preparation of carboxyic ester intermediate. Bis-(chloroethyl)cyclopropylamine hydrochloride (3.15 g, 14.4 mmol), 18-crown-6 (0.95 g, 3.6 mmol), and potassium carbonate (9.95 g, 72 mmol) were dissolved in N,N-dimethylformamide (10 mL). The mixture was heated to 85° C. The carboxyic acid from Part D (4.15 g; 12 mmol) was suspended in N,N-dimethylformamide (5 mL), and slowly added to the mixture. The temperature was increased to 125° C., and stirred for 3 hr. Afterward, the mixture was cooled to ambient temperature. 200 mL of water was added to the mixture, and the mixture was extracted with ethyl acetate (2×150 mL). The organic layer was dried over magnesium sulfate and filtered through a silica plug. Removal of the organic solvent produced 2.82 g (52%) of a carboxyic ester product.

Part F. Preparation of THP-hydroxamic acid intermediate. The carboxyic ester from Part E (2.82 g; 5.5 mmol) was dissolved in a mixture of ethanol (70 mL) and water (22 mL). Potassium hydroxide (2.21 g, 55 mmol) was added, and the resulting mixture was refluxed for 3 hr. The mixture was cooled to ambient temperature and acidified with concentrated HCl to pH~3. The desired carboxyic acid product was extracted with ethyl acetate (2×100 mL), dried over magnesium sulfate, and filtered through a silica plug. Removal of the solvent produced a crude carboxyic acid. The crude carboxyic acid was suspended in N,N,dimethylformamide (12 mL). 1-Hydroxybenzotriazole (0.912 g, 6.7 mmol), 4-methylmorpholine (1.825 g, 18 mmol), and O-(tetrahydro-2H-pyran-2yl)hydroxyamine (1.12 g, 9.5 mmol) were added to the mixture. Lastly, 1-[2-(dimethylamino) propyl]-3-ethylcarbodiimide hydrochloride (1.56 g, 8.1 mmol) was added. Afterward, the mixture was heated to 65° C., and stirred for 2 hr. The mixture was then cooled to ambient temperature, and water (500 mL) was added. Ethyl acetate (2×100 mL) was used to extract the organic product. The combined organic phases were dried over magnesium sulfate and concentrated. The residue was purified by flash chromatography, affording a THP-hydroxamic acid in the form of a white foam (0.86 g, 27%).

Part G. Preparation of 1-cyclopropyl-4-[[4-[4-(cyclopropylmethoxy)-3-fluorophenyl]-1-piperazinyl]sulfonyl]-N-hydroxy-4-piperidinecarboxamide, dihydrochloride. The THP-hydroxamic acid from Part F (0.860 g; 1.48 mmol) was diluted with methanol (15 mL). Acetyl chloride (0.2 mL, 2.8 mmol) was added. A white precipitate started to form. After 15 min, the reaction mixture was washed with diethyl ether (2×10 mL), and concentrated to produce the desired aryl hydroxamic acid in the form of a white foam (488 mg; 67%). MS MH+ calc'd. for $C_{23}H_{33}FN_4O_5S$ 497; found 497.

Example 11

Preparation of 4-[[4-(4-butoxy-3-fluorophenyl)-1-piperazinyl]sulfonyl]-N-hydroxy-1-(2-methoxy-ethyl)-4-piperidinecarboxamide, dihydrochloride

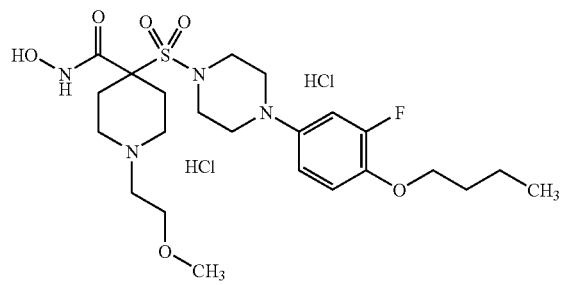

Part A. Preparation of aryl ether intermediate. 4-Bromo-2-fluoro-phenol (19.1 g; 100 mmol), cesium carbonate (39.1 g; 120 mmol), tetrabutylammonium iodide (900 mg), and bromobutane (12.8 mL; 120 mmol) were suspended in N-methylpyrrolidinone (20 mL). The mixture was then warmed to 85° C. During the course of reaction, an additional 20 mL of N-methylpyrrolidinone was added to facilitate stirring. After 2 hr, the mixture was allowed to cool, diluted with water (400 mL), and extracted with 1:1 hexane: ethyl acetate (400 mL; then 100 mL). The combined organic phases were dried over magnesium sulfate, filtered through a silica plug, and concentrated to produce an aryl ether in the form of an oil (23.72 g; 96%). The product was characterized by nuclear magnetic resonance.

Part B. Preparation of aryl piperazine dihydrochloride intermediate. The aryl ether from Part A (23.75 g; 96 mmol) was combined with t-butoxycarbonylpiperazine (21.39 g; 115 mmol), rac-2,2'-bis(diphenylphosphino)-1,1'binaphthyl (2.36 g; 3.8 mmol), sodium t-butoxide (12.0 g; 125 mmol), 1,4-dioxane (75 mL), and, lastly, tris(dibenzylideneacetone) dipalladium (0) (1.10 g; 1.2 mmol). The mixture was lowered into an oil bath set to 50° C. while being stirred. The temperature of the bath was raised over 30 min to 100° C. At that point, thin layer chromatography of the reaction mixture indicated that the reaction was complete. The mixture was allowed to cool, and was then diluted with water (500 mL) and extracted with dichloromethane (2×300 mL). The combined organic layers were dried using magnesium sulfate. Filtration through a silica plug, followed by concentration, produced an aryl BOC piperazine in the form of a dark oil (33.8 g, 95%), which was characterized by nuclear magnetic resonance. The aryl BOC piperazine was diluted with dry methanol (700 mL). Acetyl chloride (17 mL) was then added over 10 min. The solution was warmed to reflux. After 1 hr, the reaction mixture was allowed to cool to ambient temperature. The mixture was then poured into dry ether (1.6 L). An aryl piperazine dihydrochloride precipitate was collected by filtration and dried in vacuo, producing 26.23 g of an aryl piperazine dihydrochloride product as white crystals (81%). Elemental Anal. Calc'd. for $C_{14}H_{21}FN_2O$ (2HCl): C, 51.65; H, 7.07: N, 8.61; found: C, 51.89; H, 7.03: N, 8.52.

Part C. Preparation of sulfonamide intermediate. The aryl piperazine dihydrochloride from Part B (10.0 g, 39.6 mmol) was suspended in a mixture of methylene chloride (140 mL), N,N-dimethylformamide (13 mL), and triethylamine (14 g, 139 mmol). The resulting mixture was stirred for 30 min at 0° C. Methanesulfonyl chloride (4.9 g, 43 mmol) was then added dropwise. After 30 min, the ice bath was removed and the mixture was stirred for 2 hr at ambient temperature. The mixture was diluted with water (800 mL), and extracted with methylene chloride (2×150 mL). The combined organic layers were dried over magnesium sulfate and filtered through a silica plug. Concentration produced a sulfonamide product (9.7 g, 75%) in the form of a pale yellow solid.

Part D. Preparation of ester intermediate. The sulfonamide product from Part C (9.7 g, 29.5 mmol) was dissolved in tetrahydrofuran (60 mL), and then cooled to −78° C. Lithium hexamethyldisilazide (1 M in THF, 100 mL) was added over 10 min. The reaction mixture was allowed to warm to room temperature to allow for complete dissolution of the anion. The mixture was then cooled back down to −78° C. Afterward, dimethylcarbonate (2.65 g, 29.5 mmol) was added. The reaction mixture was allowed to warm to 0° C., and then poured into 600 mL of saturated ammonium chloride with vigorous swirling to quench the anion. The mixture was then extracted with ethyl acetate (3×150 mL). The combined organic phases were dried over magnesium sulfate, filtered through silica, and concentrated to produce an ester in the form of a solid (10.8 g)

Part E. Preparation of piperidine ester intermediate. To a mixture of 18-crown-6 (0.92 g, 3.49 mmol), potassium carbonate (9.56 g, 69.3 mmol), and N,N-bis(2-chloroethyl)-2-methoxyethylamine hydrochloride (3.30 g, 13.9 mmol) in DMF (23 mL) at 60° C. under an atmosphere of $N_2$ was added the ester of Part D (4.50 g, 11.6 mmol) as two portions 15 min apart. After 5 hr at 90° C., the mixture was concentrated in vacuo, diluted with water (350 mL), and extracted with ethyl acetate(3×100 mL). The organic layer was washed with water (2×100 mL) and brine (100 mL), dried over magnesium sulfate, concentrated in vacuo, and purified by flash chromatography (methyl alcohol/ethyl acetate) to produce a piperidine ester in the form of an off-white solid (3.04 g, 51% yield): MS MH$^+$ calcd. for $C_{24}H_{39}FN_3O_6S$ 516; found 516.

Part F. Preparation of O-protected hydroxamic acid intermediate. After a solution of the piperidine ester of Part E (2.90 g, 5.80 mmol) and aqueous 50% NaOH (4.64 g, 58.0 mmol) in methanol (29 mL) and THF (59 mL) was heated at reflux for 1.5 hr, the solution was concentrated in vacuo to a white solid. The solid was dissolved into a water-acetonitrile solution, and the pH was adjusted to 1 with concentrated HCl. The solution was concentrated to produce the crude acid as a HCl salt-NaCl mixture (MS MH$^+$ calcd. for $C_{23}H_{36}FN_3O_6S$ 502; found 502). A mixture of the crude acid, 1-hydroxybenzotriazole hydrate (1.38 g, 10.2 mmol), triethylamine (7.92 mL, 56.8 mmol), O-(tetrahydro-2H-pyran-2-yl)hydroxyamine (1.15 g, 9.82 mmol), and 1-(3-dimethylaminopropyl)-3-ethylcarbodiimide hydrochloride (1.89 g, 9.86 mmol) in DMF (60 mL) under an atmosphere of $N_2$ was heated at 60° C. for 16 hr. The mixture was concentrated in vacuo, diluted with ethyl acetate (300 mL), washed with water (3×100 mL) and brine (100 mL), dried over magnesium sulfate, and concentrated to produce a clear, yellow oil. Chromatographic purification (MeOH/$CH_2Cl_2$) produced an O-protected hydroxamic acid product in the form of a tan foam (1.80 g, 52% yield): MS MH$^+$ calcd. for $C_{28}H_{45}FN_4O_7S$ 601; found 601

Part G. Preparation of 4-[[4-(4-butoxy-3-fluorophenyl)-1-piperazinyl]sulfonyl]-N-hydroxy-1-(2-methoxyethyl)-4-piperidinecarboxamide, dihydrochloride. A solution of the O-protected hydroxamic acid of Part F (1.80 g, 3.00 mmol) and acetyl chloride (1.09 g, 14.4 mmol) in methanol (30 mL) was stirred at ambient temperature for 30 min. The solution was poured into ethyl ether (300 mL), and the solid was collected, washed with ether, and dried in vacuo at 40° C. overnight to produce the desired compound in the form of a white solid (1.32 g, 75% yield): Anal. Calcd. For $C_{23}H_{37}FN_4O_6S.2HCl$: C, 46.86; H, 6.67; N, 7.21; found C, 46.71; H, 7.05; N, 9.47. MS MH$^+$ calcd. for $C_{23}H_{37}FN_4O_6S.2HCl$ 517; found 517.

Example 12

Preparation of 4-{[4-(2-fluoro-1,1'-biphenyl-4-yl)piperazin-1-yl]sulfonyl}-N-hydroxytetrahydro-2H-pyran-4-carboxamide hydrochloride

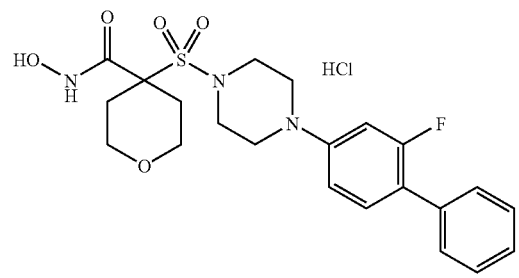

Part A. Preparation of biphenyl ester intermediate. Tert-butyl 4-(piperazin-1-ylsulfonyl)tetrahydro-2H-pyran-4-carboxylate (1.55 g, 4.6 mmol), 1-bromo-3-fluoro-biphenyl (1.16 g, 4.6 mmol), BINAP (115 mg, 0.18 mmol), sodium t-butoxide (622 mg, 6.5 mmol), and dioxane (10 mL) were combined. The resulting mixture was lowered into an 80° C. oil bath. $Pd_2(DBA)_3$ (85 mg, 0.09 mmol) was added to the mixture, and the mixture was then stirred overnight. Afterward, the reaction mixture was allowed to cool, diluted with water (400 mL), and extracted with ethyl acetate (2×150 mL). The organic layer was dried over magnesium sulfate. Concentration produced 2.3 g of a crude biphenyl ester.

Part B. Preparation of biphenyl acid intermediate. The biphenyl ester product from Part A (2.3 g, 4.5 mmol) was dissolved in trifluoroacetic acid and stirred at ambient temperature for 4 hr. The solvent was removed, azeotroping with acetonitrile. The crude biphenyl acid product was dried in vacuo.

Part C. Preparation of THP-hydroxamic acid intermediate. To the dried biphenyl acid product from Part B was added N-methylmorpholine (1.4 g, 14 mmol), O-(tetrahydro-2H-pyran-2-yl)hydroxyamine (0.91 g, 7.8 mmol), 1-hydroxybenzotriazole hydrate (0.74 g, 5.5 mmol), and N,N-dimethylformamide (15 mL). After 10 min of stirring, 1-(3-dimethylaminopropyl)-3-ethylcarbodiimide hydrochloride (1.22 g, 6.4 mmol) was added to the mixture, and the mixture was heated to 80° C. for 4 hr. The reaction mixture was allowed to cool, diluted with water (400 mL), and extracted with ethyl acetate (3×150 mL). The combined organic layers were dried over magnesium sulfate and concentrated. The resulting residue was purified by flash chromatography, affording a THP-hydroxamic acid in the form of a foam.

Part D. Preparation of 4-{[4-(2-fluoro-1,1'-biphenyl-4-yl)piperazin-1-yl]sulfonyl}-N-hydroxytetrahydro-2H-pyran-4-carboxamide hydrochloride. The THP-hydroxamic acid from Part C was dissolved in methanol. Acetyl chloride (ca. 1 mL) was added slowly. After 10 min, the product was precipitated by addition of ether (20 mL). The solid was collected and dried in a vacuum oven at 50° C., affording 520 mg of the desired biphenyl hydroxamic acid (23% from the biphenyl ester). MS MH+ calcd. for $C_{22}H_{27}N_3O_5FS$ 464.1655, found 464.1650.

Example 13

Preparation of 4-{[4-(3-fluoro-4-pentylphenyl)piperazin-1-yl]sulfonyl}-N-hydroxy-1-(2-methoxyethyl)piperidine-4-carboxamide dihydrochloride

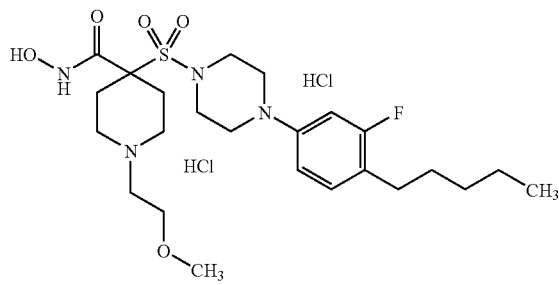

Part A. Preparation of alkene intermediate. To a mixture of 4-bromo-2-fluorobenzaldehyde (2.00 g, 9.86 mmol) and potassium carbonate (1.72 g, 12.10 mmol) in isopropyl alcohol (5 mL) under an atmosphere of $N_2$ at ambient temperature was added butyltriphenylphosphonium bromide (4.92 g, 12.3 mmol). The reaction mixture was heated at 80° C. for 18 hr, concentrated in vacuo, diluted with ether, and filtered through a silica bed. The filtrate was concentrated in vacuo to produce an alkene in the form of a clear, colorless liquid (1.78 g, 74% yield). The proton NMR spectrum was consistent for the desired alkene as a mixture of cis and trans isomers.

Part B. Preparation of aryl alkene intermediate. The alkene product from Part A (0.810 g, 3.33 mmol) was added to a 65° C. mixture of tert-butyl 1-(2-methoxyethyl)-4-(piperazin-1-ylsulfonyl)piperidine-4-carboxyate (1.23 g, 3.15 mmol), sodium tert-butoxide (0.354 g, 3.68 mmol), racemic-2,2'-bis(diphenylphosphino)-1,1'-binaphthyl(0.049 g, 0.078 mmol), and tris(dibenzylideneacetone)-dipalladium (0) (0.024 g, 0.026 mmol) in anhydrous 1,4-dioxane (5.7 mL) under an $N_2$ atmosphere. After heating the black mixture at 65° C. for 2 hr and 80° C. for 3 hr, the ambient mixture was poured into water (150 mL) and extracted with $CH_2Cl_2$ (3×50 mL). The organic layer was washed with water (2×50 mL), dried over $MgSO_4$, concentrated in vacuo, and purified by flash chromatography (silica gel; methanol/ethyl acetate) to produce an aryl alkene product in the form of a tan solid (1.29 g, 74% yield). The proton NMR spectrum was consistent for the desired structure as a mixture of cis and trans isomers.

Part C. Preparation of aryl pentane intermediate. Hydrogenation of the aryl alkene product from Part B (1.20 g, 1.81 mmol) in ethanol with 4% Pd on carbon at ambient temperature produced an aryl pentane product in the form of a white solid (0.95 g, 95% yield): MS MH+ calcd. for $C_{28}H_{47}FN_3O_5S$ 556; found 556.

Part D. Preparation of acid intermediate. A solution of the aryl pentane product from Part C (0.900 g, 1.67 mmol) in trifluoroacetic acid (10 mL) was stirred at ambient temperature for 18 hr. The solution was treated with 4N HCl in dioxane and concentrated in vacuo to produce an acid product in the form of a tan solid (0.679 g, 73% yield): MS MH+ calcd. for $C_{24}H_{39}FN_3O_5S$ 500; found 500.

Part E. Preparation of O-protected hydroxamic acid intermediate. A mixture of the acid product from Part D (0.670 g, 1.17 mmol), 1-hydroxybenzotriazole hydrate (0.237 g, 1.75 mmol), N-methylmorpholine (0.43 mL, 3.9 mmol), O-(tetrahydro-2H-pyran-2-yl)hydroxyamine (0.238 g, 2.03 mmol), and 1-(3-dimethylaminopropyl)-3-ethylcarbodiimide hydrochloride (0.278 g, 1.75 mmol) in DMF (5 mL) under an atmosphere of $N_2$ was heated at 60° C. for 18 hr. The mixture was concentrated in vacuo, diluted with acetonitrile, and concentrated in vacuo. The resulting residue was partitioned between saturated $NaHCO_3$ (150 mL) and $CH_2Cl_2$ (50 mL). The aqueous layer was extracted with $CH_2Cl_2$ (2×50 mL). The combined organic layers were washed with water (50 mL), dried over $MgSO_4$, and concentrated in vacuo to a clear, yellow oil. Chromatography purification (silica gel; methanol/ethyl acetate) produced an O-protected hydroxamic acid product in the form of a solid (0.396 g, 56% yield): MS MH+ calcd. for $C_{29}H_{48}FN_4O_6S$ 599; found 599.

Part F. Preparation of 4-{[4-(3-fluoro-4-pentylphenyl)piperazin-1-yl]sulfonyl}-N-hydroxy-1-(2-methoxyethyl)piperidine-4-carboxamide dihydrochloride. A solution of the O-protected hydroxamic acid product from Part E (0.390 g, 0.651 mmol) and acetyl chloride (0.236 g, 3.13 mmol) in methanol (6 mL) was stirred at ambient temperature for 1 hr. The solution was poured into ethyl ether (100 mL). The solid was collected, washed with ether, and dried in vacuo at 40° C. in a vacuum overnight to provide the desired compound in the form of a tan solid (0.27 g, 70% yield) MS MH+ calcd. for $C_{24}H_{40}FN_4O_5S$ 515; found 515.

Example 14

Preparation of N-hydroxy-4-({4-[4-(2-methoxyethoxy)phenyl]piperazin-1-yl}sulfonyl)tetrahydro-2H-pyran-4-carboxamide hydrochloride

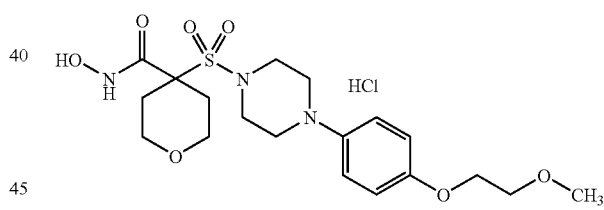

Part A: Preparation of 1-bromo-4-(2-methoxyethoxy)benzene.

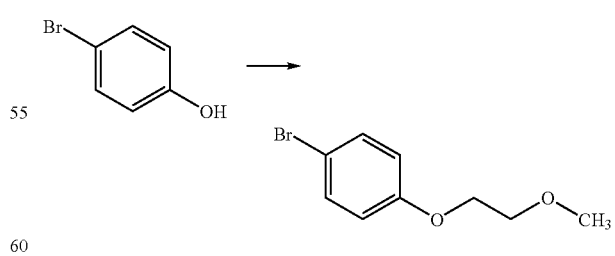

To a room temperature solution of 4-bromophenol (5 g, 28.9 mmol) in 15 mL DMF under $N_2$ was added 2-bromoethyl methyl ether (5 g, 36.4 mmol) and potassium carbonate (4.4 g, 31.8 mmol). The resulting solution was stirred overnight at ambient temperature under $N_2$. Afterward, no starting material remained. The mixture was concentrated, partially dissolved in ethyl acetate (50 mL), and filtered. The filtrate was concentrated under reduced pressure, affording 5.6 g of crude oil. ¹H NMR and mass spectrometry (MNa⁺=287.0) were consistent with the desired product.

Part B: Preparation of tert-butyl 4-({4-[4-(2-methoxyethoxy)phenyl]piperazinyl}sulfonyl)perhydro-2H-pyran-4-carboxylate.

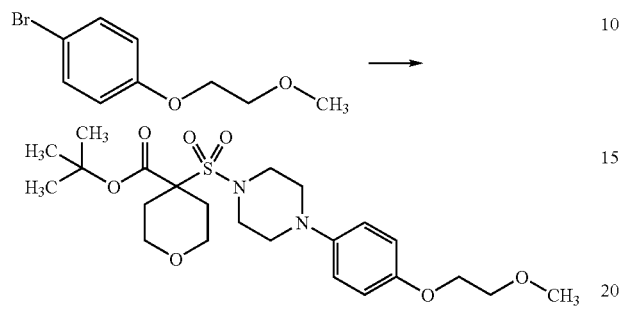

To a solution of tert-butyl 4-(piperazinylsulfonyl)perhydro-2H-pyran-4-carboxylate (1.5 g, 4.5 mmol, supplied by CarboGen) in toluene (40 mL) under N₂ were added the product from Part A (1.14 g, 4.95 mmol), sodium tert-butoxide (1.08 g, 11.25 mmol), palladium(II) acetate (10 mg, 0.045 mmol), and tert-tri-butylphosphine (7.0 mg, 0.036 mmol). The reaction was continued overnight at 60° C. under N₂. Afterward, no starting material remained. The reaction was diluted with methanol and concentrated under reduced pressure. The residue was partially dissolved in dichloromethane and filtered to afford 1.8 g (82%) of the crude product. Mass spectrometry (MH⁺=486.4) was consistent with desired product.

Part C: Preparation of 4-({4-[4-(2-methoxyethoxy)phenyl]piperazinyl}sulfonyl)perhydro-2H-pyran-4-carboxylic acid.

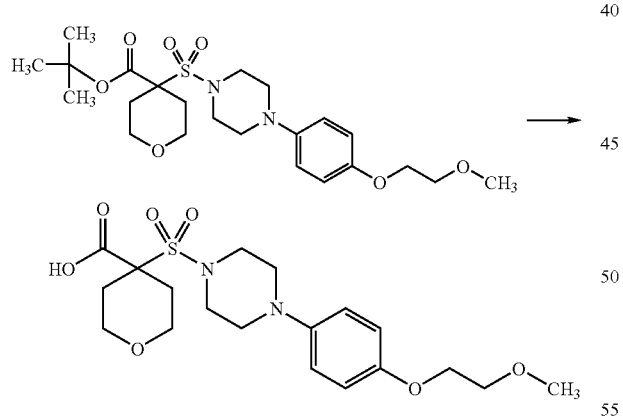

The product from Part B (1.8 g, 3.7 mmol) was dissolved in 1:1 trifluoroacetic acid/dichloromethane (10 mL). The reaction was continued overnight at room temperature under N₂. Afterward, no starting material was detected by HPLC. The mixture was concentrated under reduced pressure. Additional dichloromethane was added, and the solvent was once again removed under reduced pressure. The resulting solid was triturated with ether and filtered to afford the desired product (1.06 g (67%)) of as a white solid. ¹HNMR and mass spectrometry (MH⁺=429) was consistent with desired product.

Part D: Preparation of [4-({4-[4-(2-methoxyethoxy)phenyl]piperazinyl}sulfonyl)perhydro-2H-pyran-4-yl]-N-perhydro-2H-pyran-2-yloxycarboxamide:

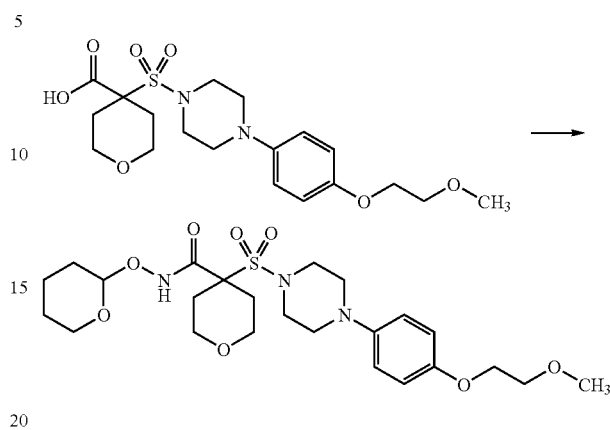

To a solution of the product from Part C (1.0 g, 2.3 mmol) dissolved in N,N-dimethylformamide (15 mL) were added triethylamine (516 mg, 5.1 rmnol), N-hyroxybenzatriazole (373 mg, 2.76 mmol), O-(tetrahydro-2H-pyran-2-yl)hydroxylamine (404 mg, 3.4 mmol), and 1-(3-dimethylaminopropyl)-3-ethylcarbodiimide hydrochloride (615 mg, 3.2 mmol). The reaction was continued overnight at ambient temperature under N₂. Afterward, no starting material was detected by HPLC. The mixture was diluted with ethyl acetate and washed with water (3×50 mL), saturated sodium bicarbonate (3×50 mL), and brine (1×50 mL). The organic layer was dried over magnesium sulfate, filtered, and concentrated to afford 1.24 g of crude oil. Mass spectrometry (MNa⁺=550) was consistent with desired product.

Part E: Preparation of N-hydroxy-4-({4-[4-(2-methoxyethoxy)phenyl]piperazin-1-yl}sulfonyl)tetrahydro-2H-pyran-4-carboxamide hydrochloride.

The product from Part D (1.2 g, 2.3 mmol) was dissolved in 4N HCl in dioxane (12 mL) and methanol (1 mL). The reaction was continued at ambient temperature for 1 h. Afterward, no starting material was detected by HPLC. The product was concentrated under reduced pressure and triturated with diethyl ether. The resulting white solid was collected by suction filtration affording 560 mg (51%) of the desired product. ¹HNMR was consistent with desired product. HRMS for $C_{19}H_{29}N_3O_7S$ showed [M+H]$_{found}$=444.1802 for [M+H]$_{calc}$=444.1799.

Example 15

Preparation of N-hydroxy-1-(2-methoxyethyl)-4-{[4-(4-pentylpheyl)piperidin-1-yl]sulfonyl}piperidine-4-carboxamide hydrochloride

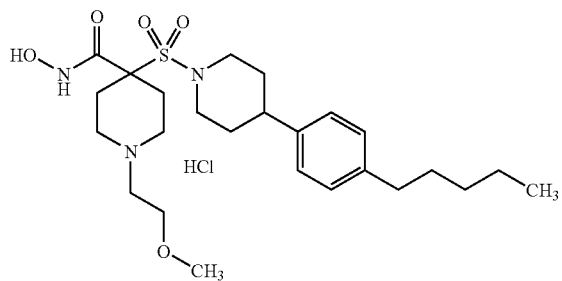

Part A. Preparation of Alcohol Intermediate. Magnesium turnings (0.606 g, 24.95 mmol) and iodine were heated in a 3-neck flask (fitted with an addition funnel and a reflux condensor) with a heat-gun until iodine vapors appeared. After cooling to ambient temperature, tetrahydrofuran (10 mL) was added, followed by the slow addition of a solution of 1-bromo-4-n-pentylbenzene (5.00 g, 22.01 mmol) in tetrahydrofuran (50 mL). The mixture was heated with a heat-gun during the addition. After the addition was complete, the mixture was heated at reflux for 1 hr. The reaction mixture was then cooled in an ice-bath, and a solution of 1-benzyl-4-piperidone (2.78 g, 14.67 mmol) in tetrahydrofuran (40 mL) was quickly added. After slowly warming over 3 hr, the reaction mixture was re-cooled in an ice-bath. Water (25 mL) was added, followed by ethyl acetate (25 mL). The organic layer was removed, and the aqueous layer was further extracted with ethyl acetate. The organic layer was washed with saturated NaCl and dried over $Na_2SO_4$. Chromatography (on silica, ethyl acetate/hexanes) produced an alcohol in the form of a pale yellow oil (4.43 g, 90%).

Part B. Preparation of Alkene Intermediate. To a solution of the alcohol of Part A (3.13 g, 9.27 mmol) in dichloromethane (10 mL) was added trifluoroacetic acid (10 mL, 129.80 mmol). The resulting mixture was stirred at ambient temperature for 3.5 hr, and then concentrated in vacuo. The residue was partitioned between diethyl ether and water. The organic layer was washed with saturated NaCl and dried over $Na_2SO_4$. Concentration in vacuo produced an alkene in the form of an amber oil (2.93 g, 99%).

Part C. Preparation of Piperidine Intermediate. To a solution of the alkene of Part B (2.93 g, 9.17 mmol) in methanol (20 mL) was added ammonium formate (1.74 g, 27.51 mmol) and 10% Pd/C (0.917 g). The resulting mixture was heated at reflux. After 7 hr, the reaction mixture was cooled to ambient temperature and filtered through a pad of Celite®, washing with methanol. The filtrate was concentrated in vacuo to produce a piperidine in the form of a yellow oil (2.10 g, quantitative yield).

Part D. Preparation of Sulfonamide Intermediate. To an ice-cold solution of the piperidine of Part C (1.00 g, 4.32 mmol) in dichloromethane (8.0 mL) was added diisopropylethylamine (1.66 mL, 9.51 mmol) and N-(benzyloxycarbonyl)-4-(chlorosulfonyl)piperidine (1.65 g, 5.19 mmol). The resulting mixture was slowly allowed to warm to ambient temperature with stirring for 2 days. The reaction mixture was then diluted with dichloromethane, washed with $H_2O$, 5% $KHSO_4$, washed with saturated NaCl, and dried over $Na_2SO_4$. Chromatography (on silica, ethyl acetate/hexanes) produced sulfonamide in the form of an off-white oily solid (1.32 g, 60%).

Part E. Preparation of Methyl Ester Intermediate. To a solution of the sulfonamide of Part D (1.32 g, 2.57 mmol) in tetrahydrofuran (5.0 mL) was slowly added lithium bis(trimethylsilyl)amide (6.44 mL, 1M in tetrahydrofuran, 6.44 mmol). After 1 hr at ambient temperature, a solution of dimethyl carbonate (0.348 g, 3.86 mmol) in tetrahydrofuran (2.0 mL) was quickly added. The resulting mixture was stirred at ambient temperature overnight. Additional lithium bis(trimethylsilyl)amide (2.57 mL, 1M in tetrahydrofuran, 2.57 mmol) was then added. After 1.5 hr, a solution of dimethyl carbonate (0.174 g, 1.93 mmol) in tetrahydrofuran (1.0 mL) was quickly added. After stirring at ambient temperature overnight, the reaction mixture was cooled in an ice-bath and quenched by the addition of saturated $NH_4Cl$. Water was added, and the organic layer was removed. The aqueous layer was further extracted with ethyl acetate. The combined organic layers were washed with 5% $KHSO_4$, washed with saturated NaCl, and dried over $Na_2SO_4$. Chromatography (on silica, ethyl acetate/hexanes) produced a methyl ester in the form of an off-white solid (0.410 g, 28%).

Part F. Preparation of Amine Intermediate. To a suspension of the methyl ester of Part E (0.923 g, 1.62 mmol) and 10% Pd/C (0.162 g) in ethyl acetate (10 mL) was bubbled $H_2$. After the uptake of $H_2$ ceased, the mixture was filtered through a pad of Celite® washing with ethyl acetate methanol, tetrahydrofuran and dichloromethane. The filtrate was concentrated in vacuo to produce an amine in the form of a gray solid (0.615 g, 87%).

Part G. Preparation of N-methoxyethyl Amine Intermediate. To a suspension of the amine of Part F (0.615 g, 1.41 mmol) and $K_2CO_3$ (0.428 g, 3.10 mmol) in N,N-dimethylformamide (6.0 mL) was added 2-bromoethyl methyl ether (0.199 mL, 2.12 mmol). The resulting mixture was heated at 50° C. for 7 hr. The reaction mixture was then diluted with acetonitrile and filtered through a pad of Celite®. The filtrate was concentrated in vacuo. Chromatography (on silica, ethyl acetate with 10% methanol/hexanes) produced an N-methoxyethyl amine in the form of a tan solid (0.446 g, 64%).

Part H. Preparation of Acid Intermediate. To a solution of the N-methoxyethyl amine of Part G (0.446 g, 0.902 mmol) in tetrahydrofuran (5.0 mL) was added potassium trimethylsilanolate (0.231 g, 1.80 mmol). The resulting mixture was stirred at ambient temperature for 24 hr. The reaction mixture was concentrated by blowing $N_2$ over the mixture. Water was added, and the reaction was neutralized with 1N HCl (pH-7) and partially concentrated in vacuo. The precipitate was collected by filtration to produce an acid in the form of a white solid (0.271 g, 62%).

Part I. Preparation of Protected Hydroxamic acid Intermediate. To a solution of the acid of Part H (0.271 g, 0.564 mmol) in N,N-dimethylformamide (5.0 mL) was added 1-Hydroxybenzotriazole hydrate (0.091 g, 0.677 mmol), triethylamine (0.236 mL, 1.69 mmol), O-(tetrahydropyranyl)hydroxylamine (0.198 g, 1.69 mmol), and 1-(3-Dimethylaminopropyl)-3-ethylcarbodiimide hydrochloride (0.162 g, 0.846 mmol). The resulting mixture was stirred at 50° C. for 8 hr, and then cooled to ambient temperature. The reaction mixture was partitioned between water and ethyl acetate. The organic layer was washed with saturated NaCl, and dried over $Na_2SO_4$. Chromatography (on silica, ethyl acetate with 10% methanol/hexanes) produced a protected hydroxamic acid in the form of a pale yellow foam (0.109 g, 33%).

Part J. Preparation of N-hydroxy-1-(2-methoxyethyl)-4-{[4-(4-pentylpheyl)piperidin-1-yl]sulfonyl}piperidine-4-carboxamide hydrochloride. To the protected hydroxamic acid of Part I (0.100 g, 0.172 mmol) was added a solution of 4N HCl in dioxane (0.500 mL, 2.00 mmol) and methanol (0.100 mL, 2.47 mmol). The resulting mixture was stirred at ambient temperature for 1.5 hr. Diethyl ether was then added. The solids were collected by filtration and washed with diethyl ether to produce the title compound in the form of a pale pink solid (0.068 g, 74%). HRMS MH⁺ calculated for $C_{25}H_{41}N_3O_5S$: 496.2845; found 496.2852.

Example 16

Preparation of 4-{[4-(4-butoxyphenyl)piperidin-1-yl]sulfonyl}-N-hydroxy-1-(2-methoxyethyl)piperidine-4-carboxamide hydrochloride

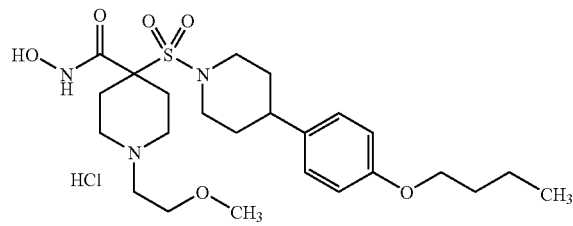

Part A. Preparation of Alcohol Intermediate. Magnesium turnings (2.40 g, 98.93 mmol) and iodine were heated in a 3-neck flask (fitted with an addition funnel and a reflux condenser) with a heat-gun until iodine vapors appeared. After cooling to ambient temperature, tetrahydrofuran (50 mL) was added, followed by slow addition of a solution of 4-bromo-butoxybenzene (20.0 g, 87.29 mmol) in tetrahydrofuran (200 mL). The mixture was heated with a heat-gun during the addition. After the addition was complete, a small amount of 1,2-dibromoethane was added, and the mixture was heated at reflux for 2.5 hr. The reaction mixture was then cooled in an ice-bath, and a solution of 1-benzyl-4-piperidone (11.01 g, 58.19 mmol) in tetrahydrofuran (200 mL) was quickly added. After slowly warming to ambient temperature overnight, the reaction mixture was re-cooled in an ice-bath and quenched by the addition of 1N HCl (100 mL). Additional water (100 mL) was added, and the organic layer was removed. The aqueous layer was further extracted with ethyl acetate. The combined organic layers were washed with saturated NaCl and dried over $Na_2SO_4$. Concentration in vacuo produced an alcohol in the form of a tan oil (26.6 g, quantitative yield).

Part B. Preparation of Alkene Intermediate. To a solution of the alcohol of Part A (19.75 g, 58.19 mmol) in dichloromethane (50 mL) was added trifluoroacetic acid (50 mL, 649.0 mmol). The resulting mixture was stirred at ambient temperature overnight, and then concentrated in vacuo. The residue was partitioned between diethyl ether and water. The aqueous layer was neutralized with 2.5 N NaOH (pH-7), and extracted with diethyl ether. The combined organic layers were washed with saturated NaCl and dried over $Na_2SO_4$. Chromatography (on silica, ethyl acetate/hexanes) produced an alkene in the form of a yellow oily solid (12.4 g, 66%).

Part C. Preparation of Piperidine Intermediate. To a solution of the alkene of Part B (12.40 g, 38.57 mmol) in methanol (80 mL) was added ammonium formate (7.30 g, 115.71 mmol) and 10% Pd/C (3.86 g). The resulting mixture was heated at reflux. After 3 hr, the reaction mixture was cooled to ambient temperature and filtered through a pad of Celite®, washing with methanol. The filtrate was concentrated in vacuo to produce a piperidine in the form of a yellow oil (9.30 g, quantitative yield).

Part D. Preparation of Sulfonamide Intermediate. To an ice-cold solution of the piperidine of Part C (9.0 g, 38.57 mmol) in dichloromethane (75.0 mL) was added triethylamine (11.83 mL, 84.85 mmol) and N-(benzyloxycarbonyl)-4-(chlorosulfonyl)piperidine (3.58 g, 46.28 mmol). The resulting mixture was slowly allowed to warm to ambient temperature with stirring for 1 hr. The reaction mixture was then concentrated in vacuo. The residue was partitioned between water and ethyl acetate. The combined organic layers were washed with $H_2O$, 5% $KHSO_4$, washed with saturated NaCl, and dried over $Na_2SO_4$. Chromatography (on silica, ethyl acetate/hexanes) produced a sulfonamide in the form of an off-white solid (3.46 g, 29%).

Part E. Preparation of Methyl Ester Intermediate. To a suspension (pre-cooled to −40° C.) of the sulfonamide of Part D (1.00 g, 3.21 mmol) and dimethyl carbonate (0.325 mL, 3.85 mmol) in tetrahydrofuran (15.0 mL) was slowly added lithium bis(trimethylsilyl)amide (8.03 mL, 1M in tetrahydrofuran, 8.03 mmol). After 30 min at −40° C., the reaction was quenched by the addition of saturated $NH_4Cl$. Water was added, and the organic layer was removed. The aqueous layer was further extracted with ethyl acetate. The combined organic layers were washed with 5% $KHSO_4$, washed with saturated NaCl, and dried over $Na_2SO_4$. Concentration in vacuo produced a methyl ester in the form of a tan solid (1.22 g, quantitative yield).

Part F. Preparation of N-Methoxyethyl Amine Intermediate. To a solution of bis(2-chloroethyl)-2-methoxyethyl amine hydrochloride (1.80 g, 7.59 mmol) in N,N-dimethylformamide (10 mL) was added $K_2CO_3$ (5.72 g, 41.4 mmol), 18-C-6 (0.182 g, 0.690 mmol) and a solution of the methyl ester of Part E (2.55 g, 6.90 mmol) in N,N-dimethylformamide (5.0 mL). The resulting mixture was heated at 60° C. for 23 hr. After cooling to ambient temperature, the reaction mixture was partitioned between ethyl acetate and water. The organic layer was washed with saturated NaCl, and dried over $Na_2SO_4$. Chromatography (on silica, ethyl acetate with 10% methanol/hexanes) produced an N-methoxyethyl amine (1.38 g, 40%).

Part G. Preparation of Acid Intermediate. To a solution of the N-methoxyethyl amine of Part F (1.38 g, 2.78 mmol) in tetrahydrofuran (10.0 mL) was added potassium trimethylsilanolate (0.731 g, 5.56 mmol). The resulting mixture was stirred at ambient temperature for 23 hr, at which time additional potassium trimethylsilanolate (0.019 g, 0.702 mmol) was added. After stirring at ambient temperature for 2.5 hr, the reaction mixture was concentrated by blowing $N_2$ over the reaction mixture. Water was added, and the reaction mixture was neutralized with 1N HCl (pH-7). Afterward, the reaction mixture was partially concentrated in vacuo. The precipitate was collected by filtration to produce an acid in the form of a white solid (0.860 g, 64%).

Part H. Preparation of Protected Hydroxamic acid Intermediate. To a solution of the acid of Part G (0.860 g, 7.18 mmol) in N,N-dimethylformamide (8.0 mL) was added 1-Hydroxybenzotriazole hydrate (0.289 g, 2.14 mmol), triethylamine (0.744 mL, 5.34 mmol), O-(tetrahydropyranyl)hydroxylamine (0.626 g, 5.34 mmol), and 1-(3-Dimethylaminopropyl)-3-ethylcarbodiimide hydrochloride (0.512 g, 2.67 mmol). The resulting mixture was stirred at 50° C. for 14 hr, at which time additional HoBt (0.072 g, 0.534 mmol) and EDC (0.128 g, 0.668 mmol) were added. After heating at 50° C. for 6 hr, the reaction was cooled to ambient temperature. The reaction mixture was partitioned between water and ethyl acetate. The organic layer was washed with saturated NaCl, and dried over $Na_2SO_4$. Chromatography (on silica, ethyl acetate with 10% methanol/hexanes) produced a protected hydroxamic acid in the form of a pale yellow foam (0.879 g, 85%).

Part I. Preparation of 4-{[4-(4-butoxyphenyl)piperidin-1-yl]sulfonyl}-N-hydroxy-1-(2-methoxyethyl)piperidine-4-carboxamide hydrochloride. To a solution of the protected hydroxamic acid of Part H (0.879 g, 1.51 mmol) in dioxane (2.0 mL) was added a solution of 4N HCl in dioxane (3.78 mL, 15.11 mmol) and methanol (0.613 mL, 15.11 mmol). The resulting mixture was stirred at ambient temperature for 1.5 hr. The mixture was then slowly added to a rapidly stirred solution of diethyl ether. The precipitate was collected by filtration and washed with diethyl ether to produce the title compound in the form of an off-white solid (0.634 g, 79%). HRMS $MH^+$ calculated for $C_{24}H_{39}N_3O_6S$: 498.2632; found 498.2622.

Example 17

Preparation of N-hydroxy-4-({4-[4-(3,3,4,4,4-pentafluorobutyl)phenyl]piperazin-1-yl}sulfonyl)tetrahydro-2H-pyran-4-carboxamide hydrochloride

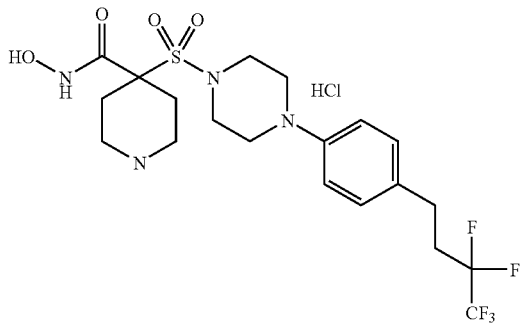

Part A. t-Butyl-2-[1-[4-(4-bromophenyl)piperazinyl]sulfonyl]acetate (Carbogen, 15 g, 35.7 mmol), $K_2CO_3$ (14.83 g, 107.3 mmol), N,N-dimethylformamide (140 mL), 2-bromoethyl ether (Aldrich, 9.13 g, 39.3 mmol), and 18-crown-6 (catalytic amount, spatula tip) were heated at 70° C. overnight with mixing under an $N_2$ atmosphere. Additional $K_2CO_3$ (4.94 g, 35.7 mmol) and 2-bromoethyl ether (3.69 g, 16 mmol) were added, and the resulting mixture was stirred overnight under $N_2$. Afterward, $K_2CO_3$ (4.94 g, 35.7 mmol) and 2-bromoethyl ether (3.69 g, 16 mmol) were added to the mixture, and the mixture was stirred overnight under $N_2$. The reaction was cooled to ambient temperature and poured into ethyl acetate (500 mL) and deionized water (200 mL). The layers were separated, and the aqueous layer was back-extracted with ethyl acetate (100 mL). The combined ethyl acetate layers were washed with 100 mL of each of a 1:1 mixture of deionized water:saturated NaCl(aq) and saturated NaCl(aq), dried over $MgSO_4$, and concentrated in vacuo to produce a yellow solid. The solid was stirred in MeOH (50 mL) for 1 hr, filtered, and washed with MeOH (15 mL). The resulting solid was dried in a vacuum oven at 50° C. overnight producing 11.1 g (64%) of the desired t-butyl ester pyran product. $^1H$ NMR confirmed the structure of the desired product.

Part B. Zn/Cu couple (1.22 g, 18.8 mmol), 1,1,1,2,2-pentafluoro-4-iodobutane, Matrix Scientific, (3.35 g, 12.2 mmol), benzene (32.5 mL), and N,N-dimethylformamide (6.5 mL) were heated together for 3 hours at 60° C. under $N_2$. The t-butyl ester pyran from Part A (2.0 g, 4.1 mmol) and [1,1'-Bis(diphenylphosphino)ferrocene]dichloropalladium (II), complex with $CH_2Cl_2$ (1:1), Aldrich, (0.166 g, 0.2 mmol) were added, and the resulting dark mixture was stirred overnight at 78° C. under $N_2$. Zn/Cu couple (1.22 g, 18.8 mmol), 1,1,1,2,2-pentafluoro-4-iodobutane, iodobutane, Matrix Scientific, (3.35 g, 12.2 mmol), benzene (32.5 mL), and N,N-dimethylformamide (6.5 mL) were heated together for 3 hr at 60° C. under $N_2$. This mixture was added to the original flask along, with an additional portion of the Pd catalyst (same amount used above). The resulting mixture was then stirred overnight at 78° C. under $N_2$. Zn/Cu couple (1.22 g, 18.8 mmol), 1,1,1,2,2-pentafluoro-4-iodobutane, Matrix Scientific, (3.35 g, 12.2 mmol), benzene (32.5 mL), and N,N-dimethylformamide (6.5 mL) were heated together for 3 hr at 60° C. under $N_2$. This mixture was then added to the original flask, and the resulting mixture was stirred overnight at 78° C. under $N_2$. Another portion of the Pd catalyst (same amount used above) was added, and the resulting mixture was stirred overnight at 78° C. under $N_2$. The reaction was allowed to cool to ambient temperature, and 25 mL saturated $NH_4Cl(aq)$ was added to the mixture. The mixture was then stirred for 15 min. The resulting mixture was filtered through a pad of Celite®, and washed with 50 mL each of deionized water and ethyl acetate. The layers were separated, and the organic layer was washed with 100 mL of saturated NaCl(aq), dried over $MgSO_4$, and concentrated in vacuo to produce a red oil (2.35 g, 103%).

Part C. The red oil from Part B was dissolved in $CH_2Cl_2$ (30 mL), and trifluoroacetic acid (30 mL) was added. The mixture was stopped with a syringe needle vent over a weekend at ambient temperature. The solution was concentrated in vacuo to produce an oil (assumed theoretical yield).

Part D. The oil from Part C dissolved in 1-hydroxybenzotriazole (Aldrich, 0.83 g, 6.1 mmol), and 1-[3-dimethylamino)propyl]-3-ethylcarbodiimide hydrochloride (Aldrich, 1.18 g, 6.1 mmol) mixed with N,N-dimethylformamide (20 mL). The mixture was stoppered at ambient temperature for 1 hr. To the resulting solution were added 4-methylmorpholine (1.76 mL, 16 mmol) and O-(tetrahydropyranyl) hydroxylamine (Carbogen, 0.71 g, 6.1 mmol). The solution was mixed at ambient temperature for 2 hr, after which time 1-hydroxybenzotriazole (Aldrich, 0.55 g, 4.1 mmol), 1-[3-dimethylamino)propyl]-3-ethylcarbodiimide hydrochloride (Aldrich, 0.79 g, 4.1 mmol), 4-methylmorpholine (0.55 mL, 5 mmol), and O-(tetrahydropyranyl)hydroxylamine (Carbogen, 0.48 g, 4.1 mmol) were added. The resulting solution was stirred while stoppered at ambient temperature overnight. 1-Hydroxybenzotriazole (Aldrich, 0.28 g, 2.1 mmol), 1-[3-dimethylamino)propyl]-3-ethylcarbodiimide hydrochloride (Aldrich, 0.4 g, 2.1 mmol), 4-methylmorpholine (0.5 mL, 4.5 mmol), and O-(tetrahydropyranyl)-hydroxylamine (Carbogen, 0.24 g, 2.1 mmol) were added to the mixture. The mixture was then allowed to mix at ambient temperature for 4 hr. The reaction mixture was poured into 250 mL ethyl acectate, 50 mL of deionized water, and 50 mL of saturated $NaHCO_3(aq)$. The layers were separated, and the organic layer was washed with 100 mL each of a 1:1 mixture of deionized water:saturated NaCl(aq) and saturated NaCl(aq), dried over $MgSO_4$, and concentrated in vacuo to produce an oil (assumed theoretical yield).

Part E. The oil from Part D was dissolved in MeOH (5 mL), and 4N HCl in dioxane (20 mL) was added. The mixed contents were stoppered overnight at ambient temperature. The solution was concentrated in vacuo to a semi-solid/oil. The crude oil was purified by chromatography (on reversed-phase silica, water/acetonitrile with 0.05% trifluoroacetic acid in both). The trifluoroacetate salt was exchanged for hydrochloride salt by 3 co-evaporations with MeOH (5 mL) and 4N HCl in dioxane (20 mL). After the last coevaporation, the solids were triturated with diethyl ether over a weekend. The solids were filtered and dried in a vacuum oven at 50° C. overnight producing 0.55 g of a white solid (24.5% overall yield from step A). MS, M+H calculated for $C_{20}H_{27}F_5N_3O_5S$: 516.1586, found: 516.1599.

Example 18

Preparation of N-hydroxy-4-({4-[4-(3,3,4,4,4-pentafluorobutyl)phenyl]piperidin-1-yl}sulfonyl)tetrahydro-2H-pyran-4-carboxamide

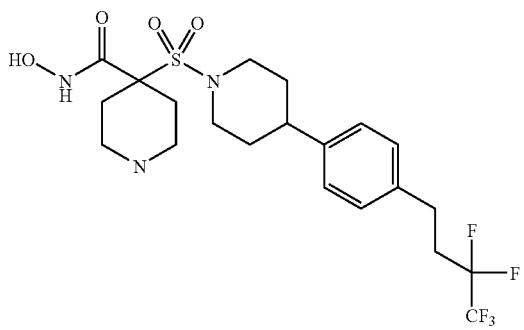

Part A. A solution of 4-(4-bromophenyl)-4-piperidinol (Aldrich, 50 g, 195 mmol), triethylamine (59.8 mL, 429 mmol), and $CH_2Cl_2$ (400 mL) was cooled to 0° C. with mixing under an $N_2$ atmosphere. To this mixture was added methanesulfonyl chloride (16.6 mL, 214 mmol) in $CH_2Cl_2$ (100 mL) dropwise, keeping the reaction temperature at less than 10° C. After the addition was complete, the ice bath was removed, and the solution was allowed to stir for 1 hr. Additional methanesulfonyl chloride (10 mL, 129 mmol) in $CH_2Cl_2$ (50 mL) was added dropwise to the mixture. The mixture was then stirred at ambient temperature under an $N_2$ atmosphere overnight. The next morning, the mixture was added to 300 mL 0.5 N HCl(aq) and 200 mL deionized water. The layers were separated, and the aqueous layer was back-extracted with $CH_2Cl_2$ (100 mL). The combined $CH_2Cl_2$ layers were washed with 300 mL of each of saturated $NaHCO_3$(aq) and saturated NaCl(aq). The $CH_2Cl_2$ layer was dried over $MgSO_4$, filtered, and concentrated in vacuo to produce a methylsulfonamide in the form of a solid (62 g, 95.6%).

Part B. To the methylsulfonamide in Part A was added $CH_2Cl_2$ (300 mL) and triethylsilane (125 mL, 778 mmol). To this slurry was added trifluoroacetic acid (300 mL, 3.9 mol). The resulting mixture was stirred while stoppered at ambient temperature for 1 hr, and was then concentrated in vacuo to produce a solid. The solid was then mixed with MeOH (150 mL) at ambient temperature for 2 days in a stoppered flask. The solid was then filtered from the slurry and washed with an additional 100 mL MeOH. The resulting solid was dried in a vacuum oven at 50° C. overnight to produce 54.14 g (91.7%) of the product. $^1$H NMR was used to analyze the structure of the product.

Part C. Zinc (dust, 325 mesh, 2.06 g, 31.5 mmol), 1,2-dibromoethane (0.243 mL, 2.8 mmol), and tetrahydrofuran (12.5 mL) were heated together at 65° C. under $N_2$ for 5 min. The slurry was cooled to ambient temperature with mixing under $N_2$. Subsequently, trimethylchlorosilane (0.336 mL, 2.64 mmol) was added. The resulting mixture was stirred at ambient temperature for 30 min. 1,1,1,2,2-Pentafluoro-4-iodobutane (Matrix Scientific, 6.45 g, 23.5 mmol) was added, and the mixture was stirred at 40° C. for 3 hr under an $N_2$ atmosphere. N,N-Dimethylaceamide (35 mL), the product from Part B (5 g, 15.7 mmol), and dichlorobis(tri-o-tolylphosphine)palladium(II) (Aldrich, 802 mg, 1.02 mmol) were then added to the mixture. The resulting mixture was heated at 80° C. under $N_2$ overnight. The mixture was cooled to less than 30° C., and 50 mL saturated $NH_4Cl$(aq) was added, followed by 200 mL ethyl acetate. This biphasic system was filtered through a pad of Celite®, washing with deionized water (50 mL) and ethyl acetate (50 mL). The layers were separated, and the ethyl acetate layer was washed with 100 mL of each of saturated $NaHCO_3$(aq) and saturated NaCl(aq). The ethyl acetate layer was then dried over $MgSO_4$, filtered, and concentrated in vacuo to produce a solid that was then slurried in hexanes (50 mL) for 1 hr. The solid was filtered, washed with hexanes (20 mL), and dried at 50° C. in a vacuum oven for 2 hr to produce 5.58 g (92%) of a solids product. $^1$H NMR was used to analyze the structure of the product.

Part D. Tetrahydrofuran (70 mL), the product from Part C (6.7 g, 17.4 mmol), and di-tert-butyl dicarbonate (Aldrich, 4.55 g, 20.9 mmol) were cooled together to –78° C. under $N_2$. To the resulting mixture was added a solution of lithium bis(trimethylsilyl)amide in tetrahydrofuran (1M, 46 mL) at such a rate that the temperature remained below –70° C. This solution was allowed to mix at –78° C. under $N_2$ for 1 hr, and was then mixed at 0° C. for 20 min. The reaction was then cooled to –40° C., and saturated $NH_4Cl$(aq) (25 mL) was added. After the addition was complete, the mixture was warmed to ambient temperature, and ethyl acetate (250 mL) and deionized water (100 mL) were added. The layers were separated, and the aqueous layer was back-extracted with ethyl acetate (100 mL). The combined ethyl acetate layers were washed with 100 mL of each of saturated $NaHCO_3$(aq) and saturated NaCl(aq), dried over $MgSO_4$, filtered, and concentrated in vacuo. The resulting solid/oil was co-evaporated several times with acetonitrile to produce a solid that was, in turn, dried in a vacuum oven at 50° C. overnight to produce 8.55 g (102%) of a t-butyl ester in the form of a solid.

Part E. The t-butyl ester from Part D (3 g, 6.2 mmol), N,N-Dimethylformamide (15 mL), $K_2CO_3$ (2.76 g, 20 mmol), 2-bromoethyl ether, Aldrich, (1.75 g, 7.6 mmol), and 18-Crown-6 (0.49 g, 1.86 mmol) were heated together at 65° C. under an $N_2$ atmosphere overnight. An additional 1 g of $K_2CO_3$ (7.2 mmol) and 0.87 g of 2-bromoethyl ether (3.78 mmol) were added to the mixture, and it was again stirred overnight at 65° C. under an $N_2$ atmosphere. The reaction mixture was cooled to ambient temperature, and then added to deionized water (75 mL) and ethyl acetate (200 mL). The layers were separated, and the aqueous layer was back-extracted with ethyl acetate (50 mL). The combined ethyl acetate layers were washed with 100 mL of each of a 1:1 mixture of deionized water:saturated NaCl(aq) and saturated NaCl(aq), dried over $MgSO_4$, filtered, and concentrated in vacuo. Chromatography (on silica, ethyl acetate/hexanes) produced 1.76 g (51.2₄%) a t-butyl ester pyran in the form of a solid.

Part F. The t-butyl ester pyran from Part E was dissolved in $CH_2Cl_2$ (11.2 mL). To this solution was added triethylsilane (4.76 mL, 29.8 mmol), trifluoroacetic acid (11.2 mL, 145 mmol), and trifluoromethanesulfonic acid (0.185 mL, 2 mmol) in that order. The resulting solution was mixed at ambient temperature while stoppered with a syringe needle vent overnight. The reaction mixture was concentrated in vacuo to produce 1.5 g (95%) of an acid product in the form of a white solid.

Part G. To the acid from Part F was added N,N-dimethylformamide (15 mL), 1-hydroxybenzotriazole (Aldrich, 0.61 g, 4.5 mmol), and 1-[3-dimethylamino)propyl]-3-ethylcarbodiimide hydrochloride (Aldrich, 0.86 g, 4.5 mmol). The resulting mixture was stirred for 30 min at ambient temperature while stoppered. To the resulting solution was added 4-methylmorpholine (1.3 mL, 12 mmol) and O-(tetrahydropyranyl)-hydroxylamine (0.53 g, 4.5 mmol). This mixture was allowed to stir overnight while stoppered at ambient temperature. To this mixture was added 250 mL ethyl acetate, 50 mL $dH_2O$, and 50 mL saturated $NaHCO_3$ (aq). The layers were then allowed to separate. The aqueous layer was back-extracted with ethyl acetate (50 mL). The combined ethyl acetate layers were then washed with 100 mL of each of a 1:1 mixture of deionized water:saturated NaCl(aq) and saturated NaCl(aq). The ethyl acetate layer was dried over $MgSO_4$, filtered, and concentrated in vacuo to produce a semi-solid. The semi-solid was, in turn, recrystallized twice from $MeOH/dH_2O$ to produce 1.25 g (69.4%) of a product in the form of a white solid.

Part H. The solid from Part G was dissolved in MeOH (2.5 mL). To this solution was added 4N HCl/Dioxane (10 mL). The resulting solution was mixed while covered at ambient temperature for 1 hr. The solution was then concentrated in vacuo to produce a solid. The solids were then co-evaporated three times with 50 mL of diethyl ether per evaporation. The dried solids were placed into a vacuum oven at 50° C. overnight to produce 0.95 g (88.4%) of a product in the form of a white solid. MS, M+H calculated for $C_{21}H_{28}F_5N_2O_5S$: 515.1634, found: 515.1620.

Example 19

Preparation of 4-{[4-(5-butylthien-2-yl)piperidin-1-yl]sulfonyl}-N-hydroxytetrahydro-2H-pyran-4-carboxamide

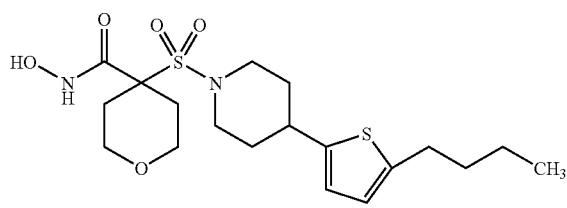

Part A. Preparation of tert-butyl 4-(5-butylthien-2-yl)-4-hydroxypiperidine-1-carboxylate. A tetrahydrofuran (80 mL) solution of 2-n-butylthiophene (Lancaster, 5.0 g, 35.7 mmol) was cooled to 0° C. under $N_2$ and then slowly treated with 1.6 M n-butyl lithium (in hexanes) (24.3 mL, 38.9 mmol) over 10 min. After stirring at 0° C. for 45 min, the resulting mixture was cooled to −78° C. and then treated with tert-butyl 4-oxo-1-piperidine carboxylate (6.46 g, 32.4 mmol) in THF (30 mL) over 10 min. After 30 min, the mixture was removed from the cold bath, stirred at ambient temperature for 2.5 hr, quenched with water (50 mL), and partitioned with diethyl ether (100 mL). The aqueous layer was separated and extracted with diethyl ether (50 mL). The combined organic layers were washed with 1:1 brine/water (2×30 mL), washed with brine (2×50 mL), dried over $Na_2SO_4$, filtered, and concentrated in vacuo. The resulting yellow oil was purified on silica, eluting with 4:1 hexanes/ethyl acetate to produce the product in the form of a clear, yellow oil (10.0 g, 90.8%). LC/MS m/z=362 [M+Na]

Part B. Preparation of 4-(5-butylthien-2-yl)piperidine hydrochloride. A methylene chloride solution (20.0 mL) of the alcohol prepared in Part A (8.58 g, 25.3 mmol) was cooled to 0° C., treated with triethylsilane (12.11 mL, 75.8 mmol) followed by trifluoroacetic acid (19.5 mL, 253 mmol). The resulting mixture was removed from the cold bath and stirred at ambient temperature for 50 min. The mixture was then concentrated in vacuo, dissolved in methanol (20.0 mL), treated with 4 N HCl in 1,4-dioxane (5.0 mL), and concentrated in vacuo. These steps were repeated two more times. Afterward, the mixture was triturated with diethyl ether. The resulting solid was filtered, washed with diethyl ether and dried in vacuo to produce the product in the form of a white solid (5.67 g, 86%). LC/MS m/z=224 [M+H]

Part C. Preparation of 4-(5-butylthien-2-yl)-1-(methylsulfonyl)piperidine. A methylene chloride solution (28.0 mL) of the amine prepared in Part B (6.25 g, 24.1 mmol) was treated under $N_2$ with triethylamine (8.38 mL, 60.1 mmol). The resulting suspension was cooled to 0° C. and slowly treated with a methylene chloride solution (20.0 mL) of methanesulfonyl chloride (2.05 mL, 26.5 mmol) over 15 min, and then removed from the cold bath. After 2 hr at ambient temperature, the reaction mixture was concentrated in vacuo and suspended in water (300 mL). The resulting solid was filtered, washed with water, and dried in vacuo to produce the product in the form of a yellow solid 6.89 g (95%). LC/MS m/z=302 [M+H], 324 [M+Na]

Part D. Preparation of tert-butyl {[4-(5-butylthien-2-yl)piperidin-1-yl]sulfonyl}acetate. A tetrahydrofuran solution (44 mL) of the methyl sulfonamide prepared in Part C (6.64 g, 22.0 mmol) and di-tert-butyl dicarbonate (5.6 g, 25.6 mmol) was cooled to −78° C. under $N_2$. The resulting yellow suspension was treated with 1M lithium bis(trimethylsilyl)amide (in tetrahydrofuran) (60.6 mL, 60.6 mmol) over 20 min. The resulting homogeneous solution was slowly warmed to ambient temperature by letting the cold bath expire. After 1.5 hr, the mixture was cooled to −78° C.; quenched with aqueous, saturated ammonium chloride (10.0 mL); and warmed to ambient temperature. The mixture was partitioned with ethyl acetate (100 mL) and water (50 mL). The organic layer was separated, washed with 5% aqueous $KHSO_4$ (50 mL), saturated $NaHCO_3$ (50 mL), washed with 1:1 brine/water (2×100 mL), washed with brine (2×50 mL), dried over $Na_2SO_4$, filtered, and concentrated in vacuo to produce the product in the form of a yellow oil (9.38 g, 100%). LC/MS m/z=424 [M+Na]

Part E. Preparation of tert-butyl 4-{[4-(5-butylthien-2-yl)piperidin-1-yl]sulfonyl}tetrahydro-2H-pyran-4-carboxylate. An N,N-dimethylformamide (20.0 mL) solution of the ester prepared in Part D (4.0 g, 9.96 mmol) was treated with potassium carbonate (3.44 g, 24.9 mmol), 18-crown-6 ether (catalytic amount; 0.1 g), and 2-bromoethyl ether (1.46 mL, 10.5 mmol) under $N_2$. The resulting mixture was stirred at 60° C. for 2.5 days. Additional potassium carbonate (1.75 g, 12.7 mmol) and 2-bromoethyl ether (0.75 mL, 5.4 mmol) were added to drive the reaction to completion. After 24 hr, the mixture was diluted with ethyl acetate (50 mL) and partitioned with water (100 mL). The organic layer was separated, washed with saturated $NaHCO_3$ (30 mL), washed with 1:1 brine/water (2×50 mL), washed with brine (2×50 mL), dried over $Na_2SO_4$, filtered, and concentrated in vacuo. The resulting oil was purified on silica, eluting with 9:1 hexanes/ethyl acetate to produce the product in the form of a white solid (3.51 g, 75%). LC/MS m/z=494 [M+Na]

Part F. Preparation of 4-{[4-(5-butylthien-2-yl)piperidin-1-yl]sulfonyl}-N-(tetrahydro-2H-pyran-2-yloxy)tetrahydro-2H-pyran-4-carboxamide. A methylene chloride solution (8.0 mL) of the ester prepared in Part E (3.27 g, 6.93 mmol) was treated with trifluoroacetic acid (8.0 mL, 104 mmol) and stirred at ambient temperature. After 4 hr, the mixture was concentrated in vacuo to approximately 8.0 mL, then treated with diethyl ether (15 mL). The resulting mixture was concentrated in vacuo to approximately 4.0 mL, then treated with diethyl ether (15 mL). The resulting precipitate was filtered, washed with diethyl ether, and dried in vacuo. The resulting white solid (2.93 g) was dissolved in N,N-dimethylformamide (14.1 mL), treated with 1-(3-dimethylaminopropyl)-3-ethylcarbodiimide hydrochloride (2.03 g, 10.6 mmol) and N-hydroxybenzo-triazole hydrate (1.43 g, 10.6 mmol), and stirred at ambient temperature under $N_2$. After 1 hr, the resulting suspension was treated with O-(tetrahydro-2H-pyran-2-yl)hydroxylamine (1.24 g, 10.6 mmol), followed by N-methylmorpholine (2.33 mL, 21.2 mmol). After 30 min, the mixture was diluted with ethyl acetate (100 mL) and partitioned with water (50 mL). The aqueous layer was separated and then extracted with ethyl acetate (25 mL). The organic layers were combined, washed with saturated $NaHCO_3$ (25 mL), washed with 1:1 brine/water (25 mL), washed with brine (25 mL), dried over $Na_2SO_4$, filtered, and concentrated in vacuo. The resulting oil was purified on silica, eluting with 1:1 hexanes/ethyl acetate to produce the product in the form of a colorless glassy solid having an 11:4 mixture of desired product/impurity (3.52 g, 98.6% mass recovery). LC/MS m/z=537 [M+Na] for desired product Part G. Preparation of 4-{[4-(5-butylthien-2-yl)piperidin-1-yl]sulfonyl}-N-hydroxytetrahydro-2H-pyran-4-carboxamide. An ethyl acetate solution (14.0 mL) of the THP hydroxymate prepared in Part F (3.52 g of 11:4 mixture, ca. 4 mmol) was treated with methanol (3.0 mL), followed by 4 N HCl in 1,4-dioxane (8.5 mL, 34.2 mmol). After stirring for 20 hr at ambient temperature, the mixture was concentrated to approximately half the volume in vacuo, and treated with diethyl ether, producing a precipitate which was stirred for 1 hr, filtered, washed with diethyl ether, and dried in vacuo. The resulting white precipitate was recrystallized in acetone, filtered, washed with cold acetone, and dried in vacuo to produce the product in the form of a white solid (0.10 g, ca. 5%). HRMS (ES+) m/z calculated for $C_{19}H_{30}N_2O_5S_2$: 431.1669, observed [M+H] 431.1688.

Example 20

Preparation of N-hydroxy-1-(2-methoxyethyl)-4-({4-[4-(4,4,4-trifluorobutoxy)phenyl]piperidin-1-yl}sulfonyl)piperidine-4-carboxamide hydrochloride

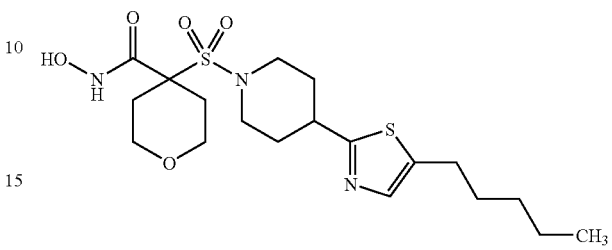

Part A. Preparation of 1-bromo-4-(4,4,4-trifluorobutoxy)benzene. An N,N-dimethylformamide (53.0 mL) solution of 4-bromophenol (Aldrich, 4.57 g, 26.4 mmol) was treated with potassium carbonate (4.57 g, 33.0 mmol) and 1-bromo-4,4,4-trifluorobutane (Lancaster, 5.30 g, 27.7 mmol) under $N_2$ and stirred at 60° C. After 1.5 days, the mixture was diluted with ethyl acetate (100 mL) and partitioned with water (50 mL). The organic layer was separated, washed with saturated $NaHCO_3$ (25 mL), washed with 2.5 N NaOH (20 mL), washed with 1:1 brine/water (3×20 mL), washed with brine (2×25 mL), dried over $Na_2SO_4$, filtered, and concentrated in vacuo to produce a product in the form of an amber oil (7.28 g, 97%). LC/MS m/z=283 [M+H].

Part B. Preparation of tert-butyl 4-hydroxy-4-[4-(4,4,4-trifluorobutoxy)phenyl]piperidine-1-carboxylate. A tetrahydrofuran (40 mL) solution of the aryl bromide prepared in Part A (5.0 g, 17.7 mmol) was cooled to −78° C. under $N_2$ and then slowly treated with 1.6 M n-butyl lithium (in hexanes) (12.2 mL, 19.4 mmol) over 10 min. The resulting homogeneous solution was stirred at −78° C. for 1 hr, and then treated with tert-butyl 4-oxo-1-piperidine carboxylate (3.52 g, 17.7 mmol) in THF (14 mL) over 10 min. After 1 hr 50 min, the mixture was warmed to 0° C. After 30 min, the mixture was quenched with aqueous, saturated ammonium chloride (20 mL), and partitioned with ethyl acetate (100 mL) and water (50 mL). The aqueous layer was separated and extracted with ethyl acetate (20 mL). The combined organic layers were washed with saturated $NaHCO_3$ (50 mL), washed with 1:1 brine/water (2×100 mL), washed brine (2×50 mL), dried over $Na_2SO_4$, filtered, and concentrated in vacuo. The resulting yellow oil was purified on silica, eluting with 3:1 hexanes/ethyl acetate to produce the product in the form of a light yellow solid (2.79 g, 39%). LC/MS m/z=426 [M+Na].

Part C. Preparation of 4-[4-(4,4,4-trifluorobutoxy)phenyl]piperidine hydrochloride. A methylene chloride solution (20.0 mL) of the alcohol prepared in Part B (2.67 g, 6.62 mmol) was cooled to 0° C., treated with triethylsilane (3.17 mL, 19.9 mmol). followed by trifluoroacetic acid (5.10 mL, 66.2 mmol). The mixture was then removed from the cold bath and stirred at ambient temperature for 1.5 hr. The mixture was concentrated in vacuo, dissolved in methanol (15.0 mL), treated with 4 N HCl in 1,4-dioxane (4.0 mL), and concentrated in vacuo. These steps were repeated once more. Afterward, the concentrated product was dried in vacuo to produce the product in the form of a yellow solid (2.68 g, 125% mass recovery; retained 1,4-dioxane). LC/MS m/z=288 [M+H].

Part D. Preparation of 1-(methylsulfonyl)-4-[4-(4,4,4-trifluorobutoxy)phenyl]piperidine. A methylene chloride solution (10 mL) of the amine prepared in Part C (2.14 g, 6.61 mmol) was treated under $N_2$ with triethylamine (2.3 mL, 16.5 mmol). The resulting suspension was cooled to 0° C. and slowly treated with a methylene chloride solution (3.2 mL) of methanesulfonyl chloride (0.56 mL, 7.27 mmol), and then removed from the cold bath. After 16 hr, the reaction mixture was further treated at ambient temperature with triethylamine (0.5 mL, 3.6 mmol) and methanesulfonyl chloride (0.20 mL, 2.60 mmol) to drive the reaction to completion. After 4 hr, the mixture was concentrated in vacuo and then partitioned with ethyl acetate (50 mL) and water (30 mL). The aqueous layer was separated, extracted with ethyl acetate (25 mL). The combined organic layers were then washed with saturated $NaHCO_3$ (25 mL), washed with 1:1 brine/water (2×20 mL), washed with brine (2×10 mL), dried over $Na_2SO_4$, filtered, and concentrated in vacuo to produce the product in the form of a light yellow solid (2.49 g, 100%). LC/MS m/z=388 [M+Na].

Part E. Preparation of tert-butyl ({4-[4-(4,4,4-trifluorobutoxy)phenyl]piperidin-1-yl}sulfonyl)acetate. A tetrahydrofuran solution (17 mL) of the methyl sulfonamide prepared in Part D (3.09 g, 8.46 mmol) and di-tert-butyl dicarbonate (2.03 g, 9.30 mmol) was cooled to −78° C. under $N_2$. The resulting yellow suspension was treated with 1M lithium bis(trimethylsilyl)amide (in tetrahydrofuran) (23.3 mL, 23.3 mmol) over 10 min. After 1 hr, the resulting homogeneous solution was warmed to 0° C. After 1 hr, the mixture was cooled to −78° C., quenched with aqueous, saturated ammonium chloride (20.0 mL), and warmed to ambient temperature. The mixture was partitioned with ethyl acetate (100 mL) and water (50 mL). The organic layer was separated, washed with saturated $NaHCO_3$ (50 mL), washed with 1:1 brine/water (50 mL), washed with brine (2×25 mL), dried over $Na_2SO_4$, filtered, and concentrated in vacuo to produce the product in the form of a yellow solid (4.09 g, 100%). LC/MS m/z=488 [M+Na].

Part F. Preparation of tert-butyl 1-(2-methoxyethyl)-4-({4-[4-(4,4,4-trifluorobutoxy)phenyl]piperidin-1-yl}sulfonyl)piperidine-4-carboxylate. An N,N-dimethylformamide (10.0 mL) solution of bis(2-chloroethyl)-2-methoxyethylamine hydrochloride (Clariant) (1.32 g, 5.59 mmol), potassium carbonate (3.56 g, 25.8 mmol), and 18-crown-6 ether (0.34 g, 1.29 mmol) was treated (under $N_2$ while being stirred at 60° C.) portion-wise with the ester prepared in Part E (total of 2.0 g, 4.30 mmol—addition protocol: 0.5 g, then 0.25 g 30 min later, followed by 0.25 g portions every 15 min until all the 2.0 g was added to the reaction mixture). After 23 hr, the mixture was diluted with ethyl acetate (30 mL) and partitioned with water (25 mL). The aqueous layer was separated, and extracted with ethyl acetate (2×20 mL). The combined organic layers were washed with saturated $NaHCO_3$ (20 mL), washed with 1:1 brine/water (20 mL), washed with brine (20 mL), dried over $Na_2SO_4$, filtered, and concentrated in vacuo. The resulting solid was purified on silica, eluting with 1:1 hexanes/ethyl acetate to produce the product in the form of a orange solid (1.57 g, 61%). LC/MS m/z=593 [M+H].

Part G. Preparation of N-hydroxy-1-(2-methoxyethyl)-4-({4-[4-(4,4,4-trifluorobutoxy)phenyl]piperidin-1-yl}sulfonyl)piperidine-4-carboxamide hydrochloride. A methylene chloride solution (5.0 mL) of the ester prepared in Part F (1.48 g, 2.50 mmol) was treated with trifluoroacetic acid (5.0 mL, 64.9 mmol) and stirred at ambient temperature. After 24 hr, the mixture was concentrated in vacuo, then treated with 4 N HCl in 1,4-dioxane (5 mL) and concentrated in vacuo. These steps were repeated once more, and the resulting material was then treated with diethyl ether (20 mL), stirred at ambient temperature for 15 min, and concentrated in vacuo. This produced a glassy solid (1.22 g), which was subsequently dissolved in N,N-dimethylformamide (5.0 mL), treated with 1-(3-dimethylaminopropyl)-3-ethylcarbodiimide hydrochloride (0.61 g, 3.19 mmol) and N-hydroxybenzo-triazole hydrate (0.43 g, 3.19 mmol), and stirred at ambient temperature under $N_2$. After 30 min, the resulting solution was treated with O-(tetrahydro-2H-pyran-2-yl)hydroxylamine (0.37 g, 3.19 mmol), followed by N-methylmorpholine (0.94 mL, 8.52 mmol). After 3.5 hr, the mixture was diluted with ethyl acetate (25 mL) and partitioned with water (20 mL). The aqueous layer was separated and then extracted with ethyl acetate (2×25 mL). The organic layers were combined, washed with saturated $NaHCO_3$ (25 mL), washed with 1:1 brine/water (20 mL), washed with brine (20 mL), dried over $Na_2SO_4$, filtered, and concentrated in vacuo. The resulting orange/brown solid (1.54 g) oil was dissolved in ethyl acetate (5.0 mL), diluted with methanol (1.0 mL), and treated with 4 N HCl in 1,4-dioxane (3.0 mL, 12.1 mmol). After stirring for 20 hr at ambient temperature, the mixture was diluted with ethyl acetate (25 mL) and partitioned with saturated $NaHCO_3$ (20 mL). The organic layer was washed with brine, dried over $Na_2SO_4$, filtered, and concentrated in vacuo. The resulting oil was purified on reverse phase HPLC (acetonitrile/water/TFA) to produce, after exchange of TFA for HCl (with 4 N HCl in 1,4-dioxane), the product in the form of a white solid (0.51 g, 36% for three steps). HRMS (ES+) m/z calculated for $C_{24}H_{36}N_3O_6SF_3$: 552.2350, observed [M+H] 552.2378.

Example 21

Preparation of N-hydroxy-4-{[4-(4-pentylphenyl)piperazin-1-yl]sulfonyl}-1-(trifluoroacetyl)piperidine-4-carboxamide hydrochloride

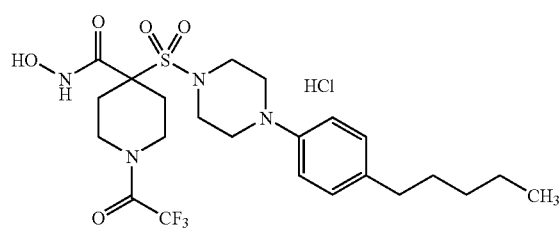

Part A. Preparation of 1-(4-bromophenyl)-4-(methylsulfonyl)piperazine. A methylene chloride solution (100 mL) of the 1-(4-bromophenyl)-piperazine hydrochloride (25.0 g, 90.1 mmol) under $N_2$ was treated with triethylamine (27.6 mL, 198 mmol). The resulting suspension was cooled to 0° C. and slowly treated with a methylene chloride solution (80 mL) of methanesulfonyl chloride (7.67 mL, 99.1 mmol). The mixture was then removed from the cold bath. After 19 hr at ambient temperature, the mixture was concentrated in vacuo and then suspended in water (200–300 mL). The suspension was stirred for 2 hr, filtered, washed with water, and dried under high vacuum to afford a yellow solid (29.54 g, >100% mass recovery due to residual solvent). HPLC: >90% clean. LC/MS m/z=319 [M+H].

Part B. Preparation of 1-(4-bromophenyl)-4-(methylsulfonyl)piperazine. A tetrahydrofuran solution (30 mL) of 1-pentene (15.6 mL, 135 mmol) was placed in a 0° C. bath and slowly treated with 0.5 M 9-borabicyclo[3.3.1]nonane in THF (270 mL, 135 mmol) over 20–30 min., keeping the temperature below 10° C. After the addition was complete, the cold bath was removed and the mixture was stirred at ambient temperature overnight. The reaction was then fitted with a reflux condensor treated with aqueous 2M $K_3PO_4$ (135 mL, 270 mmol), (dppf)$PdCl_2$ (3.11 g, 3.81 mmol), and the sulfonamide prepared in Part A (24.3 g, 76.1 mmol). The resulting reddish brown suspension was refluxed for 1.5 hr. The mixture was cooled to ambient temperature and concentrated in vacuo. The resulting residue was partitioned with ethyl acetate (400 mL) and water (400 mL). The aqueous layer was removed, and the organic layer was washed with saturated $NaHCO_3$, washed with 1:1 brine/water, washed with brine, dried over $Na_2SO_4$, filtered, and concentrated in vacuo. The crude material was dissolved in methylene chloride (100 mL), treated with decolorizing charcoal, stirred for 2 hr, and filtered through Celite, and concentrated in vacuo. The resulting reddish brown oil was then recrystallized in methanol to afford a white solid (8.28 g, 35% in three crops of crystals). LC.MS m/z=311 [M+H]; 333 [M+Na].

Part C. Preparation of tert-butyl {[4-(4-pentylphenyl)piperazin-1-yl]sulfonyl}acetate. A tetrahydrofuran solution (52 mL) of the methyl sulfonamide prepared in Part B (8.0 g, 25.8 mmol) was cooled to −78° C. under $N_2$, and then treated with 1M lithium bis(trimethylsilyl)amide (in tetrahydrofuran) (67.0 mL, 67.0 mmol) over 30 min. After 30 min at −78° C., the mixture was stirred at 0° C. for 1 hr, cooled to −78° C., and treated with di-tert-butyl dicarbonate (2.03 g, 9.30 mmol) in THF (10 mL). After 45 min at −78° C., the mixture was warmed to 0° C. to drive the reaction to completion. The mixture was then cooled to −78° C., quenched with aqueous, saturated ammonium chloride (100 mL), and warmed to ambient temperature. The mixture was partitioned with ethyl acetate (100 mL) and water (50 mL). The organic layer was separated, washed with 1:1 brine/water (50 mL), washed with brine 50 mL), dried over $Na_2SO_4$, filtered, and concentrated in vacuo. The resulting residue was recrystallized in acetonitrile and methanol to afford a white solid (5.45 g, 51%). The filtrate was further purified on silica, eluting with 1:1 hexanes/ethyl acetate to produce more of the same product as a white, yellow solid (2.02 g, 19%): total combined product (7.47 g, 70%). LC/MS m/z=411 [M+H]

Part D. Preparation of tert-butyl 1-benzyl-4-{[4-(4-pentylphenyl)piperazin-1-yl]sulfonyl}piperidine-4-carboxylate. An N,N-dimethylformamide (10.0 mL) solution of the ester prepared in Part C (5.50 g, 13.4 mmol) was treated with potassium carbonate (5.55 g, 40.0 mmol), 18-crown-6 ether (catalytic), and N-benzyl-N,N-bis(2-chloroethyl)amine (3.27 g, 14.1 mmol) under $N_2$ and stirred at 60° C. After 24 hr, the temperature was increased to 70° C. to drive reaction to completion. After 4 days, the reaction was cooled to ambient temperature, diluted with ethyl acetate (100 mL), and partitioned with water (100 mL). The aqueous layer was separated and extracted with ethyl acetate (50 mL). The combined organic layers were washed with 1:1 brine/water (60 mL), washed with brine (2×20 mL), dried over $Na_2SO_4$, filtered, and concentrated in vacuo to afford an amber oil (8.4 g, 110% mass recovery; residual DMF). LC/MS m/z=570 [M+H].

Part E. Preparation of tert-butyl 4-{[4-(4-pentylphenyl)piperazin-1-yl]sulfonyl}-1-(trifluoroacetyl)piperidine-4-carboxylate. The ester prepared in Part D (7.5 g, 13.2 mmol) was dissolved in methanol (75 mL) at 50° C., and then cooled to ambient temperature. The resulting solution was charged with ammonium formate (2.5 g, 39.6 mmol), palladium on carbon (Degussa, 10% wt Pd), 50% water) (0.75 g, 10% by wt), and heated to 50° C. for 4 hr. The resulting mixture was cooled to ambient temperature and further charged with ammonium formate (2.5 g, 39.6 mmol), palladium on carbon (Degussa, 10% wt Pd), 50% water) (0.75 g, 10% by wt), and heated to 60° C. for another 4 hr to drive the reaction to completion. Afterward, the mixture was cooled to ambient temperature, filtered through celite, washed with methanol, and concentrated in vacuo. The resulting yellow liquid was partitioned with ethyl acetate (200 mL) and 2M NaOH (100 mL). The aqueous layer was separated and extracted with ethyl acetate (50 mL). The organic layers were then combined and washed with 2M NaOH (50 mL), washed with 1:1 brine/water (50 mL), washed with brine (50 mL), dried over $Na_2SO_4$, filtered, and concentrated in vacuo to afford a yellow oil. A portion of this material (1.0 g, 2.08 mmol) was dissolved in methylene chloride (3.7 mL), and then treated with triethylamine (0.70 mL, 5.0 mmol) and trifluoroacetic anhydride (0.353 mL, 2.5 mmol). The resulting mixture was stirred at ambient temperature overnight. Afterward, the mixture was concentrated in vacuo and then partitioned with ethyl acetate (25 mL) and water (25 mL). The organic layer was separated and washed with saturated $NaHCO_3$ (10 mL), washed with 1:1 brine/water (20 mL), washed with brine (20 mL), dried over $Na_2SO_4$, filtered, and concentrated in vacuo. The crude orange oil was recrystallized in methanol (3 mL) to afford a white solid (0.64 g, 53% for two steps). LC/MS m/z=576 [M+H]; 598 [M+Na].

Part F. Preparation of tert-butyl 4-{[4-(4-pentylphenyl)piperazin-1-yl]sulfonyl}-1-(trifluoroacetyl)piperidine-4-carboxylate. A methylene chloride solution (5.0 mL) of the ester prepared in Part E (0.61 g, 1.06 mmol) was treated with trifluoroacetic acid (3.5 mL, 45.4 mmol). After 24 hr of stirring at ambient temperature, the mixture was concentrated in vacuo to approximately 25% volume, and then added to vigorously stirred diethyl ether (50 mL). After 2 hr, the resulting suspension was filtered, washed with diethyl ether, dried in vacuo, dissolved in acetonitrile (25 mL), and concentrated in vacuo (this was repeated once more) to afford a white solid (0.49 g, 73%). LC/MS m/z=520 [M+H].

Part G. Preparation of 4-{[4-(4-pentylphenyl)piperazin-1-yl]sulfonyl}-N-(tetrahydro-2H-pyran-2-yloxy)-1-(trifluoroacetyl)piperidine-4-carboxamide:

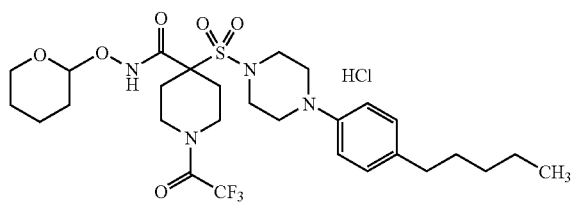

An N,N-dimethylformamide (5.0 mL) solution of the acid prepared in Part F (0.45 g, 0.71 mmol) was treated with 1-(3-dimethylamino-propyl)-3-ethylcarbodiimide hydrochloride (0.21 g, 1.07 mmol) and N-hydroxybenzo-triazole hydrate (0.14 g, 1.07 mmol), and then treated with O-(tetrahydro-2H-pyran-2-yl)hydroxylamine (0.12 g, 1.07 mmol), followed by N-methylmorpholine (0.31 mL, 2.84 mmol). The resulting mixture was stirred at ambient temperature under $N_2$. After 2.5 days, the resulting solution was diluted with ethyl acetate (15 mL) and partitioned with water (15 mL). The organic layer was separated and then washed with saturated $NaHCO_3$ (15 mL), washed with 1:1 brine/water (20 mL), washed with brine (20 mL), dried over $Na_2SO_4$, filtered, and concentrated in vacuo. The resulting amber oil was purified on silica, eluting with 3:1 hexanes/ethyl acetate, to afford a clear colorless oil (0.5 g, 100%). LC/MS m/z=619 [M+H]; 641 [M+Na].

Part H. Preparation of N-hydroxy-4-{[4-(4-pentylphenyl)piperazin-1-yl]sulfonyl}-1-(trifluoroacetyl)piperidine-4-carboxamide hydrochloride. The THP-protected hydroxamate prepared in Part G (0.42 g, 0.67 mmol) was dissolved in methanol (1.0 mL) and then treated with 4 N HCl in 1,4-dioxane (3.0 mL, 12.0 mmol). After stirring for 80 min at ambient temperature, the mixture was concentrated in vacuo to 25% volume, and then treated with diethyl ether (30 mL). The resulting suspension was filtered, washed with diethyl ether, and dried in vacuo to afford an orange/light peach solid (0.37 g, 97%). HRMS (ES+) m/z calculated for $C_{23}H_{34}N_4O_5SF_3$: 535.2197, observed [M+H] 535.2167.

Example 22

Preparation of 1-ethyl-4-{[4-(3-fluoro-4-pentylphenyl)piperazin-1-yl]sulfonyl}-N-hydroxypiperidine-4-carboxamine hydrochloride

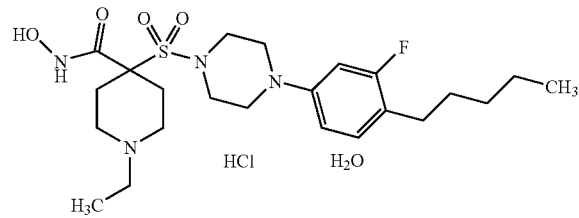

Part A. Preparation of:

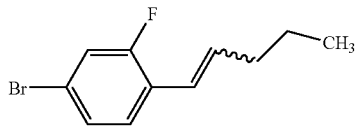

To a mixture of 4-bromo-2-fluorobenzaldehyde (2.00 g, 9.86 mmol) and potassium carbonate (1.72 g, 12.10 mmol) in isopropyl alcohol (5 mL) under $N_2$ at ambient temperature was added butyltriphenylphosphonium bromide (4.92 g, 12.3 mmol). The resulting mixture was heated at 80° C. for 18 hr. Afterward, the mixture was concentrated in vacuo. Ether was then added, and the resulting mixture was filtered through a silica bed and concentrated in vacuo to provide the alkene as a clear, colorless liquid (1.78 g, 74% yield). The proton NMR spectrum was consistent with the desired alkene as a mixture of cis and trans isomers.

Part B. Preparation of:

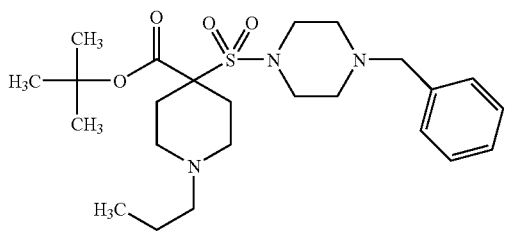

To a 75° C. mixture of 18-crown-6(3.05 g, 11.6 mmol), potassium carbonate (32.0 g, 232 mmol), and 1,5-dichloro-3-ethyl-3-azapentane hydrochloide (9.58 g, 46.4 mmol) (synthetic procedure in J. Org. Chem. 1993, 58, 1359–1366) in DMF(197 mL) under $N_2$ was added drop wise a solution of tert-butyl [(4-benzylpiperazin-1-yl)sulfonyl]acetate (13.7 g, 38.7 mmol) in DMF (73 mL). The resulting mixture was heated for 15 hr. The ambient reaction mixture was filtered, and the filtrate was concentrated in vacuo. Chromatography (silica gel; hexane/ethyl acetate) provided the piperidine as a yellow solid (9.66 g, 55% yield): HR-MS MH+ calcd. for $C_{23}H_{38}N_3O_4S$ 452.2583, found 452.2600.

Part C. Preparation of:

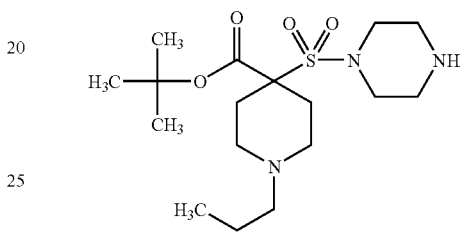

A mixture of the piperidine of Part B (9.66 g, 21.4 mmol) and a catalytic amount of 20% Pd(OH)$_2$/C in ethanol was reacted at ambient temperature under H$_2$ (50 psi). The mixtuer was then filtered and concentrated in vacuo to provide the piperazine as a white wax (7.44 g, 96% yield): MS MH+ calcd. for $C_{16}H_{32}N_3O_4S$ 362, found 362.

Part D. Preparation of:

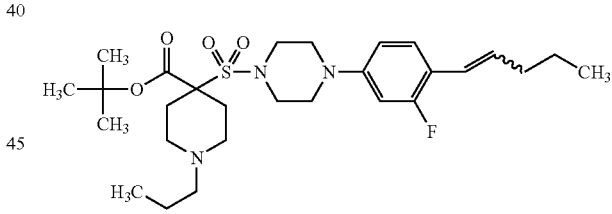

To an 82° C. mixture of the alkene of Part A (2.38 g, 9.79 mmol), the piperazine of Part C (3.35 g, 9.26 mmol), sodium t-butoxy (1.04 g, 10.8 mmol), and racemic-2,2'-bis(diphenylphosphino)-1,1'-binaphthyl (0.143 g, 0.229 mmol) in dioxane (17 mL) was added tris(dibenzylideneacetone)-dipalladium(0) (0.069 g, 0.076 mmol) under $N_2$. The resulting black mixture was heated at 80° C. for 18 hr. Afterward, the mixture was diluted with water (300 mL) and extracted with CH$_2$Cl$_2$ (3×100 mL). The organic layer was washed with water(2×100 mL) and brine(100 mL), dried over MgSO$_4$, concentrated in vacuo, and purified by flash chromatography (silica gel; methanol/CH$_2$Cl$_2$) to provide the alkenyl piperazine as an oil (3.00 g, 62% yield): MS MH+ calcd. for $C_{27}H_{43}N_3O_4SF$ 524, found 524. The proton NMR spectrum was consistent for the desired product as a mixture of cis and trans isomers.

Part E. Preparation of:

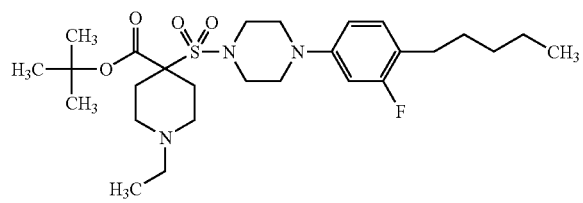

The alkenyl piperazine of Part D (1.20 g, 1.81 mmol) was hydrogenated at 5 psi in ethanol with 20% palladium hydroxide on carbon at ambient temperature for 12 hr. The resulting solution was concentrated in vacuo and purified by chromatography (silica gel; methanol/$CH_2Cl_2$) to provide the alkanyl piperazine as an impure yellow oil (2.48 g, 85% yield): MS $MH^+$ calcd. for $C_{27}H_{45}N_3O_4FS$ 526, found 526.

Part F. Preparation of:

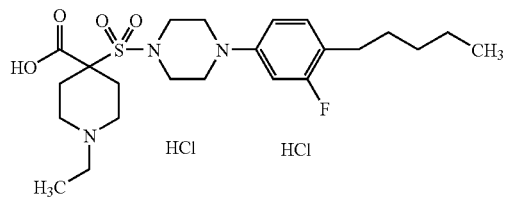

A solution of the alkanyl piperazine of Part E (2.48 g, 4.72 mmol) in 4N HCl in dioxane (12 mL, 47.2 mmol) was stirred at ambient temperature for 18 hr. The resulting solution was concentrated in vacuo, treated again for 4 hr with 4N HCl, and poured into ether (30 mL) to precipitate the acid as a pink solid (2.14 g, 84% yield): MS $MH^+$ calcd. for $C_{23}H_{37}N_3O_4FS$ 470, found 470.

Part G. Preparation of:

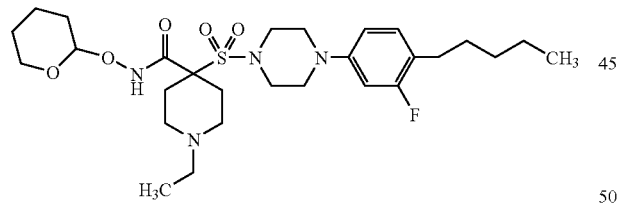

A mixture of the acid of Part F (2.04 g, 3.76 mmol), 1-hydroybenzotriazole hydrate (0.754 g, 5.58 mmol), N-methylmorpholine (1.55 mL, 14.0 mmol), O-(tetrahydro-2H-pyran-2-yl)hydroxylamine (0.761 g, 6.50 mmol), and 1-(3-dimethylaminopropyl)-3-ethylcarbodiimide hydrochloride (1.06 g, 5.52 mmol) in NMP (17 mL) under $N_2$ was stirred at ambient temperature for 18 hr, and then heated at 52° C. for 48 hr. To the mixture was added 1-(3-dimethylaminopropyl)-3-ethylcarbodiimide hydrochloride (0.600 g, 3.13 mmol) and O-(tetrahydro-2H-pyran-2-yl)hydroxylamine (0.500 g, 4.27 mmol) and was heated at 75° C. for 7 days. The ambient mixture was diluted with water (350 mL), and then extracted with ethyl acetate (3×100 mL). The organic layer was washed with water (100 mL), washed with 1N NaOH (100 mL), washed with water (2×100 mL), washed with brine (100 mL), concentrated in vacuo, and purified by chromatography (silica gel; methanol/$CH_2Cl_2$/$NH_3$) to provide the O-protected hydroxamate as a white solid (0.946 g, 44% yield): MS $MH^+$ calcd. for $C_{28}H_{46}N_4O_5FS$ 569, found 569.

Part H. Preparation of:

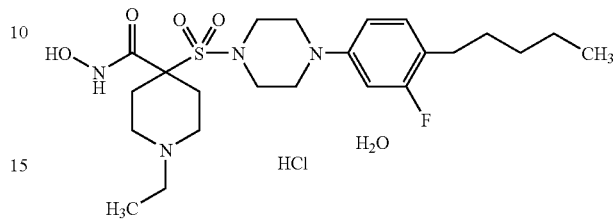

A solution of the O-protected hydroxamate of Part G (0.926 g, 1.62 mmol) and acetyl chloride (0.591 g, 7.83 mmol) in methanol (16 mL) was stirred at ambient temperature for 20 min. The resulting solution was poured into ethyl ether (300 mL), concentrated in vacuo, triturated with ether, and purified by reverse phase chromatography to provide the title compound as an off-white solid (0.49 g, 55% yield): MS $MH^+$ calcd. for $C_{23}H_{38}N_4O_4FS$ 485, found 485.

Example 23

Preparation of 4-{[4-(2-fluoro-4-pentylphenyl)piperazin-1-yl]sulfonyl}-N-hydroxytetrahydro-2H-pyran-4-carboxamide hydrochloride

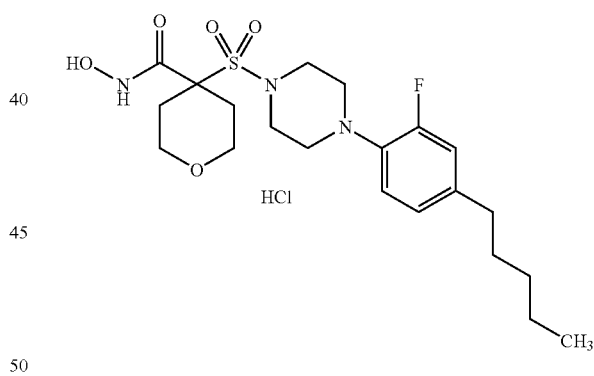

Part A. 4-Chloro-3-fluorobenzaldehyde (2.35 g, 15 mmol), n-butyltriphenylphosphonium bromide (7.38 g, 19 mmol), and potassium carbonate (2.57 g, 19 mmol) were suspended in isopropanol and heated for 48 hr at 80° C. The mixture was concentrated, and then diluted with water (150 mL) and hexane (50 mL). This mixture was filtered, and the hexane layer was separated. The aqueous layer was extracted with additional hexane (2×50 mL). The combined hexane phases were washed with water (50 mL), and then dried over magnesium sulfate. Concentration afforded the desired olefin as a clear yellow oil (2.62 g, 89%).

Part B. The olefin from Part A (1.18 g, 6.0 mmol) was subjected to hydrogenation over 5% Pd—C in ethanol for 30 min. The product was filtered through celite, and then concentrated to afford the desired aryl pentane as an oil (1.09 g, 91%)

Part C. Tert-butyl 4-(piperazin-1-ylsulfonyl)tetrahydro-2H-pyran-4-carboxylate (1.50 g, 4.5 mmol), 1-(3-fluoro, 4-chlorophenyl)pentane from Part B (1.09 g, 5.45 mmol), 2-(di-t-butylphosphino)biphenyl (89 mg, 0.3 mmol), Pd(OAc)$_2$ (45 mg, 0.2 mmol), sodium t-butoxide (538 mg, 5.6 mmol), and toluene (3 mL) were combined in a reaction vessel, which was subsequently lowered into a 90° C. oil bath. The mixture was stirred for 2 hr, and then allowed to cool. Subsequently, the mixture was diluted with water (50 mL), and extracted with ethyl acetate (2×100 mL). The combined organic layers were dried using magnesium sulfate. Concentration followed by chromatography afforded 1.15 g (51%) of a crude t-butyl ester as a solid.

Part D. The biphenyl ester from Part C (1.15 g, 2.3 mmol) was dissolved in trifluoroacetic acid. The resulting solution was briefly heated to reflux, and then stirred at ambient temperature for 1 hr. The solvent was removed, and the resulting residue was azeotroped with acetonitrile. The crude biphenyl acid was dried in vacuo, and then combined with N-methylmorpholine (ca. 1 mL), O-(tetrahydro-2H-pyran-2-yl)hydroxylamine (0.468 g, 4 mmol), 1-hydroxybenzotriazole hydrate (0.540 g, 4 mmol), and N,N-dimethylformamide (5 mL). The resulting mixture was stirred for 10 min, and then 1-(3-dimethylaminopropyl)-3-ethylcarbodiimide hydrochloride (0.764 mg, 4 mmol) was added. Stirring was then resumed for 2 hr at ambient temperature. Afterward, the mixture was diluted with water (100 mL), and was extracted with ethyl acetate (2×100 mL). The combined organic layers were dried over magnesium sulfate and concentrated. The resulting residue was purified by flash chromatography, affording the desired THP-hydroxamate as a foam (1.1 g, 87% from t-butyl ester).

Part E. The THP-hydroxamate of Part D (1.1 g, 2.0 mmol) was dissolved in methanol (50 mL). Acetyl chloride (ca. 5 mL) was added slowly. After 10 mm, the solution was concentrated. The solid was triturated with ether and dried in a vacuum oven at 40° C., affording 849 mg of the title hydroxamic acid (95%). MS MH$^-$ calc'd. for $C_{21}H_{32}FN_3O_5S$ 458.2125, found 458.2143. Anal. Calc'd for $C_{21}H_{32}FN_3O_5S(1HCl)$: C, 51.06; H, 6.73; N, 8.51. Obs.: C, 50.77; H, 7.57; N, 8.52.

Example 24

Preparation of 4-{[4-(5-butylpyridin-2-yl)piperidin-1-yl]sulfonyl}-1-cyclopropyl-N-hydroxypiperidine-4-carboxamide hydrochloride

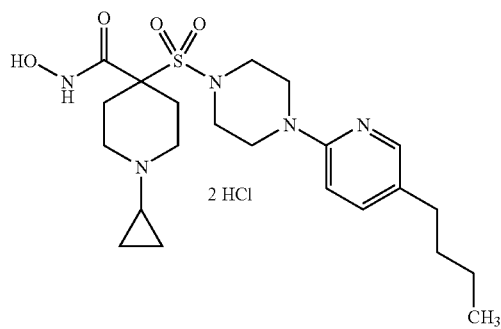

Part A. Preparation of iodo intermediate. To a solution of N-Boc-4-hydroxypiperdine (10.0 g, 49.7 mmol) in dichloromethane (200 mL) was added triphenylphosphine (16.9 g, 64.6 mmol) and imidazole (5.07 g, 74.5 mmol). The resulting slurry was cooled to 0° C. in an ice bath. Iodine (15.1 g, 59.6 mmol) was added in small portions. The solution was then stirred for 18 hr at ambient temperature. Afterward, the solution was diluted with water and extracted with diethyl ether. The organic layer was washed with water and saturated aqueous NaCl, and then dried over sodium sulfate. Concentration in vacuo followed by trituration with hexane removed the excess triphenylphosphine and triphenylphosphine oxide. The filtrate was concentrated in vacuo to provide the iodo intermediate as a colorless oil (14.4 g, 93% yield).

Part B. Preparation of tert-butyl 4-(5-bromopyridin-2-yl)piperidine-1-carboxylate intermediate. Zinc dust (6.38 g, 97.7 mmol) was suspended into tetrahydrofuran (10 mL), and 1,2-dibromoethane (0.55 mL, 6.43 mmol) was added. The slurry was heated to reflux with a heat gun 3 times. Upon cooling to ambient temperature, trimethylsilyl chloride (0.78 mL, 6.15 mmol) was added. After 15 min, the iodo compound of Part A (22.5 g, 72.3 mmol) was added. After 30 min, 2,5-dibromopyridine (17.1 g, 72.3 mmol) in N,N-dimethylacetamide(50 mL) was added, followed by tris(dibenzylideneacetone)dipalladium(0) (659 mg, 0.72 mmol) and tri-2-furylphosphine (671 mg, 2.90 mmol). The solution was then heated at 80° C. for 18 hr. Afterward, the solution was cooled to ambient temperature and filtered through Celite, rinsing with ethyl acetate and water. The filtrate was diluted with ethyl acetate, washed with water and brine, and dried over sodium sulfate. Concentration in vacuo produced tert-butyl 4-(5-bromopyridin-2-yl)piperidine-1-carboxylate as an orange oil (16.44 g, 67% yield). MS(CI) M-tBu calculated for $C_{15}H_{21}N_2O_2Br$: 286, found 286.

Part C. Preparation of amine intermediate. To a solution of the tert-butyl 4-(5-bromopyridin-2-yl)piperidine-1-carboxylate of Part B (16.4 g, 48.3 mmol) in 1,4-dioxane (30 mL) was added 4M HCl in 1,4-dioxane (30 mL). The solution was then stirred for 48 hr. Afterward, the solution was concentrated in vacuo to provide the amine as an orange solid.

Part D. Preparation of benzyl 4-{[4-(5-bromopyridin-2-yl)piperidin-1-yl]sulfonyl}piperidine-1-carboxylate intermediate. To a solution of the amine of Part C (15.6 g, 56.2 mmol) in dichloromethane (200 mL) was added diisopropylethylamine (21.5 mL, 123.5 mmol). The solution was cooled to 0° C., and benzyl 4-(chlorosulfonyl)piperidine-1-carboxylate (17 g, 53.5 mmol) was added dropwise as a solution in dichloromethane (100 mL). The solution was then stirred at ambient temperature for 18 hr. The solution was concentrated in vacuo, and the residue was dissolved into ethyl acetate. The organic solution was washed with 1M HCl, washed with saturated aqueous sodium bicarbonate, washed with saturated aqueous NaCl, and dried over sodium sulfate. Purification (silica gel/ethyl acetate/hexanes) produced benzyl 4-{[4-(5-bromopyridin-2-yl)piperidin-1-yl]sulfonyl}piperidine-1-carboxylate as a yellow solid (8.93 g, 31%). MS(CI) MH$^+$ calculated for $C_{23}H_{28}N_3O_4SBr$: 524, found 524.

Part E. Preparation of -benzyl 4-methyl 4-{[4-(5-bromopyridin-2-yl)piperidin-1-yl]sulfonyl}piperidine-1,4-dicarboxylate intermediate. To a solution of the carboxylate of Part D (6.93 g, 13.3 mmol) in tetrahydrofuran (20 mL) was added lithium bis(trimethylsilyl)amide (1.0M solution in tetrahydrofuran, 39.8 mL) dropwise over 30 min. After stirring at ambient temperature for 30 min, dimethylcarbonate (1.68 mL, 19.9 mmol) was added. The solution was stirred at ambient temperature for 2 hr. The reaction was quenched with the addition of water. The solution was concentrated in vacuo, and the residue was dissolved into ethyl acetate. The organic solution was washed with water and saturated aqueous NaCl. Concentration in vacuo followed by trituration with methanol produced 1-benzyl 4-methyl 4-{[4-(5-bromopyridin-2-yl)piperidin-1-yl]sulfonyl}piperidine-1,4-dicarboxylate as a solid (4.65 g, 60%). MS(CI) MH$^+$ calculated for $C_{25}H_{30}N_3O_6SBr$: 582, found 582.

Part F. Preparation of 1-benzyl 4-methyl 4-{[4-(5-butylpyridin-2-yl)piperidin-1-yl]sulfonyl}piperidine-1,4-dicarboxylate intermediate. To a solution of the methyl ester of Part E (3.0 g, 5.17 mmol) in tetrahydrofuran (15 mL) was added potassium phosphate (3.29 g, 15.5 mmol) in water (10 mL). To this solution was then added tributylborane (1.0 M in tetrahydrofuran, 7.76 ml) and [1,1'-bis(diphenylphosphino)-ferrocene]dichloropalladium(II).$CH_2Cl_2$ (211 mg, 0.26 mmol). The resulting solution was heated at 60° C. for 20 hr. Afterward, the solution was filtered through Celite, washing with ethyl acetate. The filtrate was then washed with water, washed with saturated aqueous NaCl, and dried over sodium sulfate. Chromatography (on silica, ethyl acetate/hexanes) produced 1-benzyl 4-methyl 4-{[4-(5-butylpyridin-2-yl)piperidin-1-yl]sulfonyl}piperidine-1,4-dicarboxylate as a yellow solid (2.82 g, quantitative yield). MS(CI) MH$^+$ calculated for $C_{29}H_{39}N_3O_6S$: 558, found 558.

Part G. Preparation of methyl 4-{[4-(5-butylpyridin-2-yl)piperidin-1-yl]sulfonyl}piperidine-4-carboxylate intermediate. A solution of the methyl ester of Part F (2.47 g, 4.43 mmol) was hydrogenated in ethanol in the presence of 20% $Pd(OH)_2$/C at 20 psi for 3 hr at ambient temperature. The solution was then filtered and concentrated to produce methyl 4-{[4-(5-butylpyridin-2-yl)piperidin-1-yl]sulfonyl}piperidine-4-carboxylate as an oil (1.65 g, 88%). MS(CI) MH$^+$ calculated for $C_{21}H_{33}N_3O_4S$: 424, found 424.

Part H. Preparation of methyl 4-{[4-(5-butylpyridin-2-yl)piperidin-1-yl]sulfonyl}-1-cyclopropylpiperidine-4-carboxylate intermediate. To a solution of the amine of Part G (500 mg, 1.18 mmol) in methanol (3 mL) was added glacial acetic acid (0.68 mL, 11.8 mmol). After 10 min of stirring at ambient temperature, (1-ethoxycyclopropyl)oxytrimethylsilane (0.31 mL, 1.53 mmol) was added. After 10 min, sodium cyanoborohydride (334 mg, 5.31 mmol) was added, and the solution was heated to reflux for 6 six hr. Afterward, the solution was stirred at ambient temperature for 18 hr. The solution was then concentrated in vacuo, and the residue was then dissolved into ethyl acetate. The organic solution was washed with water, washed with 1M NaOH, washed with saturated aqueous NaCl, and dried over sodium sulfate. Concentration in vacuo produced methyl 4-{[4-(5-butylpyridin-2-yl)piperidin-1-yl]sulfonyl}-1-cyclopropylpiperidine-4-carboxylate as a white solid (380 mg, 70% yield for 2 steps). MS(CI) MH$^+$ calculated for $C_{24}H_{37}N_3O_4S$: 464, found 464.

Part I. Preparation of acid intermediate. To a solution of the cyclopropylamine of Part H (370 mg, 0.80 mmol) in methanol (3 mL) and tetrahydrofuran (3 mL) was added NaOH (320 mg) in water (2 mL). The solution was heated to 60° C. for 6 hr. Afterward, the solution was concentrated in vacuo, and the residue was dissolved into water. The resulting solution was acidified to pH=2 with 1M HCl. The solution was then concentrated.

Part J. Preparation of 4-{[4-(5-butylpyridin-2-yl)piperidin-1-yl]sulfonyl}-1-cyclopropyl-N-(tetrahydro-2H-pyran-2-yloxy)piperidine-4-carboxamide Intermediate. To the crude acid of Part I (0.80 mmol) in N,N-dimethylformamide (3 mL) was added 1-hydroxybenztriazole (130 mg, 0.96 mmol), 4-methylmorpholine (0.44 mL, 4.0 mmol), and tetrahydropyranylamine (140 mg, 1.2 mmol). After 30 min, 1-(3-dimethylaminopropyl)-3-ethylcarbodiimide hydrochloride (215 mg, 1.12 mmol) was added, and the solution was heated at 70° C. for 18 hr. Afterward, the solution was partitioned between ethyl acetate and water. The organic layer was washed with water and saturated aqueous NaCl, and then dried over sodium sulfate. Chromatography (on silica, ethyl acetate/hexane/methanol) produced 4-{[4-(5-butylpyridin-2-yl)piperidin-1-yl]sulfonyl}-1-cyclopropyl-N-(tetrahydro-2H-pyran-2-yloxy)piperidine-4-carboxamide as an oil (160 mg, 36% yield for 2 steps). MS(CI) MH$^+$ calculated for $C_{28}H_{44}N_4O_5S$: 549, found 549.

Part K. Preparation of 4-{[4-(5-butylpyridin-2-yl)piperidin-1-yl]sulfonyl}-1-cyclopropyl-N-hydroxypiperidine-4-carboxamide hydrochloride. To a solution of the protected hydroxamate of Part J (150 mg, 0.27 mmol) in 1,4-dioxane (2 mL) was added 4M HCl in 1,4-dioxane (3 mL). The solution was stirred at ambient temperature for 1 hr. Afterward, the solution was concentrated in vacuo. The resulting residue was stirred in ethyl ether. Subsequently, vacuum filtration provided the title compound as a white solid (135 mg, 93% yield). MS(CI) MH$^+$calculated for $C_{23}H_{36}N_4O_4S$: 465, found 465. HRMS calculated for $C_{23}H_{36}N_4O_4S$: 465.2536, 465.2553. Analytical calculation for $C_{23}H_{36}N_4O_4S$: C, 48.93; H, 7.32; N, 9.92; Cl, 12.56. Found: C, 49.26; H, 7.71; N, 9.85; Cl, 12.41.

Example 25

Preparation of 1-cyclopropyl-N-hydroxy-4-({[4-[4-(2,2,2-trifluoroethoxy)phenyl]piperidin-1-yl}sulfonyl)piperidine-4-carboxamide hydrochloride

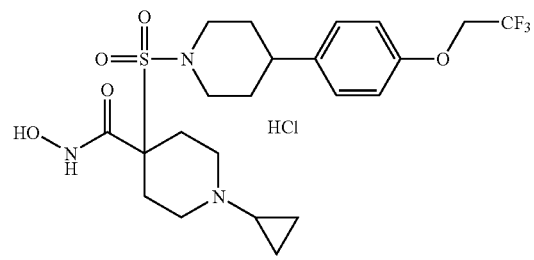

Part A:

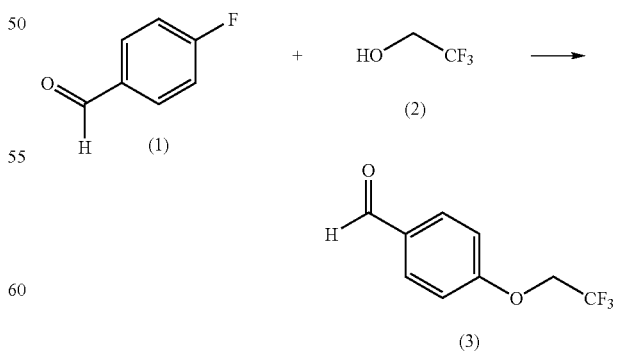

To a solution of 4-fluoro-benzaldehyde (1) (Aldrich, 8.0 g, 64.4 mmol) in N,N-dimethylformamide (120 ml) was added potassium carbonate (Aldrich, 13.4 g, 96.7 mmol) followed by 3,3,3-trifluoroethanol (2) (6.4 g, 64.4 mmol). The mixture was stirred at 80° C. for 18 hr. After cooling to room temperature, the mixture was diluted with water, and the resulting solid was filtered. The filter cake was washed with water and dried in vacuo to afford compound (3) as a white solid (12.5 g, 95% yield). $^1$H NMR indicated the desired compound (3).

Part B:

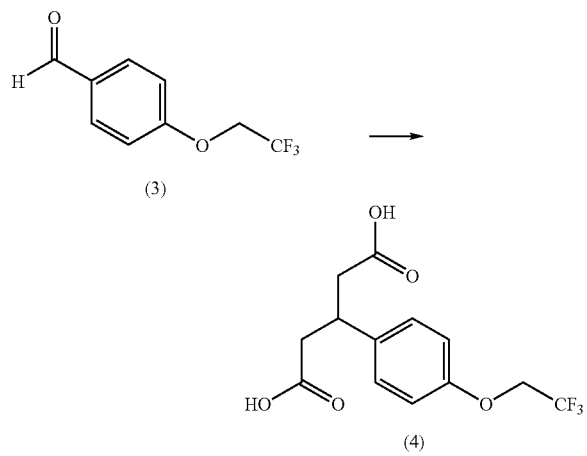

The product (3) from Part A (37 g, 181.2 mmol) and ethylacetoacetate (Aldrich, 69.3 ml, 543.7 mmol) were added neat to a round bottom flask equipped with stir bar. A catalytic amount of piperidine (1.0 ml) was added, and the mixture was stirred for 3 days to form a hard yellow solid. Ethanol (250 ml) was added to the yellow solid. The mixture was then heated to reflux for 20 min and then cooled to ambient temperature. The resulting solid was filtered, washed with hexanes, and dried. Next, a solution of KOH (50.8 g, 56.11 mmol) in water (43 ml) was heated to 80° C. The dried solid was then added portion-wise, maintaining the temperature between 80–90° C. The resulting mixture was stirred at 80° C. for 2 hr, and then poured into a flask of ice (300 g), followed by ethyl acetate (300 ml). The bi-phase mixture was separated, and the aqueous layer was titrated to pH 1 with concentrated HCl. An oil fell out which was separated from the aqueous phase. The aqueous phase was then extracted with dichloromethane (2×-150 ml). The organics were combined and added with the oil. The resulting mixture was dried over Na$_2$SO$_4$, filtered, and concentrated to form compound (4) as a pale yellow solid (27.7 g, 49.9%). $^1$H NMR indicated the desired compound (4).

Part C:

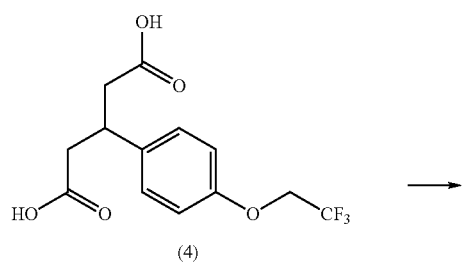

-continued

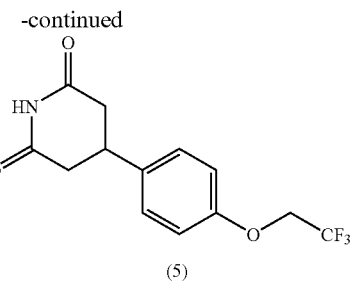

The solid product (4) from Part B (27.6 g, 91.1 mmol) was added to a round bottom flask along with urea (8.1 g, 135 mmol). The solids were heated at 150–160° C. for 2 hr, and then cooled to room temperature. Ethanol (30 ml) was added, and the mixture refluxed for 1 hr. As the mixture cooled, solids formed that were slurried in hexanes, filtered, and dried to form compound (5) as an off-white solid (24.1 g, 93%). $^1$H NMR indicated the desired product (5).

Part D:

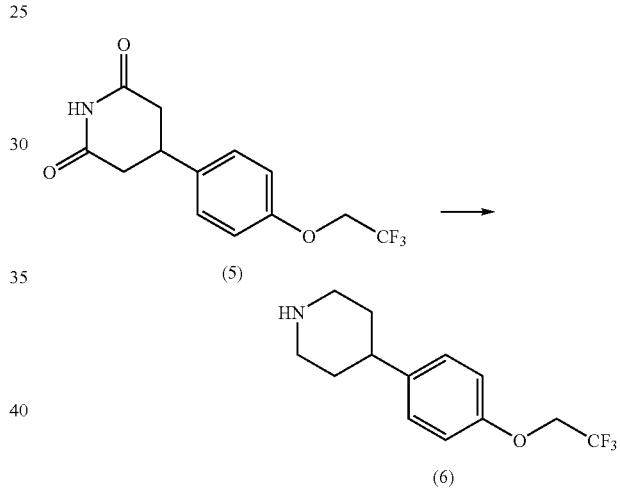

A lithium aluminum hydride ("LAH") solution (1.0 M in THF, 46 ml) was heated to 40° C. in a round bottom flask. The solid product (5) from Part C (24 g, 83.6 mmol) was added portion-wise, keeping the temperature at less than 60° C. After the addition, the mixture was heated to reflux and stirred for 1.5 hr. Afterward, the vessel was cooled to room temperature. Water (2 ml) was slowly added to quench any remaining LAH. A potassium/sodium tartrate aqueous solution (15 ml) was added, followed by Na$_2$SO$_4$ (120 g). After standing 1 hr, the solids were filtered. The resulting filtrate was dried over more Na$_2$SO$_4$, filtered, concentrated, and dried to produce compound (6) as a clear oil (17.0 g, 78%). $^1$H NMR indicated the desired product (6).

Part E:

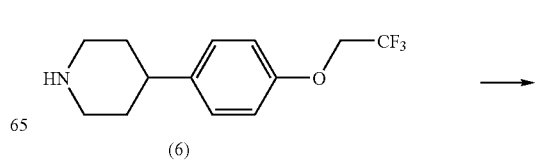

-continued

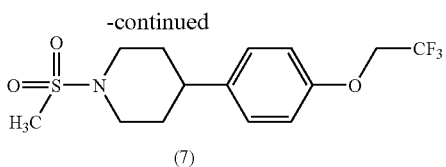

(7)

A solution of the product (6) from Part D (13.6 g, 52.3 mmol) in dichloromethane (110 ml) was cooled to 0° C. A solution of mesylchloride (Aldrich, 5.3 ml, 68.8 mmol) in dichloromethane (10 ml) was slowly dripped in over 15 min. The ice bath was removed and the mixture was warmed to room temperature. After 3 hr, the mixture was concentrated to dryness. The residue was taken up in ethyl acetate (300 ml), washed with 10% HCl (100 ml), washed with water (100 ml), washed with brine (100 ml), and dried over Na$_2$SO$_4$. After filtering, the organic was concentrated and dried to produce compound (7) as a tan solid (14.9 g, 84%). 1H NMR indicated the desired compound (7).

Part F:

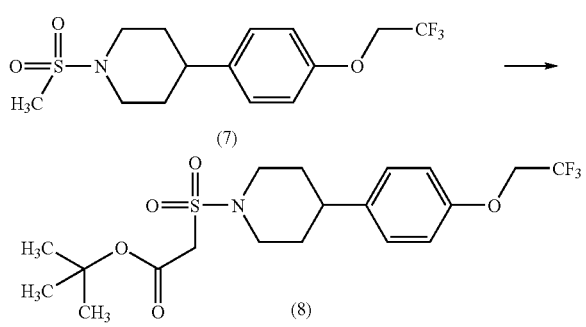

A solution of the product (7) from Part E (14.8 g, 43.9 mmol) and t-butylcarboxlyate anhydride (Aldrich, 11.5 g, 52.7 mmol) in tetrahydrofuran (80 ml) was cooled to −75° C. Lithium bis(trimethylsilyl)amide (Aldrich, 1.0 M in tetrahydrofuran, 132 ml, 132 mmol) was added slowly, keeping temperature of less than −60° C. After the addition, the mixture was warmed to 0° C. and stirred for 1 hr. The mixture was then cooled back to −75° C. and slowly quenched with saturated NH$_4$Cl$_{aq}$ (200 ml), keeping the temperature at less than −20° C. The aqueous froze into a solid chunk of ice. After warming to 5° C., the mixture was separated, and the aqueous extracted via ethylacetate (3×-200 ml). The organics were washed with saturated NH$_4$Cl (2×-200 ml), washed with water (1×-200 ml), washed with brine (1×-200 ml), dried over Na$_2$SO$_4$, and concentrated to produce a beige solid that was recrystallized from methanol to afford the product (8) (12.0 g, 62% yield). $^1$H NMR indicated the desired compound (8).

Part G:

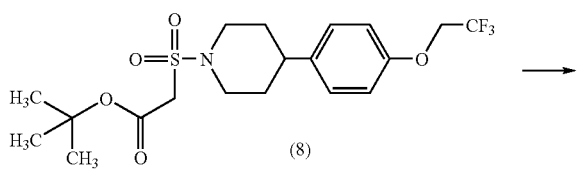

-continued

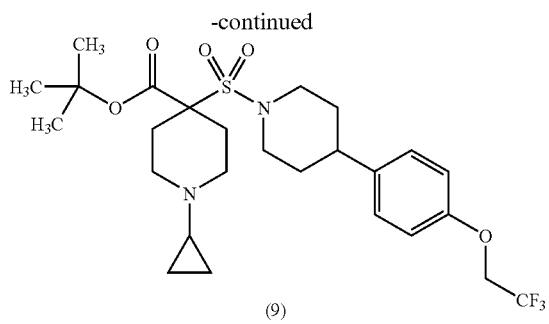

(9)

To a solution of the product (8) from Part F (4.0 g, 9.1 mmol), potassium carbonate (Aldrich, 7.6 g, 54.9 mmol), and 18-crown-6 (Aldrich, 0.5 g, cat. amt) in N,N-dimethylformamide (20 ml) was added bis(chloroethyl)-N-cyclopropylamine hydrochloride (E-4668,2.2 g, 10.0 mmol). The mixture was heated at 60° C. for 18 hr and then worked up by cooling and pouring into water (50 ml). The resulting mixture was extracted via ethylacetate (2×-150 ml). The organics were combined and washed with water (1×-100 ml), washed with brine (2×-100 ml), dried over Na$_2$SO$_4$, and concentrated to afford a brown oil. The oil was purified via silica gel (ethyl acetate: hexanes, 1:9) to afford compound (9) as a white solid (1.8 g, 36%. $^1$H NMR indicated the desired compound (9).

Part H:

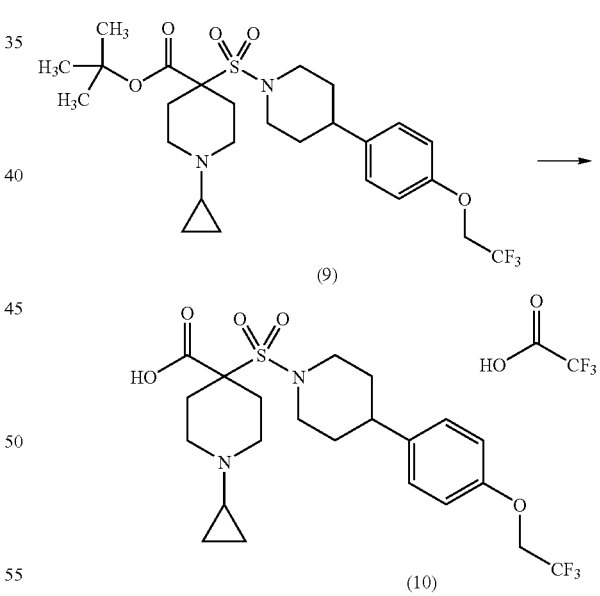

To a solution of the product (9) of Part G (1.8 g, 3.3 mmol) in methylene chloride (70 ml) was added trifluoroacetic acid (Aldrich, 15 ml, 195 mmol). The mixture was stirred overnight at room temperature. The mixture was then concentrated to one-third volume. The residue was dripped into stirring diethylether (500 ml). The resulting solid, in turn, was collected, washed with diethylether, and dried to afford the product (10) as a TFA salt (1.9 g, 95% yield). $^1$H NMR indicated the desired compound (10).

Part I:

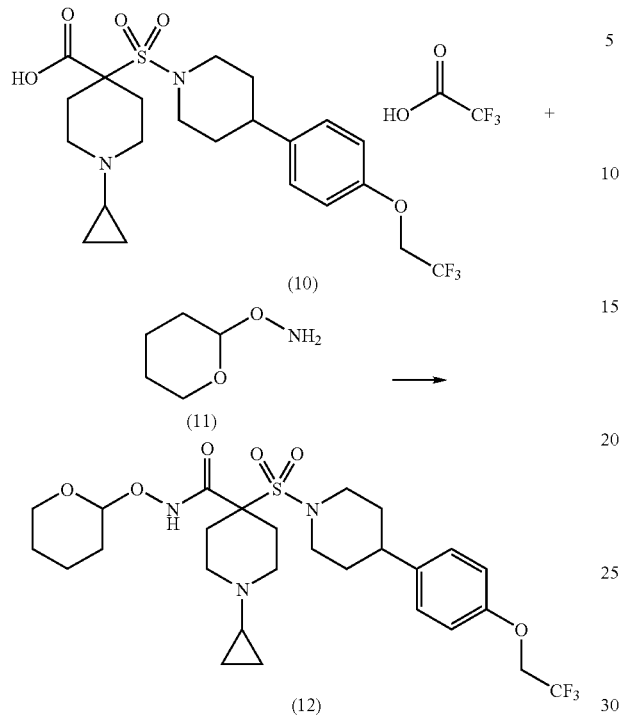

To a solution of the product (10) of Part H (1.9 g, 3.1 mmol) in N,N-dimethylformamide (10 ml) was added triethylamine (Aldrich, 1.3 ml, 9.3 mmol) followed by N-hydroxybenzotriazole hydrate (Aldrich, 0.84 g, 6.2 mmol), O-(tetrahydro-2H-pyran-2-yl)hydroxylamine (11) (0.54 g, 4.6 mmol), and, lastly, 1-(3-dimethylaminopropyl)-3-ethylcarbodiimide hydrochloride (Sigma, 1.5 g, 7.8 mmol). The resulting mixture was stirred at room temperature for 15 hr. The mixture was then diluted with water (15 ml) and ethylacetate (100 ml). The organics were separated, and the aqueous was further extracted with ethylacetate (2×-75 ml). The combined organics were then combined and washed with saturated aqueous NaHCO₃ (2×-150 ml), water (2×-100 ml), and brine (1×-200 ml). After drying over sodium sulfate, the organics were concentrated to afford compound (12) as a brown oil (1.7 g, 94% yield). $^1$H NMR indicated the desired compound (12).

Part J:

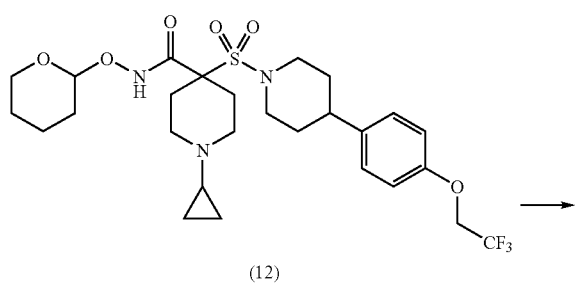

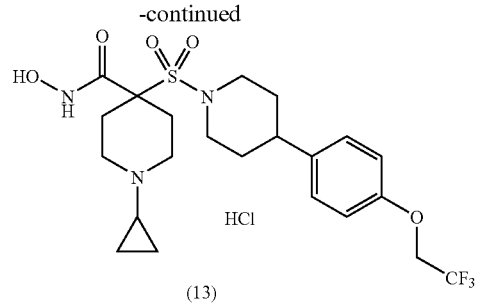

To the product (12) of Part I (1.7 g, 2.9 mmol) was added methanol (2 ml) and 4 N HCl in dioxane (10 ml) for 1 hr. The solvent was concentrated to one-third volume. Diethylether was then added. The resulting solid was filtered, washed with diethylether, and dried to afford compound (13) as a beige solid (0.82 g, 87% yield). $^1$H NMR indicated the desired compound (13). HRMS for $C_{22}H_{30}F_3N_3O_5S$ indicated $M^{+H}_{found}$=506.1915 ($M^{+H}_{calc}$=506.1931).

Example 26

Preparation of N-hydroxy-4-[(4-octylpiperidin-1-yl)sulfonyl]tetrahydro-2H-pyran-4-carboxamide

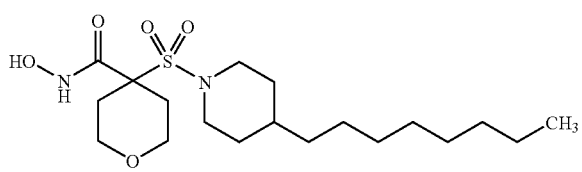

Part A. Preparation of tert-butyl 4-4{[4-(methoxymethylene)piperdin-1-yl]sulfonyl}tetrahydro-2H-pyran-4-carboxylate:

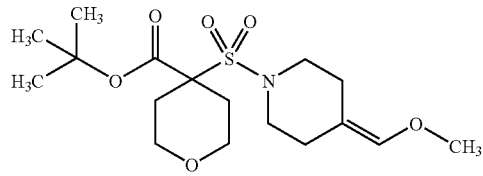

An oven-dried round-bottomed flask fitted with septa and a nitrogen needle was charged with (methoxymethyl)triphenylphosphonium chloride (4.11 g, 12 mmol) and tetrahydrofuran (50 mL). The flask was immersed in an ice bath. A 1 M solution of lithium hexamethyldisilazide in tetrahydrofuran (13 mL, 13 mmol) was then added dropwise while maintaining mixture temperature at less than 5° C. After complete addition, the mixture was stirred with cooling for 15 min. Then, a solution of tert-butyl 4-(4-oxopiperidin-1-yl)sulfonyl]tetrahydro-2H-pyran-4-carboxylate (3.47 g, 10 mmol) in tetrahydrofuran (10 mL) was added dropwise, again maintaining a reaction temperature at less than 5° C. After complete addition (approximately 30 min), the mixture was stirred with cooling for 15 min, then the cooling bath was removed. The mixture was slowly warmed to room temperature and stirred overnight. Diethyl ether (200 mL) was added to the reaction mixture, resulting in a yellow precipitate, which was removed by vacuum filtration. The filtrate was washed with 5% aqueous HCl (3×100 mL), saturated aqueous sodium bicarbonate (3×100 mL), and brine (1×100 mL). The organic layer was then dried over magnesium sulfate and concentrated in vacuo. Purification by flash column chromatography (20–40% ethyl acetate/hexane) yielded 2.82 g of the title compound as a colorless, viscous oil (75%): 1H NMR (CDCl$_3$) δ 1.51 (s, 9H), 2.05–2.30 (m, 2H), 2.29 (m, 2H), 3.29 (m, 6H), 3.95 (dd, J=11.4, 4.2 Hz, 2H), 5.84 (s, 1H); electrospray mass spectroscopy m/z=376 (M+H).

Part B. Preparation of tert-butyl 4-[(4-formylpiperidin-1-yl)sulfonyl]tetrahydro-2H-pyran-4-carboxylate:

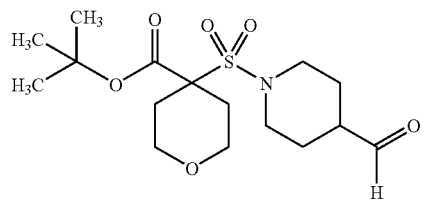

A round-bottomed flask was charged the product of Part A (0.50 g, 1.34 mmol), tetrahydrofuran (5 mL), and 5% aqueous HCl (1 mL, 1.37 mmol). The resulting mixture was stirred at room temperature for 2 hr, and then heated to 50° C. overnight. Afterward, the mixture was partitioned between diethyl ether (25 mL) and saturated aqueous sodium bicarbonate (25 mL). The organic layer was washed with brine (25 mL), dried over magnesium sulfate, and concentrated in vacuo. This resulted in isolation of 0.50 g (quantitative) product as a yellow solid: 1H NMR (CDCl$_3$) δ 1.51 (s, 9H), 1.70 (m, 2H), 1.93 (m, 2H), 2.08 (td, J=12.4, 4.8 Hz, 2H), 2.29 (d, J=12.4 Hz, 2H), 2.41 (m, 1H), 3.11 (m, 2H), 3.29 (td, J=12, 1.6 Hz, 2H), 3.70 (m, 2H), 3.95 (dd, J=11.2, 4 Hz, 2H), 9.65 (s, 1H); electrospray mass spectroscopy m/z=362 (M+H).

Part C. Preparation of tert-butyl 4-({4-[1E]-oct-1-enyl]piperdin-1-yl}sulfonyl)tetrahydro-2H-pyran-4-carboxylate:

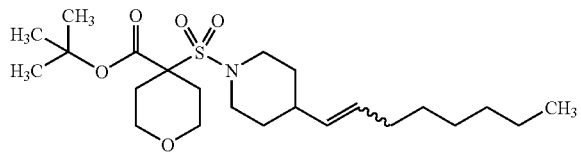

An oven-dried, round-bottomed flask fitted with septa and a nitrogen needle was charged with (heptyl)triphenylphosphonium bromide (1.1 g, 2.5 mmol) and tetrahydrofuran (10 mL), resulting in a white slurry. The flask was immersed in an ice bath. Subsequently, a 1 M solution of lithium hexamethyldisilazide in tetrahydrofuran (2.7 mL, 2.7 mmol) was added dropwise, maintaining the reaction temperature at less than 5° C. After complete addition, the mixture was stirred with cooling for 15 min. Then, a solution of the product from Part B (0.75 g, 2.07 mmol) in tetrahydrofuran (2 mL) was added dropwise, again maintaining the reaction temperature at less than 5° C. After complete addition (approximately 15 min), the mixture was stirred with cooling for 15 min. The cooling bath was then removed. The mixture was slowly warmed to room temperature and stirred for 1 hr. Diethyl ether (25 mL) was added to the mixture. This resulted in a tan precipitate, which was removed by vacuum filtration. The filtrate was washed with water (50 mL) and brine (50 mL). The organic layer was dried over magnesium sulfate and concentrated in vacuo. Purification by flash column chromatography (10% ethyl acetate/hexane) yielded 0.66 g of the title compound as a white crystalline solid (72%): 1H NMR (CDCl$_3$) δ; mass spectroscopy (electrospray) m/z=444 (M+H).

Part D. Preparation of tert-butyl 4-[(4-octylpiperdin-1-yl)sulfonyl]tetrahydro-2H-pyran-4-carboxylate:

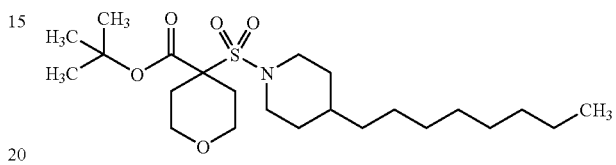

A 150 mL hydrogenation flask was charged with 10% palladium on carbon (20 mg) and a solution of the product from Part C (0.35 g, 0.79 mmol) in methanol (5 mL). The flask was placed under an H$_2$ atmosphere and agitated at room temperature for 1.5 h. Afterward, the mixture was filtered through celite and concentrated to produce 0.328 g of product as a white solid (93%): mass spectroscopy (electrospray) m/z=446 (M+H).

Part E. A 2-dram vial was charged with the product of Part D (0.307 g, 0.69 mmol) and a 1:1 mixture of trifluoroacetic acid and dichloromethane (1 mL). The mixture was stirred at room temperature for 5 hr and then concentrated in vacuo. The product was precipitated by the addition of a 1:1 mixture of diethyl ether/hexane. The resulting solid was collected by vacuum filtration. After further drying in vacuo, the yield of product was 0.232 g as a white solid (86%): mass spectroscopy (electrospray) m/z=390 (M+H).

Part F. A 2-dram vial was charged with the product from Part E (0.232 g, 0.60 mmol), a 0.5 M solution of hydroxybenotriazole in dimethylformamide (2.4 mL, 1.2 mmol), a 0.5 M solution of THP-ONH$_2$ (2.4 mL, 1.2 mmol), triethylamine (0.33 mL, 2.4 mmol), and EDC (0.228 g, 1.2 mmol). The resulting mixture was stirred at room temperature overnight, and then partitioned between water (25 mL) and ethyl acetate (25 mL). The organic layer was washed with 5% aqueous HCl (3×25 mL), washed with brine (1×100 mL), filtered through a celite column, and concentrated in vacuo. Purification by preparative reverse phase HPLC yielded 0.169 g of product as a white crystalline solid: mass spectroscopy (electrospray) m/z=506 (M+H).

Part G. Preparation of:

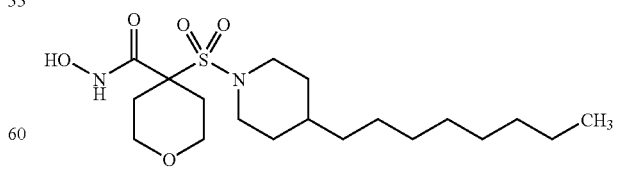

A 2-dram vial was charged with the product from Part F (0.169 g), methanol (1 mL), dioxane (1 mL), and 4 N HCl in dioxane (0.1 mL). The resulting solution was stirred at room temperature for 30 min. Then the solvents were removed in vacuo. Treatment with HCl in dioxone/methanol was repeated for 30 min. The solvents were then removed in vacuo, leaving 0.162 g of title compound as a white crystalline solid (67%—two steps): mass spectroscopy (electrospray) m/z=444 (M+H), HRMS: calculated for $C_{19}H_{37}N_2O_5S$ (M+H) 405.2418, observed 405.2398.

Example 27

Preparation of

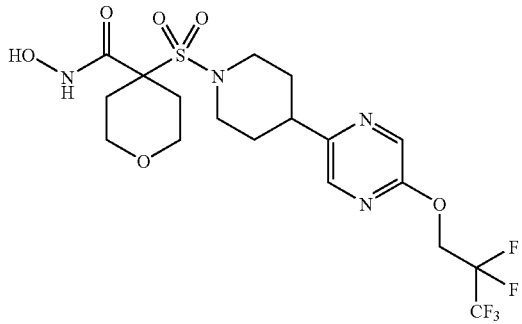

Part A. 2-Aminopyrazine (Aldrich, 20 g, 0.21 mol) was dissolved in 600 mL of $CH_2Cl_2$ and then cooled to 0° C. in an ice bath. To the resulting slurry was added N-Bromosuccinimide (Aldrich, 37.6 g, 0.211 mol) portion-wise over approximately 10 min. The slurry was allowed to mix in the ice bath for 1.5 hr. The slurry was then filtered through a bed of Celite®. The bed of Celtite® was washed with ~150 mL $CH_2Cl_2$. The filtrate was then concentrated in vacuo to solids. The resulting solids were purified by chromatography (silica, ethyl acetate/hexanes), producing 19.4 g (53%) of product. $^1H$ NMR confirmed the structure of the desired product.

Part B. Concentrated $H_2SO_4$ (55 mL) was cooled to approximately 0° C. in a round-bottomed flask. $NaNO_2$ (8.23 g, 119.3 mmol) was added portion-wise to the flask over approximately 5 min. After the addition was complete, the solution was allowed to mix and warm to ambient temperature over 30 min. The solution was cooled again in an ice bath, and a separate solution of the product from Part A (18.33 g, 105.3 mmol) in concentrated $H_2SO_4$ (90 mL) was added dropwise while maintaining a temperature of less than 10° C. After addition was complete, the solution was mixed in the ice bath for 15 min and then warmed to 40° C. for 15 min. The resulting mixture was allowed to cool to ambient temperature and then slowly poured into 500 g of ice. The resulting aqueous mixture was extracted with diethyl ether (3×500 mL). The organic extracts were dried over $MgSO_4$, filtered, and concentrated in vacuo to solids. The solids were slurried in hexanes (100 mL) at ambient temperature for approximately 1 hr, filtered, and desiccated to produce 9.55 g (51.8%) of solids.

Part C. 4.2 g (24 mmol) of the product from Part B was dissolved in pyridine (25 mL) and cooled to 0° C. in an ice bath. Triflic anhydride (Aldrich, 8.12 g, 28.8 mmol) was added in several portions over approximately 5 min. The mixture was allowed to mix, stoppered with a syringe needle vent in an ice bath for approximately 30 min, and then stoppered overnight at ambient temperature. The reaction mixture with diethyl ether (300 mL) and aqueous 1N HCl (500 mL). Separated layers and back-extracted the aqueous layer with diethyl ether (200 mL). The combined organic extracts were washed with saturated aqueous $NaHCO_3$ (2×100 mL) and saturated aqueous NaCll (200 mL). The organic layers were dried over $MgSO_4$, filtered, and concentrated in vacuo to an oil that was purified by chromatography (silica, ethyl acetate/hexanes) to produce 5.55 g (75%) of the desired product. $^1H$ NMR confirmed the structure of the product.

Part D. Tert-butyl-4-[(4-oxo-1-1piperidyl)sulfonyl]tetrahydro-2H-pyran-4-carboxylate (Carbogen, 20 g, 57.6 mmol) was added to methanol (200 mL). The mixture was cooled to 0° C. under $N_2$ in an ice bath. $NaBH_4$ (Aldrich, 2.72 g, 72 mmol) was added in small portions to the above mixture over approximately 10 min. Once addition was complete, the mixture was allowed to stir in the ice bath for approximately 10 min and then warmed to ambient temperature with mixing for approximately 1.5 hr. The mixture was placed in an ice bath and approximately 10 mL of deionized water ("d$H_2O$") was added with mixing while under $N_2$. The resulting mixture was further diluted with ethyl acetate (500 mL) and d$H_2O$ (200 mL). The layers were separated, and the organic layer was washed with 0.5 N HCl and saturated aqueous NaCl (200 mL each). The organic layer was dried over $MgSO_4$ and filtered. The resulting filtrate was concentrated in vacuo to give 19 g (94%) of solids. $^1H$ NMR confirmed the structure of the solids as the desired product.

Part E. Triphenylphosphine, polymer supported resin (Aldrich, 42.2 g, 3.0 mmol/g, 126.5 mmol) was added to methylene chloride (600 mL) and stirred for approximately 1 hr to let the resin swell. Added imidazole (Aldrich, 163.2 mmol, 11.11 g) to the above mixture and cooled in an ice bath to 0° C. Added iodine (Aldrich, 41.42 g, 163.2 mmol) to the reaction mixture and let mix approximately 10 min at 0° C. To the resulting mixture was added the solids from Part D (19.0 g, 54.4 mmol) and it was allowed to stir and warm to ambient temperature over a weekend. The polymer supported resin was filtered from the reaction mixture and washed with methylene chloride (500 mL). The filtrate was washed with saturated aqueous $NaSO_3$, 1/1 d$H_2O$/saturated aqueous NaCl and saturated aqueous NaCl (400 mL each). The methylene chloride layer was dried over $MgSO_4$, filtered, and concentrated to give 18.6 g (74.5%) of product. $^1H$ NMR confirmed the structure of the solids as the desired product.

Part F. Zinc dust (Aldrich, 325 mesh, 263 mg, 4.05 mmol) was stirred and heated in tetrahydrofuran (5 mL) with 1,2-dibromoethane (Aldrich, 68 mg, 0.364 mmol) at 65° C. under $N_2$ for approximately 5 min. The mixture was cooled to ambient temperature. Chlorotrimethylsilane (Aldrich, 39 mg, 0.364 mmol) was then added. This mixture was allowed to stir under $N_2$ at ambient temperature for approximately 30 min. The iodide from Part E (1.36 g, 3.0 mmol) was added, and the resulting mixture was stirred at 40° C. under $N_2$ for approximately 3 hr. The product from Part C (0.7 g, 2.28 mmol), N,N-Dimethylacetamide (14 mL), and [1,1'-bis(diphenylphosphino)ferrocene]dichloropalladium(II) complex with dichloromethane (Aldrich, 93 mg, 0.114 mmol) were added to the mixture. It was stirred overnight at 80° C. under $N_2$. The mixture was cooled to ambient temperature. Saturated aqueous $NH_4Cl$ (10 mL) was then added. The resulting mixture was diluted further with d$H_2O$ (50 mL) and ethyl acetate (100 mL), and then filtered through a bed of Celite®. The layers were separated, and the aqueous layer was back-extracted with ethyl acetate (50 mL). The combined organic layers were washed with 1/1 d$H_2O$/saturated aqueous NaCl and saturated aqueous NaCl (50 mL each), dried over MgSO$_4$, filtered, and concentrated in vacuo to produce an oil that was purified by chromatography (silica, ethyl acetate/hexanes) to produce 90 mg (7%) of product.

Part G. The product from Part F (180 mg, 0.322 mmol, 90 mg from Part F remainder from an additional lot), N,N-Dimethylformamide (10 mL), K$_2$CO$_3$ (89 mg, 0.64 mmol), 18-Crown-6 (Aldrich, catalytic amount), and 2,2,3,3,3-pentafluoropropan-1-ol (Aldrich, 58 mg, 0.38 mmol) were mixed in a stoppered flask at ambient temperature overnight. The resulting mixture was diluted with dH$_2$O (50 mL) and ethyl acetate (100 mL). The layers were then separated, and the aqueous layer was back-extracted with ethyl acetate (50 mL). The combined organic layers were washed with 1/1 dH$_2$O/saturated aqueous NaCl and saturated aqueous NaCl (50 mL each), dried over MgSO$_4$, filtered, and concentrated in vacuo to produce 160 mg (89%) of dark oil.

Part H. The oil from Part G (160 mg, 0.286 mmol) was dissolved in methylene chloride (5 mL) and trifluoroacetic acid (5 mL) and then mixed in a stoppered flask with syringe needle vent overnight at ambient temperature. The resulting mixture was concentrated in vacuo to an oil 130 mg (90%).

Part I. The oil from Part H (130 mg, 0.258 mmol), 1-hydroxybenzotriazole (Aldrich, 65 mg, 0.48 mmol), and 1-[3-(dimethylamino)propyl]-3-ethylcarbodiimide hydrochloride (Aldrich, 92 mg, 0.48 mmol) were dissolved in N,N-dimethyformamide (10 mL). The resulting mixture was stirred in a stoppered flask at ambient temperature for approximately 30 min. N-methylmorpholine (Aldrich, 130 mg, 1.3 mmol) and O-(tetrahydropyranyl)hydroxylamine (Carbogen, 56 mg, 0.48 mmol) were added to the above mixture, and it was allowed to mix stoppered at ambient temperature overnight. 1-Hydroxybenzotriazole (65 mg, 0.48 mmol), 1-[3-(dimethylamino)propyl]-3-ethylcarbodiimide hydrochloride (92 mg, 0.48 mmol), N-methylmorpholine (130 mg, 1.3 mmol), and O-(tetrahydropyranyl)hydroxylamine (56 mg, 0.48 mmol) were again added to the mixture, and it was allowed to mix at ambient temperature another night. The reaction mixture was diluted with dH$_2$O (50 mL) and ethyl acetate (100 mL). The layers were separated and the aqueous layer was back-extracted with ethyl acetate (50 mL). The combined organic layers were washed with 1/1 dH$_2$O/saturated aqueous NaCl and saturated aqueous NaCl (50 mL each), dried over MgSO$_4$, filtered, and concentrated in vacuo to give 130 mg (84%) of an oil.

Part J. The oil from Part I was dissolved in 1.25 N HCl in methanol (Fluka, 10 mL) and was mixed covered for approximately 1.5 hr. The solution was concentrated in vacuo, re-dissolved, and concentrated in vacuo 2 additional times with 1.25 N HCl in methanol (10 mL each time) to give an oil. The oil was purified by chromatography (reversed phase C-18 silica, Acetonitrile/dH$_2$O with 0.05% trifluoroacetic acid in each). Column fractions were concentrated in vacuo to an oil that was then co-evaporated with 1.25 N HCl in methanol 3 times (10 mL each time) to exchange salts, i.e., trifluoroacetate for HCl. The resulting residue after the third co-evaporation was dissolved in a minimum amount of acetonitrile, precipitated with dH$_2$O, and filtered to produce 45 mg (40%) of solids whose structure was confirmed by $^1$H NMR to be the desired product.

Examples 28–54

In Vitro MMP Inhibition Analysis

Several hydroxamic acids and salts thereof were analyzed in in vitro assays to determine their ability to inhibit the MMP cleavage of peptide substrates. Inhibition ($K_i$) and $IC_{50}$ constants were calculated from the assayed hydroxamic acid-MMP interactions.

Human recombinant MMP-1, MMP-2, MMP-9, MMP-13, and MMP-14 were used in this assay. All enzymes were prepared in Assignee's laboratories following usual laboratory procedures. Protocols for the preparation and use of these enzymes are available in the scientific literature. See, e.g., *Enzyme Nomenclature* (Academic Press, San Diego, Calif., 1992) (and the citations therein). See also, Freije, et al., *J Biol. Chem.*, 269(24), 16766–16773 1994).

The MMP-1 proenzyme was purified from the spent media of MMP-1-transfected HT-1080 cells provided by Dr. Harold Welgus of Washington University (St. Louis, Mo.). The protein was purified on a zinc chelating column.

The MMP-2 proenzyme was purified by gelatin Sepharose chromatography from MMP-2-transfected p2AHT2 cells provided by Dr. Gregory Goldberg of Washington University (St. Louis, Mo.).

The MMP-9 proenzyme was purified by gelatin Sepharose chromatography from spent media of MMP-9-transfected HT1080 cells provided by Dr. Howard Welgus of Washington University (St. Louis, Mo.).

The MMP-13 was obtained as a pro enzyme from a full-length cDNA clone using baculovirus, as described by V. A. Luckow, "Insect Cell Expression Technology," *Protein Engineering. Principles and Practice*, pp. 183–218 (edited by J. L. Cleland et al., Wiley-Liss, Inc., 1996). The expressed proenzyme was first purified over a heparin agarose column, and then over a chelating zinc chloride column. The proenzyme was then activated by APMA for use in the assay. Further details on baculovirus expression systems may be found in, for example, Luckow et al., *J. Virol.*, 67(8), 4566–79 (1993). See also, O'Reilly et al, Baculovirus Expression Vectors: A Laboratory Manual (W. H. Freeman and Co., New York, N.Y., 1992). See also, King et al., *The Baculovirus Expression System: A Laboratory Guide* (Chapman & Hall, London, England, 1992).

The MMP-14 full length cDNA was provided by Dr. Gregory Goldberg of Washington University (St. Louis, Mo.). The catalytic domain enzyme was expressed in *E. coli* inclusion bodies, solubilized in urea, purified on a preparative C-14 reverse phase HPLC column, and then refolded in the presence of zinc acetate and purified for use.

All MMPs were activated using 4-aminophenylmercuric acetate ("APMA", Sigma Chemical, St. Louis, Mo.) or trypsin. MMP-9 also was activated using human recombinant MMP-3 (purified in Assignee's laboratory following standard cloning and purification techniques).

Two fluorogenic, methoxycoumarin-containing polypeptide substrates were used in the MMP inhibition assays:

MCA-ProLeuGlyLeuDpaAlaArgNH$_2$ (I)

MCA-ArgProLeuGlyLeuDpaAlaArgGluArgNH$_2$ (II)

Here, "Dpa" is 3-(2,4-dinitrophenyl)-L-2,3-diaminopropionyl group, and "MCA" is 7-methoxycoumarin-4-yl acetyl. Substrate (I) was purchased from Baychem (Redwood City, Calif.), and substrate II was prepared Assignee's laboratory. Substrate I was used in the $IC_{50}$ determination assays, while substrate II was used in the $K_i$ determination assays. In the absence of MMP inhibitory activity, either substrate is cleaved at the Gly-Leu peptide bond. This cleavage separates the highly fluorogenic peptide from the 2,4-dinitrophenyl quencher, thus resulting in increase of fluorescent intensity.

The stock solutions of the assayed hydroxamic acids (or salts thereof) were prepared in 1% dimethyl sulfoxide (DMSO). These stock solutions were diluted in Buffer A (100 mM Tris-HCl, 100 mM NaCl, 10 mM $CaCl_2$, 0.05% polyoxyethylene 23 lauryl ether, pH 7.5) to obtain solutions with different hydroxamic acid concentrations, i.e., assay solutions with different concentrations of the assayed MMP inhibitory compound. The experiment controls contained the same amount of Buffer A/DMSO as the assayed sample, but contained no hydroxamic acid (or salt thereof).

The assays from which the $IC_{50}$ determinations were made were performed as follows. The MMPs were activated with either trypsin or APMA (4-aminophenylmercuric acetate, Sigma Chemical, St. Louis, Mo.). The assayed hydroxamic acid samples were incubated in Microfluor™ White Plates (Dynatech, Chantilly, Va.) and analyzed on a Perkin Elmer L550 plate reader (Norwalk, Conn.). The excitation wavelength was 328 nm, and the emission wavelength—415 nm. All samples (assayed hydroxamic acids and controls) were incubated in separate plates at room temperature in the presence of 4 μM of MMP substrate (I). As stated in the previous paragraph, samples containing varying concentrations of the same assayed hydroxamic acid were prepared. Inhibition was measured as a reduction in fluorescent intensity as a function of MMP inhibitor concentration.

The assays from which the $K_i$ determinations were made were performed as follows. The assayed hydroxamic acid samples were incubated in separate wells of untreated white polystyrene plates (Nunc Nalgene International, Rochester, N.Y.), and analyzed on a Tecan SpectraFlour Plus plate reader. The excitation wavelength was 330 nm, and the emission wavelength—420 nm. All samples (assayed hydroxamic acids and controls) were incubated in separate plate wells at room temperature for 1 hr in the presence of 4 μM of MMP substrate (II). In the absence of MMP inhibitory activity, substrate II was cleaved at the Gly-Leu bond resulting in an increase of relative fluorescence. Inhibition was observed as a reduced rate of this increase in relative fluorescence. The various hydroxamic acids were analyzed using a single low enzyme concentration with a single substrate concentration fixed at or below the $K_m$. This protocol is a modification of method by Knight et al., *FEBS Lett.*, 296(3), 263–266 (1992). Apparent inhibitory constants were determined by non-linear regression of reaction velocity as a function of inhibitor and enzyme concentration using Morrison's equation, as described by Kuzmic, Anal. Biochem. 286, 45–50 (2000). Modifications were made in the non-linear regression method to allow a common control reaction rate and effective enzyme concentration to be shared between all dose-response relationships on a given assay plate. Since the substrate concentration was chosen to be at or below the $K_m$, the apparent $K_i$'s from this analysis were reported as $K_i$'s without correction for the influence of substrate.

The above protocols were used to determine $IC_{50}$ constants and $K_i$ values for the compounds in Examples 1–27 above. The results are shown in Table 2. All values in Table 2 are given in nM units. The $IC_{50}$ measurements are in parenthesis.

TABLE 2

| Ex. # | Compound | MMP-1 $K_i$ ($IC_{50}$) | MMP-2 $K_i$ ($IC_{50}$) | MMP-9 $K_i$ ($IC_{50}$) | MMP-13 $K_i$ ($IC_{50}$) | MMP-14 $K_i$ ($IC_{50}$) |
|---|---|---|---|---|---|---|
| 28 | Example 1 | >10000 | 1.52 | 0.696 | 1.82 | 4290 |
| 29 | Example 2 | >10000 | 0.74 | 1.28 | 0.77 | 1945 |
| 30 | Example 3 | 7530 | 0.59 | 0.93 | 1.46 | 1260 |
| 31 | Example 4 | 1470 | 0.104 | 0.739 | 0.216 | 954 |
| 32 | Example 5 | >10000 | 0.62 | 0.108 | 0.522 | 1545.72 |
|  |  | (>10000) | (<0.1) | (<0.1) | (<0.1) | (4546) |
| 33 | Example 6 | >10000 | 0.501 | 0.287 | 0.27 | 2296 |
|  |  | (>10000) | (0.2) | (0.2) | (0.1) | (>10000) |
| 34 | Example 7 | >10000 | 0.497 | 7.35 | 0.17 | 4329.20 |
| 35 | Example 8 | 748 | 1.98 | 1.65 | 0.11 | 468 |
| 36 | Example 9 | >10000 | 0.223 | 2.76 | 0.05 | 5910.13 |
| 37 | Example 10 | >10000 | 0.52 | 0.97 | 3.88 | 4336 |
|  |  | (>10000) | (0.2) | (0.3) | (1.3) | (5824.0) |
| 38 | Example 11 | >10000 | 0.71 | 2.67 | 0.67 | 3603 |
|  |  | (>10000) | (0.2) | (2.3) | (0.8) | (7122) |
| 39 | Example 12 | >10000 | 0.18 | 1.0 | 0.77 | 1710 |
| 40 | Example 13 | >10000 | 0.549 | 0.712 | 0.61 | 3520 |
| 41 | Example 14 | >10000 | 3.84 | 20 | 2.67 | 9170 |
| 42 | Example 15 | >10000 | 0.89 | 0.13 | 0.23 | 2960 |
|  |  | (>10000) | (0.1) | (0.3) | (0.1) | (6169) |
| 43 | Example 16 | >10000 | 1.24 | 0.47 | 0.34 | 2930 |
| 44 | Example 17 | >10000 | 0.418 | 1.01 | 0.328 | 7970 |
| 45 | Example 18 | 7350 | 0.565 | 0.398 | 0.444 | 1770 |
| 46 | Example 19 | >10000 | 2.06 | 0.50 | 5.47 | 2190 |
| 47 | Example 20 | >10000 | 0.83 | 3.86 | 0.15 | 2670 |
| 48 | Example 21 | >10000 | 3.82 | 8.18 | 6.17 | 6910 |
| 49 | Example 22 | >10000 | 3.19 | 3.2 | 2.78 | 9320 |
| 50 | Example 23 | >10000 | 8.25 | 2.67 | 4.17 | >10000 |
| 51 | Example 24 | >10000 | 0.91 | 0.12 | 0.54 | 2900 |
| 52 | Example 25 | >10000 | 1.18 | 06 | 0.97 | 5380 |
| 53 | Example 26 | 2970 | 0.78 | 0.33 | 0.51 | 657 |
| 54 | Example 27 | 4780 | 0.59 | 0.54 | 0.50 | 6200 |

Examples 55–420

Additional piperazinyl- and piperidinyl-sulfonylmethyl hydroxamic acid compounds (and salts thereof) can be prepared by one skilled in the art using methods similar to those described in Examples 1–27 alone or in combination with techniques well known in the art. Such compounds include, for example, the compounds summarized in the following Table 3. Table 3 also summarizes in vitro MMP inhibition results obtained by Applicants with the listed hydroxamic acids. As with Table 2, all in vitro $K_i$ and $IC_{50}$ results in Table 3 are given in nM units. The $K_i$ measurements are in parenthesis.

TABLE 3

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 55 | 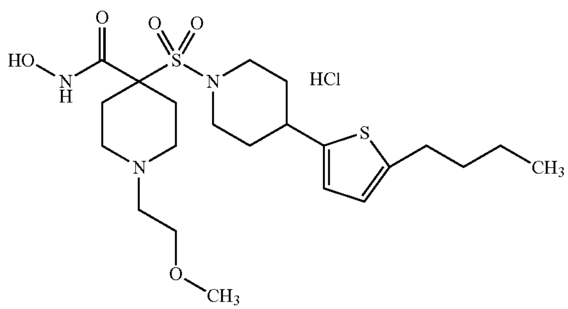 | 488.2247 | 488.2257 | >10000 | 2.2 | 0.35 | 3.94 | 2450 |
| 56 | 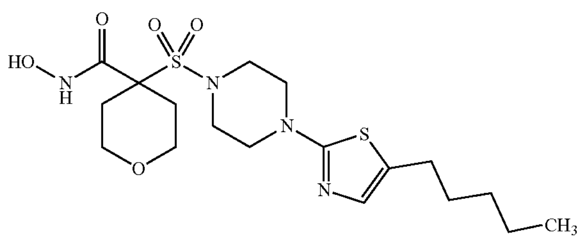 | 447.1730 | 447.1755 | >10000 | 1.02 | 3.49 | 1.74 | 795 |
| 57 | 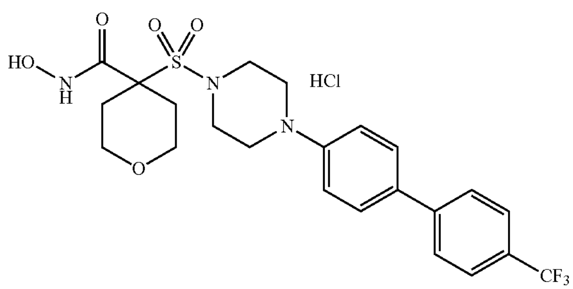 | 514 | 514 | | | | | |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 58 | 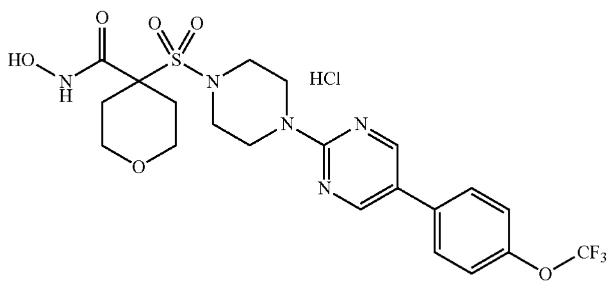 | 532.1478 | 532.1495 | | | | | |
| 59 | 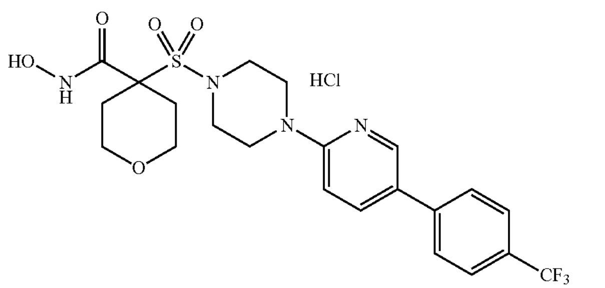 | 515.1576 | 515.1587 | | | | | |
| 60 | 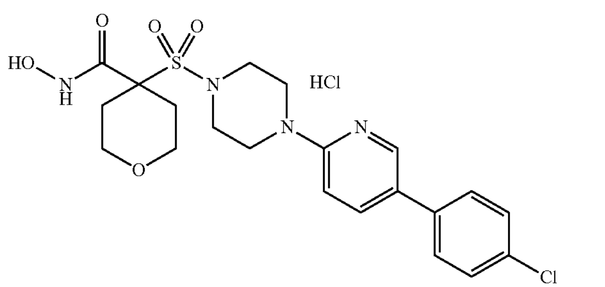 | 481.1312 | 481.1335 | 555 | 0.54 | 7.05 | 0.32 | 328 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 61 | 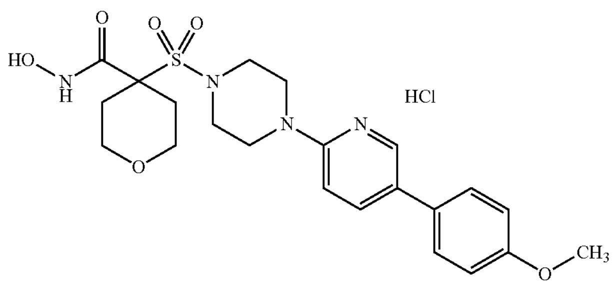 | 477.1808 | 477.1806 | 493 | 0.39 | 12.3 | 0.16 | 199 |
| 62 | 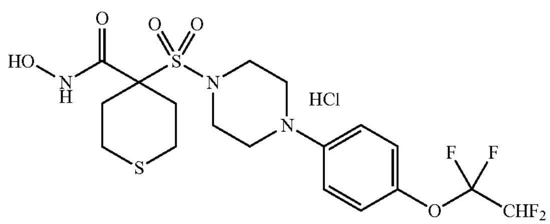 | 502.1088 | 502.1075 | 2310 | 0.22 | 1.5 | 0.50 | 1150 |
| 63 | 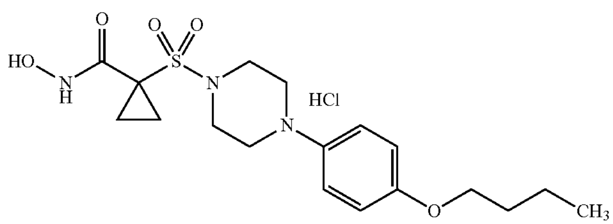 | 398.1744 | 398.1771 | >10000 | 6.77 | 7.71 | 3.16 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 64 | 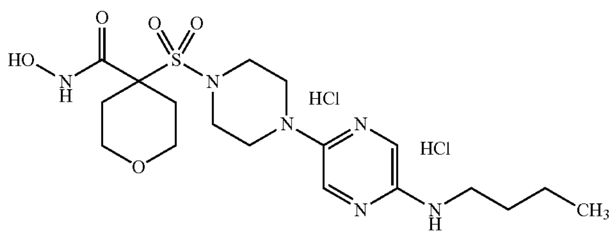 | 435.1697 | 435.1686 | >10000 | 7.44 | 2.75 | 1.31 | 6360 |
| 65 | 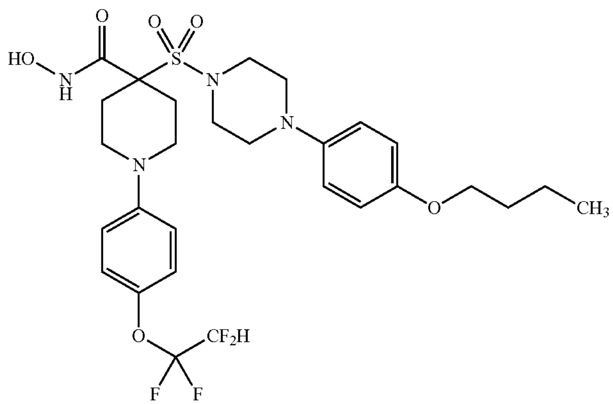 | 633.2375 | 633.2372 | >10000 | 23.6 | 128 | 32.7 | >10000 |
| 66 | 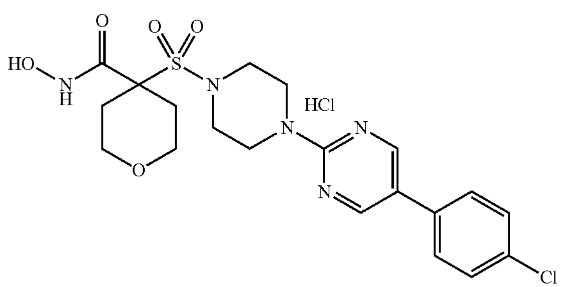 | 482.1265 | 482.1281 | 967 | 2.52 | 0.52 | 0.25 | 1120 |

TABLE 3-continued
Additional Examples of
Piperazinyl- or Piperidinylmethyl-Sulfonylmethyl Hydroxamic acid Compounds
| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 67 | 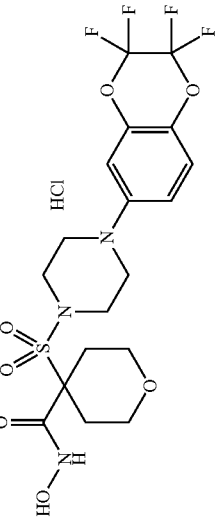 | 500.1109 | 500.113 | >10000 | 50.5 | 1380 | 156 | >10000 |
| 68 | 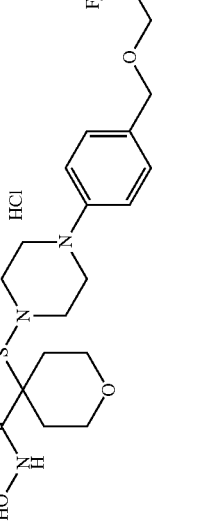 | 614.1566 | 614.1571 | >10000 | 4.69 | 208 | 1.85 | >10000 |
| 69 | 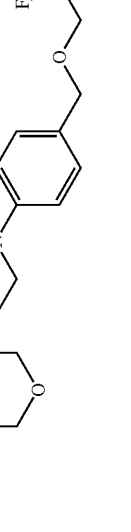 | 582.1503 | 582.1527 | >10000 | 5.44 | 202 | 2.11 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 70 | 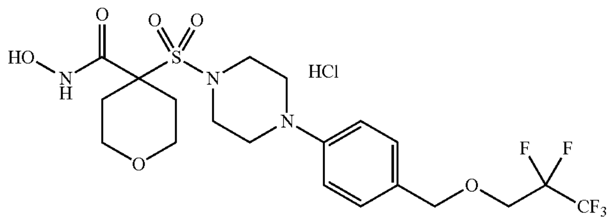 | 532.1535 | 532.1519 | >10000 | 2.57 | 49.7 | 0.61 | >10000 |
| 71 | 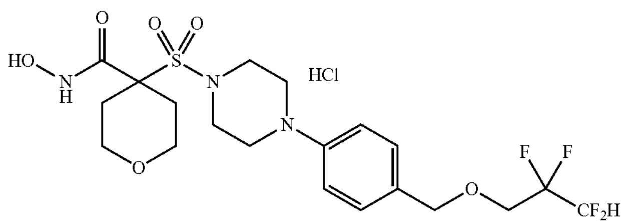 | 514.1629 | 514.1645 | >10000 | 2.35 | 13 | 0.79 | |
| 72 | 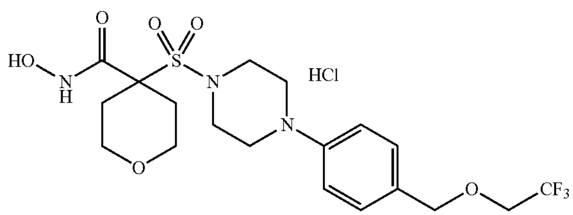 | 482 | 482 | >10000 | 2.44 | 2.86 | 0.85 | 7570 |
| 73 | 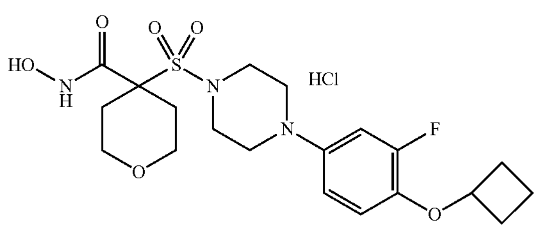 | 458 | 458 | >10000 | 2.2 | 7.97 | 9.78 | 2360 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 74 | 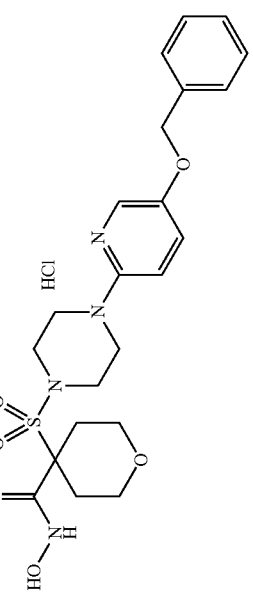 | 477.1808 | 477.1806 | 3210 | 0.5 | 4.8 | 0.06 | 454 |
| 75 | 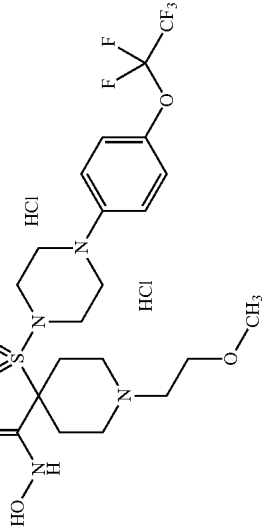 | 543.1895 | 543.1922 | 3360 | 0.10 | 0.44 | 0.14 | 1160 |
| 76 | 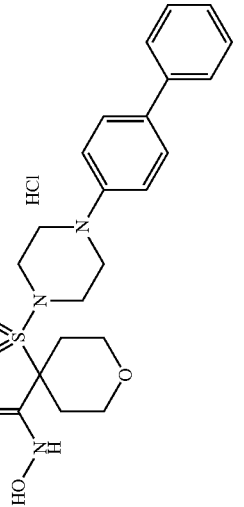 | 446 | 446 | 1340 | 0.19 | 0.50 | 0.40 | 358 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 77 | 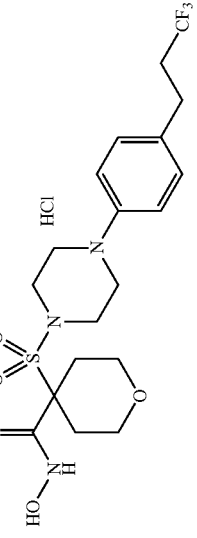 | 466.1618 | 466.1599 | >10000 | 0.38 | 0.80 | 0.84 | 1180 |
| 78 | 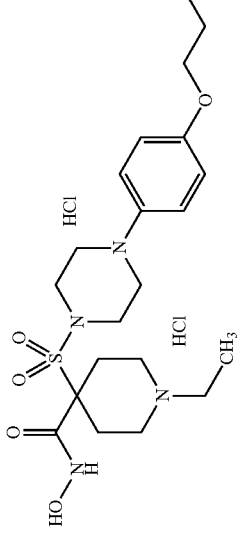 | 523.2197 | 523.2202 | >10000 | 2.56 | 22.8 | 0.43 | >10000 |
| 79 | 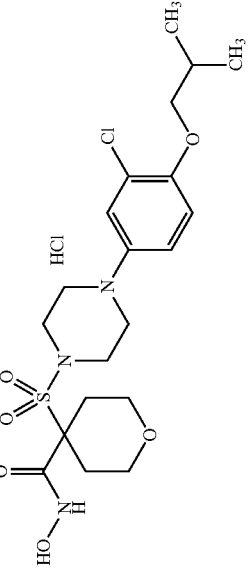 | 476 | 476 | >10000 | 10.1 | 41.5 | 6.62 | 8815 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 80 | 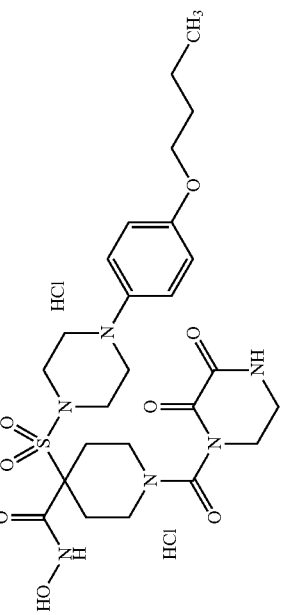 | 609.2701 | 609.2717 | 8270 | 0.52 | 1.11 | 0.22 | 1790 |
| 81 | 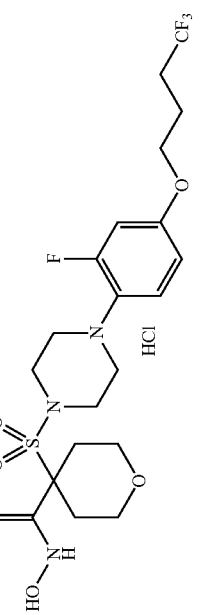 | 514 | 514 | >10000 | 0.407 | 29.2 | 0.261 | 2430 |
| 82 | 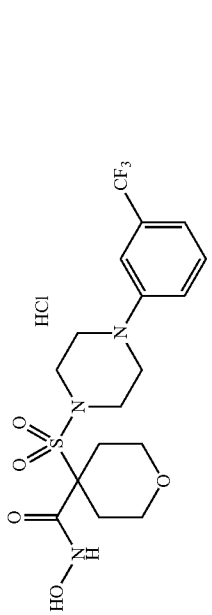 | 438 | 438 | >10000 | 8.74 | 249 | 7.49 | 1600 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 83 | 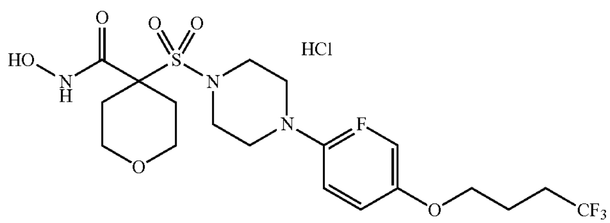 | 497.1682 | 497.1703 | 2850 | 0.251 | 4.21 | 0.048 | 981 |
| 84 | 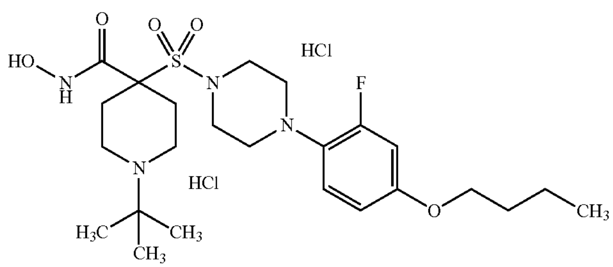 | 515 | 515 | >10000 | 7.53 | 17.9 | 1.91 | >10000 |
| 85 | 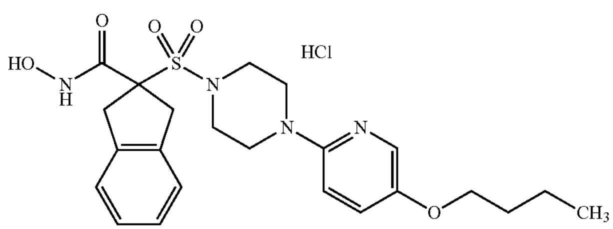 | 475.2015 | 475.2032 | 4770 | 0.64 | 1.17 | 0.25 | 1510 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 86 | 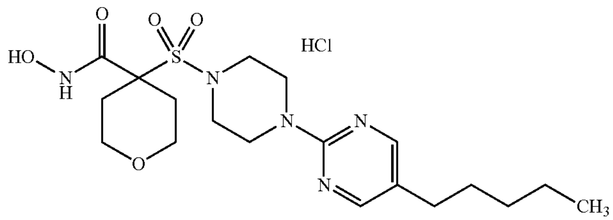 | 422.2124 | 422.2139 | >10000 | 5.51 | 1.82 | 1.20 | 4120 |
| 87 | 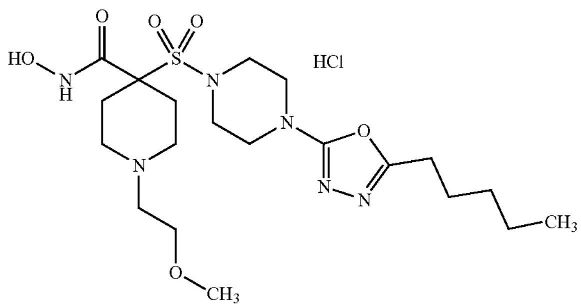 | 489.2490 | 489.2463 | >10000 | 40.7 | 25.9 | 29.8 | >10000 |
| 88 | 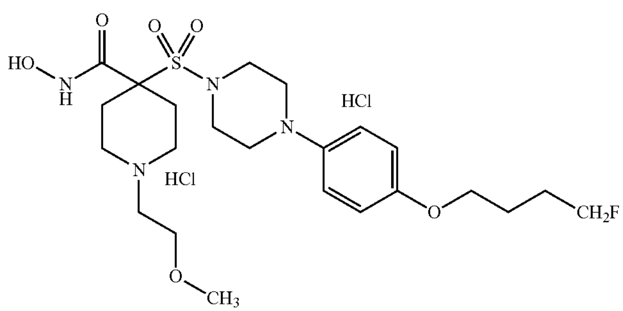 | 517.2491 | 517.2460 | >10000 | 0.54 | 2.18 | 0.18 | 2765 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 89 | 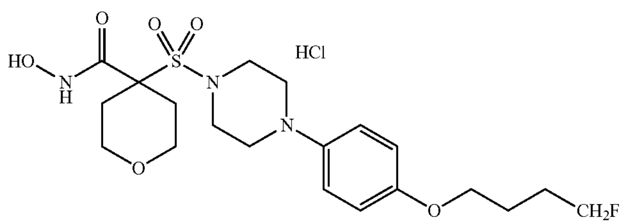 | 460.1912 | 490.1895 | >10000 | 0.49 | 2.23 | 0.17 | 2800 |
| 90 | 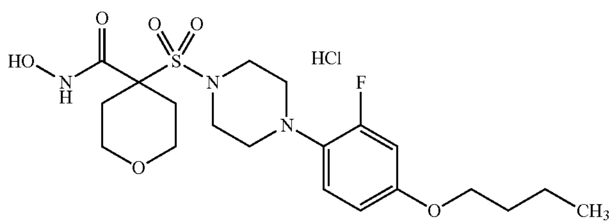 | 460 | 460 | >10000 | 1.68 | 2.15 | 0.39 | 4550 |
| 91 | 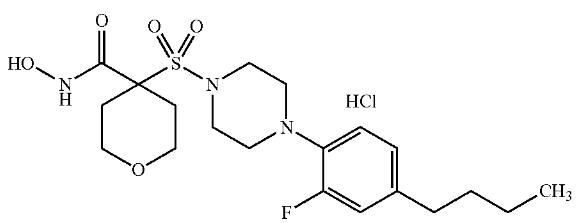 | 444 | 444 | 5110 | 1.22 | 0.452 | 1.64 | 1740 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 92 | 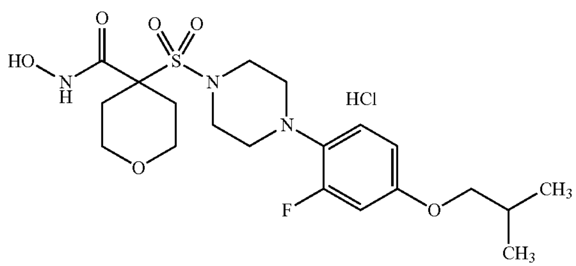 | 460 | 460 | >10000 | 1.81 | 4.55 | 0.49 | 6320 |
| 93 | 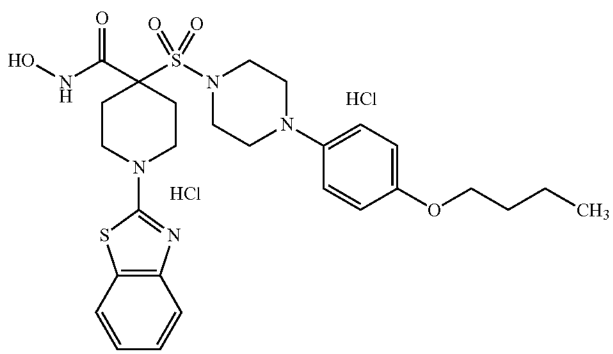 | 574.2152 | 574.2179 | >10000 | 6.92 | 60.1 | 26 | 9860 |
| 94 | 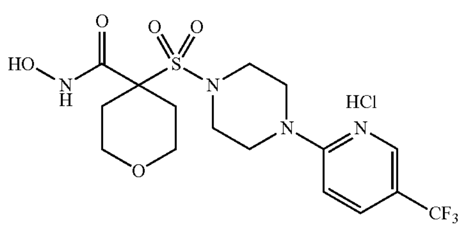 | 439.1258 | 439.1216 | 767 | 0.66 | 14.3 | 0.82 | 221 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 95 | 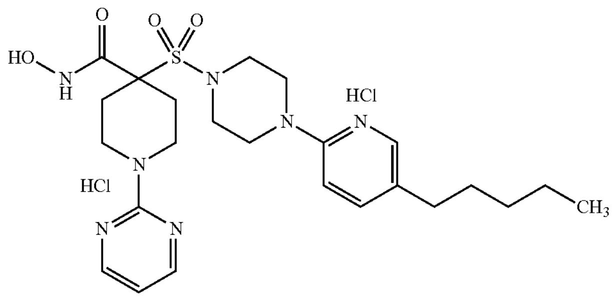 | 518.2549 | 518.2567 | >10000 | 0.64 | 0.99 | 0.68 | 597 |
| 96 | 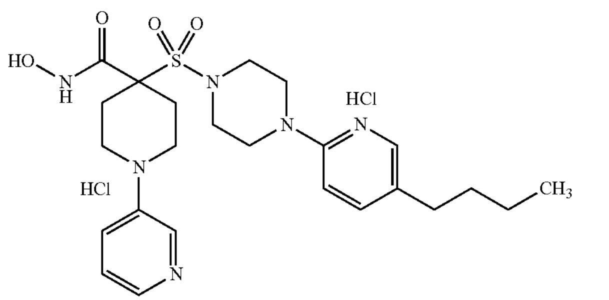 | 503.2441 | 503.2444 | >10000 | 0.20 | 0.21 | 0.44 | 816 |
| 97 | 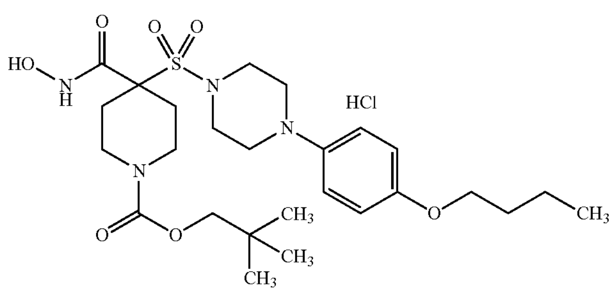 | 555.2847 | 555.2819 | >10000 | 6.69 | 21.9 | 21.9 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 98 | 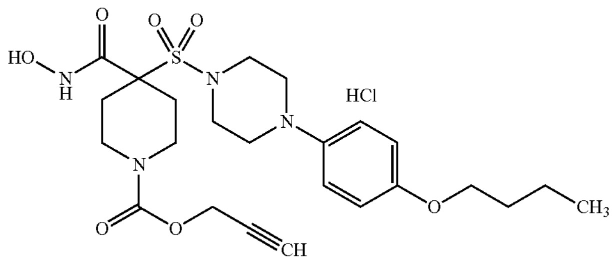 | 523.2221 | 523.2216 | >10000 | 0.5 | 1.24 | 0.38 | 1620 |
| 99 | 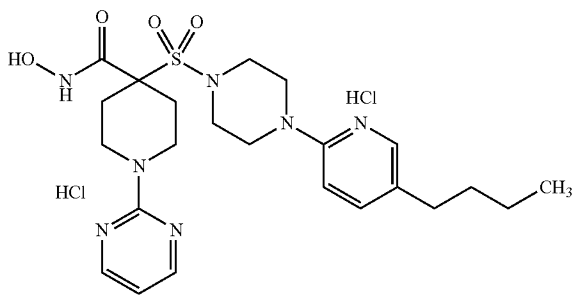 | 504.2393 | 504.2397 | 8300 | 0.17 | 0.16 | 0.30 | 225 |
| 100 | 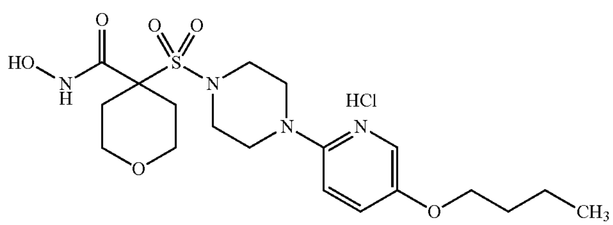 | 443.1964 | 443.1972 | 1600 | 0.13 | 0.30 | 0.06 | 411 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 101 | 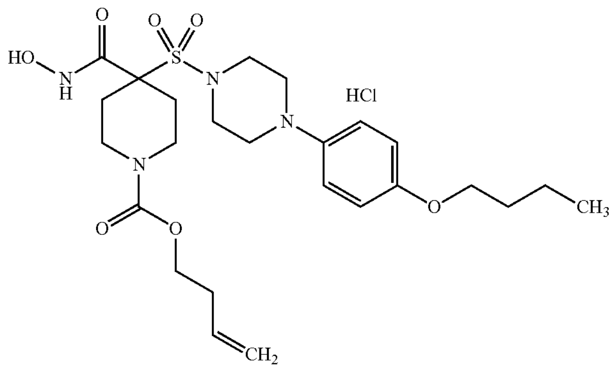 | 539.2534 | 539.2567 | >10000 | 1.64 | 3.8 | 0.92 | 4330 |
| 102 | 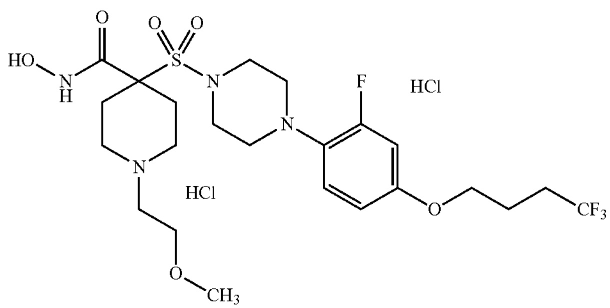 | 571 | 571 | >10000 | 1.25 | 18.1 | 0.19 | 7130 |
| 103 | 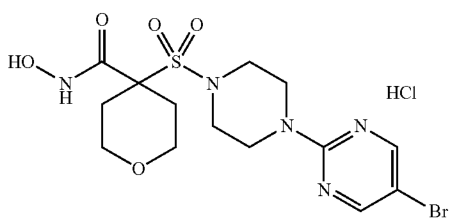 | 450.0447 | 450.0459 | 686 | 3.44 | 10.5 | 3.48 | 227 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 104 | 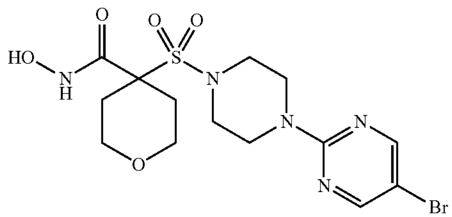 | 450.0447 | 450.0461 | 835 | 4.73 | 11.9 | 3.55 | 305 |
| 105 | 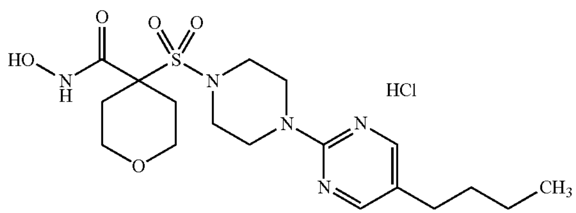 | 428.1968 | 428.1970 | 6620 | 2.94 | 0.74 | 1.88 | 1660 |
| 106 | 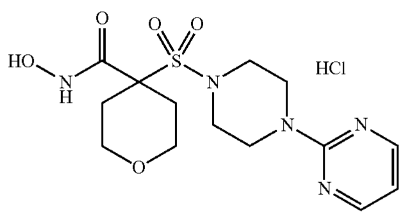 | 372.1362 | 372.1351 | 1470 | 134 | 235 | 27.2 | 7510 |
| 107 | 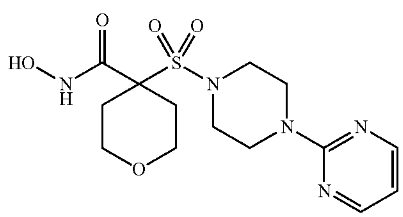 | 372.1342 | 372.1357 | 1190 | 115 | 153 | 22.4 | 6000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 108 | 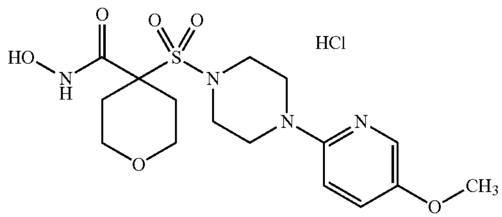 | 401.1495 | 401.1496 | >10000 | 431 | 401 | 478 | >10000 |
| 109 | 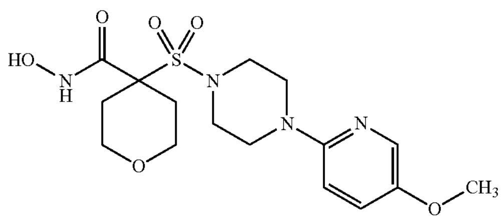 | 401.1495 | 401.1514 | >10000 | 477 | 447 | 472 | >10000 |
| 110 | 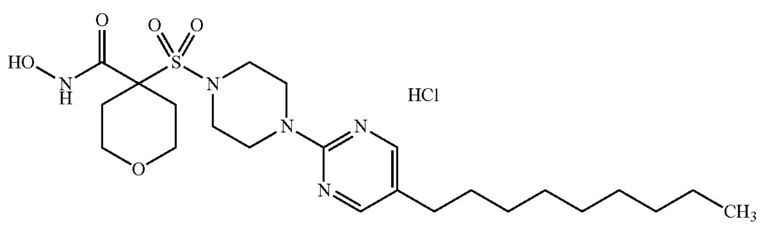 | 498.2750 | 498.2763 | >10000 | 61.7 | 40.6 | 3.23 | >10000 |
| 111 | 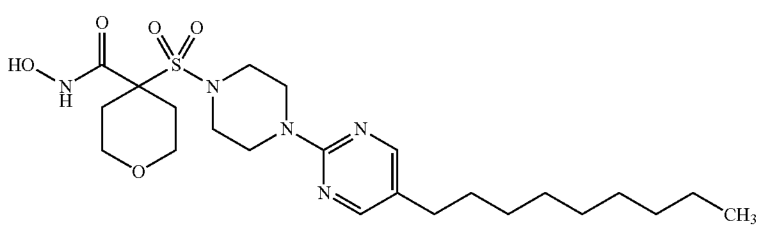 | 498.2750 | 498.2755 | >10000 | 49.6 | 30.6 | 2.58 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 112 | 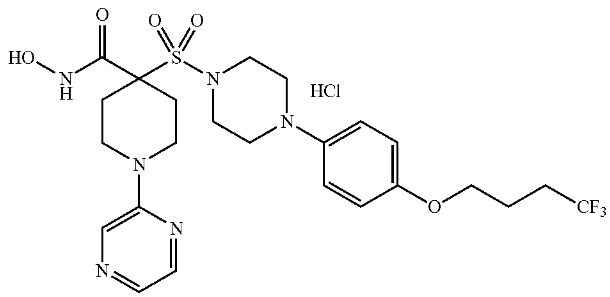 | 573.2102 | 573.2117 | >10000 | 0.69 | 15.4 | 0.27 | 1170 |
| 113 | 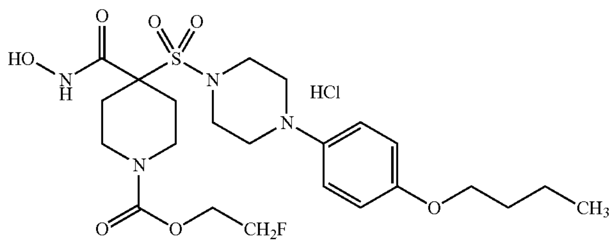 | 531.2283 | 531.2253 | >10000 | 0.4 | 1.01 | 0.25 | 2330 |
| 114 | 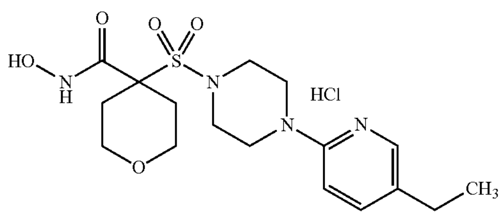 | | | 1610 | 0.367 | 2.64 | 0.748 | 97 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 115 | 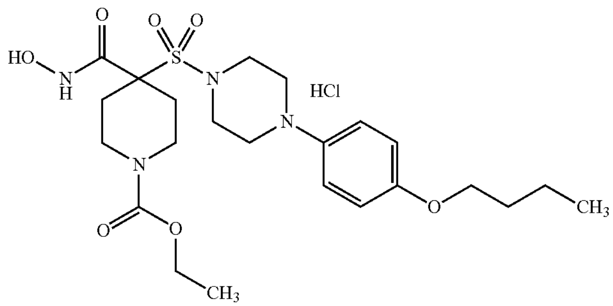 | 567.2095 | 567.2107 | >10000 | 1.48 | 4.97 | 1.17 | >10000 |
| 116 | 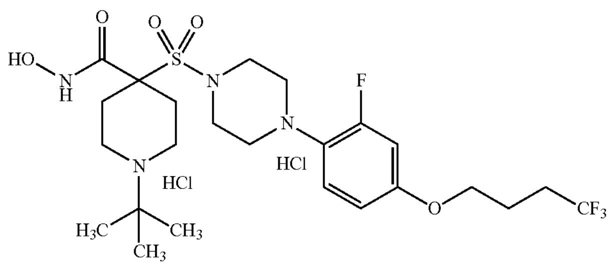 | 569 | 569 | >10000 | 4.31 | 49.5 | 1.21 | 8030 |
| 117 | 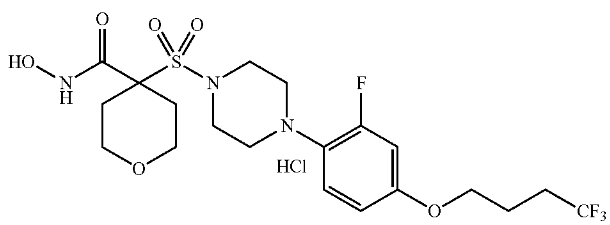 | 513 (MH) | 513 (MH) | >10000 | 2.58 | 27.7 | 0.40 | 5690 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 118 | 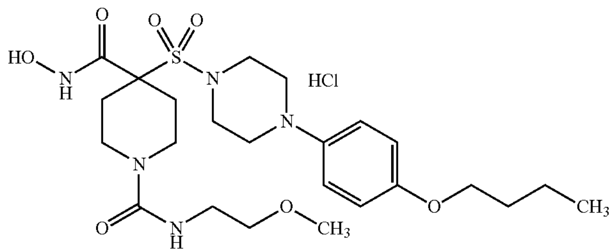 | 542.2643 | 542.2658 | >10000 | 0.75 | 1.5 | 0.43 | 2600 |
| 119 | 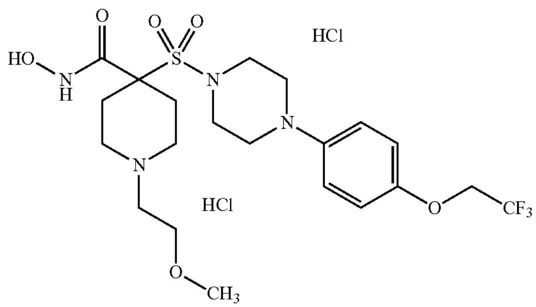 | 525.1989 | 525.1971 | >10000 | 1.19 | 1.35 | 0.79 | 4380 |
| 120 | 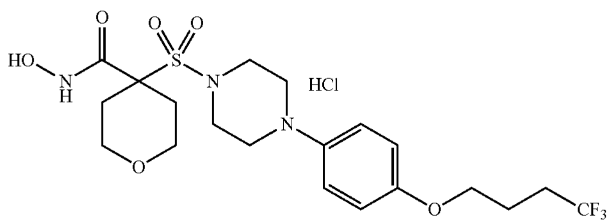 | 511 | 511 | 485 | 0.019 | 0.233 | 0.029 | 18.4 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 121 | 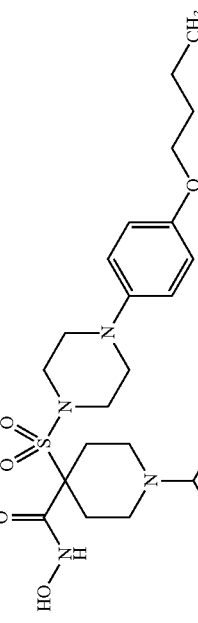 | 533.2428 | 533.2406 | >10000 | 2.15 | 3.6 | 0.68 | >10000 |
| 122 | 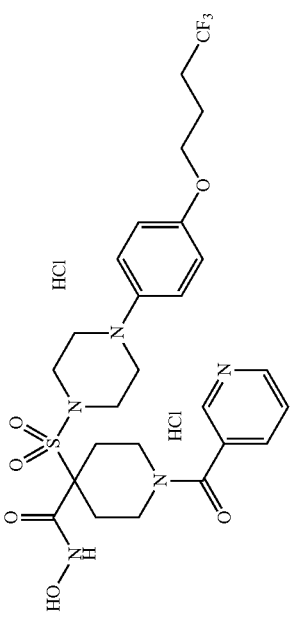 | 600.2098 | 600.2087 | >10000 | 0.34 | 0.01 | 0.03 | 3090 |
| 123 | 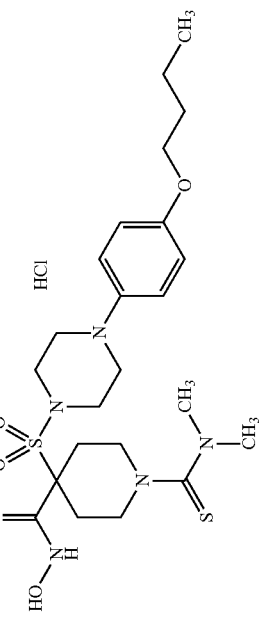 | 528.2309 | 528.2298 | >10000 | 1.28 | 2.72 | 0.74 | 5650 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 124 | 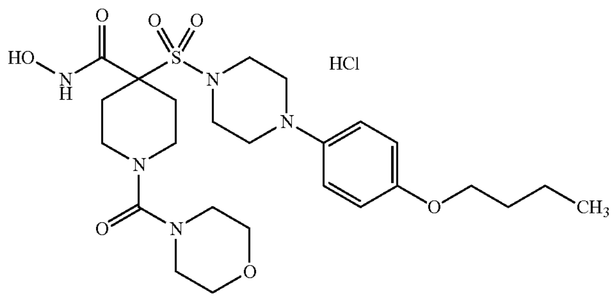 | 554.2648 | 554.2650 | >10000 | 0.193 | 0.429 | 0.121 | >10000 |
| 125 | 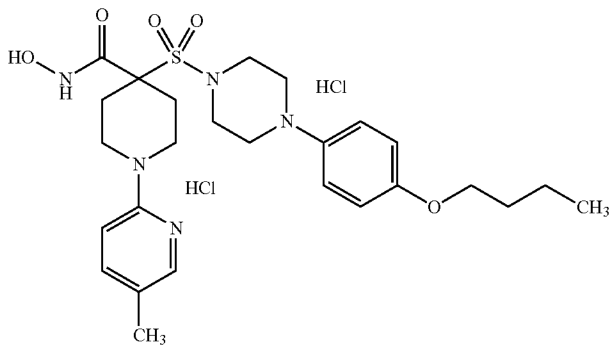 | 532.2594 | 532.2576 | >10000 | 1.8 | 7.2 | 1.67 | 2760 |
| 126 | 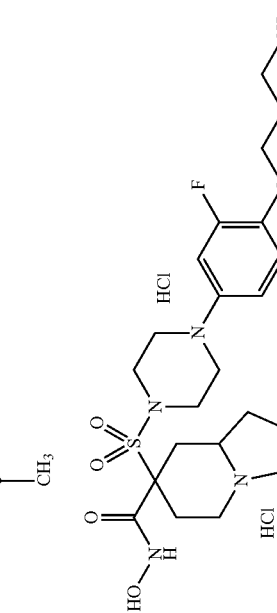 | | | >10000 | 8.24 | 19 | 7.06 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 127 | 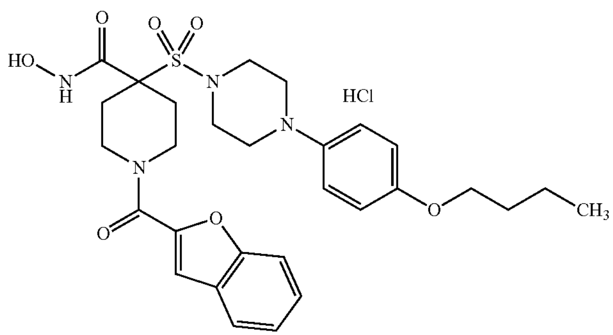 | 585.2383 | 585.2356 | >10000 | 6.02 | 24 | 6.18 | >10000 |
| 128 | 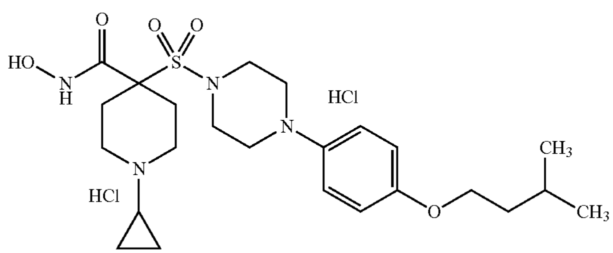 | 495.2641 | 495.2601 | >10000 | 0.785 | 1.92 | 0.211 | 5380 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 129 | 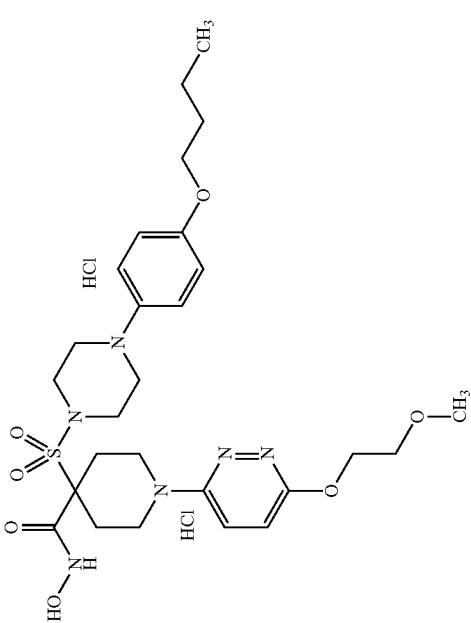 | 593.2758 | 593.2725 | >10000 | 0.508 | 1.2 | 0.302 | 1300 |
| 130 | 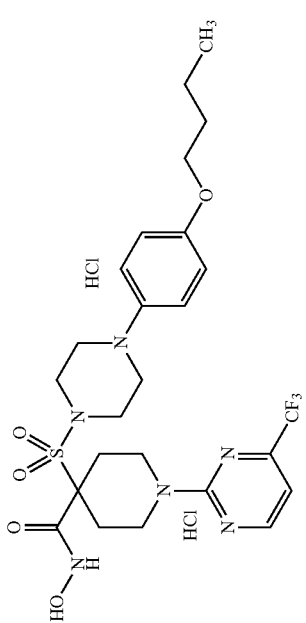 | 587.2264 | 587.2264 | >10000 | 5.23 | 23.2 | | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 131 | 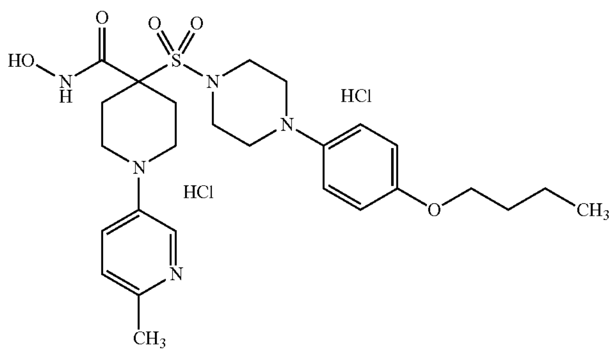 | 532.2594 | 532.2600 | >10000 | 1.39 | 3.03 | 0.621 | 3660 |
| 132 | 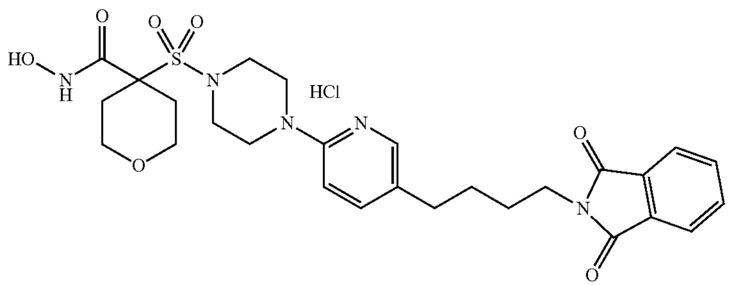 | 572.2179 | 572.2211 | 66.1 | 1.2 | 28.3 | 0.395 | 158 |
| 133 | 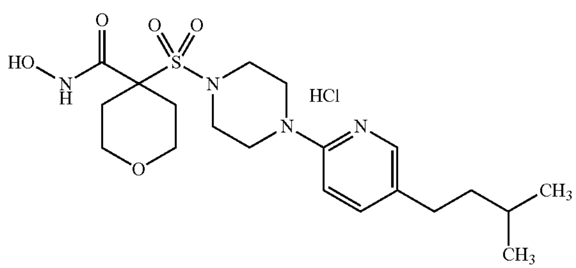 | 441.2172 | 441.2196 | >10000 | 0.251 | 0.52 | 0.227 | 2120 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 134 | 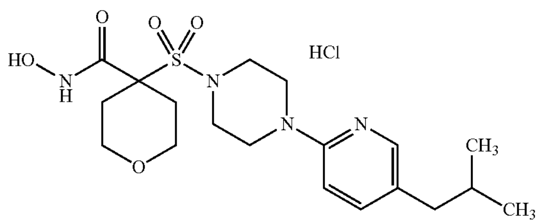 | 427.2015 | 427.2042 | 9460 | 0.926 | 9.58 | 1.68 | 1980 |
| 135 | 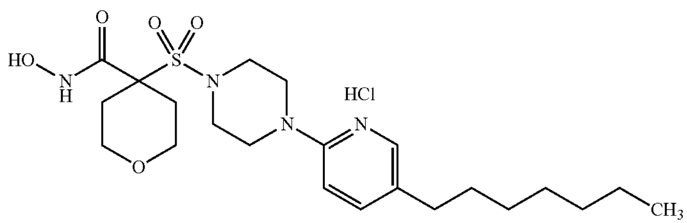 | 455.2323 | 455.2353 | >10000 | 0.169 | 0.657 | 0.134 | 1430 |
| 136 | 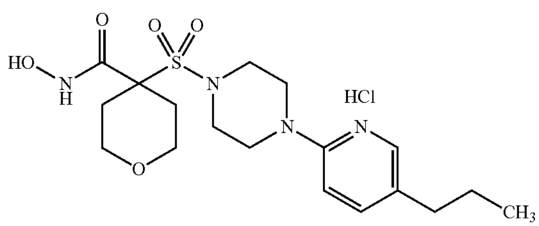 | 413.1859 | 413.1845 | 2380 | 0.142 | 0.196 | 0.423 | 159 |
| 137 | 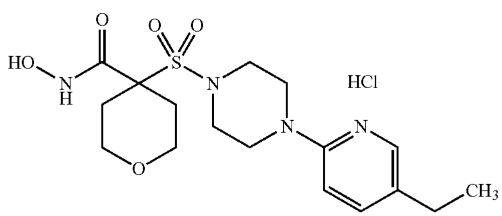 | 399.1702 | 399.174 | 1610 | 0.37 | 2.64 | 0.75 | 97.0 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 138 | 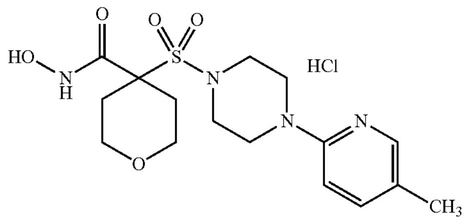 | 385.1546 | 385.1513 | 1380 | 0.469 | 5.09 | 1.15 | 66.6 |
| 139 | 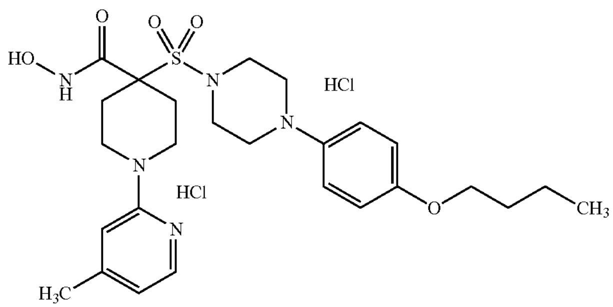 | 532.2594 | 532.2601 | 7240 | 2.18 | 7.45 | 2.03 | 1260 |
| 140 | 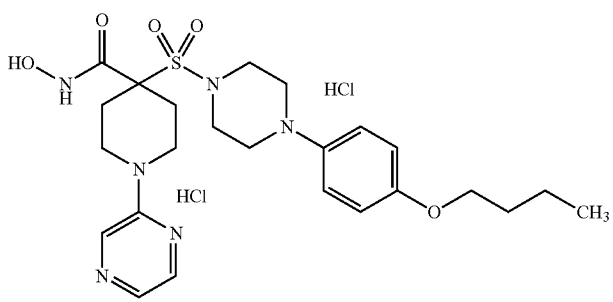 | 519.2390 | 519.2385 | >10000 | 0.672 | 1.76 | 0.446 | 945 |

TABLE 3-continued

Additional Examples of
Piperazinyl- or Piperidinylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 141 | 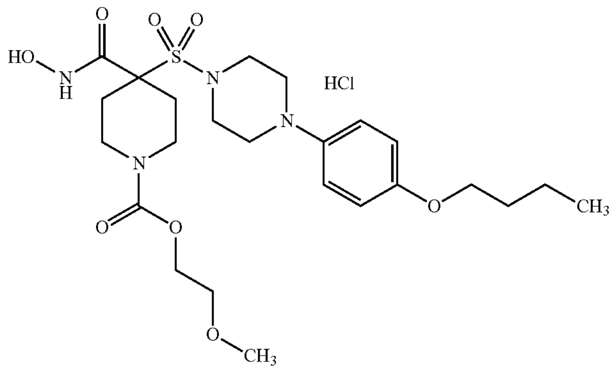 | 543.2488 | 543.2474 | 8900 | 0.266 | 5.33 | 0.151 | 1140 |
| 142 | 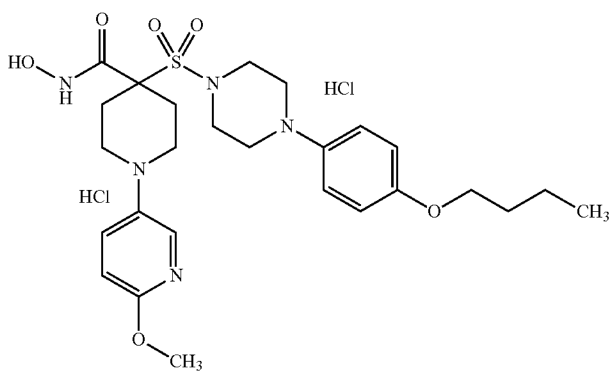 | 548.2537 | 548.2525 | >10000 | 0.978 | 2.15 | 0.505 | 2630 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 143 | 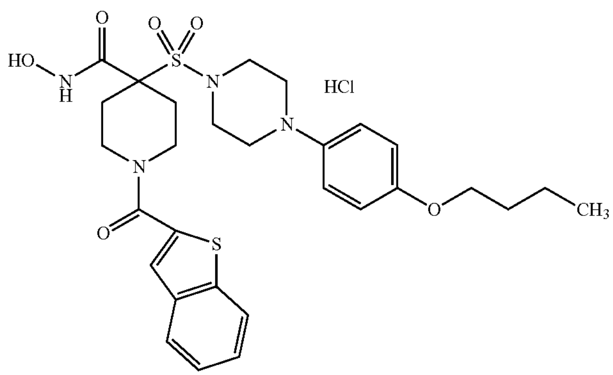 | 601.2149 | 601.2161 | >10000 | 8.97 | 29 | 7.05 | >10000 |
| 144 | 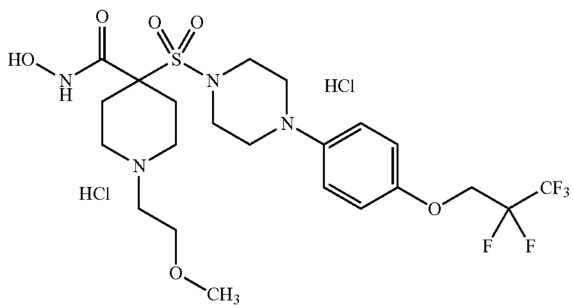 | 575.1957 | 575.1950 | >10000 | 0.69 | 2.31 | 0.306 | >10000 |
| 145 | 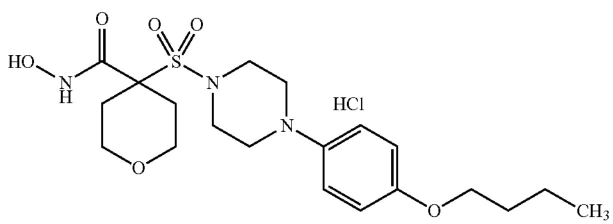 | 442.2012 | 442.2016 | >10000 | 0.695 | 1.18 | 0.347 | 2350 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 146 | 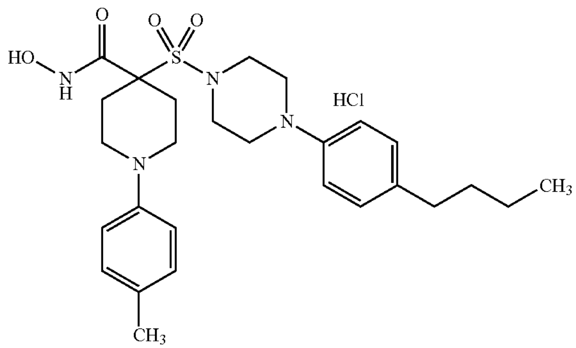 | 515.2692 | 515.2690 | >10000 | 6.41 | 2.29 | 9.38 | 8660 |
| 147 | 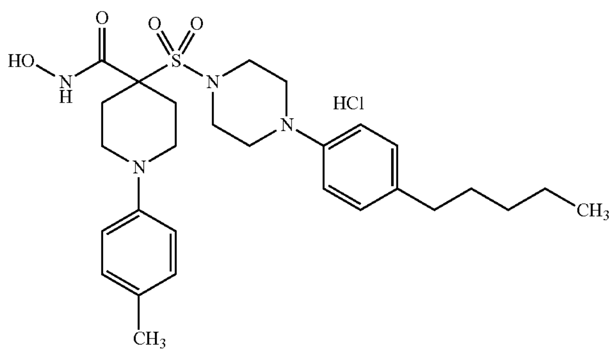 | 529.2849 | 529.2851 | >10000 | 20.5 | 13.7 | 7.35 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 148 | 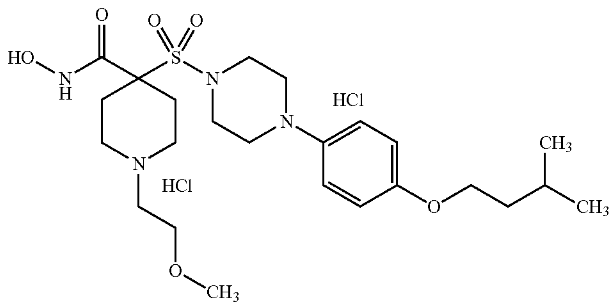 | 513.2741 | 513.2734 | >10000 | 1.19 | 2.35 | 0.24 | 6980 |
| 149 | 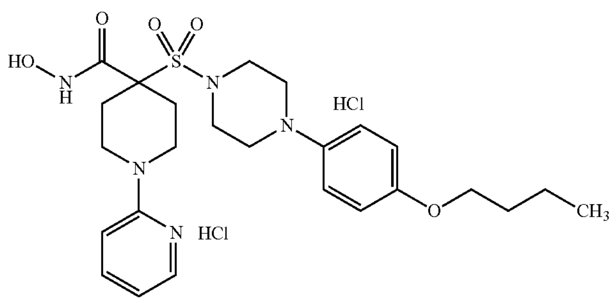 | 518.2437 | 518.2447 | >10000 | 1.89 | 5.87 | 1.31 | 2660 |

TABLE 3-continued
Additional Examples of
Piperazinyl- or Piperidinylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 150 | 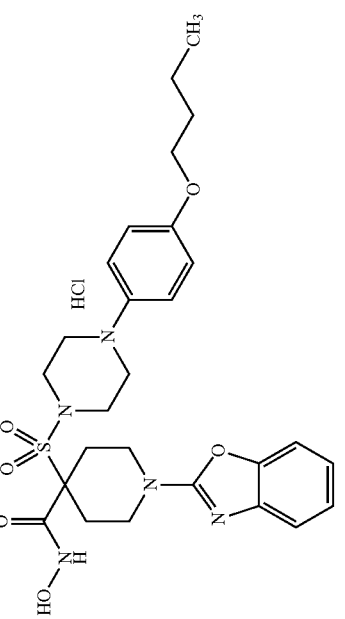 | 558.2386 | 558.2391 | >10000 | 4.25 | 31.4 | 11.2 | 8650 |
| 151 | 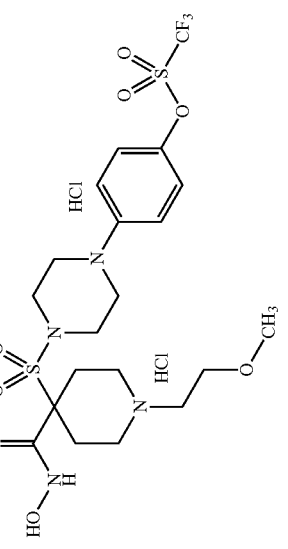 | 593 | 593 | >10000 | 0.305 | 11.5 | 0.602 | 2630 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 152 | 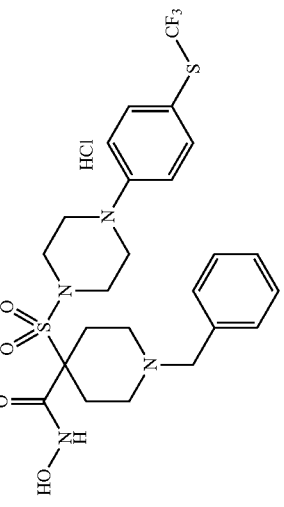 | 559.1655 | 559.1673 | >10000 | 0.871 | 90 | 5.74 | 2240 |
| 153 | 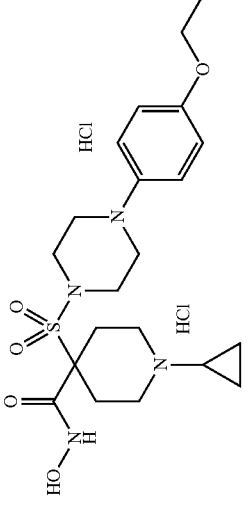 | 535.2197 | 535.2206 | >10000 | 0.502 | 6.1 | 0.099 | 6770 |
| 154 | 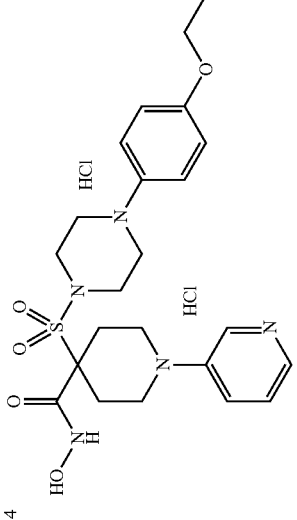 | 518.2437 | 518.2447 | >10000 | 1.07 | 2.15 | 0.561 | 3600 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 155 | 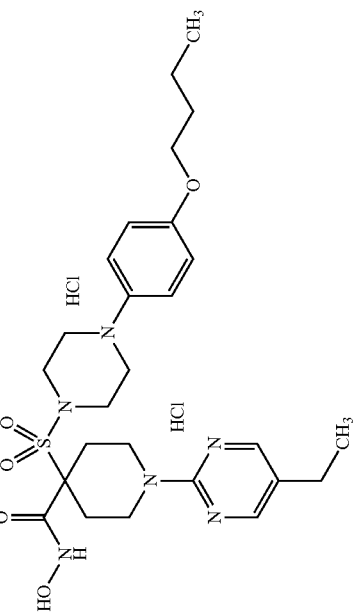 | 547.2703 | 547.2691 | >10000 | 1.83 | 9.86 | 3.36 | 5350 |
| 156 | 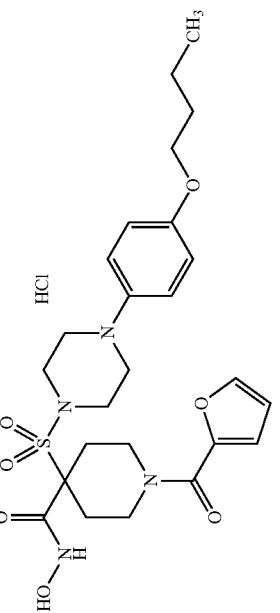 | 535.2221 | 535.2206 | >10000 | 0.75 | 1.2 | 0.31 | 2430 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 157 | HCl salt, piperazinyl-phenyl-O-butyl; piperidine-thiazole·HCl | 524.1996 | 524.2006 | >10000 | 1.47 | 4.28 | 1.02 | 2760 |
| 158 | HCl salt, piperazinyl-phenyl-O-butyl; piperidine-C(=NH)NH$_2$·HCl | 483.2384 | 483.2386 | 9340 | 0.80 | 2.09 | 0.70 | 2050 |
| 159 | 0.5 HCl salt, piperazinyl-phenyl-O-butyl; piperidine-pyrimidine | 519.2390 | 519.2399 | >10000 | 0.702 | 1.93 | 0.587 | 2060 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 160 | 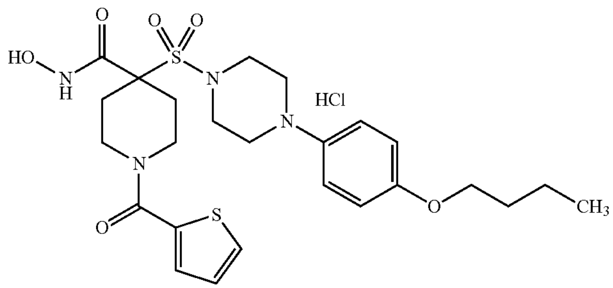 | 551.1993 | 551.1986 | >10000 | 0.599 | 1.79 | 0.417 | 2760 |
| 161 | 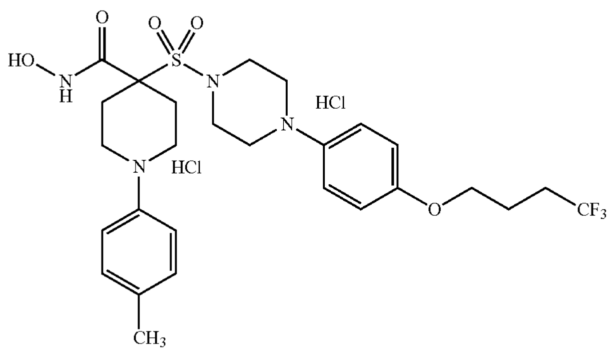 | 585.2353 | 585.2362 | >10000 | 8.26 | 134 | 2.91 | >10000 |
| 162 | 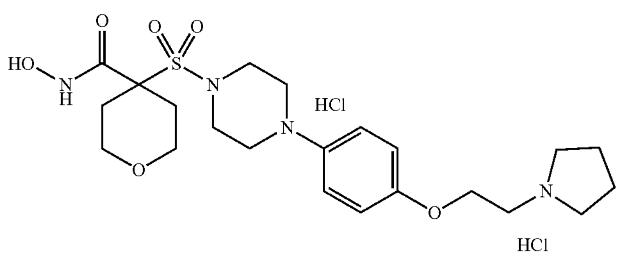 | 483.2272 | 483.2250 | >10000 | 18.4 | 402 | 7.71 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 163 | 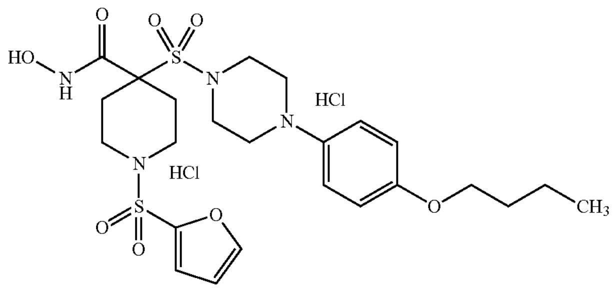 | 587.1662 | 587.1667 | >10000 | 6.3 | 16.4 | 4.01 | 9800 |
| 164 | 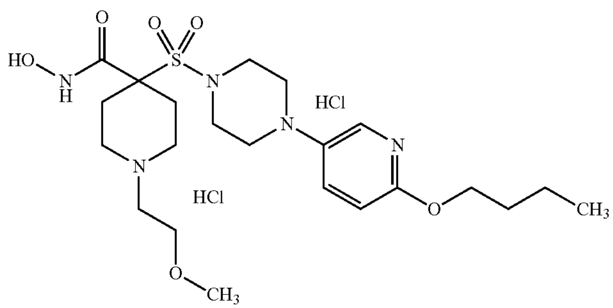 | 500.2543 | 500.2552 | >10000 | 28.6 | 7.53 | 22 | 8880 |
| 165 | 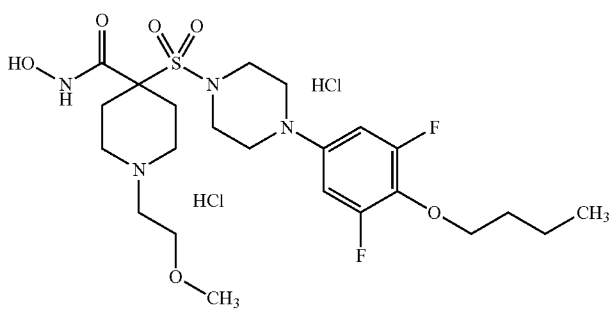 | 535 | 535 | >10000 | 0.49 | 14.7 | 1.03 | 3650 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 166 | 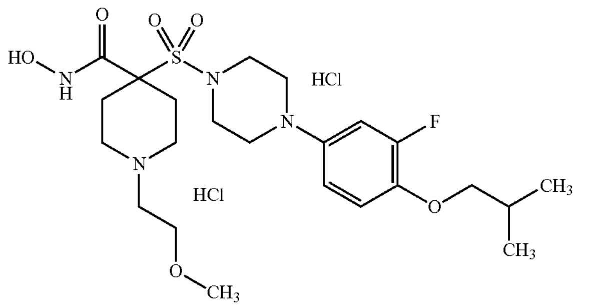 | 517 | 517 | >10000 | 0.72 | 2.22 | 0.71 | >10000 |
| 167 | 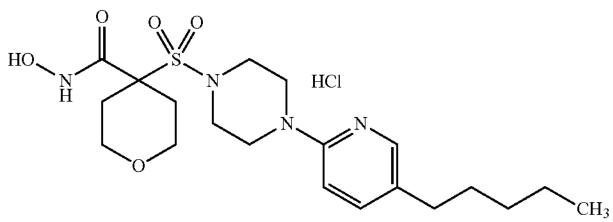 | 441.2166 | 441.2166 | 6216.67 | 0.11 | 0.20 | 0.08 | 457.7 |
| 168 | 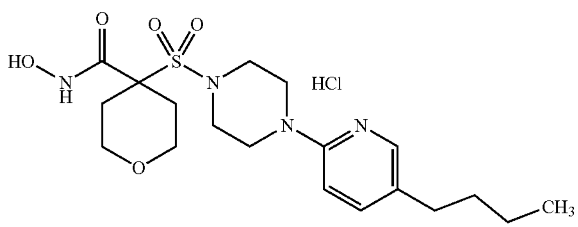 | 427.201 | 427.1988 | 6375.4 | 0.15 | 0.16 | 0.21 | 534.44 |

TABLE 3-continued

Additional Examples of
Piperazinyl- or Piperidinylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 169 | 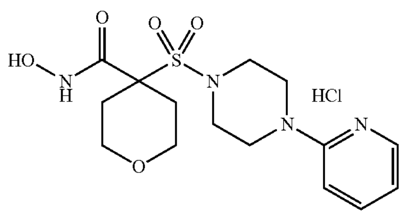 | 371.1384 | 371.1379 | 450.36 | 1.09 | 4.99 | 1.88 | 84.94 |
| 170 | 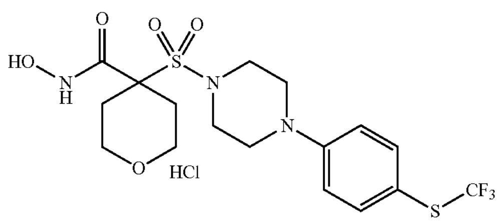 | 470.1026 | 470.1030 | 7807.88 | 0.24 | 17.10 | 0.96 | 452.68 |
| 171 | 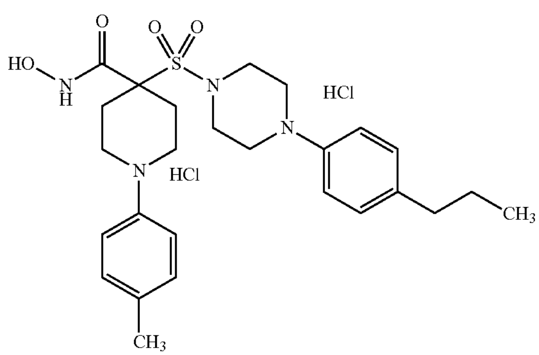 | 501.2536 | 501.2534 | >10000 | 6.82 | 6.91 | 21.5 | 4110 |

TABLE 3-continued

Additional Examples of
Piperazinyl- or Piperidinylmethyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 172 | 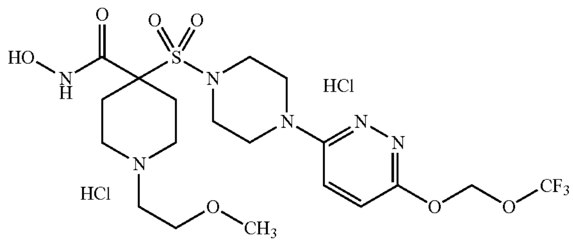 | 527.1894 | 527.1877 | >10000 | 47.33 | 112.11 | 191.89 | >10000 |
| 173 | 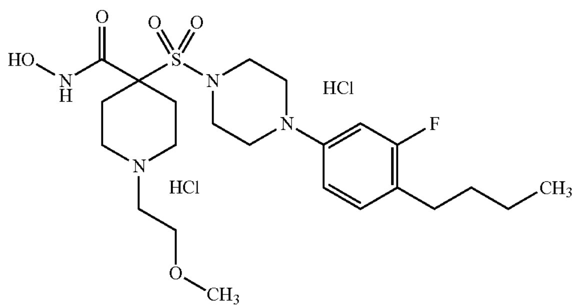 | 501 | 501 | >10000 | 0.209 | 0.149 | 0.696 | 1858.30 |
| 174 | 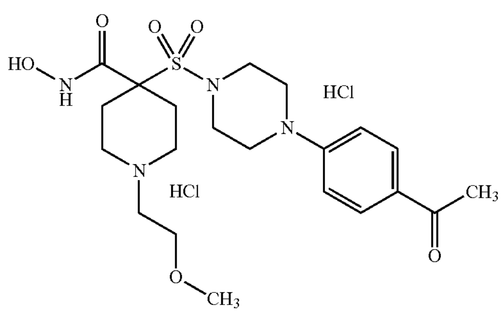 | 468.2155 | 468.2161 | 4654.81 | 2.132 | 28.938 | 3.522 | 2905.8 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 175 | 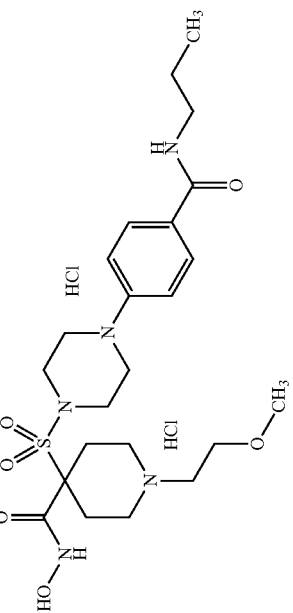 | 512.2543 | 512.2537 | >10000 | 46.87 | 439.99 | 8.25 | >10000 |
| 176 | 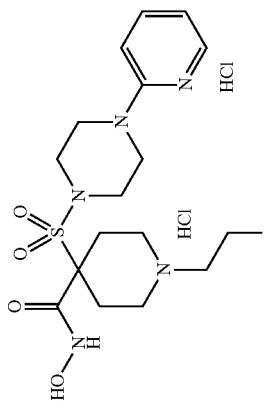 | 428.1968 | 428.1967 | 1457.26 | 1.59 | 9.63 | 1.73 | 181.20 |
| 177 | 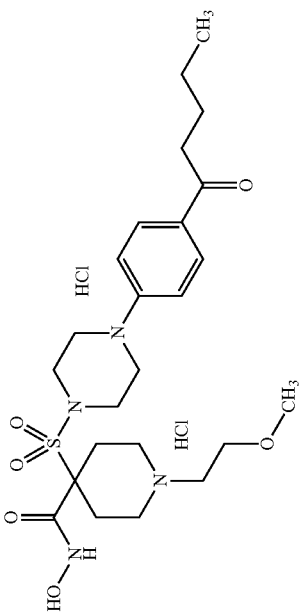 | 511.2589 | 511.2590 | 7358.60 | 2.33 | 18.64 | 0.847 | >10000 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 178 | 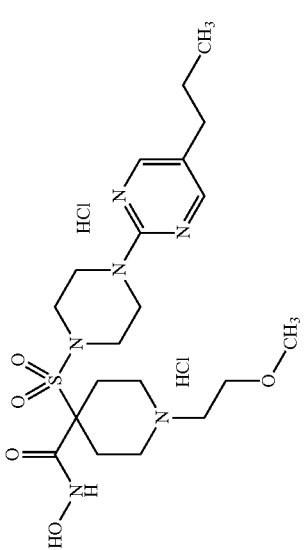 | 471.2409 | 471.2390 | >10000 | 7.88 | 2.23 | 5.26 | 2589.54 |
| 179 | 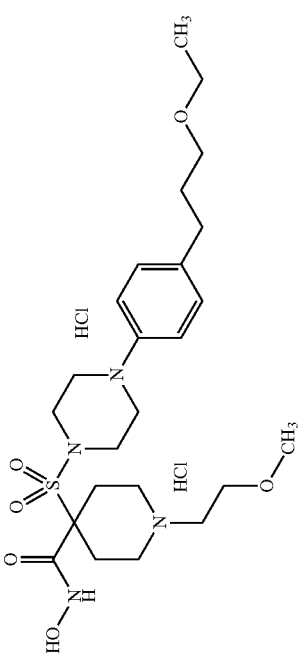 | 513.2741 | 513.2769 | (>10000) | (1.02) | (3.39) | (0.53) | (3615.48) |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 180 | 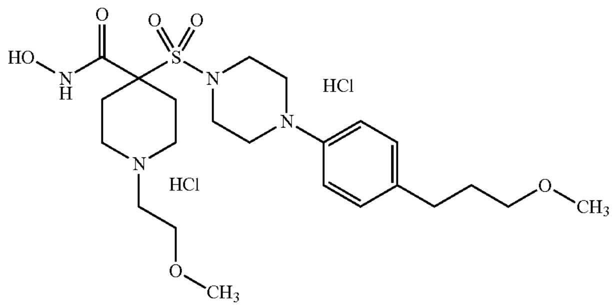 | 499.2585 | 499.261 | (>10000) | (2.14) | (2.25) | (1.21) | (5562.14) |
| 181 | 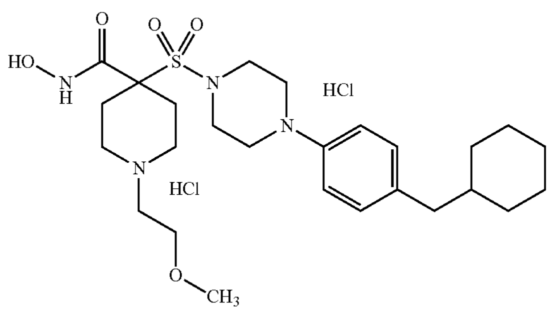 | 523.2949 | 523.2943 | (>10000) | (10.18) | (45.56) | (18.02) | (>10000) |
| 182 | 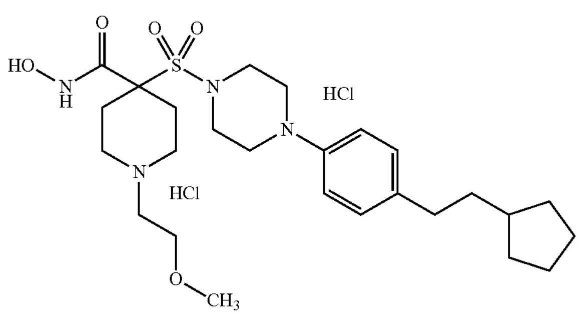 | 523.2949 | 523.2963 | (>10000) | (0.12) | (1.72) | (0.14) | (7848.42) |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 183 | 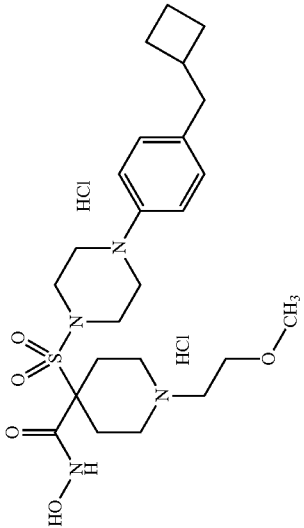 | 495.2636 | 495.2665 | (>10000) | (2.31) | (1.67) | (2.76) | (2035.88) |
| 184 | 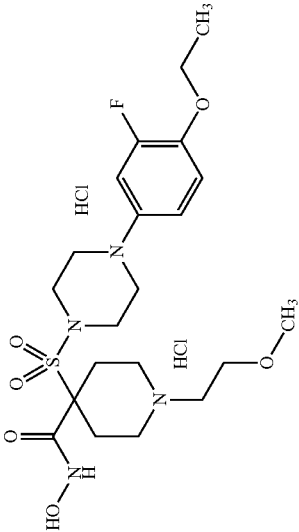 | 489 | 489 | (>10000) | (0.65) | (2.79) | (2.26) | (2400.02) |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 185 | 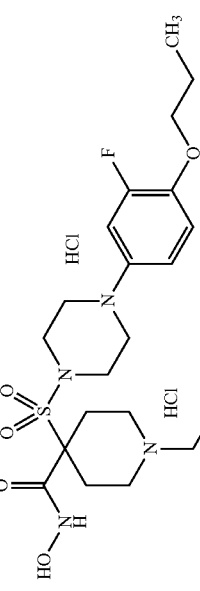 | 503 | 503 | (>10000) | (0.59) | (1.19) | (1.63) | (>10000) |
| 186 | 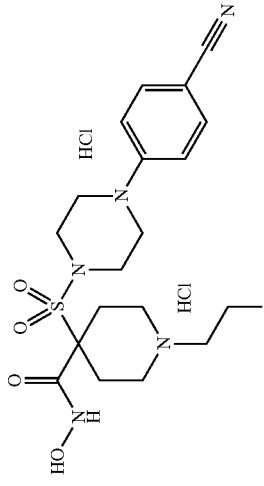 | 452 | 452 | (>10000) | (3.14) | (55.82) | (2.63) | (7483.14) |
| 187 | 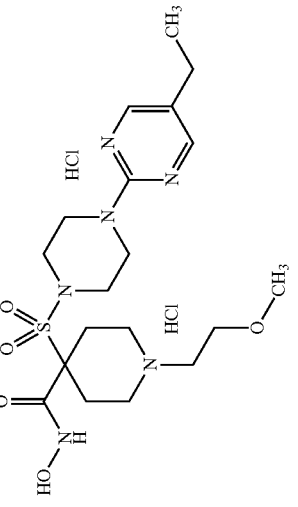 | 457.2251 | 457.2233 | (>10000) | (77.98) | (154.96) | (47.27) | (>10000) |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 188 | 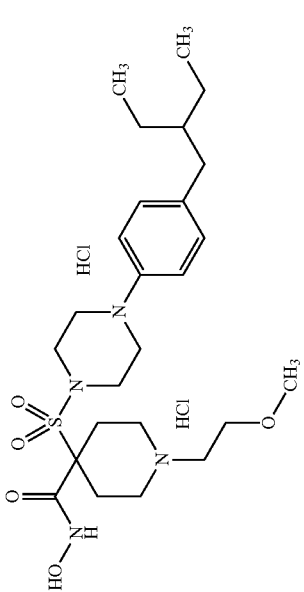 | 511.2949 | 511.296 | (>10000) | (12.45) | (33.66) | (4.01) | (>10000) |
| 189 | 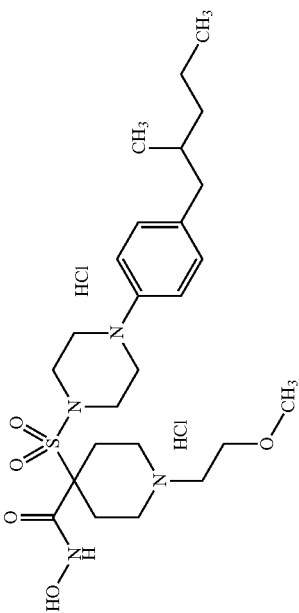 | 511.2949 | 511.2963 | >10000 | 9.78 (1.9) | 34.69 | 2.06 (1.0) | >10000 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 190 | 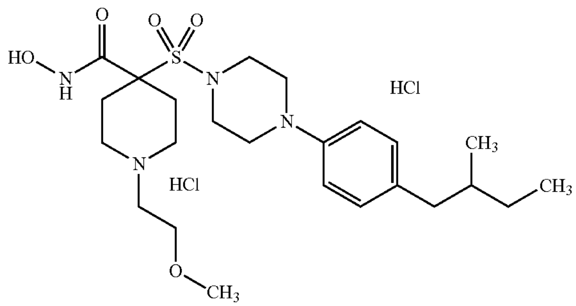 | 497.2792 | 497.2805 | >10000 | 1.49 (1.6) | 3.76 | 0.842 (2.4) | 6096.14 |
| 191 | 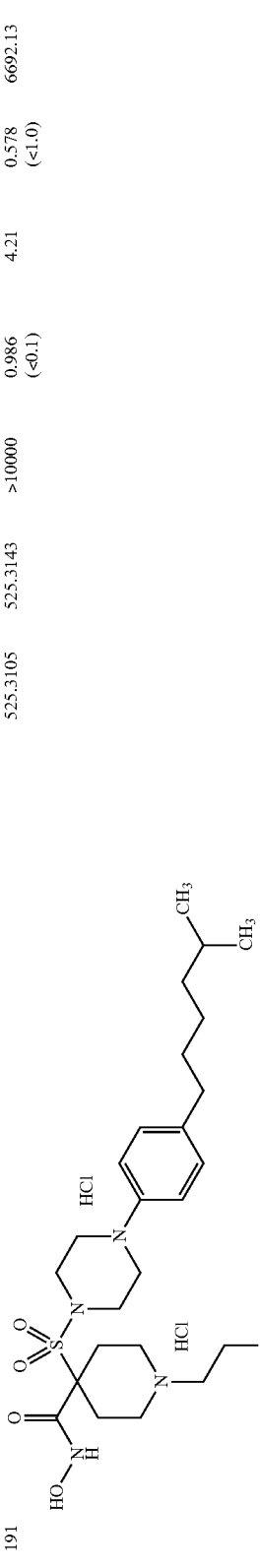 | 525.3105 | 525.3143 | >10000 | 0.986 (<0.1) | 4.21 | 0.578 (<1.0) | 6692.13 |
| 192 | 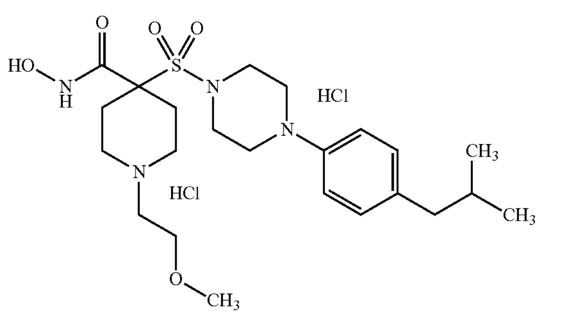 | 483.2636 | 483.2633 | >10000 | 1.90 (1.3) | 9.11 | 1.93 (3.6) | 6976.18 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 193 | 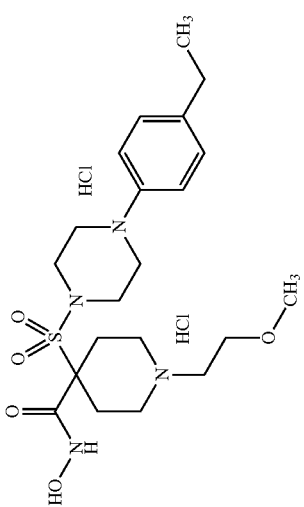 | 455.2323 | 455.2319 | 7178.46 | 1.21 (0.2) | 3.11 | 1.77 (1.9) | 403.09 |
| 194 | 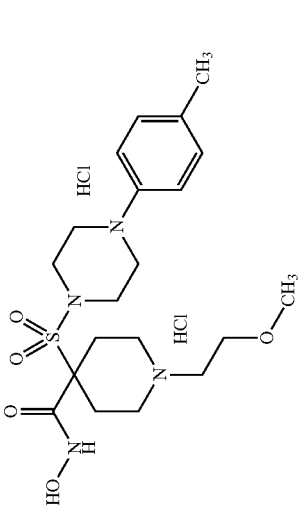 | 441.2166 | 441.2174 | 7728.05 | 1.74 (0.5) | 7.19 | 4.06 (3.1) | 307.19 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 195 | 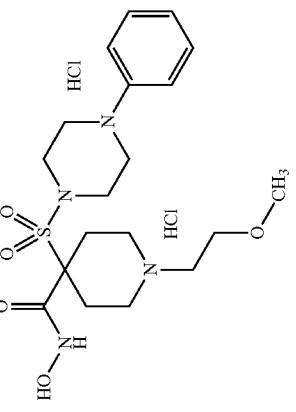 | 427.201 | 427.1996 | 2982.43 | 6.168 (2.4) | 23.20 | 8.07 (11.5) | 414.42 |
| 196 | 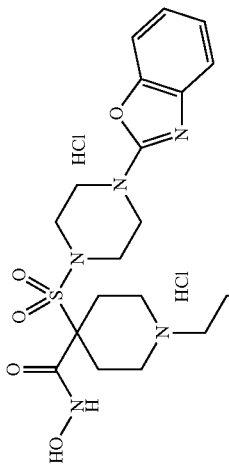 | 468.1936 | 468.1917 | >10000 | 25.14 (30.5) | 79.64 | 56.14 (177.4) | 6842.26 |
| 197 | 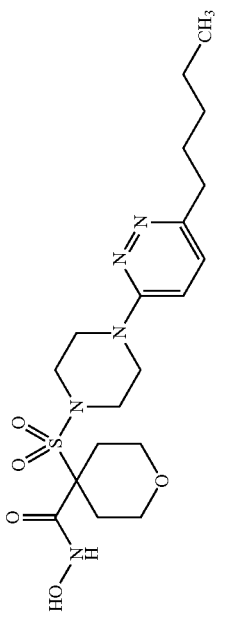 | 442.2119 | 442.2122 | >10000 | 5.78 (19.1) | 20.22 | 6.05 (35.1) | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 198 | 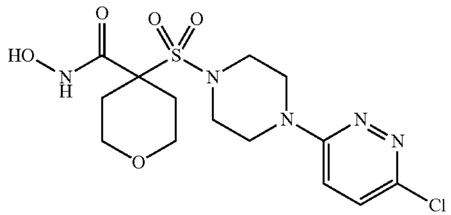 | 406.0946 | 406.0936 | 8653.80 | 8.28 (18.2) | 252.44 | 59.89 (285) | 1278.71 |
| 199 | 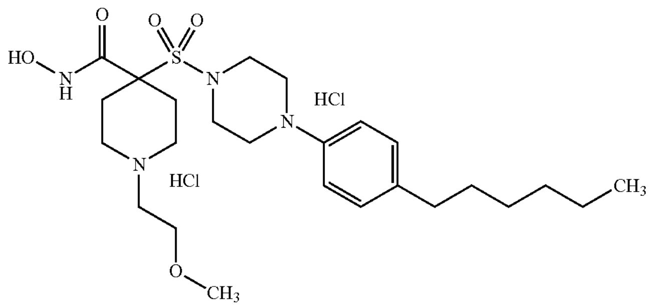 | 511.2949 | 511.2937 | >10000 (>10000) | 0.633 (<0.1) | 0.892 (1.0) | 0.397 (0.2) | 4616.01 (6709) |
| 200 | 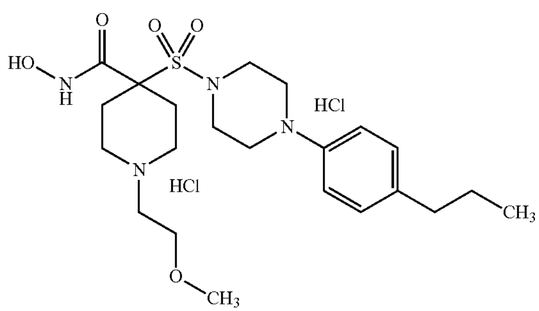 | 469.2479 | 469.2488 | >10000 (>10000) | 0.524 (<0.1) | 0.28 (<0.1) | 1.61 (0.6) | 842.4 (1487) |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 201 | (4-bromophenyl-piperazinyl sulfonyl / methoxyethyl piperidinyl hydroxamic acid · 2HCl) | 505.1115 | 505.1144 | 2730 (6853) | 0.521 (<0.1) | 3.476 (5.7) | 1.36 (0.8) | 119.7 (300.6) |
| 202 | (4-trifluoromethoxyphenyl-piperazinyl sulfonyl / methoxyethyl piperidinyl hydroxamic acid · 2HCl) | 511 | 511 | 7518 (<10000) | 0.432 (<0.1) | 4.674 (6.3) | 0.967 (0.2) | 622.7 (1170.3) |
| 203 | (4-trifluoromethoxyphenyl-piperazinyl sulfonyl / cyclopropyl piperidinyl hydroxamic acid · 2HCl) | 492 | 492 | 7356.6 (<10000) | 0.28 (<0.1) | 2.50 (3.2, 1.9) | 0.35 (0.5) | 569.03 (648) |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 204 | 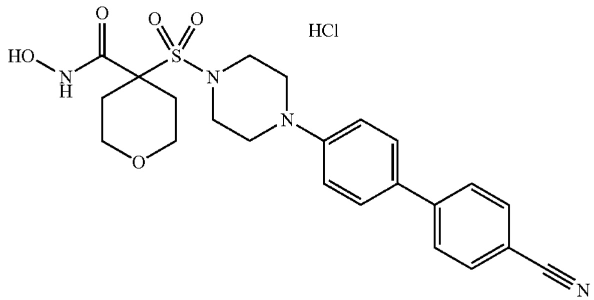 | 481 | 481 | | | | | |
| 205 | 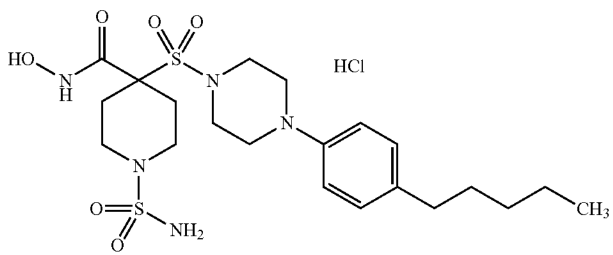 | 518.2102 | 518.2100 | >10000 | 2.03 | 248 | 2.4 | 5020 |
| 206 | 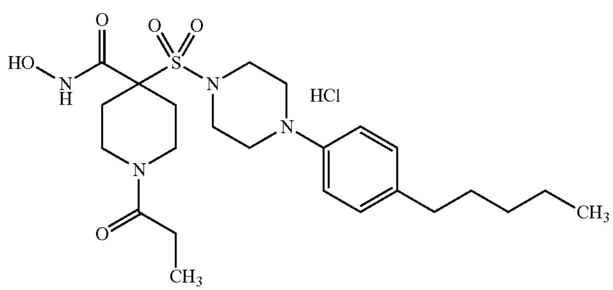 | 495.2636 | 495.2607 | >10000 | 0.63 | 0.62 | 0.41 | 110 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 207 | (4'-methyl-biphenyl piperazine sulfonyl tetrahydropyran hydroxamic acid · HCl) | 460 | 460 | 3250 | 2.02 | 12.3 | 0.94 | >10000 |
| 208 | (4'-fluoro-biphenyl piperazine sulfonyl tetrahydropyran hydroxamic acid · HCl) | 464 | 464 | 1730 | 0.24 | 0.70 | 0.36 | 621 |
| 209 | (5-(4,4,4-trifluorobutyl)pyrazine piperazine sulfonyl tetrahydropyran hydroxamic acid · HCl) | 482.168 | 482.1636 | >10000 | 3.79 | 157 | 3.32 | >10000 |

TABLE 3-continued

Additional Examples of
Piperazinyl- or Piperidinylmethyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 210 | 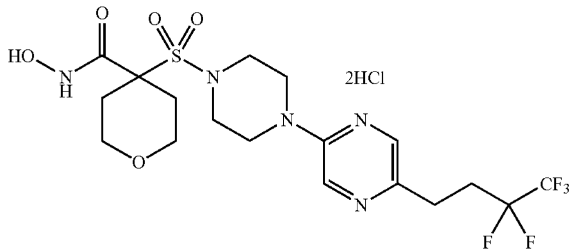 | 518.1491 | 518.1515 | >10000 | 1.04 | 141 | 0.69 | 4470 |
| 211 | 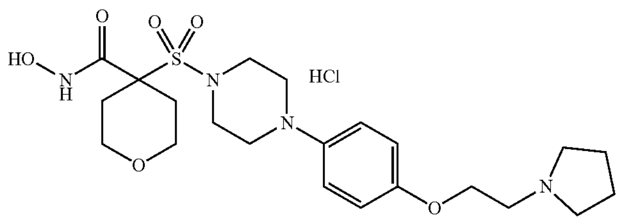 | 475.1890 | 475.1910 | >10000 | 7.41 | 22.9 | 1.16 | 2060 |
| 212 | 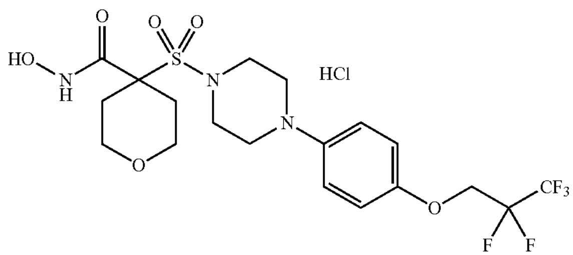 | 518.1379 | 518.1397 | 9810 | 0.54 | 2.91 | 0.30 | 5630 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 213 | 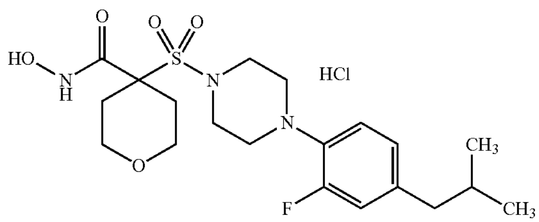 | 444 | 444 | >10000 | 12.6 | 82.4 | 16.1 | 4275 |
| 214 | 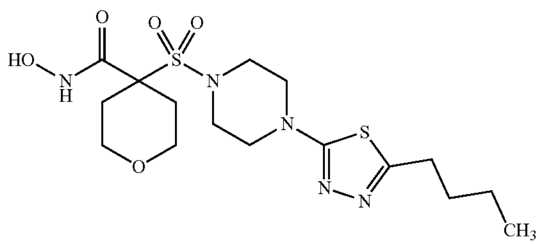 | 434.1526 | 434.155 | >10000 | 102 | 220 | 482 | >10000 |
| 215 | 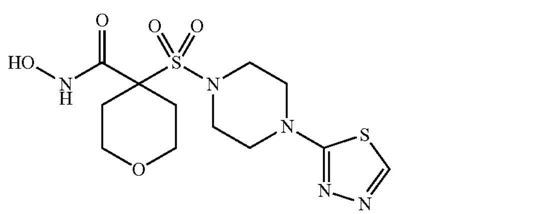 | 378.09 | 378.0921 | >10000 | 2370 | >10000 | 1890 | >10000 |
| 216 | 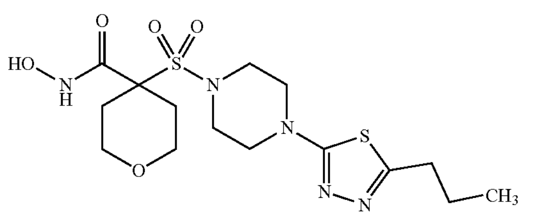 | 420.137 | 420.1412 | >10000 | 214 | 596 | 734 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 217 | 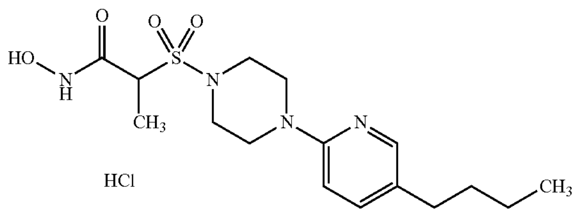 | 371.1748 | 371.1751 | >10000 | 0.29 | 0.45 | 1.21 | 1510 |
| 218 | 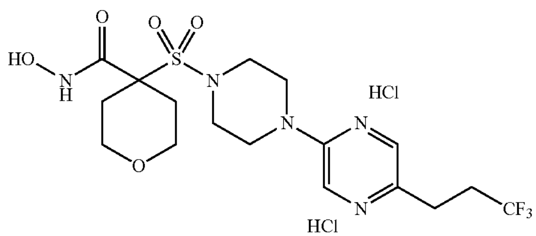 | 468.1523 | 468.1517 | >10000 | 1.39 | 2.29 | 2.03 | 4570 |
| 219 | 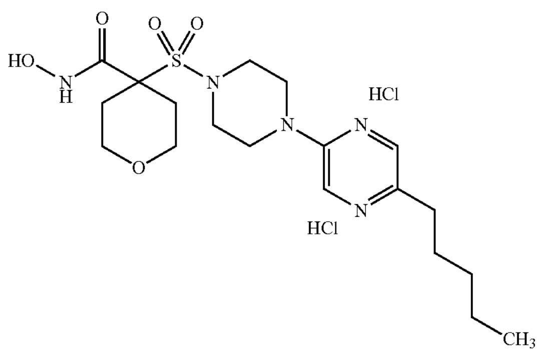 | 442.2119 | 442.2084 | >10000 | 2.5 | 0.46 | 1.11 | 3210 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 220 | 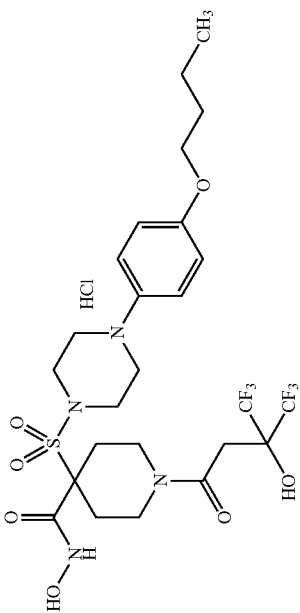 | 469.2125 | 469.2148 | >10000 | 12.7 | 38.5 | 10.7 | >10000 |
| 221 | 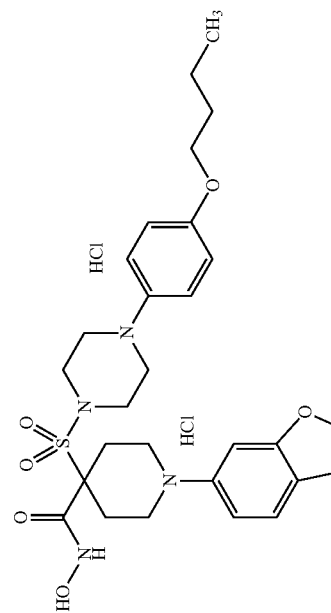 | 561.2377 | 561.2411 | >10000 | 8.53 | 14.6 | 3.52 | >10000 |
| 222 | 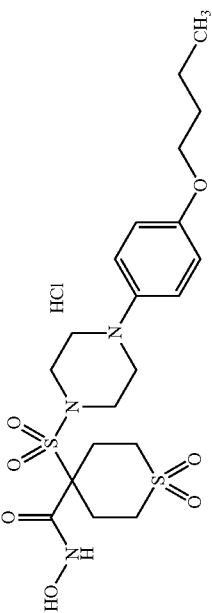 | 490.1676 | 490.1691 | >10000 | 7.88 | 21.5 | 3.99 | >10000 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 223 | 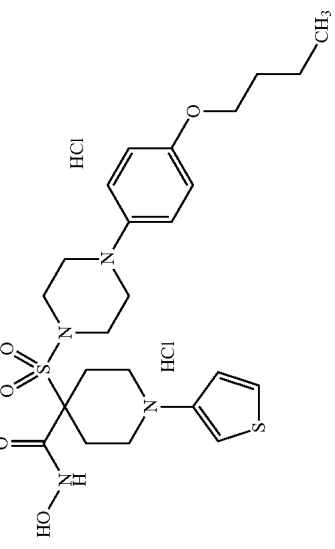 | 523.2043 | 523.2012 | >10000 | 3.46 | 66.1 | 1.4 | 7100 |
| 224 | 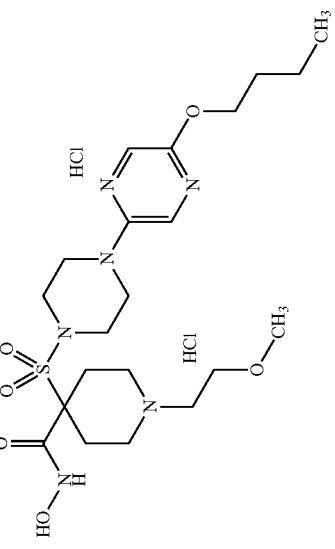 | 485.2541 | 485.2545 | >10000 | 2.46 | 0.73 | 2.32 | 7890 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 225 | 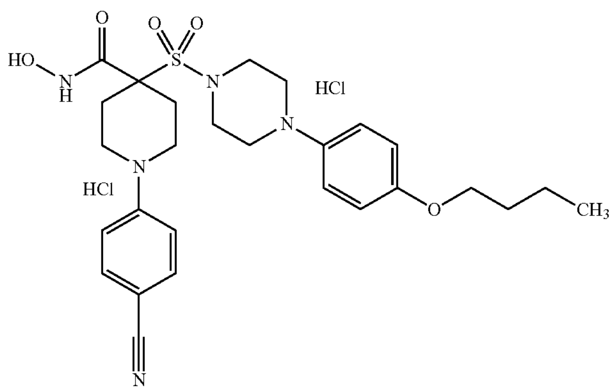 | 542.2432 | 542.246 | >10000 | 9.28 | 28.1 | 5.88 | >10000 |
| 226 | 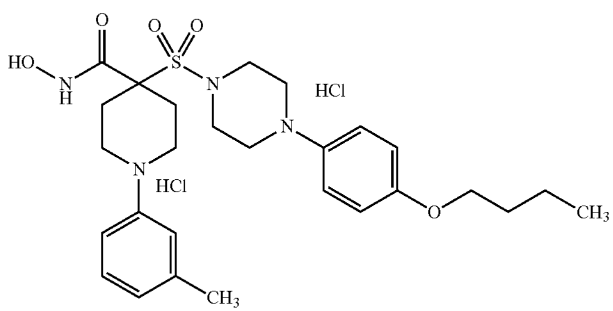 | 531.2636 | 531.263 | >10000 | 10.4 | 19 | 4.38 | >10000 |
| 227 | 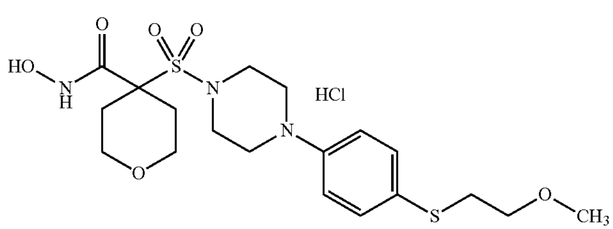 | 460.1571 | 460.1581 | 9280 | 2.47 | 17.2 | 1.79 | 1680 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 228 | 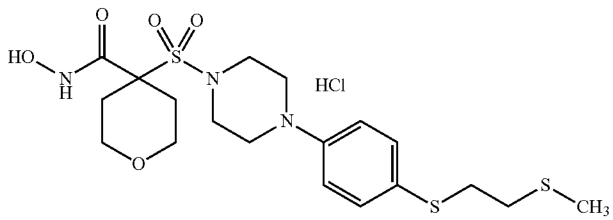 | 490.1499 | 490.1527 | >10000 | 0.70 | 8.16 | 0.67 | 1780 |
| 229 | 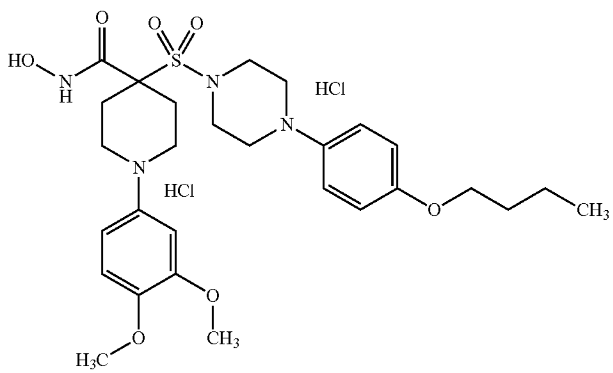 | 577.269 | 577.2686 | >10000 | 2.67 | 4.64 | 1.01 | 7880 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 230 | 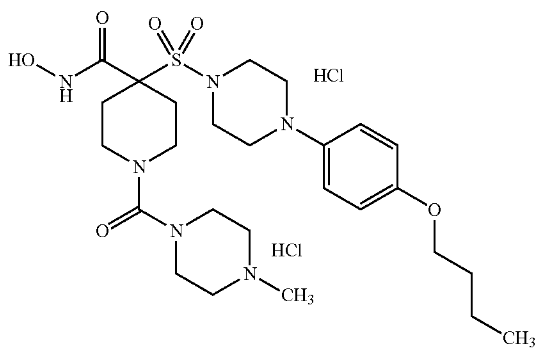 | 567.2959 | 567.2988 | >10000 | 0.46 | 0.87 | 0.27 | 2510 |
| 231 | 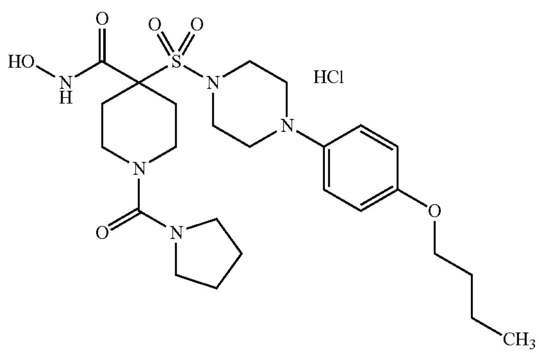 | 538.2694 | 538.2702 | >10000 | 1.32 | 0.71 | 0.17 | 1530 |
| 232 | 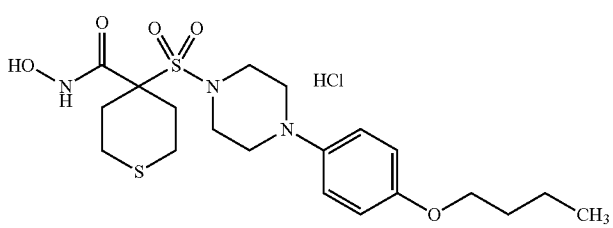 | 458.1778 | 458.1746 | >10000 | 26.5 | 2.3 | 0.56 | 3510 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 233 | 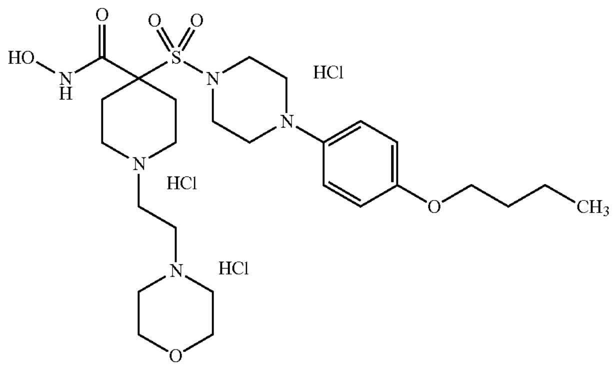 | 554.3007 | 554.2999 | >10000 | 0.771 | 0.972 | 0.26 | 3080 |
| 234 | 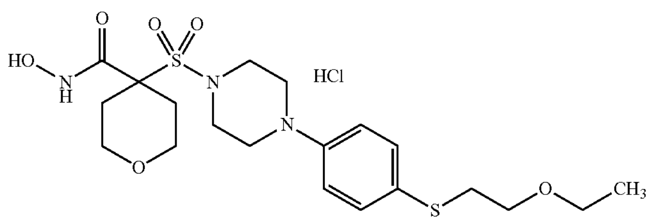 | 474.1720 | 474.1727 | >10000 | 3.16 | 33.6 | 1.61 | 2880 |
| 235 | 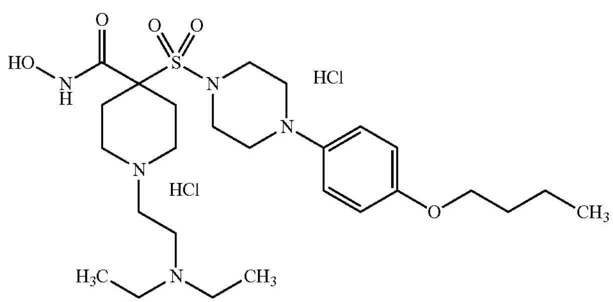 | 540.3214 | 540.3220 | >10000 | 0.76 | 0.90 | 0.30 | 3960 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 236 | 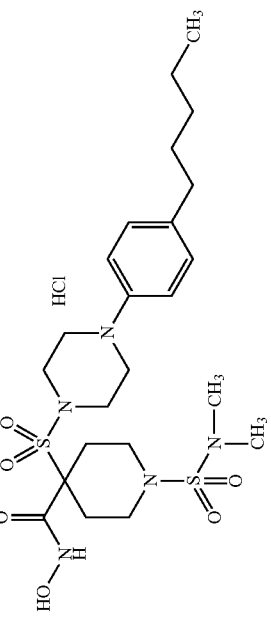 | 546.2415 | 546.2418 | >10000 | 2.58 | 2.61 | 1.47 | >10000 |
| 237 | 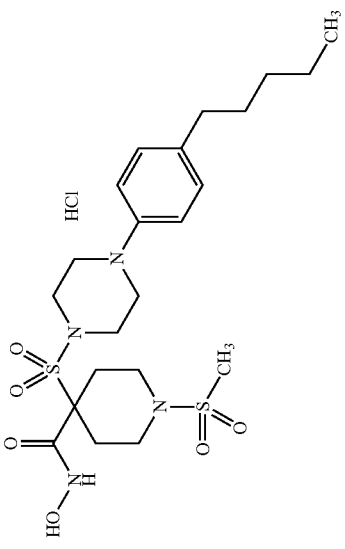 | 517.2149 | 517.2112 | >10000 | 2.03 | 2.79 | 1.69 | 7120 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 238 | 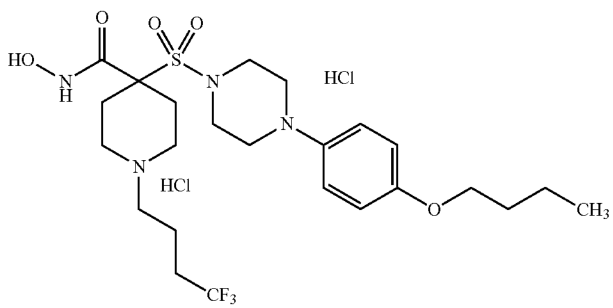 | 551.2510 | 551.2519 | >10000 | 1.63 | 2.49 | 0.53 | 6040 |
| 239 | 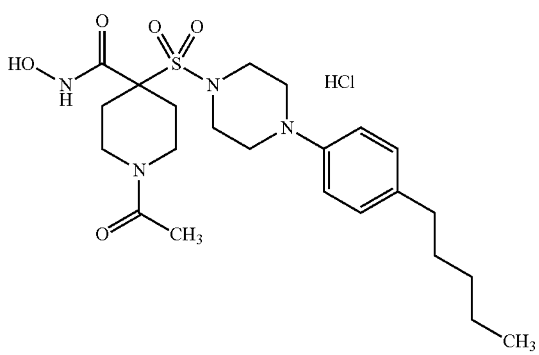 | 481.2479 | 481.2448 | >10000 | 0.54 | 0.46 | 0.37 | 1050 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 240 | 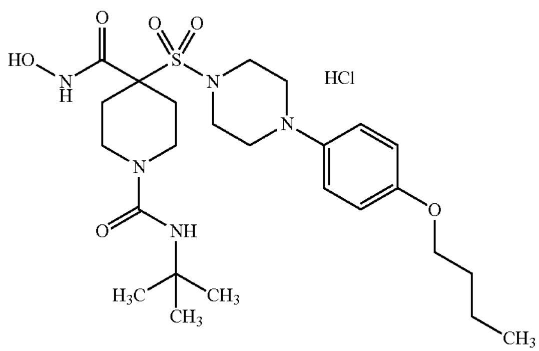 | 540.2850 | 540.2826 | >10000 | 0.536 | 1.03 | 0.327 | 3960 |
| 241 | 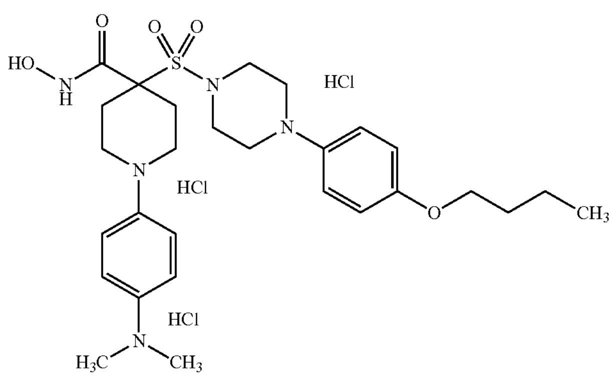 | 560.2901 | 560.2883 | >10000 | 3.64 | 4.74 | 1.06 | >10000 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 242 | 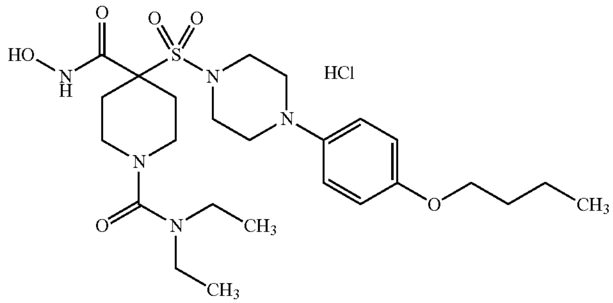 | 540.2850 | 540.2843 | >10000 | 0.591 | 1.14 | 0.331 | 2390 |
| 243 | 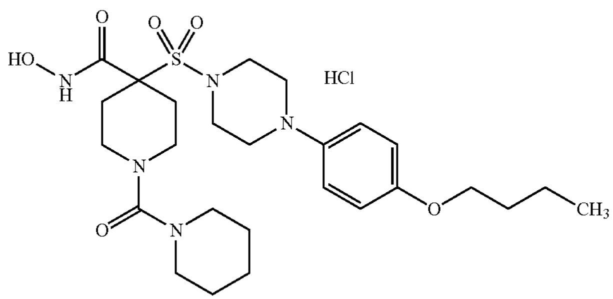 | 552.2850 | 552.2874 | >10000 | 0.34 | 0.70 | 0.24 | 2050 |
| 244 | 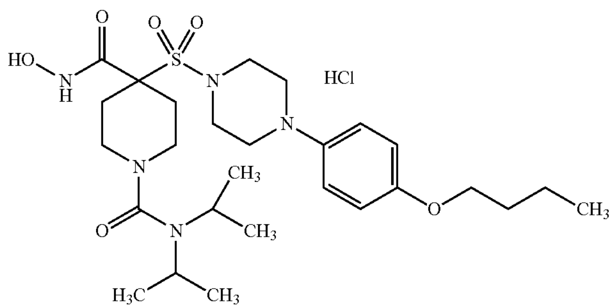 | 568.3163 | 568.3156 | >10000 | 1.57 | 3.9 | 0.57 | 5310 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 245 | 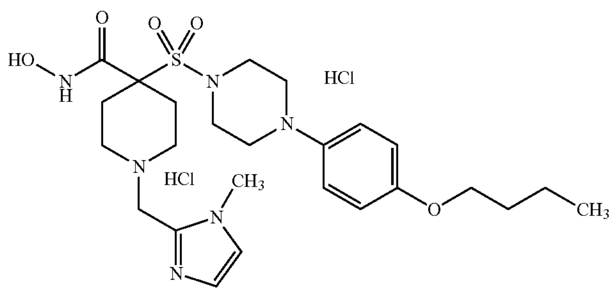 | 535.2703 | 535.2662 | >10000 | 0.475 | 0.588 | 0.177 | 2810 |
| 246 | 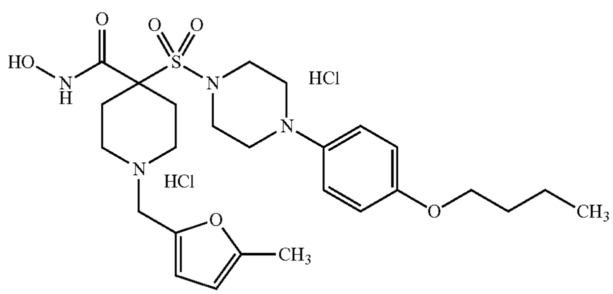 | 535.2590 | 535.2595 | >10000 | 1.2 | 1.74 | 0.396 | 5950 |
| 247 | 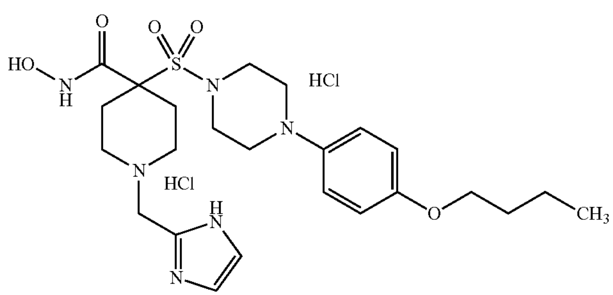 | 521.2346 | 521.2554 | >10000 | 0.686 | 0.718 | 0.166 | 1980 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 248 | 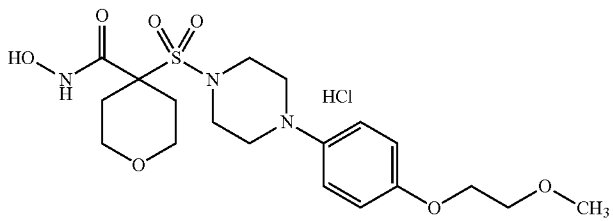 | 458.1955 | 458.1952 | >10000 | 0.877 | 25.2 | 0.564 | 7220 |
| 249 | 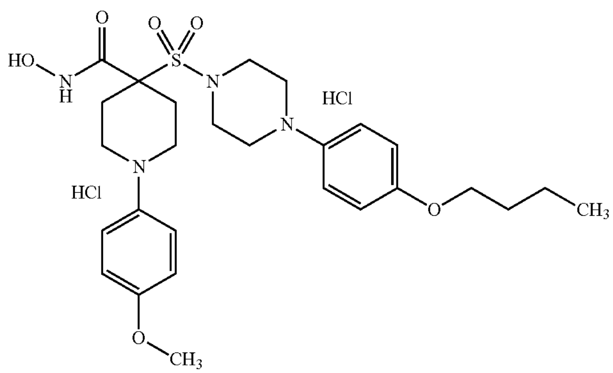 | 547.259 | 547.254 | >10000 | 4.98 | 11.3 | 2.46 | >10000 |

TABLE 3-continued
Additional Examples of
Piperazinyl- or Piperidinylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 250 | 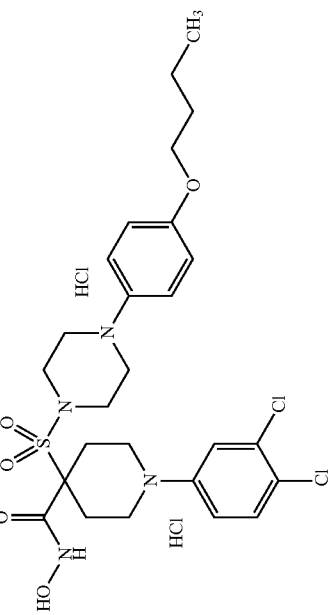 | 585.1705 | 585.1711 | >10000 | 29.9 | 73.9 | 18.4 | >10000 |
| 251 | 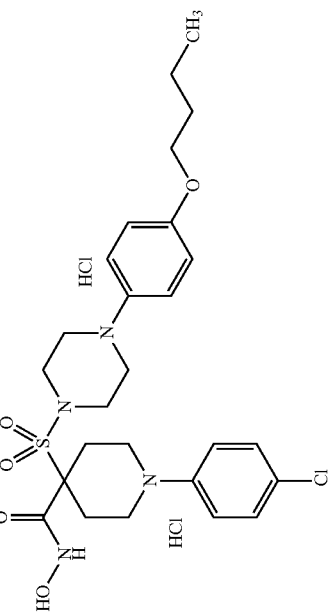 | 551.2095 | 551.2075 | >10000 | 22.5 | 57.4 | 12.9 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 252 | 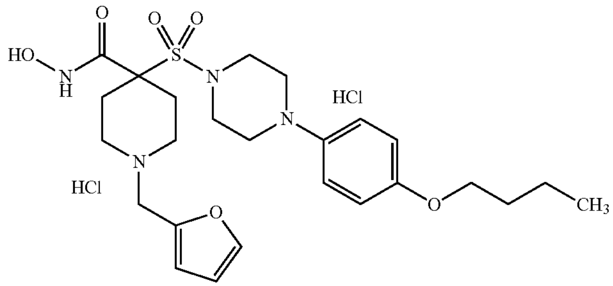 | 521.2434 | 521.2472 | >10000 | 1.38 | 1.43 | 0.373 | 5180 |
| 253 | 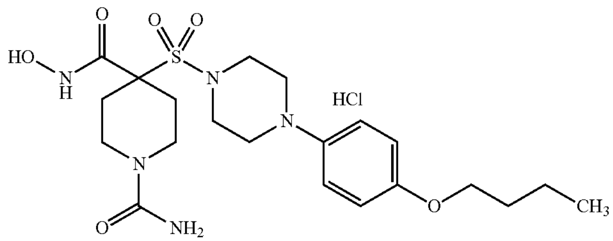 | 484.2230 | 484.2206 | >10000 | 0.761 | 1.57 | 0.357 | 1930 |
| 254 | 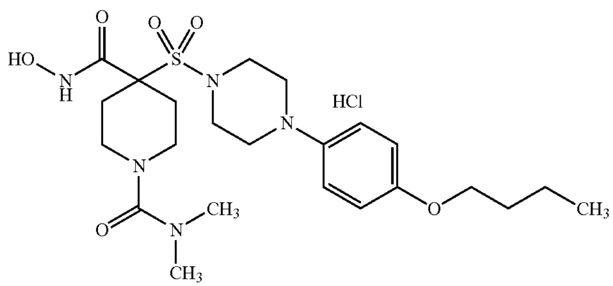 | 512.2543 | 512.2521 | >10000 | 0.309 | 0.63 | 0.10 | 856 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 255 | 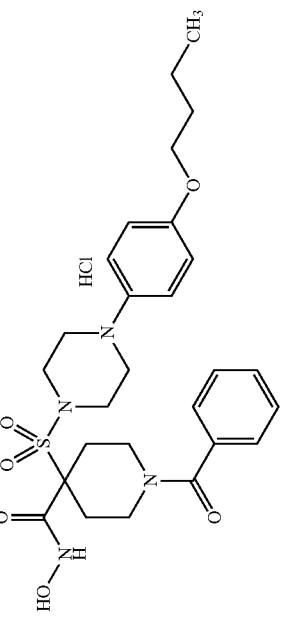 | 545.2434 | 545.2398 | >10000 | 0.858 | 2.54 | 0.39 | 5660 |
| 256 | 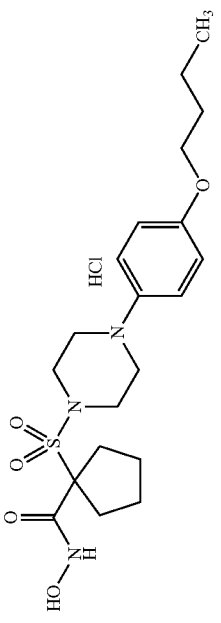 | 411.2063 | 411.2061 | >10000 | 0.17 | 0.099 | 0.161 | 416 |
| 257 | 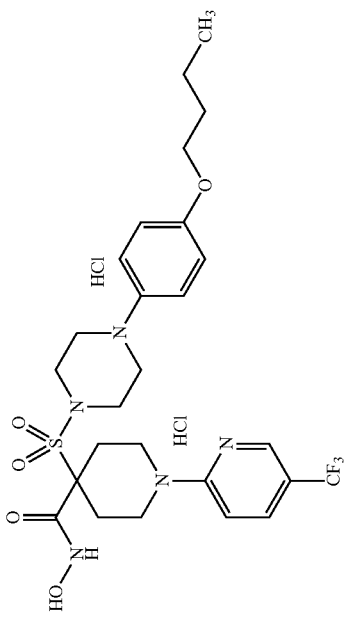 | 586.2311 | 586.2354 | >10000 | 9.64 | 37 | 12.9 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 258 | 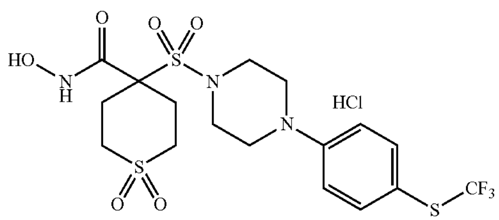 | | | >10000 | 4.06 | 457 | 30.5 | 4890 |
| 259 | 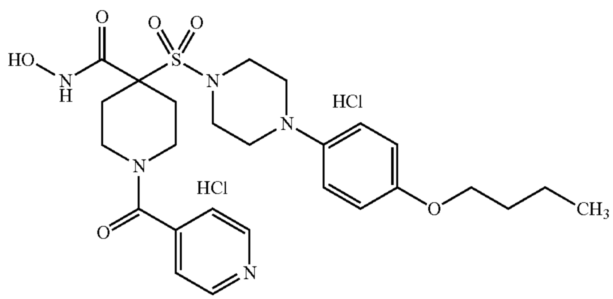 | 546.2386 | 546.2426 | >10000 | 0.468 | 1.35 | 0.359 | 2650 |
| 260 | 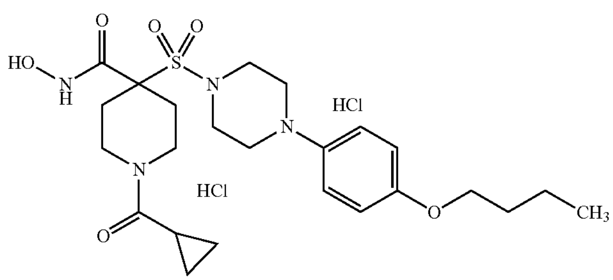 | 509.2434 | 509.2384 | >10000 | 0.467 | 0.946 | 0.301 | 2800 |

TABLE 3-continued

Additional Examples of
Piperazinyl- or Piperidinylmethyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 261 | 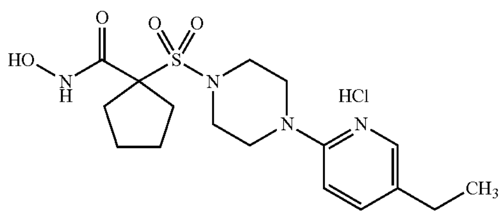 | 383.1778 | 383.1748 | 632 | 0.276 | 1.53 | 0.458 | 48.1 |
| 262 | 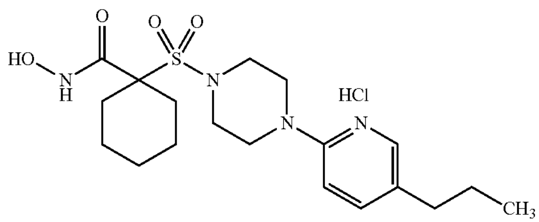 | 425.2201 | 425.2217 | 2970 | 0.106 | 0.061 | 0.132 | 299 |
| 263 | 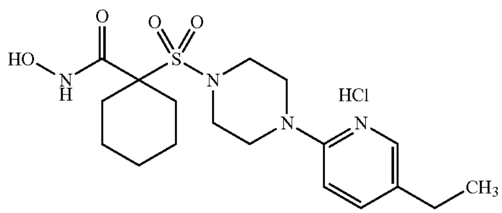 | 397.1931 | 397.1904 | 605 | 0.188 | 0.634 | 0.262 | 34 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 264 | 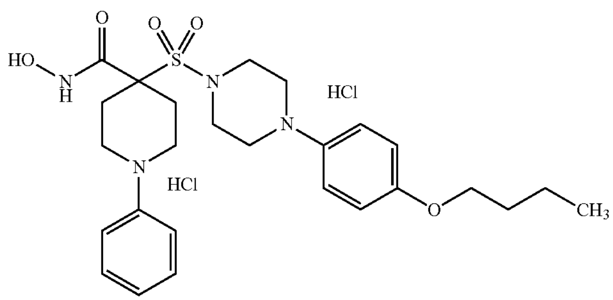 | 517.2479 | 517.2479 | >10000 | 8.23 | 20.4 | 0.048 | >10000 |
| 265 | 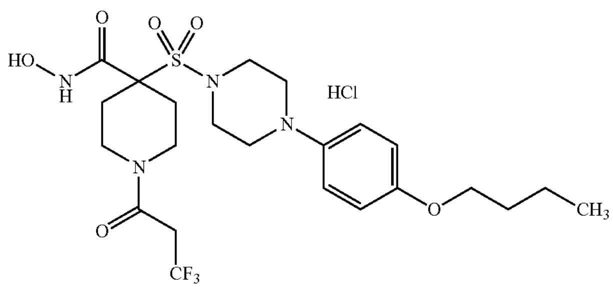 | 551.2151 | 551.2184 | >10000 | 0.878 | 2.14 | 0.637 | 3790 |
| 266 | 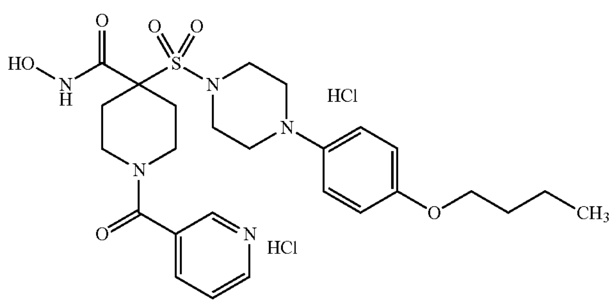 | 546.2386 | 546.2397 | >10000 | 0.422 | 0.957 | 0.308 | 2390 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 267 | 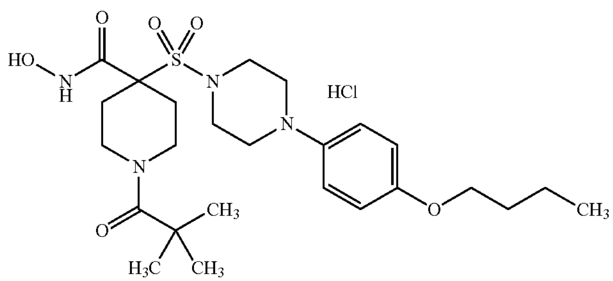 | 525.2747 | 525.2777 | >10000 | 0.836 | 2.54 | 0.64 | >10000 |
| 268 | 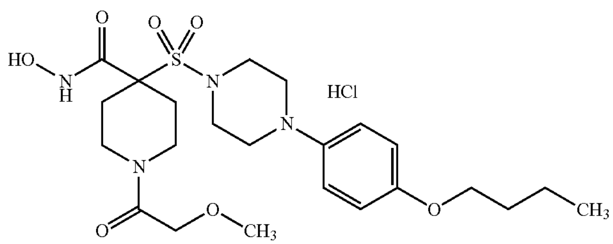 | 513.2377 | 513.2362 | 9320 | 0.564 | 1.08 | 0.311 | 1390 |
| 269 | 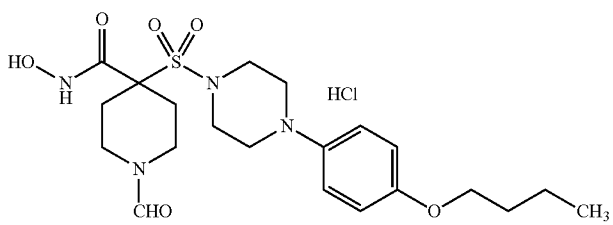 | 469.2121 | 469.2108 | 6400 | 0.436 | 0.953 | 0.25 | 1200 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 270 | 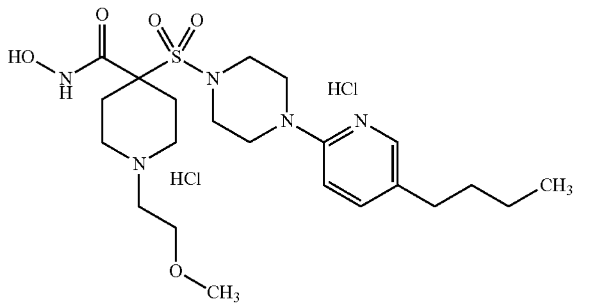 | 484.2606 | 484.2588 | >10000 | 0.176 | 0.205 | 0.339 | 1110 |
| 271 | 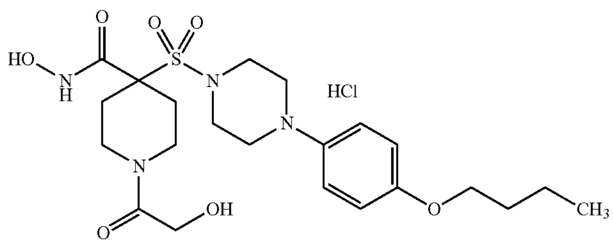 | 499.2221 | 499.2228 | 7470 | 0.668 | 1.49 | 0.452 | 1460 |
| 272 | 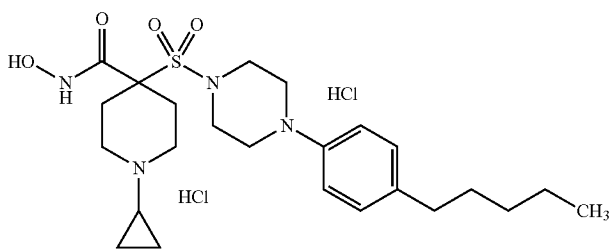 | 479.2687 | 479.2664 | >10000 | 0.662 | 0.542 | 0.33 | 4351 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 273 | 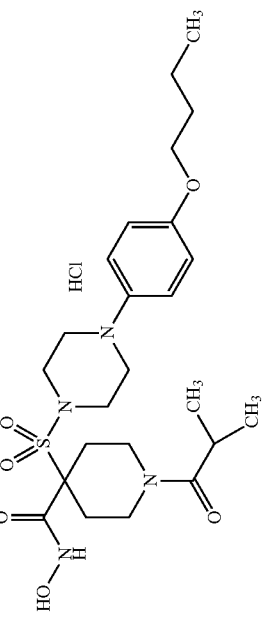 | 511.2585 | 511.2544 | >10000 | 0.622 | 1.21 | 0.313 | 5090 |
| 274 | 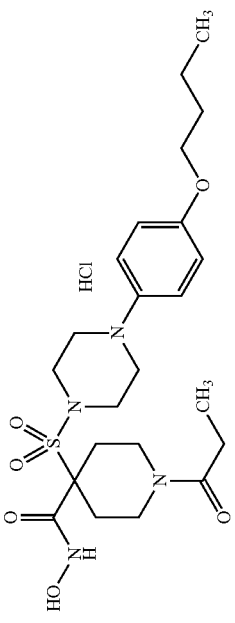 | 497.2428 | 497.2461 | >10000 | 0.826 | 1.66 | 0.484 | 3030 |
| 275 | 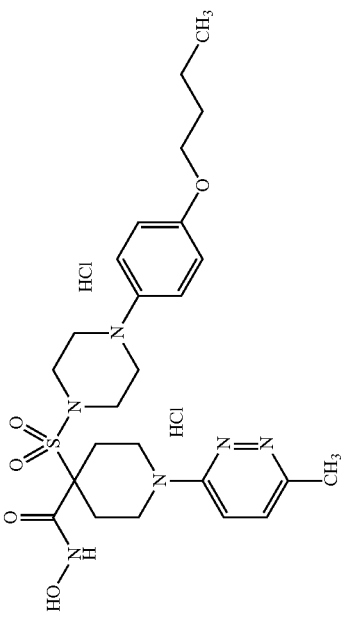 | 533.2541 | 533.2575 | >10000 | 0.381 | 0.807 | 0.216 | 818 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 276 | 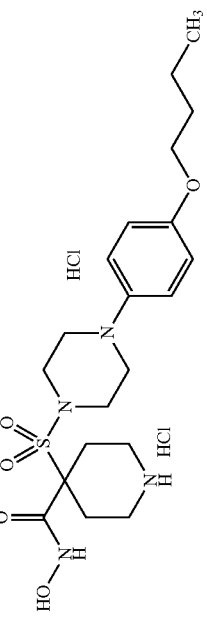 | 441.2166 | 441.2171 | >10000 | 5.7 | 9.39 | 2.49 | >10000 |
| 277 | 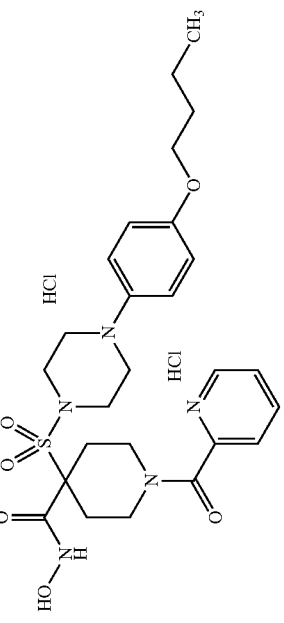 | 546.2381 | 546.2408 | >10000 | 0.42 | 0.95 | 0.23 | 3020 |
| 278 | 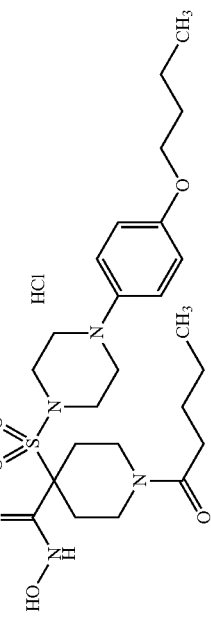 | 525.2741 | 525.2715 | >10000 | 0.81 | 2 | 0.49 | 5260 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 279 | 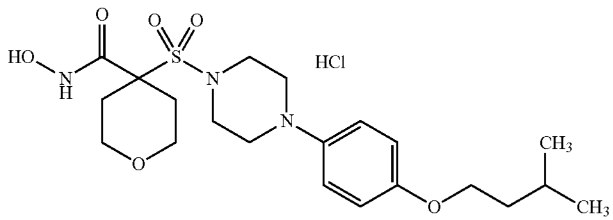 | 456.2163 | 456.2176 | >10000 | 1.11 | 3.07 | 0.32 | 4270 |
| 280 | 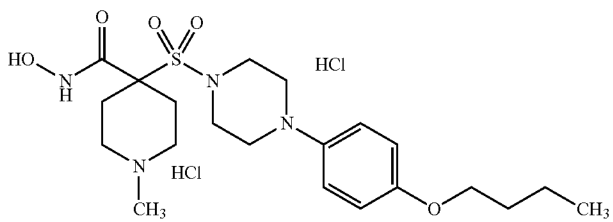 | 455.2323 | 455.2300 | >10000 | 2.76 | 3.61 | 1.02 | 7310 |
| 281 | 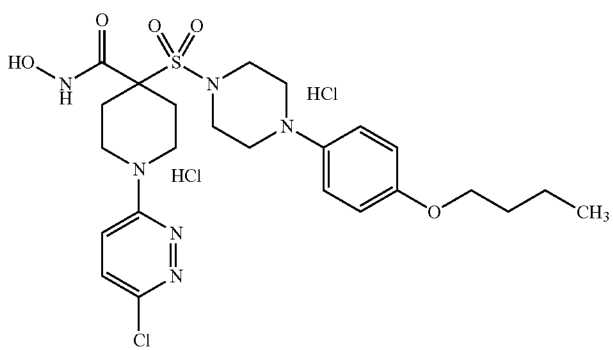 | 553.1994 | 553.1982 | >10000 | 0.769 | 2.16 | 0.442 | 1630 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 282 | 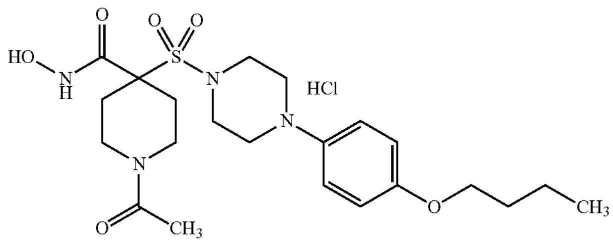 | 483.2272 | 483.2241 | >10000 | 0.50 | 0.098 | 0.27 | 1480 |
| 283 | 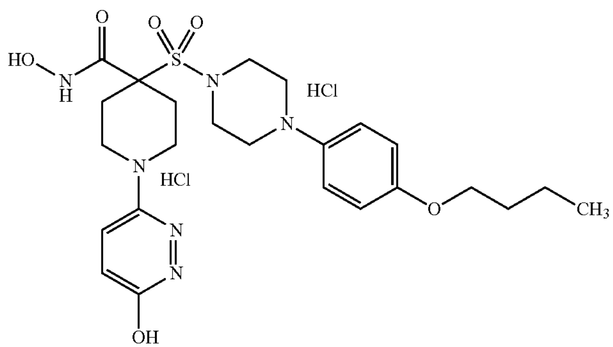 | 535.2333 | 535.2329 | 9790.62 | 0.37 | 0.69 | 0.19 | 548.90 |
| 284 | 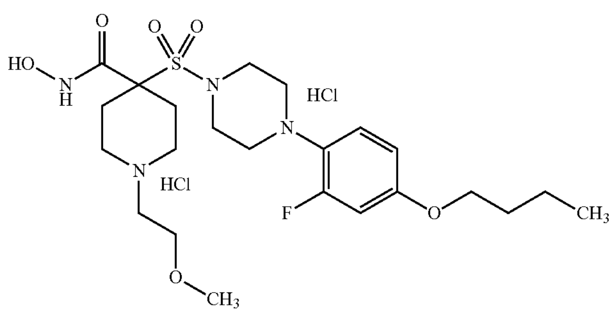 | 517 | 517 | >10000 | 0.81 | 0.99 | 0.12 | 2770 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 285 | 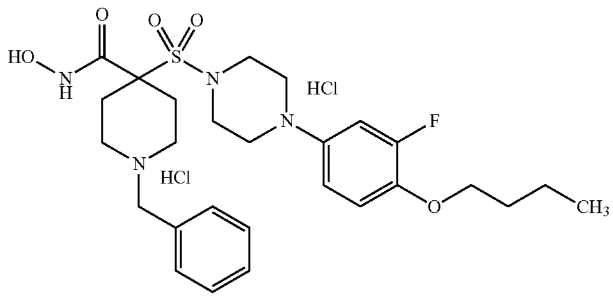 | 549 | 549 | >10000 | 1.55 | 9.83 | 2.06 | >10000 |
| 286 | 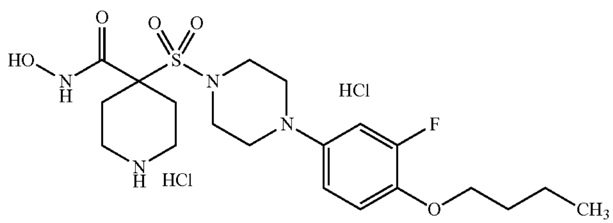 | 459 | 459 | >10000 | 5.17 | 22.31 | 5.97 | >10000 |
| 287 | 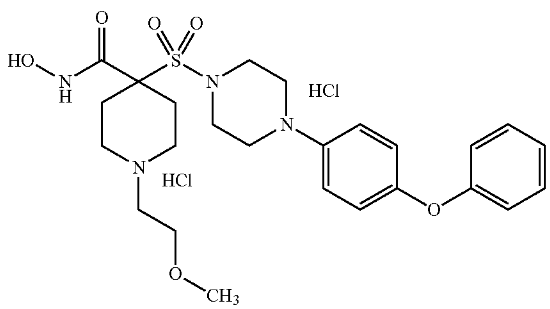 | 517 | 517 | >10000 | 9.44 | 13.92 | 3.33 | 6936.23 |

TABLE 3-continued

Additional Examples of
Piperazinyl- or Piperidinylmethyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 288 | 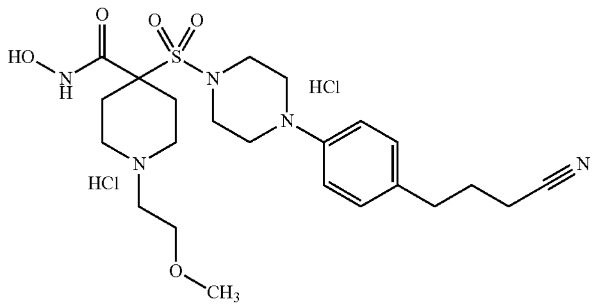 | 508.2588 | 508.2607 | >10000 | 0.227 | 1.86 | 0.31 | 2095.67 |
| 289 | 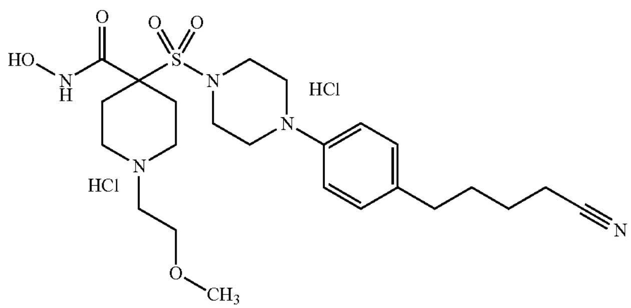 | 494.2532 | 494.2444 | >10000 | 1.229 | 7.523 | 0.82 | 4043.59 |
| 290 | 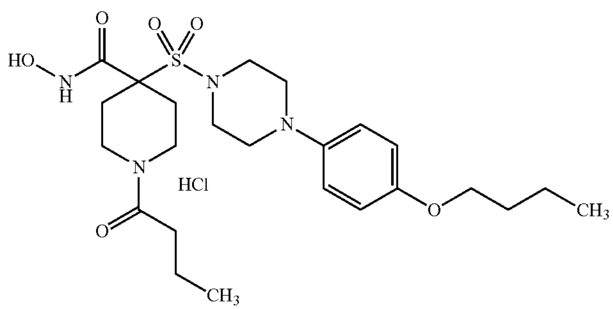 | 511.2585 | 511.2563 | (>10000) | (59.46) | (1.42) | (0.35) | (3796.20) |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 291 | 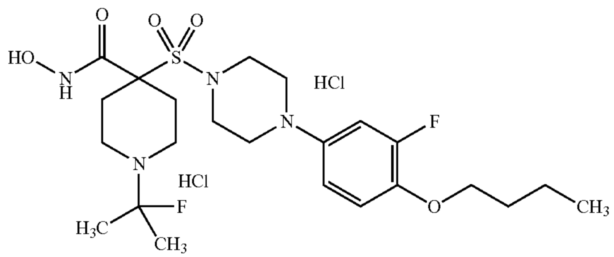 | 519 | 519 | >10000 (>10000) | 5.52 (2.83) | 24.003 (16.01) | 5.948 (3.02) | >10000 (>10000) |
| 292 | 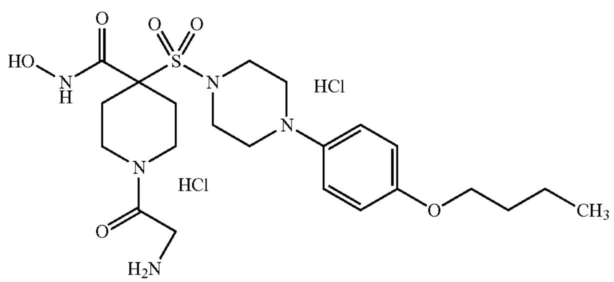 | 498.2381 | 498.2389 | >10000 | 1.74 (0.2) | 3.51 | 0.98 (0.7) | 6536.44 |
| 293 | 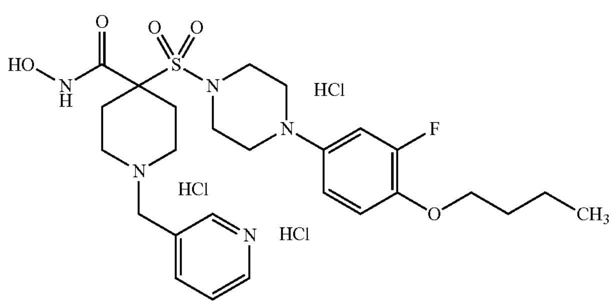 | 550 | 550 | >10000 | 0.486 (0.3) | 2.21 | 0.313 (0.8) | 5438.06 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 294 | 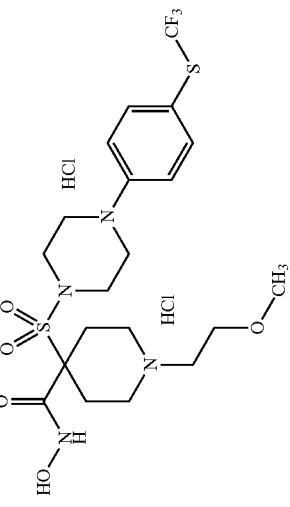 | 515 | 515 | >10000 | 0.37 (<0.1) | 32.36 | 1.27 (0.5) | 1859.51 |
| 295 | 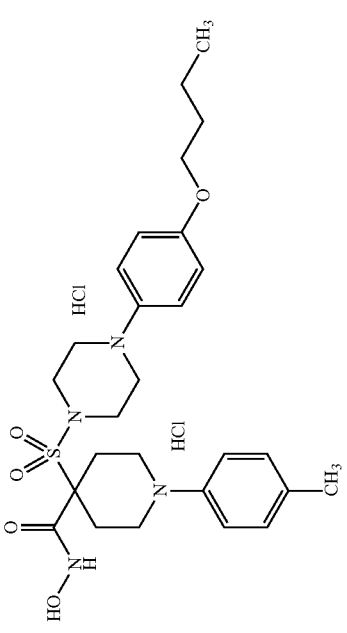 | | | >10000 (>10000) | 8.76 (>0.1) | 17.15 (0.1) | 9.133 (>0.1) | 8645 (>10000) |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 296 | 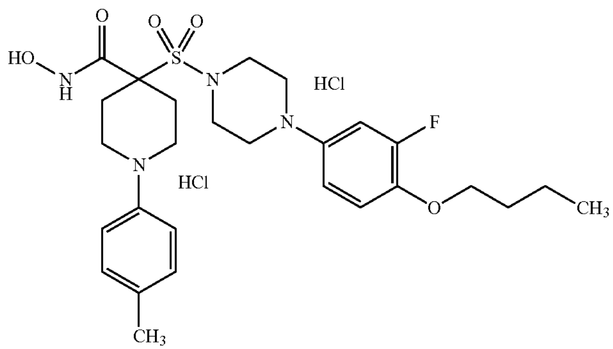 | | | >10000 (>10000) | 6.73 (>0.1) | 47.61 (115.9) | 9.22 (0.9) | (>10000) |
| 297 | 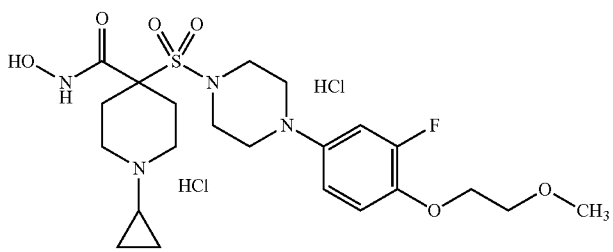 | 501 | 501 | >10000 (>10000) | 1.36 (0.4) | 19.54 (31.1) | 1.40 (1.7) | (>10000, 6469.7) |
| 298 | 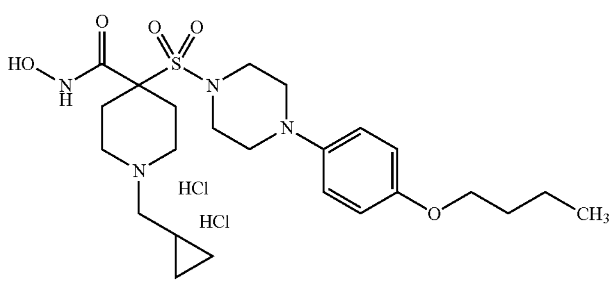 | | | >10000 (>10000) | 3.27 (1.1) | 2.99 (3.9) | 0.702 (0.9) | >10000 (>10000) |

TABLE 3-continued

Additional Examples of
Piperazinyl- or Piperidinylmethyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 299 | 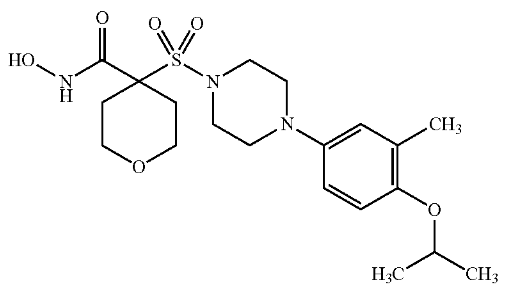 | 442.2012 | 442.1992 | >10000 | 22.49 (12.5) | 43.6 | 3.04 (9.3) | >10000 |
| 300 | 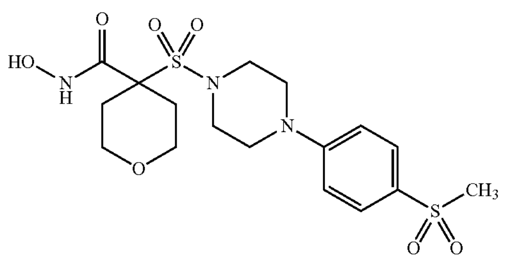 | 448.1212 | 448.1214 | >10000 | 67.05 (27.3) | 141.73 | 42.74 (61.2) | >10000 |
| 301 | 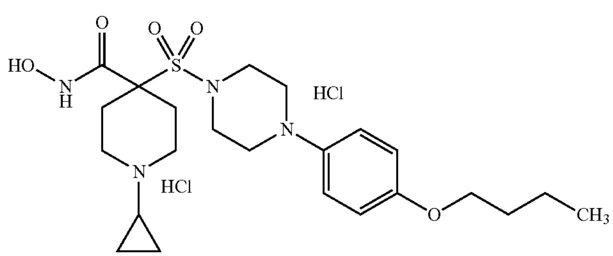 | 481 | 481 | >10000 (>10000) | 0.88 (0.2) | 9.11 (0.6) | 0.23 (0.3) | (5632) |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 302 | 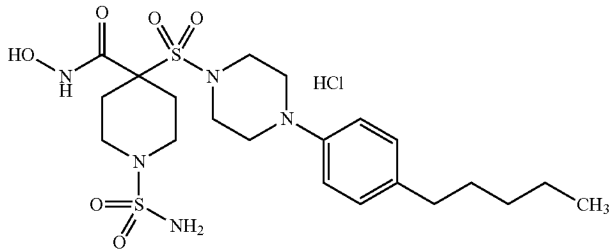 | | | | | | | |
| 303 | 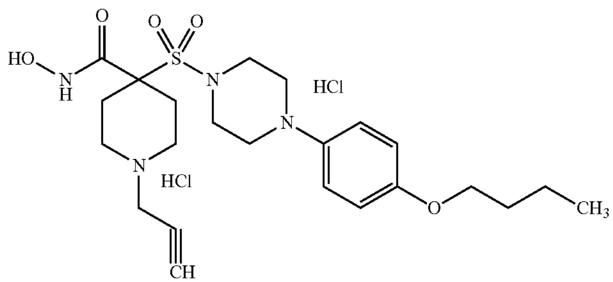 | 479 | 479 | >10000 (>10000) | 1.68 (0.1) | 1.48 (0.3) | 0.46 (0.1) | 5000.74 (2240) |
| 304 | 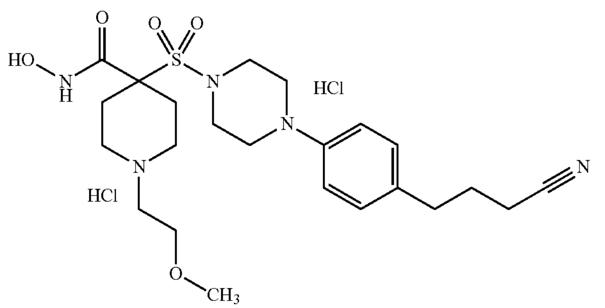 | 532.1748 | 532.1759 | (>10000) | (2.6) | (2010) | (0.9) | (>10000) |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 305 | 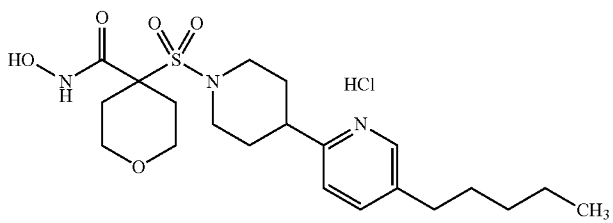 | 440.2219 | 440.2231 | 6700 | 0.407 | 0.133 | 0.136 | 645 |
| 306 | 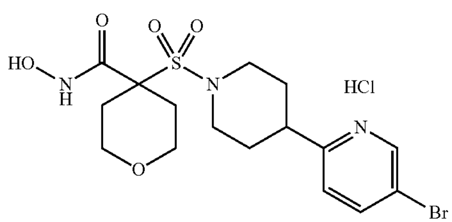 | 448.0542 | 448.0530 | 602 | 0.444 | 1.03 | 0.863 | 31.7 |
| 307 | 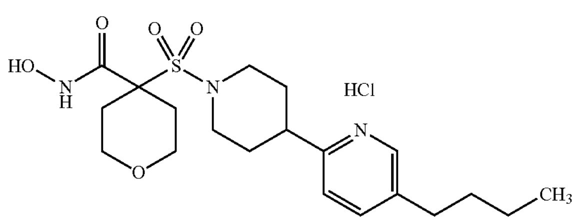 | 426.2063 | 426.2069 | 6810 | 0.505 | 0.94 | 0.654 | 1290 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 308 | 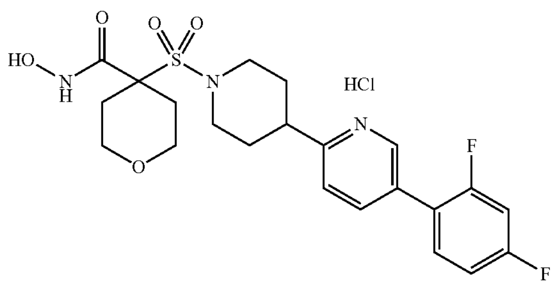 | 482.1561 | 482.1563 | 6780 | 6.36 | 11.3 | 4.26 | 1040 |
| 309 | 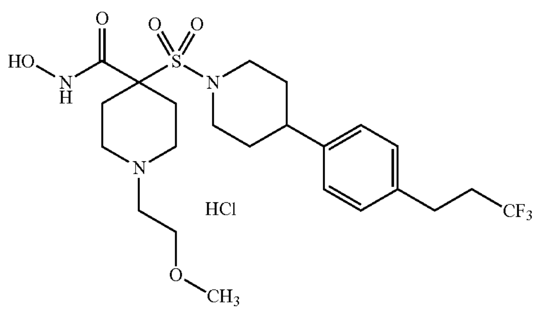 | 522.2244 | 522.2208 | >10000 | 0.328 | 0.102 | 0.355 | 1440 |
| 310 | 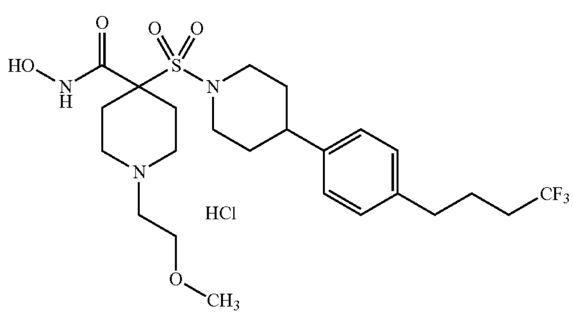 | 536.2401 | 536.2418 | >10000 | 0.919 | 0.346 | 0.268 | 4820 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 311 | 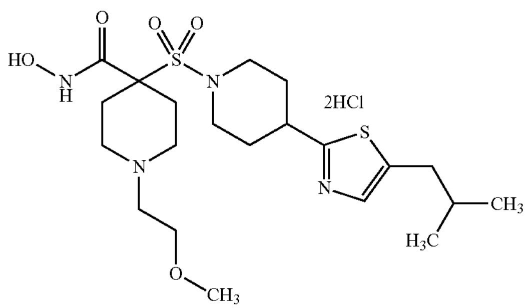 | 487.2043 | 487.2038 | >10000 | 103 | 35.7 | 1.56 | >10000 |
| 312 | 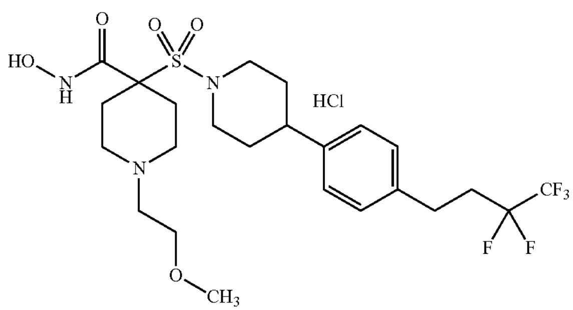 | 572.2212 | 572.2191 | >10000 | 0.52 | 0.24 | 0.2 | 2045 |
| 313 | 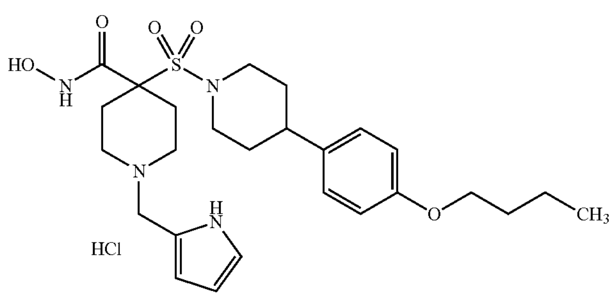 | 520.2588 | 520.2602 | >10000 | 1.47 | 1.89 | 0.44 | 5750 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 314 | 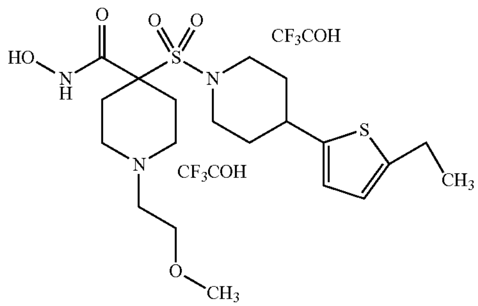 | 460.61 | 461.15 | >10000 | 9.1 | 22 | 19.6 | 1310 |
| 315 | 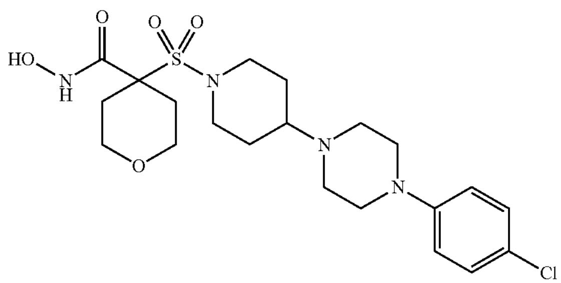 | 487.1776 | 487.1772 | >10000 | 1822.42 | 4958.8 | 419.87 | >10000 |
| 316 | 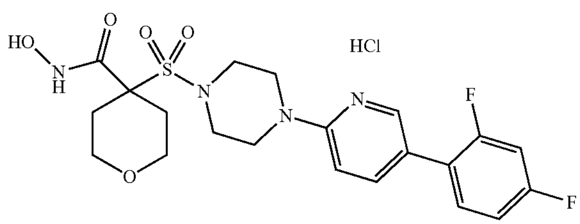 | | | 5520 | 0.73 | 2.39 | 0.77 | 910 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 317 | 2-fluorophenyl pyridine piperazine sulfonyl tetrahydropyran hydroxamic acid, HCl | | | 2410 | 0.55 | 2.18 | 0.71 | 653 |
| 318 | 2-methoxyphenyl pyridine piperazine sulfonyl tetrahydropyran hydroxamic acid, HCl | | | >10000 | 79 | 1380 | 62.3 | 1490 |
| 319 | 3-trifluoromethoxyphenyl pyridine piperazine sulfonyl tetrahydropyran hydroxamic acid, HCl | | | >10000 | 33.1 | 923 | 4.62 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 320 | 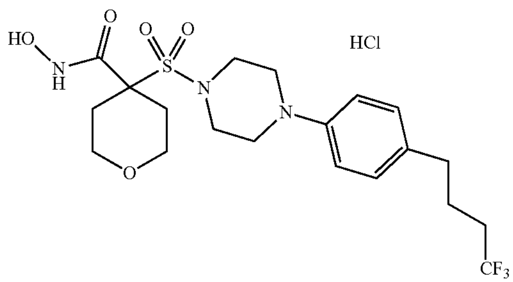 | | | >10000 | 0.842 | 1.33 | 0.501 | 3930 |
| 321 | 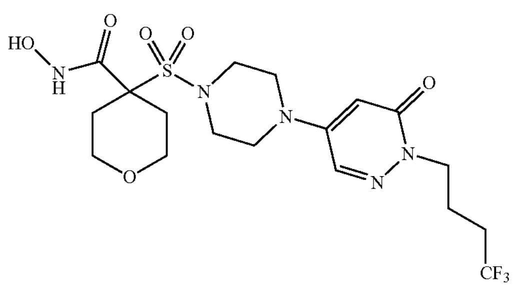 | | | >10000 | >10000 | >10000 | >10000 | >10000 |
| 322 | 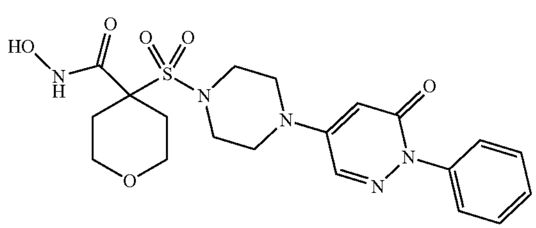 | | | >10000 | 7870 | >10000 | >10000 | >10000 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 323 | 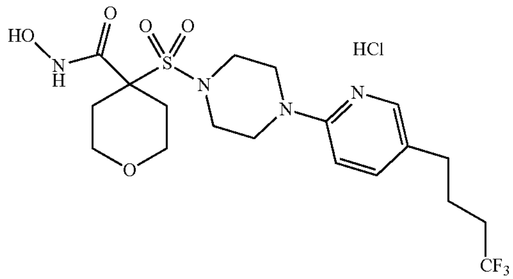 | | | 6210 | 0.50 | 0.09 | 0.65 | 1290 |
| 324 | 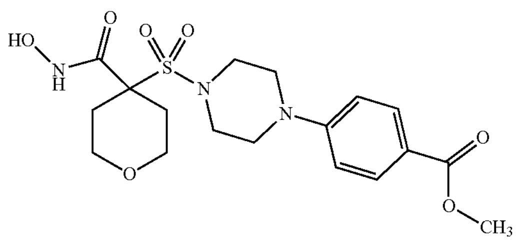 | | | 1860 | 1.22 | 2.39 | 3.55 | 1150 |
| 325 | 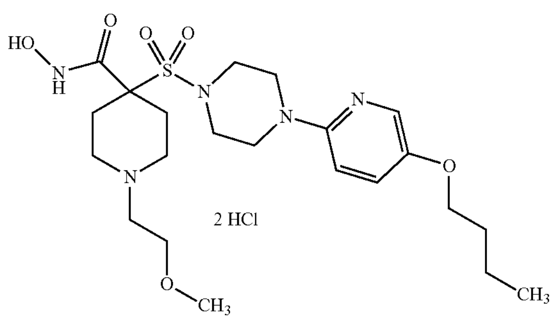 | | | 7510 | 0.18 | 0.32 | 0.09 | 912 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 326 | 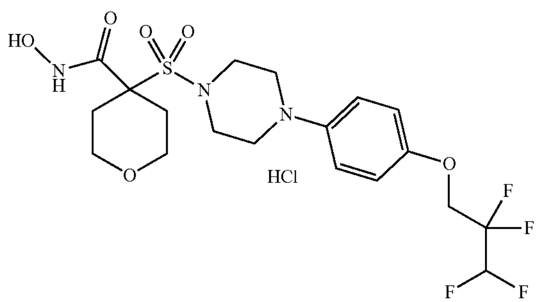 | | | 6580 | 0.34 | 2.03 | 0.31 | 2430 |
| 327 | 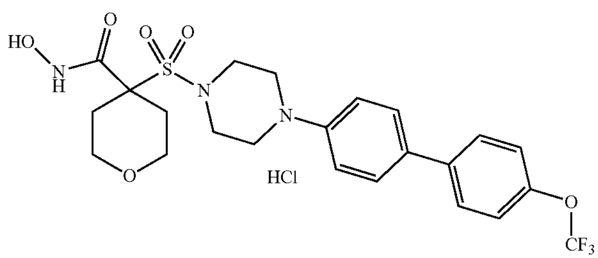 | | | 7300 | 0.97 | 35.6 | 0.499 | 1370 |
| 328 | 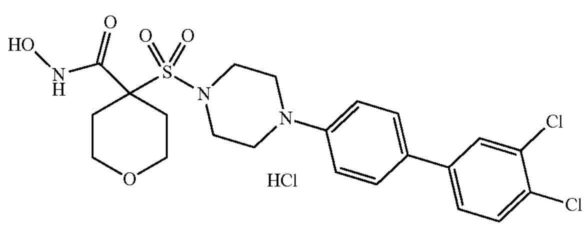 | | | 3720 | 3.58 | 95.7 | 0.71 | 2690 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 329 | 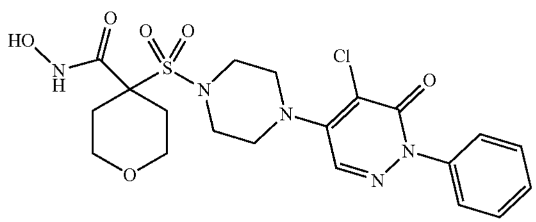 | | | >10000 | >10000 | >10000 | >10000 | >10000 |
| 330 | 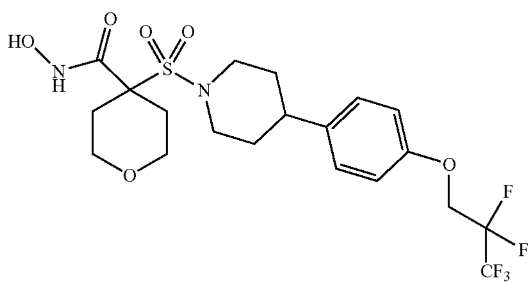 | | | 5360 | 1.18 | 3.03 | 0.92 | >10000 |
| 331 | 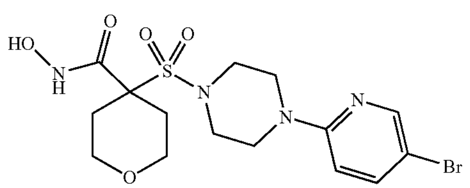 | | | 279 | 0.103 | 1.7 | 0.193 | 13.5 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 332 | 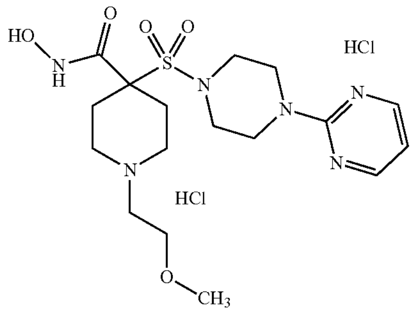 | | | 5110 | 190 | 260 | 28.2 | >10000 |
| 333 | 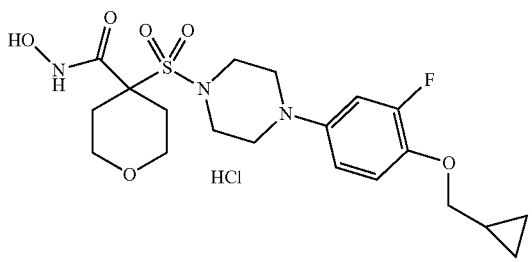 | | | >10000 | 0.58 | 1.05 | 1.12 | 2360 |
| 334 | 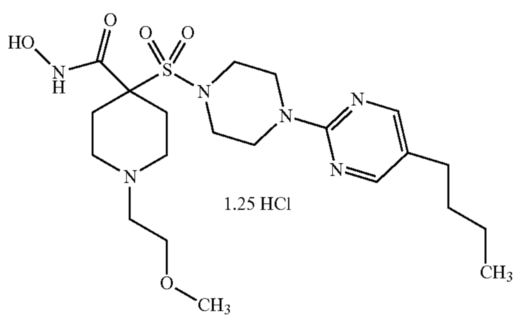 | | | >10000 | 5.99 | 1.19 | 2.75 | 5770 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 335 | 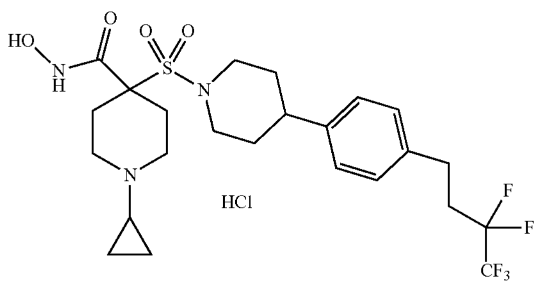 | | | >10000 | 0.618 | 0.384 | 0.489 | 9290 |
| 336 | 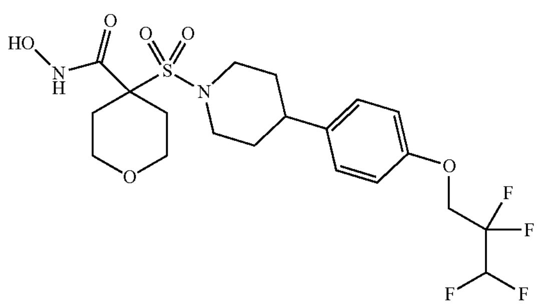 | | | 2640 | 0.606 | 1.38 | 0.522 | 2520 |
| 337 | 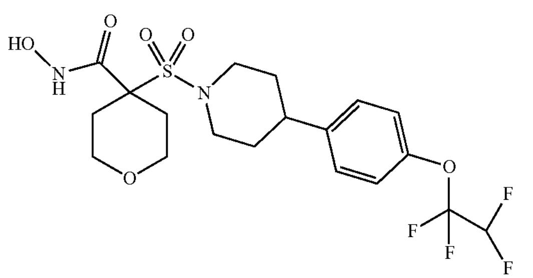 | | | 3290 | 0.427 | 0.792 | 0.708 | 1610 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 338 | 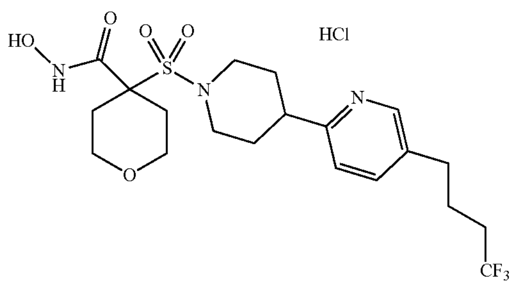 | | | 9860 | 1.09 | 0.738 | 0.302 | 1330 |
| 339 | 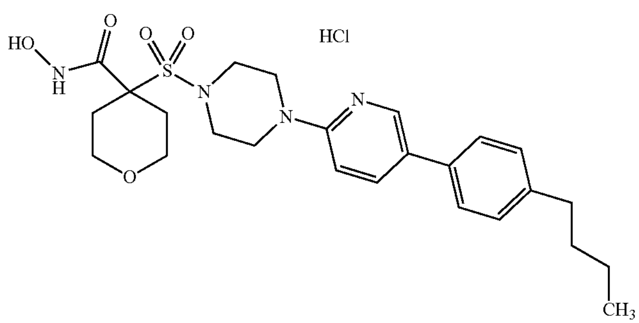 | | | >10000 | 22.9 | 160 | 2.37 | >10000 |
| 340 | 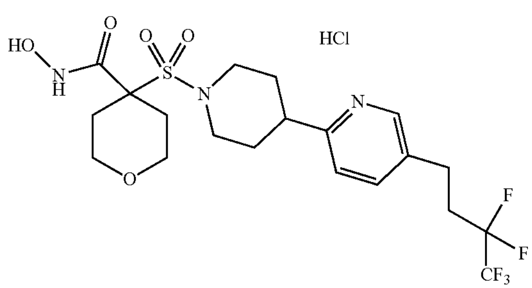 | | | 5860 | 0.26 | 0.222 | 0.107 | 1300 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 341 | (structure) HCl | | | >10000 | 0.829 | 3.77 | 2.59 | 4300 |
| 342 | (structure) HCl | | | >10000 | 16.9 | 108 | 3.89 | >10000 |
| 343 | (structure) HCl | | | 5250 | 0.113 | 0.489 | 0.167 | 34.9 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 344 | 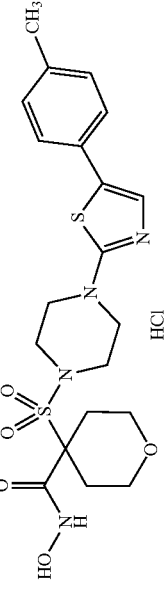 | | | 3520 | 0.177 | 0.492 | 0.267 | 75 |
| 345 | 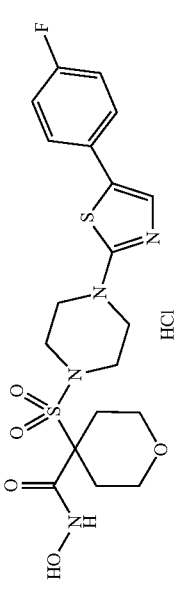 | | | 5540 | 0.169 | 0.416 | 0.236 | 38.1 |
| 346 | 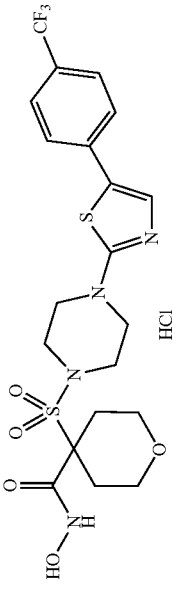 | | | 5690 | 0.215 | 2.05 | 0.167 | 114 |
| 347 | 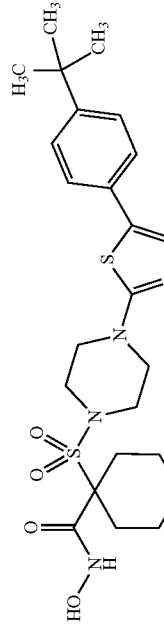 | | | 2770 | 8.57 | 6.38 | 1.48 | 84.6 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 348 | 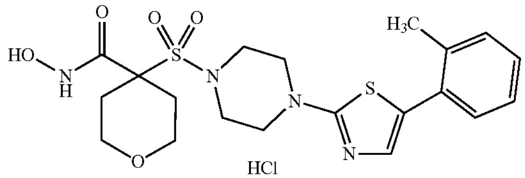 | | | >10000 | 4.61 | 9.57 | 2.99 | 650 |
| 349 | 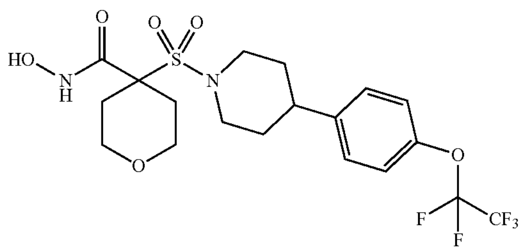 | | | >10000 | 2.12 | 29.2 | 5.08 | >10000 |
| 350 | 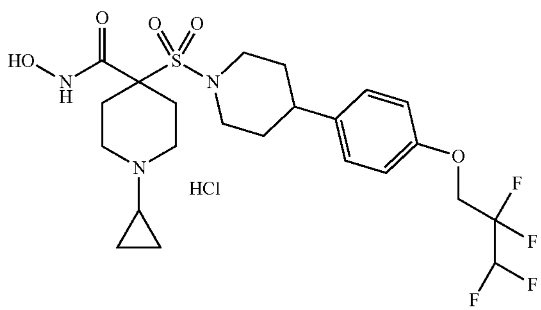 | | | >10000 | 0.891 | 1.21 | 0.523 | 4470 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 351 | 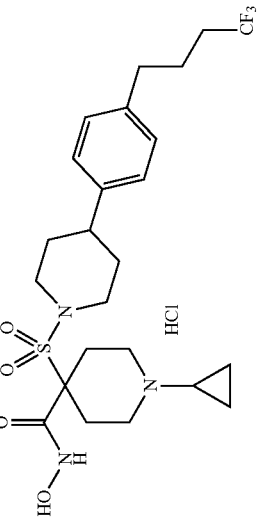 | | | >10000 | 1.26 | 0.431 | 0.359 | 4740 |
| 352 | 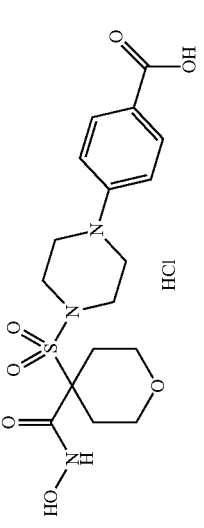 | | | >10000 | 2130 | 6610 | 3640 | >10000 |
| 353 | 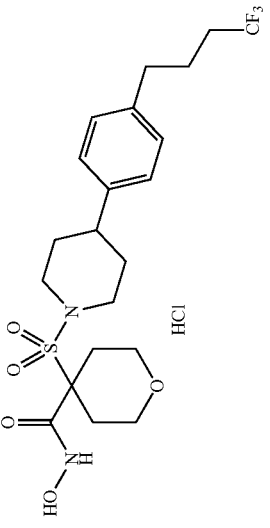 | | | 8580 | 1.29 | 0.546 | 0.378 | 2710 |

TABLE 3-continued
Additional Examples of
Piperazinyl- or Piperidinylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 354 | 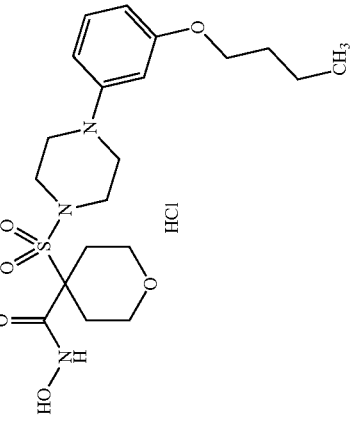 | | | >10000 | 89.4 | 786 | 165 | 4140 |
| 355 | 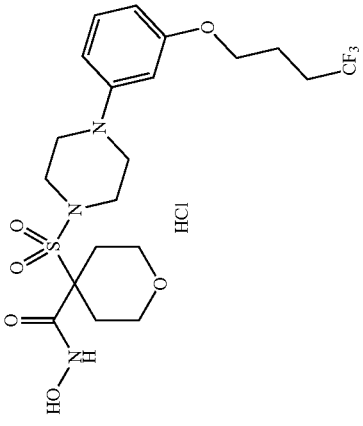 | | | >10000 | 38.3 | 638 | 51.1 | 3440 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 356 | 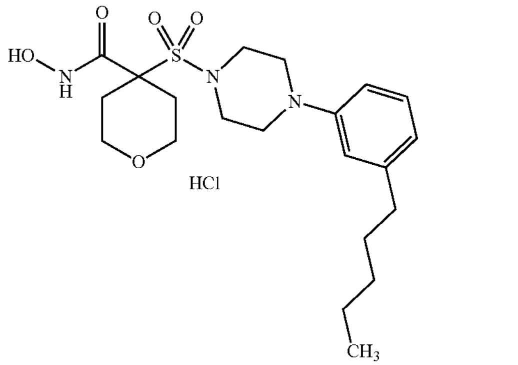 | | | >10000 | 65.7 | 184 | 35.3 | 3420 |
| 357 | 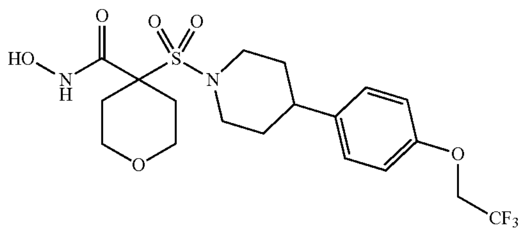 | | | 3780 | 0.919 | 0.718 | 1.2 | 2290 |
| 358 | 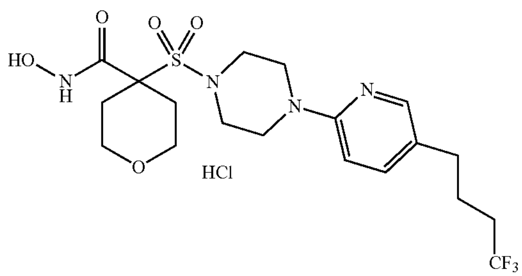 | | | >10000 | 0.281 | 0.86 | 0.15 | 2950 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 359 | (2,4-difluorophenyl-thiazole derivative) HCl | | | 2600 | 0.266 | 1.21 | 0.439 | 42.9 |
| 360 | (biphenyl-thiazole derivative) HCl | | | >2500 | 0.395 | 6.28 | 0.426 | 216 |
| 361 | (styryl-thiazole derivative) HCl | | | >2500, >2500 | 1.37, 1.39 | 36.1, 32.9 | 1.06, 1.07 | 497, 460 |
| 362 | (benzodioxole-thiazole derivative) HCl | | | 2120 | 0.333 | 1.37 | 0.408 | 150 |

TABLE 3-continued

Additional Examples of Piperazinyl- or Piperidinylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 363 | 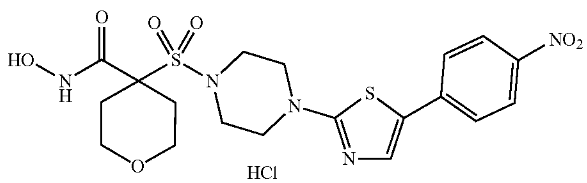 | | | 2350 | 0.056 | 1.74 | 0.076 | 27.8 |
| 364 | 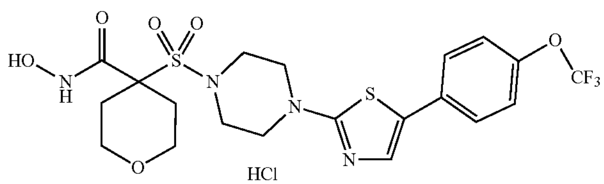 | | | 3940 | 0.187 | 0.802 | 0.106 | 69.7 |
| 365 | 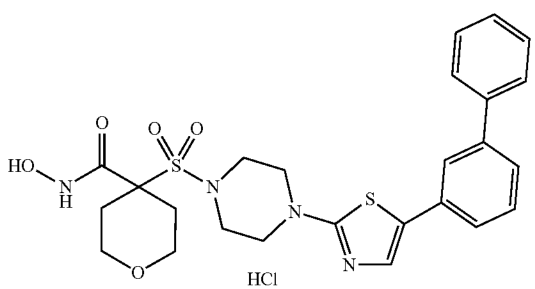 | | | >10000 | 201 | 1240 | 101 | >10000 |
| 366 | 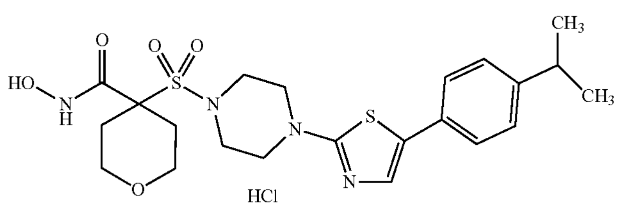 | | | 2160 | 0.264 | 2.44 | 0.182 | 50.3 |

TABLE 3-continued

Additional Examples of
Piperazinyl- or Piperidinylmethyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 367 | 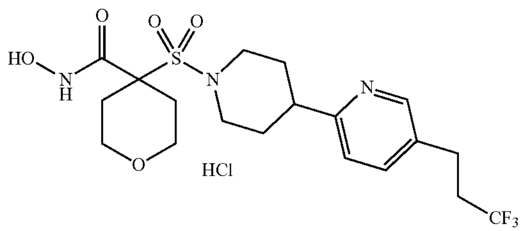 | | | 9760 | 0.978 | 0.625 | 0.835 | 3290 |
| 368 | 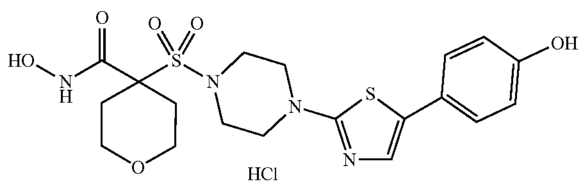 | | | 3350 | 0.225 | 0.423 | 0.329 | 180 |
| 369 | 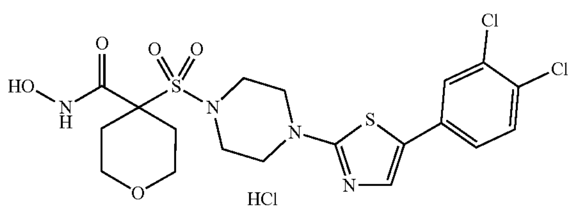 | | | >10000 | 0.879 | 22.7 | 1.35 | 343 |
| 370 | 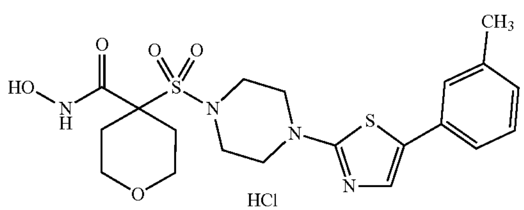 | | | 5740 | 1.34 | 9.1 | 4.16 | 341 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 371 | 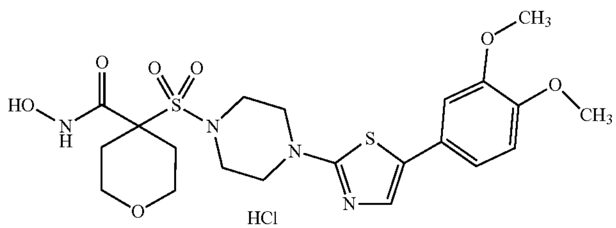 | | | 8250 | 4.14 | 6.5 | 1.35 | 1590 |
| 372 | 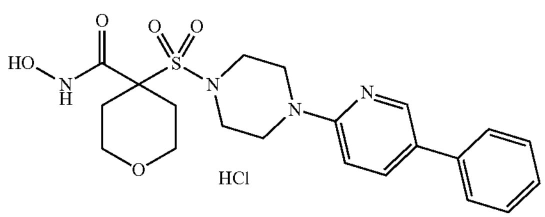 | | | 611, 795 | 0.451, 0.479 | 0.665, 0.750 | 0.485, 0.654 | 462, 470 |
| 373 | 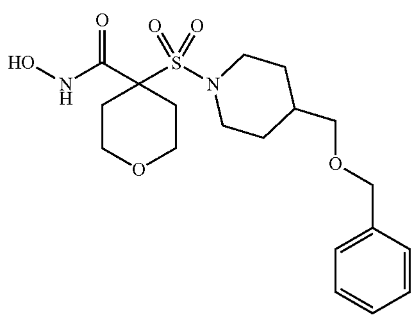 | | | >10000 | 6.12 | 7.65 | 3.37 | 79.7 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K_i (IC-50) | MMP-2 K_i (IC-50) | MMP-9 K_i (IC-50) | MMP-13 K_i (IC-50) | MMP-14 K_i (IC-50) |
|---|---|---|---|---|---|---|---|---|
| 374 | 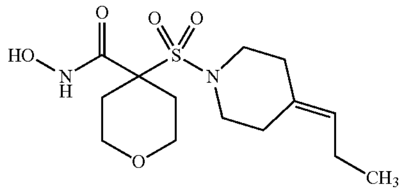 | | | 303 | 18.6 | 219 | 5.72 | 195 |
| 375 | 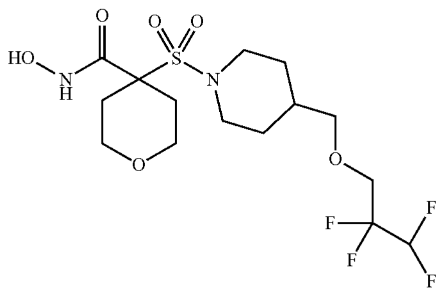 | | | >10000 | 44.1 | 105 | 509 | 2860 |
| 376 | 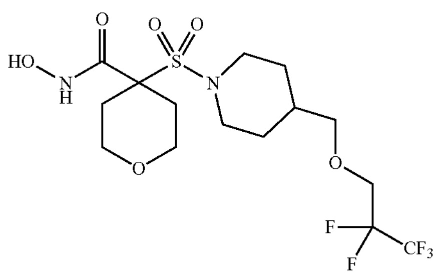 | | | >10000 | 27.1 | 114 | 31.2 | 3120 |

TABLE 3-continued

Additional Examples of Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 377 | 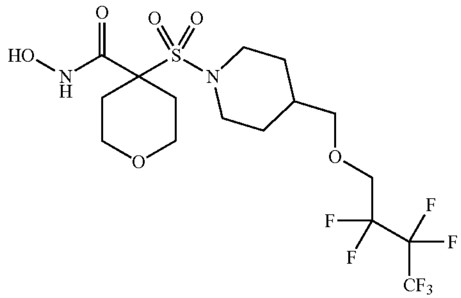 | | | >10000 | 37.5 | 174 | 87.5 | >10000 |
| 378 | 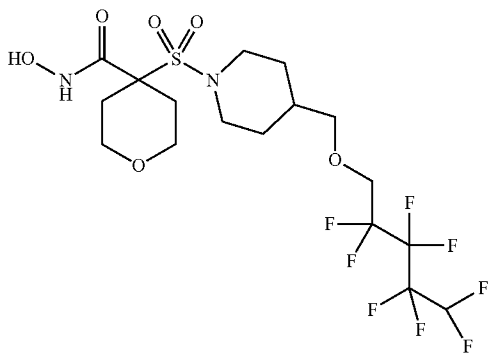 | | | >10000 | 24.8 | 219 | 48.4 | >10000 |
| 379 | 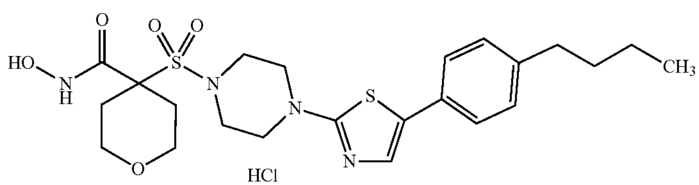 | | | >10000 | 0.14 | 3.97 | 0.167 | 283 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 380 | 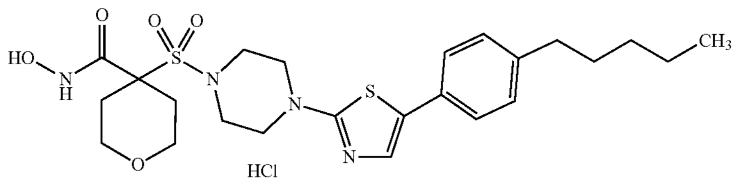 | | | >10000 | 1.39 | 16.2 | 0.651 | 3210 |
| 381 | 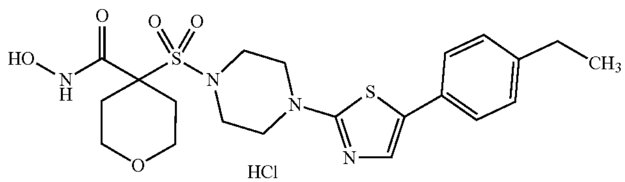 | | | 3250 | 0.209 | 1.03 | 0.074 | 54.1 |
| 382 | 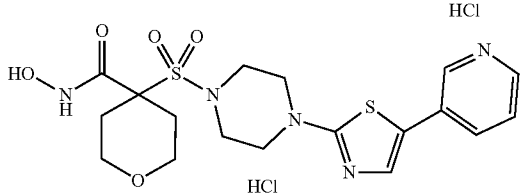 | | | 2690 | 0.68 | 4.26 | 0.647 | 778 |
| 383 | 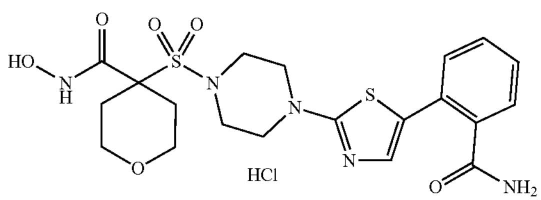 | | | >10000 | 1230 | 9520 | 104 | >10000 |

TABLE 3-continued
Additional Examples of
Piperazinyl- or Piperidinylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 384 | 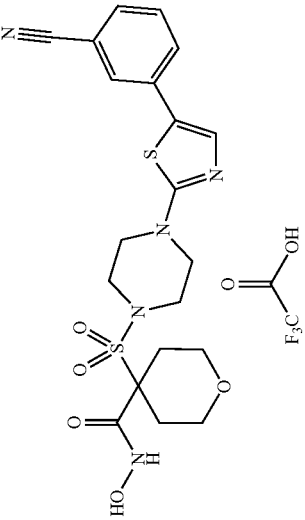 | | | 266 | 0.185 | 6.4 | 0.272 | 867 |
| 385 | 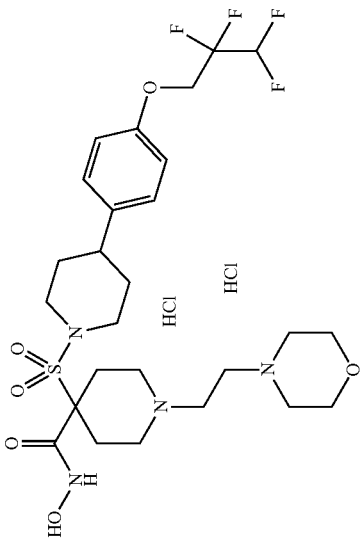 | | | >10000 | 0.573 | 0.829 | 0.378 | 2930 |

TABLE 3-continued

Additional Examples of
Piperazinyl- or Piperidinylmethyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 386 | 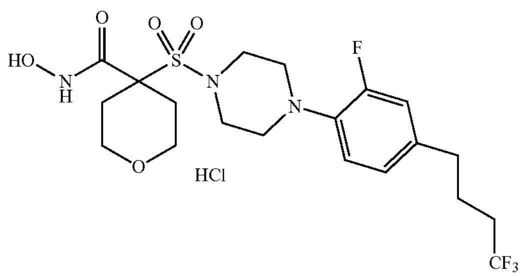 | | | >10000 | 4.88 | 4.9 | 2.29 | >10000 |
| 387 | 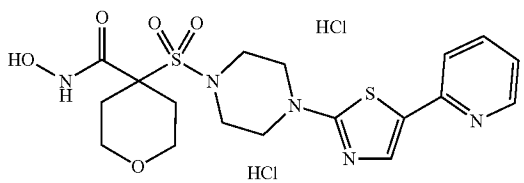 | | | >10000 | 6.71 | 34.6 | 31 | 4550 |
| 388 | 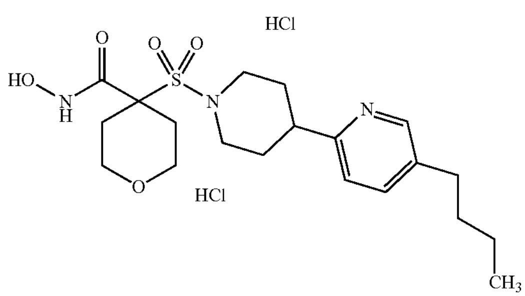 | | | >10000 | 11.2 | 2.3 | 15.1 | >10000 |

TABLE 3-continued

Additional Examples of
Piperazinyl- or Piperidinylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 389 | 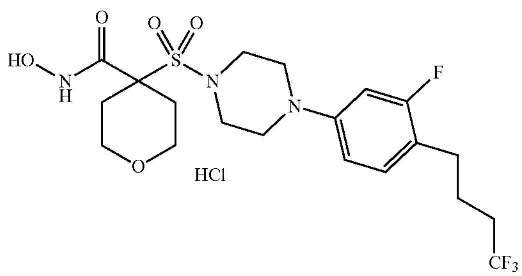 | | | >10000 | 0.38 | 1.34 | 0.47 | 3170 |
| 390 | 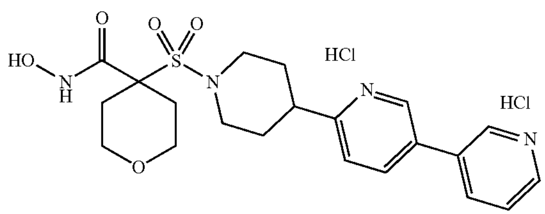 | | | 7880 | 12.3 | 53.2 | 6.72 | >10000 |
| 391 | 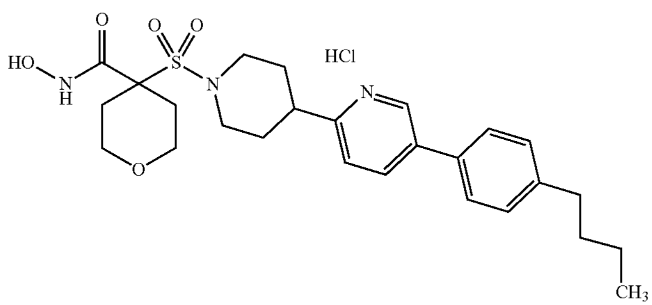 | | | 2370 | 1.93 | 4.44 | 2.48 | 136 |

TABLE 3-continued
Additional Examples of
Piperazinyl- or Piperidinyl-Sulfonylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 392 | 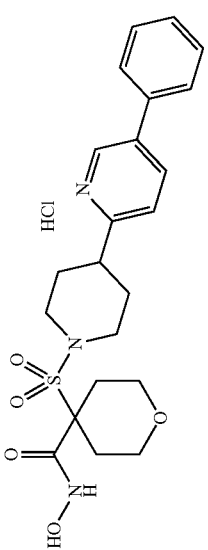 | | | 3430 | 4.02 | 2.33 | 4.23 | 1290 |
| 393 | 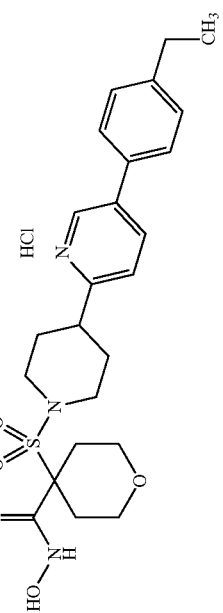 | | | 2500 | 2.23 | 4.86 | 1.09 | 194 |
| 394 | 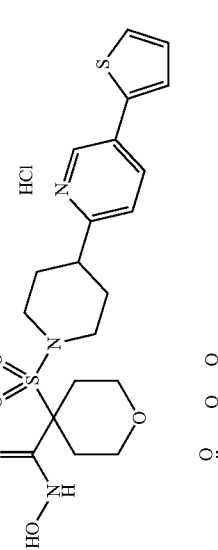 | | | 2750 | 1.8 | 1.52 | 1.73 | 931 |
| 395 | 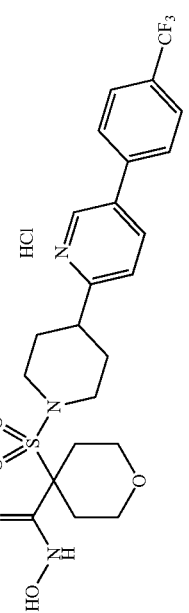 | | | >10000 | 7.17 | 29.4 | 0.89 | 1760 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 396 | 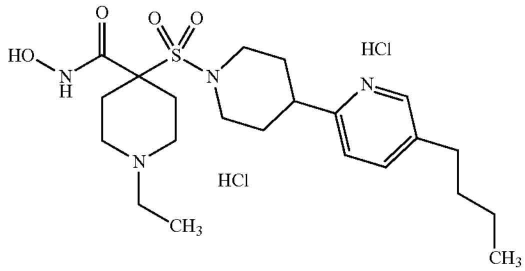 | | | >10000 | 2.32 | 0.39 | 2.19 | 7650 |
| 397 | 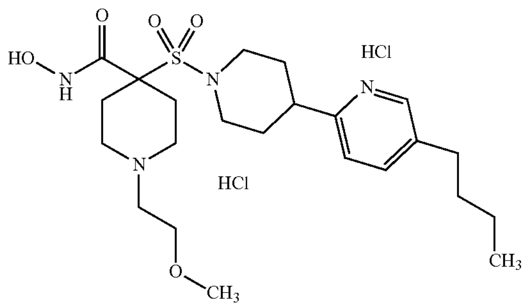 | | | >10000 | 0.69 | 0.09 | 0.54 | 2920 |
| 398 | 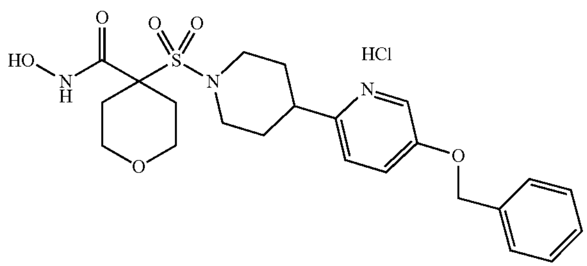 | | | 1950 | 1.31 | 5.67 | 0.15 | 514 |

TABLE 3-continued

Additional Examples of
Piperazinyl- or Piperidinylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 399 | 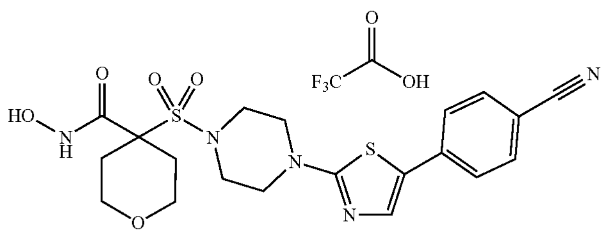 | | | 2500 | 0.05 | 0.57 | 0.04 | 9.69 |
| 400 | 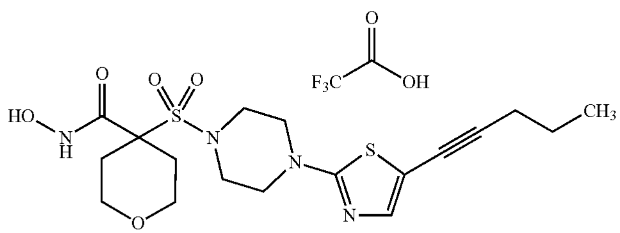 | | | 3320 | 0.71 | 1.4 | 0.28 | 724 |
| 401 | 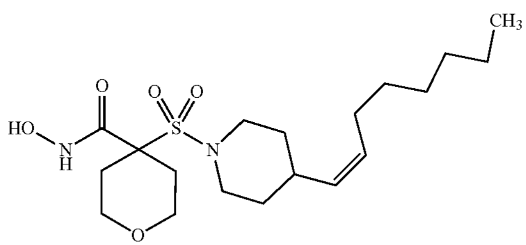 | | | >10000 | 12.8 | 4.22 | 9.05 | 2720 |
| 402 | 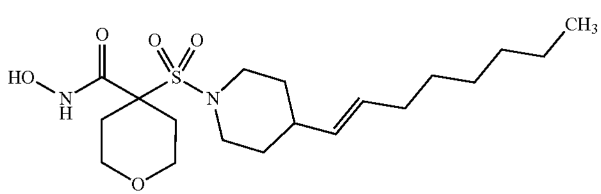 | | | 3650 | 0.83 | 0.19 | 0.58 | |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 403 | 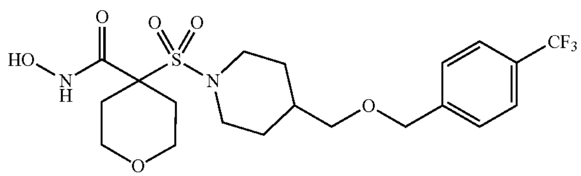 | | | >10000 | 4.96 | 7.37 | 2.47 | 129 |
| 404 | 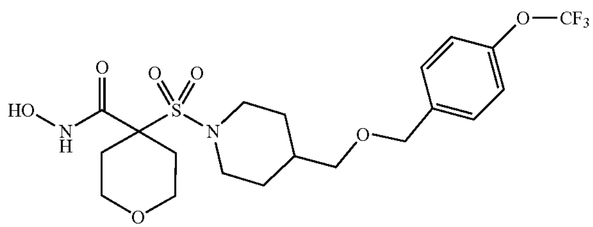 | | | >10000 | 1.41 | 2.29 | 0.33 | 71.8 |
| 405 | 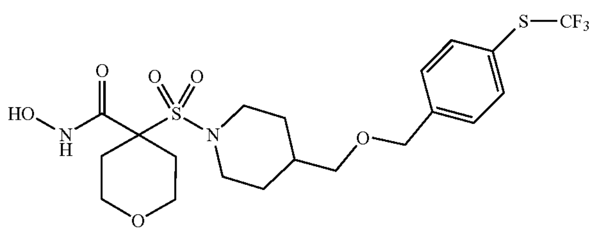 | | | 8320 | 1.27 | 3.39 | 0.18 | 95.7 |
| 406 | 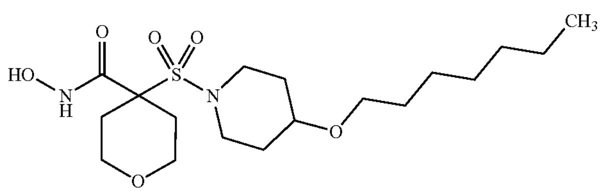 | | | 9010 | 1.76 | 0.76 | 1.28 | 1190 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 407 | (structure with thiophene, F, piperazine, HCl) | | | >10000 | 0.361 | 1.9 | 0.78 | 3030 |
| 408 | (structure with pyrrolidinyl-pyridine, piperazine, HCl) | | | >10000 | 6.48 | 10.2 | 11 | 1050 |
| 409 | (structure with pyridine, piperidine, HCl) | | | >10000 | 24.3 | 13.6 | 22.3 | 1770 |
| 410 | (structure with propoxy-pyridine, piperidine, HCl) | | | 3490 | 0.55 | 0.55 | 0.20 | 1360 |

TABLE 3-continued
Additional Examples of Piperazinyl- or Piperidinylmethyl Hydroxamic acid Compounds
| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 411 | 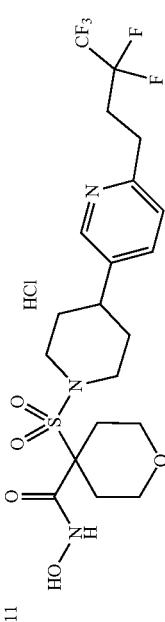 | | | >10000 | 15.3 | 2.04 | 7.75 | >10000 |
| 412 | 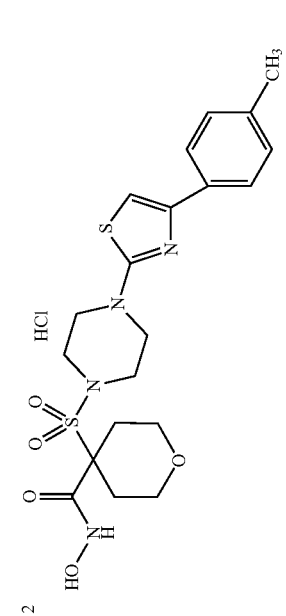 | | | >10000 | >10000 | >10000 | >10000 | >10000 |
| 413 | 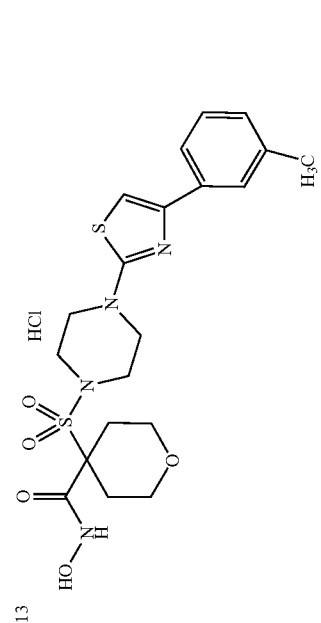 | | | >10000 | 6010 | >10000 | 4830 | >10000 |

TABLE 3-continued
Additional Examples of
Piperazinyl- or Piperidinylmethyl-Sulfonylmethyl Hydroxamic acid Compounds
| Ex. | Structure | Calc. Mass | Observed Mass | MMP-1 K$_i$ (IC-50) | MMP-2 K$_i$ (IC-50) | MMP-9 K$_i$ (IC-50) | MMP-13 K$_i$ (IC-50) | MMP-14 K$_i$ (IC-50) |
|---|---|---|---|---|---|---|---|---|
| 414 | 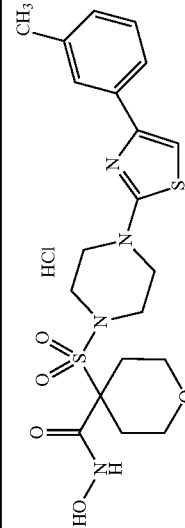 | | | >10000 | 2660 | >10000 | 4190 | >10000 |
| 415 | 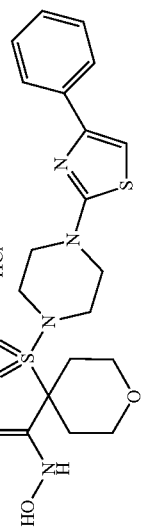 | | | >10000 | 2880 | >10000 | 2420 | >10000 |
| 416 | 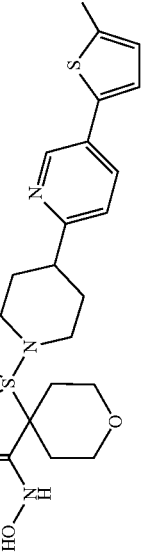 | | | 6420 | 2.07 | 1.49 | 1.35 | 506 |
| 417 | 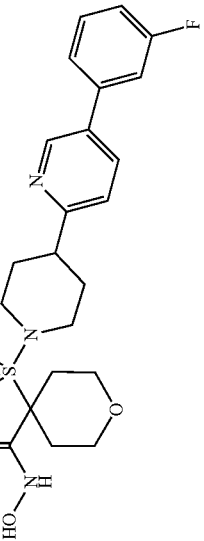 | | | 1830 | 4.13 | 4.1 | 3.84 | 1300 |

TABLE 3-continued

Additional Examples of
Piperazinyl- or Piperidinyl-Sulfonylmethyl Hydroxamic acid Compounds

| Ex. | Structure | Calc. Mass | Observed Mass | MMP-1 $K_i$ (IC-50) | MMP-2 $K_i$ (IC-50) | MMP-9 $K_i$ (IC-50) | MMP-13 $K_i$ (IC-50) | MMP-14 $K_i$ (IC-50) |
|---|---|---|---|---|---|---|---|---|
| 418 | 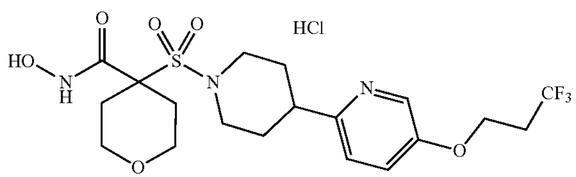 | | | 3080 | 0.97 | 1.86 | 0.46 | 5360 |
| 419 | 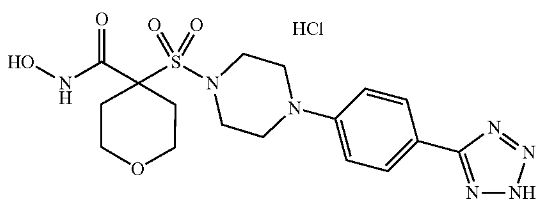 | | | >10000 | 27.9 | 112 | 34 | >10000 |
| 420 | 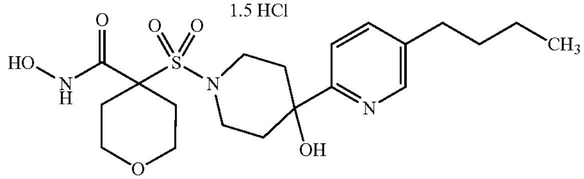 | | | >10000 | 181 | 80.3 | 175 | >10000 |

Examples A1–A67

Examples A1 thru A69 provide additional illustrations for preparing compounds of this invention.

Example A1

Preparation of 4-(4-benzyloxymethyl-piperidine-1-sulfonyl)tetrahydro-pyran-4-carboxylic acid hydroxyamide

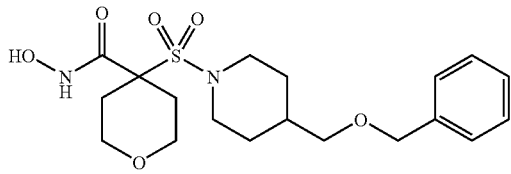

Part A. Preparation of 4-hydroxymethyl-piperidine-1-carboxylic acid tert-butyl ester:

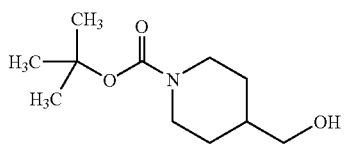

A 500 mL round-bottom flask was charged with 4-piperidinyl methanol (25.2 g, 0.22 mol) and tetrahydrofuran (125 mL). Triethylamine (33.6 mL, 0.24 mol) was added, and the flask was immersed into an ice bath. A solution of di-tert-butyl dicarbonate (50.2 g, 0.23 mol) in tetrahydrofuran (50 mL) was then added dropwise, maintaining the temperature at less than −5° C. After complete addition, the ice bath was removed and the reaction mixture was stirred overnight (18 hr). The solvent was subsequently removed in vacuo, and the residue was partitioned between ethyl acetate (300 mL) and water (150 mL). The organic layer was separated, washed with 5% HCl aqueous solution (150 mL), washed with water (150 mL), and washed with brine (150 mL). The organic layer was then dried over magnesium sulfate, filtered, and concentrated in vacuo. The crude product was triturated with hexane to form a white crystalline solid. The solid was collected by vacuum filtration, and further dried in vacuo to produce 42.7 g of a white crystalline solid product (91% yield). $^1$H NMR (CDCl$_3$) δ 1.13 (m, 2H), 1.45 (s, 9H), 1.55–1.75 (m, 3H), 2.70 (m, 2H), 3.49 (d, J=6 Hz, 2H), 4.12 (br d, J=13.5 Hz, 2H); electrospray mass spectrometry showed m/z=116 (M-Boc+H).

Part B. Preparation of 4-benzyloxymethyl-piperidine-1-carboxylic acid tert-butyl ester:

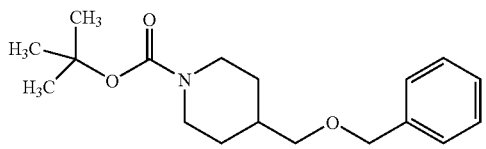

A 500 mL round-bottom flask was charged with 60% NaH oil dispersion (7.82 g, 0.2 mol) and dimethylformamide (150 mL). The flask was immersed into an ice water bath. To this suspension was added dropwise a solution of the product from Part A (35 g, 0.16 mol) in dimethylformamide (100 mL), maintaining the temperature at less than 5° C. After complete addition, the mixture was warmed to room temperature and stirred for 45 min. The flask was again immersed into an ice water bath, and a solution of benzyl bromide (25.2 mL, 0.212 mol) in dimethylformamide (25 mL) was added dropwise into the reaction mixture. After complete addition, the flask was removed from the ice bath, and the reaction mixture was warmed to 60° C. for 4 hr. The flask was then cooled to room temperature and stirred overnight. The reaction mixture was poured into 1.5 L ice water, and the aqueous layer was extracted twice with ethyl acetate (250 mL). The combined organic layers were washed with brine (400 mL), dried over magnesium sulfate, filtered, and concentrated in vacuo to afford 52.9 g of a yellow oil product. Electrospray mass spectrometry showed m/z=206 (M-Boc+H).

Part C. Preparation of 4-benzyloxymethyl-piperidine:

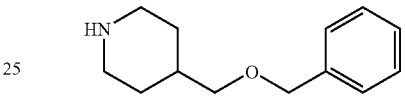

The product from Part B (52.9 g) was dissolved in 1,4-dioxane (100 mL) in a 500 mL round-bottom flask, and 4 N HCl in 1,4-dioxane (120 mL, 0.48 mol) was added. The reaction mixture was stirred at room temperature for 1 hr. Volatiles were removed in vacuo, and the residue was triturated with hexane. A white solid formed, which was collected by vacuum filtration, further washed with hexane, and dried in vacuo. The solid was partitioned between ethyl acetate (400 mL) and 10% potassium carbonate/water (400 mL). The organic layer was separated, dried over magnesium sulfate, filtered, and concentrated in vacuo to afford 18.4 g of a yellow oil product (55% yield over two reaction steps). $^1$H NMR (CDCl$_3$) δ 1.14 (m, 2H), 1.70–1.80 (m, 3H), 2.58 (m, 2H), 3.06 (br d, J=12 Hz, 2H), 3.29 (d, J=6 Hz), 4.48 (s, 2H), 7.25–7.35 (m, 5H); Electrospray mass spectrometry showed m/z=206 (M+H).

Part D. Preparation of 4-benzyloxymethyl-1-methanesulfonyl-piperidine:

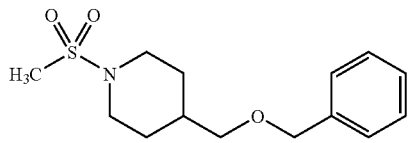

A 250 mL round-bottom flask was charged with the product from Part C (18.3 g, 89 mmol), dichloromethane (175 mL), and triethylamine (15 mL, 107 mmol). The flask was immersed into an ice water bath. A solution of methanesulfonyl chloride (7.2 mL, 93 mmol) in dichloromethane (25 mL) was then added dropwise, causing the temperature to be maintained at from 5 to 10° C. After complete addition, the flask was slowly warmed to room temperature and stirred for 18 hr. The reaction mixture was then washed sequentially with water (250 mL), 5% HCl (250 mL), and water (250 mL). The organic layer was dried over magnesium sulfate, filtered, and concentrated in vacuo to afford 23.7 g of a tan solid product (94% yield). ¹H NMR (CDCl₃) δ 1.35 (m, 2H), 1.73 (m, 1H), 1.86 (br d, J=12.8 Hz, 2H), 2.66 (m, 2H), 2.75 (s, 3H), 3.32 (d, J=6.4 Hz, 2H), 3.79 (br d, J=11.6 Hz, 2H), 4.49 (s, 2H), 7.25–7.35 (m, 5H); Electrospray mass spectrometry showed m/z=284 (M+H).

Part E. Preparation of (4-benzyloxymethyl-piperidine-1-sulfonyl)-acetic acid tert-butyl ester:

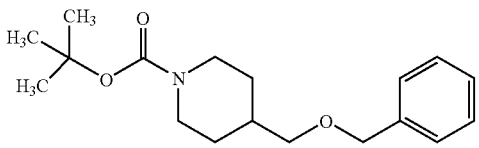

A 1 liter round-bottom flask was charged with the product from Part D (23.4 g, 83 mmol) and tetrahydrofuran (100 mL). The flask was immersed into a dry ice/acetone bath. A 1 M solution of lithium bis(trimethylsilyl)amide in tetrahydrofuran (0.25 L, 0.25 mol) was then added via an addition funnel at a rate which caused the temperature to be maintained at from −70 to −65° C. After complete addition, the reaction mixture was stirred for 10 min with cooling. A solution of di-tert-butyl dicarbonate (18.9 g, 86.7 mmol) in tetrahydrofuran (25 mL) was then added dropwise, maintaining temperature at from −70 to −65° C. After complete addition, the reaction flask was immersed into an ice water bath and stirred for 30 min. The reaction was subsequently quenched by careful addition of saturated ammonium chloride (200 mL). Afterward, the organic layer was separated, and the aqueous layer was extracted twice with ethyl acetate (250 mL). The combined organic layers were washed with 5% HCl (2×200 mL) and brine (200 mL). The organic layer was then dried over magnesium sulfate, filtered, and concentrated in vacuo to afford 29.4 g of a tan crystalline solid product (93% yield). ¹H NMR (CDCl₃) δ 1.32 (m, 2H), 1.48 (s, 9H), 1.64 (m, 1H), 1.82 (br d, J=13.6 Hz, 2H), 2.85 (m, 2H), 3.32 (d, J=6.8 Hz, 2H), 3.80 (s, 2H), 3.82 (br d, J=13 Hz, 2H), 4.48 (s, 2H), 7.25–7.35 (m, 5H); Electrospray mass spectrometry showed m/z=384 (M+H).

Part F. Preparation of 4-(4-benzyloxymethyl-piperidine-1-sulfonyl)-tetrahydro-pyran-4-carboxylic acid tert-butyl ester:

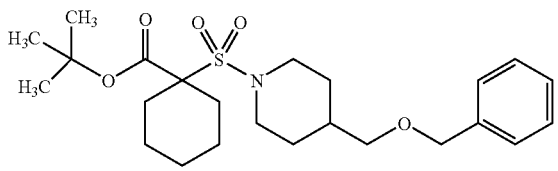

A 500 mL round-bottom flask was charged with the product from Part E (29.1 g, 76 mmol), dimethylformamide (125 mL), 18-crown-6 (6 g, 22.8 mmol), potassium carbonate (31.5 g, 228 mmol), and 2-bromoethyl ether (11.7 mL, 83.5 mmol). The resulting mixture was heated to 60° C. with vigorous stirring for 44 hr. After cooling to room temperature, the reaction mixture was poured into 500 mL ice water. The mixture was then extracted with ethyl acetate (300 mL). Afterward, the organic layer was washed with brine (400 ml). The organic layer was then dried over magnesium sulfate, filtered, and concentrated in vacuo to form 40 g of a dark yellow oil. Purification via flash column chromatography on silica gel (3×6 inch column) afforded 30.2 g of a yellow oil product (88% yield). ¹H NMR (CDCl₃) δ 1.30 (m, 2H), 1.50 (s, 9H), 1.77 (m, 3H), 2.10 (dt, J=4.6, 12.6 Hz, 2H), 2.31 (d, J=11.6 Hz, 2H), 2.94 (t, J=12.4 Hz, 2H), 3.25–3.33 (m, 4H), 3.77–3.84 (m, 2H), 3.95 (dd, J=4.2, 11.1, 2H), 4.48 (s, 2H), 7.25–7.35 (m, 5H); Electrospray mass spectrometry showed m/z=454 (M+H).

Part G. Preparation of 4-(4-benzyloxymethyl-piperidine-1-sulfonyl)-tetrahydro-pyran-4-carboxylic acid:

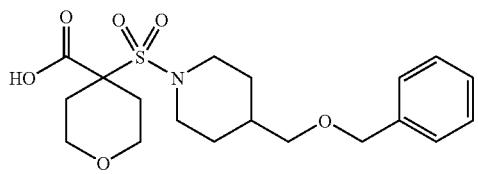

A 2-dram glass vial was charged with the product from Part F (302 mg, 0.67 mmol), dichloromethane (1 mL), and trifluoroacetic acid (1 mL). The vial was capped, and the mixture was stirred at room temperature for 2 hr. The solvent was then removed in vacuo, and the product was precipitated with diethyl ether/hexane (1:1). The white crystalline precipitate was collected by vacuum filtration and dried in vacuo. The yield after drying overnight was 210 mg (79% yield). Electrospray mass spectrometry showed m/z=398 (M+H).

Part H. Preparation of 4-(4-benzyloxymethyl-piperidine-1-sulfonyl)-tetrahydro-pyran-4-carboxylic acid (tetrahydro-pyran-2-yloxy)-amide:

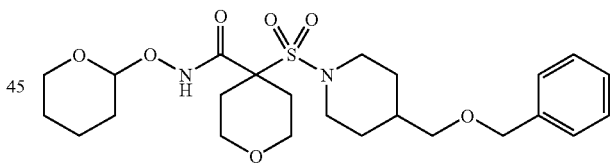

A 2-dram glass vial was charged with the product from Part G (210 mg, 0.53 mmol), a 0.5 M solution of hydroxybenzotriazole in dimethylformamide (2.1 mL, 1.05 mmol), a 0.5 M solution of tetrahydropyanyl hydroxylamine in dimethylformamide (2.1 mL, 1.05 mmol), ethyl 3-(dimethylamino)propyl carbodiimide hydrochloride (182 mg, 1.05 mmol), and triethylamine (294 uL, 2.1 mmol). The resulting mixture was stirred at room temperature for 18 hr, and then partitioned between ethyl acetate (5 mL) and water (5 mL). The organic layer was washed with 5% HCl (5 mL) and filtered through a pad of celite. The filtrate was concentrated in vacuo and purified by preparative reversed-phase high-pressure liquid chromatography using a gradient of 10–90% acetonitrile/water with 0.05% trifluoroacetic acid. This afforded 133 mg of a white solid product. Electrospray mass spectrometry showed m/z=497 (M+H).

Part I. Preparation of 4-(4-benzyloxymethyl-piperidine-1-sulfonyl)-tetrahydro-pyran-4-carboxylic acid hydroxyamide:

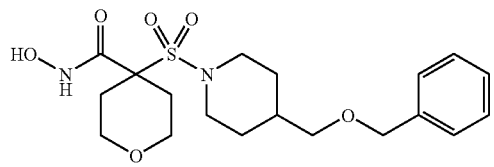

A 2-dram glass vial was charged with the product from Part H (133 mg, 0.27 mmol), 1,4-dioxane (1 mL), and methanol (1 mL). A 4 N solution of HCl in dioxane (0.1 mL, 0.4 mmol) was added, and the mixture was stirred at room temperature for 10 min. Volatiles were removed in vacuo, leaving 116 mg of a white crystalline solid product (61% yield over two reaction steps). $^1$H NMR (DMSO-d6) δ 1.12 (m, 2H), 1.64 (d, J=12 Hz, 2H), 1.69 (m, 1H), 1.83 (td, J=4.4, 12.8 Hz, 2H), 2.30 (d, J=13.2 Hz, 2H), 2.88 (t, J=11.6 Hz, 2H), 3.15 (t, J=11.4 Hz, 2H), 3.25 (d, J=6 Hz, 2H), 3.29 (s, 2H), 3.57 (d, J=12.4 Hz, 2H), 3.81 (dd, J=3.6, 11.6 Hz, 2H), 9.12 (s, 1H), 10.93 (s, 1H); Electrospray mass spectrometry showed m/z=413 (M+H). High-resolution mass spectroscopy: calculated for $C_{19}H_{29}N_2O_6S$: 413.1741; observed: 413.1745.

Example A2

Preparation of 4-(4-hydroxymethyl-piperidine-1-sulfonyl)-tetrahydro-pyran-4-carboxylic acid tert-butyl ester

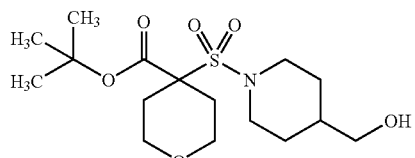

A thick-walled glass pressure vessel containing 10% palladium on carbon (1 g, 0.94 mmol) was charged with a solution of the ester from Example A1, Part F (5 g, 11 mmol) in ethyl acetate (100 mL). The flask was placed on a Parr shaker under 40 PSI hydrogen and agitated for 15 hr at room temperature. The resulting mixture was then filtered through a pad of celite. Afterward, the filtrate was concentrated in vacuo. Purification by flash column chromatography (40–75% ethyl acetate/hexane) afforded 3.21 g of a colorless crystalline solid product (80% yield). Electrospray mass spectrometry showed m/z=364 (M+H). $^1$H NMR (CDCl$_3$) δ 1.28 (m, 2H), 1.51 (s, 9H), 1.63 (m, 1H), 1.173 (br d, J=12.8 Hz, 2H), 2.10 (td, J=4.6, 12.6 Hz, 2H), 2.31 (d, J=11.2 Hz, 2H), 2.94 (td, J=2.4, 12.6 Hz, 2H), 3.29 (td, J=1.8, 12.2 Hz, 2H), 3.48 (t, J=5.6 Hz, 2H), 3.81 (m, 2H), 3.82 (dd, J=4.2, 11.4 Hz, 2H).

Example A3

Preparation of 4-(4-methanesulfonyloxymethyl-piperidine-1-sulfonyl)-tetrahydro-pyran-4-carboxylic acid tert-butyl ester

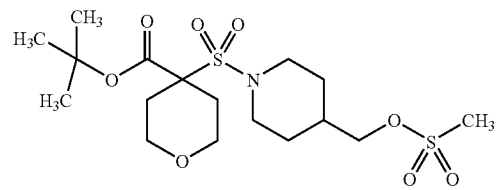

A 100 mL round-bottom flask was charged with the alcohol from Example A2 (1.18 g, 3.25 mmol) and dichloromethane (8 mL). Diisopropylethylamine (0.85 mL, 4.9 mmol) was then added dropwise. The flask was immersed into an ice water bath, and methanesulfonyl chloride (0.3 mL, 3.9 mmol) was added dropwise while maintaining temperature of the mixture at less than 5° C. The reaction mixture was then stirred with cooling for 2 hr. Afterward, the flask was removed from the cooling bath. Upon warming to room temperature, the reaction mixture was partitioned between 50 mL dichloromethane and 50 mL water. The organic layer was separated, washed with 5% HCl aqueous solution, dried over magnesium sulfate, filtered, and concentrated in vacuo. This afforded 1.38 g of a yellow solid product (96% yield). $^1$H NMR (CDCl$_3$) δ 1.37 (m, 2H), 1.52 (s, 9H), 1.78 (d, J=12.8 Hz, 2H), 1.92 (m, 1H), 2.11 (td, J=4.5, 12.6 Hz, 2H), 2.31 (d, J=12.8 Hz, 2H), 2.96 (t, J=12 Hz, 2H), 3.00 (s, 3H), 3.30 (t, J=11 Hz, 2H), 3.85 (m, 2H), 3.96 (dd, J=4, 11.6 Hz, 2H), 4.06 (d, J=6.4 Hz, 2H); Electrospray mass spectrometry showed m/z=459 (M+H).

Example A4

Preparation of 4-(4-formyl-piperidine-1-sulfonyl)-tetrahydro-pyran-4-carboxylic acid tert-butyl ester

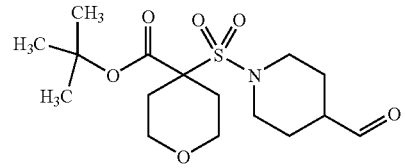

Part A. Preparation of 4-(4-methoxymethylene-piperidine-1-sulfonyl)-tetrahydro-pyran-4-carboxylic acid tert-butyl ester:

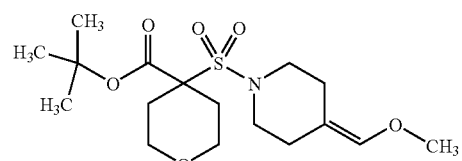

A 100 mL round-bottom flask was charged with (methoxymethyl)triphenylphosphonium chloride (4.11 g, 12 mmol) and tetrahydrofuran (50 mL). This resulted in a white slurry. The flask was then immersed into an ice bath, and a 1 M solution of lithium bis(trimethylsilyl)amide in tetrahydrofuran (13 mL, 13 mmol) was added dropwise while maintaining the temperature at less than 5° C. After complete addition, the reaction mixture was stirred with cooling for 15 min. A solution of 4-(4-oxo-piperidine-1-sulfonyl)-tetrahydro-pyran-4-carboxylic acid tert-butyl ester (3.47 g, 10 mmol) in tetrahydrofuran (20 mL) was then added dropwise, maintaining the temperature at less than 5° C. After complete addition, the flask was slowly warmed to room temperature and stirred for 72 hr. Diethyl ether was then added to the reaction mixture (200 mL), resulting in precipitation of a brown solid. The solid was filtered, and the filtrate was washed with 5% HCl solution (3×100 mL), saturated aqueous sodium bicarbonate (3×100 mL), and brine (100 mL). The organic layer was dried over magnesium sulfate, filtered, and concentrated in vacuo. Purification by flash column chromatography (20–40% ethyl acetate/hexane) afforded 2.82 g of a colorless crystalline solid product (75% yield). $^1$H NMR (CDCl$_3$) δ 1.51 (s, 9H), 2.05–2.15 (m, 4H), 2.31 (m, 4H), 3.29 (m, 6H), 3.54 (s, 3H), 3.95 (dd, J=4.2, 11.4 Hz, 2H), 5.84 (s, 1H); Electrospray mass spectrometry showed m/z=376 (M+H).

Part B. Preparation of 4-(4-formyl-piperidine-1-sulfonyl)-tetrahydro-pyran-4-carboxylic acid tert-butyl ester:

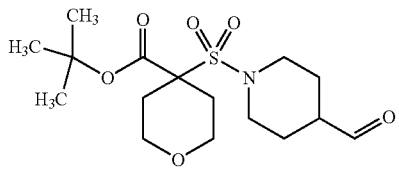

A 100 mL round-bottom flask was charged with the product from Part A (1.64 g, 4.37 mmol), tetrahydrofuran (16 mL), and a 5% solution of HCl in water (2 mL). The resulting mixture was heated to 50° C. for 2 hr, cooled to room temperature, and partitioned between ethyl acetate (100 mL) and saturated aqueous sodium bicarbonate. The organic layer was washed with brine (100 mL), filtered, and concentrated in vacuo to afford 1.64 g of a white crystalline solid product (100% yield). $^1$H NMR (CDCl$_3$) δ 1.51 (s, 9H), 1.72 (m, 2H), 1.95 (m, 2H), 2.10 (td, J=4.8, 12.6 Hz, 2H), 2.30 (d, J=12.4 Hz, 2H), 2.41 (m, 1H), 3.11 (m, 2H), 3.29 (td, J=1.8, 12.2 Hz, 2H), 3.70 (m, 2H), 3.96 (dd, J=4.4, 11.6 Hz, 2H), 9.65 (s, 1H); Electrospray mass spectrometry showed m/z=394 (M+Na).

Example A5

Preparation of 4-(4-hydroxy-piperidine-1-sulfonyl)-tetrahydro-pyran-4-carboxylic acid tert-butyl ester

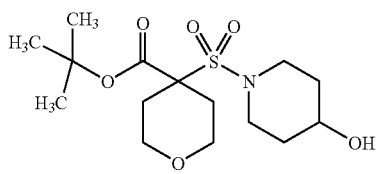

A 250 mL round-bottom flask was charged with 4-(4-oxo-piperidine-1-sulfonyl)-tetrahydro-pyran-4-carboxylic acid tert-butyl ester (10 g, 29 mmol) and methanol (100 mL). The resulting slurry was rapidly stirred with an overhead-stirring paddle, and the flask was immersed into an ice bath. Sodium borohydride (1.09 g, 29 mmol) was added in three portions over 15 min. After complete addition, the homogeneous mixture was warmed to room temperature and stirred for 30 min. The flask was again immersed into an ice water bath, and the reaction was quenched by careful addition of a saturated ammonium chloride solution (25 mL). The mixture was then warmed to room temperature, diluted with water (100 mL), and extracted with methylene chloride (3×100 mL). The combined organic layers were dried over magnesium sulfate, filtered, and concentrated in vacuo. This afforded 10 g of an off-white, crystalline solid (99% yield). $^1$H NMR (CDCl$_3$) δ 1.50 (s, 9H), 1.53–1.62 (m, 2H), 1.68 (br s, 1H), 1.86–1.92 (m, 2H), 2.11 (td, J=4.7, 12.8 Hz, 2H), 2.30 (d, J=11.2 Hz, 2H), 3.17 (m, 2H), 3.29 (t, J=12.2 Hz, 2H), 3.63 (m, 2H), 385 (m, 1H), 3.94 (dd, J=4, 11.2 Hz, 2H); Electrospray mass spectrometry showed m/z=350 (M+H)$^+$.

Example A6

Preparation of 4-[4-(2-oxo-ethyl)-piperidine-1-sulfonyl]-tetrahydro-pyran-4-carboxylic acid tert-butyl ester

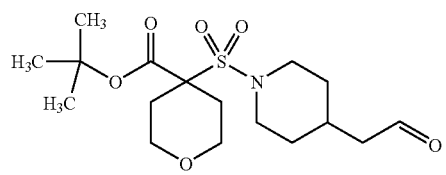

Part A. Preparation of 4-[4-(2-methoxy-vinyl)-piperidine-1-sulfonyl]-tetrahydro-pyran-4-carboxylic acid tert-butyl ester:

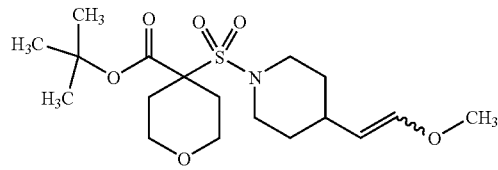

A 100 mL round-bottom flask was charged with (methoxymethyl)triphenylphosphonium chloride (3.41 g, 10 mmol) and tetrahydrofuran (15 mL). This resulted in a white slurry. The flask was then immersed into an ice bath, and a 1 M solution of lithium bis(trimethylsilyl)amide in tetrahydrofuran (10.8 mL, 10.8 mmol) was added dropwise at a rate that caused the temperature to be maintained at less than 5° C. After complete addition, the reaction mixture was stirred with cooling for 15 min. A solution of the aldehyde from Example A4 (3.0 g, 8.3 mmol) in tetrahydrofuran (5 mL) was then added dropwise, maintaining the temperature at less than 5° C. After complete addition, the flask was slowly warmed to room temperature. The mixture was then stirred for 16 hr. Subsequently, the reaction was quenched by the addition of saturated aqueous ammonium chloride (10 ml), and the mixture was partitioned between ethyl acetate (25 mL) and water (25 mL). The organic layer was washed with 5% HCl solution (2×50 mL), water (1×50 mL), and brine (1×50 mL). The organic layer was dried over magnesium sulfate, filtered, and concentrated in vacuo. Purification by flash column chromatography (20–60% ethyl acetate/hexane) afforded 2.08 g of a colorless oil product (63% yield). ¹H NMR (CDCl₃) mixture of geometric isomers in ratio of 1:1.4: δ 1.30–1.50 (m, 2H), 1.51 (s, 9H), 1.62–1.68 (m, 2H), 1.95–2.05 (m, 1H-major isomer), 2.10 (td, J=4.7, 12.8 Hz, 2H), 2.31 (d, J=11.2 Hz, 2H), 2.50–2.60 (m, 1H-minor isomer), 2.96 (t, J=12.4 Hz, 2H-major isomer), 2.99 (t, J=13.6 Hz, 2H-minor isomer), 3.30 (t, J=11.4 Hz, 2H), 3.48 (s, 3H-major isomer), 3.56 (s, 3H-minor isomer), 3.68–3.80 (m, 2H), 3.95 (dd, J=4.4, 12 Hz, 2H), 4.19 (dd, J=6.4, 8.4 Hz, 1H-minor isomer), 4.63 (dd, J=8, 12.8 Hz, 1H-major isomer), 5.82 (d, J=6.4 Hz, 1H-minor isomer), 6.31 (d, J=12.8 Hz, 1H-major isomer).

Part B. Preparation of 4-[4-(2-oxo-ethyl)-piperidine-1-sulfonyl]-tetrahydro-pyran-4-carboxylic acid tert-butyl ester:

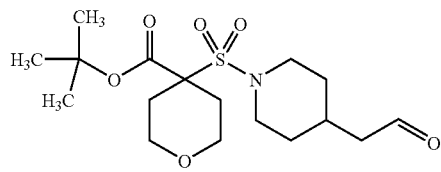

A 100 mL round-bottom flask was charged with the product from Part A (2.08 g, 5.34 mmol), tetrahydrofuran (40 mL), and a 5% solution of HCl in water (4 mL). The resulting mixture was heated to 50° C. for 0.5 hr, cooled to room temperature, and partitioned between ethyl acetate (50 mL) and saturated aqueous sodium bicarbonate (50 mL). The organic layer was washed with brine (50 mL), dried over magnesium sulfate, filtered, and concentrated in vacuo to afford 2.02 g of a white crystalline solid (100% yield). ¹H NMR (CDCl₃) δ 1.20–1.40 (m, 2H), 1.50 (s, 9H), 1.70 (d, J=12.9 Hz, 2H), 2.20–2.16 (m, 3H), 2.28 (d, J=12.9 Hz, 2H), 2.39 (d, J=6.6 Hz, 2H), 2.96 (t, J=12.7 Hz, 2H), 3.28 (t, J=12.2 Hz, 2H), 3.75 (d, J=12.6 Hz, 2H), 3.94 (dd, J=3.9, 11.7 Hz, 2H), 9.74 (s, 1H); Electrospray mass spectrometry showed m/z=394 (M+Na).

Example A7

Preparation of 4-[4-(3-hydroxy-propyl)-piperidine-1-sulfonyl]-tetrahydro-pyran-4-carboxylic acid tert-butyl ester

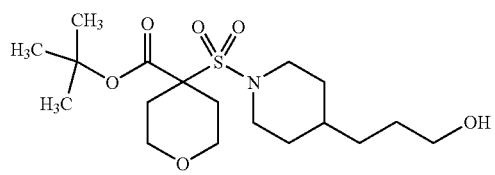

Part A. Preparation of 4-[4-(2-methoxycarbonyl-vinyl)-piperidine-1-sulfonyl]-tetrahydro-pyran-4-carboxylic acid tert-butyl ester:

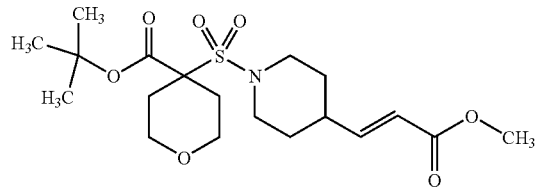

A 100 mL round-bottom flask was charged with (carbomethoxymethyl)triphenylphosphonium bromide (5.99 g, 14.4 mmol) and tetrahydrofuran (30 mL). This resulted in a white slurry. The flask was then immersed into an ice bath, and a 1 M solution of lithium bis(trimethylsilyl)amide in tetrahydrofuran (15 mL, 15 mmol) was added dropwise while maintaining the temperature at less than 5° C. After complete addition, the reaction mixture was stirred with cooling for 15 min. A solution of the aldehyde from Example A4 (4.0 g, 11.1 mmol) in tetrahydrofuran (10 mL) was then added dropwise, maintaining the temperature at less than 5° C. After complete addition, the flask was slowly warmed to room temperature and then stirred for 1 hr. The resulting mixture was diluted with diethyl ether (150 mL), resulting in a white precipitate. The solid was filtered, and the filtrate was washed with water (1×100 mL), 5% HCl solution (2×100 mL), and brine (1×100 mL). The organic layer was dried over magnesium sulfate, filtered, and concentrated in vacuo. Purification by flash column chromatography (25–40% ethyl acetate/hexane) afforded 2.09 g of a colorless crystalline solid product (45% yield). ¹H NMR (CDCl₃) predominantly one geometric isomer (>95%): δ 1.53 (s, 9H), 1.76 (d, J=13.5 Hz, 2H), 2.10 (td, J=4.7, 12.6 Hz, 2H), 2.32 (d, J=12.6 Hz, 2H), 3.00 (t, J=12.4 Hz, 2H), 3.31 (t, J=12 Hz, 2H), 3.79 (s, 3H), 3.81 (d, J=12.3 Hz, 2H), 3.97 (dd, J=4.1, 11.9 Hz, 2H), 5.81 (d, J=15.9 Hz, 1H), 6.89 (dd, J=6.6, 15.9 Hz, 1H), Electrospray mass spectrometry showed m/z=418 (M+H).

Part B. Preparation of 4-[4-(2-methoxycarbonyl-ethyl)-piperidine-1-sulfonyl]-tetrahydro-pyran-4-carboxylic acid tert-butyl ester:

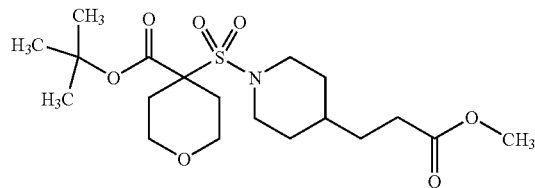

A thick-walled glass pressure vessel containing 10% palladium on carbon (0.25 g, 0.23 mmol) was charged with a solution of the ester from Part A (2.04 g, 4.9 mmol) in ethyl acetate (25 mL). The flask was placed onto a Parr shaker under 40 PSI hydrogen, and agitated for 2 hr at room temperature. The reaction mixture was then filtered through a pad of celite. Afterward, the filtrate was concentrated in vacuo to afford 2.08 g of a colorless crystalline solid product (100% yield). Electrospray mass spectrometry showed m/z 32 420 (M+H). ¹H NMR (CDCl₃) δ 1.20–1.30 (m, 2H), 1.37–1.43 (m, 1H), 1.51 (s, 9H), 1.55–1.62 (m, 2H), 1.67 (br d, J=11.6 Hz, 2H), 2.10 (td, J=4.8, 12.8 Hz, 2H), 2.27–2.34 (m, 4H), 2.91 (t, J=12.2 Hz, 2H), 3.29 (t, J=12 Hz, 2H), 3.65 (s, 3H), 3.77 (d, J=12 Hz, 2H), 3.95 (dd, J=4.4, 12 Hz, 2H).

Part C. Preparation of 4-[4-(2-carboxy-ethyl)-piperidine-1-sulfonyl]-tetrahydro-pyran-4-carboxylic acid tert-butyl ester:

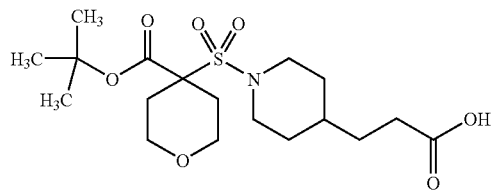

A 100 mL round-bottom flask was charged with the product from Part B (1.9 g, 4.53 mmol), ethanol (10 mL), tetrahydrofuran (10 mL), and a 1.0 M solution of aqueous lithium hydroxide (9 mL, 9 mmol). The resulting mixture was stirred at room temperature for 15 min, and then concentrated in vacuo to approximately half the original volume. The residue was dissolved in water (50 mL), and the pH was adjusted to approximately 2 using 5% aqueous HCl. The aqueous mixture was then extracted with ethyl acetate (50 mL). The organic layer was washed with water (50 mL) and brine (50 mL), dried over magnesium sulfate, filtered, and concentrated in vacuo to afford 1.82 g of a white crystalline solid product (99% yield). $^1$H NMR (CDCl$_3$) δ 1.20–1.32 (m, 2H), 1.38–1.46 (m, 1H), 1.51 (s, 9H), 1.57–1.64 (m, 2H), 1.68 (d, J=12.8 Hz, 2H), 2.10 (td, J=4.7, 12.8 Hz, 2H), 2.31 (d, J=12 Hz, 2H), 2.37 (t, J=7.6 Hz, 2H), 2.92 (t, J=12.6 Hz, 2H), 3.30 (t, J=12.2 Hz, 2H), 3.77 (d, J=11.6 Hz, 2H), 3.96 (dd, J=4, 11.6 Hz, 2H); Electrospray mass spectrometry showed m/z=406 (M+H).

Part D. Preparation of 4-[4-(3-hydroxy-propyl)-piperidine-1-sulfonyl]-tetrahydro-pyran-4-carboxylic acid tert-butyl ester:

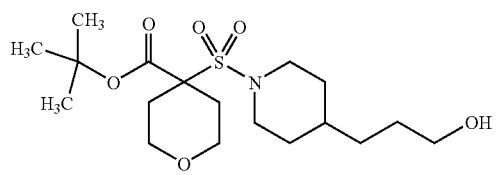

A 100 mL round-bottom flask was charged with the product from Part C (1.60 g, 3.93 mmol) and tetrahydrofuran (16 mL). A 1 M solution of borane-tetrahydrofuran complex in tetrahydrofuran (7.9 mL, 7.9 mmol) was then added dropwise over 20 min. The resulting mixture was heated to 60° C. for 1 hr, and then cooled to room temperature. The flask was immersed into an ice bath, and water (5 mL) was added carefully to quench the reaction. A 5% aqueous HCl solution was added. The mixture was then partitioned between ethyl acetate (50 mL) and saturated aqueous sodium bicarbonate (50 mL). The organic layer was washed with water (50 mL) and brine (50 mL), dried over magnesium sulfate, filtered, and concentrated in vacuo to afford 1.55 g of an off-white crystalline solid (100% yield). $^1$H NMR (CDCl$_3$) δ 1.20–1.42 (m, 5H), 1.51 (s, 9H), 1.53–1.59 (m, 2H), 1.68 (d, J=11.2 Hz, 2H), 2.10 (td, J=4.5, 12.8 Hz, 2H), 2.31 (d, J=11.2 Hz, 2H), 2.92 (t, J=12.6 Hz, 2H), 3.30 (t, J=12.4 Hz, 2H), 3.62 (t, J=6.6 Hz, 2H), 3.76 (d, J=12 Hz, 2H), 3.95 (dd, J=4, 11.6 Hz, 2H); Electrospray mass spectrometry showed m/z=392 (M+H).

Example A8

Preparation of 4-[4-(3-oxo-propyl)-piperidine-1-sulfonyl]-tetrahydro-pyran-4-carboxylic acid tert-butyl ester

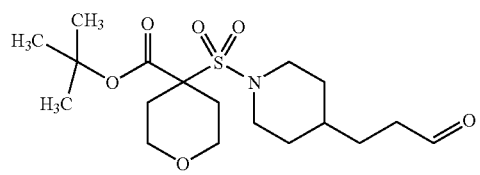

A 50 mL round-bottom flask was charged with oxalyl chloride (0.4 mL, 3.82 mmol) and methylene chloride (9 mL). The flask was then immersed into a dry ice/acetone bath. Afterward, dimethylsulfoxide (0.54 mL, 7.7 mmol) was added dropwise, maintaining the temperature at less than −65° C. After complete addition, the mixture was stirred for 15 min. A solution of the alcohol from Example A7 (1.50 g, 3.82 mmol) in methylene chloride (9 mL) was then added dropwise while maintaining the temperature at less than−65° C. The resulting mixture was stirred for 45 min after complete addition. Diisopropylethylamine (3.3 mL, 19 mmol) was then added dropwise. Subsequently, the mixture was stirred for 30 min with cooling. The dry ice/acetone bath was then removed. After 1 hr, the reaction mixture was diluted with methylene chloride (50 mL) and extracted with water (50 mL). The aqueous layer was re-extracted with methylene chloride (25 mL). The combined organic layers were then dried over magnesium sulfate, filtered, and concentrated in vacuo. Purification by flash column chromatography using a gradient of 10–30% ethyl acetate/hexane afforded a white crystalline solid (1.24 g, 83% yield). $^1$H NMR (CDCl$_3$) δ 1.20–1.42 (m, 5H), 1.51 (s, 9H), 1.53–1.59 (m, 2H), 1.68 (d, J=11.2 Hz, 2H), 2.10 (td, J=4.5, 12.8 Hz, 2H), 2.31 (d, J=11.2 Hz, 2H), 2.92 (t, J=12.6 Hz, 2H), 3.30 (t, J=12.4 Hz, 2H), 3.62 (t, J=6.6 Hz, 2H), 3.76 (d, J=12 Hz), 3.95 (dd, J=4, 11.6 Hz, 2H); Electrospray mass spectrometry showed m/z=390 (M+H).

Example A9

Preparation of 4-[4-(5-hydroxy-pentyl)-piperidine-1-sulfonyl]-tetrahydro-pyran-4-carboxylic acid tert-butyl ester

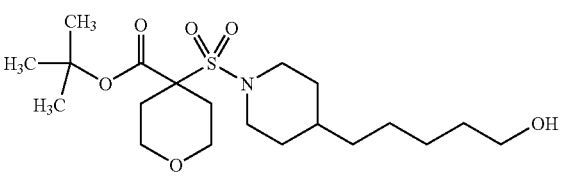

Part A. Preparation of (4-benzyloxy-butyl)-triphenyl-phosphonium; bromide:

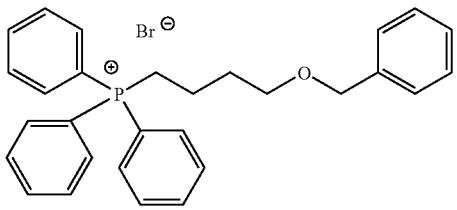

To a solution of 90% benzyloxybutyl bromide (10.01 g, 37 mmol) in methylene chloride (100 mL) was added polystyrene-bound trisamine (loading=3.42 mmol/g, 3.11 g, 10.6 mmol) to remove benzyl bromide contaminant. The resulting slurry was stirred for 16 hr at room temperature. Solids were then removed by vacuum filtration. The filtrate was concentrated in vacuo, and then re-dissolved in toluene (100 mL). Afterward, triphenylphosphine (9.77 g, 37 mmol) was added to the bromide. The resulting mixture was stirred at 80° C. for 48 hr, and then at reflux for an additional 24 hr. The mixture was then cooled to room temperature and diluted with diethyl ether (300 mL). An off-white precipitate formed, which was collected by vacuum filtration. Further drying of the solid in vacuo afforded pure phosphonium bromide in the form of a tan solid (8.92 g, 47% yield). $^1$H NMR (CDCl$_3$) δ 1.80 (m, 2H), 2.01 (p, J=6.2 Hz, 2H), 3.61 (t, J=5.6 Hz, 2H), 3.80–3.90 (m, 2H), 4.45 (s, 2H), 7.20–7.29 (m, 5H), 7.60–7.66 (m, 6H), 7.72–7.83 (m, 9H); Electrospray mass spectrometry showed m/z=425 (M for PR$_4^+$).

Part B. Preparation of 4-[4-(5-benzyloxy-pent-1-enyl)-piperidine-1-sulfonyl]-tetrahydro-pyran-4-carboxylic acid tert-butyl ester:

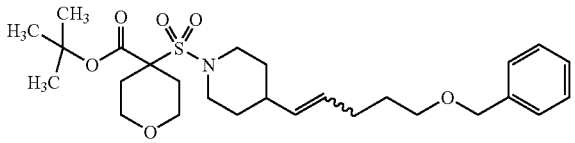

A 100 mL round-bottom flask was charged with the phosphonium bromide from Part A (7.29 g, 14.4 mmol) and tetrahydrofuran (30 mL). The flask was then immersed into an ice bath, and a 1 M solution of lithium bis(trimethylsilyl)amide in tetrahydrofuran (15.5 mL, 15.5 mmol) was added dropwise while maintaining the temperature at less than 5° C. After complete addition, the reaction mixture was stirred with cooling for 10 min. A solution of the aldehyde from Example A4 (4.0 g, 11.1 mmol) in tetrahydrofuran (10 mL) was then added dropwise, maintaining the temperature at less than 5° C. After complete addition, the flask was slowly warmed to room temperature and then stirred for 30 min. The resulting mixture was diluted with diethyl ether (50 mL), forming in a white precipitate. The solid was filtered, and the filtrate was washed with water (1×50 mL), 5% HCl solution (2×50 mL), and brine (1×50 mL). The organic layer was dried over magnesium sulfate, filtered, and concentrated in vacuo. Purification by flash column chromatography (10–25% ethyl acetate/hexane) afforded 4.15 g of desired olefin in the form of a colorless crystalline solid (73% yield). $^1$H NMR (CDCl$_3$) one major geometric isomer with several side products: δ 1.28–1.42 (m, 2H), 1.52 (s, 9H), 1.56–1.69 (m, 2H), 2.06–2.16 (m, 2H), 2.31 (d, J=12.4 Hz, 2H), 2.39–2.43 (m, 1H), 2.94 (t, J=11.6 Hz, 2H), 3.30 (t, J=11.2 Hz, 2H), 3.46 (t, J=6.4 Hz, 2H), 3.73 (d, J=12 Hz, 2H), 3.96 (dd, J=4.4, 11.6 Hz, 2H), 4.48 (s, 2H), 5.20 (t, J=10 Hz, 1H), 5.28–5.45 (m, 1H), 7.25–7.37 (m, 5H); Electrospray mass spectrometry showed m/z=508 (M+H).

Part C. Preparation of 4-[4-(5-hydroxy-pentyl)-piperidine-1-sulfonyl]-tetrahydro-pyran-4-carboxylic acid tert-butyl ester:

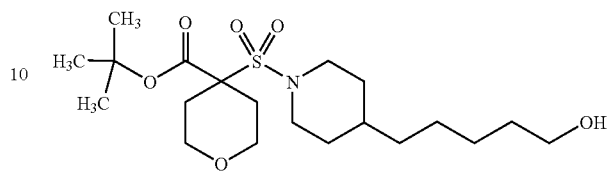

A thick-walled glass pressure vessel containing 10% palladium on carbon (1 g, 0.94 mmol) was charged with a solution of the olefin from Part B (4.15 g, 8.17 mmol) in tetrahydrofuran (25 mL). The flask was then placed onto a Parr shaker under an atmosphere of 40 PSI hydrogen and agitated for 2 hr at room temperature. The reaction mixture was then filtered through a pad of celite, and the filtrate was concentrated in vacuo. Flash column chromatography afforded the desired alcohol and two pure side products. The desired alcohol was in the form of 2.65 g of a colorless crystalline solid (77% yield). $^1$H NMR (CDCl$_3$) δ 1.16–1.38 (m, 9H), 1.51 (s, 9H), 1.53–1.59 (m, 2H), 1.65 (br d, J=12.8 Hz, 2H), 2.10 (td, J=4.7, 12.6 Hz, 2H), 2.31 (d, J=11.6 Hz, 2H), 2.90 (t, J=12.4 Hz, 2H), 3.29 (t, J=12.4 Hz, 2H), 3.62 (t, J=6.6 Hz, 2H), 3.75 (d, J=11.6 Hz, 2H), 3.95 (dd, J=4, 11.6 Hz, 2H); Electrospray mass spectrometry showed m/z=420 (M+H). The first side product was determined to be 4-(4-pentyl-piperidine-1-sulfonyl)-tetrahydro-pyran-4-carboxylic acid tert-butyl ester:

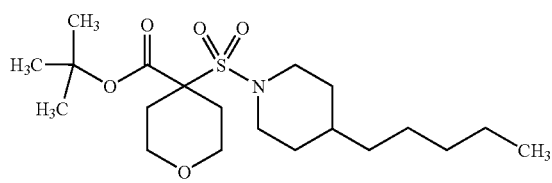

That side product was a white solid (134 mg, 4% yield) and was characterized as follows: $^1$H NMR (CDCl$_3$) δ 0.86 (t, J=7 Hz, 3H), 1.16–1.36 (m, 11H), 1.51 (s, 9H), 1.66 (br d, J=10.8 Hz, 2H), 2.11 (td, J=4.6, 12.6 Hz, 2H), 2.31 (d, J=11.6 Hz, 2H), 2.91 (t, J=12.6 Hz, 2H), 3.30 (t, J=12 Hz, 2H), 3.75 (d, J=12.4 Hz, 2H), 3.95 (dd, J=4, 11.6 Hz, 2H; Electrospray mass spectrometry showed m/z=404 (M+H). The second side product was determined to be 4-(4-phenethyl-piperidine-1-sulfonyl)-tetrahydro-pyran-4-carboxylic acid tert-butyl ester:

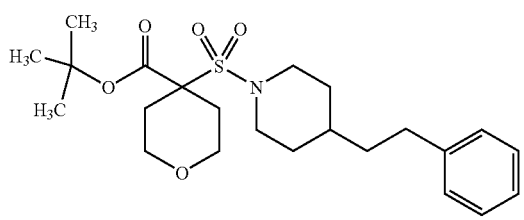

This side product also was a white solid (135 mg, 4% yield), and was characterized as follows: $^1$H NMR (CDCl$_3$) δ 1.20–1.45 (m, 3H), 1.52 (s, 9H), 1.54–1.60 (m, 2H), 1.73 (br d, J=10.4 Hz, 2H), 2.11 (td, J=4.7, 12.6 Hz, 2H), 2.32 (d, J=12.8 Hz, 2H), 2.61 (t, J=7.8 Hz, 2H), 2.91 (t, J=12.6 Hz, 2H), 3.30 (t, J=12 Hz, 2H), 3.77 (d, J=10.4 Hz, 2H), 3.96 (dd, J=4.2, 11.6 Hz, 2H), 7.10–7.30 (m, 5H); Electrospray mass spectrometry showed m/z=438 (M+H).

Example A10

Preparation of triphenyl-(4,4,4-trifluoro-butyl)-phosphonium; iodide

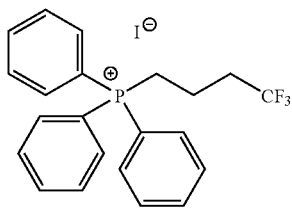

A 20 mL glass vial was charged with triphenylphosphine (3.93 g, 15 mmol), trifluorobutyl iodide (3.57 g, 15 mmol), and toluene (10 mL). The vial was capped, heated to 85° C. overnight (16 hr), and cooled to room temperature. This resulted in the formation of a white crystalline solid. This solid was collected by vacuum filtration. Further drying in vacuo afforded the title phosphine in the form of a white crystalline solid (5.48 g, 73% yield). $^1$H NMR (CDCl$_3$) δ 1.83–1.97 (m, 2H), 2.60–2.80 (m, 2H), 4.00–4.12 (m, 2H), 7.65–7.90 (m, 15H).

Example A11

Preparation of (3,3,4,4,4-pentafluoro-butyl)-triphenyl-phosphonium; iodide

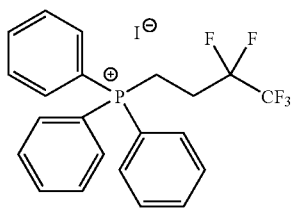

A 10 mL Teflon pressure vessel was charged with triphenylphosphine (4.27 g, 16.3 mmol), 3,3,4,4,4-pentafluoro-1-iodobutane (4.90 g, 17.9 mmol), and dimethylformamide (8 mL). The vessel was then sealed and placed into a microwave oven (MARS-5, CEM corporation). The mixture was heated to 150° C. using 150 watts of power for 60 min. Afterward, the mixture was cooled to room temperature, and concentrated in vacuo. The residue was triturated with diethyl ether (100 mL), forming a white crystalline solid product. This product was collected by vacuum filtration and dried in vacuo (8.36 g, 96% yield). $^1$H NMR (CDCl$_3$) δ 2.45–2.62 (m, 2H), 4.00–4.15 (m, 2H), 7.70–7.90 (m, 15H).

Example A12

Preparation of 4-[4-(4-hydroxy-butyl)-piperidine-1-sulfonyl]-tetrahydro-pyran-4-carboxylic acid tert-butyl ester

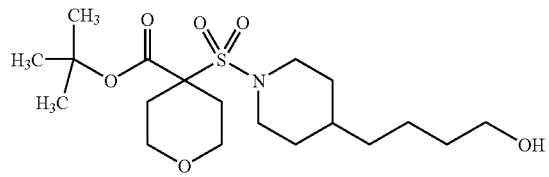

Part A. Preparation of 4-[4-(4-benzyloxy-but-1-enyl)-piperidine-1-sulfonyl]-tetrahydro-pyran-4-carboxylic acid tert-butyl ester:

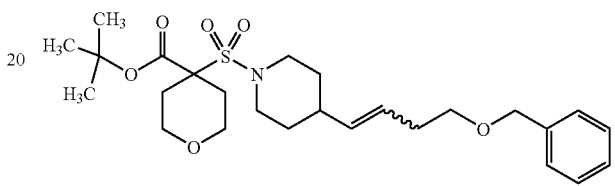

A 100 mL round-bottom flask was charged with (3-benzyloxypropyl)triphenylphosphonium bromide (7.87 g, 14.4 mmol) and tetrahydrofuran (30 mL). The flask was then immersed into an ice bath. Afterward, a 1 M solution of lithium bis(trimethylsilyl)amide in tetrahydrofuran (15.5 mL, 15.5 mmol) was added dropwise while maintaining the temperature at less than 5° C. After complete addition, the reaction mixture was stirred with cooling for 15 min. A solution of the aldehyde from Example A4 (4.0 g, 11.1 mmol) in tetrahydrofuran (10 mL) was then added dropwise while maintaining the temperature at less than 5° C. After complete addition, the flask was slowly warmed to room temperature and then stirred for 1 hr. The resulting mixture was diluted with diethyl ether (50 mL), causing a white precipitate to form. The precipitate was filtered, and the filtrate was washed with water (1×100 mL) and brine (1×100 mL). The organic layer was dried over magnesium sulfate, filtered, and concentrated in vacuo. Purification by flash column chromatography (10–25% ethyl acetate/hexane) afforded 4.65 g of desired olefin in the form of a colorless crystalline solid (85% yield). $^1$H NMR (CDCl$_3$) one major geometric isomer with several side products: δ 1.30–1.45 (m, 2H), 1.53 (s, 9H), 2.06–2.17 (m, 2H), 2.30–2.45 (m, 5H), 2.96 (t, J=12.3 Hz, 2H), 3.31 (t, J=12 Hz, 2H), 3.47 (t, J=6.9 Hz, 2H), 3.73 (d, J=11.7 2H), 3.97 (dd, J=3.7, 11.4 Hz, 2H), 4.51 (s, 2H), 5.24–5.45 (m, 2H), 7.25–7.37 (m, 5H); Electrospray mass spectrometry showed m/z=494 (M+H).

Part B. Preparation of 4-[4-(4-hydroxy-butyl)-piperidine-1-sulfonyl]-tetrahydro-pyran-4-carboxylic acid tert-butyl ester:

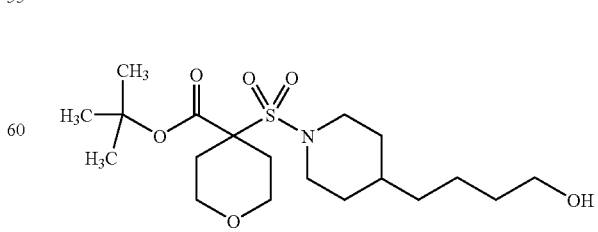

The benzyl ether from Part A (4.60 g, 9.31 mmol) in tetrahydrofuran (25 mL) with 10% Pd/C (1 g, Degussa type)

was placed onto a Parr shaker and reduced with H₂ at 40 psi for 3 hr. The resulting mixture was filtered through celite and concentrated in vacuo, forming the alcohol in the form of a crystalline solid (3.80 g, 100% yield). NMR(CDCl₃) δ 1.15–1.31 (m, 4H), 1.31–1.41 (m, 3H), 1.47–1.58 (m, 11H), 1.67 (d, 2H), 2.09 (dt, 2H), 2.32 (d, 2H), 2.92 (t, 2H), 3.29 (t, 2H), 3.63 (t, 2H), 3.76 (d, 2H), 3.96 (dd, 2H). ESMS m/z=406.37 (M+H)⁺.

Example A13

Preparation of 4-[4-(2-hydroxy-ethyl)-piperidine-1-sulfonyl]-tetrahydro-pyran-4-carboxylic acid tert-butyl ester

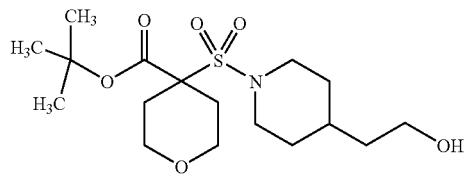

The aldehyde from Example A6 (1.43 g, 3.81 mmol) in MeOH (15 mL) at 0° C. was treated with NaBH₄ (144 mg, 3.81 mmol) in portions. Upon completion of addition, the ice bath was removed, and the mixture was stirred at room temperature for 2 hr. The reaction was then quenched with saturated NH₄Cl (~5 mL). After adding water (15 mL), the mixture was extracted with methylene chloride (3×30 mL). The organics were dried (magnesium sulfate). Concentration in vacuo afforded the alcohol as an oil (1.44 g, quantitative conversion). NMR(CDCl₃) δ 1.28 (dt, 2H), 1.33–1.42 (m, 2H), 1.47–1.65 (m, 10H), 1.70 (d, 2H), 2.10 (dt, 2H), 2.32 (d, 2H), 2.94 (dt, 2H), 3.30 (dt, 2H), 3.68 (t, 2H), 3.76 (d, 2H), 3.96 (dd, 2H).

Example A14

Preparation of 4-[4-(3-oxo-propoxy)-piperidine-1-sulfonyl]-tetrahydro-pyran-4-carboxylic acid tert-butyl ester

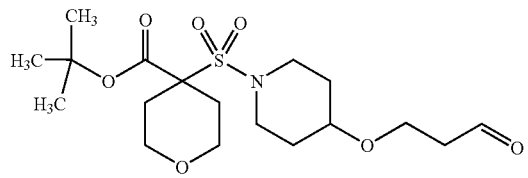

Part A. Preparation of 4-{4-[3-(tert-butyl-dimethyl-silanyloxy)-propoxy]-piperidine-1-sulfonyl}-tetrahydro-pyran-4-carboxylic acid tert-butyl ester:

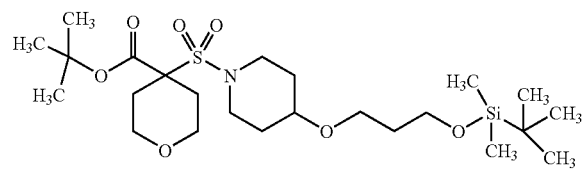

The alcohol from Example A5 (2.00 g, 5.73 mmol), tetrabutylammonium bromide (0.37 g, 1.15 mmol), and KOH (0.97 g, 17.2 mmol) were slurried in xylene (23 mL). Afterward, 3-bromopropoxy)-t-butyl-dimethylsilane (4.35 g, 17.2 mmol) was added, and the resulting mixture was stirred in a sealed vial at 100° C. for 2×30 min at 150 Watts in microwave. The mixture was filtered, and the resulting solid was washed with methylene chloride. The organics were concentrated. Chromatography (on silica, ethyl acetate/hexanes) afforded the silyl ether in the form of a colorless solid (1.74 g, 58.2% yield). NMR(CDCl₃) δ 0.03 (s, 6H), 0.86 (s, 9H), 1.52 (s, 9H), 1.58–1.88 (m, 6H), 2.10 (dd, 2H), 2.32 (d, 2H), 3.14–3.35 (m, 4H), 3.41–3.62 (m, 5H), 3.68(t, 2H), 3.96 (dd, 2H). ESMS m/z=522.53 (M+H)⁺.

Part B. Preparation of 4-[4-(3-hydroxy-propoxy)-piperidine-1-sulfonyl]-tetrahydro-pyran-4-carboxylic acid tert-butyl ester:

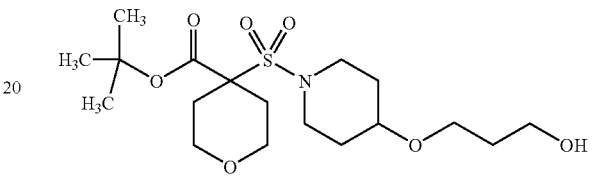

To the silyl ether from Part A (3.16 g, 6.05 mmol) in anhydrous tetrahydrofuran (60 mL) at 0° C. was added 1M TBAF (12.1 mL, 12.1 mmol). Upon completion of the addition, the ice bath was removed, and the reaction mixture was stirred at room temperature for 1.5 hr. The mixture was then poured into water (100 mL) and saturated NH₄Cl (100 mL), and extracted with ethyl acetate (2×100 mL). The organics were dried (magnesium sulfate) and concentrated. Chromatography (on silica, ethyl acetate/hexanes) afforded the alcohol in the form of a colorless crystalline solid (2.25 g, 92.4% yield). NMR(CDCl₃) δ 1.52 (s, 9H), 1.62–1.73 (m, 2H), 1.79–1.99 (m, 4H), 2.10 (dd, 2H), 2.32 (d, 2H), 3.12–3.35 (m, 4H), 3.45–3.64 (m, 5H), 3.76(t, 2H), 3.96 (dd, 2H). ESMS m/z=408.38 (M+H)⁺.

Part C. Preparation of 4-[4-(3-oxo-propoxy)-piperidine-1-sulfonyl]-tetrahydro-pyran-4-carboxylic acid tert-butyl ester:

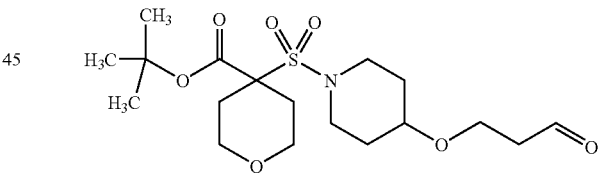

To a solution of oxalyl chloride (0.40 mL, 4.55 mmol) in anhydrous methylene chloride at −60° C. under N₂ was added anhydrous dimethylsulfoxide ("DMSO") (0.54 mL, 7.58 mmol) dropwise while maintaining the temperature at less than −50° C. This mixture was stirred for 20 min. The alcohol from Part B (1.98 g, 4.85 mmol) in 10 mol of anhydrous methylene chloride (pre-cooled) was then added dropwise while maintaining the temperature at less than −50° C. The resulting mixture was stirred at −70° C. for 1 hr. Afterward, anhydrous diisopropylethylamine (3.30 mL, 19.0 mmol) was added, and the ice bath was removed. The reaction mixture was then stirred at room temperature overnight. Subsequently, the reaction mixture was diluted with methylene chloride (175 mL), washed with water and brine, dried over magnesium sulfate, and concentrated. Chromatography (on silica, ethyl acetate/hexanes) afforded the aldehyde in the form of a colorless crystalline solid (1.59 g, 80.8% yield). NMR(CDCl₃) δ 1.52 (s, 9H), 1.60–1.72 (m, 2H), 1.77–1.98 (m, 2H), 2.09(dt, 2H), 2.32 (d, 2H), 2.66 (dt, 3H), 3.15–3.34 (m, 4H), 3.52 (bs, 2H), 3.76(t, 2H), 3.96 (dd, 2H).

Example A15

Preparation of triphenyl-(3,3,3-trifluoro-propyl)-phosphonium; iodide

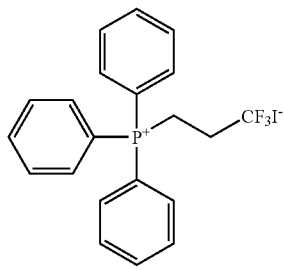

Triphenylphosphine (2.13 g, 8.12 mmol), 1,1,1-trifluoro-3-iodopropane (2.00 g, 8.93 mmol), and anhydrous dimethylformamide (4 mL) were placed into a microwave vessel and heated at 150° C. for 40 min at 600 watts. The resulting mixture was concentrated and triturated with diethyl ether to form a colorless solid. The colorless solid was collected by filtration and washed with diethyl ether. Drying under high vacuum afforded the desired salt in the form of a colorless solid (3.77 g, 95.6% yield). NMR (CDCl₃) δ 2.51–2.71 (m, 2H), 3.96–4.09 (m, 2H), 7.67–7.77 (m, 6H), 7.78–7.91 (m, 9H). ESMS m/z 32 360.30 (M+H)⁺.

Example A16

Preparation of 4-[4-(4-oxo-butyl)-piperidine-1-sulfonyl]-tetrahydro-pyran-4-carboxylic acid tert-butyl ester

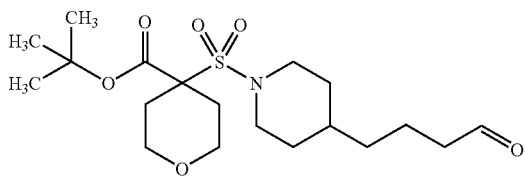

To a solution of oxalyl chloride (0.226 mL, 2.59 mmol) in anhydrous methylene chloride (5.7 mL) at −60° C. under N₂ was added anhydrous DMSO (0.31 mL, 4.32 mmol) dropwise while maintaining the temperature at less than −50° C. The resulting mixture was stirred for 20 min. Afterward, the alcohol from Example A12 (0.875 g, 2.16 mmol) in anhydrous methylene chloride (5.7 mL) (pre-cooled) was added dropwise while maintaining the temperature at less than −50° C. The resulting mixture was stirred at −70° C. for 1 hr. Subsequently, anhydrous diisopropylethylamine (1.9 mL, 10.8 mmol) was added, and the ice bath removed. The reaction mixture was then stirred at room temperature for 3 hr. Afterward, reaction mixture was diluted with methylene chloride (200 mL), washed with water (150 mL) and brine, dried over magnesium sulfate, and concentrated. Chromatography (on silica, ethyl acetate/hexanes) afforded the aldehyde in the form of a colorless crystalline solid (704.4 g, 81.1% yield). NMR(CDCl₃) δ 1.16–1.31 (m, 4H), 1.33–1.45 (m, 1H), 1.52 (s, 9H), 1.57–1.72 (m, 4H), 2.11 (dt, 2H), 2.32 (d, 2H), 2.43 (dt, 2H), 2.92 (dt, 3H), 3.30 (dt, 2H), 3.3.76 (d, 2H), 3.96 (dd, 2H), 9.75 (s, 1H).

Example A17

Preparation of tert-butyl 4-{[4-(5-hydroxypyridin-2-yl)piperidin-1-yl]sulfonyl}tetrahydro-2H-pyran-4-carboxylate]

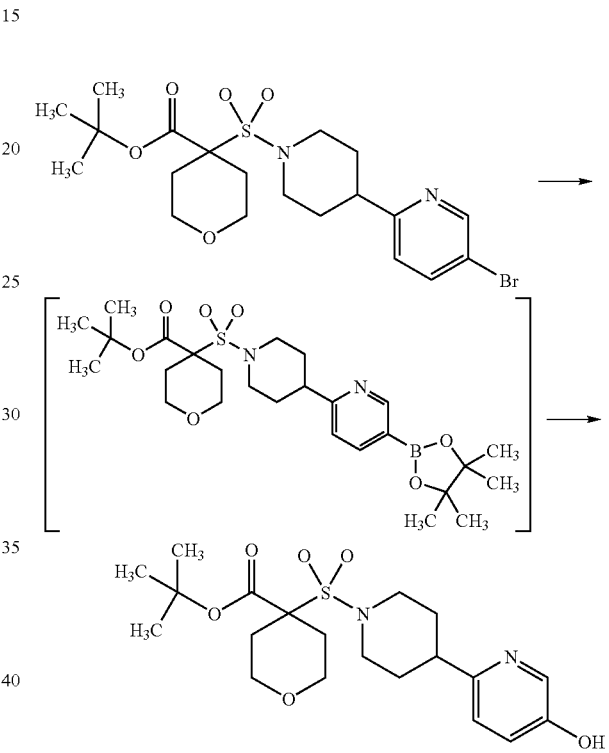

To a mixture of tert-butyl 4-{[4-(5-bromopyridin-2-yl)piperidin-1-yl]sulfonyl}tetrahydro-2H-pyran-4-carboxylate (10.0 g, 20 mmol, 1 eq.) in 100 mL of N-N' dimethylacetamide was added bis(pinacolato)diboron (5.64 g, 22 mmol, 1.1 eq.), potassium acetate (5.88 g, 60 mmol, 3 eq.), and [1,1'-bis(diphenyphosphino) ferrocene] dichloropalladium (II), CH₂Cl₂ ((500 mg, 0.6 mmol, 0.03 eq.). The resulting mixture was heated at 85° C. for 16 hr. The mixture was then cooled to room temperature, and 40 mL of methanol was added to the resulting paste, followed acetic acid (4.5 mL, 80 mmol, 4 eq.). Subsequently, H₂O₂ was added (4.0 mL 50 w/w % solution 60 mmol, 3 eq.) in four 1 mL portions. The mixture was then stirred at room temperature for 10 min. Afterward, the mixture was diluted with 400 mL of CH₂Cl₂, and then washed 3×300 mL water and 1×100 mL brine. The organic layer was dried over Na₂SO₄ and filtered through a pad of SiO₂. The product was triturated with Et₂O to afford 3.25 g. The resulting mother liquor was purified via SiO₂ chromatography (gradient 10% ethyl acetate/hexanes to 100% ethyl acetate) to afford an additional 1.08 g for a total of 4.33 g of product (51% yield). MS MH+ C20H31N2O6S calc.: 427, found: 427. 1H NMR was consistent with the desired product.

Example A18

Preparation of 4-[4-(2,2,3,3-tetrafluoro-propoxymethyl)-piperidine-1-sulfonyl]-tetrahydro-pyran-4-carboxylic acid hydroxyamide

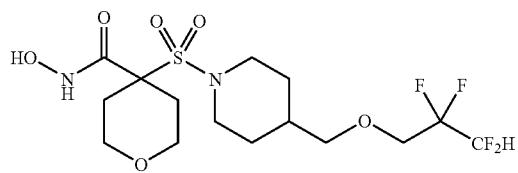

Part A. Preparation of 4-[4-(2,2,3,3-tetrafluoro-propoxymethyl)-piperidine-1-sulfonyl]-tetrahydro-pyran-4-carboxylic acid tert-butyl ester:

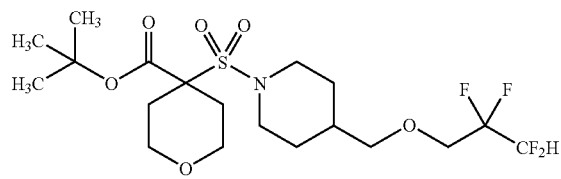

An 8 mL glass reaction vessel was charged with the mesylate from Example A3 (300 mg, 0.68 mmol), dimethylformamide (1.5 mL), 2,2,3,3-tetrafluoro-1-propanol (116 mg, 0.88 mmol), and a 60% NaH oil dispersion (35 mg, 0.88 mmol). The resulting mixture was stirred under $N_2$ at room temperature for 15 min, and then heated to 80° C. for 16 hr. The mixture was then cooled to room temperature and quenched by the addition of saturated ammonium chloride aqueous (1 mL). Afterward, the mixture was partitioned between ethyl acetate (5 mL) and water (5 mL). The organic layer was washed with brine (5 mL), and filtered through a pad of celite. The filtrate was concentrated in vacuo and purified by flash column chromatography (10–25% ethyl acetate/hexane) to afford 121 mg of a colorless oil product (37% yield). $^1$H NMR (CDCl$_3$) δ 1.30 (m, 2H), 1.52 (s, 9H), 1.67–1.82 (m, 3H), 2.11 (td, J=4.8, 12.6 Hz, 2H), 2.31 (d, J=11.2 Hz, 2H), 2.94 (td, J=1.8, 12.6 Hz, 2H), 3.30 (td, J=1.8, 12 Hz, 2H), 3.40 (d, J=6 Hz, 2H), 3.74–3.82 (m, 4H), 3.96 (dd, J=4.2, 11.4 Hz, 2H), 5.87 (tt, J=4.8, 53.2 Hz, 1H); Electrospray mass spectrometry showed m/z=478 (M+H).

Part B. Preparation of 4-[4-(2,2,3,3-tetrafluoro-propoxymethyl)-piperidine-1-sulfonyl]-tetrahydro-pyran-4-carboxylic acid:

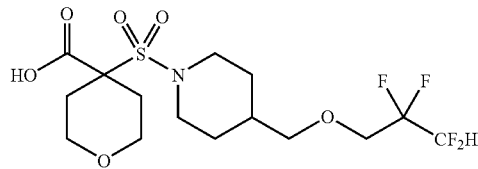

A 2-dram vial with a magnetic stirrer bar was charged with the product of Part A (120 mg, 0.25 mmol), methylene chloride (1 mL), and trifluoroacetic acid (1 mL). After the vial was capped, the mixture was stirred at room temperature for 2 hr. Afterward, the reaction mixture was concentrated in vacuo, and the residue was triturated with ethyl acetate/hexanes (1:1). The resulting solid was collected by vacuum filtration and dried in vacuo to afford a white solid product (87 mg, 82% yield). Electrospray mass spectrometry showed m/z=422 (M+H).

Part C. Preparation of 4-[4-(2,2,3,3-tetrafluoro-propoxymethyl)-piperidine-1-sulfonyl]-tetrahydro-pyran-4-carboxylic acid (tetrahydro-pyran-2-yloxy)-amide:

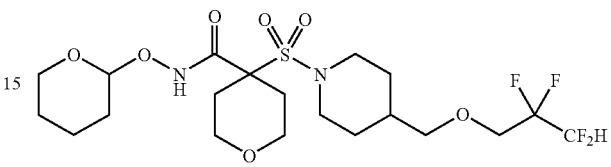

A 2-dram glass vial was charged with the product from Part B (86 mg, 0.21 mmol), a 0.5 M solution of hydroxybenzotriazole in dimethylformamide (0.8 mL, 0.4 mmol), a 0.5 M solution of tetrahydropyanyl hydroxylamine in dimethylformamide (0.8 mL, 0.4 mmol), ethyl 3-(dimethylamino)propyl carbodiimide hydrochloride (71 mg, 0.37 mmol), and triethylamine (114 uL, 0.8 mmol). The resulting mixture was stirred at room temperature for 18 hr, and then partitioned between ethyl acetate (5 mL) and water (5 mL). The organic layer was washed with 5% HCl (5 mL) and filtered through a pad of celite. The filtrate was concentrated in vacuo and purified by preparative reversed-phase high-pressure liquid chromatography using a gradient of 10–90% acetonitrile/water with 0.05% trifluoroacetic acid. This afforded 61 mg of a white solid product. Electrospray mass spectrometry showed m/z=521 (M+H).

Part D. Preparation of 4-[4-(2,2,3,3-tetrafluoro-propoxymethyl)-piperidine-1-sulfonyl]-tetrahydro-pyran-4-carboxylic acid hydroxyamide:

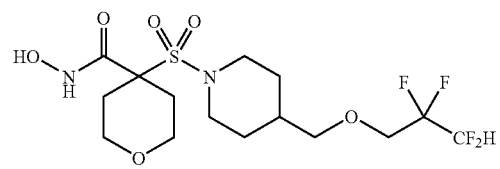

A 2-dram glass vial was charged with the product from Part C (61 mg, 0.12 mmol), 1,4-dioxane (1 mL), and methanol (1 mL). A 4 N solution of HCl in dioxane (0.1 mL, 0.4 mmol) was added, and the resulting mixture stirred at room temperature for 10 min. Volatiles were removed in vacuo, leaving 22 mg of a white crystalline solid product (24% yield over two reaction steps). $^1$H NMR (DMSO-d6) δ 1.08 (m, 2H), 1.61 (d, J=13.2 Hz, 2H), 1.71 (m, 1H), 1.83 (td, J=4.6, 12.6 Hz, 2H), 2.31 (d, J=13.2 Hz, 2H), 2.87 (t, J=11.6 Hz, 2H), 3.15 (t, J=11.4 Hz, 2H), 3.37 (d, J=6 Hz, 2H), 3.57 (d, J=12.4 Hz, 2H), 3.81 (dd, J=3.2, 12 Hz, 2H), 3.87 (t, J=14 Hz, 2H), 6.46 (tt, J=5.6, 52 Hz, 1H), 9.13 (s, 1H), 10.95 (s, 1H); Electrospray mass spectrometry showed m/z=437 (M+H). High-resolution mass spectroscopy: calculated for $C_{15}H_{25}F_4N_2O_6S$: 437.1364; observed: 437.1356.

Similar manipulations of the mesylate from Example A3 using other alcohol components as described in Part A and subsequent transformations as performed in Parts B, C, and D afforded the compounds in Table 4 corresponding to the following structure:

TABLE 4

| Example | Alcohol | R | Calc. Mass | Observed Mass |
|---|---|---|---|---|
| Example A18A | 2,2,3,3,3-pentafluoro-1-propanol | —CF$_3$ | 455.1270 | 455.1258 |
| Example A18B | 2,2,3,3,4,4,4-heptafluoro-1-butanol | —CF$_2$CF$_3$ | 505.1238 | 505.1235 |
| Example A18C | 2,2,3,3,4,4,5,5-octafluoro-1-pentanol | —CF$_2$CF$_2$CF$_2$H | 537.1300 | 537.1279 |

Example A19

Preparation of 4-[4-(4-trifluoromethyl-benzyloxymethyl)-piperidine-1-sulfonyl]-tetrahydro-pyran-4-carboxylic acid hydroxyamide

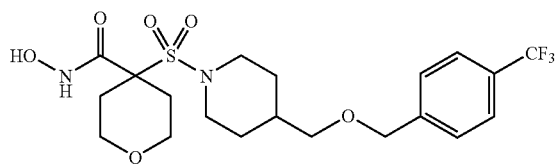

Part A. Preparation of 4-[4-(4-trifluoromethyl-benzyloxymethyl)-piperidine-1-sulfonyl]-tetrahydro-pyran-4-carboxylic acid tert-butyl ester:

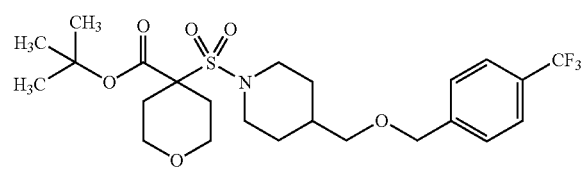

A 10 mL reaction vessel was charged with the alcohol from Example A2 (0.5 g, 1.38 mmol) and tetrahydrofuran (4 mL). A 60% NaH oil dispersion (72 mg, 1.8 mmol) was then added in 2 portions. The resulting mixture was stirred for 45 min at room temperature. 4-(trifluoromethyl)benzyl bromide (397 mg, 1.66 mmol) was then added. Afterward, the mixture was heated to 60° C. for 2 hr. The mixture was cooled to room temperature and partitioned between ethyl acetate (4 mL) and saturated aqueous ammonium chloride (4 mL). The organic layer was dried by filtration through a Celite pad, and solvent was removed in vacuo. Flash column chromatography afforded 43 mg of a white solid product (6% yield). $^1$H NMR (CDCl$_3$) δ 1.32 (m, 2H), 1.51 (s, 9H), 1.76 (d, J=12.8 Hz, 2H), 1.82 (m, 1H), 2.11 (td, J=4.7, 12.6 Hz, 2H); 2.31 (d, J=11.6 Hz, 2H), 2.95 (t, J=12.8 Hz, 2H), 3.30 (t, J=12 Hz, 2H), 3.33 (d, J=6 Hz, 2H), 3.80 (br d, J=12 Hz, 2H), 3.96 (dd, J=4.2, 11.4 Hz, 2H), 4.53 (s, 2H), 7.41 (d, J=8 Hz, 2H), 7.29 (d, J=8 Hz, 2H); Electrospray mass spectrometry showed m/z=522 (M+H).

Part B. Preparation of 4-[4-(4-trifluoromethyl-benzyloxymethyl)-piperidine-1-sulfonyl]-tetrahydro-pyran-4-carboxylic acid:

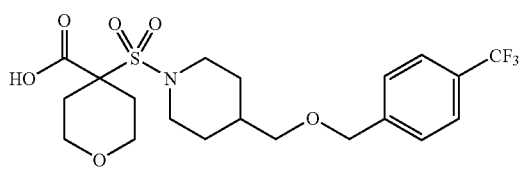

A 2-dram vial equipped with a magnetic stirring bar was charged with the product of Part A (43 mg, 0.08 mmol), methylene chloride (1 mL), and trifluoroacetic acid (1 mL). After the vial was capped, the mixture was stirred at room temperature for 3 hr. The mixture was then concentrated in vacuo, and the residue was triturated with ethyl acetate/hexanes (1:1). The resulting solid was collected by vacuum filtration and dried in vacuo to afford a white solid product (22 mg, 56% yield). Electrospray mass spectrometry showed m/z=464 (M+H).

Part C. Preparation of 4-[4-(4-trifluoromethyl-benzyloxymethyl)-piperidine-1-sulfonyl]-tetrahydro-pyran-4-carboxylic acid (tetrahydro-pyran-2-yloxy)-amide:

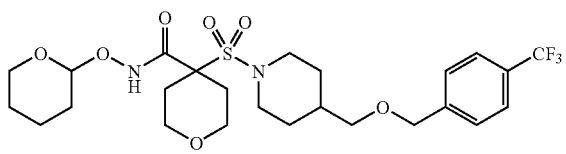

A 2-dram glass vial equipped with a magnetic stirring bar was charged with the product from Part B (22 mg, 0.05 mmol), a 0.5 M solution of hydroxybenzotriazole in dimethylformamide (0.2 mL, 0.1 mmol), a 0.5 M solution of tetrahydropyanyl hydroxylamine in dimethylformamide (0.2 mL, 0.1 mmol), ethyl 3-(dimethylamino)propyl carbodiimide hydrochloride (18 mg, 0.09 mmol), and triethylamine (26 uL, 0.2 mmol). The resulting mixture was stirred at room temperature for 18 hr, and then partitioned between ethyl acetate (5 mL) and water (5 mL). The organic layer was washed with 5% HCl (5 mL) and filtered through a pad of celite. The filtrate was concentrated in vacuo and purified by preparative reversed-phase high-pressure liquid chromatography using a gradient of 10–90% acetonitrile/water with 0.05% trifluoroacetic acid. This afforded 16 mg of a white solid product. Electrospray mass spectrometry showed m/z=582 (M+NH4).

Part D. Preparation of 4-[4-(4-trifluoromethyl-benzyloxymethyl)-piperidine-1-sulfonyl]-tetrahydro-pyran-4-carboxylic acid hydroxyamide:

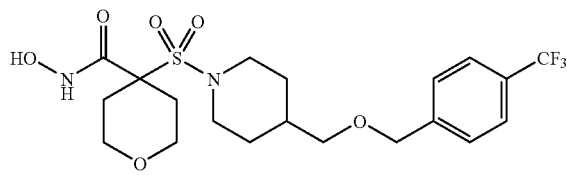

A 2-dram glass vial equipped with a magnetic stirring bar was charged with the product from Part C (16 mg, 0.05 mmol), 1,4-dioxane (1 mL), and methanol (1 mL). A 4 N solution of HCl in dioxane (0.1 mL, 0.4 mmol) was then added, and the resulting mixture was stirred at room temperature for 10 min. Volatiles were removed in vacuo, leaving 15 mg of a white crystalline solid product (69% yield over two reaction steps). $^1$H NMR (DMSO-d6) δ 1.13 (m, 2H), 1.66 (d, J=13.2 Hz, 2H), 1.71 (m, 1H), 1.84 (td, J=4.4, 12.8 Hz, 2H), 2.31 (d, J=13.2 Hz, 2H), 2.89 (t, J=11.6 Hz, 2H), 3.15 (t, J=11.4 Hz, 2H), 3.29 (d, J=5.2 Hz, 2H), 3.57 (d, J=13.2 Hz, 2H), 3.81 (dd, J=3.6, 11.6 Hz, 2H), 4.53 (s, 2H), 7.50 (d, J=8 Hz, 2H), 7.68 (d, J=8 Hz, 1H), 9.13 (s, 1H), 10.95 (s, 1H); Electrospray mass spectrometry showed m/z=481 (M+H). High-resolution mass spectroscopy: calculated for $C_{20}H_{28}F_3N_2O_6S$: 481.1615; observed: 481.1592.

Similar manipulations of the alcohol from Example A2 using other benzyl bromide components afforded the compounds in Table 5 corresponding in structure to the following formula:

TABLE 5

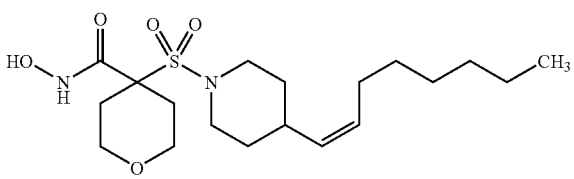

| Example | Benzyl bromide | R | Calc. Mass | Obs. Mass |
|---|---|---|---|---|
| Example A19A | 4-trifluoromethoxy benzylbromide | —OCF$_3$ | 497.1564 | 497.1559 |
| Example A19B | 4-trifluoromethyl thio-benzylbromide | —SCF$_3$ | 513.1335 | 513.1394 |

Example A20

Preparation of 4-(4-oct-1-enyl-piperidine-1-sulfonyl)-tetrahydro-pyran-4-carboxylic acid hydroxyamide

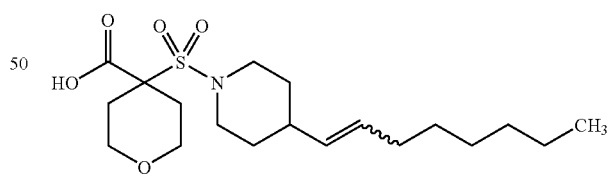

Part A. Preparation of 4-(4-oct-1-enyl-piperidine-1-sulfonyl)-tetrahydro-pyran-4-carboxylic acid tert-butyl ester:

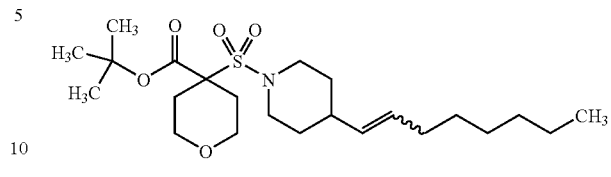

An oven-dried, 50 mL glass round-bottom flask was charged with heptyl triphenylphosphonium bromide (1.1 g, 2.5 mmol) and dry tetrahydrofuran (10 mL). The flask was then immersed into an ice bath, and a 1 M solution of lithium bis(trimethylsilyl)amide in tetrahydrofuran (2.7 mL, 2.7 mmol) was added dropwise while maintaining the temperature at less than 5° C. After complete addition, the reaction mixture was stirred with cooling for 15 min. A solution of the product from Example A4 (0.75 g, 2.1 mmol) in tetrahydrofuran (2 mL) was added dropwise while maintaining the temperature at less than 5° C. After complete addition, the mixture was stirred with cooling for 15 min, and then slowly warmed to room temperature. After stirring for an additional hr, diethyl ether was added to the mixture (25 mL). This resulted in precipitation of a brown solid. The solid was filtered, and the filtrate was washed with water (50 mL) and brine (50 mL). The organic layer was dried over magnesium sulfate, filtered and concentrated in vacuo. Purification by flash column chromatography (10% ethyl acetate/hexane) afforded 0.70 g of a colorless crystalline solid product (72% yield). $^1$H NMR (CDCl$_3$) mixture of isomers in ratio of 7:1, major isomer: δ 0.87 (t, J=6.8 Hz, 3H), 1.22–1.44 (m, 10H), 1.52 (s, 9H), 1.57 (m, 2H), 2.00 (m, 2H), 2.11 (td, J=4.7, 12.6 Hz, 2H), 2.32 (d, J=12.8 Hz, 2H), 2.39 (m, 1H), 2.99 (t, J=12.4 Hz, 2H), 3.30 (t, J=12 Hz, 2H), 3.75 (d, J=12 Hz, 2H), 3.96 (dd, J=4.2, 11.5 Hz, 2H), 5.16 (t, J=9.8 Hz, 1H), 5.33 (td, J=7.6, 10.7 Hz, 1H); Electrospray mass spectrometry showed m/z=444 (M+Na).

Part B. Preparation of 4-(4-oct-1-enyl-piperidine-1-sulfonyl)-tetrahydro-pyran-4-carboxylic acid:

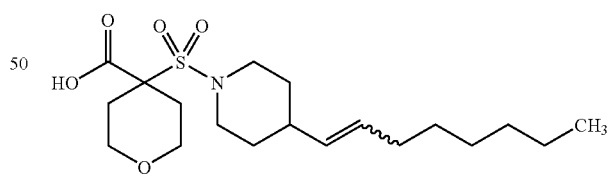

A 2-dram vial equipped with a magnetic stirring bar was charged with the product of Part A (229 mg, 0.52 mmol), methylene chloride (1 mL), and trifluoroacetic acid (1 mL). After the vial was capped, the mixture was stirred at room temperature for 3 hr. The mixture was then concentrated in vacuo, and the residue was triturated with ethyl acetate/hexanes (1:1). The solid was collected by vacuum filtration and dried in vacuo to afford a white solid product (161 mg, 81% yield). Electrospray mass spectrometry showed m/z=388 (M+H).

Part C. Preparation of 4-(4-oct-1-enyl-piperidine-1-sulfonyl)-tetrahydro-pyran-4-carboxylic acid (tetrahydro-pyran-2-yloxy)-amide:

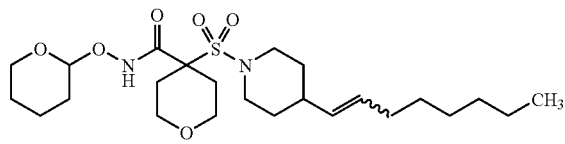

A 2-dram glass vial equipped with a magnetic stirring bar was charged with the product from Part B (161 mg, 0.42 mmol), a 0.5 M solution of hydroxybenzotriazole in dimethylformamide (1.7 mL, 0.85 mmol), a 0.5 M solution of tetrahydropyanyl hydroxylamine in dimethylformamide (1.7 mL, 0.85 mmol), ethyl 3-(dimethylamino)propyl carbodiimide hydrochloride (159 mg, 0.83 mmol), and triethylamine (232 uL, 1.67 mmol). The resulting mixture was stirred at room temperature for 18 hr, and then partitioned between ethyl acetate (5 mL) and water (5 mL). The organic layer was washed with 5% HCl (5 mL) and filtered through a pad of celite. The filtrate was concentrated in vacuo and purified by preparative reversed-phase high-pressure liquid chromatography using a gradient of 10–90% acetonitrile/water with 0.05% tnrfluoroacetic acid giving two components. Major component: 93 mg of a white solid product (46% yield), Electrospray mass spectrometry showed m/z=504 (M+NH4); Minor component: 7 mg of a white solid (4% yield), Electrospray mass spectrometry showed m/z=504 (M+NH4).

Part D. Preparation of 4-(4-Oct-1-enyl-piperidine-1-sulfonyl)-tetrahydro-pyran-4-carboxylic acid hydroxyamide:

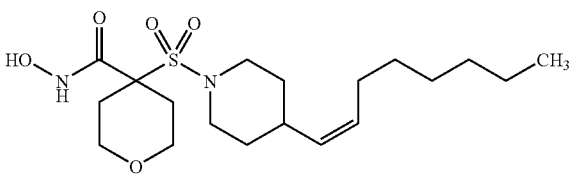

A 2-dram glass vial equipped with a magnetic stirring bar was charged with the major product from Part C (93 mg, 0.18 mmol), 1,4-dioxane (1 mL), and methanol (1 mL). A 4 N solution of HCl in dioxane (0.1 mL, 0.4 mmol) was then added, and the resulting mixture was stirred at room temperature for 10 min. Volatiles were removed in vacuo, leaving 100 mg of a white crystalline solid. $^1$H NMR (DMSO-d6) δ 0.83 (t, J=6.8 Hz, 3H), 1.22 (m, 1H), 1.47 (d, J=10.4 Hz, 2H), 1.84 (td, J=4.4, 12.8 Hz, 2H), 1.99 (q, J=6.8 Hz, 2H), 2.31 (d, J=12.8 Hz, 2H), 2.36 (m, 1H), 2.93 (t, J=11.4 Hz, 2H), 3.15 (t, J=11.6 Hz, 2H), 3.55 (d, J=12.8 Hz, 2H), 3.81 (dd, J=3.4, 11.4 Hz, 2H), 5.15 (t, J=10 Hz, 1H), 5.27 (td, J=7.2, 10.9 Hz, 1H), 9.13 (s, 1H), 10.95 (s, 1H); Electrospray mass spectrometry showed m/z=403 (M+H). High-resolution mass spectroscopy: calculated for $C_{19}H_{35}N_2O_5S$: 403.2261; observed: 403.2255.

Example A21

Preparation of 4-(4-oct-1-enyl-piperidine-1-sulfonyl)-tetrahydro-pyran-4-carboxylic acid hydroxyamide

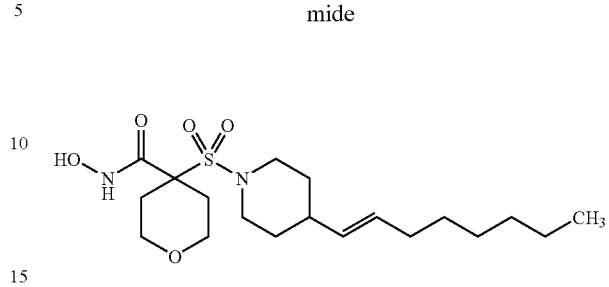

A 2-dram glass vial was charged with the major product from Example A20, Part C (7 mg, 0.02 mmol), 1,4-dioxane (1 mL), and methanol (1 mL). A 4 N solution of HCl in dioxane (0.1 mL, 0.4 mmol) was then added, and the mixture stirred at room temperature for 10 min. Volatiles were removed in vacuo, leaving 8 mg of a white crystalline solid. $^1$H NMR (DMSO-d6) δ 0.82 (t, J=6.4 Hz, 3H), 1.21 (m, 10H), 1.58 (d, J=10.8 Hz, 2H), 1.83 (td, J=4.4, 12.8 Hz, 2H), 1.91 (q, J=6.2 Hz, 2H), 2.00 (m, 1H), 2.31 (d, J=13.2 Hz, 2H), 2.89 (t, J=11.4 Hz, 2H), 3.15 (t, J=11.6 Hz, 2H), 3.54 (d, J=12.4 Hz, 2H), 3.81 (dd, J=3.6, 11.6 Hz, 2H), 5.29–5.41 (m, 2H), 9.13 (s, 1H), 10.95 (s, 1H); Electrospray mass spectrometry showed m/z=403 (M+H). High-resolution mass spectroscopy: calculated for $C_{19}H_{35}N_2O_5S$: 403.2261; observed: 403.2240.

Example A22

Preparation of 4-(4-octyl-piperidine-1-sulfonyl)-tetrahydro-pyran-4-carboxylic acid hydroxyamide (an alternative to the preparation illustrated in Example 26)

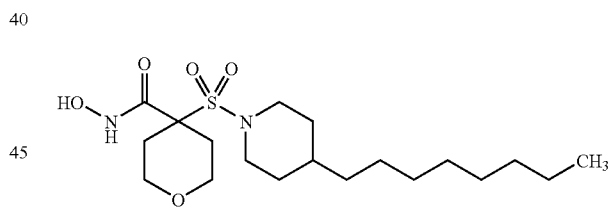

Part A. Preparation of 4-(4-octyl-piperidine-1-sulfonyl)-tetrahydro-pyran-4-carboxylic acid tert-butyl ester:

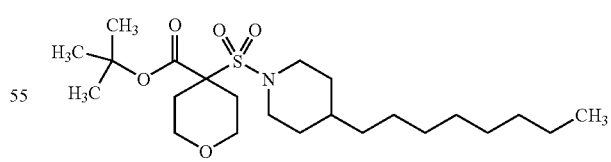

The olefin from Example A20, Part A (0.35 g, 0.79 mmol) was mixed with methanol (5 mL). Subsequently, 10% Pd/C (0.5 g) was added. The resulting mixture was agitated on a Parr shaker at 40 psi overnight. The mixture was then filtered through celite and concentrated. This afforded the alkane in the form of a white crystalline solid (328 mg, 93% yield). $^1$H NMR (CDCl$_3$) δ 0.89 (t, J=6.5 Hz, 3H), 1.27 (m, 17H), 1.54 (s, 9H), 1.69 (d, J=12.3 Hz, 2H), 2.15 (td, J=4.7, 12.5 Hz, 2H), 2.34 (d, J=12.6 Hz, 2H), 2.94 (t, J=12.2 Hz, 2H), 3.33

(t, J=11.8 Hz, 2H), 3.78 (d, J=12.6 Hz, 2H), 3.98 (dd, J=4.2, 12 Hz, 2H). Electrospray mass spectrometry showed m/z=446 (M+H)+.

Part B. Preparation of 4-(4-octyl-piperidine-1-sulfonyl)-tetrahydro-pyran-4-carboxylic acid:

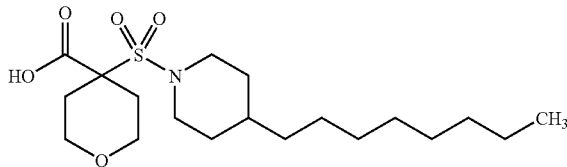

A 2-dram vial equipped with a magnetic stirring bar was charged with the product of Part A (307 mg, 0.69 mmol), methylene chloride (1 mL), and trifluoroacetic acid (1 mL). After the vial was capped, the mixture was stirred at room temperature for 3 hr. The mixture was then concentrated in vacuo, and the residue was triturated with ethyl acetate/hexanes (1:1). The resulting solid was collected by vacuum filtration and dried in vacuo to afford a white solid product (268 mg, 86% yield). Electrospray mass spectrometry showed m/z=390 (M+H).

Part C. Preparation of 4-(4-octyl-piperidine-1-sulfonyl)-tetrahydro-pyran-4-carboxylic acid (tetrahydro-pyran-2-yloxy)-amide:

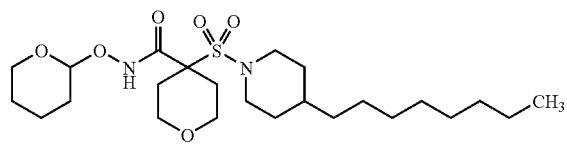

A 2-dram glass vial equipped with a magnetic stirring bar was charged with the product from Part B (232 mg, 0.60 mmol), a 0.5 M solution of hydroxybenzotriazole in dimethylformamide (2.4 mL, 1.2 mmol), a 0.5 M solution of tetrahydropyanyl hydroxylamine in dimethylformamide (2.4 mL, 1.2 mmol), ethyl 3-(dimethylamino)propyl carbodiimide hydrochloride (228 mg, 1.2 mmol), and triethylamine (332 uL, 2.4 mmol). The resulting mixture was stirred at room temperature for 18 hr, and then partitioned between ethyl acetate (5 mL) and water (5 mL). The organic layer was washed with 5% HCl (5 mL) and filtered through a pad of celite. The filtrate was concentrated in vacuo and purified by preparative reversed-phase high-pressure liquid chromatography using a gradient of 10–90% acetonitrile/water with 0.05% trifluoroacetic acid. This afforded a white solid product (169 mg, 58% yield), Electrospray mass spectrometry showed m/z=506 (M+NH4).

Part D. Preparation of 4-(4-octyl-piperidine-1-sulfonyl)-tetrahydro-pyran-4-carboxylic acid hydroxyamide:

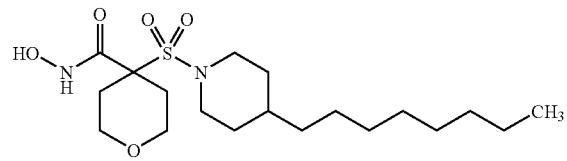

A 2-dram glass vial equipped with a magnetic stirring bar was charged with the product from Part C (93 mg, 0.18 mmol), 1,4-dioxane (1 mL), and methanol (1 mL). A 4 N solution of HCl in dioxane (0.1 mL, 0.4 mmol) was added, and the resulting mixture was stirred at room temperature for 10 min. Volatiles were removed in vacuo, leaving 162 mg of a white crystalline solid. $^1$H NMR (DMSO-d6) δ 0.82 (t, J=6.8 Hz, 3H), 1.00 (m, 2H), 1.21 (m, 11H), 1.59 (d, J=10.4 Hz, 2H), 1.83 (td, J=4.3, 12.8 Hz, 2H), 2.30 (d, J=12.8 Hz, 2H), 2.84 (t, J=11.6 Hz, 2H), 3.14 (t, J=11.6 Hz, 2H), 3.54 (d, J=12.4 Hz, 2H), 3.81 (dd, J=3.6, 11.2 Hz, 2H), 9.15 (s, 1H), 10.95 (s, 1H); Electrospray mass spectrometry showed m/z=405 (M+H). High-resolution mass spectroscopy: calculated for $C_{19}H_{37}N_2O_5S$: 405.2418; observed: 405.2398.

Example A23

Preparation of 4-(4-heptyloxy-piperidine-1-sulfonyl)-tetrahydro-pyran-4-carboxylic acid hydroxyamide

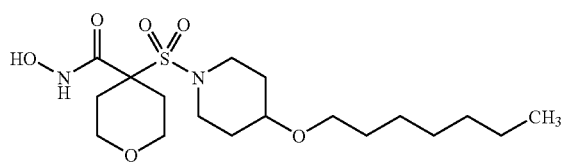

Part A. Preparation of 4-(4-heptyloxy-piperidine-1-sulfonyl)-tetrahydro-pyran-4-carboxylic acid tert-butyl ester:

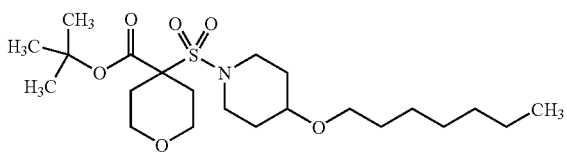

A 10 mL teflon reaction vessel was charged with the alcohol from Example A5 (0.5 g, 1.4 mmol) and tetrahydrofuran (4 mL) under N$_2$. A 60% NaH oil dispersion (74 mg, 1.9 mmol) was then added in one portion with much gassing. After stirring at room temperature for 30 min, a solution of 1-iodoheptane (0.39 g, 1.7 mmol) in tetrahydrofuran (1 mL) was added dropwise. The resulting mixture was heated to 50° C. for 26 hr, and then cooled to room temperature. Afterward, the mixture was partitioned between saturated ammonium chloride (5 mL) and ethyl acetate (5 mL). The organic layer was washed with water (5 mL), filtered through Celite, and concentrated in vacuo. Flash column chromatography on silica gel afforded a white crystalline solid product (131 mg, 20% yield). $^1$H NMR (CDCl$_3$) δ 0.88 (t, J=6.8 Hz, 3H), 1.22–1.35 (m, 8H), 1.52 (s, 9H), (m, 2H), 1.60–1.75 (m, 2H), 1.80–1.90 (m, 2H), 2.11 (td, J=4.5, 12.6 Hz, 2H), 2.32 (d, J=11.4 Hz, 2H), 3.17 (m, 2H), 3.25 (m, 2H), 3.31 (t, J=12.2 Hz, 2H), 3.40 (t, J=6.6 Hz, 2H), 3.46 (m, 1H), 3.55 (m, 2H), 3.96 (dd, J=4.2, 11.4 Hz, 2H); Electrospray mass spectrometry showed m/z=448 (M+H)+.

Part B. Preparation of 4-(4-heptyloxy-piperidine-1-sulfonyl)-tetrahydro-pyran-4-carboxylic acid:

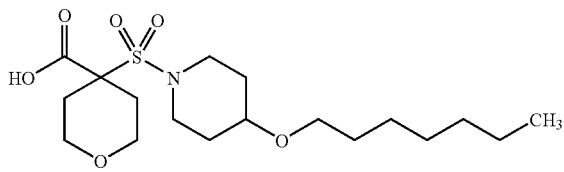

A 2-dram vial equipped with a magnetic stirring bar was charged with the product of Part A (99 mg, 0.22 mmol), methylene chloride (1 mL), and trifluoroacetic acid (1 mL). After the vial was capped, the mixture was stirred at room temperature for 3 hr. The mixture was then concentrated in vacuo, and the residue was triturated with ethyl acetate/hexanes (1:1). The resulting solid was collected by vacuum filtration and dried in vacuo to afford a white solid product (86 mg, 83% yield). Electrospray mass spectrometry showed m/z=392 (M+H).

Part C. Preparation of 4-(4-heptyloxy-piperidine-1-sulfonyl)-tetrahydro-pyran-4-carboxylic acid (tetrahydro-pyran-2-yloxy)-amide:

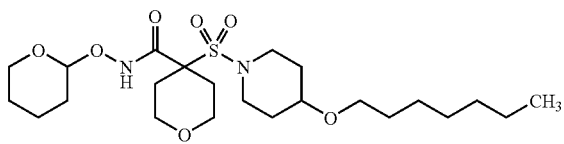

A 2-dram glass vial equipped with a magnetic stirring bar was charged with the product from Part B (72 mg, 0.18 mmol), a 0.5 M solution of hydroxybenzotriazole in dimethylformamide (0.7 mL, 0.35 mmol), a 0.5 M solution of tetrahydropyanyl hydroxylamine in dimethylformamide (0.7 mL, 0.35 mmol), ethyl 3-(dimethylamino)propyl carbodiimide hydrochloride (70 mg, 0.36 mmol), and triethylamine (102 uL, 0.73 mmol). The resulting mixture was stirred at room temperature for 18 hr, and then partitioned between ethyl acetate (5 mL) and water (5 mL). The organic layer was washed with 5% HCl (5 mL) and filtered through a pad of celite. The filtrate was concentrated in vacuo and purified by preparative reversed-phase high-pressure liquid chromatography using a gradient of 10–90% acetonitrile/water with 0.05% trifluoroacetic acid. This afforded a white solid product (55 mg, 61% yield). Electrospray mass spectrometry showed m/z=508 (M+NH4).

Part D. Preparation of 4-(4-heptyloxy-piperidine-1-sulfonyl)-tetrahydro-pyran-4-carboxylic acid hydroxyamide:

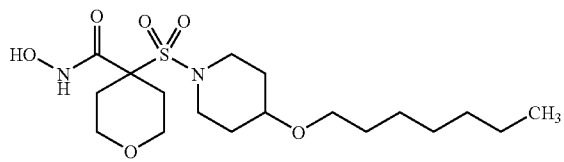

A 2-dram glass vial equipped with a magnetic stirring bar was charged with the major product from Part C (55 mg, 0.11 mmol), 1,4-dioxane (1 mL), and methanol (1 mL). A 4 N solution of HCl in dioxane (0.1 mL, 0.4 mmol) was then added, and the resulting mixture stirred at room temperature for 10 min. Volatiles were removed in vacuo, leaving 53 mg of a white crystalline solid. $^1$H NMR (DMSO-d6) δ 0.83 (t, J=6.8 Hz, 3H), 1.20–1.30 (m, 8H), 1.35–1.48 (m, 4H), 1.70–1.80 (m, 2H), 1.83 (td, J=4.4, 12.8 Hz, 2.30 (d, J=13.2 Hz, 2H), 3.00–3.10 (m, 2H), 3.14 (t, J=11.6 Hz, 2H), 3.27–3.45 (m, 5H), 3.81 (dd, J=3.8, 11.4 Hz, 2H), 9.15 (s, 1H), 10.95 (s, 1H); Electrospray mass spectrometry showed m/z=405 (M+H). High-resolution mass spectroscopy: calculated for $C_{18}H_{35}N_2O_6S$: 407.2210; observed: 407.2205.

Example A24

Preparation of N-hydroxy-4-({4-[5-(3,3,4,4,4-pentafluorobutyl)pyrazin-2-yl]piperazin-1-yl}sulfonyl)tetrahydro-2H-pyran-4-carboxamide hydrochloride

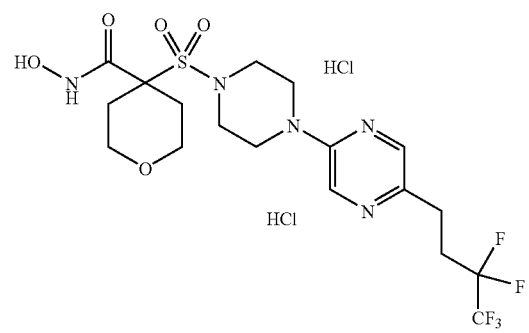

Part A. Preparation of 5'-bromo-4-methanesulfonyl-3,4,5,6-tetrahydro-2H-[1,2']bipyrazinyl:

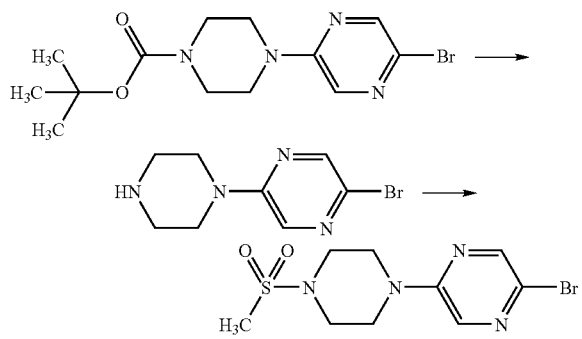

To a $CH_2Cl_2$ (150 mL) solution of Example 1, Part B (17 g, 50 mmol) in an ice bath was added trifluoroacetic acid (30 mL). The solution was stirred for 4 hr at room temperature, and then stripped in vacuo. The residue was partitioned between EtOAc (250 mL) and saturated $NaHCO_3$ (200 mL). The organic layer was separated, and the aqueous layer extracted with EtOAc and $CH_2Cl_2$ (200 mL each). The combined organic extracts were washed with brine, dried over $MgSO_4$, and evaporated to afford the crude piperazine in the form of a yellow solid (MS: m/z=243, 245 (M+H)). The resulting crude product was dissolved in $CH_2Cl_2$ (150 mL), and then cooled in an ice bath. To the resulting mixture was added $Et_3N$ (8.8 mL, 63 mmol) and methanesulfonyl chloride (4.2 mL, 55 mmol). The solution was stirred for 16 hr at room temperature. The mixture was then washed with water and brine, dried over $MgSO_4$, and evaporated to produce 14.3 g (89% yield) of the desired sulfonamide in the form of a pale yellow oil. MS: m/z=321, 323 (M+H).

Part B. Preparation of (5'-bromo-2,3,5,6-tetrahydro-[1,2']bipyrazinyl-4-sulfonyl)-acetic acid tert-butyl ester:

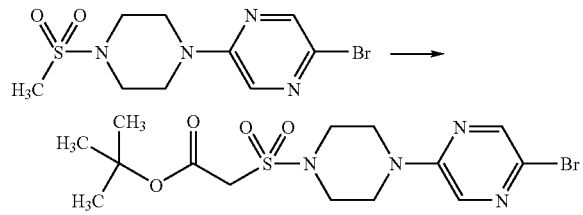

To a slurry of Part A (9.86 g, 30.7 mmol) and di-tert-butyl dicarbonate (7.37 g, 33.8 mmol) in THF (200 mL) at −78° C. was added a tetrahydrofuran ("THF") solution of lithium bis(trimethylsilyl)amide (90 mL, 1 M, 90 mmol) dropwise over 10 min. The resulting slurry was warmed to 0° C., stirred for 10 min, and quenched with saturated NH$_4$Cl (100 mL). The THF was removed by rotary evaporation, and the residue was partitioned between ethyl acetate (400 mL) and water (200 mL). The organic layer was separated, washed with brine, dried over MgSO$_4$, and evaporated to produce 12.5 g (97% yield) of the desired compound in the form of a tan solid. LCMS: m/z=443.0, 445.0 (M+H).

Part C. Preparation of 4-(5'-bromo-2,3,5,6-tetrahydro-[1,2']bipyrazinyl-4-sulfonyl)-tetrahydro-pyran-4-carboxylic acid tert-butyl ester:

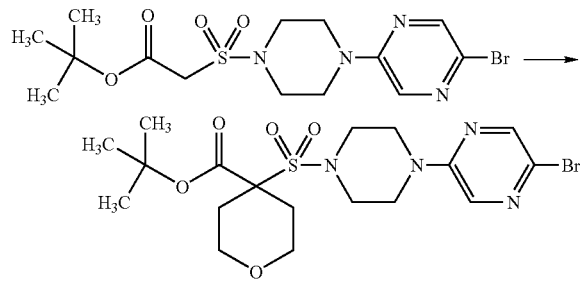

To a dimethylformamide ("DMF") (50 mL) solution of the product of Part B (6.40 g, 15.2 mmol) was added K$_2$CO$_3$ (6.6 g, 47.8 mmol), 18-crown-6 (1.2 g, 4.5 mmol), and bis(2-bromoethyl)ether (2.8 mL, 22. mmol). The resulting slurry was stirred at 60° C. for 24 hr, and then at room temperature for an additional 16 hr. The solvent was stripped in vacuo, and the residue was partitioned between ethyl acetate (150 mL) and water (100 mL). The organic layer was separated, and the aqueous layer was extracted with EtOAc (3×150 mL) and CH$_2$Cl$_2$ (100 mL). The combined organic layers were dried over MgSO$_4$ and evaporated to form a tan solid. The solid was triturated with diethyl ether, and the precipitate was isolated by filtration and washed with diethyl ether (2×25 mL) to afford 4.79 g (64% yield) of the desired acid in the form of a white solid. LCMS: m/z=513, 515 (M+H).

Part D. Preparation of 4-[5'-(3,3,4,4,4-pentafluoro-butyl)-2,3,5,6-tetrahydro-[1,2']bipyrazinyl-4-sulfonyl]-tetrahydro-pyran-4-carboxylic acid tert-butyl ester:

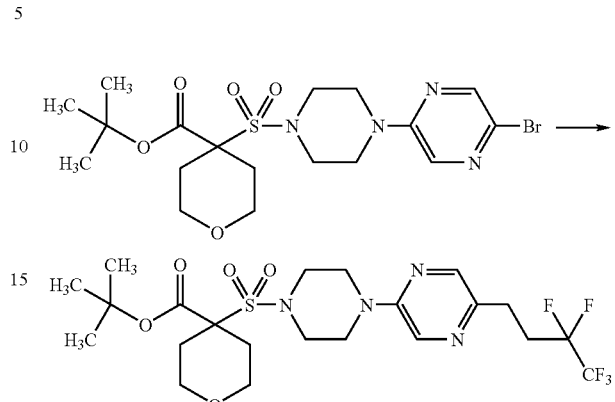

Zn/Cu couple (0.30 g, 4.6 mmol), 1,1,1,2,2-pentafluoro-4-iodobutane (0.78 g, 3.0 mmol), benzene (5 mL), and N,N-dimethylformamide (0.4 mL) were heated together for 3 hr at 60° C. under N$_2$. A solution of the product of Part C (0.49 g, 1.0 mmol) and [1,1'-bis(diphenylphosphino)ferrocene]dichloropalladium(II), complex with CH$_2$Cl$_2$ (1:1) (0.04 g, 0.05 mmol) in 1:1 DMF:THF (6 mL) was added, and the resulting slurry was stirred overnight at 60° C. under N$_2$. The mixture was subsequently poured into saturated NH$_4$Cl (50 mL), and extracted with ethyl acetate (2×50 mL). The combined organic extracts were washed with brine, dried over MgSO$_4$, and evaporated to form a brown solid. The crude material was purified on silica gel eluting with 25% ethyl acetate in hexane to produce 0.47 g (84% yield) of the desired product in the form of an off-white solid. MS: m/z=559.2 (M+H).

Part E. Preparation of 4-[5'-(3,3,4,4,4-pentafluoro-butyl)-2,3,5,6-tetrahydro-[1,2']bipyrazinyl-4-sulfonyl]-tetrahydro-pyran-4-carboxylic acid:

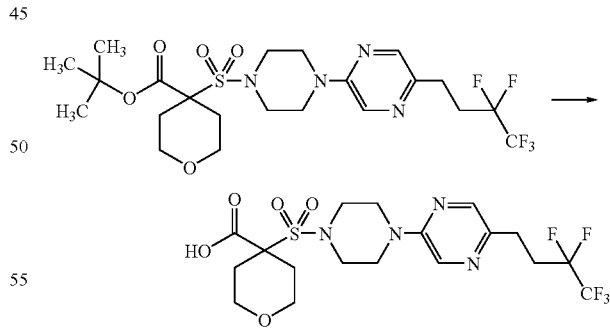

To a CH$_2$Cl$_2$ (2 mL) solution of the product of Part D (0.45 g, 0.81 mmol) was added was added trifluoroacetic acid (4 mL). The solution was stirred for 3 hr, and then stripped in vacuo to produce 0.62 g (94% yield) of the desired acid in the form of an off-white solid. The crude product was used without further purification in the next step. LCMS: m/z=503.1 (M+H).

Part F. Preparation of 4-[5'-(3,3,4,4,4-Pentafluoro-butyl)-2,3,5,6-tetrahydro-[1,2']bipyrazinyl-4-sulfonyl]-tetrahydro-pyran-4-carboxylic acid (tetrahydro-pyran-2-yloxy)-amide:

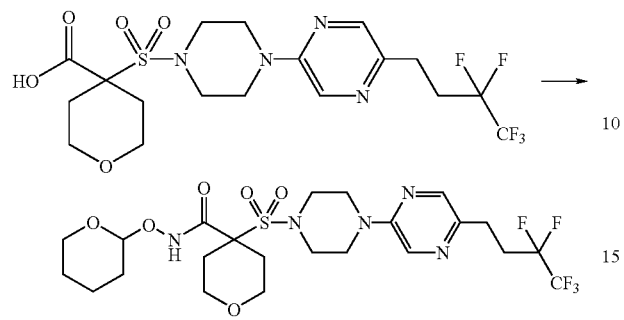

To a slurry of the product of Part E in DMF (5 mL) was added triethylamine (0.45 mL, 3.2 mmol), O-(tetrahydro-2H-pyran-2-yl)hydroxyamine (0.28 g, 2.4 mmol), 1-(3-dimethylaminopropyl)-3-ethylcarbodiimide hydrochloride (0.46 g, 2.4 mmol), and 1-hydroxybenzotriazole (0.32 g, 2.4 mmol). The reaction mixture was stirred 16 hr at room temperature. The solvent was stripped in vacuo, and the residue partitioned between ethyl acetate and water. The organic layer was separated, washed with saturated NaHCO$_3$, washed with brine, dried over MgSO$_4$, and evaporated to form an oil. The crude material was purified by flash column chromatography on silica gel eluting with 25% ethyl acetate (containing 10% MeOH) in hexane to afford 0.36 g (73% yield, based on Part D) of the desired THP-protected hydroxamic acid in the form of a white solid. LCMS: m/z=602.2 (M+H, 25%), 624.2 (M+Na, 75%).

Part G. Preparation of N-hydroxy-4-({4-[5-(3,3,4,4,4-pentafluorobutyl)pyrazin-2-yl]piperazin-1-yl}sulfonyl)tetrahydro-2H-pyran-4-carboxamide hydrochloride:

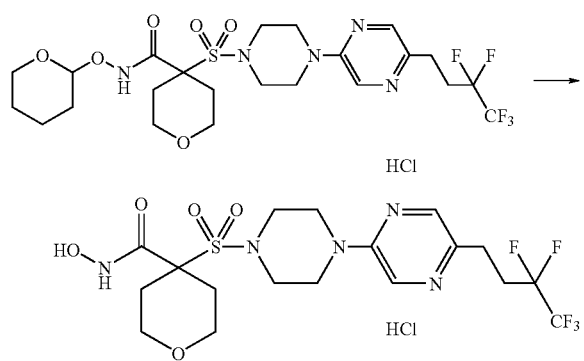

To the solid of Part F (0.35 g, 0.58 mmol) was added methanol ("MeOH") (0.5 mL) and 4 N HCl in dioxane (5.0 mL). The resulting yellow solution was stirred for 1 hr, and then added dropwise to rapidly stirring diethyl ether (50 mL). Subsequently, the slurry was stirred for 3 hr, and then filtered. The resulting solid was washed with diethyl ether (2×20 mL). The precipitate was dried in vacuo for 16 hr. Residual dioxane was removed by dissolving the solid in ethanol and stripping in vacuo at 50° C. twice. The solid was dried in vacuo for 16 hr at room temperature to afford 0.25 g (74% yield) of the desired compound. LCMS: m/z=518.1 (M+H). HRMS calcd. for C$_{18}$H$_{25}$N$_5$O$_5$SF$_5$: m/z=518.1491 [M+H]$^+$; found: 518.1515.

Example A25

Preparation of N-hydroxy-4-({4-[4-(3,3,3-trifluoropropyl)phenyl]piperazin-1-yl}sulfonyl)tetrahydro-2H-pyran-4-carboxamide hydrochloride

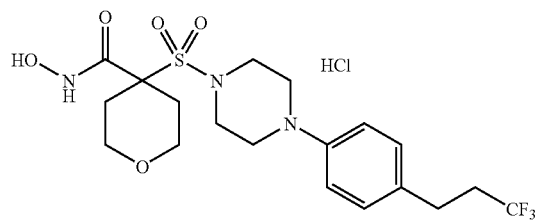

Part A. t-Butyl-2-[1-[4-(4-bromophenyl)piperazinyl]sulfonyl]acetate (15 g, 35.7 mmol, Carbogen), K$_2$CO$_3$ (14.83 g, 107.3 mmol), N,N-dimethylformamide (140 mL), 2-bromoethyl ether (9.13 g, 39.3 mmol, Aldrich), and 18-crown-6 (catalytic amount, spatula tip) were heated at 70° C. overnight with mixing under an N$_2$ atmosphere. Subsequently, additional K$_2$CO$_3$ (4.94 g, 35.7 mmol) and 2-bromoethyl ether (3.69 g, 16 mmol) were added to the mixture, and the mixture was then stirred for an additional night under N$_2$. Additional K$_2$CO$_3$ (4.94 g, 35.7 mmol) and 2-bromoethyl ether (3.69 g, 16 mmol) were once again added to the mixture, and the mixture was again stirred overnight under N$_2$. The mixture was then cooled to ambient temperature, and then poured into ethyl acetate (500 mL) and deionized water (200 mL). The layers were separated, and the aqueous was back-extracted with ethyl acetate (100 mL). The combined ethyl acetate layers were washed with 100 mL each of a 1:1 mixture of deionized water: saturated NaCl(aq) and saturated NaCl(aq), dried over MgSO$_4$, and concentrated in vacuo to form yellow solids. These solids were stirred in MeOH (50 mL) for 1 hr, filtered, and washed with MeOH (15 mL). The solids were then dried in a vacuum oven at 50° C. overnight to afford 11.1 g (64% yield) of the desired t-butyl ester pyran intermediate. $^1$H NMR confirmed structure of the intermediate.

Part B. Zn/Cu couple (0.6 g, 9.23 mmol), 1,1,1-trifluoro-3-iodopropane (1.37 g, 6.11 mmol, Aldrich), benzene (16 mL), and N,N-dimethylformamide (1 mL) were heated together for 3 hr at 60° C. under N$_2$. The t-butyl ester pyran from Part A (1.0 g, 2.04 mmol) and [1,1'-Bis(diphenylphosphino)ferrocene]dichloropalladium(II), complex with CH$_2$Cl$_2$ (1:1) (0.083 g, 0.102 mmol, Aldrich) were added, and the resulting dark mixture was stirred overnight at 69° C. under N$_2$. Zn/Cu couple (0.6 g, 9.23 mmol), 1,1,1-trifluoro-3-iodopropane (1.37 g, 6.11 mmol, Aldrich), benzene (16 mL), and N,N-dimethylformamide (1 mL) were heated together for 3 hr at 60° C. under N$_2$. This mixture was added to the original flask, and the resulting mixture was stirred overnight at 70° C. under N$_2$. An additional portion of the Pd catalyst (same amount used above) was added to the mixture, and the resulting mixture was stirred at 70° C. overnight under N$_2$. Zn/Cu couple (0.6 g, 9.23 mmol), 1,1,1-trifluoro-3-iodopropane (1.37 g, 6.11 mmol, Aldrich), benzene (16 mL), and N,N-dimethylformamide (1 mL) were heated together for 3 hr at 60° C. under N$_2$. This mixture was added to the original flask along with another portion of the Pd catalyst (same amount used above), and the resulting mixture was stirred overnight at 70° C. under N₂. The mixture was allowed to cool to ambient temperature, and 50 mL each of saturated NH₄Cl(aq) and deionized water were added to the mixture. The mixture was then stirred for 15 min. Afterward, the mixture was further diluted with 200 mL of ethyl acetate and filtered through a pad of Celite®. The filter cake was washed with 50 mL each of deionized water and ethyl acetate. The layers were separated, and the organic layer was washed with 100 mL of saturated NaCl(aq), dried over MgSO₄, and concentrated in vacuo to form a brown oil (1.43 g). Chromatography (silica, ethyl acetate/hexanes) afforded 0.80 g (78% yield) of a yellow oil.

Part C. The yellow oil from Part B was dissolved in CH₂Cl₂ (5 mL). Trifluoroacetic acid (5 mL) was then added. The mixture was agitated, and then stoppered with a syringe needle vent overnight at ambient temperature. Subsequently, the solution was concentrated in vacuo to approximately 1–2 mL. The solids were then precipitated by slow addition of 30 mL ethyl ether ("Et₂O"). The slurry was stoppered for 30 min to allow precipitation. The precipitate was then filtered and dried at 50° C. in vacuo for 2 hr to afford 0.64 g (72% yield) of solids.

Part D. The solids from Part C were dissolved with 1-hydroxybenzotriazole (0.23 g, 1.7 mmol, Aldrich) and 1-[3-dimethylamino)propyl]-3-ethylcarbodiimide hydrochloride (0.326 g, 1.7 mmol, Aldrich) in N,N-dimethylformamide (5 mL). The mixture was stoppered and mixed at ambient temperature for 30 min. Afterward, 4-methylmorpholine (0.5 mL, 6.8 mmol) and O-(tetrahydropyranyl) hydroxylamine (0.200 g, 1.7 mmol, Carbogen) were added. The resulting mixture was mixed at ambient temperature for 8 hr, after which 1-hydroxybenzotriazole (0.115 g, 0.85 mmol, Aldrich), 1-[3-dimethylamino)propyl]-3-ethylcarbodiimide hydrochloride (0.163 g, 0.85 mmol, Aldrich), 4-methylmorpholine (0.187 mL, 1.7 mmol), and O-(tetrahydropyranyl)hydroxylamine (0.1 g, 0.85 mmol, Carbogen) were added. The mixture was then stoppered and stirred overnight at ambient temperature. Subsequently, the mixture was poured into 100 mL ethyl acecate and 50 mL of saturated NaHCO₃(aq). The layers were separated, and the resulting aqueous layer was back-extracted with 50 mL ethyl acetate. The combined organic layers were washed with 50 mL each of a 1:1 mixture of deionized water:saturated NaCl(aq) and saturated NaCl(aq), dried over MgSO₄, and concentrated in vacuo to form an oil. Crystals were obtained from the resulting oil by crystallization from 10 mL methanol. The crystals were dried in vacuo at 50° C. overnight to afford of solids (0.41 g, 66% yield).

Part E. To the solids from Part D (0.28 g) dissolved in MeOH (2.5 mL) was added 4N HCl in dioxane (10 mL). This mixture was stoppered and mixed for 1 hr at ambient temperature. The mixture was then concentrated in vacuo to form solids. The crude material was purified by chromatography (on reversed-phase silica, water/acetonitrile w/0.05% trifluoroacetic acid in both). Trifluoroacetate salt was exchanged for hydrochloride salt by 3 evaporations with MeOH (5 mL) and 4N HCl in dioxane (20 mL). After the last evaporation, the solids were dissolved in 1 mL methanol and precipitated by a slow addition of 30 mL Et₂O resulting in white solids. The white solids were filtered and dried in a vacuum oven at 50° C. for 3 hr to afford 0.113 g of product (44% yield). MS, M+H calculated for C₁₉H₂₆F₃N₃O₅S: 466.1618, found: 466.1599.

Example A26

Preparation of N-hydroxy-4-({4-[4-(4,4,4-trifluorobutyl)phenyl]piperazin-1-yl}sulfonyl)tetrahydro-2H-pyran-4-carboxamide hydrochloride

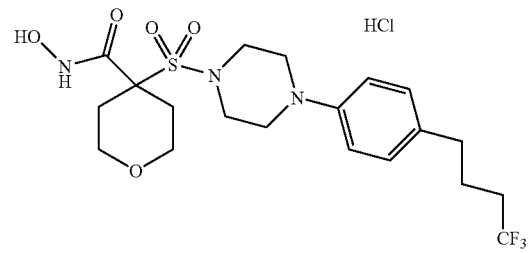

Part A. t-Butyl-2-[1-[4-(4-bromophenyl)piperazinyl] sulfonyl]acetate(15 g, 35.7 mmol, Carbogen), K₂CO₃ (14.83 g, 107.3 mmol), N,N-dimethylformamide (140 mL), 2-bromoethyl ether (9.13 g, 39.3 mmol, Aldrich), and 18-crown-6 (catalytic amount, spatula tip) were heated at 70° C. overnight with mixing under N₂. Additional K₂CO₃ (4.94 g, 35.7 mmol) and 2-bromoethyl ether (3.69 g, 16 mmol) were added to the mixture, and the mixture was again stirred overnight under N₂. Additional K₂CO₃ (4.94 g, 35.7 mmol) and 2-bromoethyl ether (3.69 g, 16 mmol) was once again added to the mixture, and the mixture was stirred overnight under N₂. The mixture was cooled to ambient temperature and then poured into ethyl acetate (500 mL) and deionized water (200 mL). The layers were separated, and the aqueous layer was back-extracted with ethyl acetate (100 mL). The combined ethyl acetate layers were washed with 100 mL each of a 1:1 mixture of deionized water:saturated NaCl(aq) and saturated NaCl(aq), dried over MgSO₄, and concentrated in vacuo to form yellow solids. These solids were stirred in MeOH (50 mL) for 1 hr, filtered, and washed with MeOH (15 mL). The solids were then dried in a vacuum oven at 50° C. overnight to afford 11.1 g (64% yield) of solids. ¹H NMR confirmed structure of the desired t-butyl ester pyran compound.

Part B. Zn/Cu couple (1.22 g, 18.8 mmol), 1,1,1-trifluoro-4-iodobutane (2.91 g, 12.2 mmol, Matrix Scientific), benzene (32.5 mL), and N,N-dimethylformamide (6.5 mL) were heated together for 3 hr at 60° C. under N₂. Afterward, the t-butyl ester pyran from Part A (2.0 g, 4.1 mmol) and [1,1'-bis(diphenylphosphino)ferrocene]dichloropalladium (II), complex with CH₂Cl₂ (1:1) (0.166 g, 0.2 mmol, Aldrich) were added, and the resulting dark mixture was stirred overnight at 78° C. under N₂. Zn/Cu couple (1.22 g, 18.8 mmol), 1,1,1-trifluoro-4-iodobutane (3.35 g, 12.2 mmol, Matrix Scientific), benzene (32.5 mL), and N,N-dimethylformamide (6.5 mL) were heated together for 3 hr at 60° C. under N₂. This mixture was then added to the original flask, along with an additional portion of the Pd catalyst (same amount used above). The resulting mixture was stirred overnight at 78° C. under N₂. The mixture was then allowed to cool to ambient temperature, and 25 mL of saturated NH₄Cl(aq) was added to the mixture. The resulting mixture was stirred for 15 min. The mixture was then further diluted with deionized water (50 mL) and ethyl acetate (100 mL) and filtered through a pad of Celite®. The filter cake was washed with 50 mL each of deionized water and ethyl acetate. The layers were separated, and the organic layer was washed with 100 mL of saturated NaCl(aq), dried over MgSO$_4$, and concentrated in vacuo to afford a red oil (2.6 g, 122% yield).

Part C. The red oil from Part B was dissolved in CH$_2$Cl$_2$ (30 mL). Trifluoroacetic acid (30 mL) was then added. The mixture was stoppered with a syringe needle vent and mixed over a weekend at ambient temperature. The resulting mixture was then concentrated in vacuo to form an oil.

Part D. The oil from Part C, 1-hydroxybenzotriazole (0.83 g, 6.1 mmol, Aldrich), and 1-[3-dimethylamino)propyl]-3-ethylcarbodiimide hydrochloride (1.18 g, 6.1 mmol, Aldrich) were dissolved in N,N-dimethylformamide (20 mL). The mixture was stoppered and mixed at ambient temperature for 1 hr. Afterward, 4-methylmorpholine (1.76 mL, 16 mmol) and O-(tetrahydropyranyl)hydroxylamine (0.71 g, 6.1 mmol, Carbogen) were added. The resulting mixture was then mixed at ambient temperature for 2 hr, after which time 1-hydroxybenzotriazole (0.55 g, 4.1 mmol, Aldrich), 1-[3-dimethylamino)propyl]-3-ethylcarbodiimide hydrochloride (0.79 g, 4.1 mmol, Aldrich), 4-methylmorpholine (0.55 mL, 5 mmol), and O-(tetrahydropyranyl)hydroxylamine (0.48 g, 4.1 mmol, Carbogen) were added. The resulting solution was stoppered and stirred at ambient temperature overnight. Subsequently, the mixture was poured into 300 mL ethyl acectate, 50 mL deionized water, and 50 mL of saturated NaHCO$_3$(aq). The layers were separated, and the organic layer was washed with 100 mL each of a 1:1 mixture of deionized water:saturated NaCl(aq) and saturated NaCl(aq), dried over MgSO$_4$, and concentrated in vacuo to afford an oil.

Part E. The oil from Part D was dissolved in MeOH (5 mL). Afterward, 4N HCl in dioxane (20 mL) was added. The resulting mixture was stoppered and mixed overnight at ambient temperature. The solution was then concentrated in vacuo to a semi-solid/oil. The crude oil was purified by chromatography (on reversed-phase silica, water/acetonitrile w/0.05% trifluoroacetic acid in both). Trifluoroacetate salt was exchanged for hydrochloride salt by 3 co-evaporations with MeOH (5 mL) and 4N HCl in dioxane (20 mL). After the last co-evaporation, the oil was triturated with diethyl ether overnight. The resulting solids were filtered and dried in a vacuum oven at 50° C. for 2 hr to afford 0.39 g (18.5% yield) of the product in the form of white solids. MS, M+H calculated for C$_{20}$H$_{28}$F$_3$N$_3$O$_5$S: 480.1775, found: 480.1763.

Example A27

Preparation of 4-{[4-(5-butylpyridin-2-yl)piperidin-1-yl]sulfonyl}-N-hydroxytetrahydro-2H-pyran-4-carboxamide hydrochloride

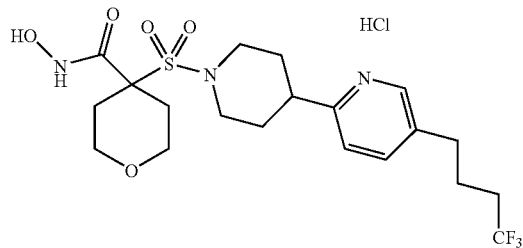

Part A. To a solution of the Boc-piperidine of Example 24, Part B (8.1 g, 23.8 mmol) in 1,4-dioxane (10 mL) was added 4M HCl in 1,4-dioxane (10 mL). Methanol (5 mL) was then added, and the resulting solution was stirred at ambient temperature for 18 hr. Additional 4M HCl in 1,4-dioxane (10 mL) was added and the reaction was complete in 15 min. The solution was concentrated in vacuo to provide the amine in the form of a yellow solid. To the crude amine suspended into methylene chloride (50 mL) was added triethylamine (8.29 mL, 59.5 mmol). The mixture was cooled to 0° C., and methanesulfonyl chloride (1.75 mL, 22.6 mmol) was added. Afterward, the mixture was stirred for 48 hr at ambient temperature. The mixture was then concentrated in vacuo. The resulting residue was dissolved into ethyl acetate. The organic layer was washed with water, saturated sodium bicarbonate, and saturated NaCl; dried over sodium sulfate; and concentrated in vacuo. Ethyl ether was added, and the resulting white solid was collected by vacuum filtration to provide the desired mesylate intermediate in the form of a white solid (4.0 g, 53% yield). MS MH$^+$ for C$_{11}$H$_{15}$BrN$_2$O$_2$S: calc. 319, found 319.

Part B. To a solution of the mesylate of Part B (3.6 g, 11.3 mmol) in tetrahydrofuran (30 mL) cooled to −50° C. was added lithium hexamethyldisilazide (1.0 M in tetrahydrofuran, 29.3 mL, 29.3 mmol) dropwise over 20 min. After 2 hr of gradually warming to ambient temperature, the mixture was cooled to −50° C. Subsequently, di-tert-butyl dicarbonate (2.59 g, 11.9 mmol) in 6 mL tetrahydrofuran was added dropwise. Upon completion of the addition, the mixture was warmed to 0° C. and then quenched by the addition of saturated ammonium chloride. Water was added, and the mixture was extracted with ethyl acetate. The organic layer was washed with water and saturated NaCl, and then dried over sodium sulfate. Concentration in vacuo afforded the t-butyl methylene intermediate in the form of an orange solid (7.6 g, quantitative yield). MS MH$^+$ for C$_{16}$H$_{23}$BrN$_2$O$_4$S: calc. 419, found 419.

Part C. To a mixture of 2-bromoethyl ether (1.70 mL, 13.6 mmol) in N, N-dimethylformamide (50 mL) was added potassium carbonate (9.36 g, 67.8 mmol) and 18-crown-6 (895 mg, 3.39 mmol). The crude t-butyl intermediate from Part B (11.3 mmol) in N,N-dimethylformamide (10 mL) was then added dropwise. The resulting mixture was heated at 80° C. for 96 hr. The mixture was then partitioned between ethyl acetate and water. The organic layer was washed with water and saturated NaCl and dried over sodium sulfate. Concentration in vacuo followed by trituration with ethyl ether afforded the t-butyl ester, alpha-tetrahydropyran intermediate in the form of a beige solid (2.56 g, 46% yield). MS MH$^+$ for C$_{20}$H$_{29}$BrN$_2$O$_5$S: calc. 489, found 489.

Part D. To a mixture of the t-butyl ester, alpha-tetrahydropyan of Part C (500 mg, 1.02 mmol) in tetrahydrofuran (3 mL) was added a solution of potassium phosphate (650 mg, 3.06 mmol) in water (2 mL), tributylborane (1M in tetrahydrofuran, 1.53 mL, 1.53 mmol), and [1,1'-bis(diphenyphosphino)ferrocene]dichloropalladium(II). CH$_2$Cl$_2$ (42 mg, 51 μmol) was then added. The mixture was heated to 60° C. for 18 hr. Afterward, the mixture was filtered through Celite, rinsing with ethyl acetate. The organic mixture was washed with water and saturated NaCl, and dried over sodium sulfate. Chromatography (on silica, ethyl acetate/hexane) afforded the desired butyl intermediate as an oil (525 mg, quantitative yield). MS MH$^+$ for C$_{24}$H$_{38}$BrN$_2$O$_5$S: calc. 467, found 467.

Part E. The butyl compound of Part D (1.02 mmol) was dissolved into neat trifluoroacetic acid (5 mL). After 1 hr, the mixture was concentrated in vacuo to provide the crude carboxylic acid. The acid was dissolved into N,N-dimethylformamide (5 mL). Afterward, 1-hydroxybenzotriazole (165 mg, 1.22 mmol), 4-methylmorpholine (0.56 mL, 5.1 mmol), O-(tetrahyrdro-2H-pyran-2-yl)hydroxylamine (179 mg, 1.53 mmol) and 1-(3-dimethylaminopropyl)-3-ethylcarbodiimide hydrochloride (274 mg, 1.43 mmol) were added. The mixture was stirred at ambient temperature for 18 hr. The mixture was then partitioned between ethyl acetate and water. The organic layer was washed with water and saturated NaCl, and dried over sodium sulfate. Chromatography (on silica, ethyl acetate, hexane) afforded the desired tetrahydropyanyl-protected hydroxamate intermediate as an oil (245 mg, 47% yield). MS MH+ for $C_{25}H_{39}N_3O_6S$: calc. 510, found 510.

Part F. The protected hydroxamate of Part E (184 mg, 0.36 mmol) was dissolved into 1,4-dioxane (3 mL). Afterward, 4M HCl in dioxane (5 mL) was added. After 1 hr, the mixture was concentrated in vacuo. Addition of ethyl ether followed by vacuum filtration afforded the title compound in the form of a white solid (155 mg, 93% yield). HRMS calc. 426.2063, found 426.2069.

Example A28

Preparation of N-hydroxy-4-({4-[5-(3,3,4,4,4-pentafluorobutyl)pyridin-2-yl]piperidin-1-yl}sulfonyl)tetrahydro-2H-pyran-4-carboxamide hydrochloride

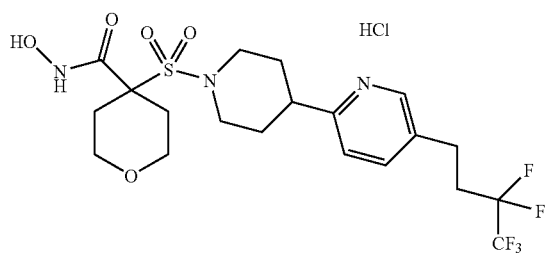

Part A. To a slurry of zinc dust (451 mg, 6.90 mmol) in tetrahydrofuran (3 mL) was added 1,2-dibromoethane (42 μL, 0.49 mmol). The slurry was heated to reflux with a heat gun 3 times. After cooling to ambient temperature the third time, trimethylsilyl chloride (70 μL, 0.55 mmol) was added. After 20 min, 1-iodo-3,3,4,4,4-pentafluorobutane (630 mg, 2.30 mmol) in tetrahydrofuran (2 mL) was added, and the mixture was heated to 40° C. until the iodide was consumed. The resulting organozinc mixture was added via syringe to a mixture of the t-butyl compound from Example A27, Part C (750 mg, 1.53 mmol) in dimethylacetamide (2 mL). Dichlorobis(tri-o-tolylphosphine)palladium(II) (78 mg, 99 μmol) was then added, and the mixture was heated to 80° C. for 18 hr. Afterward, the mixture was filtered through Celite, rinsing with ethyl acetate. The organic mixture was washed with water and saturated NaCl, and dried over sodium sulfate. Chromatography (on silica, ethyl acetate/hexane) afforded the desired pentafluorobutyl intermediate as an oil (262 mg, 31% yield). MS MH+ for $C_{24}H_{33}N_2O_5SF_5$: calc. 557, found 557.

Part B. The pentafluorobutyl of Part A (257 mg, 0.46 mmol) was dissolved into neat trifluoroacetic acid (5 mL). After 1 hr, the mixture was concentrated in vacuo to provide the crude carboxylic acid. The acid was dissolved into N,N-dimethylformamide (5 mL). Afterward, 1-hydroxybenzotriazole (74 mg, 0.55 mmol), 4-methylmorpholine (0.25 mL, 2.3 mmol), O-(tetrahydro-2H-pyran-2-yl)hydroxylamine (81 mg, 0.69 mmol), and 1-(3-dimethylaminopropyl)-3-ethylcarbodiimide hydrochloride (123 mg, 0.64 mmol) were added. The resulting mixture was stirred at ambient temperature for 18 hr, and then at 60° C. for 3 hr. The mixture was then partitioned between ethyl acetate and water. The organic layer was washed with water and saturated NaCl, and dried over sodium sulfate. Chromatography (on silica, ethyl acetate, hexane) afforded the desired tetrahydropyanyl-protected hydroxamate intermediate as an oil (100 mg, 36% yield). MS MH+ for $C_{25}H_{34}N_3O_6SF_5$: calc. 600, found 600.

Part C. The protected hydroxamate of Part B (100 mg, 0.17 mmol) was dissolved into 1,4-dioxane (2 mL). Subsequently, 4M HCl in dioxane (3 mL) was added. After 1 hr, the mixture was concentrated in vacuo. Addition of ethyl ether followed by vacuum filtration afforded the title compound in the form of a white solid (76 mg, 81% yield). HRMS calc. 516.1592, found 516.1583.

Example A29

Preparation of N-hydroxy-4-({4-[5-(4,4,4-trifluorobutyl)pyridin-2-yl]piperazin-1-yl}sulfonyl)tetrahydro-2H-pyran-4-carboxamide hydrochloride

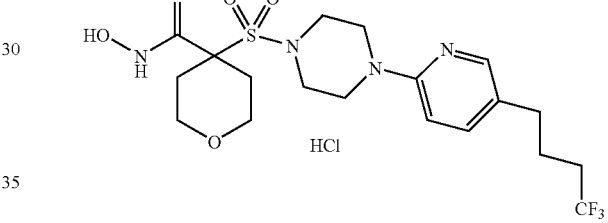

Part A. To a mixture of tert-butyl 4-(piperazinylsulfonyl) perhydro-2H-pyran-4-carboxyate (10.0 g, 29.9 mmol, Carbogen) in N,N-dimethylacetamide (40 mL) was added 2,5-dibromopyridine (6.44 g, 27.2 mmol) and cesium carbonate (17.72 g, 54.4 mmol). The mixture was heated to 120° C. for 120 hr. The mixture was then partitioned between ethyl acetate and water. The organic layer was washed with water and saturated NaCl, and dried over sodium sulfate. Concentration in vacuo followed by trituration with hexane afforded the desired bromo intermediate in the form of a yellow solid (7.0 g, 53% yield).

Part B. To a slurry of zinc dust (285 mg, 4.36 mmol) in tetrahydrofuran (3 mL) was added 1,2-dibromoethane (30 μL, 0.31 mmol). The slurry was heated to reflux with a heat gun 3 times. After cooling to ambient temperature the third time, trimethylsilyl chloride (40 μL, 0.35 mmol) was added. After 20 min, 1-iodo-4,4,4-trifluorobutane (346 mg, 1.45 mmol) in tetrahydrofuran (2 mL) was added, and the resulting mixture was heated to 40° C. until the iodide was consumed. The resulting organozinc mixture was added via syringe to a mixture of the bromo compound from Part A (475 mg, 0.97 mmol) in N,N-dimethylacetamide (2 ml). [1,1-bis(diphenyphosphino)ferrocene]dichloropalladium (II). $CH_2Cl_2$ (40 mg, 48 μmol) was then added, and the resulting mixture was heated to 80° C. for 18 hr. Afterward, the mixture was filtered through Celite, rinsing with ethyl acetate. The organic layer was then washed with water and saturated NaCl, and dried over sodium sulfate. Chromatography (on silica, ethyl acetate/hexane) afforded the desired trifluorobutyl intermediate in the form of an oil (300 mg, 59% yield). MS MH+ for $C_{23}H_{34}N_3O_5SF_3$: calc. 522, found 522.

Part C. The oil of Part B (300 mg, 0.58 mmol) was dissolved into neat trifluoroacetic acid (2 mL). After 1 hr, the mixture was concentrated in vacuo to provide the crude carboxylic acid. The acid was dissolved into N,N-dimethylformamide (2 mL). Afterward, 1-hydroxybenzotriazole (93 mg, 0.69 mmol), 4-methylmorpholine (0.32 mL, 2.9 mmol), O-(tetrahyrdro-2H-pyran-2-yl)hydroxylamine (102 mg, 0.87 mmol), and 1-(3-dimethylaminopropyl)-3-ethylcarbodiimide hydrochloride (156 mg, 0.81 mmol) were added. The resulting mixture was stirred at ambient temperature for 18 hr. The mixture was then partitioned between ethyl acetate and water. The organic layer was washed with water and saturated NaCl, and dried over sodium sulfate. Chromatography (on silica, ethyl acetate, hexane) afforded the desired protected hydroxamate intermediate in the form of an oil (230 mg, 70% yield). MS MH+ for $C_{23}H_{35}N_4O_6SF_3$: calc. 565, found 565.

Part D. The protected hydroxamate of Part C (230 mg, 0.41 mmol) was dissolved into 1,4-dioxane (2 mL). Afterward, 4M HCl in dioxane (3 mL) was added. After 1 hr, the mixture was concentrated in vacuo. Chromatography (on silica, acetonitrile/water) afforded the title compound in the form of a white solid (120 mg, 57% yield). HRMS calc. 480.1654, found 480.1700.

Example A30

Preparation of N-hydroxy-4-({4-[5-(3,3,3-trifluoropropyl)pyridin-2-yl]piperidin-1-yl}sulfonyl)tetrahydro-2H-pyran-4-carboxamide hydrochloride

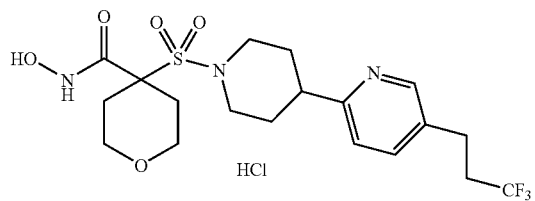

Part A. To a slurry of zinc dust (601 mg, 9.18 mmol) in tetrahydrofuran (3 mL) was added 1,2-dibromoethane (60 μL, 0.65 mmol). The slurry was heated to reflux with a heat gun 3 times. After cooling to ambient temperature the third time, trimethylsilyl chloride (90 μL, 0.73 mmol) was added. After 20 min, 3-iodo-1,1,1-trifluoropropane (0.35 mL, 3.06 mmol) in tetrahydrofuran (2 mL) was added, and the resulting mixture was heated to 40° C. until the iodide was consumed. The resulting organozinc mixture was added via syringe to a mixture of the t-butyl compound of Example A27, Part C (820 mg, 1.68 mmol) in N,N-dimethylacetamide (2 mL). Dichlorobis(tri-o-tolylphosphine) palladium (II) (86 mg, 110 μmol) was then added, and the resulting mixture was heated to 80° C. for 18 hr. Subsequently, the mixture was filtered through Celite, rinsing with ethyl acetate. The organic layer was washed with water and saturated NaCl, and dried over sodium sulfate. Chromatography (on silica, ethyl acetate/hexane) afforded the desired trifluoropropyl intermediate in the form of an oil (160 mg, 19% yield). MS MH+ for $C_{23}H_{33}N_2O_5SF_3$: calc. 507, found 507.

Part B. The trifluoropropyl compound of Part A (344 mg, 0.66 mmol) was dissolved into neat trifluoroacetic acid (2 mL). After 1 hr, the mixture was concentrated in vacuo to provide the crude carboxylic acid. The acid was dissolved into N,N-dimethylformamide (2 mL). Afterward, 1-hydroxybenzotriazole (107 mg, 0.79 mmol), 4-methylmorpholine (0.36 mL, 3.3 mmol), O-(tetrahyrdro-2H-pyran-2-yl)hydroxylamine (116 mg, 0.99 mmol), and 1-(3-dimethylaminopropyl)-3-ethylcarbodiimide hydrochloride (177 mg, 0.92 mmol) were added. The resulting mixture was stirred at ambient temperature for 18 hr. The mixture was then partitioned between ethyl acetate and water. The organic layer was washed with water and saturated NaCl, and dried over sodium sulfate. Chromatography (on silica, ethyl acetate, hexane) afforded the desired protected hydroxamate intermediate as an oil (160 mg, 44% yield). MS MH+ for $C_{24}H_{34}N_3O_6SF_3$: calc. 550, found 550.

Part C. The protected hydroxamate of Part B (160 mg, 0.29 mmol) was dissolved into 1,4-dioxane (2 mL). Afterward, 4M HCl in dioxane (3 mL) was added. After 1 hr, the mixture was concentrated in vacuo. Chromatography (on silica, acetonitrile/water(0.05% HCl) afforded the title compound in the form of a white solid (90.3 mg, 62% yield). HRMS calc. 465.1545, found 465.1543.

Example A31

Preparation of 1-cyclopropyl-N-hydroxy-4-({4-[4-(3,3,4,4,4-pentafluorobutyl)phenyl]piperidin-1-yl}sulfonyl)piperidine-4-carboxamide hydrochloride

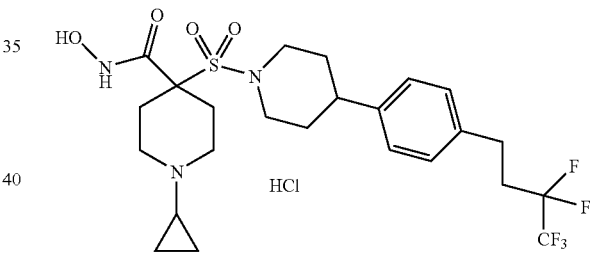

Part A. A mixture of 4-(4-bromophenyl)-4-piperidinol (50 g, 195 mmol, Aldrich), triethylamine (59.8 mL, 429 mmol), and $CH_2Cl_2$ (400 mL) was cooled to 0° C. with mixing under $N_2$. To this mixture was added methanesulfonyl chloride (16.6 mL, 214 mmol) in $CH_2Cl_2$ (100 mL) dropwise while maintaining the temperature at less than 10° C. After the addition was complete, the ice bath was removed and the mixture was stirred for 1 hr. Additional methanesulfonyl chloride (10 mL, 129 mmol) in $CH_2Cl_2$ (50 mL) was added dropwise to the mixture, and the resulting mixture was stirred at ambient temperature under $N_2$ overnight. Subsequently, the mixture was added to 300 mL of 0.5 N HCl(aq) and 200 mL of deionized water. The layers were separated, and the aqueous layer was back-extracted with $CH_2Cl_2$ (100 mL). The combined $CH_2Cl_2$ layers were washed with 300 mL each of saturated $NaHCO_3$(aq) and saturated NaCl(aq). The $CH_2Cl_2$ layer was dried over $MgSO_4$, filtered, and concentrated in vacuo to afford the desired methylsulfonamide intermediate in the form of a solid (62 g, 95.6% yield).

Part B. To the methylsulfonamide of Part A was added $CH_2Cl_2$ (300 mL) and triethylsilane (125 mL, 778 mmol), followed by trifluoroacetic acid (300 mL, 3.9 mol). The resulting mixture was stoppered and stirred at ambient temperature for 1 hr, and then concentrated in vacuo to solids. These solids were mixed with MeOH (150 mL) at ambient temperature for 2 days in a stoppered flask. The resulting solids were filtered from the slurry, and then washed with 100 mL MeOH. The washed solids were then dried in a vacuum oven at 50° C. overnight affording 54.14 g (91.7% yield) of solids. $^1$H NMR confirmed the structure of the desired product.

Part C. Zinc (dust, 325 mesh, 2.06 g, 31.5 mmol), 1,2-dibromoethane (0.243 mL, 2.8 mmol), and tetrahydrofuran (12.5 mL) were heated together at 65° C. under $N_2$ for 5 min. The slurry was then cooled to ambient temperature with mixing under $N_2$. Trimethylchlorosilane (0.336 mL, 2.64 mmol) was then added. The resulting mixture was stirred at ambient temperature for 30 min. Subsequently, 1,1,1,2,2-pentafluoro-4-iodobutane (6.45 g, 23.5 mmol, Matrix Scientific) was added, and the resulting mixture was stirred at 40° C. for 3 hr under $N_2$. Afterward, N,N-Dimethylaceamide (35 mL), the solids from Part B (5 g, 15.7 mmol), and dichlorobis(tri-o-tolylphosphine)palladium(II) (802 mg, 1.02 mmol, Aldrich) were added to the mixture. The mixture was then heated at 80° C. under $N_2$ overnight. Subsequently, the mixture was cooled to less than 30° C., and 50 mL of saturated $NH_4Cl$(aq) was added, followed by 200 mL of ethyl acetate. This biphasic system was filtered through a pad of Celite®, washing with deionized water (50 mL) and ethyl acetate (50 mL). The layers were then separated, and the ethyl acetate layer washed with 100 mL each of saturated $NaHCO_3$(aq) and saturated NaCl(aq). The ethyl acetate layer was dried over $MgSO_4$, filtered, and concentrated in vacuo to afford solids. These solids were then slurried in hexanes (50 mL) for 1 hr. Afterward, the solids were filtered, washed with hexanes (20 mL), and dried at 50° C. in a vacuum oven for 2 hr to afford 5.58 g (92% yield) of solids. $^1$H NMR confirmed the structure of the desired product.

Part D. Tetrahydrofuran (70 mL), the solids from Part C (6.7 g, 17.4 mmol), and di-tert-butyl dicarbonate (4.55 g, 20.9 mmol, Aldrich) were cooled together to −78° C. under $N_2$. To the resulting mixture, a solution of lithium bis (trimethylsilyl)amide in tetrahydrofuran (1M, 46 mL) was added at a rate such that the temperature remained at less than −70° C. This mixture was then mixed at −78° C. under $N_2$ for 1 hr, and then at 0° C. for 20 min. Subsequently, the mixture was cooled to −40° C., and saturated $NH_4Cl$(aq) (25 mL) was added. After the addition was complete, the mixture was warmed to ambient temperature, and ethyl acetate (250 mL) and deionized water (100 mL) were added. The layers were separated, and the aqueous layer was back-extracted with ethyl acetate (100 mL). The combined ethyl acetate layers were washed with 100 mL each of saturated $NaHCO_3$(aq) and saturated NaCl(aq), dried over $MgSO_4$, filtered, and concentrated in vacuo. The resulting solid/oil was co-evaporated several times with acetonitrile to afford solids, which, in turn, were dried in a vacuum oven at 50° C. overnight to afford 8.55 g (102% yield) of solids.

Part E. N,N-Dimethylformamide (20 mL), $K_2CO_3$ (5.14 g, 37.2 mmol), bis-(chloroethyl)cyclopropylamine hydrochloride (1.75 g, 7.6 mmol, Gateway Chemical), and 18-Crown-6 (0.49 g, 1.86 mmol) were heated to 65° C. under $N_2$. The solids from Part D (3.0 g, 6.2 mmol) was then added in 5 equal portions at a rate of one portion every 20 min. The mixture was then stirred overnight under $N_2$ at 65° C. An additional 1 g of $K_2CO_3$ (7.2 mmol) and 0.45 g of bis-(chloroethyl)cyclopropylamine hydrochloride (2.0 mmol, Gateway Chemical) were subsequently added, and the mixture was again stirred overnight at 65° C. under $N_2$. Subsequently, the mixture was cooled to ambient temperature. Deionized water (75 mL) and ethyl acetate (200 mL) were then added. The layers were separated, and the aqueous layer was back-extracted with ethyl acetate (50 mL). The combined ethyl acetate layers were washed with 100 mL each of a 1:1 mixture of deionized water:saturated NaCl(aq) and saturated NaCl(aq), dried over $MgSO_4$, filtered, and concentrated in vacuo to afford 4 g of solids. The solids were stirred in hexanes, filtered, washed with hexanes, and dried for several hours in vacuo at 50° C. to afford the desired t-butyl intermediate in the form of tan solids (2.22 g, 60.5% yield).

Part F. The t-butyl ester from Part E (1.76 g, 31.7 mmol) was dissolved in $CH_2Cl_2$ (11.5 mL). To this mixture were added tirethylsilane (4.9 mL, 30.7 mmol), trifluoroacetic acid (11.5 mL, 149 mmol), and trifluoromethanesulfonic acid (0.380 mL, 4.26 mmol) in that order. The resulting mixture was stoppered with a syringe needle vent and mixed at ambient temperature overnight. Subsequently, the mixture was concentrated to solids in vacuo. These solids were mixed with $Et_2O$ (50 mL) for 1 hr, filtered, washed with $Et_2O$, and dried in vacuo at 50° C. for 1 hr to afford 2.13 g (88% yield) of the desired acid intermediate.

Part G. To the acid from Part F was added N,N-dimethylformamide (15 mL), 1-hydroxybenzotriazole (0.668 g, 4.95 mmol, Aldrich), and 1-[3-dimethylamino)propyl]-3-ethylcarbodiimide hydrochloride (0.949 g, 4.95 mmol, Aldrich). The resulting mixture was stoppered and stirred for 30 min at ambient temperature. Afterward, 4-methylmorpholine (1.45 mL, 13.2 mmol) and O-(tetrahydropyranyl)hydroxylamine (0.579 g, 4.95 mmol, Carbogen) were added. The mixture was then stoppered and stirred overnight at ambient temperature. Subsequently, 4-methylmorpholine (0.363 mL, 3.3 mmol) and O-(tetrahydropyranyl)hydroxylamine (0.143 g, 1.22 mmol, Carbogen), 1-hydroxybenzotriazole (0.165 g, 1.22 mmol, Aldrich), and 1-[3-dimethylamino)propyl]-3-ethylcarbodiimide hydrochloride (0.234 g, 1.22 mmol, Aldrich) were added. The mixture was again stoppered and stirred overnight at ambient temperature. Subsequently, 200 mL of ethyl acetate, 30 mL of deionized water, and 30 mL of saturated $NaHCO_3$(aq) were added. The layers were allowed to separate. The aqueous was back-extracted with ethyl acetate (50 mL). The combined ethyl acetate layers were then washed with 75 mL each of a 1:1 mixture of deionized water: saturated NaCl(aq) and saturated NaCl(aq). The ethyl acetate layer was dried over $MgSO_4$, filtered, and concentrated in vacuo to afford a glass that was recrystallized from MeOH/deionized water to afford white solids (1.48 g, 70.5% yield).

Part H. The solids from Part G were dissolved in MeOH (2.5 mL). Afterward, 4N HCl/Dioxane (10 mL) was added. The mixture was then covered and mixed at ambient temperature for 1 hr. Subsequently, the mixture was concentrated to solids in vacuo. The solids were mixed with $Et_2O$ (50 mL) for 1 hr, filtered, and dried in vacuo at 50° C. overnight to afford 1.2 g of material. This material was purified by chromatography (on reversed-phase silica, water/acetonitrile w/0.05% trifluoroacetic acid in both). Exchanged trifluoroacetate salt for hydrochloride salt by 3 evaporations with MeOH (5 mL) and 4N HCl in dioxane (20 mL). After the last evaporation, the solids were mixed with 70 mL $Et_2O$. The white solids were filtered, washed with $Et_2O$, and dried in vacuo at 50° C. for 2 hr to afford 0.590 g of product (43% yield). MS, M+H calculated for $C_{24}H_{32}F_5N_3O_4S$: 554.2106, found: 554.2095.

Example A32

Preparation of N-hydroxy-4-({4-[4-(2,2,3,3-tetrafluoropropoxy)phenyl]piperidin-1-yl}sulfonyl)tetrahydro-2H-pyran-4-carboxamide

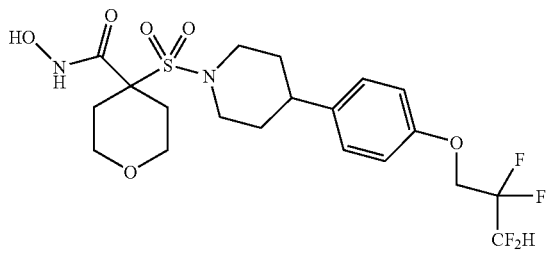

Part A. A round bottom flask was charged with 4-fluorobenzaldehyde (Aldrich, 25 g, 202 mmol) and 2,2,3,3-tetrafluoropropanol (Aldrich, 29.2 g, 222 mmol) in dimethylformamide (400 ml). Potassium carbonate (Aldrich, 41.7 g, 303 mmol) was added, and the resulting mixture was heated to 80° C. and stirred for 18 hr. The mixture was then diluted with water (500 ml) to cause a white solid to precipitate. The solid was collected by filtration, washed with water, and dried to afford the desired intermediate in the form of a white solid (43.2 g, 91% yield). $^1$H NMR showed the desired compound.

Part B. A round bottom flask was charged with the solid from Part A (41 g, 174 mmol), ethylacetoacetate (Aldrich, 44.2 ml, 347 mmol), and piperidine (Aldrich, 1.0 g, 11.7 mmol). The mixture was stirred without solvent for 3 days, resulting in a solid yellow mass. Ethanol (300 ml) was added, and the mixture was heated at reflux for 2 hr. After cooling to room temperature, precipitation occurred. The solids were filtered, washed with hexanes, and dried to afford a yellow solid. This solid was slowly added portion wise to a heated (85° C.) aqueous KOH solution (26.1 g, 470 mmol in 23 ml water). After the addition, the reaction was continued for 2 hr at 85° C., turning the mixture black. The mixture was cooled by adding ice (100 g). The cooled mixture was then washed with ethyl acetate (50 ml) and separated. The aqueous was titrated to a pH of 1 using concentrated HCl. The product was extracted out with dichloromethane (3×200 ml). The organics were combined, dried over $Na_2SO_4$, and concentrated to afford the desired di-carboxylic acid intermediate in the form of a yellowish white solid (26.9 g, 46% yield over three steps). $^1$H NMR showed the desired compound.

Part C. A round bottom flask was charged with the di-carboxylic acid from Part B (26.8 g, 79.3 mmol) and urea (7.1 g, 118.9 mmol). The mixture was heated to 170° C. for 2 hr and then cooled to 80° C. Ethanol (40 ml) was added, and the mixture was stirred at reflux for 30 min. The mixture was then cooled to 0° C. and filtered. The resulting solids were washed with hexanes and dried to afford the desired diketopiperdine intermediate in the form of a beige solid (22.3 g, 88% yield). $^1$H NMR showed the desired compound.

Part D. A round bottom flask was charged with a lithium aluminum hydride solution (208 ml, 1.0 M), and then heated to 40–60° C. The solid from Part C (22.2 g, 69.5 mmol) was added portion wise while maintaining the temperature at less than 60° C. After the addition, the flask was equipped with a condenser and refluxed for 1.5 hr. The mixture was then cooled to room temperature. Water (2 ml) was carefully added, and the resulting mixture was slurried with sodium sulfate (100 g). The solids were removed by filtration, and the filtrate was again dried over sodium sulfate. Concentration afforded the desired piperidine intermediate in the form of an orange oil (17.6 g, 87% yield). $^1$H NMR showed the desired compound.

Part E. A round bottom flask was charged with the piperidine from Part D (12.3 g, 42.2 mmol) and triethylamine (Aldrich, 10.1 ml, 72.5 mmol) in dichloromethane (100 ml). After cooling to 0° C., a solution of methylsulfonyl chloride (4.9 ml, 63.4 mmol in dichloromethane (10 ml)) was added dropwise. After the addition, the ice bath was removed, and the mixture stirred at room temperature for 18 hr. The mixture was concentrated to dryness, and the residue was combined with ethyl acetate (200 ml). The organic was washed with 10% HCl(aq), water, and brine; dried over sodium sulfate; and concentrated to afford a mix of orange and white solids. The solids were recrystallized from methanol, collected, washed with hexanes, and dried affording the desired intermediate (10.1 g, 65% yield). $^1$H NMR showed the desired compound.

Part F. A mixture of the product from Part E (11.2 g, 30.3 mmol) and t-butylcarboxlyate anhydride (Aldrich, 7.9 g, 36.4 mmol) in tetrahydrofuran (Aldrich, 60 ml) was cooled to −75° C. A solution of lithium bis(trimethylsilyl)amide (Aldrich, 1.0 M in tetrahydrofuran, 90.9 ml, 90.9 mmol) was slowly added, keeping the temperature at less than −65° C. After the addition, the mixture was warmed to 0° C. and stirred 1 hr. The mixture was then cooled back to −75° C. and quenched with a saturated solution of ammonium chloride (aqueous). The mixture was then warmed to room temperature and separated. The aqueous was extracted with ethyl acetate (twice). The organics were combined and washed with water (twice), washed with brine (twice), dried over $Na_2SO_4$, and concentrated to afford a brown residue. The residue was slurried on diethyl ether and filtered to afford the desired intermediate (12.7 g 89% yield). $^1$H NMR showed desired intermediate.

Part G. The product of Part F (5.0 g, 10.6 mmol), 18-crown-6 (Aldrich, 0.5 g, catalytic amount), potassium carbonate (Aldrich, 4.4 g, 31.8 mmol), and bis(bromoethyl) ether (Aldrich, 4.9 g, 21.2 mmol) were slurried in N,N-dimethylformamide (20 ml) and stirred at 65° C. for 15 hr. Afterward, the mixture was diluted with water (50 ml) and extracted with ethyl acetate (3×100 ml). The organics were combined and washed with water (twice), washed with brine (twice), dried over $Na_2SO_4$, and concentrated for a tan oil. The oil was washed with hexanes, and then dried to afford a tan oil. The tan oil was recrystallized from methanol to afford the desired intermediate in the form of a white solid (2.5 g, 44% yield). $^1$H NMR and LCMS showed desired intermediate.

Part H. To a mixture of the product from Part G (2.5 g, 4.6 mmol) in dichloromethane (5 ml) was added trifluoroacetic acid (Aldrich, 5 ml). The mixture stirred overnight at room temperature. Subsequently, the mixture was concentrated to one-third volume. The residue was then dripped into stirring diethyl ether (500 ml). The resulting solid was collected, washed with diethyl ether, and dried to afford the desired intermediate in the form of a white solid (1.9 g, 84% yield). $^1$H NMR showed the desired compound.

Part I. To the product of Part H (1.9 g, 3.9 mmol) in N,N-dimethylformamide (10 ml) was added triethylamine (Aldrich, 0.82 ml, 5.8 mmol), followed by N-hydroxybenzotriazole hydrate (Aldrich, 1.16 g, 8.6 mmol), O-(tetrahydro-2H-pyran-2-yl)hydroxylamine (0.91 g, 7.8 mmol), and 1-(3-dimethylaminopropyl)-3-ethylcarbodiimide hydrochloride (Sigma, 1.9 g, 9.8 mmol) in that order. The resulting mixture stirred at room temperature for 5 hr. The mixture was then diluted with water (15 ml) and ethyl acetate (100 ml). The organic layer was separated, and the aqueous was further extracted with ethyl acetate (2×75 ml). The organics were combined and washed with sat. NaHCO₃(aq) (2×150 ml), water (2×100 ml), and brine (1×200 ml). After drying over sodium sulfate, the organics were concentrated to a foamy oil and then crystallized from methanol to afford the desired intermediate in the form of a white solid (1.7 g, 74% crude yield). $^1$H NMR showed the desired compound.

Part J. To the product of Part 1 (1.7 g, 2.9 mmol) was added methanol (1 ml) and 4 N HCl in dioxane (10 ml). After stirring for 2 hr, the solvent was concentrated to one-third volume. Diethyl ether was added was then added. The resulting solid was filtered, washed with diethyl ether, and dried to afford the desired product in the form of a white solid (1.25 g, 87% yield). $^1$H NMR showed the desired compound. HRMS for $C_{20}H_{26}F_4N_2O_6S$ showed $M^{+H}_{found}$=499.1507 ($M^{+H}_{calc}$=499.1520).

Example A33

Preparation of 4-({4-[4-(1,1,2,2-tetrafluoroethoxy)phenyl]piperidinyl}sulfonyl)perhydro-2H-pyran-4-carbohydroxamic acid

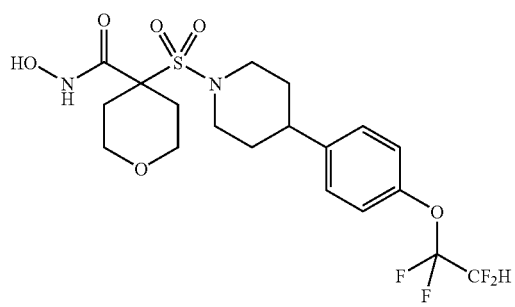

Part A. Preparation of tert-butyl 4-({4-hydroxy-4-[4-(1,1,2,2-tetrafluoroethoxy)phenyl]piperidinyl}sulfonyl)perhydro-2H-pyran-4-carboxylate:

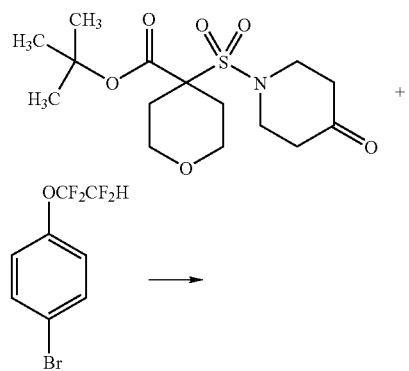

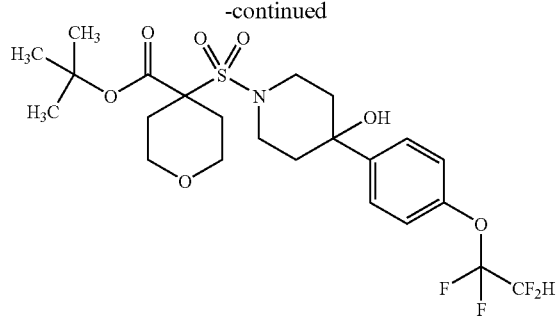

1-Bromo-4-tetrafluoroethoxybenzene (2.0 g, 7.3 mmol) was dissolved in THF (50 mL) and cooled to −78° C. under N₂. Isopropylmagnesium chloride (8.8 mmol, 4.4 mL of a 2M solution in THF) was subsequently added. The ice bath was removed, and the mixture was stirred for 36–48 hr (until no starting material was detected by reverse phase HPLC). Afterward, the mixture was once again cooled to −78° C., and 4-(4-oxo-piperidine-1-sulfonyl)-tetrahydro-pyran-4-carboxylic acid tert-butyl ester (2.5 g, 7.3 mmol, Carbogen) in THF (25 mL) was added. After 4 hr, water was added, and the product was extracted into ethyl acetate. The organic layer was washed with water and saturated NaCl before drying over anhydrous sodium sulfate. Filtration and evaporation of the solvent under reduced pressure eventually produced a solid. The solid was triturated with methanol, and the resulting white solid was collected by suction filtration to afford 1.4 g of the intermediate (35% yield). $^1$H NMR and mass spectrometry (MH⁺=542) were consistent with the desired intermediate.

Part B. Preparation of 4-({4-[4-(1,1,2,2-tetrafluoroethoxy)phenyl]piperidinyl}sulfonyl)perhydro-2H-pyran-4-carboxylic acid:

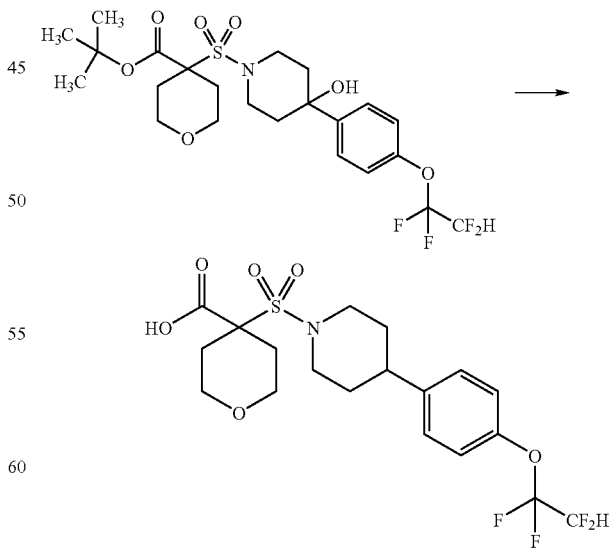

The product of Part A (13.3 g, 24.6 mmol) was suspended in dichloromethane (30 mL) and cooled to 0° C. Triethylsilane (8.6 g, 73.8 mmol, 11.8 mL) was then added, followed by trifluoroacetic acid (28.0 g, 246 mmol, 19 mL). As the trifluoroacetic acid was added, all the material gradually went into solution. The ice bath was removed, and the reaction was continued overnight at room temperature. Because there was still a small amount of dehydrated t-butyl ester remaining, additional trifluoroacetic acid (10 mL) was added, and the reaction was once again continued overnight. Afterward, no starting material remained (determined by HPLC). The mixture was concentrated under reduced pressure to afford a white solid (12.0 g, quantitative yield). Mass spectrometry (MH$^+$=470.1) was consistent with the desired intermediate.

Part C. Preparation of N-perhydro-2H-pyran-2-yloxy[4-({4-[4-(1,1,2,2-tetrafluoroethoxy)phenyl]piperidinyl}sulfonyl)perhydro-2H-pyran-4-yl]carboxamide:

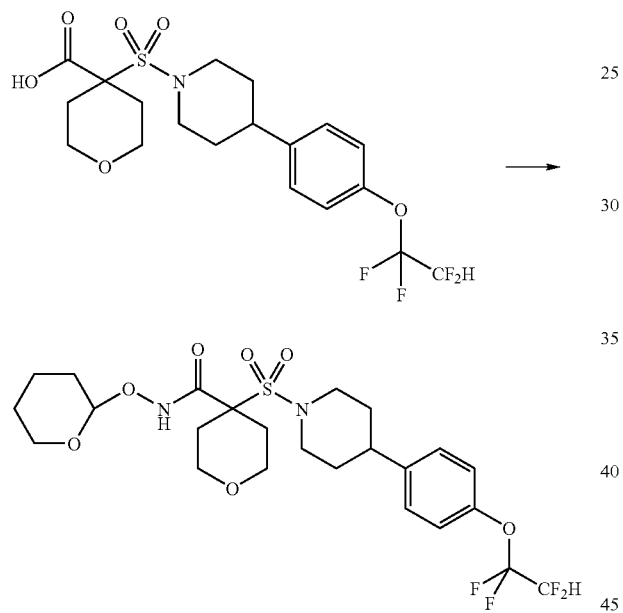

To a mixture of the product from Part B (12.0 g, 25.6 mmol) in N,N-dimethylformamide (470 mL) were added N-hydroxybenzotriazole (4.84 g, 35.8 mmol), 4-methylmorpholine (10.4 g, 11.3 mL, 102 mmol), 1-(3-dimethylaminopropyl)-3-ethylcarbodiimide hydrochloride (12.5 g, 64.0 mmol), and O-(tetrahydro-2H-pyran-2-yl)hydroxylamine (7.50 g, 70.4 mmol). The reaction was continued overnight at room temperature. Afterward, no starting material was detected by HPLC. The reaction mixture was diluted with ethyl acetate. The combined organic layer was extracted with water (3 times) and saturated sodium bicarbonate (3 times), washed with saturated NaCl; and dried over anhydrous sodium sulfate. Filtration and evaporation of the solvent under reduced pressure afforded a white solid (13.5 g). The crude material was purified by flash chromatography using dichloromethane with a methanol gradient (0–1%) to afford a white foam (11.7 g, 81% yield). $^1$H NMR and mass spectrometry (MH+Na$^+$=591.1) were consistent with the desired intermediate.

Part D. Preparation of 4-({4-[4-(1,1,2,2-tetrafluoroethoxy)phenyl]piperidinyl}sulfonyl)perhydro-2H-pyran-4-carbohydroxamic acid:

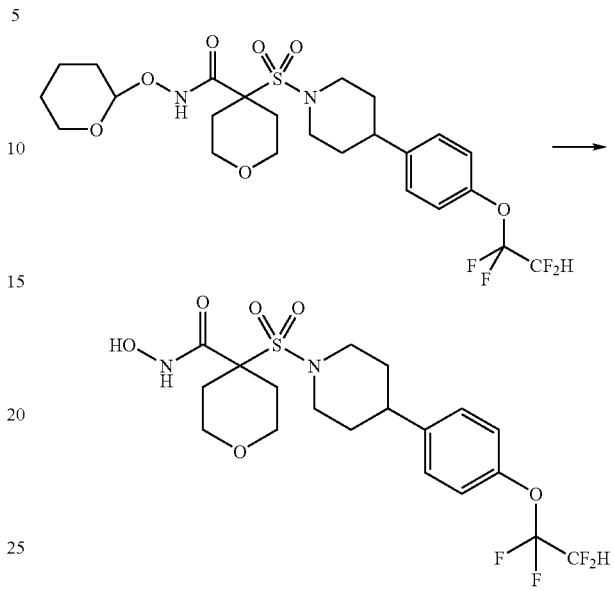

The product of Part C (11.6 g, 20.4 mmol) was dissolved in dioxane (70 mL), 4N HCl in dioxane (90 mL), and methanol (9 mL). The reaction was continued at ambient temperature overnight. Afterward, HPLC indicated that the reaction was complete. The mixture was then concentrated under reduced pressure. The residue was triturated with diethyl ether, and the resulting white solid was collected by suction filtration and dried under high vacuum (9.56 g, 97% yield). $^1$H NMR and high resolution mass spectrometry (theoretical M–H=483.1207, actual M–H=483.1181) were consistent with the desired product.

Example A34

Preparation of 1-cyclopropyl-N-hydroxy-4-({4-[4-(4,4,4-trifluorobutyl)phenyl]piperidin-1-yl}sulfonyl)piperidine-4-carboxamide hydrochloride

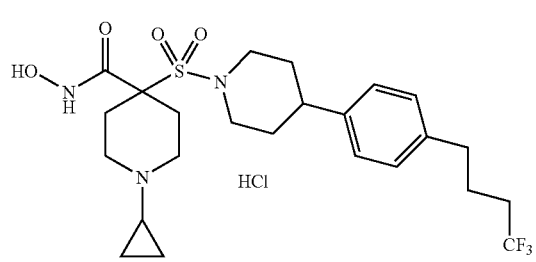

Part A. A mixture of 4-(4-Bromophenyl)-4-piperidinol (50 g, 195 mmol, Aldrich), triethylamine (59.8 mL, 429 mmol), and CH$_2$Cl$_2$ (400 mL) was cooled to 0° C. with mixing under N$_2$. To this mixture was added methanesulfonyl chloride (16.6 mL, 214 mmol) in CH$_2$Cl$_2$ (100 mL) dropwise while maintaining the temperature at less than 10° C. After the addition was complete, the ice bath was removed, and the mixture was stirred for 1 hr. Additional methanesulfonyl chloride (10 mL, 129 mmol) in CH$_2$Cl$_2$ (50 mL) was added dropwise to the mixture. Afterward, the mixture was stirred at ambient temperature under N$_2$ overnight. The reaction mixture was then added to 300 mL 0.5 N HCl(aq) and 200 mL deionized water. Subsequently, the layers were separated, and the aqueous layer was back-extracted with CH$_2$Cl$_2$ (100 mL). The combined CH$_2$Cl$_2$ layers were washed with 300 mL each of saturated NaHCO$_3$(aq) and saturated NaCl (aq). The CH$_2$Cl$_2$ layer was dried over MgSO$_4$, filtered, and concentrated in vacuo to afford the desired methylsulfonamide in the form of solids (62 g, 95.6% yield).

Part B. To the methylsulfonamide in Part A was added CH$_2$Cl$_2$ (300 mL) and triethylsilane (125 mL, 778 mmol) to form a slurry. Trifluoroacetic acid (300 mL, 3.9 mol) was then added. The resulting mixture was stoppered and stirred at ambient temperature for 1 hr and then concentrated in vacuo to solids. The solids were mixed with MeOH (150 mL) at ambient temperature for 2 days in a stoppered flask. Subsequently, the solids were filtered from the slurry and washed with 100 mL MeOH. The solids were then dried in a vacuum oven at 50° C. overnight to afford 54.14 g (91.7% yield) of solids. $^1$H NMR confirmed the structure of the desired intermediate.

Part C. Zinc (dust, 325 mesh, 2.06 g, 31.7 mmol), 1,2-dibromoethane (0.243 mL, 2.8 mmol), and tetrahydrofuran (12.5 mL) were heated together at 65° C. under N$_2$ for 5 min. The resulting slurry was cooled to ambient temperature with mixing under N$_2$. Trimethylchlorosilane (0.336 mL, 2.64 mmol) was subsequently added. This mixture was then stirred at ambient temperature for 30 min. Afterward, 1,1,1-trifluoro-4-iodobutane (5.6 g, 23.5 mmol, SynQuest) was added, and the resulting mixture was stirred at 40° C. for 3 hr under N$_2$. Subsequently, N,N-dimethylaceamide (35 mL), product from Part B (5 g, 15.7 mmol), and dichlorobis(tri-o-tolylphosphine)palladium(II) (802 mg, 1.02 mmol, Aldrich) were added. The mixture was then heated at 80° C. under N$_2$ overnight. The mixture was then cooled to less than 30° C., and 25 mL saturated NH$_4$Cl(aq) was added, followed by 200 mL ethyl acetate and 75 mL of deionized water. The biphasic system was filtered through a pad of Celite® washing with deionized water (25 mL) and ethyl acetate (50 mL). The layers were separated, and the ethyl acetate layer was washed with 100 mL each of saturated NaHCO$_3$(aq) and saturated NaCl(aq). The ethyl acetate layer was dried over MgSO$_4$, filtered, and concentrated in vacuo to afford solids. The solids were then slurried in hexanes (100 mL) for 1 hr, filtered, washed with hexanes (20 mL), and dried at 50° C. in a vacuum oven for 2 hr to afford 4.94 g (90% yield) of solids.

Part D. Tetrahydrofuran (42 mL), the product from Part C (4.85 g, 13.88 mmol), and di-tert-butyl dicarbonate (3.64 g, 16.66 mmol, Aldrich) were cooled together to −78° C. under N$_2$. To the resulting mixture, a solution of lithium bis(trimethylsilyl)amide in tetrahydrofuran (1 M, 36 mL) was added at a rate such that the temperature remained at less than −70° C. The resulting mixture was mixed at −78° C. under N$_2$ for 1 hr, and then at 0° C. for 20 min. Subsequently, the mixture was cooled to −40° C., and saturated NH$_4$Cl(aq) (25 mL) was added. After the addition was complete, the mixture was warmed to ambient temperature, and ethyl acetate (250 mL) and deionized water (100 mL) were added. The layers were separated, and the aqueous layer was back-extracted with ethyl acetate (50 mL). The combined ethyl acetate layers were washed with 100 mL each of 1:1 NaHCO$_3$(aq):deionized water, 1:1 saturated NaCl(aq): deionized water, and saturated NaCl(aq); dried over MgSO$_4$; filtered; and concentrated in vacuo to afford 6.6 g (106% yield) of solids.

Part E. N,N-Dimethylformamide (20 mL), K$_2$CO$_3$ (5.76 g, 41.64 mmol), bis-(chloroethyl)cyclopropylamine hydrochloride (1.97 g, 9.0 mmol, Gateway Chemical), and 18-Crown-6 (0.55 g, 2.1 mmol) were heated to 65° C. under N$_2$. The product from Part D (3.12 g, 6.94 mmol) was added to the mixture in 5 equal portions at a rate of one portion every 20 min. The resulting mixture was then stirred overnight under N$_2$ at 65° C. An additional 1.2 g of K$_2$CO$_3$ (8.68 mmol) and 0.5 g of bis-(chloroethyl)cyclopropylamine hydrochloride (2.29 mmol, Gateway Chemical) were added to the mixture. The mixture was again stirred overnight at 65° C. under N$_2$. Subsequently, the mixture was cooled to ambient temperature. Deionized water (100 mL) and ethyl acetate (200 mL) were then added. The layers were separated, and the aqueous layer was back-extracted with ethyl acetate (100 mL). The combined ethyl acetate layers were washed with 75 mL each of a 1:1 mixture of deionized water:saturated NaCl(aq) and saturated NaCl(aq), dried over MgSO$_4$, filtered, and concentrated in vacuo to afford 3.88 g of the desired t-butyl ester intermediate in the form of an oil.

Part F. The t-butyl ester from Part E (3.88 g, 6.94 mmol) was dissolved in CH$_2$Cl$_2$ (24 mL). To this mixture were added tirethylsilane (10.4 mL, 65 mmol), trifluoroacetic acid (24 mL, 310 mmol), and trifluoromethanesulfonic acid (0.405 mL, 4.55 mmol) in that order. The resulting mixture was stoppered with a syringe needle vent and mixed at ambient temperature overnight. Subsequently, the mixture was concentrated to solids in vacuo to afford solids. These solids were mixed with Et$_2$O (50 mL) for 1 hr, filtered, washed with Et$_2$O, and dried in vacuo at 50° C. for 1 hr to afford 3.78 g (88% yield) of the desired acid intermediate.

Part G. To the acid from Part F was added N,N-dimethylformamide (25 mL), 1-hydroxybenzotriazole (1.24 g, 9.2 mmol, Aldrich), and 1-[3-dimethylamino)propyl]-3-ethylcarbodiimide hydrochloride (1.76 g, 9.2 mmol, Aldrich). The resulting mixture was stooppered and stirred for 30 min at ambient temperature. Subsequently, 4-methylmorpholine (2.7 mL, 24.5 mmol) and O-(tetrahydropyranyl)hydroxylamine (1.08 g, 9.2 mmol, Carbogen) were added. The mixture was then stoppered and stirred overnight at ambient temperature. Afterward, 200 mL of ethyl acetate and 75 mL of deionized water were added to this mixture. The layers were then allowed to separate. The aqueous layer was back-extracted with ethyl acetate (50 mL), and then the combined ethyl acetate layers were washed with 75 mL each of a 1:1 mixture of deionized water:saturated NaCl(aq) and saturated NaCl(aq), dried over MgSO$_4$, filtered, and concentrated in vacuo to form an oil that was recrystallized from MeOH/deionized water to afford 1.67 g (45% yield) of white solids.

Part H. The solids from Part G were dissolved in MeOH (5 mL) and combined with 4N HCl/Dioxane (20 mL). The resulting mixture was covered and mixed at ambient temperature for 2 hr. The mixture was then concentrated to solids in vacuo. The solids were mixed with Et$_2$O (75 mL) for 1 hr, filtered, and dried in vacuo at 50° C. overnight to afford 1.35 g of product (88% yield). MS, M+H calculated for C$_{24}$H$_{34}$F$_3$N$_3$O$_4$S: 518.2295, found: 518.2278.

Example A35

Preparation of 4-{4-[5-(2,2,2-trifluoro-ethoxy)-pentyl]-piperidine-1-sulfonyl}-tetrahydro-pyran-4-carboxylic acid hydroxyamide

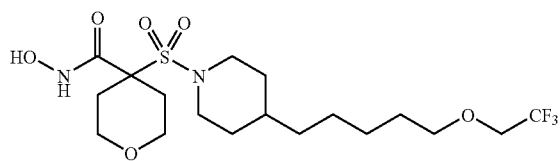

Part A. Preparation 4-[4-(5-methanesulfonyloxy-pentyl)-piperidine-1-sulfonyl]-tetrahydro-pyran-4-carboxylic acid tert-butyl ester:

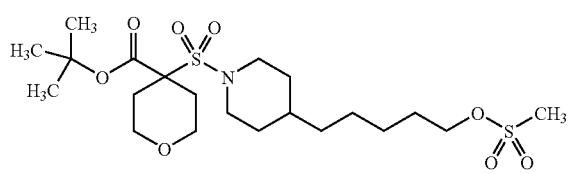

A 100 ml round-bottom flash was charged with the alcohol from Example A9, Part C (1.5 g, 3.58 mmol) and dichloromethane (9 mL). Diisopropylethylamine (0.93 mL, 5.4 mmol) was then added dropwise. Afterward, the flask was immersed into ice water bath, and methanesulfonyl chloride (0.333 mL, 4.3 mmol) was added dropwise while maintaining the temperature at less than 5° C. The resulting mixture was stirred with cooling for 30 min, and then the flask was removed from the cooling bath. Upon warming to room temperature, the reaction mixture was partitioned between dichloromethane (50 mL) and water (50 mL). The organic layer was separated, washed with 5% HCl aqueous solution (50 mL), dried over magnesium sulfate, filtered, and concentrated in vacuo. This afforded 1.88 g of a yellow viscous oil product (quantitative). $^1$H NMR (CDCl$_3$) δ 1.15–1.51 (m, 9H), 1.51 (s, 9H), 1.65 (d, J=10.4 Hz, 2H), 1.73 (p, J=6.9 Hz, 2H), 2.10 (td, J=4.7, 12.6 Hz, 2H), 2.30 (d, J=11.6 Hz, 2H), 2.91 (t, J=12.6 Hz, 2H), 2.98 (s, 3H), 3.30 (t, J=12 Hz, 2H), 3.75 (d, J=12.4 Hz, 2H), 3.95 (dd, J=4, 11.6 Hz, 2H), 4.19 (d, J=6.4 Hz, 2H); Electrospray mass spectrometry showed m/z=498 (M+H).

Part B. Preparation of 4-{4-[5-(2,2,2-trifluoro-ethoxy)-pentyl]-piperidine-1-sulfonyl}-tetrahydro-pyran-4-carboxylic acid tert-butyl ester:

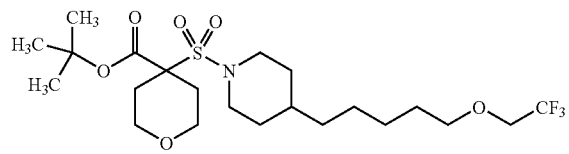

A 15 mL glass reaction vessel was charged with a 60% NaH oil dispersion (140 mg, 3.5 mmol and dimethylformamide (2 mL)). 2,2,3,3-tetrafluoro-1-ethanol (300 mg, 3 mmol) was then added dropwise over 10 min. Afterward, the vial was stirred under N$_2$ at room temperature for 10 min. A solution of the mesylate from Part A (0.5 g, 1 mmol) in dimethylformamide (1 mL) was then added. The reaction vessel was subsequently heated to 80° C. for 3 hr, and then cooled to room temperature. The resulting mixture was diluted with ice water (20 mL), causing a white crystalline solid to be formed. The solid was collected by vacuum filtration and then further dried in vacuo to afford 502 mg of a white crystalline solid product (77% yield). $^1$H NMR (CDCl$_3$) δ 1.15–1.38 (m, 9H), 1.52 (s, 9H), 1.54–1.60 (m, 2H), 2.11 (td, J=4.8, 12.6 Hz, 2H), 2.31 (d, J=11.2 Hz, 2H), 2H), 2.91 (t, J=12.6 Hz, 2H), 3.30 (t, J=12 Hz, 2H), 3.58 (d, J=6.4 Hz, 2H), 3.74–3.82 (m, 4H), 3.96 (dd, J=4.2, 11.4 Hz, 2H); Electrospray mass spectrometry showed m/z=502 (M+H).

Part C. Preparation of 4-{4-[5-(2,2,2-trifluoro-ethoxy)-pentyl]-piperidine-1-sulfonyl}-tetrahydro-pyran-4-carboxylic acid:

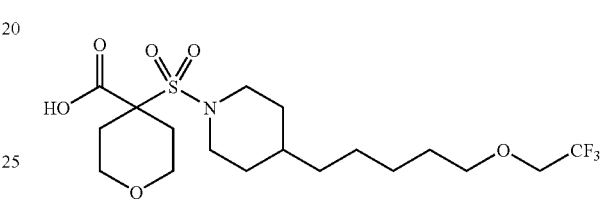

A 2-dram vial equipped with a magnetic stirring bar was charged with the ester from Part B (386 mg, 0.77 mmol), methylene chloride (2 mL), and trifluoroacetic acid (2 mL). After the vial was capped, the mixture was stirred at room temperature for 2 hr. The reaction mixture was concentrated in vacuo, forming a white solid product (253 mg, 100% yield). Electrospray mass spectrometry showed m/z=446 (M+H).

Part D. Preparation of 4-{4-[5-(2,2,2-trifluoro-ethoxy)-pentyl]-piperidine-1-sulfonyl}-tetrahydro-pyran-4-carboxylic acid (tetrahydro-pyran-2-yloxy)-amide:

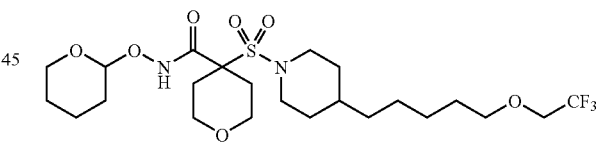

A 2-dram glass vial equipped with a magnetic stirring bar was charged with the product from Part C (353 mg, 0.79 mmol), a 0.5 M solution of hydroxybenzotriazole in dimethylformamide (3.2 mL, 1.6 mmol), a 0.5 M solution of tetrahydropyanyl hydroxylamine in dimethylformamide (3.2 mL, 1.6 mmol), ethyl 3-(dimethylamino)propyl carbodiimide hydrochloride (304 mg, 1.6 mmol), and triethylamine (331 uL, 2.4 mmol). The resulting mixture was stirred at room temperature for 18 hr, and then partitioned between ethyl acetate (50 mL) and water (50 mL). The organic layer was washed with 5% HCl (2×5 mL) and water (5 mL), and then filtered through a pad of celite. The filtrate was concentrated in vacuo and purified by flash column chromatography on silica gel to afford a white solid product (386 mg, 89% yield). Electrospray mass spectrometry showed m/z=545 (M+H)$^+$.

Part E. Preparation of 4-{4-[5-(2,2,2-trifluoro-ethoxy)-pentyl]-piperidine-1-sulfonyl}-tetrahydro-pyran-4-carboxylic acid hydroxyamide:

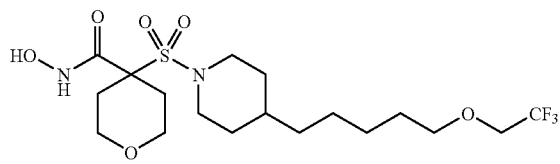

A 2-dram glass vial equipped with a magnetic stirring bar was charged with the major product from Part D (386 mg, 0.71 mmol), 1,4-dioxane (2 mL), and methanol (2 mL). A 4 N solution of HCl in dioxane (0.1 mL, 0.4 mmol) was added, and the mixture was stirred at room temperature for 15 min. Volatiles were removed in vacuo, leaving 320 mg of a white crystalline solid product. $^1$H NMR (CDCl$_3$) δ 1.13–1.38 (m, 9H), 1.58 (p, J=6.8 Hz, 2H), 1.67 (d, J=11.2 Hz, 2H), 2.15–2.25 (m, 4H), 2.89 (t, J=11.6 Hz, 2H), 3.43 (td, J=3.2, 11.6 Hz, 2H), 3.57 (t, J=6.4 Hz, 2H), 3.71, (d, J=13.2 Hz, 2H), 3.77 (q, J=8.8 Hz, 2H), 3.93–3.97 (m, 2H); Electrospray mass spectrometry showed m/z=461 (M+H). High-resolution mass spectroscopy: calculated for C$_{18}$H$_{32}$F$_3$N$_2$O$_6$S: 461.1928; observed: 461.1882.

Example A36

Preparation of 4-(4-hexyloxy-piperidine-1-sulfonyl)-tetrahydro-pyran-4-carboxylic acid hydroxyamide

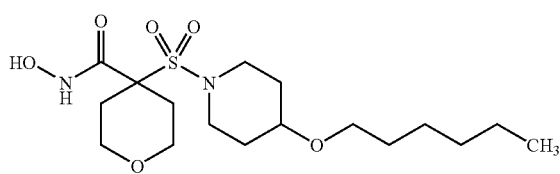

Part A. Preparation of 4-(4-hexyloxy-piperidine-1-sulfonyl)-tetrahydro-pyran-4-carboxylic acid tert-butyl ester:

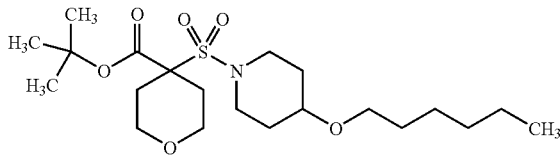

A 10 mL Teflon pressure vessel was charged with the product of Example A5 (0.35 g, 1.0 mmol), iodohexane (0.44 mL, 3 mmol), tetrabutylammonium bromide (64 mg, 0.2 mmol), powdered KOH (0.17 g, 3 mmol), and xylenes (5 mL). The reaction vessel was then sealed and placed into a microwave oven (MARS-5, CEM corporation). The mixture was heated to 80° C. using 300 watts for 30 min. After cooling to room temperature, the mixture was diluted with methylene chloride (40 mL), filtered, and concentrated in vacuo. Purification by flash column chromatography afforded a white crystalline solid product (289 mg, 67% yield). $^1$H NMR (CDCl$_3$) δ 0.87 (t, J=7 Hz, 3H), 1.22–1.35 (m, 6H), 1.51 (s, 9H), 1.54 (m, 2H), 1.60–1.70 (m, 2H), 1.78–1.88 (m, 2H), 2.09 (td, J=4.7, 12.8 Hz, 2H), 2.31 (d, J=11.6 Hz, 2H), 3.23 (m, 2H), 3.29 (t, J=12.2 Hz, 2H), 3.39 (t, J=6.6 Hz 2H), 3.44 (m, 1H), 3.55 (m, 2H), 3.95 (dd, J=4.2, 11.4 Hz, 2H); Electrospray mass spectrometry showed m/z=434 (M+H)$^+$.

Part B. Preparation of 4-(4-hexyloxy-piperidine-1-sulfonyl)-tetrahydro-pyran-4-carboxylic acid:

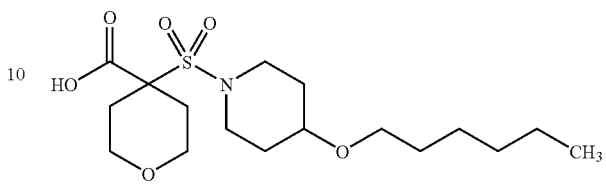

A glass 15 mL test tube equipped with a magnetic stirring bar was charged with the product from Part A (247 mg, 0.57 mmol), methylene chloride (2 mL), and trifluoroacetic acid (2 mL). The vessel was then sealed, and the mixture was stirred at room temperature for 3 hr. Afterward, the mixture was concentrated in vacuo, and the residue was triturated with an ethyl acetate/hexane mixture (1:1, 5 mL). The resulting solid was collected by vacuum filtration, washed with ethyl acetate/hexane (1:1, 2 mL), and dried in vacuo to afford the carboxylic acid product (216 mg, 100% yield). Electrospray mass spectrometry showed m/z=378 (M+H)$^+$.

Part C. Preparation of 4-(4-Hexyloxy-piperidine-1-sulfonyl)-tetrahydro-pyran-4-carboxylic acid (tetrahydro-pyran-2-yloxy)-amide:

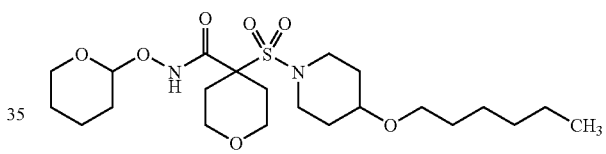

A glass 15 mL test tube equipped with a magnetic stirring bar was charged with the product from Part B (165 mg, 0.44 mmol). Next, the following were added sequentially: 0.5 M hydroxybenzotriazole in dimethylformamide (1.7 mL, 0.85 mmol), 0.5 M tetrahydropyanyl hydroxylamine in dimethylformamide (1.7 mL, 0.85 mmol), triethylamine (0.24 mL, 1.7 mmol), and ethyl 3-(dimethylamino)propyl carbodiimide hydrochloride (167 mg, 0.87 mmol). The resulting mixture was placed under N$_2$ and stirred at room temperature for 14 hr. The mixture was then partitioned between ethyl acetate (25 mL) and water (25 mL). The organic layer was washed with 5% HCl (25 mL) and water (25 mL), filtered through celite, and concentrated in vacuo. Flash column chromatography on silica gel afforded a white solid product (177 mg, 85% yield). Electrospray mass spectrometry showed m/z=477 (M+H)$^+$.

Part D. Preparation of 4-(4-hexyloxy-piperidine-1-sulfonyl)-tetrahydro-pyran-4-carboxylic acid hydroxyamide:

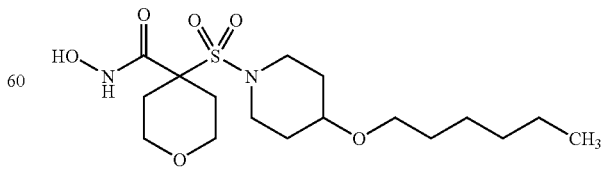

A 2-dram glass vial equipped with a magnetic stirring bar was charged with the major product from Part C (177 mg, 0.34 mmol), 1,4-dioxane (1 mL), and methanol (1 mL). A 4 N solution of HCl in dioxane (0.1 mL, 0.4 mmol) was then added, and the resulting mixture stirred at room temperature for 2.5 hr. Volatiles were removed in vacuo, leaving 139 mg of a white crystalline solid product. H NMR (DMSO-d6) δ 0.85 (t, J=6.6 Hz, 3H), 1.20–1.35 (m, 6H), 1.35–1.52 (m, 4H), 1.70–1.95 (m, 4H), 2.32 (d, J=12.9 Hz, 2H), 3.00–3.10 (m, 2H), 3.17 (t, J=11.7 Hz, 2H), 3.25–3.45 (m, 5H), 3.75–3.87 (m, 2H), 9.15 (s, 1H), 10.95 (s, 1H); Electrospray mass spectrometry showed m/z=393 (M+H). High-resolution mass spectroscopy: calculated for $C_{17}H_{33}N_2O_6S$: 393.2054; observed: 393.2038.

Similar manipulations of the alcohol from Example A5 using other alkyl halide components ("R-X") were used to prepare the compounds in Table 6 corresponding in structure to the following formula:

TABLE 6

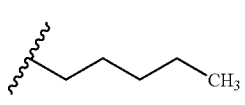

| Example | Alkyl Halide (R-X) | R | calc. mass | obs. mass |
|---|---|---|---|---|
| Example A36A | 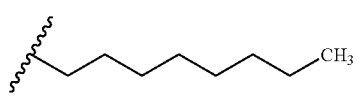 | 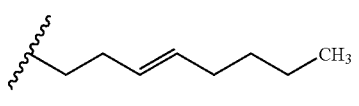 | 379.1897 | 379.1929 |
| Example A36B | 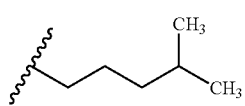 | 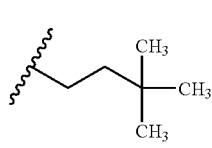 | 421.2367 | 421.2355 |
| Example A36C | 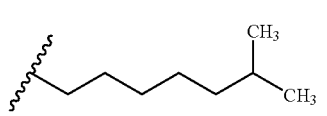 | 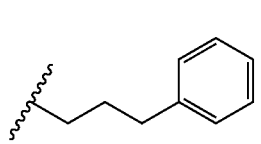 | 419.2210 | 419.2231 |
| Example A36D | 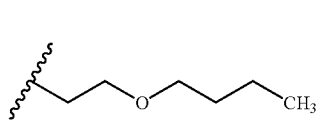 | | 393.2054 | 393.2031 |
| Example A36E | | | 393.2054 | 393.2055 |
| Example A36F | | | 421.2367 | 421.2359 |
| Example A36G | | | 427.1897 | 427.1895 |
| Example A36H | | | 409.2003 | 409.2052 |

Following the procedure described in Part A above, the compounds in Table 7 were obtained by the reaction of the alcohol from Example A7 with different alkyl halide components ("R-X") and subsequent transformations as described in Parts B, C and D above:

TABLE 7

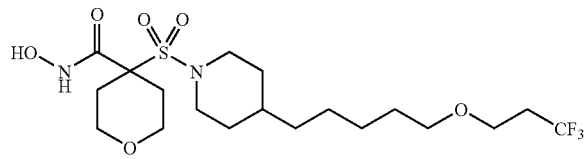

| Example | R-X | R | calc. mass | obs. mass |
|---|---|---|---|---|
| Example A36I | I//CH₃ | ///CH₃ | 407.2210 | 407.2226 |
| Example A36J | I//CF₃ | ///CF₃ | 461.1928 | 461.1906 |

Example A37

Preparation of 4-{4-[5-(3,3,3-Trifluoro-propoxy)-pentyl]-piperidine-1-sulfonyl}-tetrahydro-pyran-4-carboxylic acid hydroxyamide

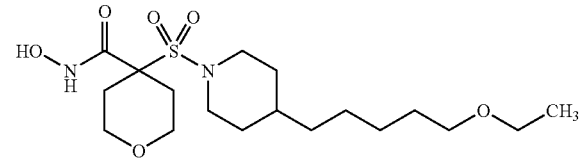

As described in Example A35, Part B, reaction of the mesylate from Example A35, Part A (0.5 g, 1 mmol) with 3,3,3-trifluoroethanol (342 mg, 3 mmol) and subsequent transformation of the t-butyl ester into the hydroxamic acid as described in Example A35, Parts C, D and E afforded 313 mg of a white crystalline solid. $^1$H NMR (CDCl$_3$) δ 1.13–1.38 (m, 9H), 1.54 (p, J=6.9 Hz, 2H), 1.67 (d, J=11.2 Hz, 2H), 2.15–2.26 (m, 4H), 2.31–2.43 (m, 2H), 2.88 (t, J=11.6 Hz, 2H), 3.87–3.47 (m, 4H), 3.60 (t, J=6.6 Hz), 3.71, (d, J=12.8 Hz, 2H), 3.93–3.97 (m, 2H); Electrospray mass spectrometry showed m/z=475 (M+H). High-resolution mass spectroscopy: calculated for C$_{19}$H$_{34}$F$_3$N$_2$O$_6$S: 475.2084; observed: 475.2110.

Example A38

Preparation of 4-[4-(5-ethoxy-pentyl)-piperidine-1-sulfonyl]-tetrahydro-pyran-4-carboxylic acid hydroxyamide Part A. Preparation of 4-[4-(5-ethoxy-pentyl)-piperidine-1-sulfonyl]-tetrahydro-pyran-4-carboxylic acid tert-butyl ester:

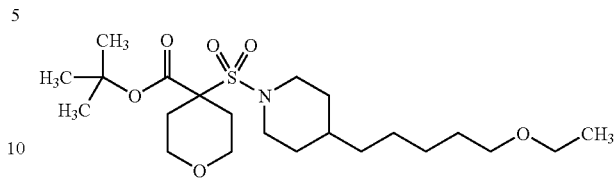

A 10 mL round-bottom flask was charged with the alcohol from Example A9, Part C (0.25 g, 0.6 mmol) and tetrahydrofuran (2 mL). A 1.0 M solution of potassium t-butoxide in tetrahydrofuran (0.9 mL, 0.9 mmol) was then added dropwise. The resulting mixture was stirred for 10 min at room temperature, and then iodoethane (95 ug, 1.2 mmol) was added. This produced a white precipitate. The mixture was stirred at room temperature for 16 hr, and then quenched by the addition of water (1 mL). Afterward, the mixture was partitioned between ethyl acetate (25 mL) and water (25 mL). The organic layer was washed with brine (25 mL), dried over magnesium sulfate, filtered, and concentrated in vacuo. Flash column chromatography (10–20% ethyl acetate/hexane) afforded a white solid product (119 mg, 44% yield). $^1$H NMR (CDCl$_3$) δ 1.18 (t, J=7 Hz, 3H), 1.22–1.35 (m, 9H), 1.51 (s, 9H), 1.54–1.58 (m, 2H), 1.66 (d, J=10.4 Hz, 2H), 2.10 (td, J=4.5, 12.6 Hz, 2H), 2.31 (d, J=12.4 Hz, 2H), 2.91 (t, J=11.6 Hz, 2H), 3.30 (t, J=11.6 Hz, 2H), 3.38 (t, J=6.6 Hz, 2H), 3.44 (q, J=6.8 Hz, 2H), 3.75 (d, J=11.6 Hz, 2H), 3.95 (dd, J=4, 11.6 Hz, 2H); Electrospray mass spectrometry showed m/z=448 (M+H).

Part B. Preparation of 4-[4-(5-ethoxy-pentyl)-piperidine-1-sulfonyl]-tetrahydro-pyran-4-carboxylic acid:

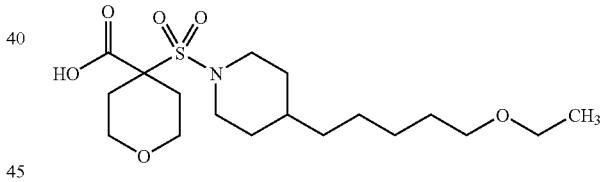

A 2-dram vial equipped with a magnetic stirring bar was charged with the ester from Part A (119 mg, 0.27 mmol), methylene chloride (1 mL), and trifluoroacetic acid (1 mL). After the vial was capped, the mixture was stirred at room temperature for 2 hr. The mixture was then concentrated in vacuo, affording a white solid product (104 mg, 100% yield). Electrospray mass spectrometry showed m/z=392 (M+H).

Part C. Preparation of 4-[4-(5-ethoxy-pentyl)-piperidine-1-sulfonyl]-tetrahydro-pyran-4-carboxylic acid (tetrahydro-pyran-2-yloxy)-amide:

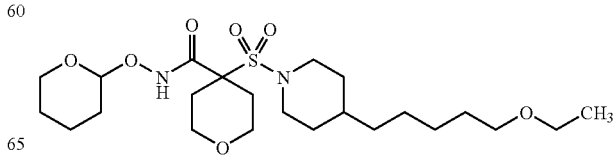

A 2-dram glass vial equipped with a magnetic stirring bar was charged with the product from Part B (104 mg, 0.26 mmol), a 0.5 M solution of hydroxybenzotriazole in dimethylformamide (1.1 mL, 0.55 mmol), a 0.5 M solution of tetrahydropyanyl hydroxylamine in dimethylformamide (1.1 mL, 0.55 mmol), ethyl 3-(dimethylamino)propyl carbodiimide hydrochloride (101 mg, 0.53 mmol), and triethylamine (110 uL, 0.79 mmol). The resulting mixture was stirred at room temperature for 18 hr, and then partitioned between ethyl acetate (5 mL) and water (5 mL). The organic layer was washed with 5% HCl (2×5 mL) and water (5 mL), and then filtered through a pad of celite. Afterward, the filtrate was concentrated in vacuo and purified by flash column chromatography on silica gel to afford a white solid product (109 mg, 84% yield). Electrospray mass spectrometry showed m/z=491 (M+H)+.

Part D. Preparation of 4-[4-(5-ethoxy-pentyl)-piperidine-1-sulfonyl]-tetrahydro-pyran-4-carboxylic acid hydroxyamide:

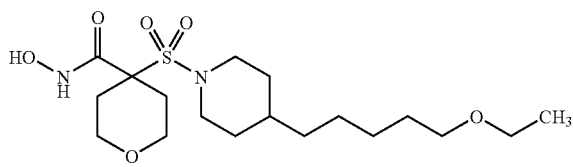

A 2-dram glass vial equipped with a magnetic stirring bar was charged with the major product from Part C (386 mg, 0.71 mmol), 1,4-dioxane (1 mL), and methanol (1 mL). A 4 N solution of HCl in dioxane (0.1 mL, 0.4 mmol) was then added, and the resulting mixture stirred at room temperature for 15 min. Volatiles were removed in vacuo, leaving 320 mg of a white crystalline solid. ¹H NMR (CDCl₃) δ 1.18 (t, J=7 Hz, 3H), 1.19–1.38 (m, 9H), 1.58 (p, J=6.7 Hz, 2H), 1.67 (d, J=11.2 Hz, 2H), 2.15–2.26 (m, 4H), 2.88 (t, J=11.6 Hz, 2H), 3.36–3.48 (m, 6H), 3.71, (d, J=12.8 Hz, 2H), 3.93–3.97 (m, 2H); Electrospray mass spectrometry showed m/z=407 (M+H). High-resolution mass spectroscopy: calculated for C₁₈H₃₅N₂O₆S: 407.2210; observed: 407.2176.

Example A39

Preparation of 4-[4-(4-propoxy-butyl)-piperidine-1-sulfonyl]-tetrahydro-pyran-4-carboxylic acid hydroxyamide

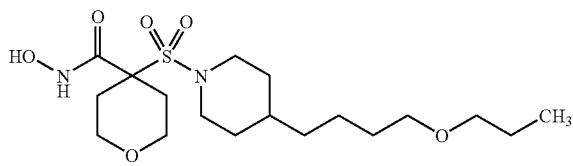

Part A. Preparation of 4-[4-(4-propoxy-butyl)-piperidine-1-sulfonyl]-tetrahydro-pyran-4-carboxylic acid tert-butyl ester:

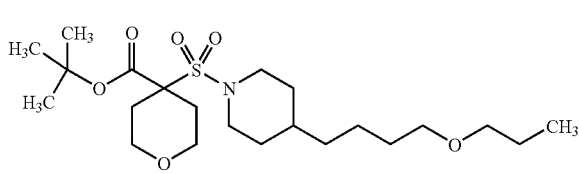

The alcohol of Example A12 (0.50 g, 1.23 mmol), tetrabutylammonium bromide (79 mg, 0.246 mmol), and KOH (207 mg, 3.69 mmol) were slurried in xylene (5 mL), Afterward, 1-iodopropane (0.36 mL, 3.69 mmol) was added, and the resulting mixture was stirred in a sealed vial at 80° C. over the weekend. Subsequently, the mixture was filtered through celite, and concentrated under N₂. Chromatography (on silica, ethyl acetate/hexanes) afforded the ether in the form of a colorless oil (389.6 mg, 70.7% yield). NMR (CDCl₃) δ 0.90 (t, 3H), 1.14–1.44 (m, 7H), 1.47–1.63 (m, 13H), 1.64–1.72 (m, 2H), 2.10 (dt, 2H), 2.32 (d, 2H), 2.90 (t, 2H), 3.26–3.41 (m, 6H), 3.75 (d, 2H), 3.95 (dd, 2H). ESMS m/z=448.44 (M+H)+.

Part B. Preparation of 4-[4-(4-propoxy-butyl)-piperidine-1-sulfonyl]-tetrahydro-pyran-4-carboxylic acid:

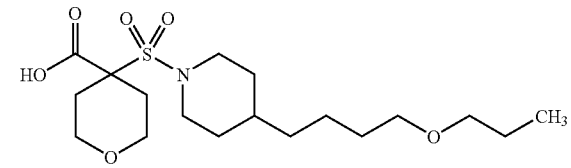

The ester of Part A (389.6 mg, 0.87 mmol) was hydrolyzed in 1:1 trifluoroacetic acid:methylene chloride (6 mL) at room temperature overnight. The resulting mixture was concentrated under N₂ and triturated with ethyl acetate/hexane to afford the carboxylic acid in the form of a solid (321.9 mg, 94.5% yield). This material was used in the next step without further purification.

Part C. Preparation of 4-[4-(4-propoxy-butyl)-piperidine-1-sulfonyl]-tetrahydro-pyran-4-carboxylic acid (tetrahydropyran-2-yloxy)-amide:

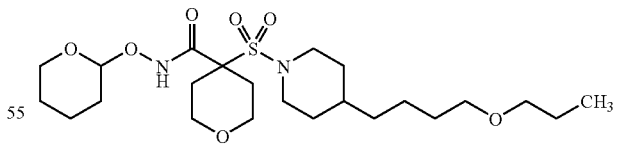

To a mixture of the crude acid from Part B (321.9 mg, 0.82 mmol), 1-hydrozybenzotriazole hydrate (166 mg, 1.23 mmol), THP-ONH₂ (135 mg, 1.15 mmol), and triethylamine (0.34 mL, 2.5 mmol) in dimethylformamide (5.0 mL) was added 1-(3-dimethylaminopropyl)-3-ethylcarbodiimide hydrochloride (220 mg, 1.15 mmol). After heating to 40° C., the acid slowly went into solution. The mixture was then stirred at 40–45° C. overnight. Subsequently, the mixture was concentrated; combined with ethyl acetate (5 mL); and extracted with 1N HCl (5 mL), water (5 mL) and brine (5 mL). The resulting material was filtered through a 3 mL Chem-Elut tube and concentrated. Chromatography (on silica, ethyl acetate/hexanes) afforded the protected hydroxamate in the form of a colorless oil (271.4 mg, 67.5% yield). NMR(CDCl$_3$) δ 0.90 (t, 3H), 1.12–1.28 (m, 4H), 1.28–1.42 (m, 2H), 1.47–1.64 (m, 8H), 1.67 (d, 2H), 1.75–1.88 (m, 2H), 2.13–2.26 (m, 4H), 2.90 (t, 2H), 3.31–3.40 (m, 4H), 3.48 (dq, 2H), 3.58–3.66 (m, 2H), 3.73–3.83 (m, 2H), 3.89–3.99 (m, 3H), 4.97 (s, 1H), 9.19 (s, 1H). ESMS m/z=508.48 (M+NH$_4$)$^+$.

Part D. Preparation of 4-[4-(4-propoxy-butyl)-piperidine-1-sulfonyl]-tetrahydro-pyran-4-carboxylic acid hydroxyamide:

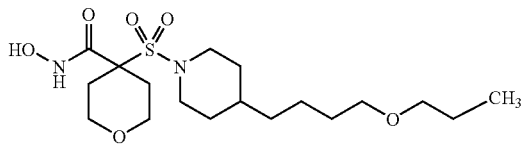

To the THP-protected hydroxamate from Part C (271.4 mg, 0.55 mmol) in methanol (1.0 mL) and 1,4-dioxane (1.0 mL) was added 4M HCl in 1,4-dioxane (200 μL). After stirring for 1 hr, the mixture was concentrated under N$_2$ and triturated with ethyl acetate/hexane to afford an off-white amorphous solid (197.8 mg, 88.0% yield). NMR (DMSO) δ 0.83 (t, 3H), 0.95–1.07 (m, 2H), 1.13–1.21 (m, 2H), 1.21–1.35 (m, 3H), 1.38–1.52 (m, 4H), 1.59 (d, 2H), 1.84 (dt, 2H), 2.30 (d, 2H), 2.85 (t, 2H), 3.14 (d, 2H), 3.23–3.33 (m, 4H), 3.55 (d, 2H), 3.80 (d, 2H), 9.13 (s, 1H), 10.94 (s, 1H). ESMS m/z=407.2 (M+H)$^+$. HRMS calcd. for C$_{18}$H$_{35}$N$_2$O$_6$S H: 407.2210 (M+H)$^+$. Found: 407.2210.

Example A40

Preparation of 4-{4-[4-(4,4,4-trifluoro-butoxy)-butyl]-piperidine-1-sulfonyl}-tetrahydro-pyran-4-carboxylic acid hydroxyamide

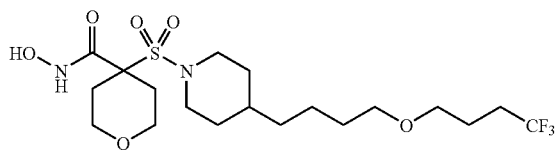

Part A. Preparation of 4-{4-[4-(4,4,4-trifluoro-butoxy)-butyl]-piperidine-1-sulfonyl}-tetrahydro-pyran-4-carboxylic acid tert-butyl ester:

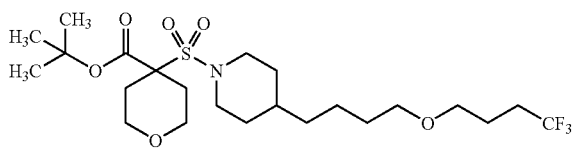

The alcohol of Example A12 (0.50 g, 1.23 mmol), tetrabutylammonium bromide (79 mg, 0.246 mmol), and KOH (207 mg, 3.69 mmol) were slurried in xylene (5 mL). Afterward, 4,4,4-trifluoromethyl-1-iodobutane (0.88 g, 3.69 mmol) was added, and the resulting mixture was stirred in a sealed vial at 80° C. over the weekend. Subsequently, the mixture was filtered through celite and concentrated under N$_2$. Chromatography (on silica, ethyl acetate/hexanes) afforded the ether in the form of a colorless oil (296.4 mg, 46.7% yield). NMR(CDCl$_3$) δ 1.25–1.42 (m, 7H), 1.52 (s, 9H), 1.55 (d, 2H), 1.67 (d, 2H), 1.75–1.84 (m, 2H), 2.06–2.24 (m, 4H), 2.32 (d, 2H), 2.92 (t, 2H), 3.40 (t, 2H), 3.38 (t, 2H), 3.43 (t, 2H), 3.72–3.82 (m, 2H), 3.95 (dd, 2H). ESMS m/z=516.44 (M+H)$^+$.

Part B. Preparation of 4-{4-[4-(4,4,4-trifluoro-butoxy)-butyl]-piperidine-1-sulfonyl}-tetrahydro-pyran-4-carboxylic acid:

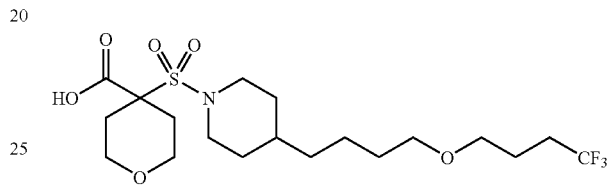

The ester of Part A (290.1 mg, 0.56 mmol) was hydrolyzed in 1:1 trifluoroacetic acid:methylene chloride (6 mL) at room temperature overnight. The resulting mixture was concentrated under N$_2$, and triturated with ethyl acetate/hexane to afford the desired acid in the form of a solid (251.5 mg, 97.7% yield). This material was used in the next step without further purification.

Part C. Preparation of 4-{4-[4-(4,4,4-trifluoro-butoxy)-butyl]-piperidine-1-sulfonyl}-tetrahydro-pyran-4-carboxylic acid (tetrahydro-pyran-2-yloxy)-amide:

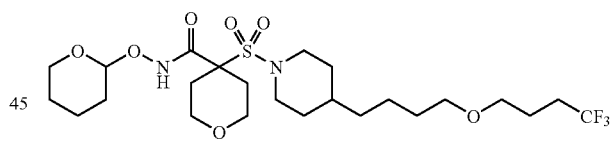

To a mixture of the crude acid from Part B (251.2 mg, 0.55 mmol), 1-hydrozybenzotriazole hydrate (111 mg, 0.822 mmol), THP—ONH$_2$ (90 mg, 0.77 mmol), and triethylamine (0.23 mL, 1.6 mmol) in dimethylformamide (3.0 mL) was added 1-(3-dimethylaminopropyl)-3-ethylcarbodiimide hydrochloride (146 mg, 0.76 mmol). The resulting mixture was stirred at 40–45° C. overnight. Subsequently, the mixture was concentrated; combined with ethyl acetate (5 mL); and extracted with 1N HCl (5 mL), water (5 mL), and brine (5 mL). The resulting material was dried by filtering through a 3 mL Chem-Elut tube and concentrated. Chromatography (on silica, ethyl acetate/hexanes) afforded the protected hydroxamate in the form of a colorless oil (255.3 mg, 83.5% yield). NMR (CDCl$_3$) δ 1.12–1.42 (m, 7H), 1.47–1.73 (m, 8H), 1.75–1.89 (m, 5H), 2.09–2.26 (m, 6H), 2.90 (t, 2H), 3.37 (t, 2H), 3.40–3.54 (m, 4H), 3.59–3.66 (m, 1H), 3.73–3.82 (m, 2H), 3.89–3.99 (m, 3H), 4.97 (s, 1H), 9.19 (s, 1H). ESMS m/z=576.51 (M+NH$_4$)$^+$.

Part D. Preparation of 4-{4-[4-(4,4,4-trifluoro-butoxy)-butyl]-piperidine-1-sulfonyl}-tetrahydro-pyran-4-carboxylic acid hydroxyamide:

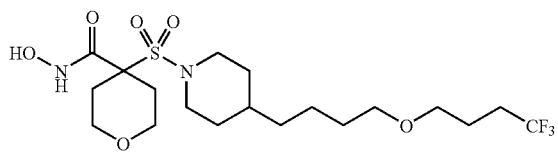

To the THP-protected hydroxamate from Part C (255.3 mg, 0.46 mmol) in methanol (1.0 mL) and 1,4-dioxane (1.0 mL) was added 4M HCl in 1,4-dioxane (200 µL). After stirring for 1 hr, the mixture was concentrated under $N_2$, and triturated with ethyl acetate/hexane to afford an off-white amorphous solid (203.4 mg, 93.8% yield). NMR (DMSO) δ 0.94–1.07 (m, 2H), 1.13–1.35 (m, 5H), 1.39–1.48 (m, 2H), 1.55–1.70 (m, 4H), 1.84 (dt, 2H), 2.16–2.35 (m, 4H), 2.85 (t, 2H), 3.14 (t, 2H), 3.26–3.39 (m, 4H), 3.55 (d, 2H), 3.80 (dd, 2H), 9.22 (bs, 1H), 10.94 (s, 1H). ESMS m/z=475.2 (M+H)⁺. HRMS calcd. for $C_{19}H_{34}F_3N_2O_6SH$: 475.2084 (M+H)⁺. Found: 475.2102.

Example A41

Preparation of 4-(4-hexyloxymethyl-piperidine-1-sulfonyl)-tetrahydro-pyran-4-carboxylic acid hydroxyamide

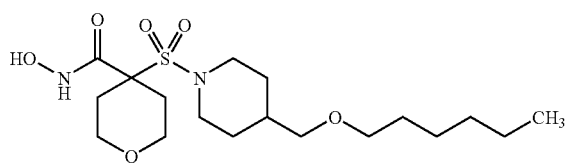

Part A. Preparation of 4-(4-hexyloxymethyl-piperidine-1-sulfonyl)-tetrahydro-pyran-4-carboxylic acid tert-butyl ester:

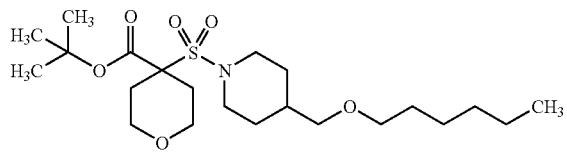

The alcohol of Example A2 (0.30 g, 0.826 mmol), tetrabutylammonium bromide (53 mg, 0.165 mmol), and KOH (139 mg, 2.48 mmol) were slurried in xylene (3.3 mL). Next, 1-iodohexane (0.37 mL, 2.48 mmol) was added, and the resulting mixture was stirred in a sealed vial at 80° C. for 6 hr. The mixture was then filtered through celite and concentrated under $N_2$. Chromatography (on silica, ethyl acetate/hexanes) afforded the ether in the form of a colorless oil (261.1 mg, 70.6% yield). NMR(CDCl₃) δ 0.86 (t, 3H), 1.20–1.34 (m, 8H), 1.47–1.56 (m, 2H), 1.52 (s, 9H), 1.67–1.78 (m, 3H), 2.12 (dt, 2H), 2.32 (d, 2H), 2.93 (t, 2H), 3.23 (d, 2H), 3.40 (t, 2H), 3.47 (t, 2H), 3.79 (d, 2H), 3.95 (dd, 2H). ESMS m/z=448.43 (M+H)⁺.

Part B. Preparation of 4-(4-hexyloxymethyl-piperidine-1-sulfonyl)-tetrahydro-pyran-4-carboxylic acid:

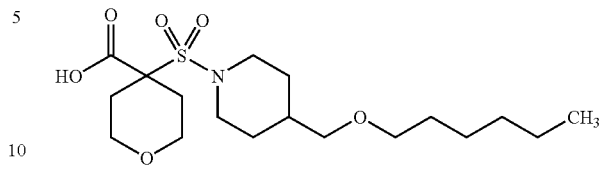

The ester of Part A (520.2 mg, 1.16 mmol) was hydrolyzed in 1:1 trifluoroacetic acid:methylene chloride (6 mL) at room temperature overnight. Afterward, the mixture was concentrated under $N_2$, and triturated with ethyl acetate/hexane to afford the desired acid in the form of a solid (424.9 mg, 93.6% yield). This material was used without further purification.

Part C. Preparation of 4-(4-hexyloxymethyl-piperidine-1-sulfonyl)-tetrahydro-pyran-4-carboxylic acid (tetrahydro-pyran-2-yloxy)-amide:

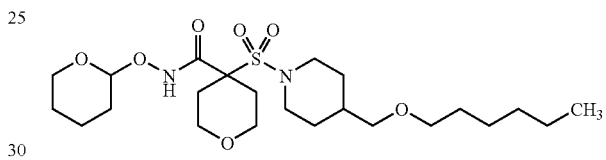

To a mixture of the crude acid from Part B (424.9 mg, 1.09 mmol), 1-hydrozybenzotriazole hydrate (220 mg, 1.63 mmol), THP—ONH₂ (178 mg, 1.52 mmol), and triethylamine (0.45 mL, 3.23 mmol) in dimethylformamide (5.0 mL) was added 1-(3-dimethylaminopropyl)-3-ethylcarbodiimide hydrochloride (290 mg, 1.52 mmol). After heating at 40° C., the acid slowly went into solution. The mixture was then stirred at 40–45° C. overnight. Subsequently, the mixture was concentrated; combined with ethyl acetate (5 mL); and extracted with 1N HCl (5 mL), water (5 mL), and brine (5 mL). The resulting material was dried by filtering through 3 mL Chem-Elut tube and concentrated. Chromatography (on silica, ethyl acetate/hexanes) afforded the protected hydroxamate in the form of a colorless oil (464.3 mg, 86.8% yield). NMR(CDCl₃) δ 0.86 (t, 3H), 1.17–1.35 (m, 8H), 1.47–1.89 (m, 10H), 2.13–2.27 (m, 4H), 2.93 (t, 2H), 3.23 (d, 2H), 3.36 (t, 2H), 3.48 (dq, 2H), 3.58–3.66 (m, 1H), 3.76–3.85 (m, 2H), 3.89–3.99 (m, 3H), 4.97 (s, 1H), 9.19 (s, 1H). ESMS m/z=508.47 (M+NH₄)⁺.

Part D. Preparation of 4-(4-hexyloxymethyl-piperidine-1-sulfonyl)-tetrahydro-pyran-4-carboxylic acid hydroxyamide:

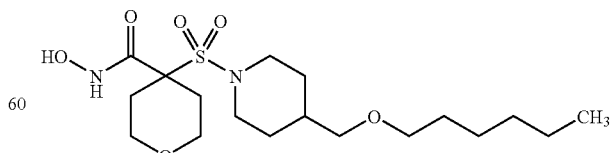

To the THP-protected hydroxamate from Part C (464.3 mg, 0.95 mmol) in methanol (1.0 mL) and 1,4-dioxane (1.0 mL) was added 4M HCl in 1,4-dioxane (200 µL). After stirring for 1 hr, the mixture concentrated under $N_2$, and triturated with ethyl acetate/hexane to afford an off-white amorphous solid (377.6 mg, 98.2% yield). NMR (DMSO) δ 0.83 (t, 3H), 1.01–1.14 (m, 2H), 1.17–1.30 (m, 6H), 1.39–1.48 (m, 2H), 1.56–1.67 (m, 3H), 1.87 (dt, 2H), 2.30 (d, 2H), 2.86 (t, 2H), 3.08 3.19(m, 4H), 3.25–3.34 (m, 2H), 3.57 (d, 2H), 3.82 (dd, 2H), 9.15 (s, 1H), 10.94 (s, 1H). ESMS m/z=407.2 (M+H)$^+$. HRMS calcd. for $C_{18}H_{35}N_2O_6SH$: 407.2210 (M+H)$^+$. Found: 407.2189.

Example A42

Preparation of 4-[4-(4,4,4-trifluoro-butoxymethyl)-piperidine-1-sulfonyl]-tetrahydro-pyran-4-carboxylic acid hydroxyamide

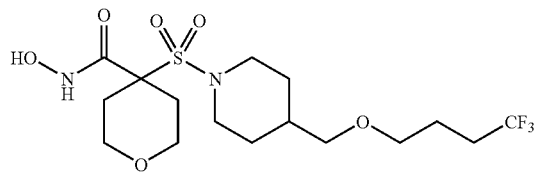

Part A. Preparation of 4-[4-(4,4,4-trifluoro-butoxymethyl)-piperidine-1-sulfonyl]-tetrahydro-pyran-4-carboxylic acid tert-butyl ester:

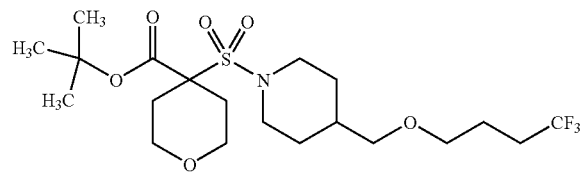

The alcohol of Example A2 (0.50 g, 1.38 mmol), tetrabutylammonium bromide (89 mg, 0.0.276 mmol), and KOH (232 mg, 4.14 mmol) were slurried in xylene (5.5 mL). Afterward, 1,1,1-trifluoro-4-iodobutane (0.98 g, 4.14 mmol) was added, and the resulting mixture was stirred in a sealed vial at 80° C. over the weekend. Subsequently, the mixture was filtered through celite and concentrated under $N_2$. Chromatography (on silica, ethyl acetate/hexanes) afforded the ether in the form of a colorless oil (430.5 mg, 65.8% yield). NMR (CDCl$_3$) δ 1.22–1.36 (m, 2H), 1.51 (s, 9H), 1.66–1.74 (m, 5H), 2.06–2.22 (m, 4H), 2.32 (d, 2H), 2.94 (t, 2H), 3.24 (d, 2H), 3.40 (t, 2H), 3.43 (t, 2H), 3.79 (d, 2H), 3.96 (dd, 2H). ESMS m/z=491.42 (M+NH$_4$)$^+$.

Part B. Preparation of 4-[4-(4,4,4-trifluoro-butoxymethyl)-piperidine-1-sulfonyl]-tetrahydro-pyran-4-carboxylic acid:

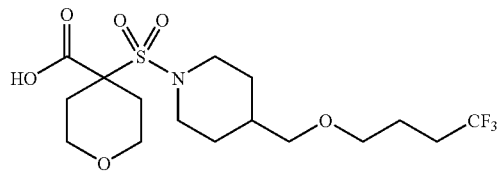

The ester of Part A (429.5 mg, 0.91 mmol) was hydrolyzed in 1:1 trifluoroacetic acid:methylene chloride (6 mL) at room temperature overnight. The mixture was then concentrated under $N_2$, and triturated with ethyl acetate/hexane to afford the desired acid in the form of a solid (334.2 mg, 88.0% yield). This material was used in the next step without further purification.

Part C. Preparation of 4-[4-(4,4,4-trifluoro-butoxymethyl)-piperidine-1-sulfonyl]-tetrahydro-pyran-4-carboxylic acid (tetrahydro-pyran-2-yloxy)-amide:

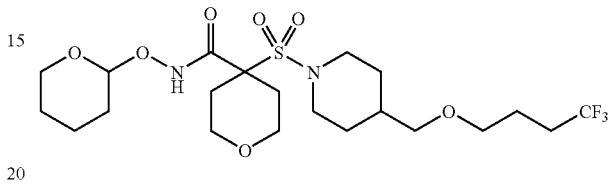

To a mixture of the crude acid from Part B (334.2 mg, 0.80 mmol), 1-hydrozybenzotriazole hydrate (162 mg, 1.2 mmol), THP—ONH$_2$ (131 mg, 1.12 mmol), and triethylamine (0.33 mL, 2.37 mmol) in dimethylformamide (5.0 mL) was added 1-(3-dimethylaminopropyl)-3-ethylcarbodiimide hydrochloride (214 mg, 1.12 mmol). After heating at 40° C., the acid slowly went into solution. The mixture was then stirred at 40–45° C. overnight. Subsequently, the mixture was concentrated; combined with ethyl acetate (5 mL); and extracted with 1N HCl (5 mL), water (5 mL), and brine (5 mL). The resulting material was dried by filtering through 3 mL Chem-Elut tube and concentrated. Chromatography (on silica, ethyl acetate/hexanes) afforded the protected hydroxamate in the form of a colorless oil (356.6 mg, 86.3% yield). NMR(CDCl$_3$) δ 1.19–1.24 (m, 2H), 1.54–1.89 (m, 10H), 2.07–2.38 (m, 6H), 2.93 (t, 2H), 3.23 (d, 2H), 3.43 (t, 2H), 3.48 (dq, 2H), 3.58–3.66 (m, 1H), 3.76–3.85 (m, 2H), 3.89–3.99 (m, 3H), 4.97 (s, 1H), 9.19 (s, 1H), ESMS m/z=534.42 (M+NH$_4$)$^+$.

Part D. Preparation of 4-[4-(4,4,4-trifluoro-butoxymethyl)-piperidine-1-sulfonyl]-tetrahydro-pyran-4-carboxylic acid hydroxyamide:

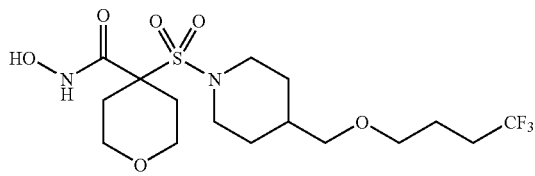

To the THP-protected hydroxamate from Part C (356.6 mg, 0.69 mmol) in methanol (1.0 mL) and 1,4-dioxane (1.0 mL) was added 4M HCl in 1,4-dioxane (200 μL). After stirring for 1 hr, the mixture was concentrated under $N_2$, and triturated with ethyl acetate/hexane to afford an off-white amorphous solid (269.8 mg, 90.4% yield). NMR (DMSO) 1.00–1.15 (m, 2H), 1.56–1.72 (m, 5H), 1.84 (dt, 2H), 2.16–2.35 (m, 4H), 2.86 (t, 2H), 3.15 (t, 2H), 3.19(d, 2H), 3.37 (t, 2H), 3.56 (d, 2H), 3.81 (dd, 2H), 9.15 (s, 1H), 10.94 (s, 1H). ESMS m/z=433.2 (M+H)$^+$. HRMS calcd. for $C_{16}H_{28}F_3N_2O_6S$: 433.1615 (M+H)$^+$. Found: 433.1617.

Example A43

Preparation of 4-[4-(6,6,6-Trifluoro-hexyl)-piperidine-1-sulfonyl]-tetrahydro-pyran-4-carboxylic acid hydroxyamide

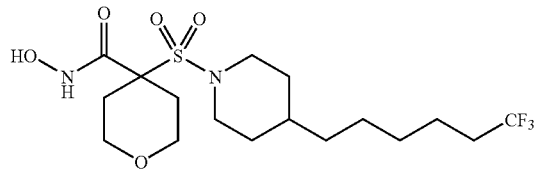

Part A. Preparation of 4-[4-(6,6,6-trifluoro-hex-2-enyl)-piperidine-1-sulfonyl]-tetrahydro-pyran-4-carboxylic acid tert-butyl ester:

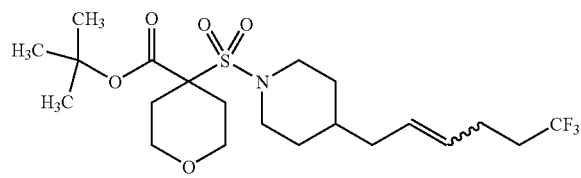

To the phosphine from Example A10 (800 mg, 1.6 mmol) in anhydrous tetrahydrofuran (6.6 mL) at 0° C. was added 1M LiN(TMS) (1.7 mL, 1.7 mmol) dropwise while maintaining the temperature at less than 5° C. Upon completion of the addition, the mixture was stirred at 0° C. for 15 min. The aldehyde from Example A6 (500 mg, 1.33 mmol) in anhydrous tetrahydrofuran (2.7 mL) was then added dropwise while maintaining the temperature at less than 4° C. Afterward, the mixture was allowed to warm to room temperature overnight. The mixture was subsequently poured into stirring ether (75 mL) and filtered. The filtrate was washed with 1N HCl (3×75 mL), saturated sodium bicarbonate (3×75 mL), and brine (100 mL); dried over MgSO$_2$; and concentrated to crude oil. Chromatography (on silica, ethyl acetate/hexanes) afforded the alkene in the form of a clear yellow oil (377.1 mg, 60.4% yield). NMR(CDCl$_3$) δ 1.5 (q, 2H), 1.36–1.58 (m, 10H), 1.67 (d, 2H), 1.93–2.18 (m, 6H), 2.22–2.36 (m, 4H), 2.93 (t, 2H), 3.30 (t, 2H), 3.79 (d, 2H), 3.96 (dd, 2H), 5.34–5.48 (m, 2H). ESMS m/z=470.39 (M+H)$^+$.

Part B. Preparation of 4-[4-(6,6,6-trifluoro-hexyl)-piperidine-1-sulfonyl]-tetrahydro-pyran-4-carboxylic acid tert-butyl ester:

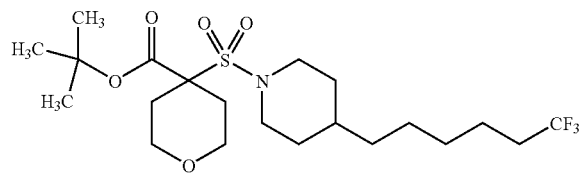

The alkene from Part A (388 mg, 0.826 mmol) was combined with tetrahydrofuran (10 mL). Afterward, 10% Pd/C (0.20 g) was added. The resulting mixture was agitated on a Parr shaker at 40 psi overnight. Afterward, the mixture was filtered through celite and concentrated, providing the alkane in the form of a colorless solid (368.6 mg, 94.7% yield). NMR(CDCl$_3$) δ 1.17–1.39 (m, 9H), 1.48–1.58 (m, 11H), 1.66 (d, 2H), 1.97–2.16 (m, 4H), 2.32 (d, 2H), 2.91 (t, 2H), 3.30 (dt, 2H), 3.76 (d, 2H), 3.96 (dd, 2H). ESMS m/z=416.33 (M+H)$^+$.

Part C. Preparation of 4-[4-(6,6,6-trifluoro-hexyl)-piperidine-1-sulfonyl]-tetrahydro-pyran-4-carboxylic acid:

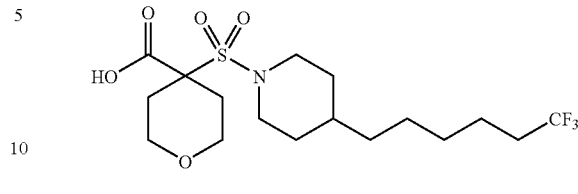

The ester of Part B (368.6 mg, 0.78 mmol) was hydrolyzed in 1:1 trifluoroacetic acid:methylene chloride (6 mL) at room temperature overnight. The mixture was then concentrated under N$_2$, and triturated with ethyl acetate/hexane to afford the desired acid in the form of a solid (303.9 mg, 93.8% yield). This material was used in the next step without further purification.

Part D. Preparation of 4-[4-(6,6,6-trifluoro-hexyl)-piperidine-1-sulfonyl]-tetrahydro-pyran-4-carboxylic acid (tetrahydro-pyran-2-yloxy)-amide:

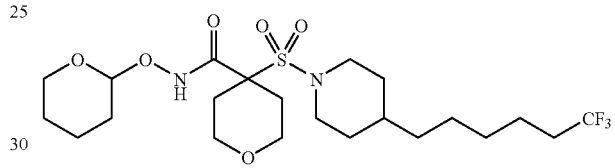

To a mixture of the crude acid from Part C (303.9 mg, 0.73 mmol), 1-hydrozybenzotriazole hydrate (148 mg, 1.10 mmol), THP—ONH$_2$ (120 mg, 1.03 mmol), and triethylamine (0.31 mL, 2.23 mmol) in dimethylformamide (5.0 mL) was added 1-(3-dimethylaminopropyl)-3-ethylcarbodiimide hydrochloride (196 mg, 1.03 mmol). After heating at 40° C., the acid slowly went into solution. The mixture was then stirred at 40–45° C. overnight. Subsequently, the mixture was concentrated; combined with ethyl acetate (5 mL); and extracted with 1N HCl (5 mL), water (5 mL), and brine (5 mL). The resulting material was dried by filtering through 3 mL Chem-Elut tube and concentrated. Chromatography (on silica, ethyl acetate/hexanes) afforded the protected hydroxamate in the form of a colorless oil (346.8 mg, 92.3% yield). NMR(CDCl$_3$) δ 1.13–1.38 (m, 10H), 1.48–1.72 (m, 6H), 1.75–1.89 (m, 4H), 1.97–2.11 (m, 2H), 2.13–2.27 (m, 4H), 2.91 (t, 2H), 3.48 (dq, 2H), 3.59–3.66 (m, 1H), 3.73–3.83 (m, 2H), 3.90–3.99 (m, 3H), 4.97 (s, 1H), 9.19 (s, 1H). ESMS m/z=514.40 (M+H)$^+$.

Part E. Preparation of 4-[4-(6,6,6-trifluoro-hexyl)-piperidine-1-sulfonyl]-tetrahydro-pyran-4-carboxylic acid hydroxyamide:

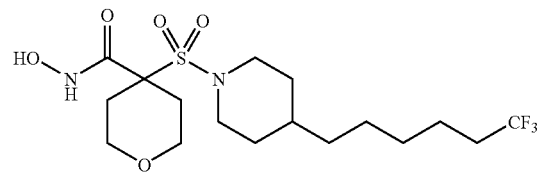

To the THP-protected hydroxamate from Part D (346.8 mg, 0.67 mmol) in methanol (1.0 mL) and 1,4-dioxane (1.0 mL)

was added 4M HCl in 1,4-dioxane (200 μL). After stirring for 1 hr, the mixture was concentrated under $N_2$, and triturated with ethyl acetate/hexane to afford the desired compound as an off-white amorphous solid (259.9 mg, 89.6% yield). NMR (DMSO) 1.01 (q, 2H), 1.12–1.34 (m, 7H), 1.38–1.48 (m, 2H), 1.60 (d, 2H), 1.83 (dt, 2H), 2.13–2.26 (m, 2H), 2.40 (d, 2H), 2.85 (t, 2H), 3.15 (t, 2H), 3.55 (d, 2H), 3.81 (dd, 2H), 9.15 (s, 1H), 10.94 (s, 1H). ESMS m/z=431.2 (M+H)$^+$. HRMS calcd. for $C_{17}H_{30}F_3N_2O_5S$: 431.1822 (M+H)$^+$. Found: 431.1818.

Example A44

Preparation of 4-[4-(2-butoxy-ethyl)-piperidine-1-sulfonyl]-tetrahydro-pyran-4-carboxylic acid hydroxyamide

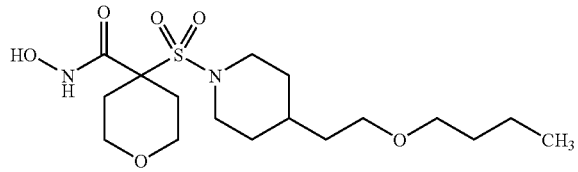

Part A. Preparation of 4-[4-(2-butoxy-ethyl)-piperidine-1-sulfonyl]-tetrahydro-pyran-4-carboxylic acid tert-butyl ester:

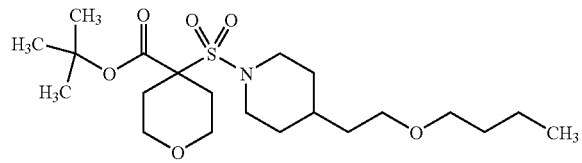

The alcohol of Example A13 (0.70 g, 1.85 mmol), tetrabutylammonium bromide (119 mg, 0.376 mmol), and KOH (311 mg, 5.55 mmol) were slurried in xylene (7.5 mL). Afterward, 1-iodobutane (0.63 mL, 5.55 mmol) was added, and the resulting mixture was stirred in a sealed vial at 80° C. over the weekend. Subsequently, the mixture was filtered through celite and concentrated under $N_2$. Chromatography (on silica, ethyl acetate/hexanes) afforded the ether in the form of a colorless oil (559.2 mg, 69.7% yield). NMR (CDCl$_3$) δ 0.90 (t, 3H), 1.19–1.39 (m, 4H), 1.47–1.61 (m, 14H), 1.68 (d, 2H), 2.10 (dt, 2H), 2.32 (d, 2H), 2.93 (dt, 2H), 3.40 (dt, 2H), 3.37 (t, 2H), 3.42 (t, 2H), 3.75 (d, 2H), 3.96 (dd, 2H). ESMS m/z=434.44 (M+H)$^+$.

Part B. Preparation of 4-[4-(2-butoxy-ethyl)-piperidine-1-sulfonyl]-tetrahydro-pyran-4-carboxylic acid:

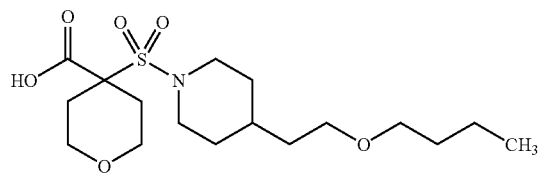

The ester of Part A (559.2 mg, 1.29 mmol) was hydrolyzed in 1:1 trifluoroacetic acid:methylene chloride (6 mL) at room temperature overnight. The mixture was then concentrated under $N_2$, and triturated with ethyl acetate/hexane to afford the desired acid in the form of a solid (445.9 mg, 91.6% yield). This material was used in the next step without further purification.

Part C. Preparation of 4-[4-(2-butoxy-ethyl)-piperidine-1-sulfonyl]-tetrahydro-pyran-4-carboxylic acid (tetrahydro-pyran-2-yloxy)-amide:

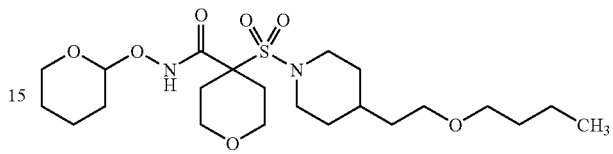

To a mixture of the crude acid from Part B (445.9 mg, 1.18 mmol), 1-hydrozybenzotriazole hydrate (239 mg, 1.77 mmol), THP—ONH$_2$ 194 mg, 1.66 mmol), and triethylamine (0.49 mL, 3.5 mmol) in dimethylformamide (5.0 mL) was added 1-(3-dimethylaminopropyl)-3-ethylcarbodiimide hydrochloride (316 mg, 1.65 mmol). After heating at 40° C., the acid slowly went into solution. The mixture was then stirred at 40–45° C. overnight. Subsequently, the mixture was concentrated; combined with ethyl acetate (5 mL); and extracted with 1N HCl (5 mL), water (5 mL), and brine (5 mL). The resulting material was dried by filtering through 3 mL Chem-Elut tube and concentrated. Chromatography (on silica, ethyl acetate/hexanes) afforded the protected hydroxamate in the form of a colorless oil (487.7 mg, 86.7% yield). NMR (CDCl$_3$) δ 0.90 (t, 3H), 1.15–1.39 (m, 4H), 1.46–1.89 (m, 12H), 2.12–2.27 (m, 4H), 2.92 (dt, 2H), 3.36 (t, 2H), 3.41 (t, 2H), 3.48 (dq, 2H), 3.58–3.66 (m, 1H), 3.73–3.83 (m, 2H), 3.89–3.99 (m, 3H), 4.97 (s, 1H), 9.19 (s, 1H). ESMS m/z=477.41 (M+H)$^+$.

Part D. Preparation of 4-[4-(2-butoxy-ethyl)-piperidine-1-sulfonyl]-tetrahydro-pyran-4-carboxylic acid hydroxyamide:

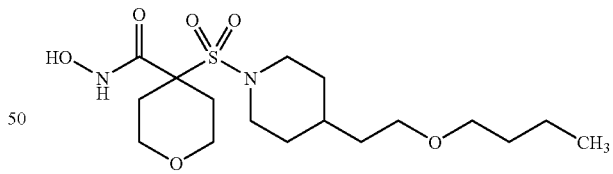

To the THP-protected hydroxamate from Part C (487.7 mg, 1.02 mmol) in methanol (1.0 mL) and 1,4-dioxane (1.0 mL) was added 4M HCl in 1,4-dioxane (200 μL). After stirring for 1 hr, the mixture was concentrated under $N_2$, and triturated with ethyl acetate/hexane to afford the desired compound as an off-white amorphous solid (360.4 mg, 89.7% yield). NMR(DMSO) δ 0.83 (t, 3H), 0.96–1.13 (m, 2H), 1.21–1.32 (m, 2H), 1.35–1.49 (m, 5H), 1.60 (d, 2H), 1.83 (dt, 2H), 2.30 (d, 2H), 2.84 (t, 2H), 3.14 (d, 2H), 3.26–3.37 (m, 4H), 3.55 (d, 2H), 3.81 (dd, 2H), 9.13 (s, 1H), 10.94 (s, 1H). ESMS m/z=393.2 (M+H)$^+$. HRMS calcd. for $C_{17}H_{33}N_2O_6SH$: 393.2054 (M+H)$^+$. Found: 393.2035.

Example A45

Preparation of 4-{4-[2-(4,4,4-trifluoro-butoxy)-ethyl]-piperidine-1-sulfonyl}-tetrahydro-pyran-4-carboxylic acid hydroxyamide

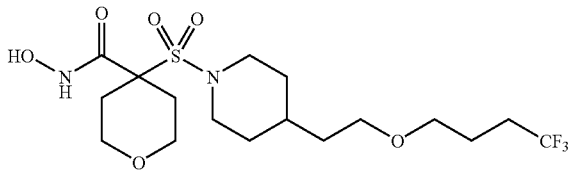

Part A. Preparation of 4-{4-[2-(4,4,4-trifluoro-butoxy)-ethyl]-piperidine-1-sulfonyl}-tetrahydro-pyran-4-carboxylic acid tert-butyl ester:

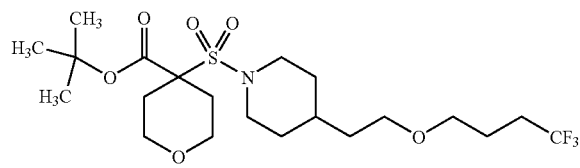

The alcohol of Example A13 (0.70 g, 1.85 mmol), tetrabutylammonium bromide (119 mg, 0.376 mmol), and KOH (311 mg, 5.55 mmol) were slurried in xylene (7.5 mL). Afterward, 4,4,4-trifluoro-1-iodobutane (1.32 g, 5.55 mmol) was added, and the reaction mixture was stirred in a sealed vial at 80° C. over the weekend. Subsequently, the mixture was filtered through celite and concentrated under $N_2$. Chromatography (on silica, ethyl acetate/hexanes) afforded the ether in the form of a pale yellow oil (551.8 mg, 61.1% yield). NMR(CDCl$_3$) δ 1.19–1.32 (m, 2H), 1.47–1.60 (m, 12H), 1.68 (d, 2H), 1.74–1.84 (m, 2H), 2.05–2.23 (m, 4H), 2.32 (d, 2H), 2.93 (dt, 2H), 3.39 (dt, 2H), 3.43 (dt, 4H), 3.76 (d, 2H), 3.96 (dd, 2H). ESMS m/z=488.42 (M+H)$^+$.

Part B. Preparation of 4-{4-[2-(4,4,4-trifluoro-butoxy)-ethyl]-piperidine-1-sulfonyl}-tetrahydro-pyran-4-carboxylic acid:

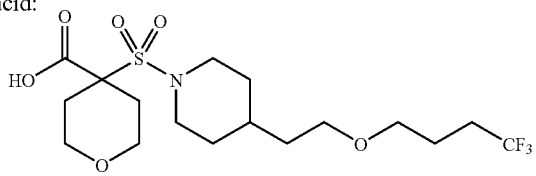

The ester of Part A (551.8 mg, 1.13 mmol) was hydrolyzed in 1:1 trifluoroacetic acid:methylene chloride (6 mL) at room temperature overnight. The mixture was then concentrated under $N_2$, and triturated with ethyl acetate/hexane to afford the desired acid in the form of a solid (444.7 mg, 91.2% yield). This material was used in the next step without further purification.

Part C. Preparation of 4-{4-[2-(4,4,4-trifluoro-butoxy)-ethyl]-piperidine-1-sulfonyl}-tetrahydro-pyran-4-carboxylic acid (tetrahydro-pyran-2-yloxy)-amide:

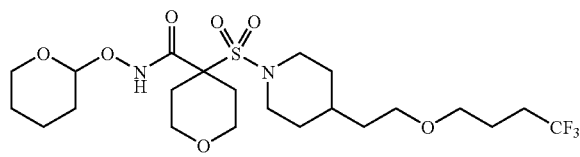

To a mixture of the crude acid from Part B (444.7 mg, 1.03 mmol), 1-hydrozybenzotriazole hydrate (209 mg, 1.55 mmol), THP—ONH$_2$ (169 mg, 1.44 mmol), and triethylamine (0.43 mL, 3.1 mmol) in dimethylformamide (5.0 mL) was added 1-(3-dimethylaminopropyl)-3-ethylcarbodiimide hydrochloride (276 mg, 1.45 mmol). After heating at 40° C., the acid slowly went into solution. The mixture was then stirred at 40–45° C. overnight. Subsequently, the mixture was concentrated; combined with ethyl acetate (5 mL); and extracted with 1N HCl (5 mL), water (5 mL), and brine (5 mL). The resulting material was dried by filtering through 3 mL Chem-Elut tube and concentrated. Chromatography (on silica, ethyl acetate/hexanes) afforded the protected hydroxamate in the form of a colorless oil (447.5 mg, 81.9% yield). NMR(CDCl$_3$) δ 1.16–1.30 (m, 2H), 1.46–1.89 (m, 12H), 2.07–2.26 (m, 6H), 2.92 (dt, 2H), 3.42 (t, 4H), 3.48 (dq, 2H), 3.58–3.66 (m, 1H), 3.73–3.83 (m, 2H), 3.89–4.00 (m, 3H), 4.97 (s, 1H), 9.19 (s, 1H). ESMS m/z=531.40 (M+H)$^+$.

Part D. Preparation of 4-{4-[2-(4,4,4-trifluoro-butoxy)-ethyl]-piperidine-1-sulfonyl}-tetrahydro-pyran-4-carboxylic acid hydroxyamide:

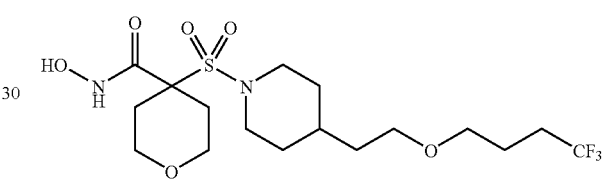

To the THP-protected hydroxamate from Part C (447.5 mg, 0.84 mmol) in methanol (1.0 mL) and 1,4-dioxane (1.0 mL) was added 4M HCl in 1,4-dioxane (200 μL). After stirring for 1 hr, the mixture was concentrated under $N_2$, and triturated with ethyl acetate/hexane to afford the desired compound as an off-white amorphous solid (361.9 mg, 96.1% yield). NMR(DMSO) δ 0.95–1.13 (m, 2H), 1.37–1.49 (m, 3H), 1.56–1.71 (m, 4H), 1.83 (dt, 2H), 2.26–2.34 (m, 4H), 2.86 (t, 2H), 3.14 (t, 2H), 3.36 (t, 4H), 3.55 (d, 2H), 3.81 (dd, 2H), 9.13 (s, 1H), 10.94 (s, 1H). ESMS m/z=447.2 (M+H)$^+$. HRMS calcd. for $C_{17}H_{30}F_3N_2O_6SH$: 447.1771 (M+H)$^+$. Found: 447.1757.

Example A46

Preparation of 4-{4-[4-(3,3,3-trifluoro-propoxy)-butyl]-piperidine-1-sulfonyl}-tetrahydro-pyran-4-carboxylic acid hydroxyamide

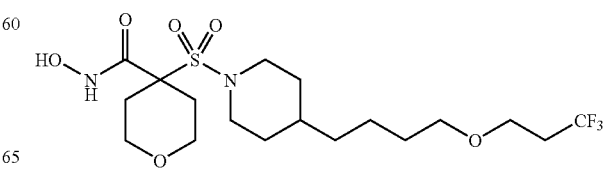

Part A. Preparation of 4-[4-(4-methanesulfonyloxy-butyl)-piperidine-1-sulfonyl]-tetrahydro-pyran-4-carboxylic acid tert-butyl ester:

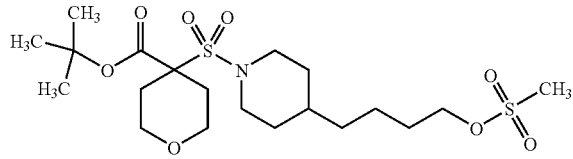

The alcohol from Example A12 (703 mg, 1.73 mmol) combined with methylene chloride (9 mL). Triethylamine (0.32 mL, 2.2 mmol) was then added. Afterward, the mixture was cooled to 0° C. Methanesulfonyl chloride (0.15 mL, 1.9 mmol) was then added dropwise. The resulting mixture was allowed to warm to room temperature overnight. Subsequently, additional triethylamine (0.16 mL, 1.15 mmol) and methanesulfonyl chloride (0.07 mL, 0.90 mmol) were added to drive the reaction to completion. After 2 hr, the mixture was diluted with methylene chloride (20 mL) and washed with water (30 mL), 10% citric acid (30 mL), 5% sodium bicarbonate, and brine (30 mL). The organics were dried (magnesium sulfate) and concentrated. Chromatography (on silica, ethyl acetate/hexanes) afforded the mesylate in the form of a colorless oil (747.8 mg, 89.6% yield). NMR (CDCl$_3$) δ 1.17–1.46 (m, 7H), 1.52 (s, 9H), 1.63–1.77 (m, 4H), 2.10 (dt, 2H), 2.32 (d, 2H), 2.91 (dt, 2H), 3.02 (s, 3H), 3.30 (dt, 2H), 3.77 (d, 2H), 3.96 (dd, 2H), 4.21 (t, 2H).

Part B. Preparation of 4-{4-[4-(3,3,3-trifluoro-propoxy)-butyl]-piperidine-1-sulfonyl}-tetrahydro-pyran-4-carboxylic acid tert-butyl ester:

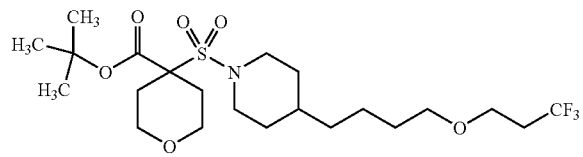

The 3,3,3-trifluoropropan-1-ol (546 mg, 4.79 mmol) was placed into an oven-dried flask. Anhydrous dimethylformamide (4.5 mL) was then added, followed by the addition of a 60% NaH oil dispersion (230 mg, 5.74 mmol) in 2 portions. After 15 min, the mesylate from Part A (732 mg, 1.51 mmol) in anhydrous dimethylformamide (1.5 mL) was added, and the resulting mixture was heated at 80° C. for 2 hr. The mixture was then cooled to room temperature, poured into saturated NH$_4$Cl (20 mL) and water (20 mL), and extracted with ethyl acetate (2×20 mL). The organics were washed with brine, dried over magnesium sulfate, and concentrated. Chromatography (on silica, ethyl acetate/hexanes) afforded the ether in the form of a colorless oil (541.9 mg, 71.5% yield). NMR(CDCl$_3$) δ 1.15–1.40 (m, 6H), 1.48–1.57 (m, 12H), 1.66 (d, 2H), 2.11 (dt, 2H), 2.28–2.45 (m, 4H), 2.92 (dt, 2H), 3.39 (dt, 2H), 3.42 (t, 4H), 3.62 (t, 2H), 3.76 (d, 2H), 3.96 (dd, 2H). ESMS m/z=502.45 (M+H)$^+$.

Part C. Preparation of 4-{4-[4-(3,3,3-trifluoro-propoxy)-butyl]-piperidine-1-sulfonyl}-tetrahydro-pyran-4-carboxylic acid:

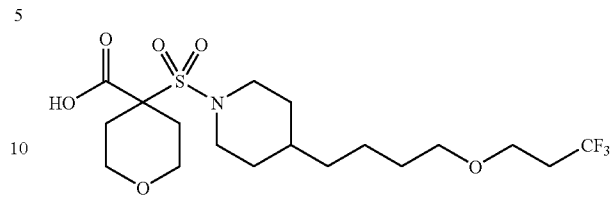

The ester of Part B (541.6 mg, 1.08 mmol) was hydrolyzed in 1:1 trifluoroacetic acid:methylene chloride (4 mL) at room temperature for 2 hr. The mixture was then concentrated under N$_2$, and triturated with ethyl acetate/hexane to afford the desired acid in the form of a solid (477.5 mg, 99.1% yield). This material was used in the next step without further purification. NMR(CDCl$_3$) δ 1.15–1.43 (m, 7H), 1.47–1.59 (m, 2H), 1.70 (d, 2H), 2.18 (dt, 2H), 2.29–2.44 (m, 4H), 2.93 (t, 2H), 3.33–3.45 (m, 4H), 3.61 (t, 2H), 3.79 (d, 2H), 4.00 (dd, 2H). ESMS m/z=464.31 (M+H)$^+$.

Part D. Preparation of 4-{4-[4-(3,3,3-trifluoro-propoxy)-butyl]-piperidine-1-sulfonyl}-tetrahydro-pyran-4-carboxylic acid (tetrahydro-pyran-2-yloxy)-amide:

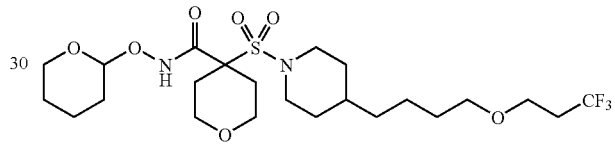

To a mixture of the crude acid from Part C (473.5 mg, 1.06 mmol), 1-hydrozybenzotriazole hydrate (215 mg, 1.59 mmol), THP—ONH$_2$ (174 mg, 1.48 mmol), and triethylamine (0.44 mL, 3.2 mmol) in dimethylformamide (3.2 mL) was added 1-(3-dimethylaminopropyl)-3-ethylcarbodiimide hydrochloride (283 mg, 1.48 mmol). After heating at 40° C., the acid slowly went into solution. The mixture was then stirred at 40–45° C. overnight. Subsequently, the mixture was partition between ethyl acetate (20 mL) and water (20 mL). The organics were extracted with 1N HCl (20 mL) and brine (20 mL), dried over magnesium sulfate, and concentrated. Chromatography (on silica, ethyl acetate/hexanes) afforded the protected hydroxamate in the form of a colorless oil (511.2 mg, 88.6% yield). NMR(CDCl$_3$) δ 1.13–1.39 (m, 8H), 1.48–1.72 (m, 7H), 1.73–1.89 (m, 3H), 2.13–2.26 (m, 4H), 2.31–2.44 (m, 2H), 2.90 (t, 2H), 3.40 (t, 2H), 3.48 (dq, 2H), 3.58–3.66 (m, 3H), 3.73–3.82 (m, 2H), 3.88–4.00 (m, 3H), 4.97 (s, 1H), 9.19 (s, 1H). ESMS m/z=545.41 (M+H)$^+$.

Part E. Preparation of 4-{4-[4-(3,3,3-trifluoro-propoxy)-butyl]-piperidine-1-sulfonyl}-tetrahydro-pyran-4-carboxylic acid hydroxyamide:

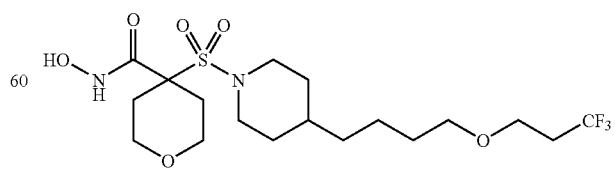

To the THP-protected hydroxamate from Part D (503 mg, 0.923 mmol) in methanol (1.0 mL) and 1,4-dioxane (1.0 mL) was added 4M HCl in 1,4-dioxane (200 μL). After stirring for 1 hr, the mixture was concentrated under $N_2$, and triturated with ethyl acetate/hexane to afford the desired compound as an off-white amorphous solid (393.5 mg, 92.6% yield). NMR(DMSO) δ 0.93–1.07(m, 2H), 1.11–1.35 (m, 5H), 1.38–1.48 (m, 2H), 1.59 (d, 2H), 1.83 (dt, 2H), 2.30 (d, 2H), 2.42–2.54 (m, 2H), 2.85 (t, 2H), 3.14 (t, 2H), 3.34 (t, 2H), 3.48–3.58 (m, 4H), 3.80 (dd, 2H), 9.13 (bs, 1H), 10.94 (s, 1H). ESMS m/z=461.2 (M+H)$^+$. HRMS calcd. for $C_{18}H_{32}F_3N_2O_6SH$: 461.1928 (M+H)$^+$. Found: 461.1933.

Example A47

Preparation of 4-[4-(2-pentyloxy-ethyl)-piperidine-1-sulfonyl]-tetrahydro-pyran-4-carboxylic acid hydroxyamide

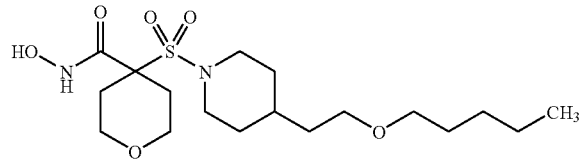

Part A. Preparation of 4-[4-(2-pentyloxy-ethyl)-piperidine-1-sulfonyl]-tetrahydro-pyran-4-carboxylic acid tert-butyl ester:

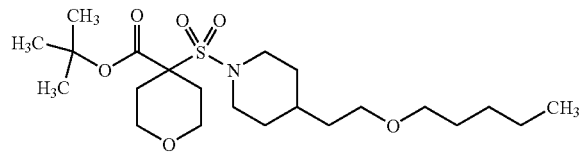

The alcohol of Example A13 (257 mg, 0.680 mmol), tetrabutylammonium bromide (44 mg, 0.136 mmol), and KOH (114 mg, 2.04 mmol) were slurried in xylene (2.7 mL). Afterward, 1-iodopentane (0.27 mL, 2.04 mmol) was added, and the resulting mixture was stirred in a sealed vial at 80° C. overnight. Subsequently, the mixture was filtered through celite and concentrated under $N_2$. Chromatography (on silica, ethyl acetate/hexanes) afforded the ether in the form of a colorless oil (202.7 mg, 66.6% yield). NMR(CDCl$_3$) δ 0.88 (t, 3H), 1.19–1.34 (m, 6H), 1.45–1.63 (m, 14H), 1.68 (d, 2H), 2.10 (dd, 2H), 2.32 (d, 2H), 2.93 (dt, 2H), 3.40 (dt, 2H), 3.36 (t, 2H), 3.42 (t, 2H), 3.76 (d, 2H), 3.96 (dd, 2H). ESMS m/z=448.47 (M+H)$^+$.

Part B. Preparation of 4-[4-(2-pentyloxy-ethyl)-piperidine-1-sulfonyl]-tetrahydro-pyran-4-carboxylic acid:

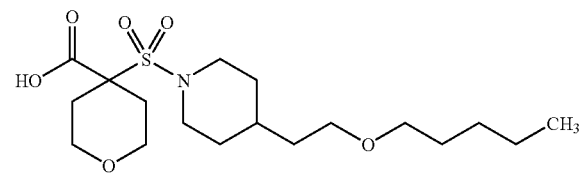

The ester of Part A (202.8 mg, 0.453 mmol) was hydrolyzed in 1:1 trifluoroacetic acid:methylene chloride (4 mL) at room temperature for 2 hr. The mixture was then concentrated under $N_2$ to afford the desired acid (177.9 mg, 100% yield). This material was used in the next step without further purification. NMR(CDCl$_3$) δ 0.88 (t, 3H), 1.19–1.35 (m, 6H), 1.49–1.63 (m, 5H), 1.71 (d, 2H), 2.18 (dt, 2H), 2.35 (d, 2H), 2.94 (t, 2H), 3.34–3.43 (m, 4H), 3.46(t, 2H), 3.79 (d, 2H), 4.00 (dd, 2H). ESMS m/z=392.38 (M+H)$^+$.

Part C. Preparation of 4-[4-(2-pentyloxy-ethyl)-piperidine-1-sulfonyl]-tetrahydro-pyran-4-carboxylic acid (tetrahydro-pyran-2-yloxy)-amide:

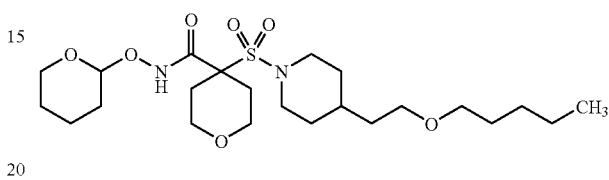

To a mixture of the crude acid from Part B (177.5 mg, 0.453 mmol), 1-hydrozybenzotriazole hydrate (92 mg, 0.68 mmol), THP—ONH$_2$ (74 mg, 0.63 mmol), and triethylamine (0.19 mL, 1.4 mmol) in dimethylformamide (2.5 mL) was added 1-(3-dimethylaminopropyl)-3-ethylcarbodiimide hydrochloride (121 mg, 0.63 mmol). After heating at 40° C., the acid slowly went into solution. The mixture was then stirred at 40–45° C. overnight. Subsequently, the mixture was poured onto 10 mL Chem-Elut tube prewetted with 0.5N HCl (8 mL), eluted with ethyl acetate ("EtOAc"), and concentrated. Chromatography (on silica, ethyl acetate/hexanes) afforded the protected hydroxamate in the form of a colorless oil (109.5 mg, 49.2% yield). NMR(CDCl$_3$) δ 0.90 (t, 3H), 1.13–1.39 (m, 6H), 1.45–1.92 (m, 10H), 2.12–2.30 (m, 4H), 2.94 (t, 2H), 3.30–3.56 (m, 8H), 3.59–3.84 (m, 4H), 3.88–4.03 (m, 4H), 4.97 (s, 1H), 9.19 (s, 1H). ESMS m/z=491.38 (M+H)$^+$.

Part D. Preparation of 4-[4-(2-pentyloxy-ethyl)-piperidine-1-sulfonyl]-tetrahydro-pyran-4-carboxylic acid hydroxyamide:

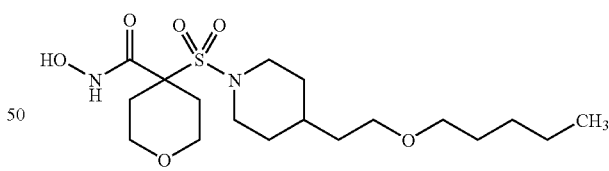

To the THP-protected hydroxamate from Part C (103 mg, 0.21 mmol) in methanol (1.0 mL) and 1,4-dioxane (1.0 mL) was added 4M HCl in 1,4-dioxane (200 μL). After stirring for 1.5 hr, the mixture was concentrated under $N_2$. Reverse phase chromatography (acetonitrile:water:0.05% trifluoroacetic acid) and lyophylization afforded the desired compound as an off-white amorphous solid (72.1 mg, 84.5% yield). NMR (CDCl$_3$) δ 0.88 (t, 3H), 1.13–1.39 (m, 5H), 1.44–1.78 (m, 8H), 2.10–2.33 (m, 4H), 2.92 (t, 2H), 3.32–3.53 (m, 6H), 3.72 (d, 2H), 3.96 (d, 2H), 6.92 (bs, 1H), 9.20 (bs, 1H). ESMS m/z=407.2 (M+H)$^+$. HRMS calcd. for $C_{18}H_{35}N_2O_6SH$: 407.2210 (M+H)$^+$. Found: 407.2209.

Example A48

Preparation of 4-[4-(7,7-trifluoro-heptyloxy)-piperidine-1-sulfonyl]-tetrahydro-pyran-4-carboxylic acid hydroxyamide

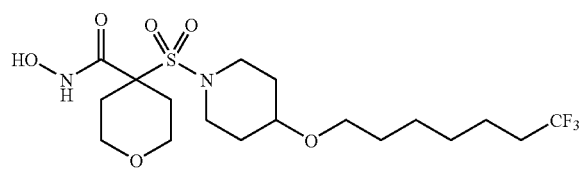

Part A. Preparation of 4-[4-(7,7-trifluoro-hept-3-enyloxy)-piperidine-1-sulfonyl]-tetrahydro-pyran-4-carboxylic acid tert-butyl ester:

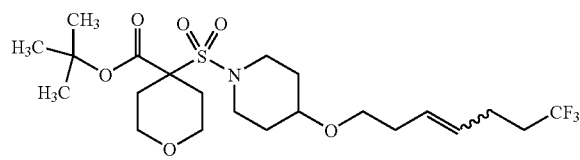

To the phosphine from Example A10 (800 mg, 1.6 mmol) in anhydrous tetrahydrofuran (5.9 mL) at 0° C. was added 1M LiN(TMS) (1.5 mL, 1.5 mmol) dropwise while maintaining the temperature at less than 5° C. Upon completion of the addition, the mixture was stirred at 0° C. for 15 min. The aldehyde from Example A14, Part D (500 mg, 1.23 mmol) in anhydrous tetrahydrofuran (2.5 mL) was then added dropwise while maintaining the temperature at less than 4° C. Afterward, the mixture was allowed to warm to room temperature over several hours. The mixture was then poured into stirring ether (75 mL) and filtered. The filtrate was washed with 1N HCl (3×75 mL), saturated sodium bicarbonate (3×75 mL), and brine (100 mL); dried over magnesium sulfate; and concentrated to form a crude oil. Chromatography (on silica, ethyl acetate/hexanes) afforded the alkene in the form of a colorless crystalline oil (498.8 mg, 81.1% yield). NMR(CDCl$_3$) δ 1.52 (s, 9H), 1.60–1.74 (m, 2H), 1.77–1.90 (m, 2H), 2.04–2.20 (m, 4H), 2.22–2.36 (m, 6H), 3.16–3.36 (m, 4H), 3.38–3.65 (m, 5H), 3.96 (dd, 2H), 5.35–5.54 (m, 2H). ESMS m/z=500.45 (M+H)$^+$.

Part B. Preparation of 4-[4-(7,7-trifluoro-heptyloxy)-piperidine-1-sulfonyl]-tetrahydro-pyran-4-carboxylic acid tert-butyl ester:

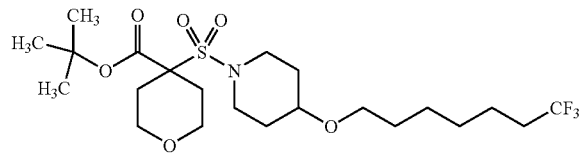

The alkene from Part A (483.4 mg, 0.968 mmol) was combined with tetrahydrofuran (5 mL). Subsequently, 10% Pd/C (0.24 g) was added. The resulting mixture was stirred on a Parr hydrogenator at 40 psi for 2 hr. The mixture was then filtered through celite and concentrated. Chromatography (on silica, using ethyl acetate/hexanes) afforded a crystalline solid product (363.1 mg, 74.8% yield). NMR(CDCl$_3$) δ 1.29–1.46 (m, 2H), 1.46–1.75 (m, 15H), 1.75–1.92 (m, 2H), 1.98–2.20 (m, 4H), 2.32 (d, 2H), 3.12–3.64 (m, 9H), 3.96 (dd, 2H). ESMS m/z=446.37 (M+H-t-Bu)$^+$.

Part C. Preparation of 4-[4-(7,7-trifluoro-heptyloxy)-piperidine-1-sulfonyl]-tetrahydro-pyran-4-carboxylic acid:

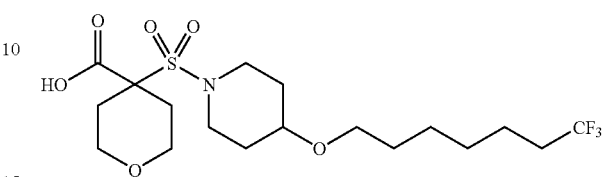

The ester of Part B (349.7 mg, 0.697 mmol) was hydrolyzed in 1:1 trifluoroacetic acid:methylene chloride (4 mL) at room for 2 hr. The mixture was then concentrated under N$_2$ to afford the desired acid (307–1 mg, 98.9% yield). This material was used in the next step without further purification. NMR (CDCl$_3$) δ 1.28–1.45 (m, 4H), 1.48–1.74 (m, 6H), 1.77–1.92 (m, 2H), 1.97–2.27 (m, 4H), 2.35 (d, 2H), 3.19–3.65 (m, 9H), 4.12 (dd, 2H). ESMS m/z=463.37 (M+NH$_4$)$^+$.

Part D. Preparation of 4-[4-(7,7-trifluoro-heptyloxy)-piperidine-1-sulfonyl]-tetrahydro-pyran-4-carboxylic acid (tetrahydro-pyran-2-yloxy)-amide:

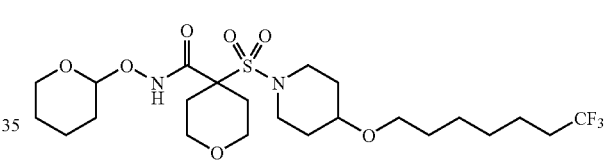

To a mixture of the crude acid from Part C (305.1 mg, 0.685 mmol), 1-hydrozybenzotriazole hydrate (139 mg, 1.03 mmol), THP—ONH$_2$ (112 mg, 0.96 mmol), and triethylamine (0.29 mL, 2.08 mmol) in dimethylformamide (3.0 mL) was added 1-(3-dimethylaminopropyl)-3-ethylcarbodiimide hydrochloride (183 mg, 0.96 mmol). The resulting mixture was stirred at 50° C. overnight. Subsequently, the mixture was concentrated; combined with ethyl acetate (5 mL); and washed with water (5 mL), 1N HCl (4 mL), and saturated sodium bicarbonate. Chromatography (on silica, ethyl acetate/hexanes) afforded the protected hydroxamate in the form of a colorless oil (336.7 mg, 90.3% yield). NMR (CDCl$_3$) δ 1.31–1.46 (m, 4H), 1.51–1.73 (m, 10H), 1.75–1.92 (m, 4H), 1.97–2.31 (m, 6H), 3.18–3.32 (m, 2H), 3.35–3.70 (m, 8H), 3.89–4.05 (m, 3H), 4.97 (s, 1H), 9.19 (s, 1H). ESMS m/z=545.45 (M+H)$^+$.

Part E. Preparation of 4-[4-(7,7-trifluoro-heptyloxy)-piperidine-1-sulfonyl]-tetrahydro-pyran-4-carboxylic acid hydroxyamide:

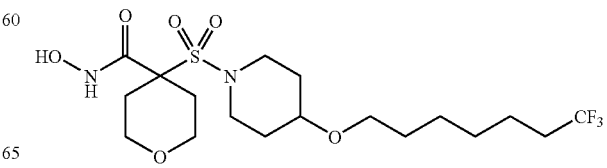

To the THP-protected hydroxamate from Part D (336.7 mg, 0.618 mmol) in methanol (2.0 mL) was added 4M HCl in 1,4-dioxane (200 μL). After stirring for 1 hr, the mixture was concentrated under $N_2$ to afford the desired compound in the form of a white amorphous solid (270.4 mg, 95.0% yield). NMR (CD3OD) δ 1.35–1.44 (m, 4H), 1.49–1.60 (m, 6H), 1.80–1.90 (m, 2H), 2.02–2.19 (m, 4H), 2.32 (d, 2H), 3.12–3.22 (m, 2H), 3.36 (t, 2H), 3.46 (t, 3H), 3.52–3.61 (m, 2H), 3.90 (dd, 2H). ESMS m/z=461.2 (M+H)$^+$. HRMS calcd. for $C_{18}H_{32}F_3N_2O_6SH$: 461.1928 (M+H)$^+$. Found: 461.1911.

Example A49

Preparation of 4-[4-(6,6,6-trifluoro-hexyloxy)-piperidine-1-sulfonyl]-tetrahydro-pyran-4-carboxylic acid hydroxyamide

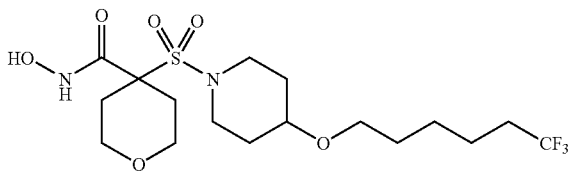

Part A. Preparation of 4-[4-(6,6,6-trifluoro-hex-3-enyloxy)-piperidine-1-sulfonyl]-tetrahydro-pyran-4-carboxylic acid tert-butyl ester:

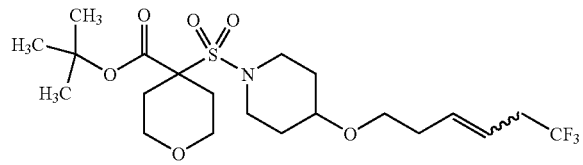

To the phosphine from Example A15 (778 mg, 1.6 mmol) in anhydrous tetrahydrofuran (5.9 mL) at 0° C. was added 1M LiN(TMS) (1.5 mL, 1.5 mmol) dropwise while maintaining the temperature at less than 5° C. Upon completion of the addition, the mixture was stirred at 0° C. for 15 min. The aldehyde from Example A14, Part D (500 mg, 1.23 mmol) in anhydrous tetrahydrofuran (2.5 mL) was then added dropwise while maintaining the temperature at less than 4° C. The cooling bath was then removed, and the mixture was stirred at room temperature for 3 hr. Subsequently, the mixture was poured into stirring ether (75 mL) and filtered. The filtrate was washed with 1N HCl (3×75 mL), saturated sodium bicarbonate (3×75 mL), and brine (100 mL); dried over magnesium sulfate; and concentrated to form a crude oil. Chromatography (on silica, ethyl acetate/hexanes) afforded the alkene in the form of a colorless crystalline solid (529.6, 88.6% yield). NMR (CDCl$_3$) δ 1.52 (s, 9H), 1.60–1.72 (m, 2H), 1.77–1.90 (m, 2H), 2.11 (dt, 2H), 2.33 (d, 4H), 2.74–2.96 (m, 2H), 3.18–3.36 (m, 4H), 3.40–3.64 (m, 5H), 3.96 (dd, 2H), 5.42–5.54 (m, 1H), 5.69–5.82 (m, 1H). ESMS m/z=486.41 (M+H)$^+$.

Part B. Preparation of 4-[4-(6,6,6-trifluoro-hexyloxy)-piperidine-1-sulfonyl]-tetrahydro-pyran-4-carboxylic acid tert-butyl ester:

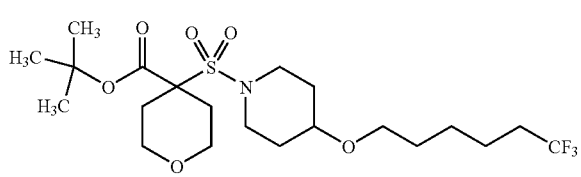

The alkene from Part A (519.2 mg, 1.07 mmol) was combined with tetrahydrofuran (5 mL). Afterward, 10% Pd/C (0.26 g) was added. The resulting mixture was stirred on a Parr hydrogenator at 40 psi for 2 hr. The mixture was then filtered through celite and concentrated. Chromatography (on silica, using ethyl acetate/hexanes) afforded a crystalline solid (408.4 mg, 78.3% yield). NMR(CDCl$_3$) δ 1.35–1.74 (m, 13H), 1.76–1.91 (m, 2H), 1.98–2.20 (m, 4H), 2.32 (d, 2H), 3.12–3.63 (m, 9H), 3.96 (dd, 2H). ESMS m/z=510.39 (M+Na)$^+$.

Part C. Preparation of 4-[4-(6,6,6-trifluoro-hexyloxy)-piperidine-1-sulfonyl]-tetrahydro-pyran-4-carboxylic acid:

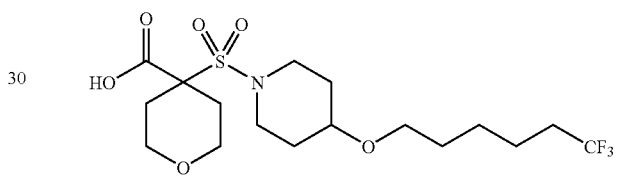

The ester of Part B (400.7 mg, 0.822 mmol) was hydrolyzed in 1:1 trifluoroacetic acid:methylene chloride (4 mL) at room temperature for 2 hr. The mixture was then concentrated under $N_2$ to afford the desired acid (355.4 mg, 100% yield). This material was used in the next step without further purification. NMR (CDCl$_3$) δ 1.36–1.52 (m, 2H), 1.52–1.75 (m, 6H), 1.78–1.93 (m, 2H), 2.00–2.26 (m, 4H), 2.37 (d, 2H), 3.20–3.66 (m, 9H), 4.03 (dd, 2H). ESMS m/z=432.31 (M+H)$^+$.

Part D. Preparation of 4-[4-(6,6,6-trifluoro-hexyloxy)-piperidine-1-sulfonyl]-tetrahydro-pyran-4-carboxylic acid (tetrahydro-pyran-2-yloxy)-amide:

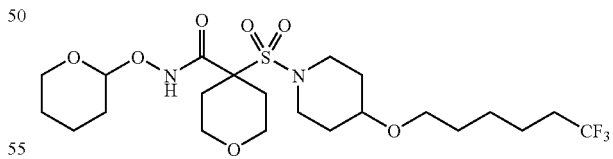

To a mixture of the crude acid from Part C (350.5 mg, 0.812 mmol), 1-hydrozybenzotriazole hydrate (164 mg, 1.21 mmol), THP—ONH$_2$ (133 mg, 1.14 mmol), and triethylamine (0.34 mL, 2.44 mmol) in dimethylformamide (4.0 mL) was added 1-(3-dimethylaminopropyl)-3-ethylcarbodiimide hydrochloride (217 mg, 1.14 mmol). The resulting mixture was stirred at 50° C. overnight. Subsequently, the mixture was concentrated; combined with ethyl acetate (5 mL); and washed with water (5 mL), 1N HCl (4 mL), and saturated sodium bicarbonate. Chromatography (on silica, ethyl acetate/hexanes, followed by acetonitrile/water/0.05% trifluoroacetic acid on C18) afforded a mix of the protected hydroxamate and predominantly de-protected material in the form of a colorless oil (291.0 mg). NMR (CDCl$_3$) δ 1.37–1.77 (m, 8H), 1.77–1.91 (m, 2H), 1.98–2.31 (m, 6H), 3.16–3.32 (m, 2H), 3.37–3.59 (m, 7H), 3.99 (s, 3H), 6.83 (bs, 1H), 9.19 (bs, 1H). ESMS m/z=447.33 (M+H-THP)$^+$.

Part E. Preparation of 4-[4-(6,6,6-trifluoro-hexyloxy)-piperidine-1-sulfonyl]-tetrahydro-pyran-4-carboxylic acid hydroxyamide:

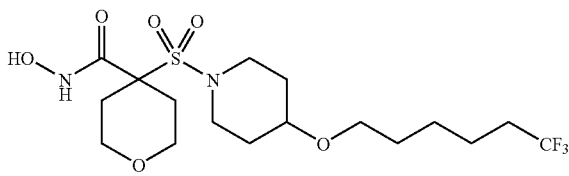

To the partially THP-protected hydroxamate from Part D (291.0 mg, 0.651 mmol) in methanol (2.0 mL) was added 4M HCl in 1,4-dioxane (200 µL). After stirring for 1 hr, the mixture was concentrated under N$_2$ to afford the desired compound as an off-white amorphous solid (272.9 mg, 93.9% yield). NMR (CD3OD) δ 1.40–1.49 (m, 2H), 1.50–1.62 (m, 6H), 1.79–1.89 (m, 2H), 2.02–2.20 (m, 4H), 2.32 (d, 2H), 3.12–3.23 (m, 2H), 3.36 (t, 2H), 3.46 (t, 3H), 3.51–3.61 (m, 2H), 3.90 (dd, 2H). ESMS m/z=447.2 (M+H)$^+$. HRMS calcd. for C$_{17}$H$_{30}$F$_3$N$_2$O$_6$S H: 447.1771 (M+H)$^+$. Found: 447.1756.

Example A50

Preparation of 4-[4-(6,6,7,7,7-pentafluoro-heptyloxy)-piperidine-1-sulfonyl]-tetrahydro-pyran-4-carboxylic acid hydroxyamide

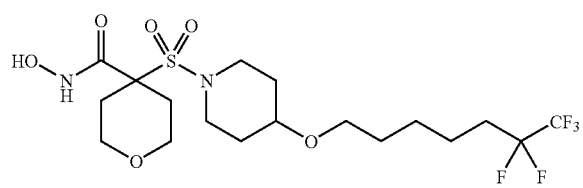

Part A. Preparation of 4-[4-(6,6,7,7,7-pentafluoro-hept-3-enyloxy)-piperidine-1-sulfonyl]-tetrahydro-pyran-4-carboxylic acid tert-butyl ester:

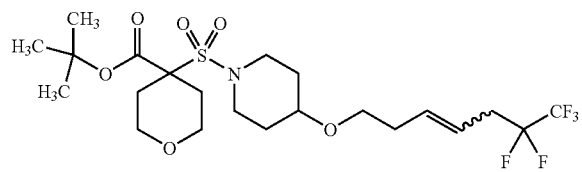

To the phosphine from Example A11 (981 mg, 1.83 mmol) in anhydrous tetrahydrofuran (6.8 mL) at 0° C. was added 1M LiN(TMS) (1.7 mL, 1.7 mmol) dropwise while maintaining the temperature at less than 5° C. Upon completion of addition, the mixture was stirred at 0° C. for 15 min. The aldehyde from Example A14, Part D (573 mg, 1.41 mmol) in anhydrous tetrahydrofuran (2.9 mL) was then added dropwise while maintaining the temperature at less than 4° C. The cooling bath was then removed, and the mixture was stirred at room temperature overnight. Subsequently, the mixture was poured into stirring ether (75 mL) and filtered. The filtrate was washed with 1N HCl (3×75 mL), saturated sodium bicarbonate (3×75 mL), and brine (100 mL); dried over magnesium sulfate; and concentrated to form a crude oil. Chromatography (on silica, ethyl acetate/hexanes) afforded the alkene as an off-white crystalline solid (620.2, 82.3% yield). NMR (CDCl$_3$) δ 1.52 (s, 9H), 1.58–1.74 (m, 2H), 1.76–1.90 (m, 2H), 2.11 (dt, 2H), 2.25–37 (m, 4H), 2.84 (dd, 2H), 3.18–3.37 (m, 4H), 3.40–3.65 (m, 5H), 3.97 (dd, 2H), 5.49 (q, 1H), 5.71–5.83 (m, 1H). ESMS m/z=536.41 (M+H)$^+$.

Part B. Preparation of 4-[4-(6,6,7,7,7-pentafluoro-heptyloxy)-piperidine-1-sulfonyl]-tetrahydro-pyran-4-carboxylic acid tert-butyl ester:

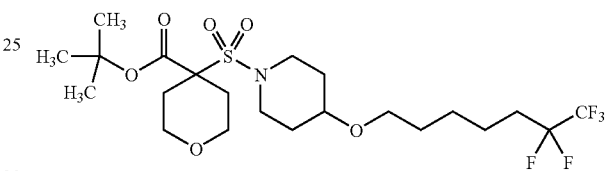

The alkene from Part A (609.7 mg, 1.14 mmol) was combined with tetrahydrofuran (5 mL). Afterward, 10% Pd/C (0.31 g) was added. The resulting mixture was stirred on a Parr hydrogenator at 40 psi for 2 hr. The mixture was then filtered through celite and concentrated. Chromatography (on silica, using ethyl acetate/hexanes) afforded the ester in the form of a crystalline solid (498.6 mg, 81.5% yield). NMR (CDCl$_3$) δ 1.37–1.74 (m, 17H), 1.77–1.91 (m, 2H), 1.93–2.20 (m, 4H), 2.32 (d, 2H), 3.12–3.63 (m, 9H), 3.96 (dd, 2H). ESMS m/z=560.41 (M+Na)$^+$.

Part C. Preparation of 4-[4-(6,6,7,7,7-pentafluoro-heptyloxy)-piperidine-1-sulfonyl]-tetrahydro-pyran-4-carboxylic acid:

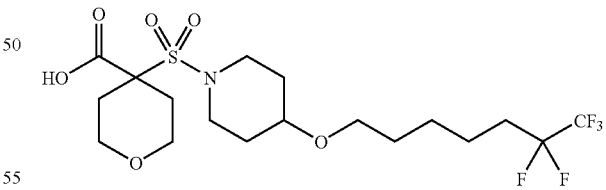

The ester of Part B (493.4 mg, 0.918 mmol) was hydrolyzed in 1:1 trifluoroacetic acid:methylene chloride (4 mL) at room temperature for 2 hr. The mixture was then concentrated under N$_2$ to afford the desired acid (442.7 mg, 100% yield). The resulting material was used in the next step without further purification. NMR (CDCl$_3$) δ 1.37–1.51 (m, 2H), 1.54–1.74 (m, 6H), 1.70–1.94 (m, 2H), 1.94–2.26 (m, 4H), 2.37 (d, 2H), 3.20–3.64 (m, 9H), 4.03 (dd, 2H). ESMS m/z=482.34 (M+H)$^+$.

Part D. Preparation of 4-[4-(6,6,7,7,7-pentafluoro-heptyloxy)-piperidine-1-sulfonyl]-tetrahydro-pyran-4-carboxylic acid (tetrahydro-pyran-2-yloxy)-amide:

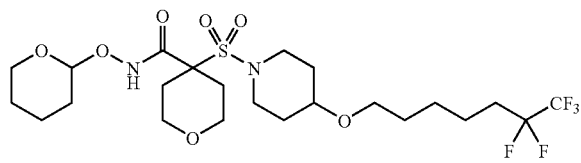

To a mixture of the crude acid from Part C (437.4 mg, 0.908 mmol), 1-hydrozybenzotriazole hydrate (184 mg, 1.36 mmol), THP—ONH$_2$(149 mg, 1.27 mmol), and triethylamine (0.38 mL, 2.73 mmol) in dimethylformamide (4.0 mL) was added 1-(3-dimethylaminopropyl)-3-ethylcarbodiimide hydrochloride (243 mg, 1.27 mmol). The resulting mixture was stirred at 50° C. overnight. Subsequently, the mixture was concentrated; combined with ethyl acetate (5 mL); and washed with water (5 mL), 1N HCl (4 mL), and saturated sodium bicarbonate. Chromatography (on silica, ethyl acetate/hexanes, followed by acetonitrile/water/0.05% trifluoroacetic acid on C18) afforded a mix of the protected hydroxamate and predominantly de-protected material in the form of a colorless oil (351.1 mg). NMR (CDCl$_3$) δ 1.37–1.52 (m, 2H), 1.52–1.75 (m. 6H), 1.75–1.92 (m, 2H), 1.92–2.34 (m, 8H), 3.13–3.30 (m, 2H), 3.33–3.60 (m, 7H), 3.99 (d, 3H). ESMS m/z=497.32 (M+H-THP)$^+$.

Part E. Preparation of 4-[4-(6,6,7,7,7-pentafluoro-heptyloxy)-piperidine-1-sulfonyl]-tetrahydro-pyran-4-carboxylic acid hydroxyamide:

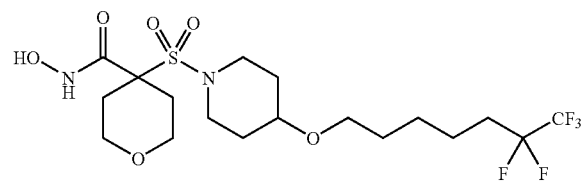

To the partially THP-protected hydroxamate from Part D (351.1 mg, 0.605 mmol) in methanol (2.0 mL) was added 4M HCl in 1,4-dioxane (200 µL). After stirring for 1 hr, the mixture was concentrated under N$_2$ to afford the desired compound as an off-white amorphous solid (303.6 mg, 100% yield). NMR (CD$_3$OD) δ 1.41–1.64 (m, 8H), 1.79–1.91 (m, 2H), 2.00–2.18 (m, 4H), 2.32 (d, 2H), 3.12–3.23 (m, 2H), 3.36 (t, 2H), 3.47 (t, 3H), 3.50–3.61 (m, 2H), 3.91 (dd, 2H). ESMS m/z=497.2 (M+H)$^+$. HRMS calcd. for C$_{18}$H$_{30}$F$_5$N$_2$O$_6$SH: 497.1739 (M+H)$^+$. Found: 497.1725.

Example A51

Preparation of 4-[4-(7,7,8,8,8-pentafluoro-octyl)-piperidine-1-sulfonyl]-tetrahydro-pyran-4-carboxylic acid hydroxyamide

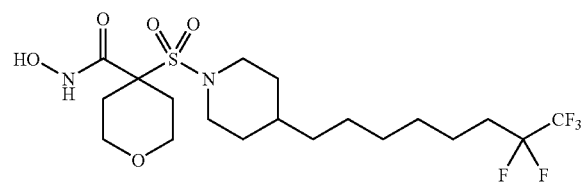

Part A. Preparation of 4-[4-(7,7,8,8,8-pentafluoro-oct-4-enyl)-piperidine-1-sulfonyl]-tetrahydro-pyran-4-carboxylic acid tert-butyl ester:

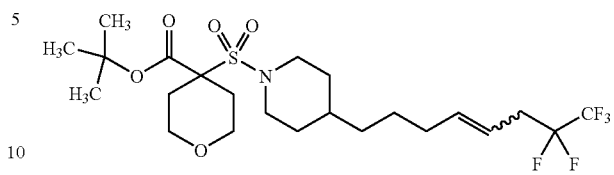

To the phosphine from Example A11 (552 mg, 1.03 mmol) in anhydrous tetrahydrofuran (4.1 mL) at 0° C. was added 1M LiN(TMS) (1.1 mL, 1.1 mmol) dropwise while maintaining the temperature at less than 5° C. Upon completion of addition, the mixture was stirred at 0° C. for 15 min. The aldehyde from Example A16 (348 mg, 0.861 mmol) in anhydrous tetrahydrofuran (1.7 mL) was then added dropwise while maintaining temperature at less than 4° C. The cooling bath was then removed, and the mixture was stirred at room temperature overnight. Subsequently, the mixture was poured into stirring ether (75 mL) and filtered. The filtrate was washed with 1N HCl (3×75 mL), saturated sodium bicarbonate (3×75 mL), and brine (100 mL); dried over magnesium sulfate; and concentrated to crude oil. Chromatography (on silica, ethyl acetate/hexanes) afforded the alkene in the form of a colorless oil (275.2, 59.9% yield). NMR (CDCl$_3$) δ 1.26–1.43 (m, 7H), 1.52 (s, 9H), 1.66 (d, 2H), 2.20 (q, 2H), 2.11 (dt, 2H), 2.31 (d, 2H), 2.78 (dt, 2H), 2.91 (d, 2H), 3.30 (t, 2H), 3.76 (d, 2H), 3.97 (dd, 2H), 5.39 (q, 1H), 5.70 (q, 1H), ESMS m/z=534.44 (M+H)$^+$.

Part B. Preparation of 4-[4-(7,7,8,8,8-pentafluoro-octyl)-piperidine-1-sulfonyl]-tetrahydro-pyran-4-carboxylic acid tert-butyl ester:

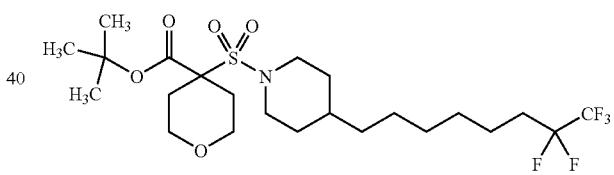

The alkene from Part A (270 mg, 0.506 mmol) was combined with tetrahydrofuran (20 mL). Afterward, 10% Pd/C (0.27 g) was added. The resulting mixture was stirred on a Parr hydrogenator at 40 psi for 1.5 hr. The mixture was then filtered through celite and concentrated, affording the ester in the form of a colorless oil (276.2 mg, quantitative conversion). NMR (CDCl$_3$)δ 1.25–1.40(m, 111H), 1.47–1.61 (m, 11H), 1.66(d, 22H), 1.91–2.06 (m, 2H), 2.21 (dt, 2H), 2.32 (d, 2H), 2.90 (t, 2H), 3.30 (d, 2H), 3.75 (d, 2H), 3.96 (dd, 2H). ESMS m/z=560.41 (M+Na)$^+$.

Part C. Preparation of 4-[4-(7,7,8,8,8-pentafluoro-octyl)-piperidine-1-sulfonyl]-tetrahydro-pyran-4-carboxylic acid:

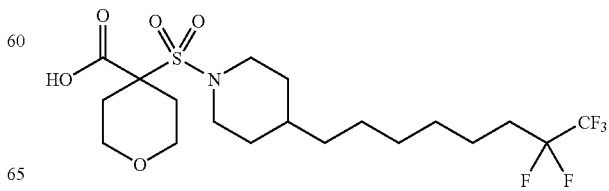

The ester of Part B (262.1 mg, 0.489 mmol) was hydrolyzed in 1:1 trifluoroacetic acid:methylene chloride (4 mL) at room temperature for 2 hr. The mixture was then concentrated under $N_2$ to afford the desired acid (230.2, 100% yield). This material was used in the next step without further purification. NMR (CDCl$_3$) δ 1.15–1.44 (m, 11H) 1.52–1.63 (m, 2H), 1.72 (d, 2H), 1.91–2.10 (m, 2H), 2.13–2.28 (m, 2H), 2.38 (d, 2H), 2.94 (t, 2H), 3.20 (t, 2H), 3.82 (d, 2H), 4.02 (dd, 2H). ESMS m/z=480.35 (M+H)$^+$.

Part D. Preparation of 4-[4-(7,7,8,8,8-pentafluoro-octyl)-piperidine-1-sulfonyl]-tetrahydro-pyran-4-carboxylic acid (tetrahydro-pyran-2-yloxy)-amide:

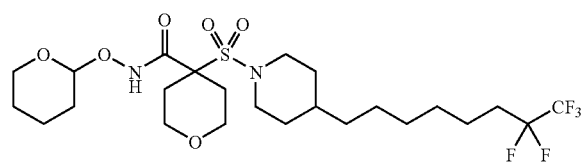

To a mixture of the crude acid from Part C (226.1 mg, 0.472 mmol), 1-hydrozybenzotriazole hydrate (95.5 mg, 0.71 mmol), THP—ONH$_2$ (77.3 mg, 0.66 mmol), and triethylamine (0.20 mL, 1.44 mmol) in dimethylformamide (2.0 mL) was added 1-(3-dimethylaminopropyl)-3-ethylcarbodiimide hydrochloride (126.1 mg, 0.66 mmol). The resulting mixture was stirred at 50° C. overnight. Subsequently, the mixture was concentrated; combined with ethyl acetate (5 mL); and washed with water (5 mL), 1N HCl (4 mL), and saturated sodium bicarbonate. Chromatography (on silica, ethyl acetate/hexanes) afforded the protected hydroxamate in the form of a colorless oil (224.5 mg, 82.3% yield). NMR (CDCl$_3$) δ 1.13–1.44 (m, 10H), 1.52–1.74 (m, 8H), 1.77–2.12 (m, 5H), 2.14–2.33 (m, 4H), 2.93 (t, 2H), 3.50 (dq, 2H), 3.60–3.70 (m, 1H), 3.74–3.86 (m, 2H), 3.90–4.03 (m, 3H), 4.99 (s, 1H), 9.02 (s, 1H). ESMS m/z=579.47 (M+H)$^+$.

Part E. Preparation of 4-[4-(7,7,8,8,8-pentafluoro-octyl)-piperidine-1-sulfonyl]-tetrahydro-pyran-4-carboxylic acid hydroxyamide:

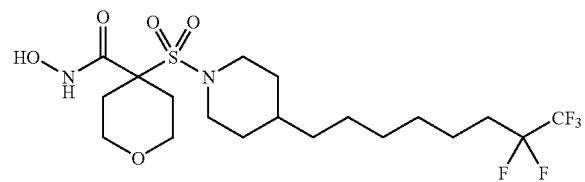

To the THP-protected hydroxamate from Part D (224.5 mg, 0.388 mmol) in methanol (2.0 mL) was added 4M HCl in 1,4-dioxane (200 µL). After stirring for 1 hr, the mixture was concentrated under $N_2$ to afford the desired compound as an off-white amorphous solid (184.8 mg, 96.3% yield). NMR (CD$_3$OD) δ 1.07–1.20 (m, 2H), 1.22–1.44 (m, 9H), 1.51–1.61 (m, 2H), 1.68 (d, 2H), 1.99–2.16 (m, 4H), 2.33 (d, 2H), 2.93 (dt, 2H), 3.36 (t, 2H), 3.73 (d, 3H), 3.90 (dd, 2H). ESMS m/z=495.2 (M+H)$^+$. HRMS calcd. for $C_{19}H_{32}F_5N_2O_5SH$: 495.1947 (M+H)$^+$. Found: 495.1922.

Example A52

Preparation of 4-[4-(8,8,8-trifluoro-octyl)-piperidine-1-sulfonyl]-tetrahydro-pyran-4-carboxylic acid hydroxyamide

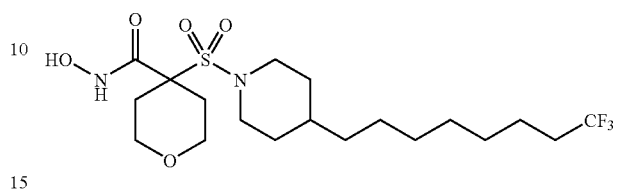

Part A. Preparation of 4-[4-(8,8,8-trifluoro-oct-4-enyl)-piperidine-1-sulfonyl]-tetrahydro-pyran-4-carboxylic acid tert-butyl ester:

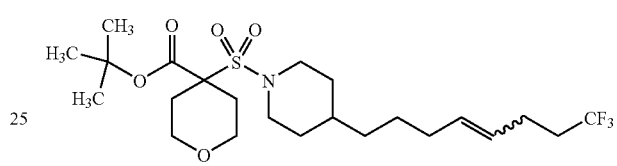

To the phosphine from Example A10 (515 mg, 1.03 mmol) in anhydrous tetrahydrofuran (4.1 mL) at 0° C. was added 1M LiN(TMS) (1.1 mL, 1.1 mmol) dropwise while maintaining the temperature at less than 5° C. Upon completion of addition, the mixture was stirred at 0° C. for 15 min. Afterward, the aldehyde from Example A16 (348 mg, 0.861 mmol) in anhydrous tetrahydrofuran (1.7 mL) was added dropwise while maintaining the temperature at less than 4° C. The cooling bath was then removed, and the mixture was stirred at room temperature overnight. The mixture was then poured into stirring ether (75 mL) and filtered. The filtrate was washed with 1N HCl (3×75 mL), saturated sodium bicarbonate (3×75 mL), and brine (100 mL); dried over magnesium sulfate; and concentrated to form a crude oil. Chromatography (on silica, ethyl acetate/hexanes) afforded the alkene as colorless oil (275.2, 59.9% yield). NMR (CDCl$_3$) δ 1.26–1.42 (m, 7H), 1.53 (s, 9H), 1.66 (d, 2H), 1.93–2.17 (m, 6H), 2.19–2.35 (m, 4H), 2.91 (d, 2H), 3.30 (t, 2H), 3.76 (d, 2H), 3.97 (dd, 2H), 5.27–5.52 (m, 2H). ESMS m/z=498.45 (M+H)$^+$.

Part B. Preparation of 4-[4-(8,8,8-trifluoro-octyl)-piperidine-1-sulfonyl]-tetrahydro-pyran-4-carboxylic acid tert-butyl ester:

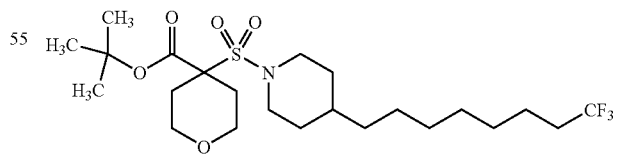

The alkene from Part A (235 mg, 0.472 mmol) was combined with tetrahydrofuran (20 mL). Afterward, 10% Pd/C (0.24 g) was added. The resulting mixture was stirred on a Parr hydrogenator at 40 psi for 1.5 hr. The mixture was then filtered through celite and concentrated, affording the ester in the form of a crystalline solid (247.5 mg, quantitative conversion). NMR (CDCl₃) δ 1.14–1.40 (m, 13H), 1.47–1.58 (m, 11H), 1.66 (d, 2H), 1.96–2.17 (m, 4H), 2.32 (d, 2H), 2.91 (t, 2H), 3.30 (d, 2H), 3.76 (d, 2H), 3.96 (dd, 2H). ESMS m/z=500.46 (M+H)⁺.

Part C. Preparation of 4-[4-(8,8,8-trifluoro-octyl)-piperidine-1-sulfonyl]-tetrahydro-pyran-4-carboxylic acid:

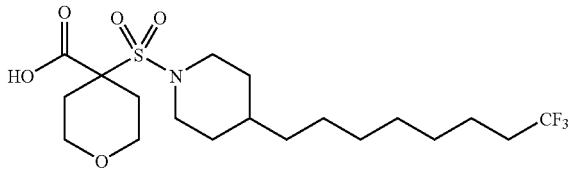

The ester of Part B (236.7 mg, 0.474 mmol) was hydrolyzed in 1:1 trifluoroacetic acid:methylene chloride (4 mL) at room temperature for 2 hr. The mixture was then concentrated under N₂ to afford the desired acid (207.8, 98.9% yield). This material was used in the next step without further purification. NMR (CDCl₃) δ 1.15–1.44 (m, 13H) 1.46–1.61 (m, 2H), 1.69 (d, 2H), 1.94–2.28 (m, 4H), 2.37 (d, 2H), 2.94 (t, 2H), 3.40 (t, 2H), 3.80 (d, 2H), 4.02 (dd, 2H). ESMS m/z=444.37 (M+H)⁺.

Part D. Preparation of 4-[4-(8,8,8-trifluoro-octyl)-piperidine-1-sulfonyl]-tetrahydro-pyran-4-carboxylic acid (tetrahydro-pyran-2-yloxy)-amide:

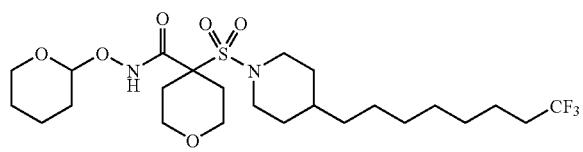

To a mixture of the crude acid from Part C (204.8 mg, 0.462 mmol), 1-hydrozybenzotriazole hydrate (93.5 mg, 0.69 mmol), THP—ONH₂ (75.7 mg, 0.65 mmol), and triethylamine (0.19 mL, 1.37 mmol) in dimethylformamide (2.0 mL) was added 1-(3-dimethylaminopropyl)-3-ethylcarbodiimide hydrochloride (123.5 mg, 0.65 mmol). The resulting mixture was stirred at 50° C. overnight. Subsequently, the mixture was concentrated; combined with ethyl acetate (5 mL); and washed with water (5 mL), 1N HCl (4 mL), and saturated sodium bicarbonate. Chromatography (on silica, ethyl acetate/hexanes) afforded the protected hydroxamate in the form of a colorless oil (224.5 mg, 82.3% yield). NMR (CDCl₃) δ 1.11–1.44 (m, 12H), 1.47–1.74 (m, 8H), 1.77–1.93 (m, 3H), 1.95–2.13 (m, 2H), 2.14–2.32 (m, 4H), 2.93 (t, 2H), 3.51 (dq, 2H), 3.59–3.69 (m, 1H), 3.74–3.87 (m, 2H), 3.90–4.04 (m, 3H), 4.99 (s, 1H), 9.02 (s, 1H). ESMS m/z=560.50 (M+NH₄)⁺.

Part E. Preparation of 4-[4-(8,8,8-trifluoro-octyl)-piperidine-1-sulfonyl]-tetrahydro-pyran-4-carboxylic acid hydroxyamide:

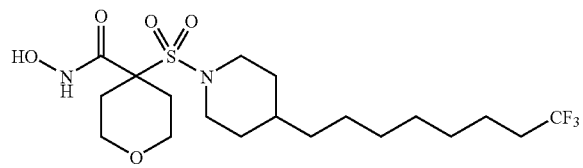

To the THP-protected hydroxamate from Part D (200.0 mg, 0.369 mmol) in methanol (2.0 mL) was added 4M HCl in 1,4-dioxane (200 μL). After stirring for 1 hr, the mixture was concentrated under N₂ to afford the desired compound as an off-white amorphous solid (163.7 mg, 96.9% yield). NMR (CD₃OD) δ 1.07–1.20 (m, 2H), 1.21–1.44 (m, 11H), 1.67 (d, 2H), 2.03–2.17 (m, 4H), 2.32 (d, 2H), 2.93 (t, 2H), 3.36 (t, 2H), 3.73 (d, 3H), 3.90 (dd, 2H). ESMS m/z=459.2 (M+H)⁺. HRMS calcd. for C₁₉H₃₄F₃N₂O₅S H: 459.2135 (M+H)⁺. Found: 459.2100.

Example A53

Preparation of 4-[4-(5,5,6,6,6-pentafluoro-hexyl)-piperidine-1-sulfonyl]-tetrahydro-pyran-4-carboxylic acid hydroxyamide

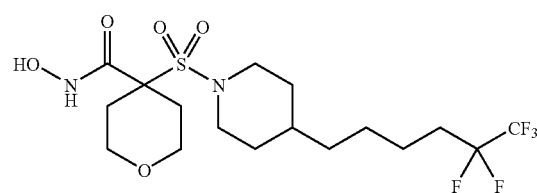

Part A. Preparation of 4-[4-(5,5,6,6,6-pentafluoro-hex-2-enyl)-piperidine-1-sulfonyl]-tetrahydro-pyran-4-carboxylic acid tert-butyl ester:

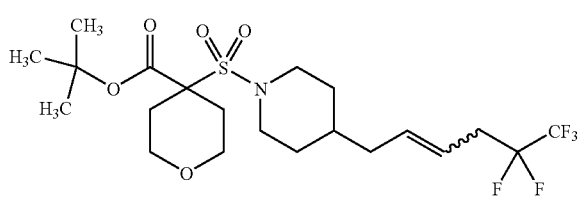

To the phosphine from Example A11 (943 mg, 1.76 mmol) in anhydrous tetrahydrofuran (7.0 mL) at 0° C. was added 1M LiN(TMS) (1.9 mL, 1.9 mmol) dropwise while maintaining the temperature at less than 5° C. Upon completion of addition, the mixture was stirred at 0° C. for 15 min. The aldehyde from Example A6 (550 mg, 1.47 mmol) in anhydrous tetrahydrofuran (2.8 mL) was then added dropwise while maintaining the temperature at less than 5° C. Afterward, the cooling bath was removed, and the mixture was stirred at room temperature overnight. Subsequently, the mixture was poured into stirring ether (75 mL) and filtered. The filtrate was washed with 1N HCl (3×75 mL), saturated sodium bicarbonate (3×75 mL), and brine (100 mL); dried over magnesium sulfate; and concentrated to crude oil. Chromatography (on silica, ethyl acetate/hexanes) afforded the alkene as an off-white crystalline solid (644.2, 86.4% yield). NMR (CDCl₃) δ 1.16–1.36 (m, 2H), 1.40–1.57 (m, 10H), 1.60–1.76 (m, 2H), 1.94–2.18 (m, 4H), 2.33 (d, 2H), 2.65–2.97 (m, 4H), 3.29 (t, 2H), 3.78 (d, 2H), 3.96 (dd, 2H), 5.43–5.54 (m, 1H), 5.65–5.78 (m, 1H). ESMS m/z=506.38 (M+H)⁺.

Part B. Preparation of 4-[4-(5,5,6,6,6-pentafluoro-hexyl)-piperidine-1-sulfonyl]-tetrahydro-pyran-4-carboxylic acid tert-butyl ester:

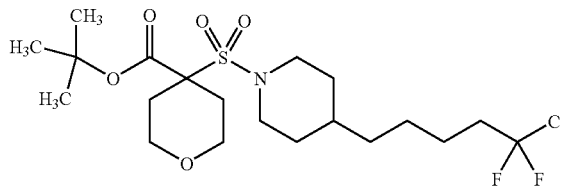

The alkene from Part A (638.3 mg, 1.263 mmol) was combined with tetrahydrofuran (5 mL). Afterward, 10% Pd/C (0.32 g) was added. The resulting mixture was stirred on a Parr hydrogenator at 40 psi for 1 hr. The mixture was then filtered through celite and concentrated, affording the ester (640.4 mg, 100% yield). NMR (CDCl$_3$) δ 1.15–1.44 (m, 7H), 1.47–1.61 (m, 11H), 1.67 (d, 2H), 1.89–2.18 (m, 4H), 2.33 (d, 2H), 2.93 (t, 2H), 3.31 (d, 2H), 3.77 (d, 2H), 3.97 (dd, 2H). ESMS m/z=508.36 (M+H)$^+$.

Part C. Preparation of 4-[4-(5,5,6,6,6-pentafluoro-hexyl)-piperidine-1-sulfonyl]-tetrahydro-pyran-4-carboxylic acid:

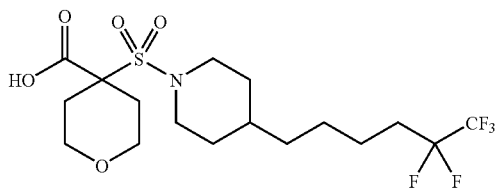

The ester of Part B (633.1 mg, 1.247 mmol) was hydrolyzed in 1:1 trifluoroacetic acid:methylene chloride (4 mL) at room temperature for 1 hr. The mixture was then concentrated under N$_2$ to afford the desired acid in the form of a solid (555.1, 98.6% yield). The resulting material was used in the next step without further purification. NMR (CD$_3$OD) δ 1.07–1.23 (m, 2H), 1.25–1.33 (m, 2H), 1.36–1.46 (m, 3H), 1.50–1.60 (m, 2H), 1.70 (d, 2H), 2.00–2.17 (m, 4H), 2.32 (d, 2H), 2.95 (dt, 2H), 3.34 (dt, 2H), 3.94 (dd, 2H). ESMS m/z=469.33 (M+NH$_4$)$^+$.

Part D. Preparation of 4-[4-(5,5,6,6,6-pentafluoro-hexyl)-piperidine-1-sulfonyl]-tetrahydro-pyran-4-carboxylic acid (tetrahydro-pyran-2-yloxy)-amide:

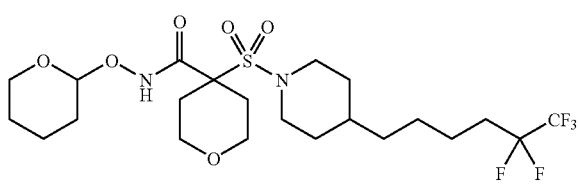

To a mixture of the crude acid from Part C (550.7 mg, 1.22 mmol), 1-hydrozybenzotriazole hydrate (247 mg, 1.83 mmol), THP—ONH$_2$ (200 mg, 1.71 mmol), and triethylamine (0.51 mL, 3.67 mmol) in dimethylformamide (4.0 mL) was added 1-(3-dimethylaminopropyl)-3-ethylcarbodiimide hydrochloride (326 mg, 1.71 mmol). The resulting mixture was stirred at 45° C. overnight. Subsequently, the mixture was concentrated, partitioned between ethyl acetate and water, and poured onto 20 mL Chem-Elut tubes. The crude product was eluted with methylene chloride and ethyl acetate. Chromatography (on silica, ethyl acetate/hexanes) afforded the protected hydroxamate in the form of a colorless oil (624.2 mg, 92.9% yield). NMR (CDCl$_3$) δ 1.13–1.43 (m, 7H), 1.50–1.73(m, 8H), 1.76–1.88 (m, 3H), 1.92–2.06 (m, 2H), 2.14–2.27 (m, 4H), 2.92 (t, 2H), 3.43–3.54 (m, 2H), 3.59–3.66 (m, 1H), 3.74–3.84 (m, 2H), 3.90–3.99 (m, 3H), 4.97 (s, 1H), 9.18 (s, 1H). ESMS m/z=568.43 (M+NH$_4$)$^+$.

Part E. Preparation of 4-[4-(5,5,6,6,6-pentafluoro-hexyl)-piperidine-1-sulfonyl]-tetrahydro-pyran-4-carboxylic acid hydroxyamide:

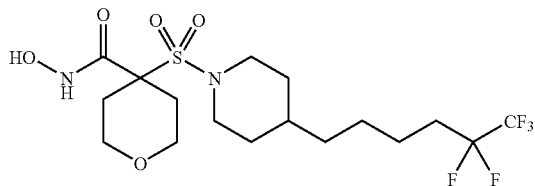

To the THP-protected hydroxamate from Part D (616.1 mg, 1.12 mmol) in methanol (4.0 mL) was added 4M HCl in 1,4-dioxane (200 μL). After stirring for 1.5 hr, the mixture was concentrated under N$_2$ to afford the desired compound in the form of a colorless crystalline solid (343.7 mg, 75.4% yield). NMR (DMSO) δ 0.94–1.09 (m, 2H), 1.16–1.24 (m, 2H), 1.25–1.38 (m, 3H), 1.60 (d, 2H), 1.83 (dt, 2H), 2.07–2.24 (m, 2H), 2.31 (d, 2H), 2.86 (t, 2H), 3.14 (t, 2H), 3.55 (d, 3H), 3.81 (dd, 2H), 9.15 (s, 1H), 10.95 (s, 1H). ESMS m/z=467.2 (M+H)$^+$. HRMS calcd. for C$_{17}$H$_{28}$F$_5$N$_2$O$_5$S H: 467.1634 (M+H)$^+$. Found: 467.1627.

Example A54

Preparation of 4-[4-(6,6,7,7,7-pentafluoro-heptyl)-piperidine-1-sulfonyl]-tetrahydro-pyran-4-carboxylic acid hydroxyamide

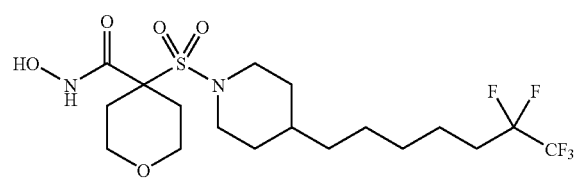

Part A. Preparation of 4-[4-(6,6,7,7,7-pentafluoro-hept-3-enyl)-piperidine-1-sulfonyl]-tetrahydro-pyran-4-carboxylic acid tert-butyl ester:

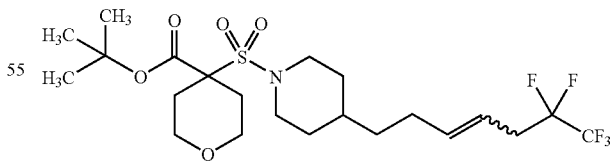

To the phosphine from Example A11 (842 mg, 1.57 mmol) in anhydrous tetrahydrofuran (6.3 mL) at 0° C. was added 1M LiN(TMS) (1.7 mL, 1.7 mmol) dropwise while maintaining the temperature at less than 5° C. Upon completion of addition, the mixture was stirred at 0° C. for 15 min. Afterward, the aldehyde from Example A8 (511.5 mg, 1.31 mmol) in anhydrous tetrahydrofuran (1.8 mL) was added dropwise while maintaining the temperature at less than 5°

C. The cooling bath was then removed, and the mixture was stirred at room temperature overnight. Subsequently, the mixture was poured into stirring ether (75 mL) and filtered. The filtrate was washed with 1N HCl (3×75 mL), saturated sodium bicarbonate (3×75 mL), and brine (100 mL); dried over magnesium sulfate; and concentrated to crude oil. Chromatography (on silica, ethyl acetate/hexanes) afforded the alkene in the form of a colorless oil (626.8, 92.4% yield). NMR (CDCl$_3$) δ 1.17–1.43 (m, 5H), 1.53 (s, 9H), 1.68 (d, 2H), 2.02–2.18 (m, 4H), 2.33 (d, 2H), 2.79 (dt, 2H), 2.93 (t, 2H), 3.31 (dt, 2H), 3.78 (d, 2H), 3.97 (dd, 2H), 5.33–5.47 (m, 1H), 5.64–5.77 (m, 1H). ESMS m/z=520.41 (M+H)$^+$.

Part B. Preparation of 4-[4-(6,6,7,7,7-pentafluoro-heptyl)-piperidine-1-sulfonyl]-tetrahydro-pyran-4-carboxylic acid tert-butyl ester:

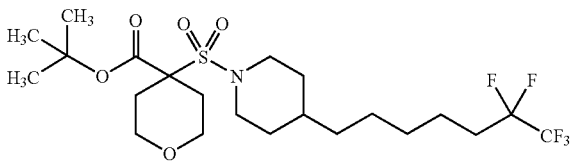

The alkene from Part A (613.5 mg, 1.181 mmol) was combined with tetrahydrofuran (5 mL). Afterward, 10% Pd/C (0.31 g) was added. The mixture was then stirred on a Parr hydrogenator at 40 psi for 1 hr. Subsequently, the mixture was filtered through celite and concentrated, affording the ester in the form of a crystalline solid (609.9 mg, 99.0% yield). NMR (CDCl$_3$) δ 1.16–1.44 (m, 8H), 1.49–1.76 (m, 14H), 1.90–2.20 (m, 4H), 2.34 (d, 2H), 2.94 (t, 2H), 3.33 (d, 2H), 3.79 (d, 2H), 3.98 (dd, 2H). ESMS m/z=522.39 (M+H)$^+$.

Part C. Preparation of 4-[4-(6,6,7,7,7-pentafluoro-heptyl)-piperidine-1-sulfonyl]-tetrahydro-pyran-4-carboxylic acid:

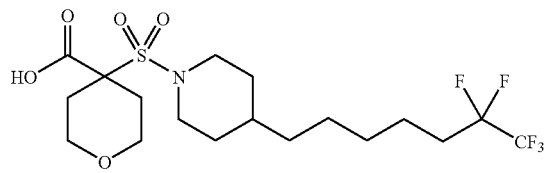

The ester of Part B (602.8 mg, 1.156 mmol) was hydrolyzed in 1:1 trifluoroacetic acid:methylene chloride (4 mL) at room temperature for 1 hr. The mixture was then concentrated under N$_2$ to afford the desired acid (537.2, 99.9% yield). This material was used in the next step without further purification. NMR (CD$_3$OD) δ 1.09–1.45 (m, 9H)1.51–1.62 (m, 2H), 1.70 (d, 2H), 2.00–2.16 (m, 4H), 2.32 (d, 2H), 2.94 (dt, 2H), 3.34 (dt, 2H), 3.76 (d, 2H), 3.93 (dd, 2H). ESMS m/z=483.34 (M+NH$_4$)$^+$.

Part D. Preparation of 4-[4-(6,6,7,7,7-pentafluoro-heptyl)-piperidine-1-sulfonyl]-tetrahydro-pyran-4-carboxylic acid (tetrahydro-pyran-2-yloxy)-amide:

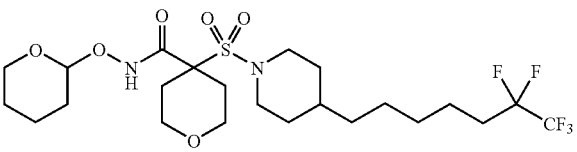

To a mixture of the crude acid from Part C (533.2 mg, 1.145 mmol), 1-hydrozybenzotriazole hydrate (232 mg, 1.72 mmol), THP—ONH$_2$(188 mg, 1.61 mmol), and triethylamine (0.48 mL, 3.45 mmol) in dimethylformamide (4.0 mL) was added 1-(3-dimethylaminopropyl)-3-ethylcarbodiimide hydrochloride (306 mg, 1.6 mmol). The resulting mixture was stirred at 45° C. overnight. Subsequently, the mixture was concentrated, partitioned between ethyl acetate and water, and poured onto 20 mL Chem-Elut tubes. The crude product was eluted with methylene chloride and ethyl acetate. Chromatography (on silica, ethyl acetate/hexanes) afforded the protected hydroxamate in the form of a colorless oil (599.3 mg, 92.7% yield). NMR (CDCl$_3$) δ 1.13–1.41 (m, 8H), 1.51–1.72 (m, 8H), 1.74–1.88 (m, 3H), 1.91–2.07 (m, 2H), 2.13–2.27 (m, 4H), 2.90 (t, 2H), 3.48 (dq, 2H), 3.59–3.66 (m, 1H), 3.73–3.84 (m, 2H), 3.89–3.99 (m, 3H), 4.97 (s, 1H), 9.18 (s, 1H). ESMS m/z=582.45 (M+NH$_4$)$^+$.

Part E. Preparation of 4-[4-(6,6,7,7,7-pentafluoro-heptyl)-piperidine-1-sulfonyl]-tetrahydro-pyran-4-carboxylic acid hydroxyamide:

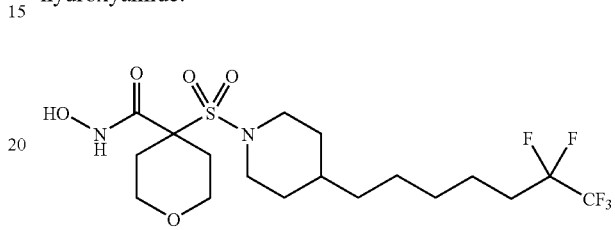

To the THP-protected hydroxamate from Part D (589.5 mg, 1.04 mmol) in methanol (4.0 mL) was added 4M HCl in 1,4-dioxane (200 μL). After stirring for 1 hr, the mixture was concentrated under N$_2$ to afford the desired compound in the form of a colorless crystalline solid (482.9 mg, 96.3% yield). NMR (DMSO) δ 0.95–1.07 (m, 2H), 1.11–1.20 (m, 2H), 1.22–1.46 (m, 5H), 1.43–1.52 (m, 2H), 1.61 (d, 2H), 1.84 (dt, 2H), 2.06–2.24 (m, 2H), 2.30 (d, 2H), 2.84 (t, 2H), 3.14 (t, 2H), 3.55 (d, 2H), 3.82 (dd, 2H), 9.15 (s, 1H), 10.95 (s, 1H). ESMS m/z=481.2 (M+H)$^+$. HRMS calcd. for C$_{18}$H$_{30}$F$_5$N$_2$O$_5$S H: 481.1790 (M+H)$^+$. Found: 481.1824.

Example A55

Preparation of N-hydroxy-1-({4-[5-(3,3,4,4,4-pentafluorobutyl)pyridin-2-yl]piperidin-1-yl}sulfonyl)cyclopentanecarboxamide hydrochloride

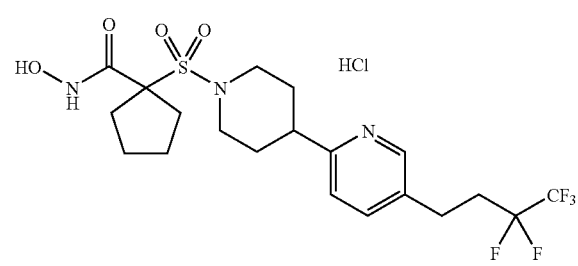

Part A. To a slurry of zinc dust (6.32 g, 96.6 mmol) in tetrahydrofuran (20 mL) was added 1,2-dibromoethane (0.58 mL, 6.7 mmol). The slurry was heated to reflux with a heat gun 3 times. After cooling to ambient temperature the third time, trimethylsilyl chloride (0.96 mL, 7.6 mmol) was added. After 20 min, 1-iodo-3,3,4,4,4-pentafluorobutane (19.62 g, 71.6 mmol) was added. The iodide was consumed after 1 hr of stirring at ambient temperature. The resulting organozinc mixture was added via syringe to a mixture of the t-butyl methylene compound of Example A27, Part B (20.0 g, 47.7 mmol) in N,N-dimethylacetamide (40 mL). Dichlorobis(benzonitrile)palladium(II) (695 mg, 1.8 mmol)

and 2-(dicyclohexylphosphino)biphenyl (919 mg, 2.62 mmol) were then added, and the resulting mixture was heated to 50° C. for 18 hr. Subsequently, the mixture was filtered through Celite, rinsing with ethyl acetate. The organic mixture was then washed with water and saturated NaCl, and dried over sodium sulfate. Trituration with hexane afforded the desired pentafluorobutyl methylene intermediate in the form of a yellow solid (20.5 g, 88% yield). MS MH$^+$ for $C_{20}H_{27}N_2O_4SF_5$: calc. 487, found 487.

Part B. To a mixture of the methylene compound of Part A (1.0 g, 2.06 mmol) in N,N-dimethylformamide (5 mL) was added potassium carbonate (1.70 g, 12.3 mmol) and 18-crown-6 (163 mg, 0.62 mmol). 1,4-Dibromobutane (0.29 mL, 2.47 mmol) was then added, and the resulting mixture was heated to 80° C. for 18 hr. Subsequently, the mixture was partitioned between ethyl acetate and water. The organic layer was washed with water and saturated NaCl, and dried over sodium sulfate. Chromatography (on silica, ethyl acetate/hexane) afforded the desired cyclopentyl intermediate as an oil (415 mg, 37% yield). MS MH$^+$ for $C_{24}H_{33}N_2O_4SF_5$: calc. 541, found 541.

Part C. The cyclopentyl compound of Part B (400 mg, 0.74 mmol) was dissolved into neat trifluoroacetic acid (5 mL). After one hr the mixture was concentrated in vacuo to provide the crude carboxylic acid. The acid was dissolved into N,N-dimethylformamide (3 mL) and 1-hydroxybenzotriazole (120 mg, 0.89 mmol), 4-methylmorpholine (0.41 mL, 3.7 mmol), O-(tetrahyrdro-2H-pyran-2-yl)hydroxylamine (130 mg, 1.11 mmol) and 1-(3-dimethylaminopropyl)-3-ethylcarbodiimide hydrochloride (198 mg, 1.04 mmol) were added. The mixture was stirred at ambient temperature for 18 hr. The mixture was partitioned between ethyl acetate and water. The organic layer was washed with water and saturated NaCl and dried over sodium sulfate. Chromatography (on silica, ethyl acetate, hexane) afforded the desired THP hydroxamate intermediate as an oil (292 mg, 68% yield). MS MH$^+$ for $C_{25}H_{34}N_3O_5SF_5$: calc. 584, found 584.

Part D. The protected hydroxamate of Part C (282 mg, 0.48 mmol) was dissolved into 1,4-dioxane (1 mL) and methanol (1 mL). Afterward, 4M HCl in dioxane (3 mL) was added. After 1 hr, the mixture was concentrated in vacuo. Addition of ethyl ether followed by vacuum filtration afforded the title compound in the form of a white solid (205 mg, 80% yield). HRMS calc. 500.1642, found 500.1663.

Example A56

Preparation of N-hydroxy-1-({4-[5-(3,3,4,4,4-pentafluorobutyl)pyridin-2-yl]piperidin-1-yl}sulfonyl)cyclohexanecarboxamide hydrochloride

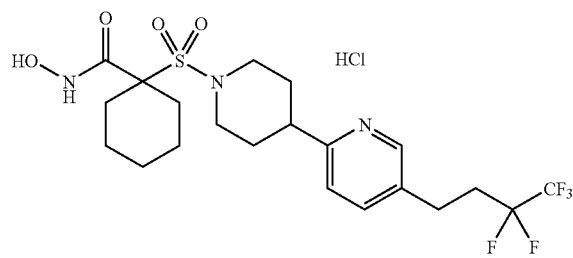

Part A. To a mixture of the methylene compound of Example A55, Part A (1.0 g, 2.06 mmol) in N,N-dimethylformamide (5 mL) was added a 60% NaH suspension in mineral oil (206 mg, 5.15 mmol). Subsequently, 1,5-Dibromopentane (0.34 mL, 2.47 mmol) was added, and the resulting mixture was heated to 80° C. for 18 hr. The mixture was then partitioned between ethyl acetate and water. The organic layer was washed with water and saturated NaCl, and dried over sodium sulfate. Chromatography (on silica, ethyl acetate/hexane) afforded a cyclohexyl intermediate in the form of an oil (183 mg, 16% yield). MS MH+for $C_{25}H_{35}N_2O_4SF_5$: calc. 555, found 555.

Part B. The cyclohexyl compound of Part A (180 mg, 0.32 mmol) was dissolved into neat trifluoroacetic acid (3 mL). After 1 hr, the mixture was concentrated in vacuo to provide the crude carboxylic acid. The acid was dissolved into N,N-dimethylformamide (3 mL). Afterward, 1-hydroxybenzotriazole (53 mg, 0.39 mmol), 4-methylmorpholine (0.18 mL, 1.6 mmol), O-(tetrahydro-2H-pyran-2-yl)hydroxylamine (56 mg, 0.48 mmol), and 1-(3-dimethylaminopropyl)-3-ethylcarbodiimide hydrochloride (86 mg, 0.45 mmol) were added. The resulting mixture was stirred at ambient temperature for 18 hr. The mixture was then partitioned between ethyl acetate and water. The organic layer was washed with water and saturated NaCl, and dried over sodium sulfate. Chromatography (on silica, ethyl acetate, hexane) afforded the desired protected hydroxamate intermediate as an oil (100 mg, 52% yield). MS MH$^+$ for $C_{26}H_{36}N_3O_5SF_5$: calc. 598, found 598.

Part C. The protected hydroxamate of Part B (97 mg, 0.16 mmol) was dissolved into 1,4-dioxane (2 mL) and methanol (1 mL). Afterward, 4M HCl in dioxane (2 mL) was added. After 1 hr, the mixture was concentrated in vacuo. Chromatography (on silica, acetonitrile/water) afforded the title compound in the form of a white solid (50 mg, 57% yield). HRMS calc. 514.1799, found 514.1801.

Example A57

Preparation of N-hydroxy-4-({4-[5-(2,2,2-trifluoroethoxy)pyridin-2-yl]piperidin-1-yl}sulfonyl)tetrahydro-2H-pyran-4-carboxamide hydrochloride

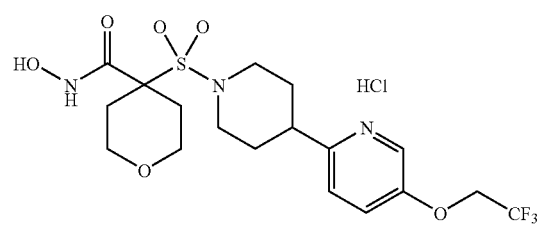

Part A. To a mixture of tert-butyl 4-{[4-(5-hydroxypyridin-2-yl)piperidin-1-yl]sulfonyl}tetrahydro-2H-pyran-4-carboxylate (1.0 g, 2.34 mmol, 1 eq.) was added $Cs_2CO_3$ (1.5 g, 4.68 mmol, 2 eq.), followed by 2,2,2-trifluoroethyl trifluoromethanesulfonate (600 mg, 2.6 mmol, 1.1 eq.). The resulting slurry was stirred at room temperature for 4 hr. The mixture was then diluted with 75 mL of ethyl acetate and washed 3×75 mL of water and 1×74 mL of brine. The organic layer was dried over $Na_2SO_4$, and the solvent was removed in vacuo. The resulting oil was purified via $SiO_2$ chromatography (gradient: 10% ethyl acetate/hexanes to 100% ethyl acetate). This afforded 1.1 g of the desired t-butyl ester intermediate (92% yield). MS MH+

C22H31F3N2O6S calc.: 509, found: 509. 1H and 19F NMR were consistent with the desired intermediate.

Part B. The t-butyl ester from Part A (1.1 g 2.16 mmol, 1 eq.) was combined with neat trifluoroacetic acid (3 mL). The resulting mixture was stirred at room temperature for 4 hr. Excess trifluoroacetic acid was then removed in vacuo. This afforded the desired carboxylic acid intermediate in the form of a paste. The paste was used in the next step without further purification. MS MH+ C18H24F3N2O6S calc: 453 found 453.

Part C. The carboxylic acid from Part B was combined with 11 mL of N-N' dimethyl formamide. Afterward, N-methyl morpholine (1.1 g, 10.8 mmol, 5 eq.) and 1-hydroxybenzotriazole (351 mg, 2.6 mmol, 1.2 eq.) were added. The resulting mixture was stirred at room temperature for 5 min. Subsequently, 1-(3-dimethylaminopropyl)-3-ethylcarbodiimide hydrochloride (580 mg, 3.02 mmol, 1.4 eq.) was added, followed by O-(tetrahydro-2H-pyran-2-yl)hydroxylamine (380 mg, 3.24 mmol, 1.5 eq.). The resulting mixture was stirred at room temperature for 18 hr. Afterward, the mixture was diluted with 75 mL of ethyl acetate; washed with 3×75 mL of water and 1×75 mL of brine; and dried over Na2SO4. After removing the solvent in vacuo, the resulting oil was purified via SiO2 chromatography (gradient 10% ethyl acetate/hexanes to 100% ethyl acetate) to afford 940 mg of the desired THP-protected intermediate (79% yield). MS MH+ C23H33F3N3O7S calc.: 552 found: 552. 1H and 19F NMR were consistent with the desired intermediate.

Part D. The THP-protected compound from Part C was suspended in 5 mL 4.0 N HCl/dioxane, and stirred at room temperature for 4 hr. The mixture was then diluted with methanol, and the solvent was removed in vacuo to afford 700 mg of the title compound as the HCl salt (88% yield). Elemental analysis C18H25ClF3N3O6S calc: C: 42.90, H: 5.00, N: 8.34, Cl: 7.04, S: 6.36. found: C: 43.04, H: 5.33, N: 8.33, Cl: 7.15, S: 6.27. 1H and 19F NMR were consistent with the desired product.

Example A58

Preparation of N-hydroxy-4-({4-[5-(2,2,3,3,3-pentafluoropropoxy)pyridin-2-yl]piperidin-1-yl}sulfonyl)tetrahydro-2H-pyran-4-carboxamide hydrochloride

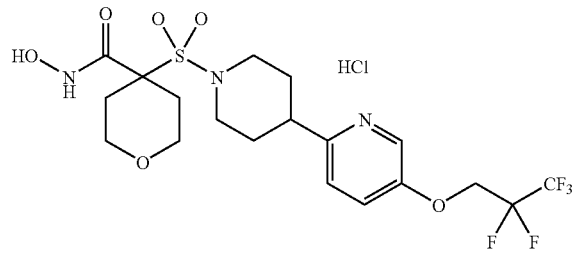

Part A. To a mixture of tert-butyl 4-{[4-(5-hydroxypyridin-2-yl)piperidin-1-yl]sulfonyl}tetrahydro-2H-pyran-4-carboxylate (500 mg, 1.17 mmol, 1 eq.) was added Cs2CO3 (762 mg, 2.34 mmol, 2 eq.), followed by 3,3,3,2,2,-pentafluoropropyl trifluoromethanesulfonate (428 mg, 1.52 mmol, 1.1 eq.). The resulting slurry was stirred at room temperature for 4 hr. The mixture was then diluted with 50 mL of ethyl acetate and washed with 3×50 mL of water and 1×50 mL of brine. The organic layer was dried over Na2SO4, and the solvent was removed in vacuo. The resulting oil was purified via SiO2 chromatography (gradient: 10% ethyl acetate/hexanes to 100% ethyl acetate) to 422 mg of the desired t-butyl ester product (64% yield). MS MH+ C23H32F5N2O6S calc: 559 found 559. 1H and 19F NMR were consistent with the desired intermediate.

Part B. The t-butyl ester from Part A (390 mg 0.70 mmol, 1 eq.) was combined with neat trifluoroacetic acid (3 mL). The resulting mixture was stirred at room temperature for 4 hr, after which excess trifluoroacetic acid was removed in vacuo to afford the desired carboxylic acid intermediate in the form of a paste. The paste was used in the next step without further purification. MS MH+ C19H24F5N2O6S calc 503 found 503.

Part C. The carboxylic acid from Part B was combined with 5 mL of N-N' dimethyl formamide. Afterward, N-methyl morpholine (354 mg, 3.5 mmol, 5 eq.), and 1-hydroxybenzotriazole (113 mg, 0.84 mmol, 1.2 eq.) were added, and the resulting mixture was stirred at room temperature for 5 min. Subsequently, 1-(3-dimethylaminopropyl)-3-ethylcarbodiimide hydrochloride (187 mg, 0.98 mmol, 1.4 eq.) was added, followed by O-(tetrahyrdro-2H-pyran-2-yl)hydroxylamine (123 mg, 1.05 mmol, 1.5 eq.). The resulting mixture was stirred at room temperature for 18 hr. The mixture was then diluted with 75 mL of ethyl acetate, washed with 3×75 mL of water and 1×75 mL of brine, and dried over Na2SO4. After removing the solvent in vacuo, the resulting oil was purified via SiO2 chromatography (gradient 10% ethyl acetate/hexanes to 100% ethyl acetate) to afford 940 mg of the desired THP-protected intermediate (79% yield). MS MH+ C24H33F5N3O7S calc: 602 found: 602. 1H and 19F NMR were consistent with the desired intermediate.

Part D. The THP-protected compound from Part C was suspended in 5 mL 4.0 N HCl dioxane. This mixture was then stirred at room temperature for 4 hr. Subsequently, the mixture was diluted with methanol, and the solvent was removed in vacuo to afford 290 mg (70% yield) of the title compound as an HCl salt. Elemental analysis C19H25ClF5N3O6S calc: C: 41.20, H: 4.55, N: 7.59, Cl: 6.40, S: 5.79. found: C: 41.12, H: 4.73, N: 7.50, Cl: 6.90, S: 6.31. 1H and 19F NMR were consistent with the desired product.

Example A59

Preparation of N-hydroxy-4-({4-[5-(2,2,3,3-tetrafluoropropoxy)pyridin-2-yl]piperidin-1-yl}sulfonyl)tetrahydro-2H-pyran-4-carboxamide hydrochloride

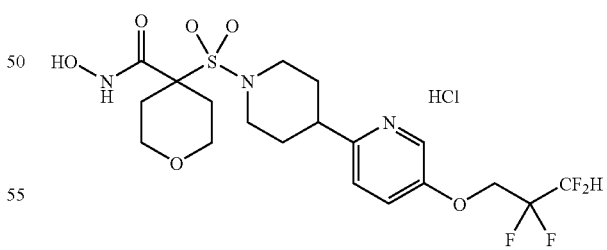

Part A. To a mixture of tert-butyl 4-{[4-(5-hydroxypyridin-2-yl)piperidin-1-yl]sulfonyl}tetrahydro-2H-pyran-4-carboxylate (750 mg, 1.75 mmol, 1 eq.) was added Cs2CO3 (1.14 g, 3.5 mmol, 2 eq.), followed by 3,3,2,2,-tetrafluoropropyl trifluoromethanesulfonate (600 mg, 2.27 mmol, 1.3 eq.). The resulting slurry was stirred at room temperature for 16 hr. The mixture was then diluted with 50 mL of ethyl acetate and washed 3× with 50 mL of water and 1×50 mL of brine. The organic layer was dried over Na2SO4, and the solvent was removed in vacuo affording an oil. The oil was purified via SiO₂ chromatography (gradient: 10% ethyl acetate/hexanes to 100% ethyl acetate) to afford 857 mg of the desired t-butyl ester intermediate (90% yield). MS MH+ C23H33F4N2O6S calc: 541 found 541. 1H and 19F NMR were consistent with the desired intermediate.

Part B. The t-butyl ester from Part A (857 mg 1.58 mmol, 1 eq.) was combined with neat trifluoroacetic acid (5 mL). The resulting mixture was stirred at room temperature for 4 hr, after which the excess trifluoroacetic acid was removed in vacuo to afford the desired carboxylic acid intermediate in the form of a paste. The paste was used in the next step without further purification. MS MH+ C19H25F4N2O6S calc 485 found 485.

Part C. The carboxylic acid from Part B was combined with 10 mL of N-N' dimethyl formamide. Subsequently, N-methyl morpholine (800 mg, 7.9 mmol, 5 eq.) and 1-hydroxybenzotriazole (255 mg, 1.89 mmol, 1.2 eq.) were added. The resulting mixture was stirred at room temperature for 5 min. Then, 1-(3-dimethylaminopropyl)-3-ethylcarbodiimide hydrochloride (423 mg, 2.21 mmol, 1.4 eq.) was added, followed by O-(tetrahyrdro-2H-pyran-2-yl)hydroxylamine (277 mg, 2.37 mmol, 1.5 eq.). The resulting mixture was stirred at room temperature for 18 hr. Afterward, the mixture was diluted with 75 mL of ethyl acetate, washed with 3×75 mL of water and 1×75 mL of brine, and dried over Na₂SO₄. The solvent was removed in vacuo to afford an oil. The oil was purified via SiO₂ chromatography (gradient 10% ethyl acetate/hexanes to 100% ethyl acetate) to afford 700 mg of the desired THP-protected intermediate (76% yield). MS MH+ C24H34F4N3O7S calc: 584 found: 584. 1H and 19F NMR were consistent with the desired intermediate.

Part D. The THP-protected compound from Part C was suspended in 5 mL 4.0 N HCl/dioxane. The resulting mixture was then stirred at room temperature for 4 hr. Afterward, the mixture was diluted with methanol, and the solvent was removed in vacuo to afford 442 mg (75% yield) of the title compound as an HCl salt. Elemental analysis C19H26ClF4N3O6S calc: C: 41.20, H: 4.55, N: 7.59, Cl: 6.40, S: 5.79. found: C: 41.12, H: 4.73, N: 7.50, Cl: 6.90, S: 6.31. 1H and 19F NMR were consistent with the desired product.

Example A60

Preparation of 2-ethyl-N-hydroxy-2-({4-[5-(3,3,4,4,4-pentafluorobutyl)pyridin-2-yl]piperidin-1-yl}sulfonyl)butanamide hydrochloride

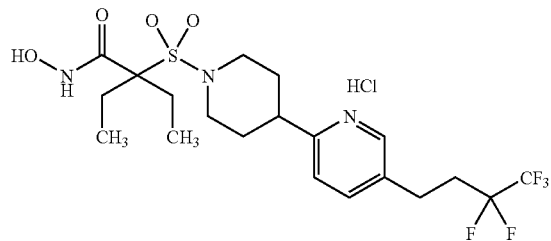

Part A. To tert-butyl ({4-[5-(3,3,4,4,4-pentafluorobutyl)pyridin-2-yl]piperidin-1-yl}sulfonyl)acetate (1.0 g, 2.05 mmol, 1 eq.) and a 60% (w/w) NaH dispersion in mineral oil (205 mg 5.15 mmol 2.5 eq.) under argon was added 10 mL of dry N-N' dimethylformamide with some effervescence. This slurry was stirred at room temperature for 30 min. Afterward, ethyl iodide (935 mg, 6.0 mmol, 3 eq.) was added in one portion, and the mixture was stirred at room temperature under argon for 18 hr. Water (5 ml) was then added dropwise. The resulting mixture was diluted with 50 mL of ethyl acetate, and washed 3× with 50 mL of water and 1×50 mL of brine. The organic layer was dried over Na₂SO₄, and the solvent was removed in vacuo to afford an oil. The oil was purified via SiO₂ chromatography (gradient: 10% ethyl acetate/hexanes to 100% ethyl acetate) to afford 720 mg of the desired t-butyl ester intermediate (65% yield). MS MH+ C24H36F5N2O4S calc: 543 found 543. 1H and 19F NMR were consistent with the desired intermediate.

Part B. The t-butyl ester from Part A (670 mg 1.23 mmol, 1 eq.) was combined with neat trifluoroacetic acid (5 mL). The resulting mixture was stirred at room temperature for 4 hr. Excess trifluoroacetic acid was then removed in vacuo to afford the desired carboxylic acid intermediate in the form of a paste. This paste was used in the next step without further purification. MS MH+ C20H29F5N2O4S calc 487 found 487.

Part C. The carboxylic acid from Part B was combined with 10 mL for N-N' dimethyl formamide. Afterward, n-methyl morpholine (622 mg, 6.15 mmol, 5 eq.) and 1-hydroxybenzotriazole (200 mg, 1.47 mmol, 1.2 eq.) were added. The resulting mixture was then stirred at room temperature for 5 min. Subsequently, 1-(3-dimethylaminopropyl)-3-ethylcarbodiimide hydrochloride (330 mg, 1.72 mmol, 1.4 eq.) was added, followed by O-(tetrahyrdro-2H-pyran-2-yl)hydroxylamine (215 mg, 1.84 mmol, 1.5 eq.). The resulting mixture was stirred at room temperature for 18 hr. The mixture was then diluted with 75 mL of ethyl acetate, washed 3×75 mL of water and 1×75 mL brine, and dried over Na₂SO₄. The solvent was removed in vacuo to afford an oil. This oil was purified via SiO₂ chromatography (gradient 10% ethyl acetate/hexanes to 100% ethyl acetate) to afford 420 mg of the desired THP-protected intermediate (58% yield). MS MH+ C25H37F5N3O5S calc: 586 found: 586. 1H and 19F NMR were consistent with the desired intermediate.

Part D. The THP-protected compound from Part C was suspended in 5 mL 4.0 N HCl dioxane. This mixture was then stirred at room temperature for 4 hr. Subsequently, the mixture was diluted with methanol, and the solvent was removed in vacuo to afford 300 mg of the title compound as an HCl salt (87% yield). MS MH+ C20H28F5N3O4S calc: 502 found: 502. 1H and 19F NMR were consistent with the desired product.

Example A61

Preparation of N-hydroxy-4-methoxy-2-(2-methoxyethyl)-2-({4-[5-(3,3,4,4,4-pentafluorobutyl)pyridin-2-yl]piperidin-1-yl}sulfonyl)butanamide hydrochloride

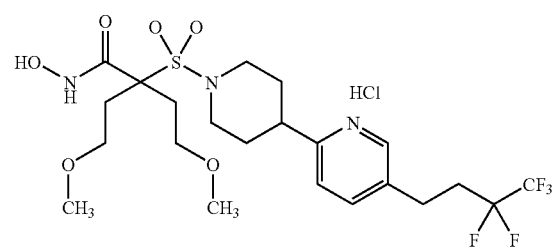

Part A. To tert-butyl ({4-[5-(3,3,4,4,4-pentafluorobutyl)pyridin-2-yl]piperidin-1-yl}sulfonyl)acetate (1.5 g, 3.08 mmol, 1 eq.) and a 60% (w/w) NaH dispersion in mineral oil (308 mg, 7.71 mmol, 2.5 eq.) was added 10 mL of dry N-N' dimethylformamide with some effervescence. This slurry was stirred at room temperature for 30 min. Afterward, bromoethylmethyl ether (1.07 g 7.71 mmol, 2.5 eq.) was added in one portion. The mixture was then heated at 75° C. under argon for 75 hr. At 24 and 48 hr, 2 more equivalents of NaH and bromoethylmethyl ether were added, respectively. Water (5 mL) was then added dropwise. The resulting mixture was diluted with 75 mL of ethyl acetate, amd washed 3× with 75 mL of water and 1×50 mL of brine. The organic layer was dried over Na₂SO₄, and the solvent was removed in vacuo to afford an oil. The oil was purified via SiO₂ chromatography (gradient: 10% ethyl acetate/hexanes to 100% ethyl acetate) to afford 625 mg of the desired t-butyl ester intermediate (33% yield). MS MH+ C26H40F5N2O6S calc: 603 found 603. 1H and 19F NMR were consistent with the desired intermediate.

Part B. The t-butyl ester from Part A (600 mg 1.0 mmol, 1 eq.) was combined with neat trifluoroacetic acid (4 mL). The resulting mixture was stirred at room temperature for 4 hr. Excess trifluoroacetic acid was then removed in vacuo to afford the desired carboxylic acid in the form of a paste. The paste was used in the next step without further purification. MS MH+ C22H32F5N2O6S calc 547 found 547.

Part C. The carboxylic acid from Part B was combined with 5 mL for N-N' dimethyl formamide. Afterward, N-methyl morpholine (505 mg, 5 mmol, 5 eq.) and 1-hydroxybenzotriazole (162 mg, 1.2 mmol, 1.2 eq.) were added. The resulting mixture was stirred at room temperature for 5 min. Subsequently, 1-(3-dimethylaminopropyl)-3-ethylcarbodiimide hydrochloride (268 mg, 1.4 mmol, 1.4 eq.) was added, followed by O-(tetrahyrdro-2H-pyran-2-yl)hydroxylamine (175 mg, 1.5 mmol, 1.5 eq.). The resulting mixture was stirred at room temperature for 18 hr. The mixture was then diluted with 50 mL of ethyl acetate, washed 3×50 mL of water and 1×50 mL of brine, and dried over Na₂SO₄. The solvent was removed in vacuo to afford an oil. The oil was purified via SiO₂ chromatography (gradient 10% ethyl acetate/hexanes to 100% ethyl acetate) to yield 200 mg of the desired THP-protected intermediate (31% yield). MS MH+ C27H40F5N3O7S calc: 646 found: 646. 1H and 19F NMR were consistent with the desired intermediate.

Part D. The THP-protected compound from Part C was suspended in 5 mL 4.0 N HCl dioxane. The resulting mixture was stirred at room temperature for 4 hr. Afterward, the mixture was diluted with methanol, and the solvent was removed in vacuo. The product was then purified by reverse phase prep HPLC to afford 60 mg of the title compound as an HCl salt (32% yield). MS MH+ C22H33F5N3O6S calc: 562 found: 562. 1H and 19F NMR were consistent with the desired product.

Example A62

Preparation of 1-cyclopropyl-4-({4-[3-fluoro-4-(4,4, 4-trifluorobutyl)phenyl]piperazin-1-yl}sulfonyl)-N-hydroxypiperidine-4-carboxamide hydrochloride

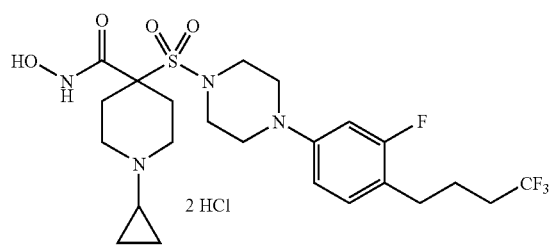

Part A. Preparation of triphenyl-(4,4,4-trifluoro-butyl)-phosphonium, iodide:

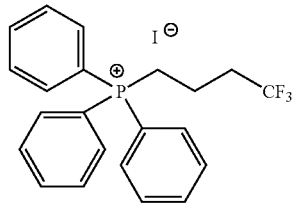

A mixture of triphenylphosphine (1.62 g, 6.18 mmol) and 1,1,1-trifluoro-4-iodo-propane (1.53 g, 6.83 mmol) in DMF (3 mL) was placed into a microwave at 150° C. under 75 watts for 30 min. The mixture was then concentrated in vacuo to afford an oil. The oil was triturated with ether several times to afford 2.86 g (95% yield) of the desired compound in the form of a white solid. MS: m/z=359 (M+).

Part B. Preparation of 4-chloro-2-fluoro-1-(4,4,4-trifluoro-but-1-enyl)-benzene:

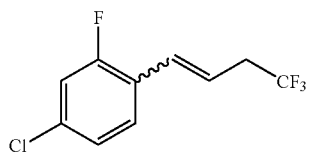

A mixture of the product from Part A (5.81 g, 11.9 mmol), K₂CO₃ (1.80 g, 13.0 mmol), and 4-chloro-2-fluorobenzaldehyde (1.83 g, 11.6 mmol) in IPA (37 mL) were combined and heated for 3.5 hr at 80° C. The resulting mixture was then cooled to ambient temperature, diluted with water (300 mL), and extracted with hexane (3×100 mL). The organic layer was washed with water (2×100 mL), dried over MgSO₄, and concentrated in vacuo to afford 2.26 g (82% yield) of the desired compound in the form of a clear, colorless liquid. Proton NMR in CDCl₃ was consistent with the desired product in the form of a mixture of cis and trans isomers.

Part C. Preparation of 4-chloro-2-fluoro-1-(4,4,4-trifluoro-butyl)-benzene:

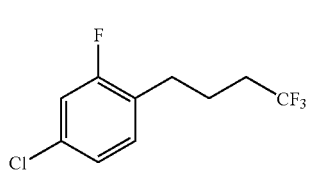

The product from Part B (2.20 g, 9.22 mmol) in ethanol was hydrogenated at 5 psi for 2 hr over a catalytic amount of 5% Pt/C. The mixture was then diluted with water (300 mL) and extracted with ethyl acetate (3×100 mL). The organic layer was washed with water (3×100 mL) and brine (100 mL), dried over MgSO₄, and concentrated in vacuo to afford 1.88 g (85% yield) of the desired compound in the form of a clear, colorless liquid. Proton NMR in CDCl₃ was consistent with the desired product.

Part D. Preparation of 4-methanesulfonyl-piperazine-1-carboxylic acid tert-butyl ester:

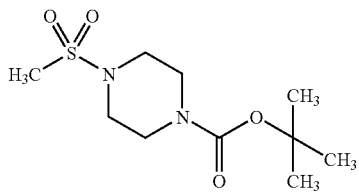

To a 14° C. CH$_2$Cl$_2$ mixture (500 mL) of t-butyl 1-piperazinecarboxylate (50.0 g, 246 mmol) and triethylamine (68.6 mL, 492 mmol) was added (dropwise) a CH$_2$Cl$_2$ solution (150 mL) of methanesulfonyl chloride (17.1 mL, 222 mmol). The resulting mixture was stirred at ambient temperature for 2 hr. The mixture was then washed with 1.0 N HCl$_{aq}$(200 mL), saturated NaCO$_{3aq}$ (200 mL), water (2×200 mL) and brine (200 mL); dried over MgSO$_4$; and concentrated in vacuo to afford 57.7 g (98% yield) of the desired compound in the form of a white solid.

Part E. Preparation of 4-tert-butoxycarbonylmethanesulfonyl-piperazine-1-carboxylic acid tert-butyl ester:

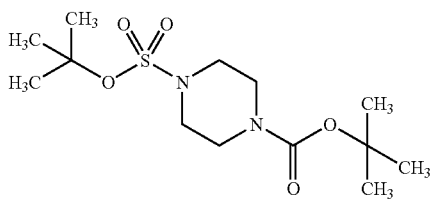

To a −79° C. tetrahydrofuran solution (100 mL) of Part D (8.88 g, 33.6 mmol) was added dropwise 1.0 N lithium bis(trimethylsilyl)amide in tetrahydrofuran (100 mL, 100 mmol). After the addition, the mixture was warmed up to 0° C., and then cooled again to −79° C. A tetrahydrofuran solution (10 mL) of t-butylcarboxylate anhydride (9.10 g, 41.7 mmol) was then added dropwise to the mixture. The mixture was then allowed to warm up to 0° C. Subsequently, the reaction was quenched with saturated NH$_4$Cl(aq) (1100 mL), and extracted with ethyl acetate (3×250 mL). The organic layer was washed with water (2×250 mL) and brine (250 mL), dried over MgSO$_4$, and concentrated in vacuo to afford a solid. The solid was recrystallized from an ethyl acetate/hexane solution to afford 9.99 g (82% yield) of the desired compound in the form of a white, crystalline solid. MS: m/z=364 (M+).

Part F. Preparation of 4-(1-benzyl-4-tert-butoxycarbonyl-piperidine-4-sulfonyl)-piperazine-1-carboxylic acid tert-butyl ester:

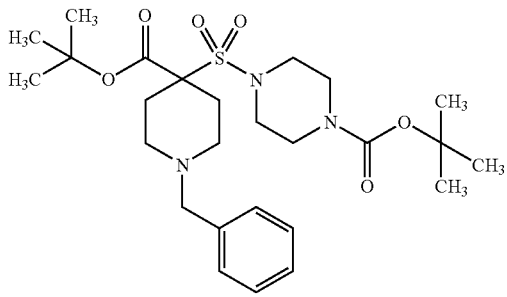

A mixture of the product from Part E (9.90 g, 27.2 mmol), bis(2-chloroethyl)benzylamine (7.57 g, 32.6 mmol), 18-crown-6 ether (2.39 g, 9.07 mmol), and K$_2$CO$_3$ (11.2 g, 81.5 mmol) in DMF (50 mL) was heated at 57° C. for 18 hr. Subsequently, the mixture was cooled to ambient temperature, diluted with water (350 mL), and extracted with ethyl acetate (3×100 mL). The organic layer was washed with water (2×100 mL) and brine (100 mL), dried over MgSO$_4$, and concentrated in vacuo to afford a solid. The solid was triturated with hot methanol (1 mL per g of solid), collected by filtration, and washed with ethyl ether to afford 7.61 g (54% yield) of the desired compound in the form of a white solid. MS: m/z=524 (M+H).

Part G. Preparation of 4-(4-tert-butoxycarbonyl-piperidine-4-sulfonyl)-piperazine-1-carboxylic acid tert-butyl ester:

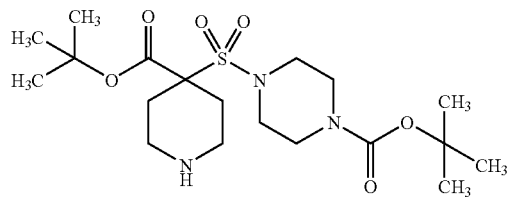

The product from Part F (7.42 g, 14.2 mmol) in ethanol-tetrahydrofuran was hydrogenated at 60 psi for 5 hr over a catalytic amount of 20% Pd(OH)$_2$/C at ambient temperature. Afterward, the mixture was filtered, concentrated in vacuo, triturated with ethyl ether, and concentrated in vacuo to afford 6.00 g (97% yield) of the desired compound in the form of a solid. MS: m/z=434 (M+H).

Part H. Preparation of 4-(4-tert-butoxycarbonyl-1-cyclopropyl-piperidine-4-sulfonyl)-piperazine-1-carboxylic acid tert-butyl ester:

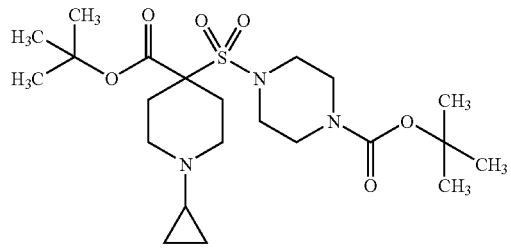

To a methanol solution (58 mL) of the product of Part G (3.00 g, 6.92 mL) and concentrated acetic acid (4.03 g, 69.2 mmol) was added [(1-ethoxycyclopropyl)oxy]trimethylsilane (1.81 mL, 9.02 mmol). After 10 min, sodium cyanoborohydride (1.96 g, 31.2 mmol) also was added. After refluxing for 2.5 hr, the mixture was concentrated in vacuo, diluted with ethyl acetate (150 mL), washed with 1.0 N NaOH(aq) (2×25 mL), water (2×50 mL), and brine (50 mL); dried over MgSO$_4$; and concentrated in vacuo to afford 3.08 g (94% yield) of the desired compound in the form of a white solid. MS: m/z=474 (M+H).

Part I. Preparation of 4-(4-tert-butoxycarbonyl-1-cyclopropyl-piperidine-4-sulfonyl)-piperazine-1-carboxylic acid tert-butyl ester, 2HCl:

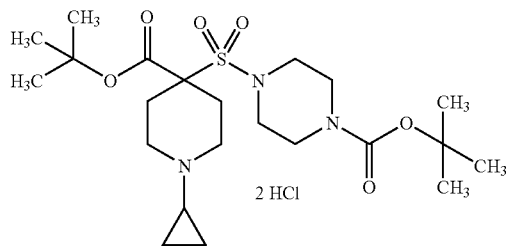

To a methanol solution (2 mL) of the product of Part H (0.500 g, 1.06 mmol) was added a methanol solution (3 mL) of acetyl chloride (0.239 g, 3.17 mmol). The resulting mixture was stirred at ambient temperature for 3 days. Subsequently, the mixture was diluted with ethyl ether, and the solid was collected to afford 0.409 g (86% yield) of the desired compound in the form of a white solid. MS: m/z=374 (M+H).

Part J. Preparation of 1-cyclopropyl-4-{4-[3-fluoro-4-(4,4,4-trifluoro-butyl)-phenyl]-piperazine-1-sulfonyl}-piperidine-4-carboxylic acid tert-butyl ester:

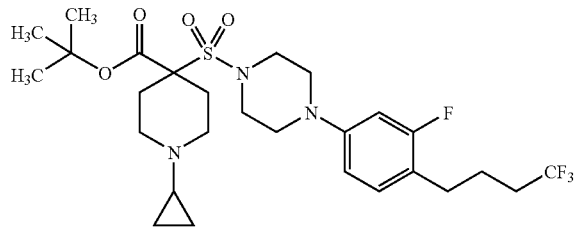

A mixture of the product of Part I (2.78 g, 6.22 mmol), the product of Part C (1.80 g, 7.48 mmol), palladium(II) acetate (0.070 g, 0.312 mmol), sodium t-butoxide (0.836 g, 8.69 mmol), and 2-(di-t-butylphosphino)biphenyl (0.185, 0.621 mmol) in toluene was heated at 90° C. for 18 hr. The mixture was then diluted with water (350 mL) and extracted with ethyl acetate (3×100 mL). The organic layer was filtered through celite, washed with water (2×100 mL) and brine (100 mL), dried over MgSO$_4$, and concentrated in vacuo to afford a yellow oil. The oil was purified on silica gel (70 g), eluting with 0–100% ethyl acetate in hexane, to afford 0.638 g (17% yield) of the desired compound in the form of a yellow oil. MS: m/z=578 (M+H).

Part K. Preparation of 1-cyclopropyl-4-{4-[3-fluoro-4-(4,4,4-trifluoro-butyl)-phenyl]-piperazine-1-sulfonyl}-piperidine-4-carboxylic acid, 2HCl:

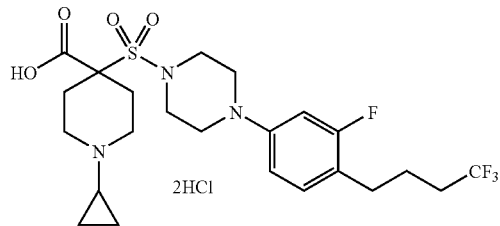

A solution of Part J (0.630 g, 1.09 mmol) in 4N HCl in dioxane (2.7 mL, 10.9 mmol) was heated at 50° C. until LCMS analysis indicated that the reaction was complete. The ambient solution was poured into ethyl ether, and a white precipitate was collected to afford 0.543 g (84% yield) of the desired compound in the form of a tan solid. MS: m/z=522 (M+H).

Part L. Preparation of 1-cyclopropyl-4-{4-[3-fluoro-4-(4,4,4-trifluoro-butyl)-phenyl]-piperazine-1-sulfonyl}-piperidine-4-carboxylic acid (tetrahydro-pyran-2-yloxy)-amide:

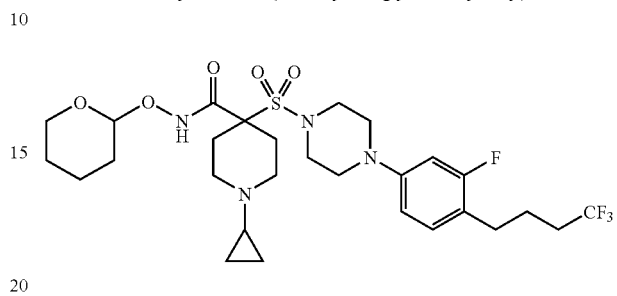

To a mixture of the product of Part K (0.533 g, 0.897 mmol), N-hydroxybenzotriazole (0.180 g, 1.33 mmol), and triethylamine (3.81 g, 3.77 mmol) in 1-methyl-2-pyrrolidinone (3.83 mL) was added O-(tetrahydro-2H-pyran-2-yl)hydroxylamine (0.179 g, 1.53 mmol), followed by 1-(3-dimethylaminopropyl)-3-ethylcarbodiimide hydrochloride (0.251 g, 1.31 mmol). After 18 hr at ambient temperature, more O-(tetrahydro-2H-pyran-2-yl)hydroxylamine (0.050 g, 0.37 mmol) and 1-(3-dimethylaminopropyl)-3-ethylcarbodiimide hydrochloride (0.050 g, 0.26 mmol) were added to the mixture. The mixture was then stirred for an additional 24 hr. Subsequently, the mixture was diluted with water (200 mL) and extracted with ethyl acetate (3×50 mL). The organic layer was washed with water (2×50 mL) and brine (50 mL), dried over MgSO$_4$, and concentrated in vacuo to afford an oil. The crude material was purified on silica gel (20 g), eluting with 0–100% ethyl acetate in hexane. to afford 0.466 g (84% yield) of the desired compound in the form of a yellow oil.

Part M. Preparation of 1-cyclopropyl-4-({4-[3-fluoro-4-(4,4,4-trifluorobutyl)phenyl]piperazin-1-yl}sulfonyl)-N-hydroxypiperidine-4-carboxamide hydrochloride:

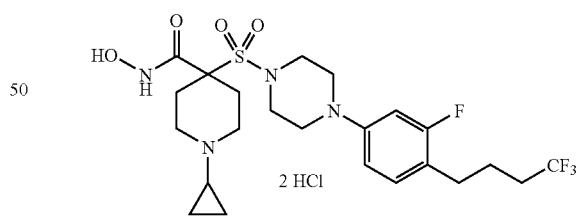

To a methanol solution (4.8 mL) of the product of Part L (0450 g, 0.725 mmol) was added in one portion a methanol solution (2.4 mL) of acetyl chloride (0.273 g, 3.61 mmol). A solid began to precipitate after 5 min at ambient temperature. The solution was diluted with ethyl ether and concentrated in vacuo, and then diluted again with ethyl ether and concentrated in vacuo to afford 0.345 g (78% yield) of the desired compound in the form of a white solid. HRMS for $C_{23}H_{33}N_4O_4F_4S$ showed $M^{+H}_{found}$=537.2142 ($M^{+H}_{calc}$=537.2159)

Example A63

Preparation of 4-({4-[5-(3,3-difluorobutyl)pyridin-2-yl]piperidin-1-yl}sulfonyl)-N-hydroxytetrahydro-2H-pyran-4-carboxamide hydrochloride

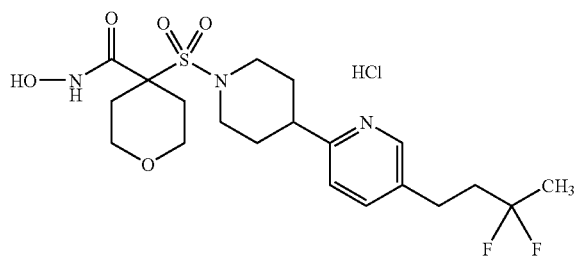

Part A. To a mixture of 2-chloro-5-iodopyridine (6.76 g, 28.2 mmol) in 50 mL N,N-dimethylformamide was added 1-buten-3-ol (24.4 mL, 282.3 mmol), palladium acetate (0.64 g, 2.82 mmol), tetrabutylammonium chloride (0.79 g, 2.82 mmol), and sodium bicarbonate (5.94 g, 70.6 mmol). The resulting mixture was stirred at 50° C. for 5 hr, and then quenched with water (20 mL). Subsequently, the mixture was diluted with 20 mL of ethyl acetate and filtered through a pack of celite. The organic layer was separated from the filtrate, and the aqueous layer was further extracted with ethyl acetate. The organics were combined, washed with saturated NaCl solution, and dried over magnesium sulfate. Chromatography (on silica, ethyl acetate/hexane) afforded the desired 4-(6-chloropyridin-3-yl)butan-2-one intermediate in the form of a yellow oil (4.01 g, 77% yield). MS MH+ for $C_9H_{10}ClNO$: calc. 184, found 184.

Part B. To a solution of the product of Part A (1.83 g, 10 mmol) in 5 mL of methylene chloride was added [bis(2-methoxyethyl)amino] sulfur trifluoride (3.76 g, 17 mmol) and 92 mg of ethanol. The mixture was stirred at ambient temperature for 40 hr. Subsequently, the mixture was poured into a 25 mL saturated sodium bicarbonate solution. After carbon dioxide evolution ceased, the mixture was extracted with methylene chloride. The resulting organics were dried over magnesium sulfate. Chromatography (on silica, ethyl acetate/hexane) afforded the desired 2-chloro-5-(3,3-difluorobutyl)pyridine intermediate in the form of a colorless oil (1.30 g, 63% yield). MS MH+ for $C_9H_{10}ClF_2N$: calc. 206, found 206.

Part C. To a solution of the product of Part B (0.50 g, 2.44 mmol) in 12 mL ethylene glycol dimethyl ether was added tert-butyl 4-{[4-(4,4,5,5-tetramethyl-1,3,2-dioxaborolan-2-yl)-3,6-dihydropyridin-1(2H)-yl]sulfonyl}tetrahydro-2H-pyran-4-carboxylate (1.28 g, 2.80 mmol), tetrakis(tri-phenylphosphine) palladium (145 mg), and potassium carbonate (0.42 g, 3.05 mmol) in 2 mL of water. The mixture was stirred at 73° C. under $N_2$ for 15 hr. The mixture was then partitioned between ethyl acetate and water. The organic layer was washed with saturated NaCl and dried over magnesium sulfate. Some solid precipitated during the concentration. The solid was triturated with ethyl acetate/hexane and filtered. The filtrate was concentrated and chromatographed (on silica, ethyl acetate/hexane) to afford an additional quantity of the desired tert-butyl 4-{[5-(3,3-difluorobutyl)-3',6'-dihydro-2,4'-bipyridin-1'(2'H)-yl]sulfonyl}tetrahydro-2H-pyran-4-carboxylate intermediate. This procedure afforded a total of 0.99 g of this compound in the form of a yellow solid (81% yield). MS MH+ for $C_{24}H_{34}F_2N_2O_5S$: calc. 501, found 501.

Part D. The product from Part C (665 mg, 1.33 mmol) was dissolved in ethanol, and then hydrogenated under 40 psi at room ambient temperature for 12 hr using chlorotris(triphenylphosphine) rhodium as a catalyst. The mixture was then concentrated and chromatographed (on silica, ethyl acetate/hexane) to afford the desired tert-butyl 4-({4-[5-(3,3-difluorobutyl)pyridin-2-yl]piperidin-1-yl}sulfonyl)tetrahydro-2H-pyran-4-carboxylate intermediate in the form of a yellow solid (550 mg, 82% yield). MS MH+ for $C_{24}H_{36}F_2N_2O_5S$: calc. 503, found 503.

Part E. The product from Part D (700 mg, 1.39 mmol) was dissolved in neat trifluoroacetic acid (10 mL). After 2 hr, the mixture was concentrated in vacuo to provide the crude carboxylic acid. The acid was dissolved in N,N-dimethylformamide (10 mL). Subsequently, 1-hydroxybenzotriazole (221 mg, 1.63 mmol), 4-methylmorpholine (0.60 mL, 5.42 mmol), 0-(tetrahyrdro-2H-pyran-2-yl)hydroxylamine (407 mg, 3.48 mmol), and 1-(3-dimethylaminopropyl)-3-ethylcarbodiimide hydrochloride (666 mg, 3.48 mmol) were added. The mixture was stirred at ambient temperature for 18 hr. The mixture was then partitioned between ethyl acetate and water. The organic layer was washed with saturated NaCl and dried over magnesium sulfate. Chromatography (on silica, ethyl acetate/hexane) afforded the desired 4-({4-[5-(3,3-difluorobutyl)pyridin-2-yl]piperidin-1-yl}sulfonyl)-N-(tetrahydro-2H-pyran-3-yloxy)tetrahydro-2H-pyran-4-carboxamide intermediate in the form of a white solid (580 mg, 77% yield). MS MH+ for $C_{25}H_{37}F_2N_3O_6S$: calc. 545, found 545.

Part F. The product of Part E (580 mg, 1.06 mmol) was dissolved in 4M HCl in dioxane (10 mL). After 15 hr, the mixture was concentrated in vacuo. The residue was triturated with acetone and filtered. The solid was washed with additional acetone and dried under high vacuum at 65° C. for 12 hr to afford the title compound in the form of a white solid (437 mg, 89% yield). MS MH+ for $C_{20}H_{29}F_2N_3O_5S$: calc. 462, found 462.

Example A64

Preparation of N-hydroxy-4-{[4-(4-{3-[4-(trifluoromethoxy)phenyl]-1,2,4-oxadiazol-5-yl}butyl)piperidin-1-yl]sulfonyl}tetrahydro-2H-pyran-4-carboxamide

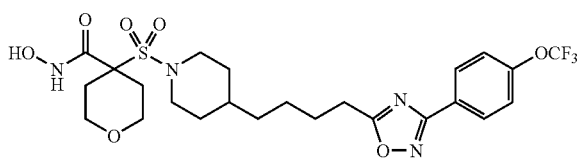

Part A. Preparation of tert-butyl 4-4{[4-(methoxymethyl)piperdin-1-yl]sulfonyl}tetrahydro-2H-pyran-4-carboxylate:

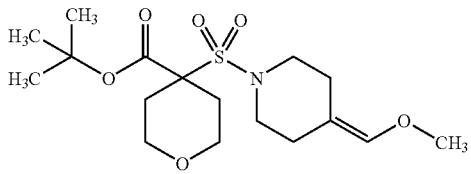

An oven-dried round-bottom flask (fitted with septa and a nitrogen needle) was charged with (methoxymethyl)triphenylphosphonium chloride (4.11 g, 12 mmol) and tetrahydrofuran (50 mL). The flask was immersed in an ice bath. A 1 M solution of lithium hexamethyldisilazide in tetrahydrofuran (13 mL, 13 mmol) was then added dropwise while maintaining the temperature at less than 5° C. After complete addition, the mixture was stirred with cooling for 15 min. Subsequently, a solution of tert-butyl 4-(4-oxopiperidin-1-yl)sulfonyl]tetrahydro-2H-pyran-4-carboxylate (3.47 g, 10 mmol) in tetrahydrofuran (10 mL) was added dropwise while maintaining the temperature at less than 5° C. After complete addition (approximately 30 min), the mixture was stirred with cooling for 15 min. The cooling bath was then removed, and the mixture was slowly warmed to room temperature and stirred overnight. Subsequently, diethyl ether (200 mL) was added, which resulted in the formation of a yellow precipitate. This precipitate was removed by vacuum filtration. The filtrate was washed with 5% aqueous HCl (3×100 mL), saturated aqueous sodium bicarbonate (3×100 mL), and brine (1×100 mL). The organic layer was then dried over magnesium sulfate and concentrated in vacuo. Purification by flash column chromatography (20–40% ethyl acetate/hexane) afforded 2.82 g of the title compound in the form of a colorless, viscous oil (75% yield): 1H NMR (CDCl$_3$) δ 1.51 (s, 9H), 2.05–2.30 (m, 2H), 2.29 (m, 2H), 3.29 (m, 6H), 3.95 (dd, J=11.4, 4.2 Hz, 2H), 5.84 (s, 1H); LCMS m/z=376 (M+H).

Part B. Preparation of tert-butyl 4-[(4-formylpiperidin-1-yl)sulfonyl]tetrahydro-2H-pyran-4-carboxylate:

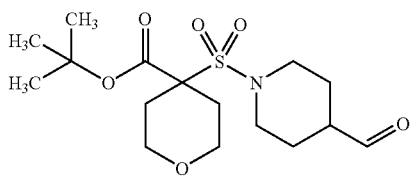

A round-bottom flask was charged with the product of Part A (0.50 g, 1.34 mmol), tetrahydrofuran (5 mL), and 5% aqueous HCl (1 mL, 1.37 mmol). The resulting mixture was stirred at room temperature for 2 hr, and then heated to 50° C. overnight. Afterward, the mixture was partitioned between diethyl ether (25 mL) and saturated aqueous sodium bicarbonate (25 mL). The organic layer was washed with brine (25 mL), dried over magnesium sulfate, and concentrated in vacuo. This resulted in isolation of 0.50 g (quantitative) product in the form of a yellow solid: 1H NMR (CDCl$_3$) δ 1.51 (s, 9H), 1.70 (m, 2H), 1.93 (m, 2H), 2.08 (td, J=12.4, 4.8 Hz, 2H), 2.29 (d, J=12.4 Hz, 2H), 2.41 (m, 1H), 3.11 (m, 2H), 3.29 (td, J=12, 1.6 Hz, 2H), 3.70 (m, 2H), 3.95 (dd, J=11.2, 4 Hz, 2H), 9.65 (s, 1H); LCMS m/z=362 (M+H).

Part C. Preparation of: tert-butyl 4-({4-[(1E,3E)-5-ethoxy-5-oxopenta-1,3-dienyl]piperidin-1-yl}sulfonyl)tetrahydro-2H-pyran-4-carboxylate:

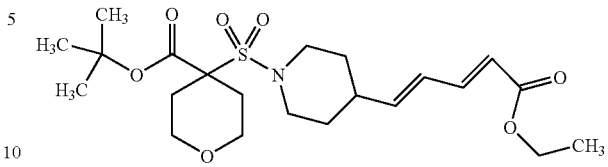

A round-bottom flask (fitted with septa and an N$_2$ gas inlet) was charged with triethyl 4-phosphonocrotonate 90% (Aldrich, 3.8 g, 15.2 mmol), the product from Part B, lithium hydroxide hydrate (460 mg, 11 mmol), molecular sieves (4 angstrom, 10 g), and tetrahydrofuran (25 mL). The resulting white slurry was heated at 70° C. for 6 hr. Afterward, the heating mantle was then removed. Water (50 mL) and ethyl acetate (100 mL) were added, and the resulting mixture was filtered through a pad of celite by vacuum filtration. The filtrate was washed with water (50 mL) and brine (50 mL). The organic layer was dried over sodium sulfate and concentrated in vacuo. Crystallization occurred on standing to afford 3 g of the product in the form of a white crystalline solid (59% yield): 1H NMR (CDCl$_3$) δ; LCMS m/z=458.55 (M+H).

Part D. Preparation of 5-(1-{[4-(tert-butoxycarbonyl)tetrahydro-2H-pyran-4-yl]sulfonyl}piperidin-4-yl)pentanoic acid:

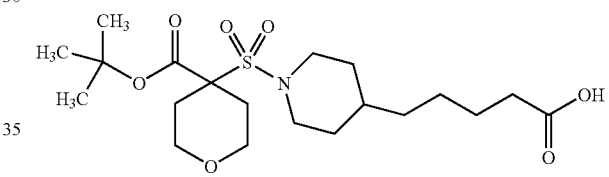

A 150 mL Parr shaker flask was charged with 10% palladium on carbon (degussa type, 2 g) and a solution of the product from Part C (2.8 g, 6.0 mmol) in ethyl acetate (75 mL). The flask was placed under an H$_2$ atmosphere and agitated at room temperature for 2.5 hr. Afterward, the mixture was filtered through celite and concentrated to afford an oil. The oil was dissolved in tetrahydrofuran (25 mL). Methanol (5 mL) and aqueous NaOH (2.5N, 5 mL) were then added. The resulting mixture was stirred for 12–15 hr at room temperature. Afterward, water (50 mL) and ethyl acetate were added. The organic layer was separated and washed with 6N aqueous HCl, dried over sodium sulfate, and concentrated in vacuo. Crystallization occurred on standing to afford 2 g of the product in the form of a white crystalline solid (77% yield): LCMS m/z=434.03 (M+H).

Part E. Preparation of: tert-Butyl-4-{[4-(4-{3-[4-(trifluoromethoxy)phenyl]-1,2,4-oxadiazol-5-yl}butyl)piperidin-1-yl]sulfonyl}tetrahydro-2H-pyran-4-pentanoate:

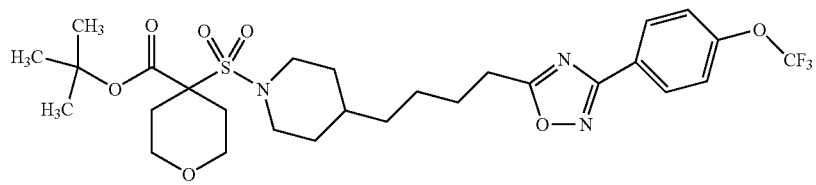

In round bottom flask under N₂, the butyric acid from Part D. (2 g, 4.6 mmol) was dissolved in dry dimethylacetamide (20 mL). Next, the following reagents were added in the following order: N-hydroxybenzotriazole hydrate (1 g, 7 mmol), triethylamine (2 mL, 25.0 mmol), 4-(trifluoromethoxy)benzamidoxime (1.5 g, 6.8 mmol), and 1-(3-dimethylaminopropyl)-3-ethylcarbodiimide hydrochloride (2 g, 10.0 mmol). After 24 hr at 70° C., the mixture was concentrated in vacuo. The residue was combined with ethyl acetate; washed with water, saturated NaHCO₃, saturated NaCl solution; dried over Na₂SO₄; filtered; and concentrated in vacuo. Chromatography (on silica, ethyl acetate/methanol/hexanes) afforded the desired oxadiazole compound in the form of a light yellow oil (600 mg, 23% yield). LCMS m/z=618[M+H]⁺.

Part F. Preparation 4-{[4-(4-{3-[4-(trifluoromethoxy)phenyl]-1,2,4-oxadiazol-5-yl}butyl)piperidin-1-yl]sulfonyl}tetrahydro-2H-pyran-4-pentanoic acid:

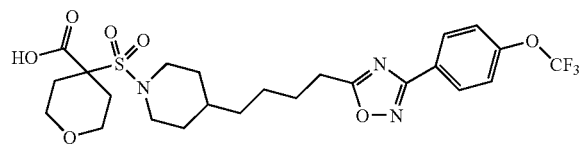

A round bottom flask was charged with the product of Part E (0.600 g, 0.69 mmol) and a 1:1 mixture of trifluoroacetic acid and dichloromethane (1 mL). The mixture was stirred at room temperature for 5 hr and then concentrated in vacuo. The product was precipitated by the addition of diethyl ether. The resulting solid was collected by vacuum filtration. Further drying in vacuo afforded 540 mg of the desired compound in the form of a white solid (95% yield): LCMS m/z=562 (M+H).

Part G. Preparation of 4-(4-{4-[3-(4-trifluoromethoxyphenyl)-[1,2,4]oxadiazol-5-yl]-butyl}-piperidine-1-sulfonyl)-tetrahydro-pyran-4-carboxylic acid (tetrahydro-pyran-2-yloxy)-amide:

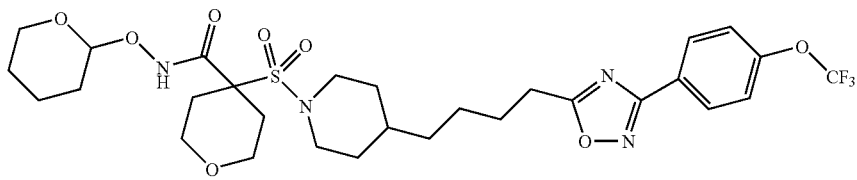

A round bottom flask was charged with the product from Part F (0.54 g, 0.96 mmol), hydroxybenotriazole,(100 mg, 0.7 mmol), a 0.5 M solution of THP—ONH₂ (0.17 g, 1.8 mmol), triethylamine (0.33 mL, 2.4 mmol), and EDC (0.350 mg, 1.8 mmol). The resulting mixture was stirred at room temperature overnight, and then partitioned between water (25 mL) and ethyl acetate (25 mL). The organic layer was washed with 5% aqueous HCl (3×25 mL), washed with brine (1×100 mL), filtered through a celite column, and concentrated in vacuo. Purification using chromatography (on silica, ethyl acetate/methanol/hexanes) afforded the desired compound in the form of a light yellow oil.

Part H. Preparation of N-hydroxy-4-{[4-(4-{3-[4-(trifluoromethoxy)phenyl]-1,2,4-oxadiazol-5-yl}butyl)piperidin-1-yl]sulfonyl}tetrahydro-2H-pyran-4-carboxamide:

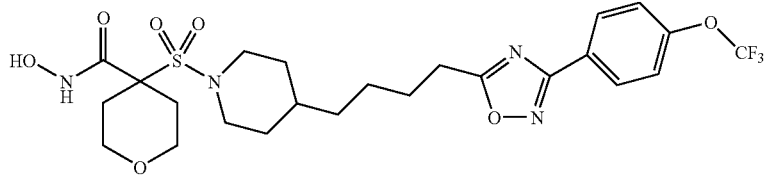

A round bottom flask was charged with the oil from Part G in acetonitrile (10 mL) and 6 N aqueous HCl (2 mL). The resulting solution was stirred at room temperature for 60 min. The volatile solvents were removed by passing a N₂ line over the surface of the vigorously stirring mixture. This resulted in the product separating from solution as a white solid. This solid was filtered and dried (220 mg) (50% yield after two reaction steps). LCMS m/z=568 (M+H).

Example A65

Preparation of N-hydroxy-4-({4-[5-(3,3,4,4,4-pentafluorobutyl)pyrazin-2-yl]piperidin-1-yl}sulfonyl)tetrahydro-2H-pyran-4-carboxamide

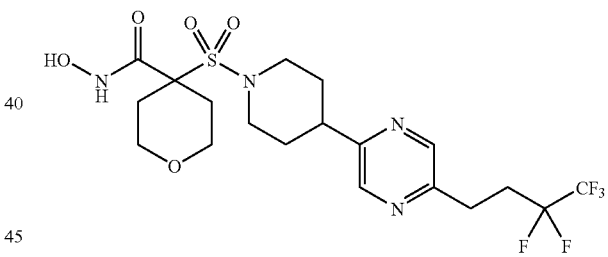

Part A. Tert-butyl 4-{[4-(4,4,5,5-tetramethyl-1,3,2-dioxaborolan-2-yl)-3,6-dihydropyridin-1-(2H)-yl]sulfonyl}tetrahydro-2H-pyran-4-carboxylate (10 g, 21.86 mmol, Gateway Chemical), 2-bromo-5-iodopyrazine (6.23 g, 21.86 mmol, Gateway Chemical), toluene (105 mL), ethanol (32 mL), 2M Na₂CO₃(aq) (64 mL), and [1,1'-bis(diphenylphosphino)ferrocene]dichloropalladium(II), complex with CH₂Cl₂ (1:1) (0.892 g, 1.1 mmol, Aldrich) were heated together under N₂ at 73° C. for 3 hr and then cooled to ambient temperature overnight. The resulting mixture was diluted with ethyl acetate (300 mL) and deionized water (200 mL). The layers were separated, and the aqueous was back-extracted with ethyl acetate (100 mL). The combined ethyl acetate layers were washed with 150 mL each of sat. NaHCO$_3$(aq) and brine, dried over MgSO$_4$, filtered, and concentrated to afford an oil in vacuo. The oil was purified by chromatography on silica (heaxnes/ethyl acetate) to afford 7.68 g (72% yield) of solids.

Part B. Zn (dust, 325 mesh, 17.05 g, 262 mmol, Aldrich) and THF (60 mL) were combined and stirred under N$_2$ at ambient temperature for 10 min. 1,2-Dibromoethane (1.81 mL, 21 mmol, Aldrich) was then added, and the resulting mixture was brought to reflux 3 times under N$_2$, cooling to ambient after each reflux in a water bath. The mixture was then cooled to 0° C. in an ice bath, and chlorotrimethylsilane (2.93 mL, 23 mmol, Aldrich) was added over a few minutes under N$_2$. The mixture was stirred at 0° C. for 5 min, and then allowed to warm to ambient temperature over 20 min with stirring under N$_2$. Subsequently, 1,1,1,2,2-pentafluoro-4-iodobutane (36 g, 131.16 mmol, Matrix Scientific) was added to the mixture. The mixture was then mixed at 40° C. under N$_2$ for 90 min. The estimated concentration of organozinc iodide was 1.4 mmol/mL THF. The product from Part A (7.68 g, 15.72 mmol), N,N-dimethylacetamide (150 mL), 33.7 mL (47.16 mmol) of the organo-zinc iodide in THF, bis(benzonitrile)dichloropalladium(II) (386 mg, 1 mmol, Aldrich), and 2-(dicyclohexylphosphino)-2'-methylbiphenyl (613 mg, 1.68 mmol, Strem Chemicals) were combined and stirred at 55° C. under N$_2$ for 3 hr and then cooled to ambient temperature overnight. Subsequently, the mixture was diluted with ethyl acetate (400 mL) and deionized water (200 mL), and filtered through a bed of Celite®. The filter cake wash rinsed with ethyl acetate (100 mL), and the resulting filtrate layers were separated. The aqueous layer was back-extracted with ethyl acetate (200 mL). The combined ethyl acetate layers were washed with 200 mL each of sat. NaHCO$_3$(aq) and brine, dried over MgSO$_4$, filtered, and concentrated. The resulting residue was triturated with hexanes, filtered, and dried in vacuo at 50° C. for 2 hr to afford 8.0 g (92% yield) of the desired intermediate.

Part C. The product from Part B was dissolved in CH$_2$Cl$_2$ (100 mL). Trifluoroacetic acid (100 mL) was then added. The resulting mixture was stoppered with a syringe needle vent overnight at ambient temperature. Subsequently, the solution was concentrated in vacuo to afford a residue that was triturated with Et$_2$O/hexanes to form solids. The solids were filtered, washed with hexanes, and dried in vacuo at 50° C. for 2 hr to afford 6.67 g (93% yield) of the desired intermediate in the form of solids.

Part D. The solids from Part C (6.6 g, 13.21 mmol), 1-hydroxybenzotriazole (5.35 g, 39.63 mmol, Aldrich), and 1-[3-dimethylamino)propyl]-3-ethylcarbodiimide hydrochloride (7.6 g, 39.63 mmol, Aldrich) were dissolved in N,N-dimethylformamide (20 mL). The mixture was stoppered at ambient temperature for 10 min. Subsequently, 4-methylmorpholine (10.9 mL, 99 mmol) and O-(tetrahydropyranyl)hydroxylamine (4.64 g, 39.63 mmol, Carbogen) were added. The resulting mixture was mixed at ambient temperature overnight, and then poured into 300 mL ethyl acecetate and 150 mL deionized water. The layers were separated and the aqueous layer was back-extracted with ethyl acetate (150 mL). The combined ethyl acetate layers were washed with 150 mL each of sat. NaHCO$_3$(aq), a 1:1 mixture of deionized water:saturated NaCl(aq) and saturated NaCl(aq), dried over MgSO$_4$, and concentrated in vacuo to an oil. The oil was triturated with Et$_2$O/hexanes to form solids that were slurried for 2 hr, filtered, and dried to a constant weight in vacuo at 50° C. to afford 7.0 g (88.5% yield) of the desired intermediate. $^1$H NMR confirmed structure of the compound.

Part E. The product from Part D (6.0 g, 10.02 mmol) was dissolved in methanol (60 mL). Palladium on carbon (Degussa type, 10% Pd on C, 50% water by weight, 1.3 g, Aldrich) was then added. The solution was deoxygenated and placed under a 50 p.s.i. H$_2$ atmosphere at ambient temperature. The mixture was mixed for 2.5 hr while maintaining the H$_2$ pressure at 50 psi. The resulting mixture was filtered through a pre-wetted (with methanol) bed of Celite®. The filter cake was washed with methanol (200 mL), and the filtrate was concentrated in vacuo to afford the desired intermediate in the form of an oil (5.5 g, 91.7% yield).

Part F. The oil from Part E (5.5 g, 9.16 mmol) was added to 1.25 N HCl/methanol (60 mL). The resulting mixture was heated to make the solution homogeneous. The mixture was allowed to cool to ambient temperature over 45 minutes of mixing. The mixture was then concentrated in vacuo to form solids. The solids were evaporated with 2 portions of 1.25 N HCl/methanol (50 mL each portion), concentrating to dryness during each evaporation. Solids were then precipitated from 1.25 N HCl/methanol and deionized water. After stirring at ambient temperature for 30 min, the solids were filtered, washed with deionized water, and dried in vacuo at 50° C. to a constant weight. This afforded 3.8 g (80% yield) of product. MS, M+H calculated for C$_{19}$H$_{25}$F$_5$N$_4$O$_5$S: 517.1539, found: 517.1523.

Example A66

Preparation of N-hydroxy-4-methoxy-2-({4-[4-(3,3,4,4,4-pentafluorobutyl)phenyl]piperidin-1-yl}sulfonyl)butanamide

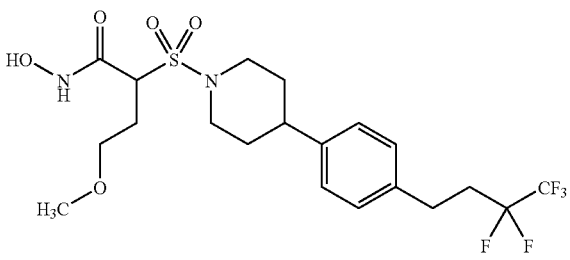

Part A. A mixture of 4-(4-bromophenyl)-4-piperidinol (50 g, 195 mmol, Aldrich), triethylamine (59.8 mL, 429 mmol), and CH$_2$Cl$_2$ (400 mL) was cooled to 0° C. with mixing under N$_2$. To this mixture was added methanesulfonyl chloride (16.6 mL, 214 mmol) in CH$_2$Cl$_2$ (100 mL) dropwise while maintaining the temperature at less than 10° C. After addition was complete, the ice bath was removed and the solution was stirred for 1 hr. Methanesulfonyl chloride (10 mL, 129 mmol) in CH$_2$Cl$_2$ (50 mL) was then added dropwise. The resulting mixture was stirred at ambient temperature under N$_2$ overnight. Subsequently, the mixture was added to 300 mL of 0.5 N HCl(aq) and 200 mL of deionized water. The layers were separated, and the aqueous layer was back-extracted with CH$_2$Cl$_2$ (100 mL). The combined CH$_2$Cl$_2$ layers were washed with 300 mL each of saturated NaHCO$_3$(aq) and saturated NaCl(aq). The CH$_2$Cl$_2$ layer was then dried over MgSO$_4$, filtered, and concentrated in vacuo to afford the desired methylsulfonamide in the form of solids (62 g, 95.6% yield).

Part B. To the methylsulfonamide product of Part A was added CH$_2$Cl$_2$ (300 mL) and triethylsilane (125 mL, 778 mmol). To this slurry was added trifluoroacetic acid (300 mL, 3.9 mol). The resulting mixture was stoppered and stirred at ambient temperature for 1 hr, and then concentrated in vacuo to solids. These solids were mixed with MeOH (150 mL) at ambient temperature for 2 days in a stoppered flask. The solids filtered from that slurry, in turn, were washed with 100 mL MeOH and then dried in a vacuum oven at 50° C. overnight to afford 54.14 g (91.7% yield) of solids. $^1$H NMR confirmed the structure of the desired intermediate.

Part C. Zinc (dust, 325 mesh, 2.06 g, 31.5 mmol), 1,2-dibromoethane (0.243 mL, 2.8 mmol), and tetrahydrofuran (12.5 mL) were heated together at 65° C. under N$_2$ for 5 min. The slurry was cooled to ambient temperature with mixing under N$_2$, and trimethylchlorosilane (0.336 mL, 2.64 mmol) was added. The resulting mixture was then stirred at ambient temperature for 30 min. Subsequently, 1,1,1,2,2-pentafluoro-4-iodobutane (6.45 g, 23.5 mmol, Matrix Scientific) was added, and the mixture was stirred at 40° C. for 3 hr under N$_2$. Next, N,N-dimethylaceamide (35 mL), the product from Part B (5 g, 15.7 mmol), and dichlorobis(tri-o-tolylphosphine)palladium(II) (802 mg, 1.02 mmol, Aldrich) were added to the mixture. The mixture was then heated at 80° C. under N$_2$ overnight. Subsequently, the mixture was cooled to less than 30° C., and 50 mL of saturated NH$_4$Cl(aq) was added to the mixture, followed by 200 mL ethyl acetate. The resulting biphasic system was filtered through a pad of Celite®, and washed with deionized water (50 mL) and ethyl acetate (50 mL). The layers were separated, and the ethyl acetate layer was washed with 100 mL each of saturated NaHCO$_3$(aq) and saturated NaCl(aq). The ethyl acetate layer was dried over MgSO$_4$, filtered, and concentrated in vacuo to form solids. The solids, in turn, were slurried in hexanes (50 mL) for 1 hr, filtered, washed with hexanes (20 mL), and dried at 50° C. in a vacuum oven for 2 hr to afford 5.58 g (92% yield) of solids. $^1$H NMR confirmed the structure of the desired intermediate.

Part D. Tetrahydrofuran (70 mL), the product from Part C (6.7 g, 17.4 mmol), and di-tert-butyl dicarbonate (4.55 g, 20.9 mmol, Aldrich) were cooled together to −78° C. under N$_2$. To the resulting mixture, a solution of lithium bis(trimethylsilyl)amide in tetrahydrofuran (1 M, 46 mL) was added at a rate such that the temperature remained at less than −70° C. This mixture was the mixed at −78° C. under N$_2$ for 1 hr, and then at 0° C. for 20 min. Subsequently, the mixture was cooled to −40° C., and saturated NH$_4$Cl(aq) (25 mL) was added. After the addition was complete, the mixture was warmed to ambient temperature, and ethyl acetate (250 mL) and deionized water (100 mL) were added. The layers were separated, and the aqueous layer was back-extracted with ethyl acetate (100 mL). The combined ethyl acetate layers were washed with 100 mL each of saturated NaHCO$_3$(aq) and saturated NaCl(aq), dried over MgSO$_4$, filtered, and concentrated in vacuo. The resulting solid/oil was co-evaporated several times with acetonitrile to afford solids. The solids were dried in a vacuum oven at 50° C. overnight to afford 8.55 g (102% yield) of solids.

Part E. Product from Part D (1.5 g, 3.08 mmol), DMF (20 mL), and a 60% NaH dispersion in mineral oil (0.310 g, 7.7 mmol, Aldrich) were combined and stirred at ambient temperature for 20 min under N$_2$. To the resulting mixture was added 2-bromoethyl methyl ether (0.695 mL, 7.4 mmol, Aldrich). The mixture was then mixed overnight at 60° C. under N$_2$. Subsequently, the mixture was cooled to ambient temperature. An additional amount of NaH (2 times the amount of NaH used initially) was then added. After mixing at ambient temperature for 20 min, additional 2-bromoethyl methyl ether was added (2 times the amount of used above). The resulting mixture was heated to 60° C. overnight under N$_2$. Subsequently, the mixture was cooled to ambient temperature, and another additional amount of NaH (i.e., 2 times the amount of NaH used initially) was added. After mixing at ambient temperature for 20 min, another additional amount of the added 2 times the amount of was added (i.e., 2 times the amount used above). The resulting mixture was heated to 60° C. overnight under N$_2$. Subsequently, the mixture was cooled to ambient temperature and diluted with ethyl acetate (250 mL) and deionized water (100 mL). The layers were separated, and the aqueous layer was back-extracted aqueous with ethyl acetate (100 mL). The combined ethyl acetate layers were washed with 100 mL each of saturated NaHCO$_3$(aq), 1:1 deionized water: saturated NaCl (aq), and saturated NaCl(aq). The ethyl acetate layers were then dried over MgSO$_4$, filtered, and concentrated in vacuo to afford an oil (2.0 g, 108% yield). The intended product was the dialkylated intermediate. A monoalkylated compound, however, also was formed as a side product, and was isolated as well.

Part F. The t-butyl ester from Part E was dissolved in CH$_2$Cl$_2$ (25 mL). Trifluoroacetic acid (25 mL) was then added. The resulting mixture was stoppered with a syringe needle vent and mixed at ambient temperature overnight. The mixture was then concentrated in vacuo to afford an oil (2.0 g, 119% yield)

Part G. To the acid from Part F was added N,N-dimethylformamide (30 mL), 1-hydroxybenzotriazole (1.25 g, 9.24 mmol, Aldrich), 1-[3-dimethylamino)propyl]-3-ethylcarbodiimide hydrochloride (1.77 g, 9.24 mmol, Aldrich), and 4-methylmorpholine (2.55 mL, 23.1 mmol). The resulting mixture was stoppered and stirred for 10 min at ambient temperature. To the resulting solution was added O-(tetrahydropyranyl)hydroxylamine (1.08 g, 9.24 mmol). This mixture was then stoppered and stirred for 10 hr at ambient temperature. Subsequently, O-(tetrahydropyranyl)hydroxylamine (1.0 g, 8.55 mmol) was added. The mixture was stoppered and mixed overnight at ambient temperature. Ethyl acetate (200 mL) and deionized water (100 mL) were then added, and the layers were separated. The aqueous layer was back-extracted with ethyl acetate (100 mL). The combined ethyl acetate layers were then washed with 100 mL each of a 1:1 mixture of deionized water:saturated NaCl(aq) and saturated NaCl(aq). The ethyl acetate layer was then dried over MgSO$_4$, filtered, and concentrated in vacuo to give afford an oil (3.0 g, 150% yield).

Part H. The oil from Part G was added to 1.25 N HCl/methanol (30 mL). The resulting mixture was stirred at ambient temperature for 30 min. Afterward, the mixture was concentrated in vacuo to afford solids. The solids were evaporated with 2 portions of 1.25 N HCl/methanol (30 mL each portion) and concentrated to dryness after each evaporation. The product material was then purified by chromatography (on reversed-phase silica, water/acetonitrile w/0.05% trifluoroacetic acid in both). Exchanged trifluoroacetate salt for hydrochloride salt by 3 evaporations with 1.25 N HCl/methanol (30 mL). After the last evaporation, the material was dissolved in acetonitrile/deionized water and lyophilized to afford 60 mg of solids. MS, M+H calculated for C$_{20}$H$_{27}$F$_5$N$_2$O$_5$S: 503.1634, found: 503.1613.

Example A67

Preparation of 4-({4-[5-(2-cyclopropylethoxy)pyrazin-2-yl]piperidin-1-yl}sulfonyl)-N-hydroxytetrahydro-2H-pyran-4-carboxamide

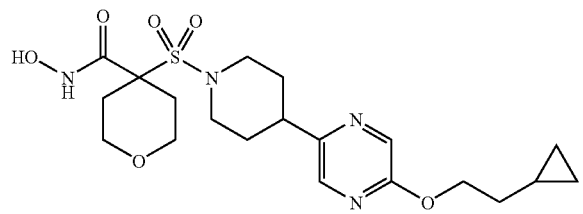

Part A. A 60% NaH dispersion in mineral oil (0.504 mg, 12.66 mmol, Aldrich) was added to a mixture of 2-cyclopropylethanol (1.0 g, 11.61 mmol, Lancaster) in THF (60 mL). The resulting mixture was stirred at ambient temperature under $N_2$ for 20 min. Subsequently, 2-bromo-5-iodopyrazine (3.0 g, 10.55 mmol, Gateway Chemical) was added, and the resulting mixture was stirred at 65° C. under $N_2$ for 3.5 hr. The mixture was then allowed to cool to ambient temperature overnight. THF was removed in vacuo, and the residue was diluted with ethyl acetate (150 mL) and deionized water (75 mL). The layers were separated, and the aqueous was back-extracted with ethyl acetate (50 mL). The combined ethyl acetate layers were then washed with 75 mL each of sat. $NaHCO_3$(aq) and brine, dried over $MgSO_4$, filtered, and concentrated to an oil in vacuo 3.0 g (~100%). It was observed that the alkoxide did not selectively displace the iodide versus bromide in this reaction. Thus, a mixture of the monoalkoxylated product resulted. This, however, did not matter for the next reaction Part B. Tert-butyl 4-{[4-(4,4,5,5-tetramethyl-1,3,2-dioxaborolan-2-yl)-3,6-dihydropyridin-1-(2H)-yl]sulfonyl}tetrahydro-2H-pyran-4-carboxylate (1.72 g, 3.75 mmol, Gateway Chemical), the product from Part A (1.0 g, 3.75 mmol), toluene (18 mL), ethanol (5.5 mL), 2M $Na_2CO_3$ (aq) (11 mL), and [1,1'-bis(diphenylphosphino)ferrocene]dichloropalladium(II), complex with $CH_2Cl_2$ (1:1) (0.153 g, 0.187 mmol, Aldrich) were heated together under $N_2$ at 73° C. for 3 hr and then cooled to ambient temperature overnight. The mixture was then diluted with ethyl acetate (150 mL) and deionized water (75 mL). The layers were separated, and the ethyl acetate layer was washed with 75 mL each of sat. $NaHCO_3$(aq) and brine, dried over $MgSO_4$, filtered and, concentrated in vacuo to afford an oil (2.12 g, 114% yield).

Part C. The product from Part B was dissolved in $CH_2Cl_2$ (20 mL). Trifluoroacetic acid (20 mL) was then added. The mixture was stoppered with a syringe needle vent and mixed for 5 hr at ambient temperature, and then concentrated in vacuo to afford an oil (quantitative conversion).

Part D. The oil from Part C, 1-hydroxybenzotriazole (1.52 g, 11.25 mmol, Aldrich), and 1-[3-dimethylamino)propyl]-3-ethylcarbodiimide hydrochloride (2.16 g, 11.25 mmol, Aldrich) were dissolved in N,N-dimethylformamide (20 mL). The mixture was stoppered and mixed at ambient temperature for 10 min. To the resulting mixture was added 4-methylmorpholine (3.1 mL, 28.1 mmol) and O-(tetrahydropyranyl)hydroxylamine (1.32 g, 11.25 mmol, Carbogen). The mixture was then mixed at ambient temperature overnight. Subsequently, the mixture was poured into 125 mL ethyl acectate and 75 mL deionized water. The layers were separated, and the aqueous layer was back-extracted with ethyl acetate (75 mL). The combined ethyl acetate layers were washed with 75 mL each of sat. $NaHCO_3$(aq), a 1:1 mixture of deionized water:saturated NaCl(aq), and saturated NaCl(aq); dried over $MgSO_4$; and concentrated in vacuo to afford an oil (quantitative conversion).

Part E. The oil from Part D was dissolved in methanol (60 mL). Palladium on carbon to solution (Degussa type, 10% Pd on C, 50% water by weight, 0.5 g, Aldrich) was then added. The mixture was deoxygenated and placed under a 50 psi. $H_2$ atmosphere at ambient temperature. The mixture was mixed for an hour while maintaining the $H_2$ pressure at 50 psi. Additional palladium on carbon (Degussa type, 10% Pd on C, 50% water by weight, 0.5 g, Aldrich) was added to the mixture. The mixture again was deoxygenated and placed under a 50 psi $H_2$ atmosphere at ambient temperature. The mixture was mixed for 3 hr while maintaining the $H_2$ pressure at 50 psi. Further palladium on carbon (Degussa type, 10% Pd on C, 50% water by weight, 0.5 g, Aldrich) was added to the mixture, and the mixture was again deoxygenated and placed under a 50 psi $H_2$ atmosphere at ambient temperature where it was mixed for 90 min while the $H_2$ pressure was maintained at 50 psi. The mixture was filtered through a pre-wetted (with methanol) bed of Celite®. The filter cake was washed with methanol (200 mL), and the filtrate was concentrated in vacuo to afford an oil. The oil was purified by chromatography [silica, ethyl acetate (w/10% MeOH)/hexanes] to afford 1.1 g (55% yield) of solids.

Part F. The solids from Part E were added to 1.25 N HCl/methanol (30 mL). The mixture was stirred at ambient temperature for 30 min. The solution was concentrated in vacuo to solids. The solids were evaporated with 2 portions of 1.25 N HCl/methanol (30 mL each portion) and concentrated to dryness after each evaporation. The product material was then purified by chromatography (on reversed-phase silica, water/acetonitrile w/0.05% trifluoroacetic acid in both). Exchanged trifluoroacetate salt for hydrochloride salt by 3 evaporations with 1.25 N HCl/methanol (30 mL). The residue was triturated with $Et_2O$, filtered, dried in vacuo at 50° C. overnight to afford 0.375 g (34% yield) of product. MS, M+H calculated for $C_{20}H_{30}N_4O_6S$: 455.1975, found: 455.1959.

Example A68

Preparation of 1-cyclopropyl-N-hydroxy-4-({4-[4-(2,2,3,3-tetrafluoropropoxy)phenyl]piperidin-1-yl}sulfonyl)piperidine-4-carboxamide hydrochloride

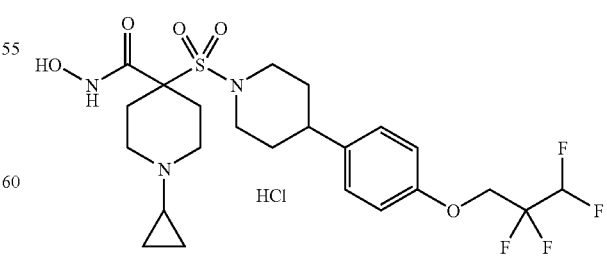

Part A. A round bottom flask was charged with 4-fluorobenzaldehyde (25 g, 202 mmol, Aldrich) and 2,2,3,3-tetrafluoropropanol (29.2 g, 222 mmol, Aldrich) in dimethylformamide (400 ml). Potassium carbonate (41.7 g, 303 mmol, Aldrich) was added, the reaction was heated to 80° C., and stirred for 18 hr. Then the reaction was diluted with water (500 ml) precipitating a white solid. The solid was collected by filtration, washed with water, and dried to afford the product as a white solid (43.2 g, 91% yield). $^1$H NMR showed the desired compound.

Part B. A round bottom flask was charged with the product from Part A (41 g, 174 mmol), ethylacetoacetate (44.2 ml, 347 mmol, Aldrich), and piperidine (1.0 g, 11.7 mmol, Aldrich). The reaction mixture was stirred without solvent for 3 days, resulting in a solid yellow mass. Ethanol (300 ml) was added, and the reaction mixture was heated at reflux for 2 hr. The reaction mixture was cooled to room temperature. After cooling to room temperature, precipitation occurred. The solids were filtered, washed with hexanes, and dried to afford a yellow solid. This solid was slowly added portion wise to a heated (85° C.) aqueous potassium hydroxide solution (26.1 g, 470 mmol in 23 ml water). After the addition, the reaction continued for 2 hr at 85° C., turning the reaction black. The reaction was cooled by adding ice (100 g). The resulting mixture was washed with ethyl acetate (50 ml) and separated. The aqueous was titrated to a pH of 1 using concentrated HCl. The product was extracted out with dichloromethane (3×-200 ml). The organics were combined, dried over $Na_2SO_4$, and concentrated to yield the dicarboxylic acid as a yellowish white solid (26.9 g, 46% yield over three steps). $^1$H NMR showed the desired compound.

Part C. A round bottom flask was charged with the product from Part B (26.8 g, 79.3 mmol) and urea (7.1 g, 118.9 mmol). The reaction was heated to 170° C. for 2 hr, and then cooled to 80° C. Ethanol (40 ml) was added, and the reaction was stirred at reflux for 30 min. The reaction was cooled to 0° C., then filtered for solids. The solids were collected, washed with hexanes, and dried to afford the diketopiperidine product as a beige solid (22.3 g, 88% yield). $^1$H NMR showed the desired compound.

Part D. A round bottom flask was charged with a lithium aluminum hydride solution (208 ml, 1.0 M), and then heated to 40–60° C. The solid from Part C (22.2 g, 69.5 mmol) was added portion wise keeping the temperature below 60° C. After the addition, the reaction flask was equipped with a condenser and refluxed for 1.5 hr. Work up consisted of cooling the mixture to room temperature, carefully adding water (2 ml), and then slurring with sodium sulfate (100 g). The solids were removed by filtration, the filtrate was dried over sodium sulfate, and concentrated affording the piperidine product as an orange oil (17.6 g, 87% yield). $^1$H NMR showed the desired compound.

Part E. A round bottom flask was charged with the product from Part D (12.3 g, 42.2 mmol) and triethyl amine (10.1 ml, 72.5 mmol, Aldrich) in dichloromethane (100 ml). After cooling to 0° C., a solution of methylsulfonyl chloride (4.9 ml, 63.4 mmol in dichloromethane (10 ml)) was added drop wise. After the addition, the ice bath was removed, and the reaction stirred at room temperature for 18 hr. The reaction was concentrated to dryness, and the residue was taken up in ethyl acetate (200 ml). The organic was washed with 10% $HCl_{aq}$, water, and brine, dried over sodium sulfate, and concentrated for a mix of orange and white solids. The solids were recrystallized from methanol, collected, washed with hexanes, and dried affording the desired product (10.1 g, 65% yield). $^1$H NMR showed the desired compound.

Part F. A solution of the product from Part E (11.2 g, 30.3 mmol) and t-butylcarboxylate anhydride (7.9 g, 36.4 mmol, Aldrich) in tetrahydrofuran (60 ml, Aldrich) was cooled to −75° C. A solution of lithium bis(trimethylsilyl)amide (1.0 M (Aldrich) in tetrahydrofuran, 90.9 ml, 90.9 mmol) was slowly added, keeping the temperature below −65° C. After the addition, the mixture was warmed to 0° C., and stirred 1 hr. The mixture was then cooled back to −75° C., and quenched with a saturated aqueous solution of ammonium chloride. The mixture was warmed to room temperature and separated. The aqueous was extracted twice with ethyl acetate. The organics were combined, washed twice with water, washed twice with brine, dried over $Na_2SO_4$, and concentrated for brown residue. The residue was slurried on diethyl ether, and filtered affording the desired product (12.7 g, 89% yield). $^1$H NMR showed the desired product.

Part G. The product from Part F (3.5 g, 7.4 mmol), 18-crown-6 (0.5 g, catalytic amount, Aldrich), potassium carbonate (6.1 g, 44.4 mmol, Aldrich), and bis(chloroethyl)-N-cyclopropylamine (1.7 g, 7.8 mmol) were slurried in 20 ml of N,N-dimethylformamide, and stirred at 65° C. for 15 hr. Once complete, the mixture was diluted with 50 ml of water, and extracted with ethyl acetate (3×-100 ml). The organics were combined, washed twice with water, washed with brine, dried over $Na_2SO_4$, and concentrated for a tan oil. The oil was washed with hexanes, and dried for a tan oil. The oil was recrystallized from methanol to afford the product as a white solid (2.5 g, 58% yield). $^1$H NMR and LCMS showed the desired product.

Part H. To a solution of the product from Part G (2.5 g, 4.3 mmol) in dichloromethane (5 ml) was added trifluoroacetic acid (5 ml, Aldrich). The reaction was stirred overnight at room temperature. Work up consisted of concentrating the mixture to one-third volume, and then dripping the residue into stirring diethyl ether (500 ml). The resulting solid was collected, washed with diethyl ether, and dried to afford the product as a white solid (1.9 g, 70% yield). $^1$H NMR showed the desired compound.

Part I. To the product of Part H (1.8 g, 2.8 mmol) in 6 ml of N,N-dimethyl formamide was added triethylamine (1.2 ml, 8.5 mmol, Aldrich) followed by N-hydroxybenzotriazole hydrate (0.83 g, 6.2 mmol, Aldrich), O-(tetrahydro-2H-pyran-2-yl)hydroxylamine (0.66 g, 5.6 mmol), and, lastly, 1-(3-dimethylaminopropyl)-3-ethyl carbodiimide hydrochloride (1.3 g, 7.0 mmol, Sigma). The mixture was stirred at room temperature for 5 hr. Workup consisted of diluting with water (15 ml) and ethyl acetate (100 ml). The organic was separated, and the aqueous was further extracted with ethyl acetate (2×-75 ml). The organics were combined, and washed with saturated $NaHCO_{3aq}$ (2×-150 ml), water (2×-100 ml), and brine (1×-200 ml). After drying over sodium sulfate, the organics were concentrated to a foamy oil, and crystallized from methanol to give the product as a white solid (1.7 g, 100% crude yield). $^1$H NMR showed the desired compound.

Part J. To the product of Part I (1.7 g, 2.8 mmol) were added methanol (1 ml) and 4N HCl in dioxane (10 ml). After stirring for 2 hr, the solvent was concentrated to one-third volume, and then diethyl ether was added. The resulting solid was filtered, washed with diethyl ether, and dried to afford the desired product as a pale yellow solid (1.6 g, 100% yield). $^1$H NMR showed the desired compound. HRMS for $C_{23}H_{31}F_4N_3O_5S$ showed $M^{+H}_{found}$=538.1978 ($M^{+H}_{calc}$=538.1993).

Example A69

Preparation of N-hydroxy-4-({4-[4-(2,2,2-trifluoroethoxy)phenyl]piperidin-1-yl}sulfonyl)tetrahydro-2H-pyran-4-carboxamide

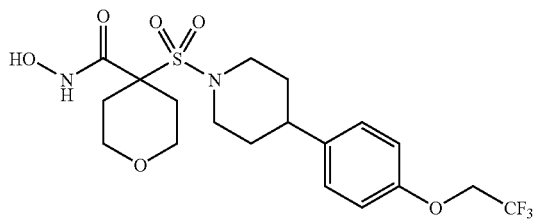

Part A. A round bottom flask was charged with 4-fluorobenzaldehyde (25 g, 202 mmol, Aldrich) and 3,3,3-trifluoroethanol (22.2 g, 222 mmol, Aldrich) in dimethylformamide (400 ml). Potassium carbonate (41.7 g, 303 mmol, Aldrich) was added, the reaction was heated to 80° C., and stirred for 18 hr. The reaction was diluted with water (500 ml) precipitating a white solid. The solid was collected by filtration, washed with water, and then dried to afford the product as a white solid (37 g, 90% yield). $^1$H NMR showed the desired compound.

Part B. A round bottom flask was charged with the product from Part A (37 g, 181.2 mmol), ethylacetoacetate (69.3 ml, 543.7 mmol, Aldrich), and piperidine (1.0 g, 11.7 mmol, Aldrich). The reaction was stirred without solvent for 3 days, resulting in a solid yellow mass. Ethanol (300 ml) was added, and the reaction was heated at reflux for 2 hr. After cooling to room temperature, precipitation occurred. The solids were filtered, washed with hexanes, and dried to afford a yellow solid. This solid was slowly added portion wise to a heated (85° C.) aqueous potassium hydroxide solution (26.1 g, 470 mmol in 23 ml water). After the addition, the reaction continued for 2 hr at 85° C., turning the reaction black. The reaction was cooled by adding ice (100 g). The resulting mixture was washed with ethyl acetate (50 ml) and separated. The aqueous was titrated to pH 1 with concentrated HCl. The product was extracted out with dichloromethane (3×-200 ml). The organics were combined, dried over Na$_2$SO$_4$, and concentrated to yield the dicarboxylic acid as a yellow solid (27.7 g, 50% yield over three steps). $^1$H NMR showed the desired compound.

Part C. A round bottom flask was charged with the product from Part B (27.6 g, 90.1 mmol) and urea (8.1 g, 135 mmol). The reaction was heated to 170° C. for 2 hr, and then cooled to 80° C. Ethanol (40 ml) was added, and the reaction stirred at reflux for 30 min. The reaction was cooled to 0° C., and then filtered for solids. The solids were collected, washed with hexanes, and dried to afford the diketopiperidine product as a beige solid (24.1 g, 93% yield). $^1$H NMR showed the desired compound.

Part D. A round bottom flask was charged with a lithium aluminum hydride solution (251 ml, 1.0 M), and then heated to 40–60° C. The solid from Part C (42 g, 84 mmol) was added portion wise keeping the temperature below 60° C. After the addition, the reaction flask was equipped with a condenser and refluxed for 1.5 hr. Work up consisted of cooling the mixture to room temperature, carefully adding water (2 ml), and then slurring with sodium sulfate (100 g). The solids were removed by filtration. The filtrate was dried over sodium sulfate, and concentrated affording the piperidine product as an orange oil (17 g, 78% yield). $^1$H NMR showed the desired compound.

Part E. A round bottom flask was charged with the product from Part D (17.0 g, 65.6 mmol) and triethyl amine (9.6 ml, 68.8 mmol, Aldrich) in dichloromethane (110 ml). After cooling to 0° C., a solution of methylsulfonyl chloride (5.3 ml, 68.8 mmol) in dichloromethane (10 ml) was added drop wise. After the addition, the ice bath was removed, and the reaction stirred at room temperature for 18 hr. The reaction was concentrated to dryness, and the residue was taken up in ethyl acetate (200 ml). The organic was washed with 10% HCl$_{aq}$, water, and brine, dried over sodium sulfate, and concentrated for a mix of orange and white solids. The solids were recrystallized from methanol, collected, washed with hexanes, and dried affording the desired product (14.9 g, 67% yield). $^1$H NMR showed the desired compound.

Part F. A solution of the product from Part E (14.8 g, 43.9 mmol) and t-butylcarboxlyate anhydride (11.5 g, 52.7 mmol, Aldrich) in tetrahydrofuran (80 ml, Aldrich) was cooled to −75° C. A solution of lithium bis(trimethylsilyl)amide (1.0 M (Aldrich) in tetrahydrofuran, 132 ml, 132 mmol) was slowly added, keeping the temperature below −65° C. After the addition, the mixture was warmed to 0° C., and stirred 1 hr. The mixture was then cooled back to −75° C., and quenched with a saturated aqueous solution of ammonium chloride. The mixture was warmed to room temperature, and then separated. The aqueous was extracted twice with ethyl acetate. The organics were combined and washed twice with water, washed with brine, dried over Na$_2$SO$_4$, and concentrated for brown residue. The residue was slurried on diethyl ether, and filtered affording the desired product (12.0 g, 62% yield). $^1$H NMR showed the desired product.

Part G. The product from Part F (4.0 g, 9.1 mmol), 18-crown-6 (0.5 g, catalytic amount, Aldrich), potassium carbonate (5.0 g, 36.6 mmol, Aldrich), and bis(bromoethyl) ether (4.2 g, 18.2 mmol, Aldrich) were slurried in N,N-dimethylformamide (15 ml), and stirred at 65° C. for 15 hr. Once complete, the mixture was diluted with water (50 ml), and extracted with ethyl acetate (3×-100 ml). The organics were combined, washed twice with water, washed with brine, dried over Na$_2$SO$_4$, and concentrated for a tan oil. The oil was washed with hexanes, and dried for a tan oil. The oil was recrystallized from methanol to afford the product as a white solid (2.5 g, 54% yield). $^1$H NMR and LCMS showed the desired product.

Part H. To a solution of the product from Part G (2.5 g, 4.9 mmol) in dichloromethane (5 ml) was added trifluoroacetic acid (5 ml, Aldrich). The reaction was stirred overnight at room temperature. Work up consisted of concentrating the mixture to one-third volume, and then dripping the residue into stirring diethyl ether (500 ml). The resulting solid was collected, washed with diethyl ether, and dried to afford the product as a white solid (1.8 g, 82% yield). $^1$H NMR showed the desired compound.

Part I. To the product of Part H (1.8 g, 4.0 mmol) in N,N-dimethylformamide (10 ml) was added triethylamine (0.6 ml, 4.0 mmol, Aldrich) followed by N-hydroxybenzotriazole hydrate (1.1 g, 8.0 mmol, Aldrich), O-(tetrahydro-2H-pyran-2-yl)hydroxylamine (0.94 g, 8.0 mmol), and, lastly, 1-(3-dimethylaminopropyl)-3-ethylcarbodiimide hydrochloride (1.7 g, 8.8 mmol, Sigma). The mixture was stirred at room temperature for 5 hr. Workup consisted of diluting with water (15 ml) and ethyl acetate (100 ml). The organic was separated, and the aqueous was further extracted with ethyl acetate (2×-75 ml). The organics were combined and washed with saturated NaHCO$_{3aq}$ (2×-150 ml), water (2×-100 ml), and brine (1×-200 ml). After drying over sodium sulfate, the organics were concentrated to a foamy oil, and crystallized from methanol to give the product as a white solid (2.2 g, 100% crude yield). $^1$H NMR showed the desired compound.

Part J. To the product of Part 1 (2.2 g, 4.0 mmol) were added methanol (1 ml) and 4N HCl in dioxane (10 ml). After stirring for 2 hr, the solvent was concentrated to one-third volume, and then diethyl ether was added. The resulting solid was filtered, washed with diethyl ether, and dried to afford the desired product as a white solid (1.2 g, 67% yield). $^1$H NMR showed the desired compound. HRMS for $C_{19}H_{25}F_3N_2O_6S$ showed $M^{+H}_{found}$=467.1431 ($M^{+H}_{calc}$=467.1464).

Table 8 below lists MMP inhibition $K_i$ values for the compounds of Examples A35 thru A67. As with the tables above, all $K_i$ values are given in nM units.

TABLE 8

| Compound Example | Structure | MMP-1 Ki | MMP-2 Ki | MMP-9 Ki | MMP-13 Ki | MMP-14 Ki |
| --- | --- | --- | --- | --- | --- | --- |
| A35 | 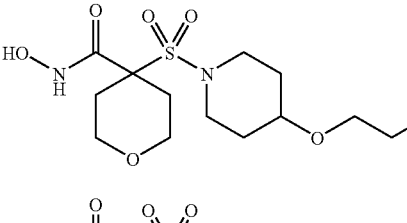 | 5290 | 2.22 | 2.68 | 0.28 | 1710 |
| A36 | 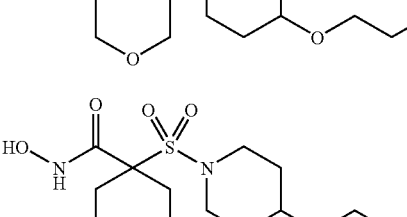 | >10000 | 3.51 | 0.95 | 5.92 | 1940 |
| A36A | 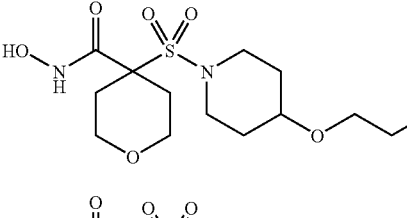 | >10000 | 6 | 2.65 | 9.36 | 816 |
| A36B | 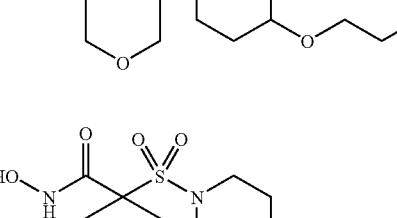 | >10000 | 1.87 | 1.34 | 0.63 | 1080 |
| A36C | 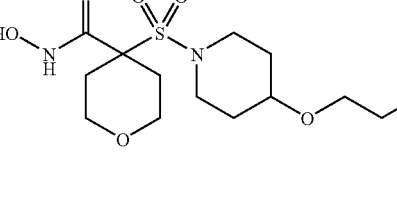 | >10000 | 3.93 | 3.41 | 1.22 | 1900 |
| A36D | 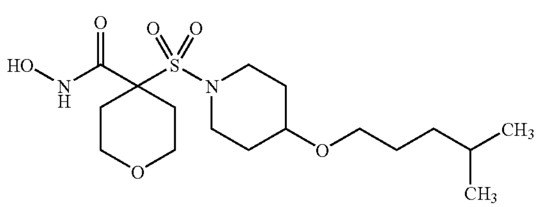 | >10000 | 11.9 | 39.1 | 19.9 | 4060 |
| A36E | 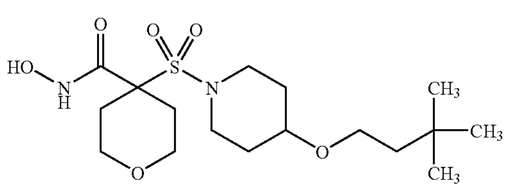 | >10000 | 112 | 365 | 65.8 | 4250 |

TABLE 8-continued
| Compound Example | Structure | MMP-1 Ki | MMP-2 Ki | MMP-9 Ki | MMP-13 Ki | MMP-14 Ki |
|---|---|---|---|---|---|---|
| A36F | 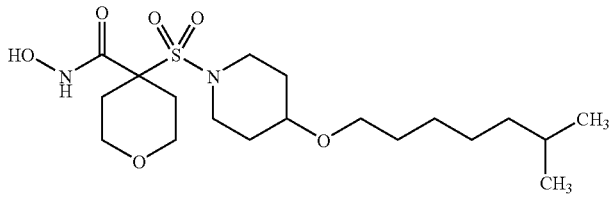 | >10000 | 2.47 | 2.26 | 1.11 | 1900 |
| A36G | 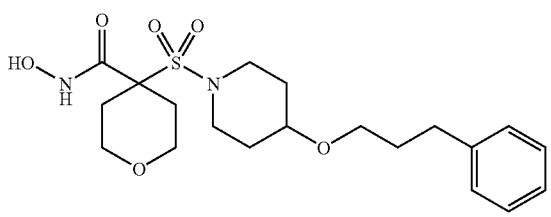 | >10000 | 31.1 | 16.4 | 30.2 | 2610 |
| A36H | 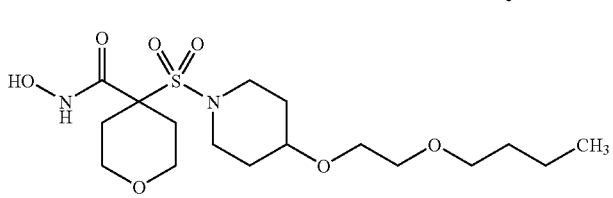 | >10000 | 60.1 | 45.7 | 70.5 | >10000 |
| A36I | 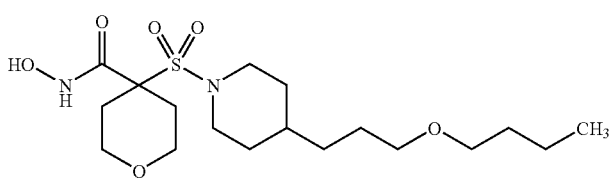 | >10000 | 9.08 | 2.57 | 7.7 | 6370 |
| A36J | 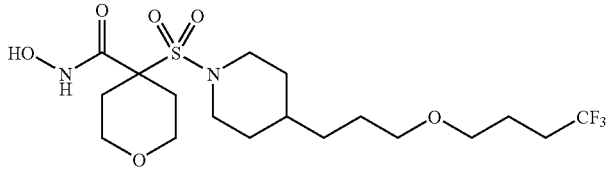 | >10000 | 7.8 | 10.3 | 4.38 | 6550 |
| A37 | 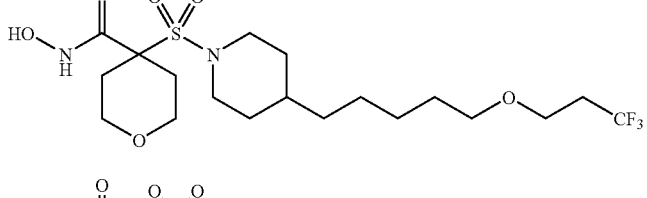 | 6710 | 0.97 | 0.30 | 0.30 | 690 |
| A38 | 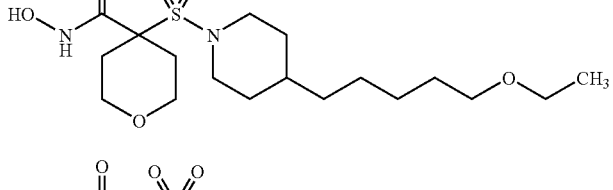 | 4580 | 0.72 | 2.25 | 0.52 | 1190 |
| A39 | 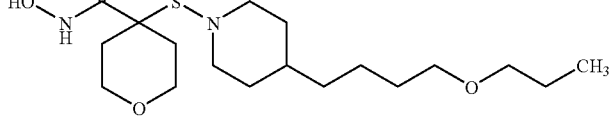 | 1990 | 12.5 | 10 | 1.99 | 1410 |

TABLE 8-continued

| Compound Example | Structure | MMP-1 Ki | MMP-2 Ki | MMP-9 Ki | MMP-13 Ki | MMP-14 Ki |
|---|---|---|---|---|---|---|
| A40 | 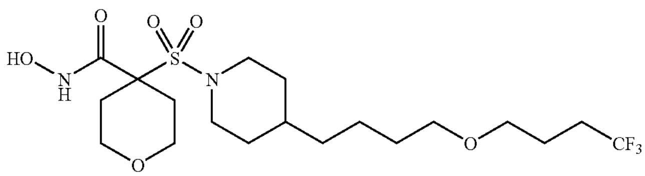 | 4260 | 6.99 | 46.4 | 0.60 | 3420 |
| A41 | 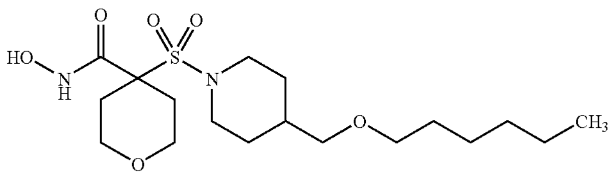 | >10000 | 8.38 | 1.79 | 7.95 | 7210 |
| A42 | 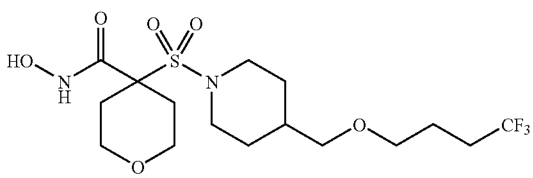 | >10000 | 22 | 28.6 | 33.3 | >10000 |
| A43 | 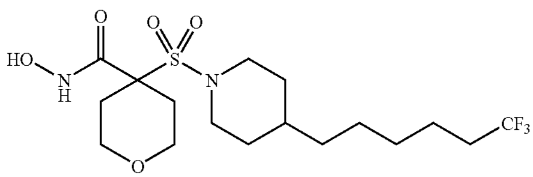 | 3100 | 0.33 | 0.19 | 0.58 | 757 |
| A44 | 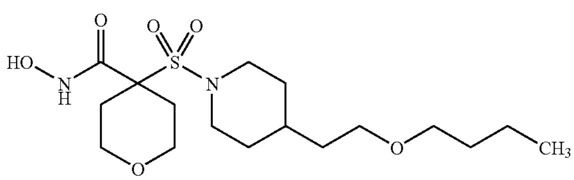 | >10000 | 27.3 | 12.5 | 38.2 | >10000 |
| A45 | 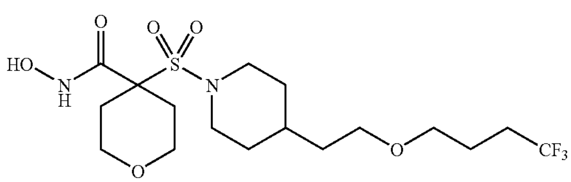 | >10000 | 23.6 | 16.8 | 12.2 | >10000 |
| A46 | 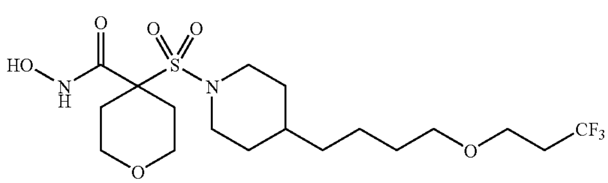 | 1500 | 5.97 | 17.5 | 0.52 | 3610 |
| A47 | 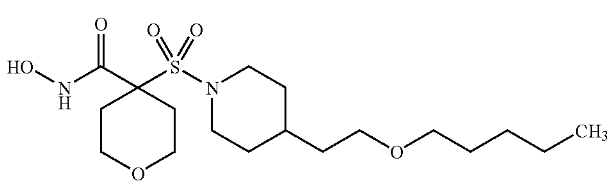 | >10000 | 18.6 | 10.2 | 12.7 | >10000 |

TABLE 8-continued

| Compound Example | Structure | MMP-1 Ki | MMP-2 Ki | MMP-9 Ki | MMP-13 Ki | MMP-14 Ki |
|---|---|---|---|---|---|---|
| A48 | 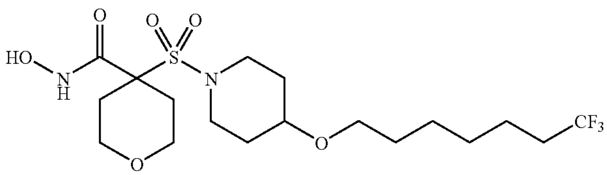 | >10000 | 3.49 | 8.23 | 1.13 | 2710 |
| A49 | 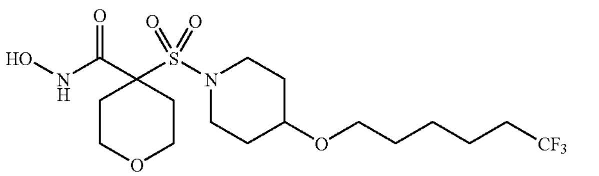 | >10000 | 3.81 | 3.1 | 2.87 | 6740 |
| A50 | 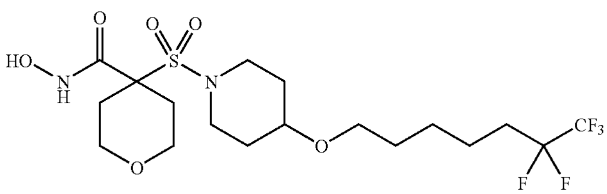 | >10000 | 1.57 | 7.1 | 0.60 | 4560 |
| A51 | 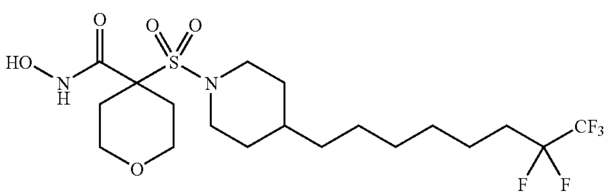 | 5110 | 0.27 | 1.01 | 0.27 | 1260 |
| A52 | 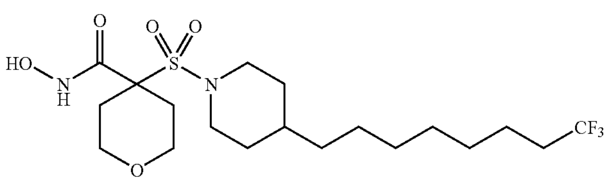 | 3930 | 0.55 | 1.03 | 0.23 | 922 |
| A53 | 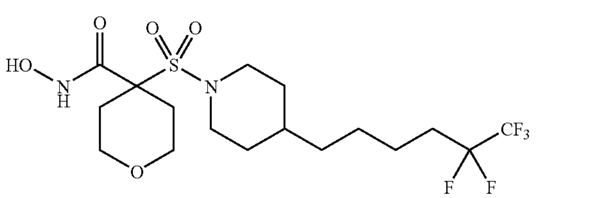 | 2880 | 1.10 | 2.46 | 2.45 | 2360 |
| A54 | 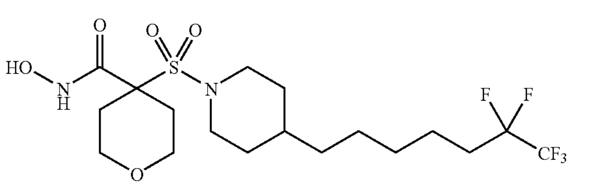 | >10000 | 1.06 | 0.81 | 0.67 | 3410 |

TABLE 8-continued

| Compound Example | Structure | MMP-1 Ki | MMP-2 Ki | MMP-9 Ki | MMP-13 Ki | MMP-14 Ki |
|---|---|---|---|---|---|---|
| A55 | 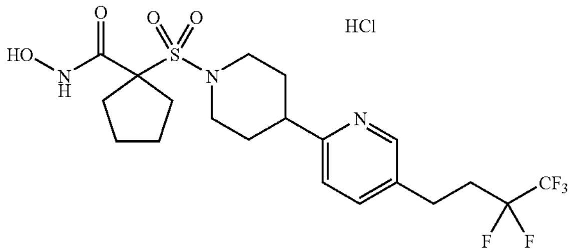 | 1610 | 0.27 | 0.13 | 0.06 | 700 |
| A56 | 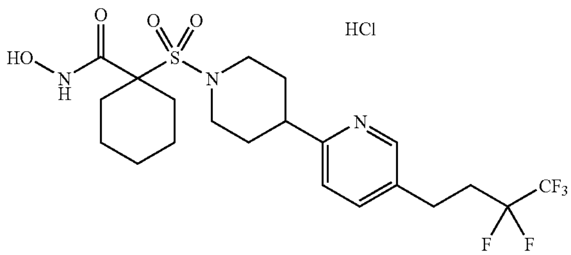 | 2470 | 0.47 | 0.15 | 0.14 | 1010 |
| A57 | 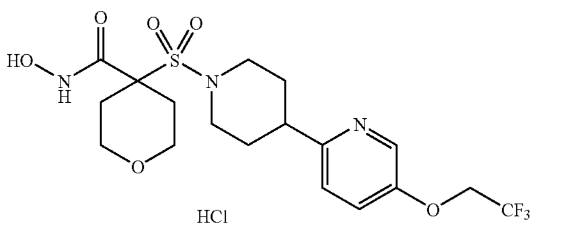 | 1570 | 0.53 | 0.48 | 0.34 | 2020 |
| A58 | 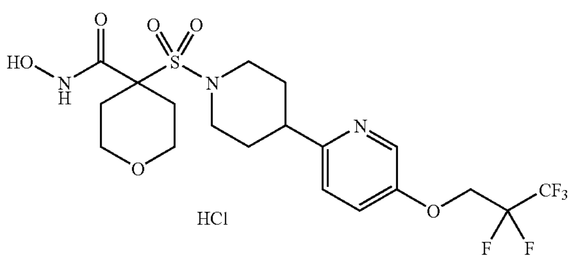 | 1550 | 0.52 | 1.37 | 0.24 | 6230 |
| A59 | 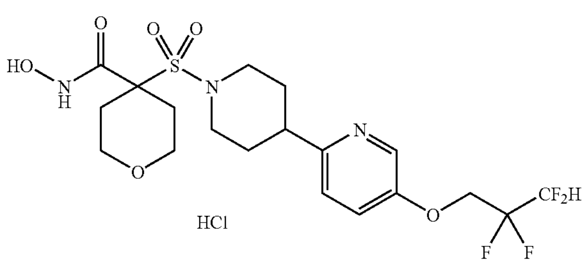 | 1660 | 0.76 | 1.54 | 0.62 | 5150 |
| A60 | 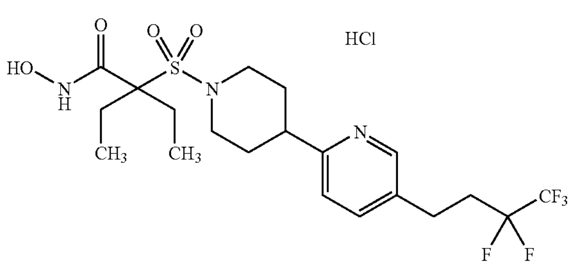 | 9180 | 1.23 | 0.63 | 0.40 | 6070 |

TABLE 8-continued

| Compound Example | Structure | MMP-1 Ki | MMP-2 Ki | MMP-9 Ki | MMP-13 Ki | MMP-14 Ki |
|---|---|---|---|---|---|---|
| A61 | 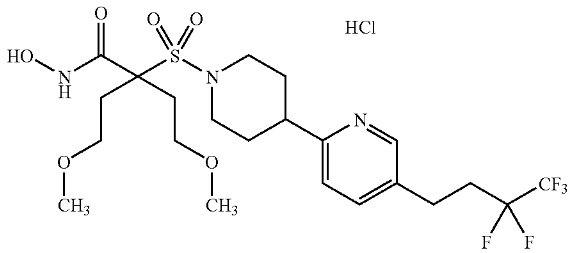 | 3530 | 0.98 | 0.38 | 0.16 | 4170 |
| A62 | 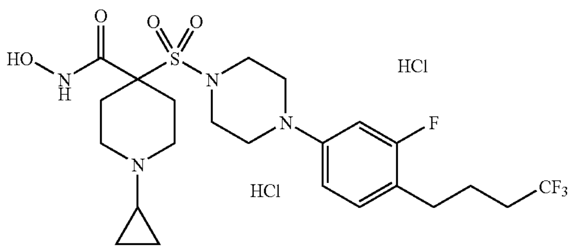 | >10000 | 0.73 | 1.74 | 0.56 | 9050 |
| A63 | 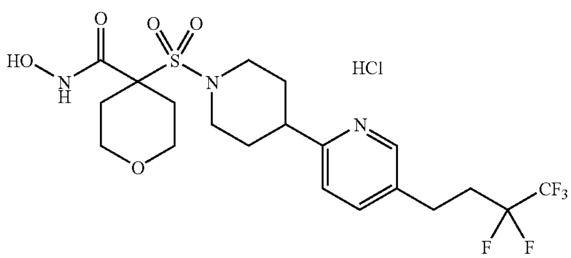 | 4370 | 0.50 | 0.22 | 0.39 | 1840 |
| A64 | 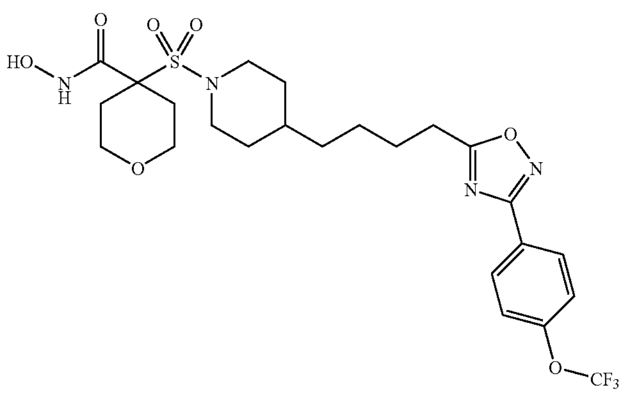 | 8880 | 63.8 | 273 | 0.51 | >10000 |
| A65 | 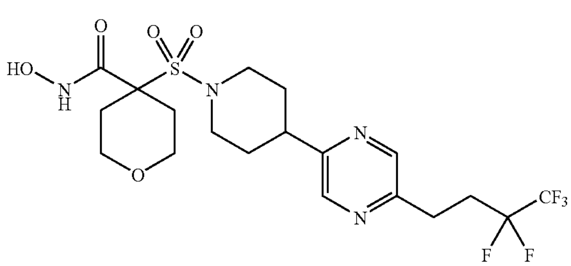 | >10000 | 2.15 | 0.19 | 0.47 | 3870 |

TABLE 8-continued

| Compound Example | Structure | MMP-1 Ki | MMP-2 Ki | MMP-9 Ki | MMP-13 Ki | MMP-14 Ki |
|---|---|---|---|---|---|---|
| A66 | 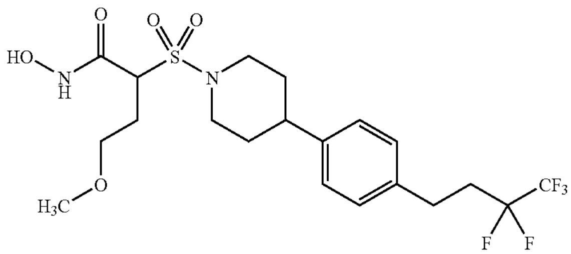 | >10000 | 2.15 | 1.15 | 1.28 | 9640 |
| A67 | 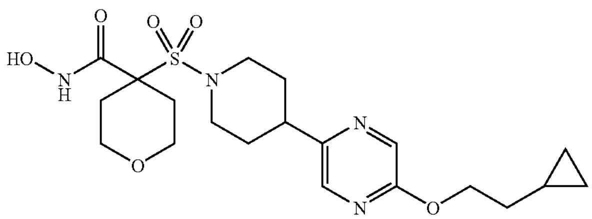 | 4450 | 0.66 | 0.07 | 0.22 | 1350 |

Examples A70–207

Further examples of compounds contemplated by this invention are shown in Table 9, along with corresponding mass spectroscopy and MMP inhibition data obtained by Applicants. As with earlier tables, all in vitro $K_i$ results in Table 9 are given in nM units,

TABLE 9

Additional Examples of Piperazinyl- or Piperidinyl-Sulfonylmethyl Hydroxamic acid Compounds

| Ex. | Structure | Calc. Mass | Observed Mass | MMP-1 $K_i$ (IC-50) |
|---|---|---|---|---|
| A70 | 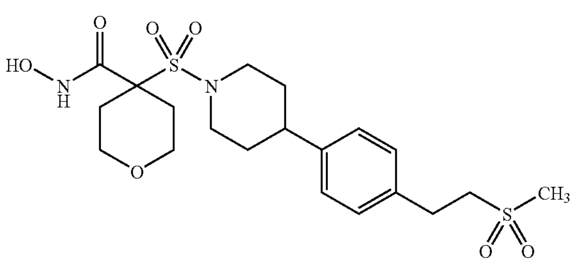 | 497 | 497 | |
| A71 | 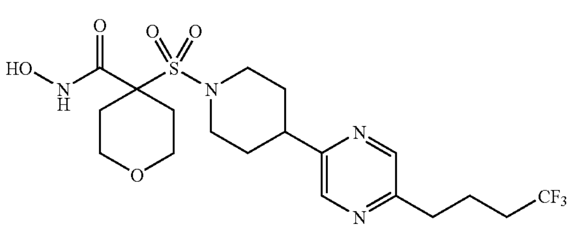 | 481.1727 | 481.1720 | |

TABLE 9-continued

Additional Examples of
Piperazinyl- or Piperidinyl-Sulfonylmethyl Hydroxamic acid Compounds

| ID | Structure | | | |
|---|---|---|---|---|
| A72 | 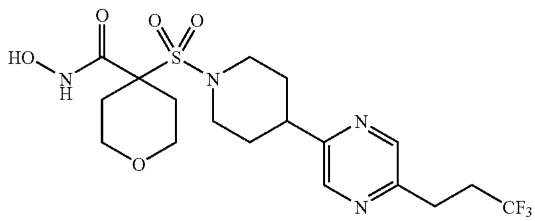 | | | >10000 |
| A73 | 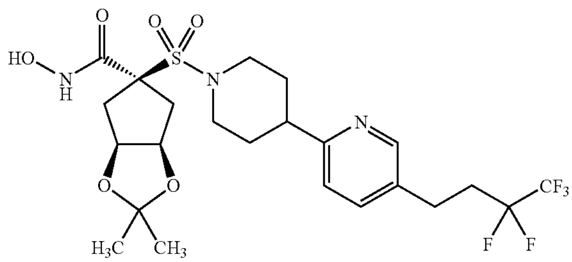 | 572.2000 | 572.1800 | 716 |
| A74 | 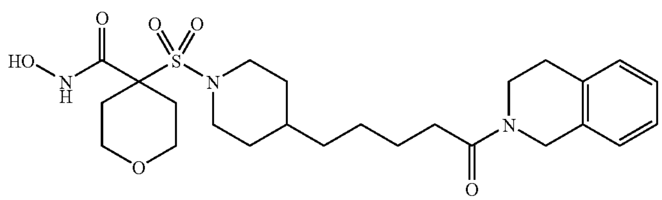 | 508.2476 | 508.2481 | 512 |
| A75 | 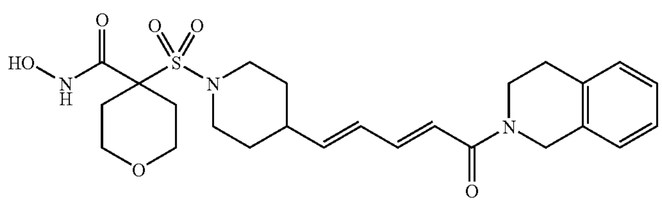 | 504.2163 | 504.2149 | 6150 |
| A76 | 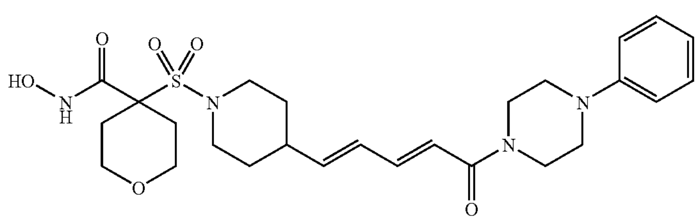 | 533.2428 | 533.2443 | >10000 |
| A77 | 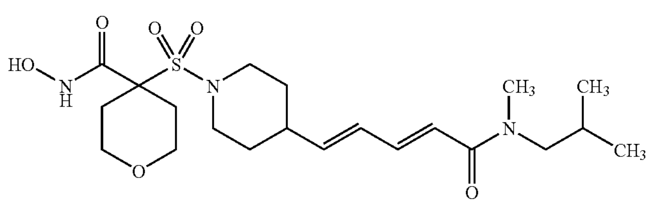 | 458.2319 | 458.2339 | 6200 |
| A78 | 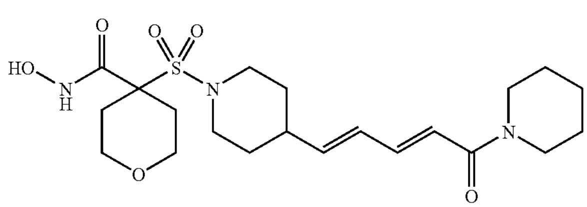 | 456.2163 | 456.2197 | 2420 |

TABLE 9-continued

Additional Examples of
Piperazinyl- or Piperidinyl-Sulfonylmethyl Hydroxamic acid Compounds

| | | | | |
|---|---|---|---|---|
| A79 | [structure] | 484.2476 | 484.2464 | >10000 |
| A80 | [structure] | 490.2006 | 490.2004 | 5450 |
| A81 | [structure] | 496.2476 | 496.2479 | 4440 |
| A82 | [structure] | 490.2006 | 490.1994 | >10000 |
| A83 | [structure] | 444.2163 | 444.2185 | 277 |
| A84 | [structure] | 504.2144 | 504.2161 | 9770 |
| A85 | [structure] | 462.2268 | 462.2293 | 3420 |

TABLE 9-continued

Additional Examples of
Piperazinyl- or Piperidinyl-Sulfonylmethyl Hydroxamic acid Compounds

| | | | | |
|---|---|---|---|---|
| A86 | | 406.2006 | 406.2031 | 516 |
| A87 | | 494.2319 | 494.2335 | 927 |
| A88 | | 500.2789 | 500.2763 | 2780 |
| A89 | | 552.1986 | 552.2122 | 1030 |
| A90 | | 445 | 445 | 1190 |
| A91 | | 462.2632 | 462.2618 | 2580 |
| A92 | | 460.2476 | 460.2478 | 3910 |

TABLE 9-continued

Additional Examples of
Piperazinyl- or Piperidinyl-Sulfonylmethyl Hydroxamic acid Compounds

| | | | | |
|---|---|---|---|---|
| A93 | | 500.2225 | 500.2260 | 1050 |
| A94 | | 482.2319 | 482.2304 | 2820 |
| A95 | | 479 | 479 | 7630 |
| A96 | | 488.2789 | 488.2775 | 1110 |
| A97 | | 446.2319 | 446.2302 | 496 |
| A98 | | 537.2741 | 537.2725 | 1620 |

TABLE 9-continued

Additional Examples of
Piperazinyl- or Piperidinyl-Sulfonylmethyl Hydroxamic acid Compounds

| | | | | |
|---|---|---|---|---|
| A99 | [structure] | 486.2268 | 486.2228 | 356 |
| A100 | [structure] HCl | 473 | 473 | >10000 |
| A101 | [structure] HCl | 498.1487 | 498.1485 | 721 |
| A102 | [structure] | 479 | 479 | 6280 |
| A103 | [structure] | 407.1874 | 407.1840 | 363 |
| A104 | [structure] HCl | 526.1800 | 526.1815 | 8590 |

TABLE 9-continued

Additional Examples of
Piperazinyl- or Piperidinyl-Sulfonylmethyl Hydroxamic acid Compounds

| | | | | |
|---|---|---|---|---|
| A105 | (structure) HCl | 450.1674 | 450.1691 | 2170 |
| A106 | (structure) HCl | 465 | 465 | 5460 |
| A107 | (structure) | 561.2052 | 561.2026 | 4440 |
| A108 | (structure) | 502.1676 | 502.166 | 1630 |
| A109 | (structure) HCl | 587.1963 | 587.196 | 8300 |
| A110 | (structure) | 439.201 | 439.2021 | >10000 |

TABLE 9-continued
Additional Examples of
Piperazinyl- or Piperidinyl-Sulfonylmethyl Hydroxamic acid Compounds
| | | | | |
|---|---|---|---|---|
| A111 | 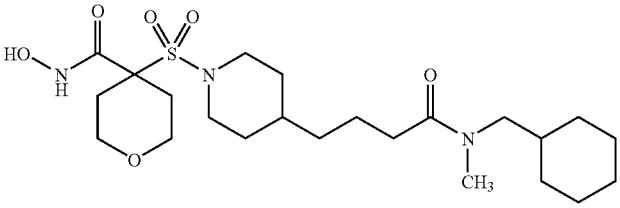 | 488.2789 | 488.2796 | >10000 |
| A112 | 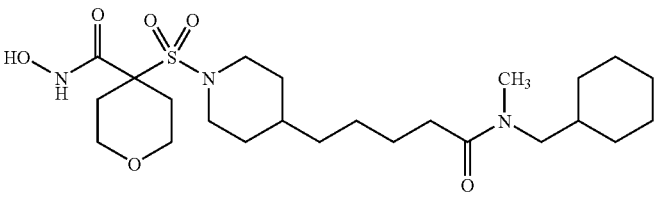 | 502.2945 | 502.2912 | 708 |
| A113 | 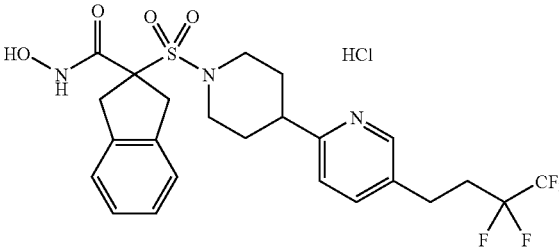 | 548.1642 | 548.166 | 9730 |
| A114 | 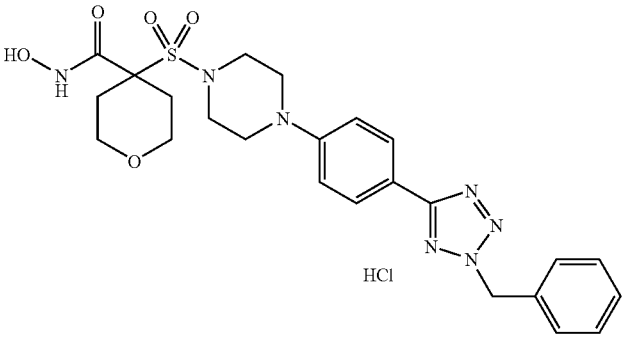 | | | 5410 |
| A115 | 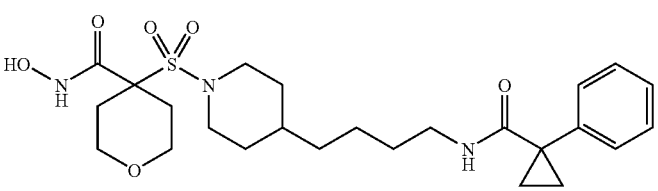 | 508.2476 | 508.246 | >10000 |
| A116 | 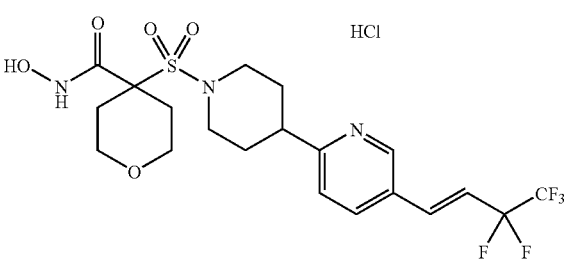 | 514.1436 | 514.1427 | 1700 |

TABLE 9-continued

Additional Examples of
Piperazinyl- or Piperidinyl-Sulfonylmethyl Hydroxamic acid Compounds

| ID | Structure | Calc. Mass | Obs. Mass | IC50 |
|---|---|---|---|---|
| A117 | | 441.2066 | 441.2148 | >10000 |
| A118 | | 573.1806 | 573.1823 | 6600 |
| A119 | | 461.2428 | 461.2388 | >10000 |
| A120 | | 451 | 451 | 4910 |
| A121 | | 524.1676 | 524.168 | >10000 |
| A122 | | 474.1487 | 474.1476 | 3100 |

TABLE 9-continued
Additional Examples of
Piperazinyl- or Piperidinyl-Sulfonylmethyl Hydroxamic acid Compounds
| | | | | | |
|---|---|---|---|---|---|
| A123 | 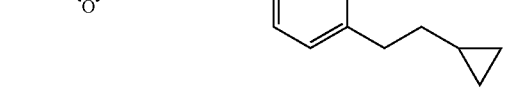 | | 437 | 437 | 5160 |
| A124 |  | | 426.2063 | 426.2060 | 3040 |
| A125 | 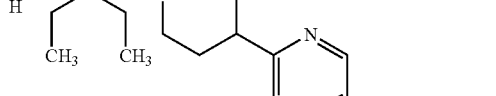 | | 489.2741 | 489.2728 | >10000 |
| A126 | 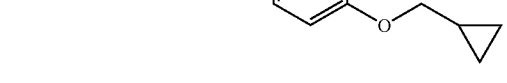 | | 486.1486 | 486.1492 | 2750 |
| A127 | 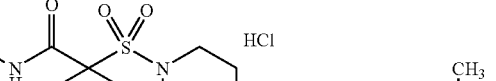 | | 398.1750 | 398.1750 | 1610 |
| A128 | 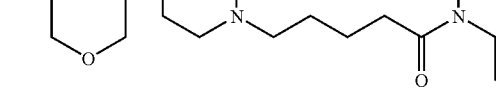 | | 516.1592 | 516.1608 | 5190 |

TABLE 9-continued
Additional Examples of
Piperazinyl- or Piperidinyl-Sulfonylmethyl Hydroxamic acid Compounds
| | | | | |
|---|---|---|---|---|
| A129 | 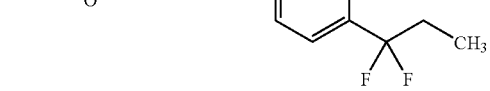 HCl | 448.1718 | 447.173 | 3650 |
| A130 | 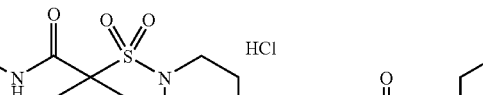 HCl | 475.2585 | 475.2603 | >10000 |
| A131 | 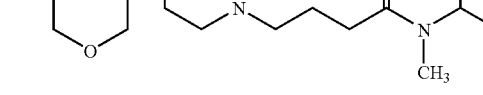 2HCl | 606.2173 | 606.2197 | >10000 |
| A132 | 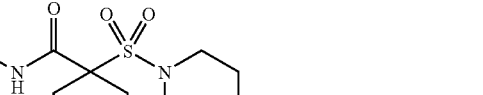 | 443.1959 | 443.1934 | 7170 |
| A133 | 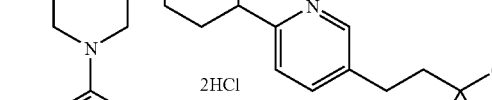 HCl | 437.1621 | 438.00 | 1900 |
| A134 |  HCl | 482.1750 | 482.1772 | 1250 |

TABLE 9-continued
Additional Examples of
Piperazinyl- or Piperidinyl-Sulfonylmethyl Hydroxamic acid Compounds
| | | | | |
|---|---|---|---|---|
| A135 | 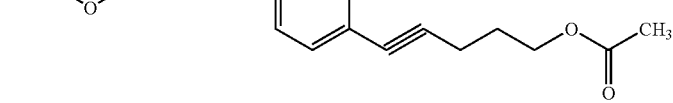 | 492.1804 | 492.1829 | 2620 |
| A136 |  | 492.1804 | 492.1801 | 4300 |
| A137 | 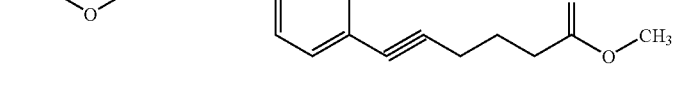 | 448.1906 | 448.1923 | 1260 |
| A138 | 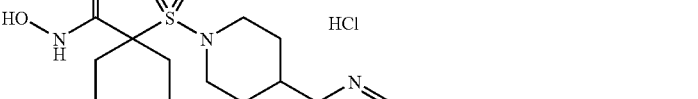 | 448.1906 | 448.1920 | 3440 |
| A139 | 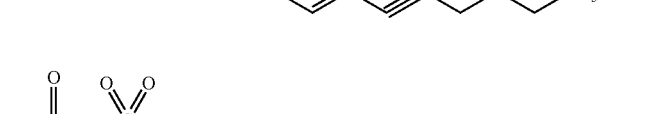 | | | 2340 |
| A140 | 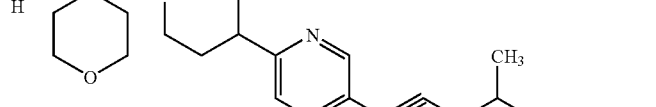 | 538.1829 | 538.1824 | >10000 |

TABLE 9-continued

Additional Examples of
Piperazinyl- or Piperidinyl-Sulfonylmethyl Hydroxamic acid Compounds

| | | | | |
|---|---|---|---|---|
| A141 | [structure with HCl] | 472.2112 | 472.2134 | 6900 |
| A142 | [structure] | 482.2319 | 482.2328 | >10000 |
| A143 | [structure] | 468.2163 | 468.2160 | >10000 |
| A144 | [structure] | 474.2632 | 474.2609 | >10000 |
| A145 | [structure] | 496.2470 | 496.2465 | >10000 |
| A146 | [structure] | 486.2069 | 486.2071 | >10000 |

TABLE 9-continued

Additional Examples of
Piperazinyl- or Piperidinyl-Sulfonylmethyl Hydroxamic acid Compounds

| A147 | | 482.2319 | 482.2291 | >10000 |
| --- | --- | --- | --- | --- |
| A148 | | 415.1509 | 415.1525 | 2710 |
| A149 | | 444.1805 | 444.1792 | >10000 |
| A150 | | 538.1829 | 538.1814 | >10000 |
| A151 | | 441.1802 | 441.1781 | >10000 |
| A152 | | 447 | 447 | >10000 |

TABLE 9-continued

Additional Examples of
Piperazinyl- or Piperidinyl-Sulfonylmethyl Hydroxamic acid Compounds

| | | | | |
|---|---|---|---|---|
| A153 | | | | >10000 |
| A154 | | 451.1764 | 451.1768 | >10000 |
| A155 | | 467.1423 | 467.1441 | 1220 |
| A156 | | 462.1874 | 462.1878 | 4550 |
| A157 | | 498.1686 | 498.1699 | >10000 |

TABLE 9-continued

Additional Examples of
Piperazinyl- or Piperidinyl-Sulfonylmethyl Hydroxamic acid Compounds

| ID | Structure | Calc'd | Found | IC50 |
|---|---|---|---|---|
| A158 | (structure; 2HCl) | 625.1675 | 625.1684 | >10000 |
| A159 | (structure; HCl) | 440.1855 | 440.187 | 1840 |
| A160 | (structure) | 562.1709 | 563.1776 | >10000 |
| A161 | (structure; HCl) | 447 | 447 | 2970 |
| A162 | (structure; HCl) | 453 | 453 | 4510 |
| A163 | (structure) | 566.2142 | 566.2154 | 1490 |

TABLE 9-continued

Additional Examples of
Piperazinyl- or Piperidinyl-Sulfonylmethyl Hydroxamic acid Compounds

| | | | |
|---|---|---|---|
| A164 | | | >10000 |
| A165 | | 592.2017 | 592.2023 | >10000 |
| A166 | | 442.2012 | 442.2023 | >10000 |
| A167 | | 591.2064 | 591.2079 | >10000 |
| A168 | | 464.1668 | 464.1661 | 2290 |

TABLE 9-continued
Additional Examples of
Piperazinyl- or Piperidinyl-Sulfonylmethyl Hydroxamic acid Compounds
| | | | | |
|---|---|---|---|---|
| A169 | 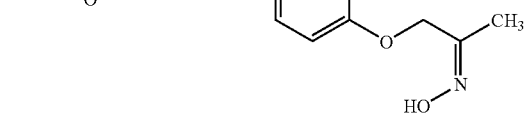 | 457.2 | 457.2 | 5370 |
| A170 | 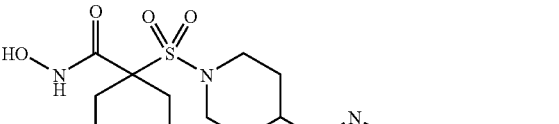 | 515.1751 | 515.1754 | >10000 |
| A171 | 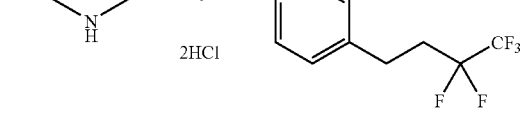 | 438.1699 | 438.1701 | 4180 |
| A172 | 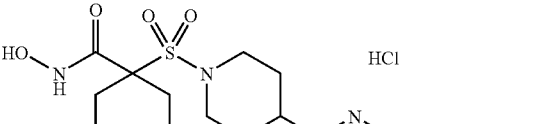 | 440.1856 | 440.1845 | 4070 |
| A173 | 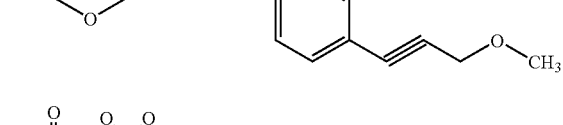 | 481 | 481 | >10000 |
| A174 | 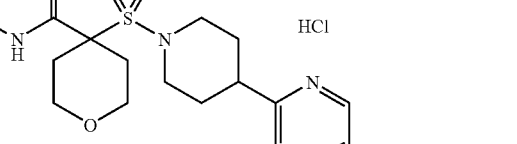 | 605.2221 | 605.2232 | >10000 |

TABLE 9-continued
Additional Examples of
Piperazinyl- or Piperidinyl-Sulfonylmethyl Hydroxamic acid Compounds
| | | | | |
|---|---|---|---|---|
| A175 | 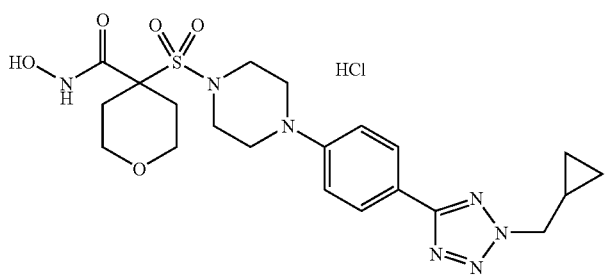 | 492.2029 | 292.2053 | 854 |
| A176 | 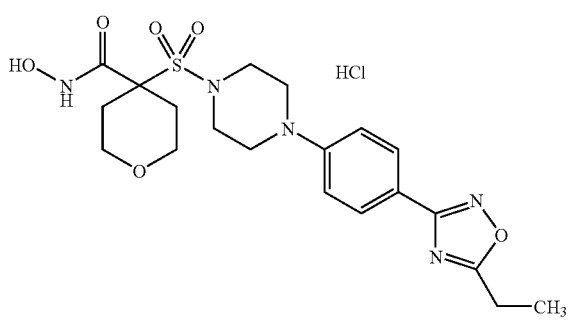 | 466.176 | 466.1779 | 1710 |
| A177 | 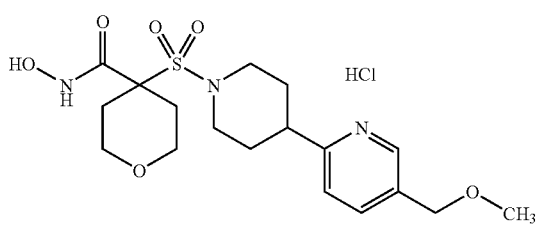 | 413 | 413 | >10000 |
| A178 | 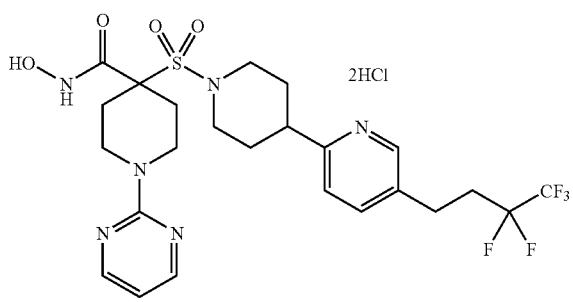 | 593.1969 | 593.1967 | >10000 |
| A179 | 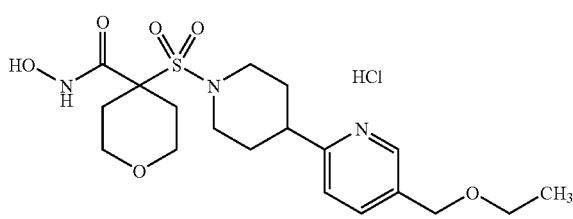 | 427 | 427 | >10000 |

TABLE 9-continued

Additional Examples of
Piperazinyl- or Piperidinyl-Sulfonylmethyl Hydroxamic acid Compounds

| | | | | |
|---|---|---|---|---|
| A180 | [structure with tetrahydropyran, sulfonyl-piperazine, 3-fluoro-4-cyanophenyl; HCl] | 413.1295 | 413.1314 | 8890 |
| A181 | [structure with N-ethyl piperidine, sulfonyl-piperidine, pyridine-CH2CH2CF3; 2HCl] | 543.2064 | 543.2057 | >10000 |
| A182 | [structure with N-(2-methoxyethyl)piperidine, sulfonyl-piperidine, pyridine-CH2CH2CF3; 2HCl] | 573.217 | 573.217 | >10000 |
| A183 | [structure with N-(CH2CF3) piperidine, sulfonyl-piperazine, phenyl-CH2CH2CH2CF3; HCl] | 561.197 | 561.1969 | >10000 |
| A184 | [structure with tetrahydropyran, sulfonyl-piperazine, pyridine-CH2CH2CF3; HCl] | 467.1576 | 467.1584 | 7050 |
| A185 | [structure with tetrahydropyran, sulfonyl-piperidine, CH2CH2-phenyl] | 397.1792 | 397.1814 | 1720 |

TABLE 9-continued

Additional Examples of
Piperazinyl- or Piperidinyl-Sulfonylmethyl Hydroxamic acid Compounds

| | | | | |
|---|---|---|---|---|
| A186 | | 466.1873 | 466.1878 | 924 |
| A187 | | 453.1266 | 453.1277 | 936 |
| A188 | | 436.1655 | 436.1665 | 3310 |
| A189 | | 557 | 557 | >10000 |
| A190 | | 517.1544 | 517.1533 | >10000 |

TABLE 9-continued

Additional Examples of
Piperazinyl- or Piperidinyl-Sulfonylmethyl Hydroxamic acid Compounds

| | | | |
|---|---|---|---|
| A191 | 460.1577 | 460.1574 | 1710 |
| A192 | 579.1876 | 579.1883 | >10000 |
| A193 | 450.1811 | 450.1827 | 4710 |
| A194 | 436.1681 | 436.1667 | >10000 |
| A195 | 465.1608 | 465.1625 | 1570 |

TABLE 9-continued
Additional Examples of
Piperazinyl- or Piperidinyl-Sulfonylmethyl Hydroxamic acid Compounds
| A196 | 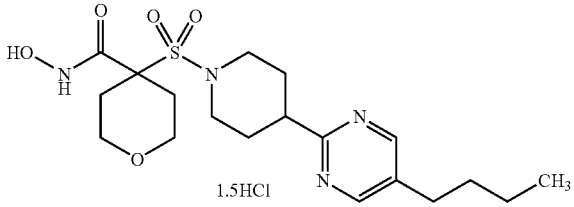 1.5HCl | 426 | 426 | >10000 |
|---|---|---|---|---|
| A197 | 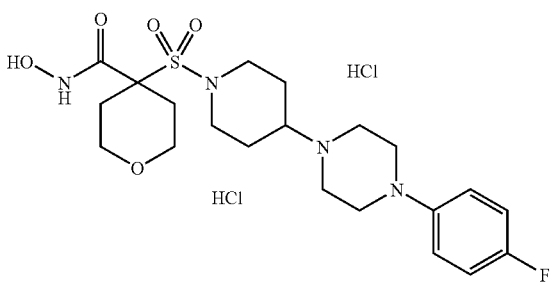 | | | >10000 |
| A198 | 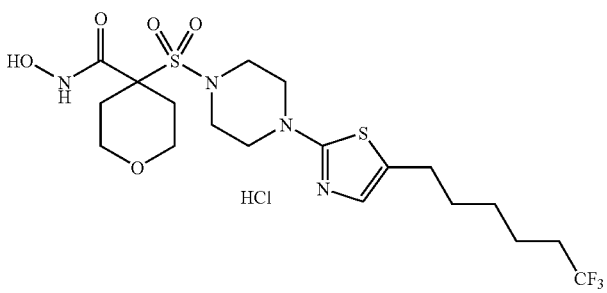 | 515.1604 | 515.1591 | >10000 |
| A199 | 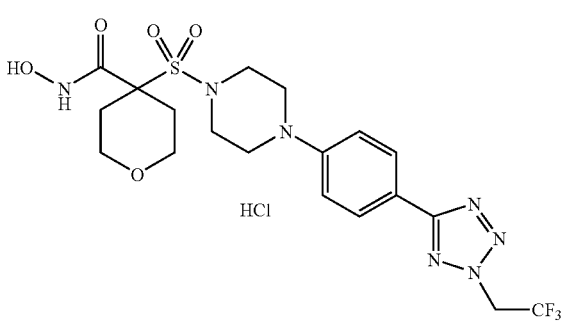 | 520.159 | 520.1586 | 287 |
| A200 | 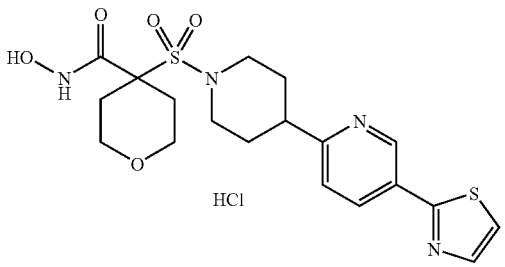 | 453.1266 | 453.1285 | >10000 |

TABLE 9-continued
Additional Examples of
Piperazinyl- or Piperidinyl-Sulfonylmethyl Hydroxamic acid Compounds
| | | | | |
|---|---|---|---|---|
| A201 | 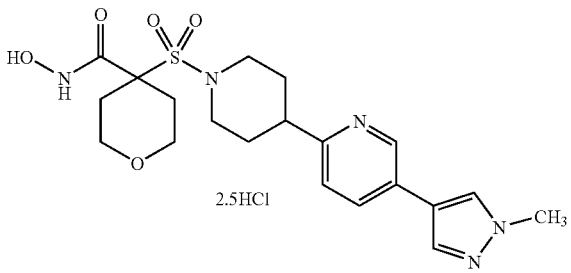 2.5HCl | 450.1811 | 450.1821 | 5850 |
| A202 | 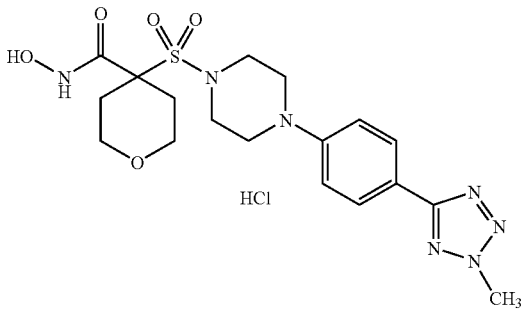 HCl | | | 2300 |
| A203 | 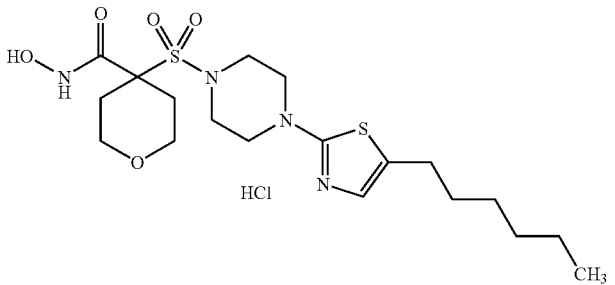 HCl | 461.1887 | 461.1881 | >10000 |
| A204 | 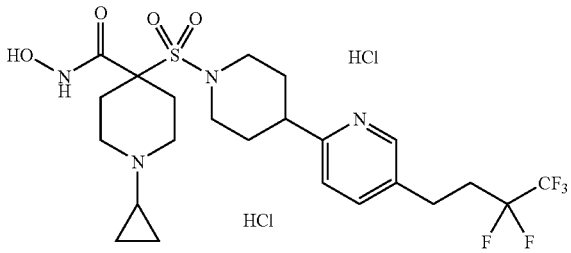 HCl HCl | 555.2064 | 555.2081 | >10000 |
| A205 | 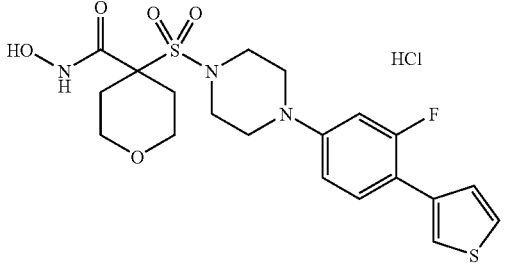 HCl | | | 3590 |

TABLE 9-continued

Additional Examples of
Piperazinyl- or Piperidinyl-Sulfonylmethyl Hydroxamic acid Compounds

| Ex. | Structure | | | |
|---|---|---|---|---|
| A206 | 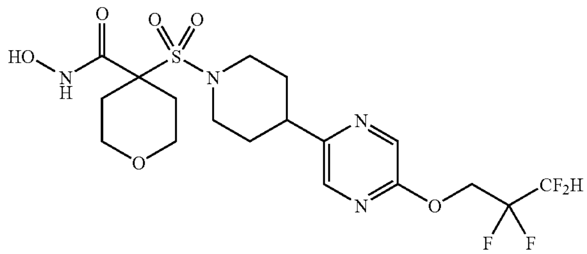 | 501.1425 | 501.1414 | 4460 |
| A207 | (HCl) | 467.1417 | 467.1412 | >10000 |
| A208 | 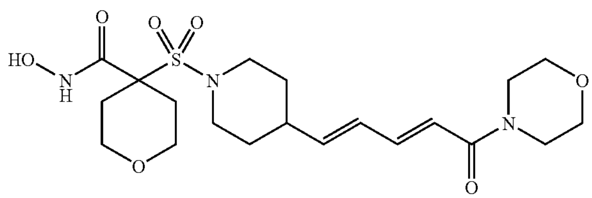 | 458.1955 | 458.1985 | 7360 |

| Ex. | Structure | MMP-2 $K_i$ (IC-50) | MMP-9 $K_i$ (IC-50) | MMP-13 $K_i$ (IC-50) |
|---|---|---|---|---|
| A70 | 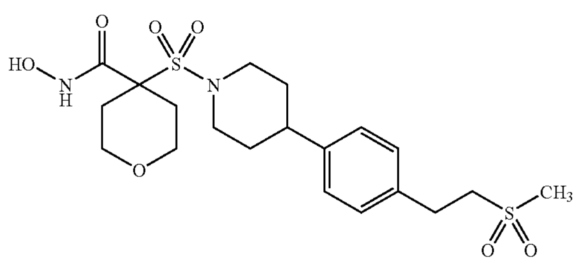 | | | |
| A71 | 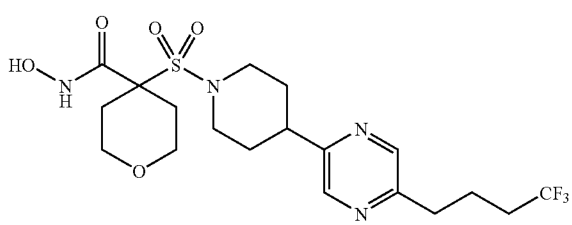 | | | |
| A72 | 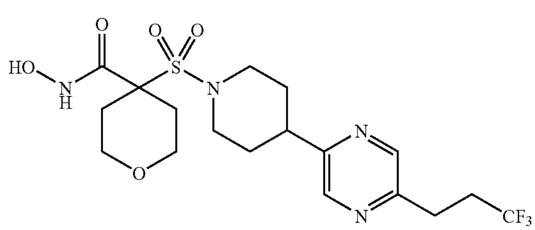 | 3.8 | 1.4 | 2.0 |

TABLE 9-continued

Additional Examples of
Piperazinyl- or Piperidinyl-Sulfonylmethyl Hydroxamic acid Compounds

| | | | | |
|---|---|---|---|---|
| A73 | [structure] | 0.22 | 0.16 | 0.09 |
| A74 | [structure] | 21.8 | 65.8 | 0.18 |
| A75 | [structure] | 228 | 501 | 0.41 |
| A76 | [structure] | 356 | 1780 | 6.79 |
| A77 | [structure] | 1100 | 5910 | 6.79 |
| A78 | [structure] | 172 | 428 | 0.52 |
| A79 | [structure] | 2450 | >10000 | 5.94 |

TABLE 9-continued

Additional Examples of
Piperazinyl- or Piperidinyl-Sulfonylmethyl Hydroxamic acid Compounds

| | | | | |
|---|---|---|---|---|
| A80 | [structure] | 239 | 1890 | 0.389 |
| A81 | [structure] | 213 | 274 | 0.92 |
| A82 | [structure] | 1080 | 8280 | 0.901 |
| A83 | [structure] | 60 | 382 | 1.58 |
| A84 | [structure] HCl | 2.88 | 0.738 | 1.82 |
| A85 | [structure] | 82.3 | 553 | 3 |
| A86 | [structure] | 23.8 | 307 | 8.19 |

TABLE 9-continued

Additional Examples of
Piperazinyl- or Piperidinyl-Sulfonylmethyl Hydroxamic acid Compounds

| | | | | |
|---|---|---|---|---|
| A87 | | 17.2 | 107 | 0.01 |
| A88 | | 38.0 | 50.7 | 2.01 |
| A89 | | 29.3 | 471 | 0.66 |
| A90 | | 0.296 | 0.075 | 0.249 |
| A91 | | 781 | 3800 | 5.08 |
| A92 | | 237 | 1100 | 2.01 |
| A93 | | 92.3 | 336 | 0.82 |

US 7,119,203 B2
TABLE 9-continued
Additional Examples of
Piperazinyl- or Piperidinyl-Sulfonylmethyl Hydroxamic acid Compounds
| | | | | |
|---|---|---|---|---|
| A94 | 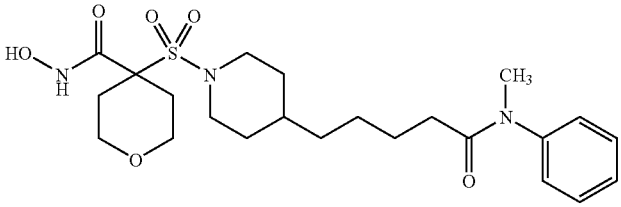 | 197 | 823 | 1.18 |
| A95 | 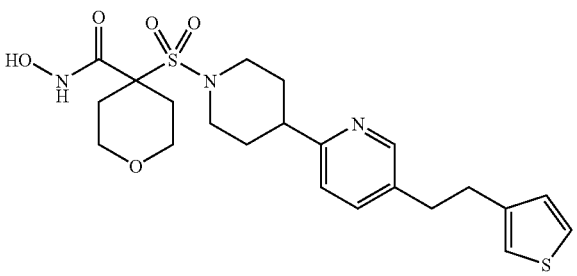 | 2.13 | 7.97 | 0.376 |
| A96 | 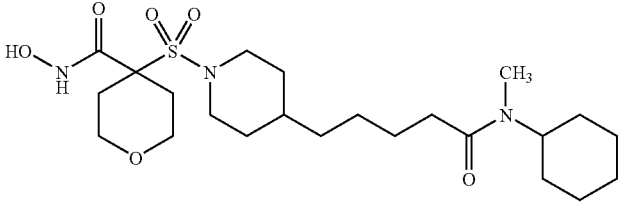 | 240 | 726 | 1.1 |
| A97 | 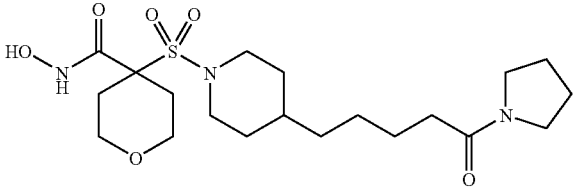 | 135 | 592 | 1.63 |
| A98 | 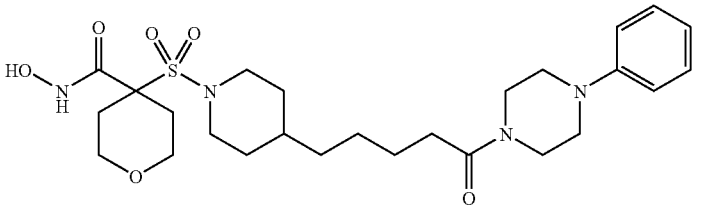 | 38.2 | 191 | 0.17 |
| A99 | 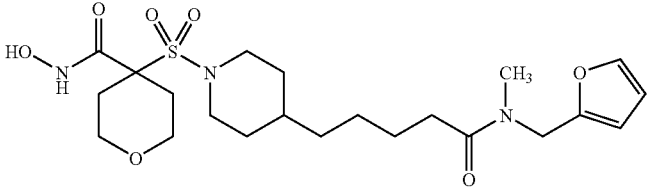 | 50.8 | 241 | 0.79 |

TABLE 9-continued

Additional Examples of
Piperazinyl- or Piperidinyl-Sulfonylmethyl Hydroxamic acid Compounds

| | | | | |
|---|---|---|---|---|
| A100 | (structure) HCl | 5.27 | 13.2 | 0.45 |
| A101 | (structure) HCl | 0.9 | 0.33 | 0.17 |
| A102 | (structure) | 1.3 | 3.84 | 0.215 |
| A103 | (structure) | 3.84 | 3.39 | 1.08 |
| A104 | (structure) HCl | 2.04 | 1.01 | 0.82 |
| A105 | (structure) HCl | 0.52 | 0.18 | 0.23 |

TABLE 9-continued

Additional Examples of
Piperazinyl- or Piperidinyl-Sulfonylmethyl Hydroxamic acid Compounds

| | | | |
|---|---|---|---|
| A106 | 0.54 | 1.05 | 0.14 |
| A107 | 2.89 | 0.86 | 0.85 |
| A108 | 3.25 | 55.5 | 0.16 |
| A109 | 0.60 | 26.8 | 0.42 |
| A110 | 7.78 | 1.03 | 4.40 |
| A111 | 364 | 1710 | 9.09 |

TABLE 9-continued

Additional Examples of
Piperazinyl- or Piperidinyl-Sulfonylmethyl Hydroxamic acid Compounds

| | | | | |
|---|---|---|---|---|
| A112 | (structure) | 190 | 1820 | 0.92 |
| A113 | (structure) HCl | 1.28 | 0.80 | 0.34 |
| A114 | (structure) HCl | 0.38 | 0.94 | 0.80 |
| A115 | (structure) | 98.5 | 1350 | 0.81 |
| A116 | (structure) HCl | 0.19 | 0.14 | 0.08 |
| A117 | (structure) | 9.91 | 0.96 | 2.8 |

TABLE 9-continued
Additional Examples of
Piperazinyl- or Piperidinyl-Sulfonylmethyl Hydroxamic acid Compounds
| | | | | |
|---|---|---|---|---|
| A118 | 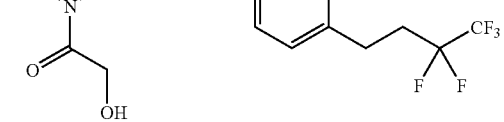 | 0.56 | 0.40 | 0.18 |
| A119 | 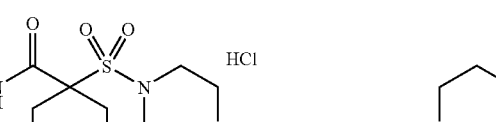 | >10000 | >10000 | 154 |
| A120 | 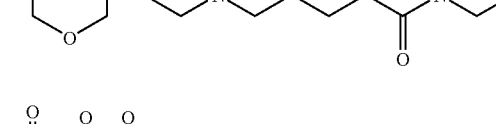 | 0.42 | 0.16 | 0.15 |
| A121 | 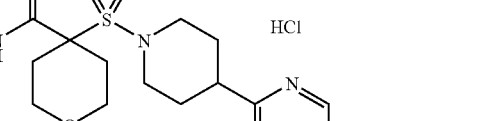 | 52.8 | 237 | 4.94 |
| A122 | 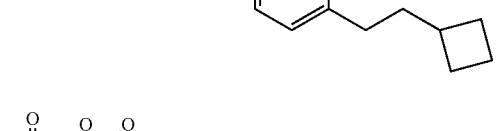 | 0.37 | 0.27 | 0.12 |
| A123 | 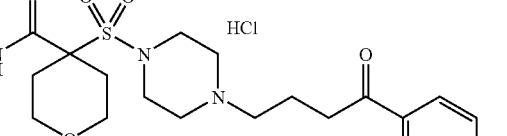 | 0.58 | 0.08 | 0.43 |

TABLE 9-continued

Additional Examples of
Piperazinyl- or Piperidinyl-Sulfonylmethyl Hydroxamic acid Compounds

| | | | | |
|---|---|---|---|---|
| A124 | | 3.42 | 0.59 | 3.11 |
| A125 | | >10000 | >10000 | 106 |
| A126 | | 0.27 | 0.14 | 0.06 |
| A127 | | 1.62 | 0.52 | 1.71 |
| A128 | | 3.33 | 8.82 | 0.84 |
| A129 | | 2.96 | 10.8 | 2.81 |

TABLE 9-continued

Additional Examples of
Piperazinyl- or Piperidinyl-Sulfonylmethyl Hydroxamic acid Compounds

| ID | Structure | | | |
|---|---|---|---|---|
| A130 | (structure) | >10000 | >10000 | 2910 3080 |
| A131 | (structure) | 1.2 | 0.57 | 0.34 |
| A132 | (structure) | 2.29 | 0.45 | 1.48 |
| A133 | (structure) | 0.77 | 1.07 | 1.12 |
| A134 | (structure) | 0.65 | 1.25 | 0.109 |
| A135 | (structure) | 0.31 | 0.48 | 0.28 |

TABLE 9-continued
Additional Examples of
Piperazinyl- or Piperidinyl-Sulfonylmethyl Hydroxamic acid Compounds
| | | | | |
|---|---|---|---|---|
| A136 | 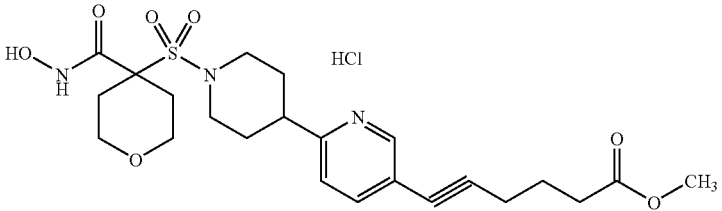 | 0.33 | 2.03 | 0.48 |
| A137 | 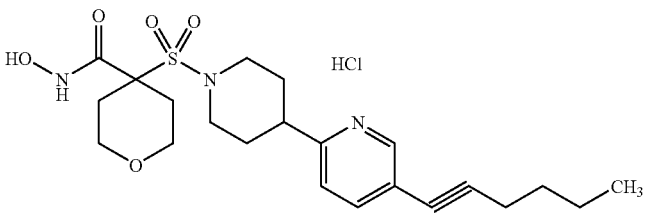 | 0.37 | 0.32 | 0.09 |
| A138 | 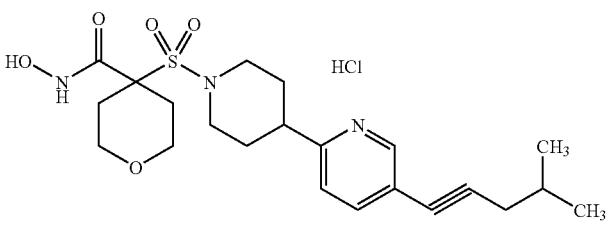 | 0.68 | 0.24 | 0.14 |
| A139 | 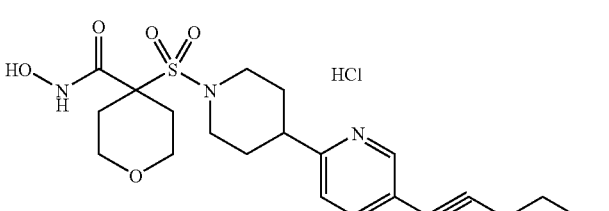 | 0.50 | 0.15 | 0.17 |
| A140 | 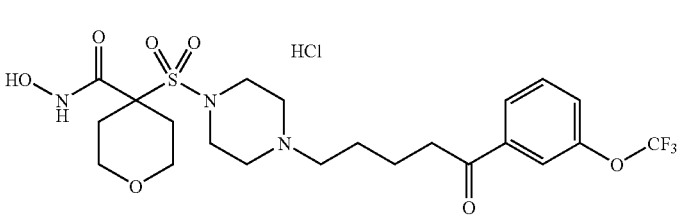 | 390 | 814 | 12.5 |
| A141 | 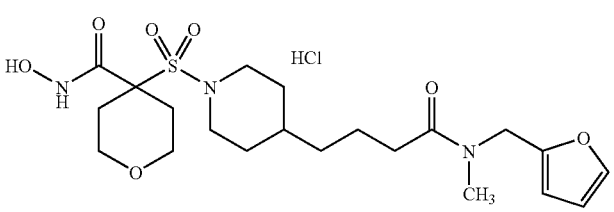 | 219 | 348 | 3.4 |
| A142 | 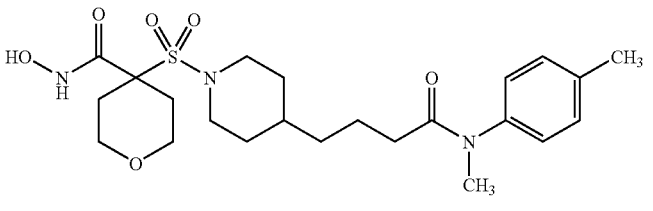 | 358 | 184 | 66.4 |

TABLE 9-continued

Additional Examples of
Piperazinyl- or Piperidinyl-Sulfonylmethyl Hydroxamic acid Compounds

| | | | | |
|---|---|---|---|---|
| A143 | [structure] | 686 | 389 | 50.8 |
| A144 | [structure] | 958 | 1520 | 22.2 |
| A145 | [structure] | 26.3 | 15.2 | 23 |
| A146 | [structure] | 344 | 262 | 31.8 |
| A147 | [structure] | 76.1 | 42.9 | 44.8 |
| A148 | [structure] | 6.67 | 3.79 | 5.21 |

TABLE 9-continued

Additional Examples of
Piperazinyl- or Piperidinyl-Sulfonylmethyl Hydroxamic acid Compounds

| | | | | |
|---|---|---|---|---|
| A149 | | 4.42 | 7.04 | 2.63 |
| A150 | | 243 | 1030 | 19.8 |
| A151 | | 1.34 | 0.72 | 1.53 |
| A152 | | 2.36 | 9.85 | 5.25 |
| A153 | | 175 | 1910 | 0.37 |
| A154 | | 88.9 | 715 | 95.5 |

TABLE 9-continued
Additional Examples of
Piperazinyl- or Piperidinyl-Sulfonylmethyl Hydroxamic acid Compounds
| | | | | |
|---|---|---|---|---|
| A155 | 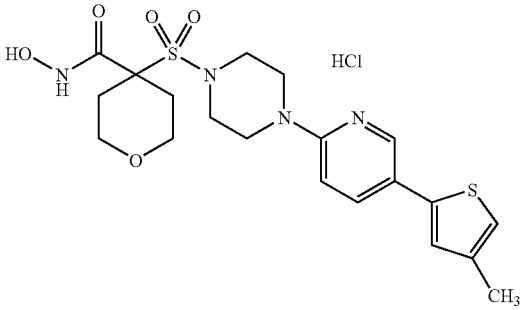 | 0.48 | 6.59 | 0.15 |
| A156 | 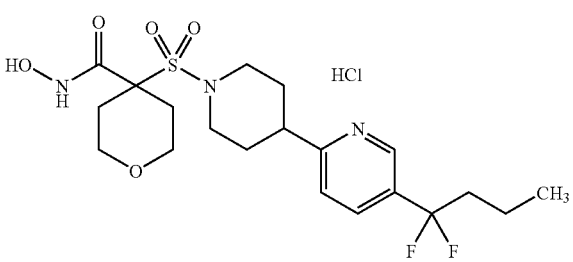 | 3.14 | 9.5 | 1.57 |
| A157 | 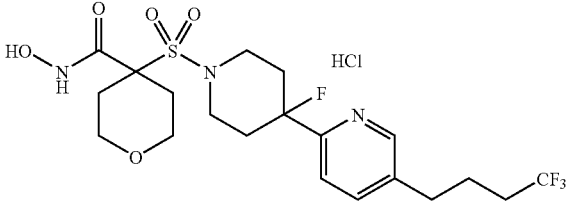 | 36.5 | 2.94 | 2.54 |
| A158 | 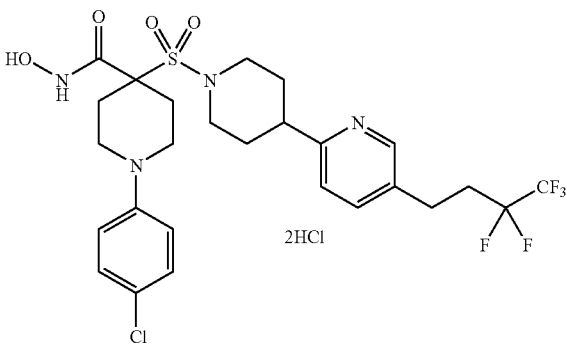 | 14.6 | 13.4 | 8.98 |
| A159 | 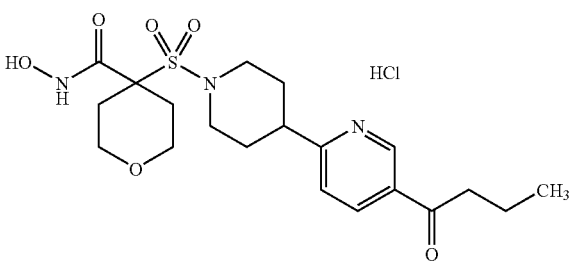 | 2.65 | 3.99 | 1.91 |

TABLE 9-continued
Additional Examples of
Piperazinyl- or Piperidinyl-Sulfonylmethyl Hydroxamic acid Compounds
| | | | | |
|---|---|---|---|---|
| A160 |  | 529 | 613 | 40.9 |
| A161 |  | 0.513 | 0.223 | 0.474 |
| A162 | 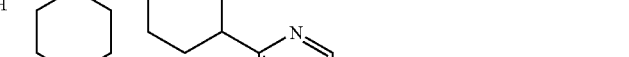 | 1.15 | 0.194 | 0.301 |
| A163 | 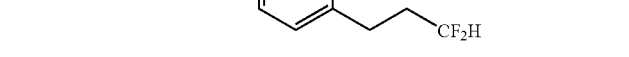 | 225 | 1630 | 2.53 |
| A164 |  | 63 | 2970 | 42.2 |
| A165 | 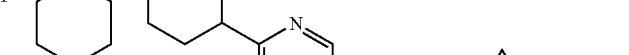 | 1.67 | 0.979 | 0.647 |

TABLE 9-continued
Additional Examples of
Piperazinyl- or Piperidinyl-Sulfonylmethyl Hydroxamic acid Compounds
| | | | | |
|---|---|---|---|---|
| A166 | 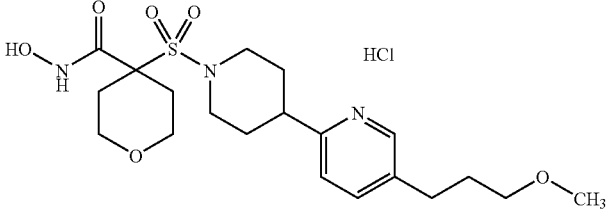 | 1.93 | 1.77 | 1.03 |
| A167 | 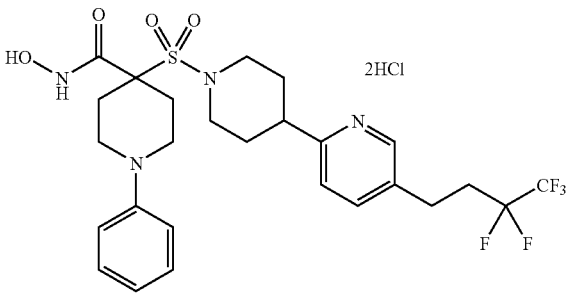 | 3.04 | 2.21 | 1.54 |
| A168 | 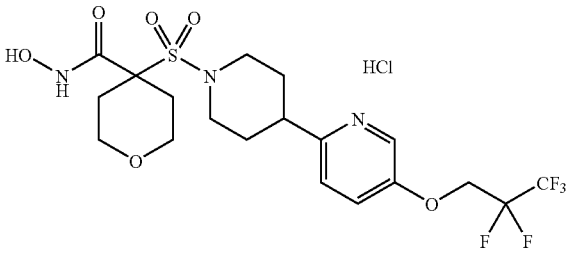 | 1.7 | 1.5 | 1.72 |
| A169 | 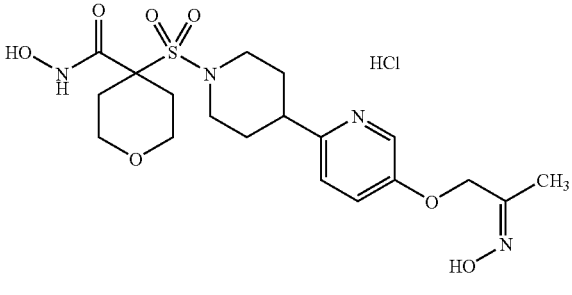 | 3.5 | 10.2 | 4.53 |
| A170 | 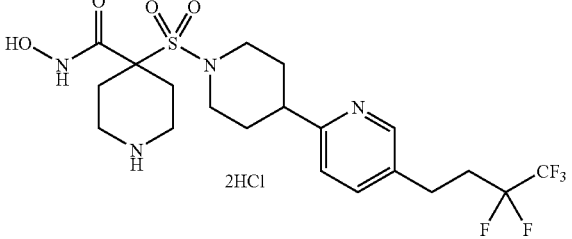 | 4.21 | 4.01 | 1.55 |

TABLE 9-continued
Additional Examples of
Piperazinyl- or Piperidinyl-Sulfonylmethyl Hydroxamic acid Compounds
| A171 | 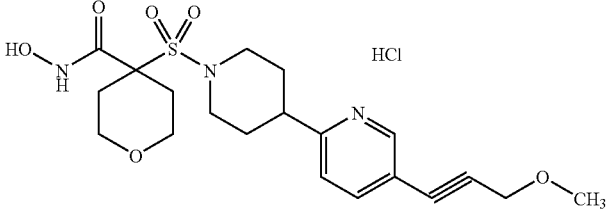 | 0.42 | 0.54 | 0.31 |
| A172 | 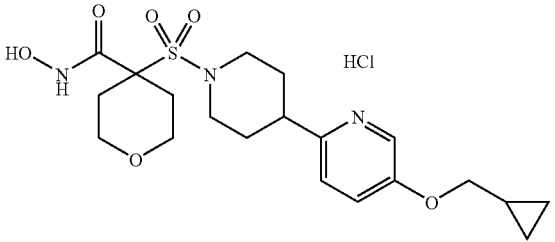 | 1.31 | 0.36 | 1.24 |
| A173 | 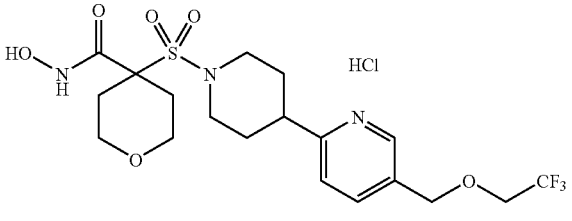 | 7.59 | 1.84 | 1.91 |
| A174 | 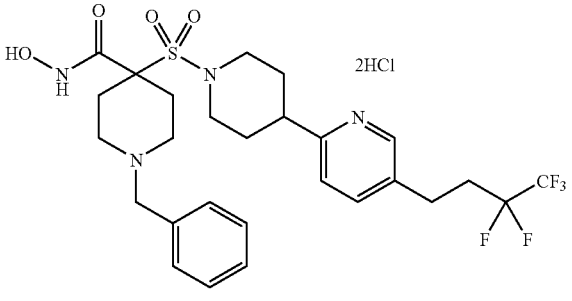 | 1.31 | 0.73 | 0.52 |
| A175 | 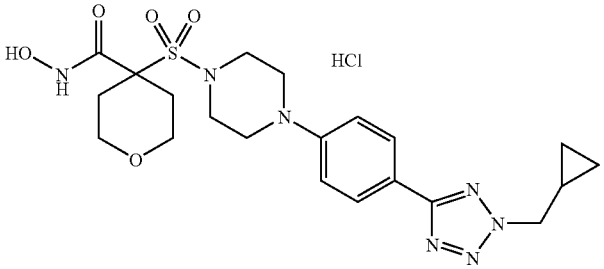 | 0.07 | 1.37 | 0.09 |

TABLE 9-continued

Additional Examples of
Piperazinyl- or Piperidinyl-Sulfonylmethyl Hydroxamic acid Compounds

| | | | | |
|---|---|---|---|---|
| A176 | [structure with HCl] | 0.08 | 0.81 | 0.15 |
| A177 | [structure with HCl] | 3.83 | 0.88 | 6.81 |
| A178 | [structure with 2HCl] | 0.881 | 0.596 | 0.437 |
| A179 | [structure with HCl] | 2.51 | 0.49 | 1.9 |
| A180 | [structure with HCl] | 2.35 | 96.1 | 2.1 |
| A181 | [structure with 2HCl] | 2.36 | 1.33 | 0.61 |

TABLE 9-continued

Additional Examples of
Piperazinyl- or Piperidinyl-Sulfonylmethyl Hydroxamic acid Compounds

| | | | | |
|---|---|---|---|---|
| A182 | (structure) 2HCl | 0.93 | 0.39 | 0.30 |
| A183 | (structure) HCl | 2.06 | 307 | 1.07 |
| A184 | (structure) HCl | 0.38 | 0.52 | 0.41 |
| A185 | (structure) | 1.1 | 1.69 | 0.95 |
| A186 | (structure) HCl | 0.23 | 0.55 | 0.21 |

TABLE 9-continued
Additional Examples of
Piperazinyl- or Piperidinyl-Sulfonylmethyl Hydroxamic acid Compounds
| | | | | |
|---|---|---|---|---|
| A187 | 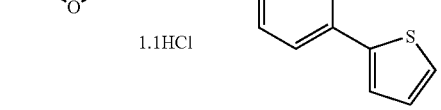 1.1HCl | 0.54 | 2.14 | 0.56 |
| A188 | 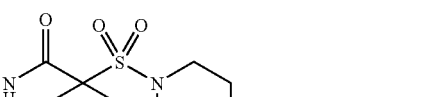 1.75HCl | 7.61 | 54.7 | 3.89 |
| A189 | 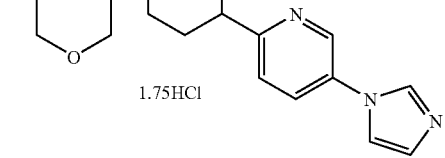 HCl | 45.5 | 4.35 | 4.443 |
| A190 |  HCl | 0.39 | 1.09 | 0.22 |
| A191 | 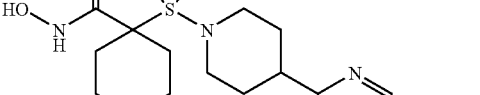 HCl | 0.31 | 0.27 | 0.13 |
| A192 | 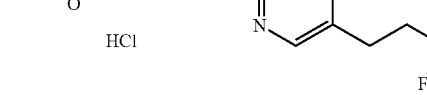 HCl | 3.25 | 10 | 4.11 |

TABLE 9-continued
Additional Examples of
Piperazinyl- or Piperidinyl-Sulfonylmethyl Hydroxamic acid Compounds
| | | | | |
|---|---|---|---|---|
| A193 | 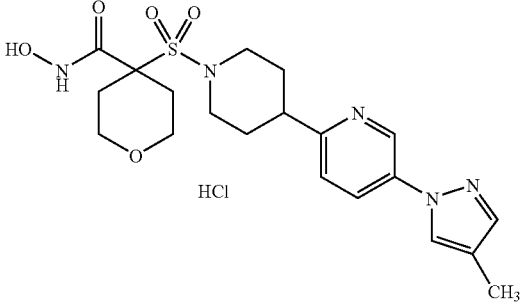 HCl | 4.7 | 8.24 | 2.09 |
| A194 | 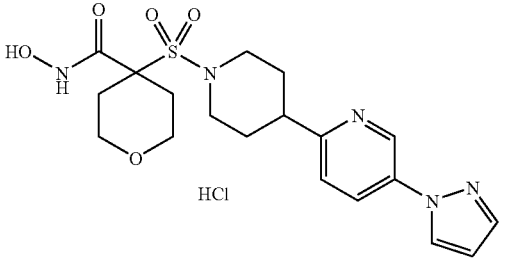 HCl | 8.71 | 12.6 | 8.86 |
| A195 | 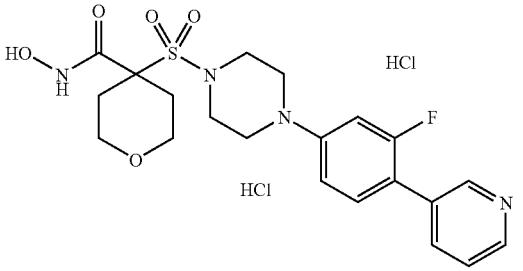 HCl   HCl | 0.18 | 6.81 | 0.34 |
| A196 | 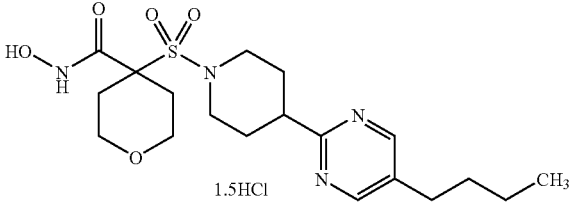 1.5HCl | 70 | 2.02 | 21.8 |
| A197 | 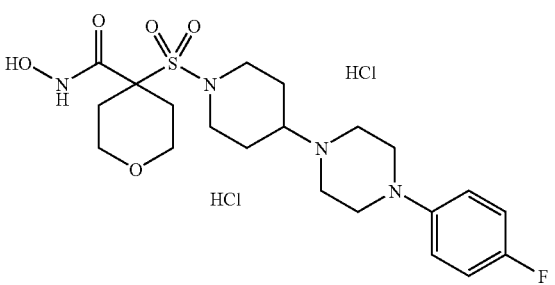 HCl   HCl | 770 | 1620 | 496 |

TABLE 9-continued

Additional Examples of
Piperazinyl- or Piperidinyl-Sulfonylmethyl Hydroxamic acid Compounds

| | | | | |
|---|---|---|---|---|
| A198 | [structure] HCl | 1.44 | 32.9 | 0.53 |
| A199 | [structure] HCl | 0.06 | 0.84 | 0.04 |
| A200 | [structure] HCl | 8.83 | 6.77 | 6.77 |
| A201 | [structure] 2.5HCl | 4.25 | 16.8 | 2.14 |
| A202 | [structure] HCl | 0.46 | 0.92 | 2.08 |

TABLE 9-continued
Additional Examples of
Piperazinyl- or Piperidinyl-Sulfonylmethyl Hydroxamic acid Compounds
| | | | | |
|---|---|---|---|---|
| A203 | 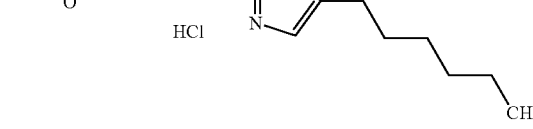 | 1.25 | 6.93 | 0.61 |
| A204 | 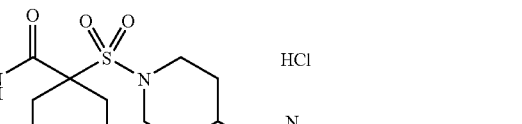 | 0.65 | 0.29 | 0.23 |
| A205 | 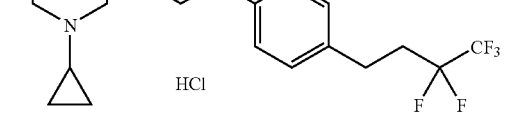 | 0.33 | 1.16 | 0.93 |
| A206 | 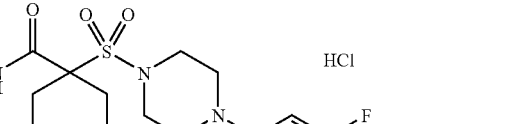 | 0.71 | 0.84 | 0.90 |
| A207 | 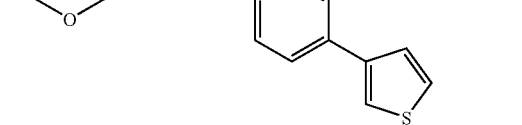 | 6130 | >10000 | 4140 |
| A208 | 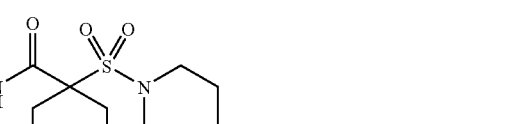 | 178 | 1590 | 1.94 |

TABLE 9-continued

Additional Examples of
Piperazinyl- or Piperidinyl-Sulfonylmethyl Hydroxamic acid Compounds

| Ex. | Structure | MMP-14 $K_i$ (IC-50) |
|---|---|---|
| A70 | 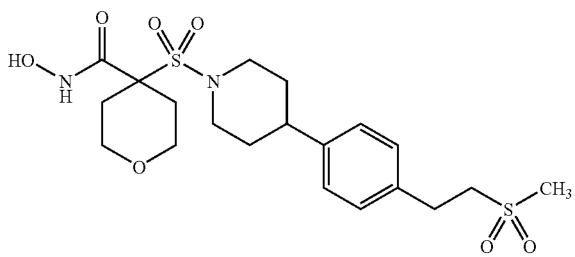 | |
| A71 | 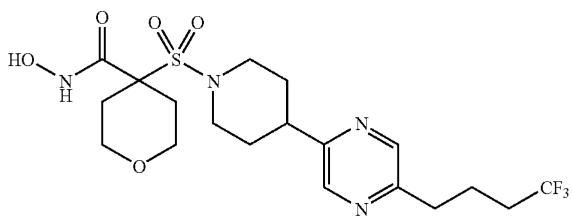 | |
| A72 | 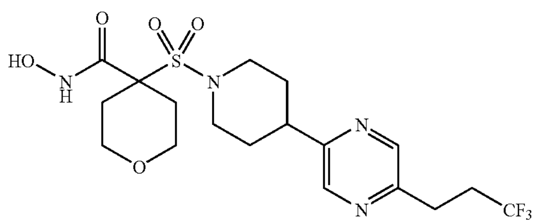 | >10000 |
| A73 | 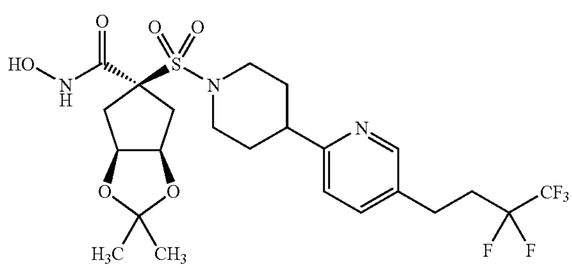 | 140 |
| A74 | 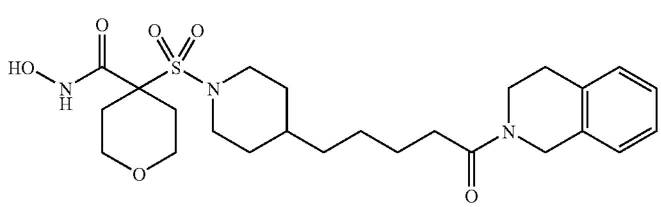 | 7960 |
| A75 | 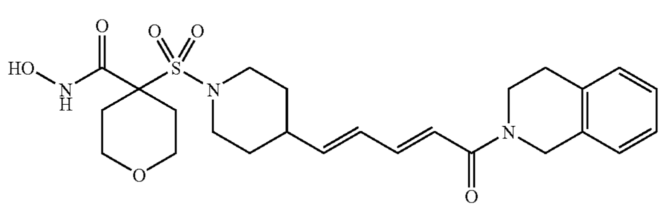 | >10000 |

TABLE 9-continued

Additional Examples of
Piperazinyl- or Piperidinyl-Sulfonylmethyl Hydroxamic acid Compounds

| A76 | | >10000 |
| A77 | | >10000 |
| A78 | | >10000 |
| A79 | | >10000 |
| A80 | | >10000 |
| A81 | | >10000 |
| A82 | | >10000 |

TABLE 9-continued

Additional Examples of
Piperazinyl- or Piperidinyl-Sulfonylmethyl Hydroxamic acid Compounds

| | | |
|---|---|---|
| A83 | (structure) | >10000 |
| A84 | (structure) HCl | 5390 |
| A85 | (structure) | >10000 |
| A86 | (structure) | 7540 |
| A87 | (structure) | >10000 |
| A88 | (structure) | 5360 |
| A89 | (structure) | 8570 |

TABLE 9-continued
Additional Examples of
Piperazinyl- or Piperidinyl-Sulfonylmethyl Hydroxamic acid Compounds
A90 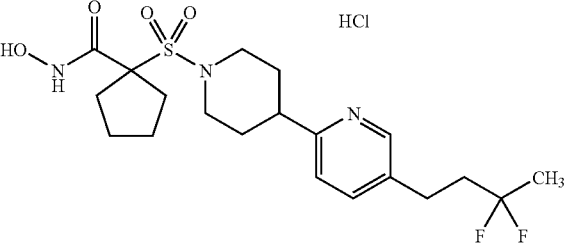 1040
A91 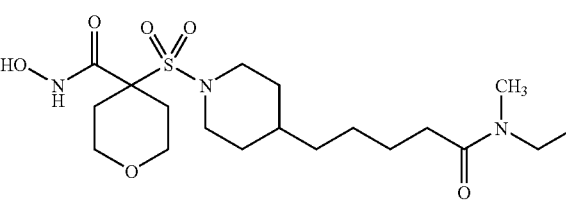 >10000
A92 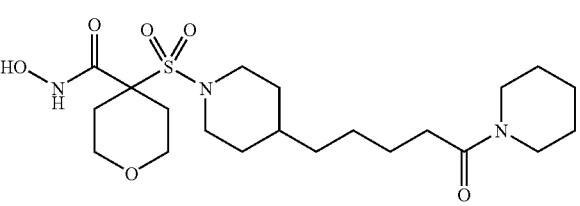 >10000
A93 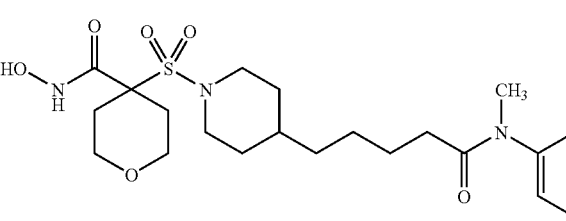 >10000
A94 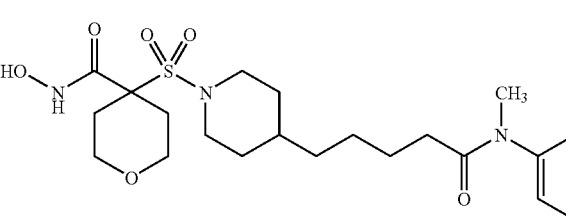 >10000
A95 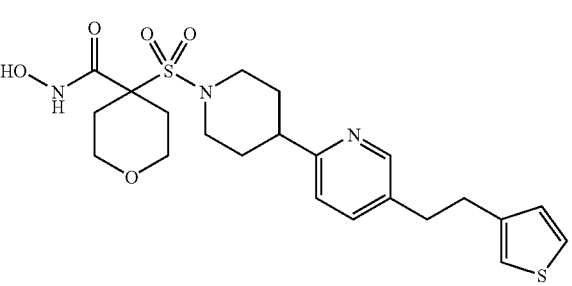 2270

TABLE 9-continued
Additional Examples of
Piperazinyl- or Piperidinyl-Sulfonylmethyl Hydroxamic acid Compounds
A96 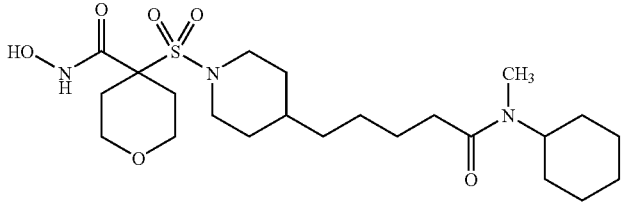 >10000
A97 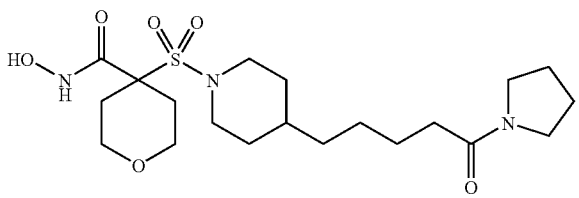 >10000
A98 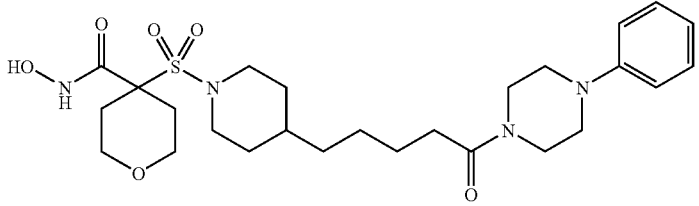 >10000
A99 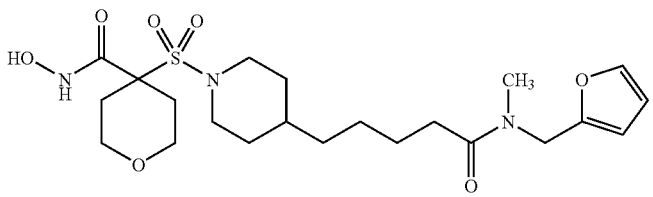 >10000
A100 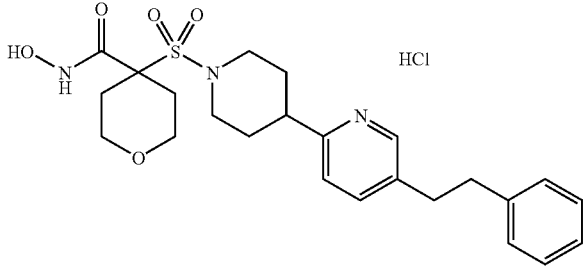 1770
A101 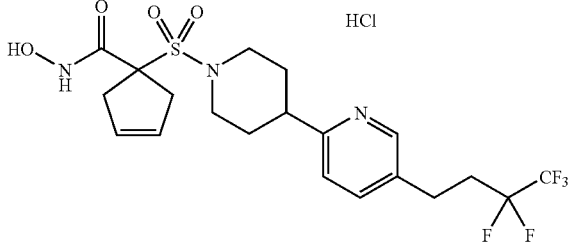 2640

TABLE 9-continued

Additional Examples of
Piperazinyl- or Piperidinyl-Sulfonylmethyl Hydroxamic acid Compounds

| | |
|---|---|
| A102 | 2160 |
| A103 | 2880 |
| A104 | 6540 |
| A105 | 1130 |
| A106 | 1250 |
| A107 | 3370 |

TABLE 9-continued

Additional Examples of
Piperazinyl- or Piperidinyl-Sulfonylmethyl Hydroxamic acid Compounds

| A108 | | 4520 |
| A109 | HCl | 3720 |
| A110 | | 9210 |
| A111 | | >10000 |
| A112 | | >10000 |
| A113 | HCl | 4410 |

TABLE 9-continued

Additional Examples of
Piperazinyl- or Piperidinyl-Sulfonylmethyl Hydroxamic acid Compounds

| A114 | 1150 |
| A115 | >10000 |
| A116 | 331 |
| A117 | >10000 |
| A118 | 3600 |
| A119 | >10000 |

TABLE 9-continued

Additional Examples of
Piperazinyl- or Piperidinyl-Sulfonylmethyl Hydroxamic acid Compounds

| | | |
|---|---|---|
| A120 | | 1280 |
| A121 | | 3320 |
| A122 | | 2600 |
| A123 | | 1280 |
| A124 | | 7290 |
| A125 | | >10000 |

TABLE 9-continued

Additional Examples of
Piperazinyl- or Piperidinyl-Sulfonylmethyl Hydroxamic acid Compounds

| A126 | 1300 |
| A127 | 4710 |
| A128 | >10000 |
| A129 | 4540 |
| A130 | >10000 |

TABLE 9-continued

Additional Examples of
Piperazinyl- or Piperidinyl-Sulfonylmethyl Hydroxamic acid Compounds

| | | |
|---|---|---|
| A131 | | 1910 |
| A132 | | 5290 |
| A133 | | 3870 |
| A134 | | 191 |
| A135 | | 609 |

TABLE 9-continued

Additional Examples of
Piperazinyl- or Piperidinyl-Sulfonylmethyl Hydroxamic acid Compounds

| | | |
|---|---|---|
| A136 | | 1150 |
| A137 | | 221 |
| A138 | | 763 |
| A139 | | 401 |
| A140 | | >10000 |
| A141 | | >10000 |
| A142 | | >10000 |

TABLE 9-continued

Additional Examples of
Piperazinyl- or Piperidinyl-Sulfonylmethyl Hydroxamic acid Compounds

| | | |
|---|---|---|
| A143 | | >10000 |
| A144 | | >10000 |
| A145 | | 6520 |
| A146 | | >10000 |
| A147 | | >10000 |
| A148 | | 1730 |

TABLE 9-continued

Additional Examples of
Piperazinyl- or Piperidinyl-Sulfonylmethyl Hydroxamic acid Compounds

| | | |
|---|---|---|
| A149 | | 6550 |
| A150 | | >10000 |
| A151 | | 3100 |
| A152 | | 4330 |
| A153 | | >10000 |
| A154 | | >10000 |

TABLE 9-continued

Additional Examples of
Piperazinyl- or Piperidinyl-Sulfonylmethyl Hydroxamic acid Compounds

| Cmpd | Structure | Activity |
|---|---|---|
| A155 | (tetrahydropyran-hydroxamic acid)-SO2-piperazinyl-pyridyl-(4-methylthiophene), HCl | 859 |
| A156 | (tetrahydropyran-hydroxamic acid)-SO2-piperidinyl-pyridyl-C(F)(F)-CH2CH2CH3, HCl | >10000 |
| A157 | (tetrahydropyran-hydroxamic acid)-SO2-piperidinyl(F)-pyridyl-CH2CH2CF3, HCl | >10000 |
| A158 | (piperidinyl(4-chlorophenyl)-hydroxamic acid)-SO2-piperidinyl-pyridyl-CH2CH2CF2CF3, 2HCl | >10000 |
| A159 | (tetrahydropyran-hydroxamic acid)-SO2-piperidinyl-pyridyl-C(O)CH2CH3, HCl | 8580 |

TABLE 9-continued
Additional Examples of
Piperazinyl- or Piperidinyl-Sulfonylmethyl Hydroxamic acid Compounds
| A160 | 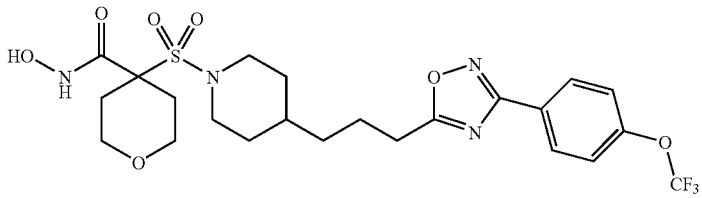 | >10000 |
| A161 | 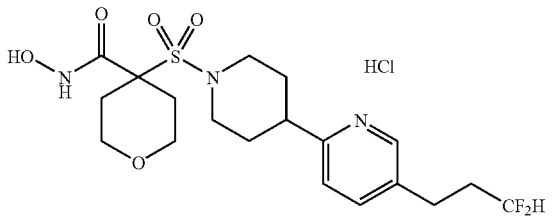 | 1670 |
| A162 | 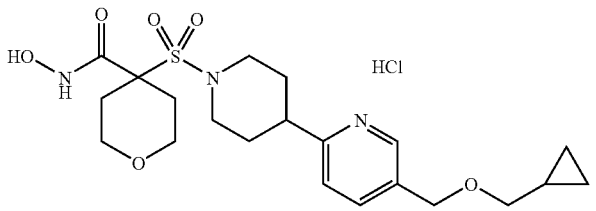 | 2290 |
| A163 | 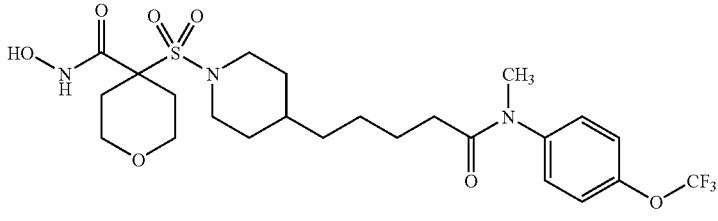 | >10000 |
| A164 | 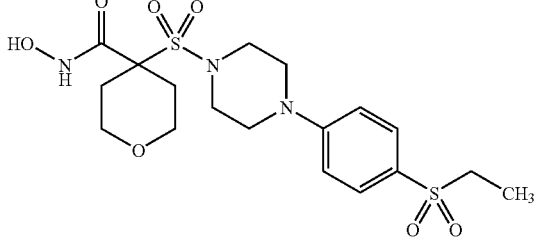 | >10000 |
| A165 | 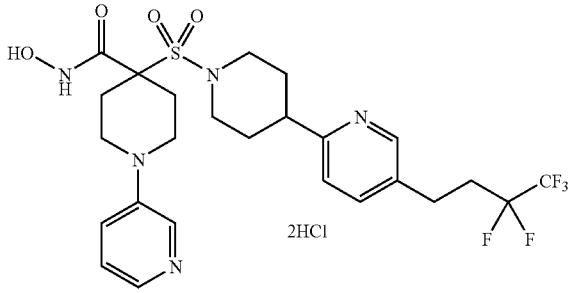 | 7210 |

TABLE 9-continued
Additional Examples of
Piperazinyl- or Piperidinyl-Sulfonylmethyl Hydroxamic acid Compounds
| A166 | 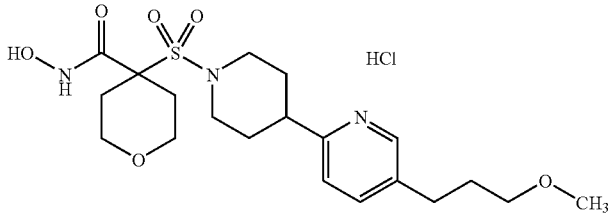 | 5060 |
| A167 | 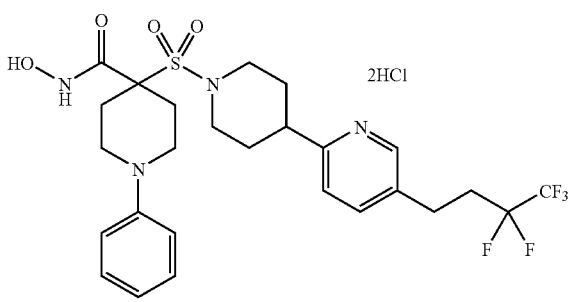 | >10000 |
| A168 | 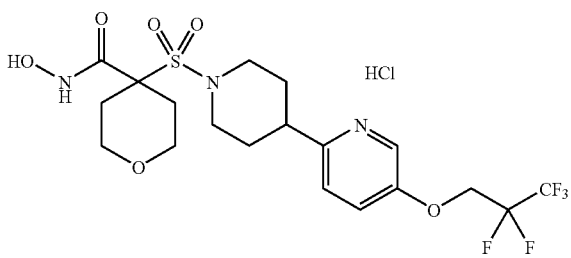 | 8570 |
| A169 | 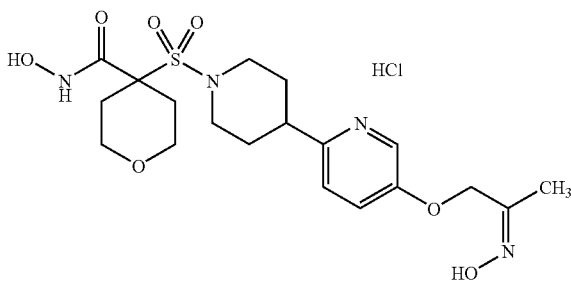 | 9300 |
| A170 | 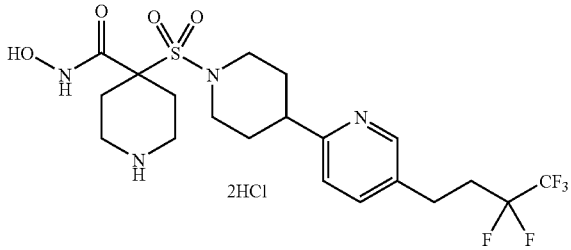 | >10000 |

TABLE 9-continued
Additional Examples of
Piperazinyl- or Piperidinyl-Sulfonylmethyl Hydroxamic acid Compounds
| A171 | 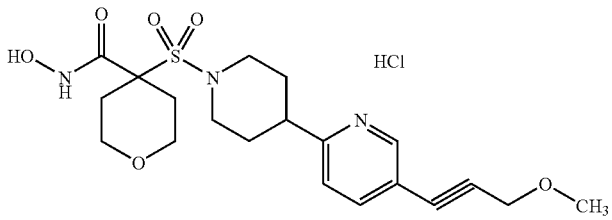 HCl | 604 |
| A172 | 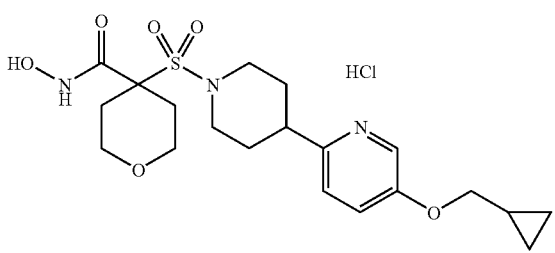 HCl | 3620 |
| A173 | 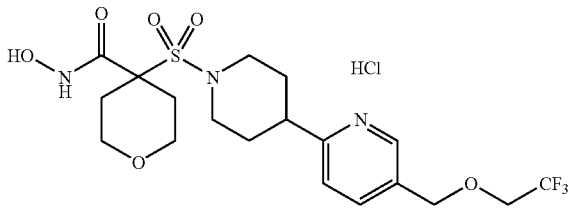 HCl | >10000 |
| A174 | 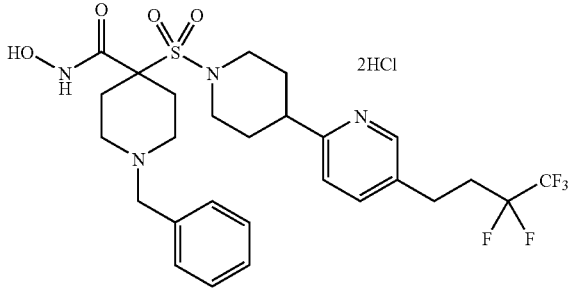 2HCl | 6520 |
| A175 | 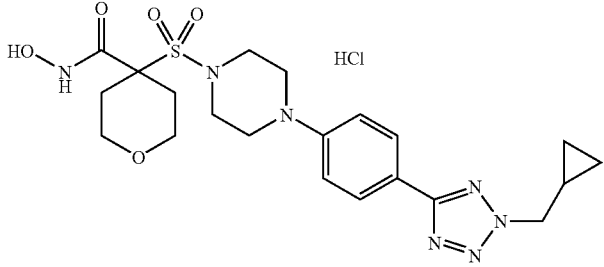 HCl | 591 |

TABLE 9-continued

Additional Examples of
Piperazinyl- or Piperidinyl-Sulfonylmethyl Hydroxamic acid Compounds

| ID | Structure | Value |
|---|---|---|
| A176 | (tetrahydropyran-4-yl hydroxamic acid)-SO₂-piperazine-phenyl-[5-ethyl-1,2,4-oxadiazol-3-yl], HCl | 184 |
| A177 | (tetrahydropyran-4-yl hydroxamic acid)-SO₂-piperidine-[pyridin-2-yl-5-CH₂OCH₃], HCl | 3360 |
| A178 | (1-(pyrimidin-2-yl)piperidin-4-yl hydroxamic acid)-SO₂-piperidine-[pyridin-2-yl-5-CH₂CH₂CF₂CF₃], 2HCl | 1950 |
| A179 | (tetrahydropyran-4-yl hydroxamic acid)-SO₂-piperidine-[pyridin-2-yl-5-CH₂OCH₂CH₃], HCl | 4280 |
| A180 | (tetrahydropyran-4-yl hydroxamic acid)-SO₂-piperazine-[4-phenyl-3-F-4-CN], HCl | 1300 |
| A181 | (1-ethylpiperidin-4-yl hydroxamic acid)-SO₂-piperidine-[pyridin-2-yl-5-CH₂CH₂CF₂CF₃], 2HCl | >10000 |

TABLE 9-continued
Additional Examples of
Piperazinyl- or Piperidinyl-Sulfonylmethyl Hydroxamic acid Compounds
A182 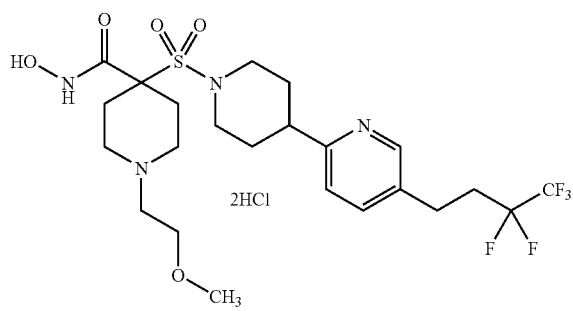 5890
A183 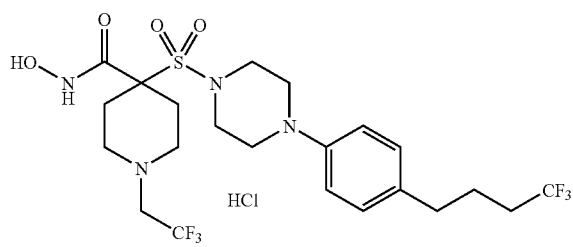 >10000
A184 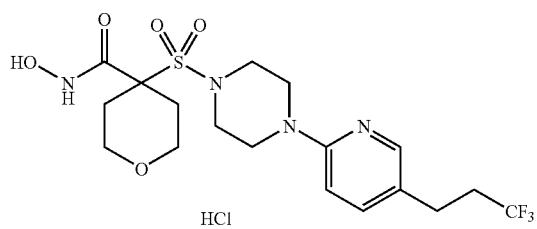 985
A185 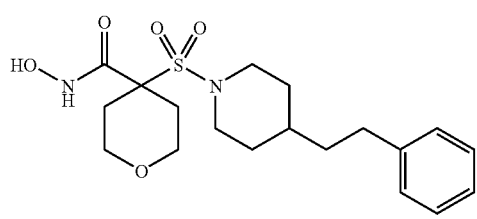 42.7
A186 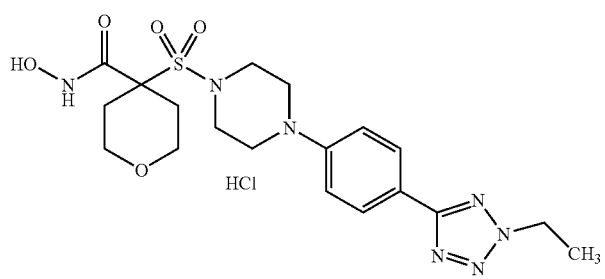 421

TABLE 9-continued
Additional Examples of
Piperazinyl- or Piperidinyl-Sulfonylmethyl Hydroxamic acid Compounds
| A187 | 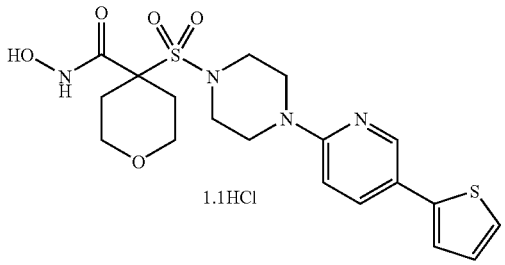 1.1HCl | 1240 |
| A188 | 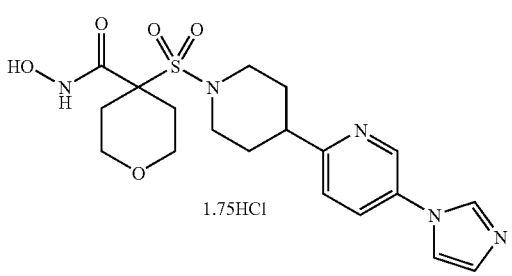 1.75HCl | 6200 |
| A189 | 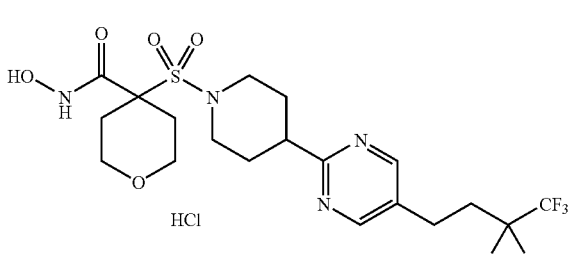 HCl | >10000 |
| A190 | 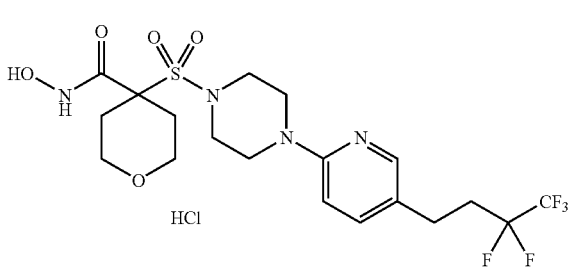 HCl | 3350 |
| A191 | 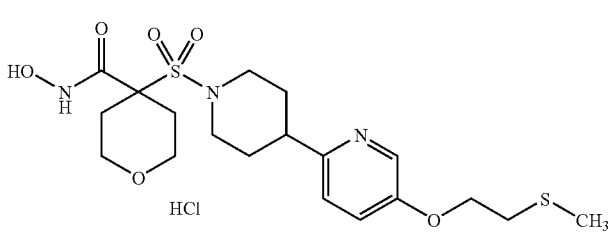 HCl | 470 |
| A192 | 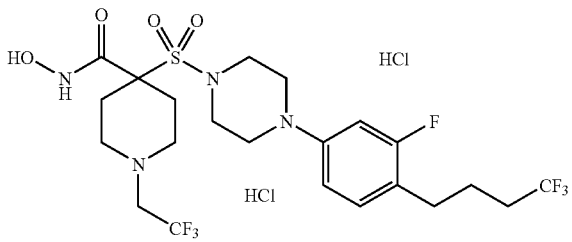 HCl HCl | >10000 |

TABLE 9-continued
Additional Examples of
Piperazinyl- or Piperidinyl-Sulfonylmethyl Hydroxamic acid Compounds
A193 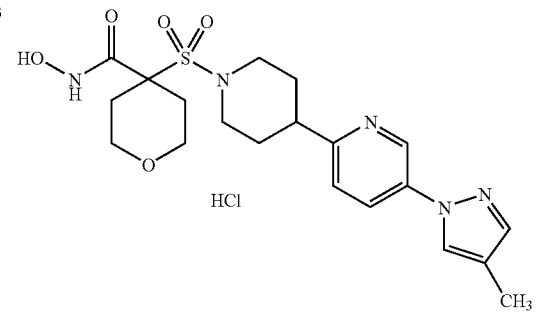 2820
A194 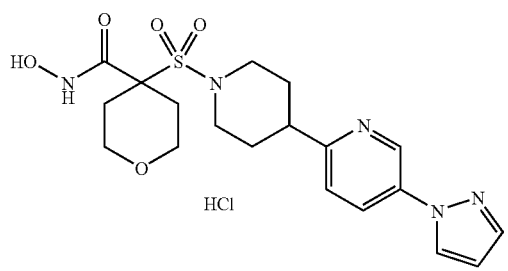 1700
A195 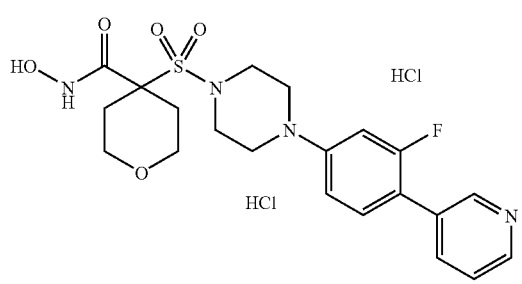 2430
A196 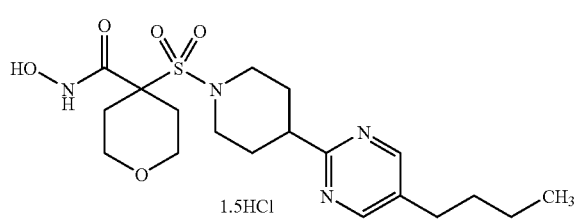 >10000
A197 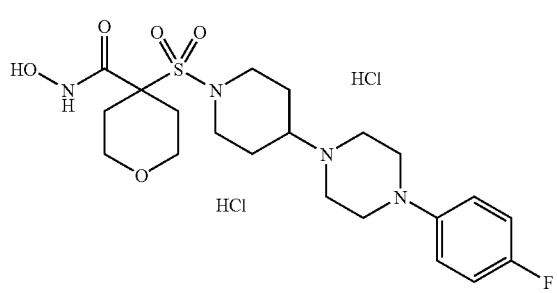 >10000

TABLE 9-continued

Additional Examples of
Piperazinyl- or Piperidinyl-Sulfonylmethyl Hydroxamic acid Compounds

| A198 | 577 |
| A199 | 287 |
| A200 | >10000 |
| A201 | 3380 |
| A202 | 1230 |

TABLE 9-continued
Additional Examples of
Piperazinyl- or Piperidinyl-Sulfonylmethyl Hydroxamic acid Compounds
| | | |
|---|---|---|
| A203 | 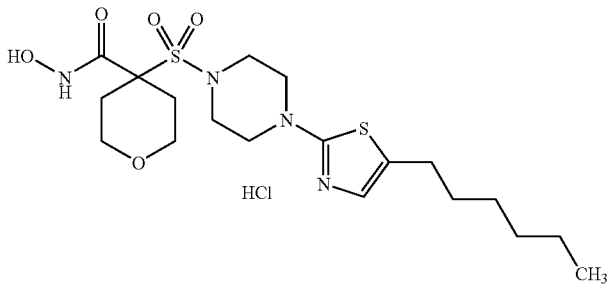 | 554 |
| A204 | 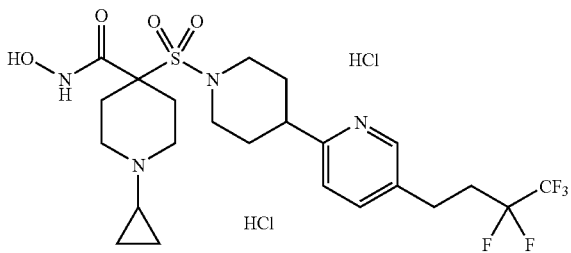 | 5100 |
| A205 | 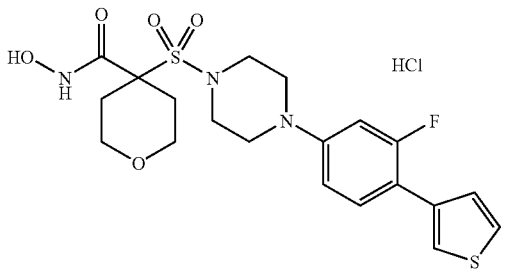 | 297 |
| A206 | 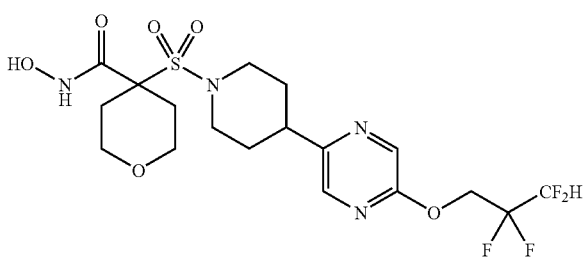 | 5750 |
| A207 | 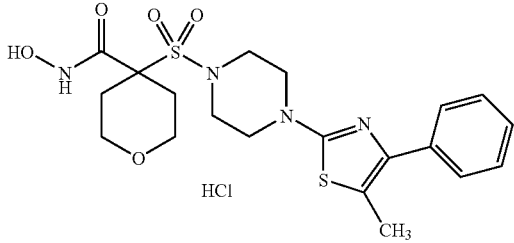 | >10000 |

TABLE 9-continued

Additional Examples of
Piperazinyl- or Piperidinyl-Sulfonylmethyl Hydroxamic acid Compounds

A208 >10000

Example 421

In Vivo Angiogenesis Assay

The study of angiogenesis depends on a reliable and reproducible model for the stimulation and inhibition of a neovascular response. The corneal micropocket assay provides such a model of angiogenesis in the cornea of a mouse. See, Kenyon, B. M, et al., "A Model of Angiogenesis in the Mouse Cornea", Investigative Ophthalmology & Visual Science, pp. 1625–1632, Vol. 37, No. 8 (July 1996).

In this assay, uniformly sized Hydron™ pellets containing bFGF and sucralfate are prepared and surgically implanted into the stroma mouse cornea adjacent to the temporal limbus. The pellets are formed by making a suspension of 20 µL sterile saline containing 10 µg recombinant bFGF, 10 mg of sucralfate and 10 µL of 12 percent Hydron™ in ethanol. The slurry is then deposited on a 10×10 mm piece of sterile nylon mesh. After drying, the nylon fibers of the mesh are separated to release the pellets.

The corneal pocket is made by anesthetizing a 7 week old C57B1/6 female mouse, then proptosing the eye with a jeweler's forceps. Using a dissecting microscope, a central, intrastromal linear keratotomy of approximately 0.6 mm in length is performed with a #15 surgical blade, parallel to the insertion of the lateral rectus muscle. Using a modified cataract knife, a lamellar micropocket is dissected toward the temporal limbus. The pocket is extended to within 1.0 mm of the temporal limbus. A single pellet is placed on the corneal surface at the base of the pocket with a jeweler's forceps. The pellet is then advanced to the temporal end of the pocket. Antibiotic ointment is then applied to the eye.

Mice are dosed on a daily basis for the duration of the assay. Dosing of the animals is based on bioavailability and overall potency of the compound. An exemplary dose is 10 or 50 mg/kg (mpk) bid, po. Neovascularization of the corneal stroma is permitted to continue under the influence of the assayed compound for 2 days. At that point, the degree of angiogenic inhibition is scored by viewing the neovascular progression with a slit lamp microscope.

The mice are anesthetized and the studied eye is once again proptosed. The maximum vessel length of neovascularization, extending from the limbal vascular plexus toward the pellet is measured. In addition, the contiguous circumferential zone of neovascularization is measured as clock hours, where 30 degrees of arc equals one clock hour. The area of angiogenesis is calculated as follows.

$$\text{area} = \frac{(0.4 \times \text{clock hours} \times 3.14 \times \text{vessel length (in mm)})}{2}$$

Five to six mice should be utilized for each compound in each study. The studied mice are thereafter compared to control mice and the difference in the area of neovascularization is recorded as an averaged value. A contemplated compound typically exhibits about 25 to about 75 percent inhibition, whereas the vehicle control exhibits zero percent inhibition.

Example 422

Tumor Necrosis Factor Assays

Cell Culture.

The cells used in the assay are the human moncytic line U-937 (ATCC CRL-1593). The cells are grown in RPMI w/10% FCS and PSG supplement (R-10) and are not permitted to overgrow. The assay is carried out as follows:

1. Count, then harvest cells by centrifugation. Resuspend the pellet in R-10 supplement to a concentration of 1.540× $10^6$ cells/mL.

2. Add test compound in 65 uL R-10 to the appropriate wells of a 96-well flat bottom tissue culture plate. The initial dilution from a DMSO stock (100 mM compound) provides a 400 uM solution, from which five additional three-fold serial dilutions are made. Each dilution of 65 ul (in triplicate) yields final compound test concentrations of 100 µM, 33.3 µM, 11.1 µM, 3.7 µM, 1.2 µM and 0.4 µM.

3. The counted, washed and resuspended cells (200,000 cells/well) in 130 µL are added to the wells.

4. Incubation is for 45 min to 1 hr at 37° C. in 5% $CO_2$ in a water saturated container.

5. R-10 (65 uL) containing 160 ng/mL PMA (Sigma) is added to each well.

6. The test system is incubated at 37° C. in 5% CO2 overnight (18–20 hr) under 100% humidity.

7. Supernatant, 150 µL, is carefully removed from each well for use in the ELISA assay.

8. For toxicity, a 50 μL aliquot of working solution containing 5 mL R-10, 5 mL MTS solution [CellTiter 96 AQueous One Solution Cell Proliferation Assay Cat.#G358/0,1 (Promega Biotech)] and 250 ul PMS solution are added to each well containing the remaining supernatant and cells and the cells incubated at 37° C. in 5% $CO_2$ until the color develops. The system is excited at 570 nm and read at 630 nm.

TNF Receptor II ELISA Assay

1. Plate 100 μL/well 2 ug/mL mouse anti-human TNFrII antibody (R&D Systems #MAB226) in 1×PBS (pH 7.1, Gibco) on NUNC-Immuno Maxisorb plate. Incubate the plate at 4° C. overnight (about 18–20 hr).
2. Wash the plate with PBS-Tween (1×PBS w/0.05% Tween).
3. Add 200 μL 5% BSA in PBS and block at 37° C. in a water saturated atmosphere for 2 hr.
4. Wash the plate with PBS-Tween.
5. Add sample and controls (100 ul of each) to each well. The standards are 0, 50, 100, 200, 300 and 500 pg recombinant human TNFrII (R&D Systems #226-B2) in 100 μL 0.5% BSA in PBS. The assay is linear to between 400–500 pg of standard.
6. Incubate at 37° C. in a saturated atmosphere for 1.5 hr.
7. Wash the plate with PBS-Tween.
8. Add 100 μL goat anti-human TNFrII polyclonal (1.5 μg/mL R&D Systems #AB226-PB in 0.5% BSA in PBS).
9. Incubate at 37° C. in a saturated atmosphere for 1 hr.
10. Wash the plate with PBS-Tween.
11. Add 100 μL anti-goat IgG-peroxidase (1:50,000 in 0.5% BSA in PBS, Sigma #A5420).
12. Incubate at 37° C. in a saturated atmosphere for 1 hr.
13. Wash the plate with PBS-Tween.
14. Add 10 μL KPL TMB developer, develop at room temperature (usually about 10 min), then terminate with phosphoric acid and excite at 450 nm and read at 570 nm.

TNFα ELISA Assay.

Coat Immulon® 2 plates with 0.1 mL/well of 1 ug/mL Genzyme mAb in 0.1 M NaHCO3 pH 8.0 buffer overnight (about 18–20 hr) at 4° C., wrapped tightly in Saran® wrap.

Flick out coating solution and block plates with 0.3 mL/well blocking buffer overnight at 4° C., wrapped in Saran® wrap.

Wash wells thoroughly 4× with wash buffer and completely remove all wash buffer. Add 0.1 mL/well of either samples or rhTNFα standards. Dilute samples if necessary in appropriate diluent (e.g. tissue culture medium). Dilute standard in same diluant. Standards and samples should be in triplicates.

Incubate at 37° C. for 1 hr in humified container.

Wash plates as above. Add 0.1 mL/well of 1:200 dilution of Genzyme rabbit anti-hTNFa.

Repeat incubation.

Repeat wash. Add 0.1 mL/well of 1 μg/mL Jackson goat anti-rabbit IgG (H+L)-peroxidase.

Incubate at 37° C. for 30 min.

Repeat wash. Add 0.1 mL/well of peroxide-ABTS solution.

Incubate at room temperature for 5–20 min.

Read OD at 405 nm.

12 Reagents are:

Genzyme mouse anti-human TNF monoclonal (Cat.#80-3399-01)

Genzyme rabbit anti-human TNF polyclonal (Cat.#IP-300)

Genzyme recombinant human TNF (Cat.#TNF-H).

Jackson Immunoresearch peroxide-conjugated goat anti-rabbit IgG (H+L) (Cat.#111-035-144).

Kirkegaard/Perry peroxide ABTS solution (Cat#50-66-01).

Immulon 2 96-well microtiter plates.

Blocking solution is 1 mg/mL gelatin in PBS with 1× thimerasol.

Wash buffer is 0.5 mL Tween® 20 in 1 liter of PBS.

Example 423

In Vitro Aggrecanase Inhibition Analysis

Assays for measuring the potency ($IC_{50}$) of a compound toward inhibiting aggrecanase are known in the art.

One such assay, for example, is reported in European Patent Application Publ. No. EP 1 081 137 A1. In that assay, primary porcine chondrocytes from articular joint cartilage are isolated by sequential trypsin and collagenase digestion followed by collagenase digestion overnight and are plated at $2\times10^5$ cells per well into 48 well plates with 5 μCi/ml$^{35}$S (1000 Ci/mmol) sulphur in type 1 collagen coated plates. Cells are allowed to incorporate label into their proteoglycan matrix (approximately 1 week) at 37° C. under an atmosphere of 5% $CO_2$. The night before initiating the assay, chondrocyte monolayers are washed 2 times in DMEM/1% PSF/G and then allowed to incubate in fresh DMEM/1% FBS overnight. The next morning, chondrocytes are washed once in DMEM/1% PSF/G. The final wash is allowed to sit on the plates in the incubator while making dilutions. Media and dilutions are made as described in the following Table 10:

TABLE 10

| | |
|---|---|
| control media | DMEM alone |
| IL-1 media | DMEM + IL-1 (5 ng/ml) |
| drug dilutions | Make all compound stocks at 10 mM in DMSO. Make a 100 μM stock of each compound in DMEM in 96-well plate. Store in freezer overnight. The next day, perform serial dilutions in DMEM with IL-1 to 5 μM, 500 nM, and 50 nM. Aspirate final wash from wells and add 50 μM of compound from above dilutions to 450 μL of IL-1 media in appropriate wells of the 48 well plates. Final compound concentrations equal 500 nM, 50 nM, and 5 nM. All samples completed in triplicate with control and IL-1 alone on each plate. |

Plates are labeled and only the interior 24 wells of the plate are used. On one of the plates, several columns are designated as IL-1 (no drug) and control (no IL-1, no drug). These control columns are periodically counted to monitor 35S-proteoglycan release. Control and IL-1 media are added to wells (450 μL) followed by compound (50 μL) so as to initiate the assay. Plates are incubated at 37° C with 5% $CO_2$ atmosphere. At 40–50% release (when CPM from IL-1 media is 4–5 times control media) as assessed by liquid scintillation counting (LSC) of media samples, the assay is terminated (about 9 to about 12 hours). Media is removed from all wells and placed into scintillation tubes. Scintillate is added and radioactive counts are acquired (LSC). To solubilize cell layers, 500 μL of papain digestion buffer (0.2 M Tris, pH 7.0, 5 mM DTT, and 1 mg/ml papain) is added to each well. Plates with digestion solution are incubated at 60° C. overnight. The cell layer is removed from the plates the next day and placed in scintillation tubes. Scintillate is then added, and samples counted (LSC). The percent of released counts from the total present in each well is determined. Averages of the triplicates are made with control background subtracted from each well. The percent of compound inhibition is based on IL-1 samples as 0% inhibition (100% of total counts).

Another assay for measuring aggrecanase inhibition is reported in WIPO Int'l Publ. No. WO 00/59874. That assay reportedly uses active aggrecanase accumulated in media from stimulated bovine cartilage (BNC) or related cartilage sources and purified cartilage aggrecan monomer or a fragment thereof as a substrate. Aggrecanase is generated by stimulation of cartilage slices with interleukin-1 (IL-1), tumor necrosis factor alpha (TNF-α), or other stimuli. To accumulate BNC aggrecanase in culture media, cartilage reportedly is first depleted of endogenous aggrecan by stimulation with 500 ng/ml human recombinant IL-β for 6 days with media changes every 2 days. Cartilage is then stimulated for an additional 8 days without media change to allow accumulation of soluble, active aggrecanase in the culture media. To decrease the amounts of matrix metalloproteinases released into the media during aggrecanase accumulation, agents which inhibit MMP-1, -2, -3, and -9 biosynthesis are included during stimulation. This BNC conditioned media containing aggrecanase activity is then used as the source of aggrecanase for the assay. Aggrecanase enzymatic activity is detected by monitoring production of aggrecan fragments produced exclusively by cleavage at the Glu373-Ala374 bond within the aggrecan core protein by Western analysis using the monoclonal antibody, BC-3 (Hughes, et al., *Biochem J*, 305(3):799–804 (1995)). This antibody reportedly recognizes aggrecan fragments with the N-terminus, 374ARGSVIL, generated upon cleavage by aggrecanase. The BC-3 antibody reportedly recognizes this neoepitope only when it is at the N-terminus and not when it is present internally within aggrecan fragments or within the aggrecan protein core. Only products produced upon cleavage by aggrecanase reportedly are detected. Kinetic studies using this assay reportedly yield a Km of 1.5+/−0.35 μM for aggrecanase. To evaluate inhibition of aggrecanase, compounds are prepared as 10 mM stocks in DMSO, water, or other solvents and diluted to appropriate concentrations in water. Drug (50 μL) is added to 50 μL of aggrecanase-containing media and 50 μL of 2 mg/ml aggrecan substrate and brought to a final volume of 200 μL in 0.2 M Tris, pH 7.6, containing 0.4 M NaCl and 40 mM CaCl$_2$. The assay is run for 4 hr at 37° C., quenched with 20 mM EDTA, and analyzed for aggrecanase-generated products. A sample containing enzyme and substrate without drug is included as a positive control and enzyme incubated in the absence of substrate serves as a measure of background. Removal of the glycosaminoglycan side chains from aggrecan reportedly is necessary for the BC-3 antibody to recognize the ARGSVIL epitope on the core protein. Therefore, for analysis of aggrecan fragments generated by cleavage at the Glu373-Ala374 site, proteoglycans and proteoglycan fragments are enzymatically deglycosylated with chondroitinase ABC (0.1 units/10 μg GAG) for 2 hr at 37° C. and then with keratanase (0.1 units/10 μg GAG) and keratanase II (0.002 units/10 μg GAG) for 2 hr at 37° C. in buffer containing 50 mM sodium acetate, 0.1 M Tris/HCl, pH 6.5. After digestion, aggrecan in the samples is precipitated with 5 volumes of acetone and resuspended in 30 μL of Tris glycine SDS sample buffer (Novex) containing 2.5% beta mercaptoethanol. Samples are loaded and then separated by SDS-PAGE under reducing conditions with 4–12% gradient gels, transferred to nitrocellulose and immunolocated with 1:500 dilution of antibody BC3. Subsequently, membranes are incubated with a 1:5000 dilution of goat anti-mouse IgG alkaline phosphatase second antibody and aggrecan catabolites visualized by incubation with appropriate substrate for 10–30 minutes to achieve optimal color development. Blots are quantitated by scanning densitometry and inhibition of aggrecanase determined by comparing the amount of product produced in the presence versus absence of compound.

The above detailed description of preferred embodiments is intended only to acquaint others skilled in the art with the invention, its principles, and its practical application so that others skilled in the art may adapt and apply the invention in its numerous forms, as they may be best suited to the requirements of a particular use. This invention, therefore, is not limited to the above embodiments, and may be variously modified.

We claim:

1. A compound or salt thereof wherein the compound corresponds in structure to a formula selected from the group consisting of:

(77-1)

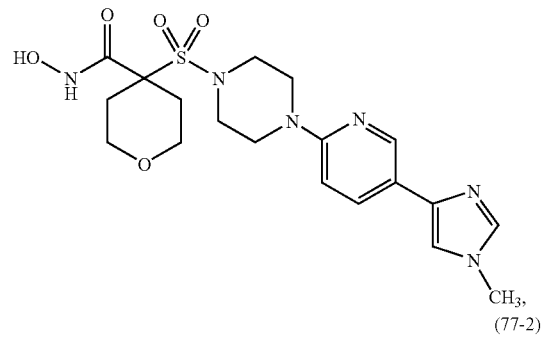

(77-2)

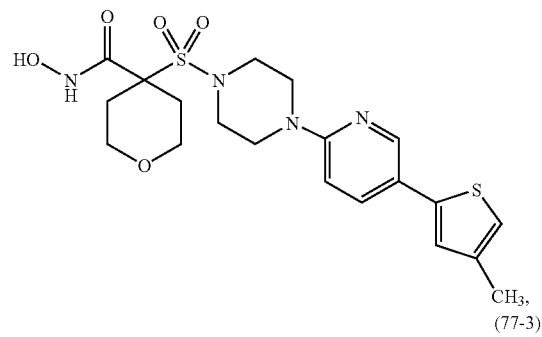

(77-3)

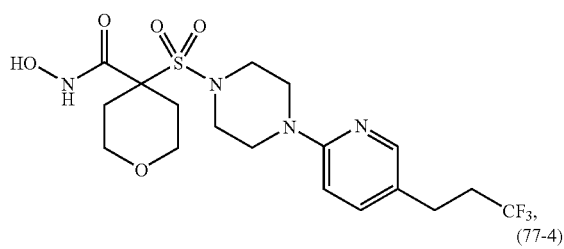

(77-4)

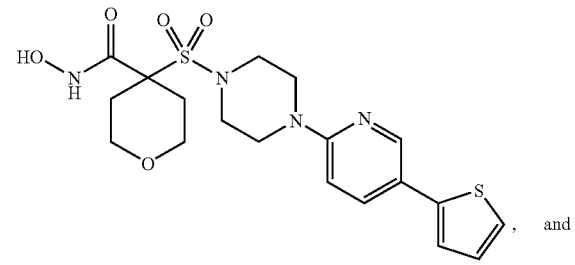

, and

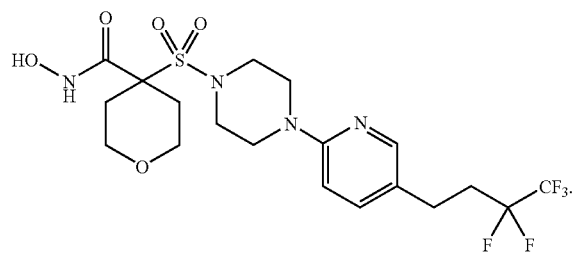
(77-5)
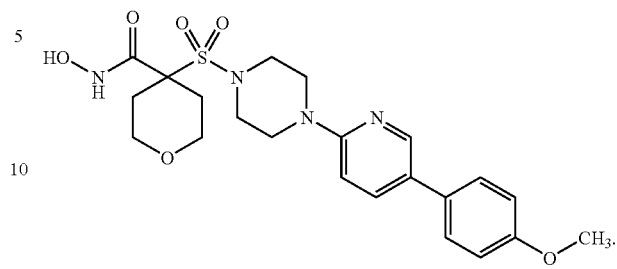
(78-1)
2. A compound or salt thereof wherein the compound corresponds in structure to the following formula:
* * * * *